US005663164A

United States Patent [19]

[11] Patent Number: 5,663,164

[45] **Date of Patent: *Sep. 2, 1997**

Teutsch et al.

[54] 1-DETHIA-2-THIA-CEPHALOSPORANIC ACIDS

[75] Inventors: Jean-Georges Teutsch, Pantin; Alain Bonnet, Livery-Gargan; Jozsef Aszodi, Choisy-le-Roi; Germain Costerousse, Saint Maurice; Solange Gouin d'Ambrieres, Paris, all of France

[73] Assignee: Roussel Uclaf, France

[ * ] Notice: The term of this patent shall not extend beyond the expiration date of Pat. No. 4,908,359.

[21] Appl. No.: 429,600

[22] Filed: Apr. 27, 1995

Related U.S. Application Data

[63] Continuation of Ser. No. 115,471, Nov. 5, 1993, abandoned, which is a continuation of Ser. No. 152,864, Feb. 5, 1988, abandoned, which is a continuation-in-part of Ser. No. 834,894, Feb. 28, 1986, abandoned, which is a continuation-in-part of Ser. No. 700,690, Feb. 12, 1985, abandoned.

[30] Foreign Application Priority Data

| | | | |
|---|---|---|---|
| Feb. 13, 1984 | [FR] | France | 84-02138 |
| Aug. 9, 1985 | [FR] | France | 85-12217 |
| Feb. 6, 1987 | [FR] | France | 87-01455 |

[51] Int. Cl.$^6$ .......... C07D 417/12; A61K 31/54

[52] U.S. Cl. .......... 514/210; 540/214

[58] Field of Search .......... 540/214, 210

[56] References Cited

U.S. PATENT DOCUMENTS

| | | | |
|---|---|---|---|
| 4,072,674 | 2/1978 | Gleason | 540/214 |
| 4,166,816 | 9/1979 | Gleason | 540/214 |
| 4,908,359 | 3/1990 | Costerousse | 514/210 |
| 5,385,897 | 1/1995 | Teutsch | 540/214 |

*Primary Examiner*—Matthew V. Grumbling
*Assistant Examiner*—King Lit Wong
*Attorney, Agent, or Firm*—Bierman, Muserlian & Lucas

[57] ABSTRACT

Novel 1-dethia-2-thia-cephalosporanic acid derivatives of the formula

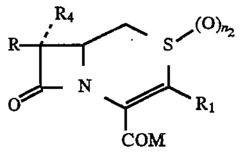

wherein R is selected from the group consisting of

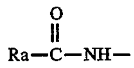 and 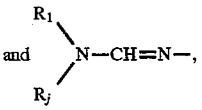

Ra is an organic radical, $R_i$ and $R_j$ are individually selected from the group consisting of hydrogen, aliphatic, aromatic and heterocycle or taken together with the nitrogen atom to which they are attached form an optionally substituted cycle or $R_bNH$—, $R_b$ is optionally substituted carbocyclic or heterocyclic aryl, $R_1$ and —COM are as defined in the specification, $R_4$ is hydrogen or methoxy, $n_2$ is 0, 1 or 2 and their non-toxic, pharmaceutically acceptable acid addition salts in racemic or optically active form having antibiotic activity and their preparation and novel intermediates.

54 Claims, No Drawings

1-DETHIA-2-THIA-CEPHALOSPORANIC ACIDS

PRIOR APPLICATIONS

This application is a continuation of U.S. patent application Ser. No. 08/115,471 filed Nov. 5, 1993, now abandoned which is a continuation of U.S. patent application Ser. No. 07/152,864 filed Feb. 5, 1988, which is a continuation-in-part of U.S. patent application Ser. No. 06/834,894 filed Feb. 28, 1986 which is a continuation-in-part of our U.S. patent application Ser. No. 06/700,690 filed Feb. 12, 1985, now all abandoned.

STATE OF THE ART

Commonly assigned U.S. Pat. No. 4,476,124 describes optically active isomers and racemates of 7-[2-(2-amino-4-thiazolyl)-2-oxyimino-acetamido]-bicyclooctene-carboxylic acid derivatives of the formula

I

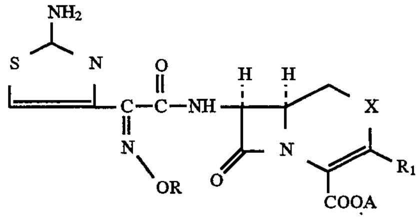

and French Patent No. 2,324,639 describes other 1-dethia-2-thia-cephalosporanic acids. Also pertinent to compounds of this type are Chem. Abracts, Vol. 98, No. 28.02.83, No. 71800v p. 602; "Recent advances in the chemistry of β-lactam antibiotica" No. 38.30.06–2.07.80 p. 8.0–87; Chem. Abstracts Vol. 72, No. 25, 22.06.70 No. 132401c p. 333; E.P. application No. 0 031 982; Can. J. of Chemistry Vol. 60 No. 21, 1982, p. 2707–2710; Chem. Abstracts Vol. 80, No. 7, 18.02.74, No. 86678t, p. 260; Chem. Abstracts, Vol. 84, No. 1, 5.01.76, No. 4315p, p. 369; and Org. Chem., Vol. 44, No. 25 7.12.79, p. 4741–4742.

OBJECTS OF THE INVENTION

It is an object of the invention to provide the novel compounds of formula I and their non-toxic, pharmaceutically acceptable salts and a process for their preparation and intermediates.

It is another object of the invention to provide novel antibacterial compositions and a novel method of combatting bacterial infections in warm-blooded animals.

These and other objects and advantages of the invention will become obvious from the following detailed description.

THE INVENTION

The novel compounds of the invention are selected from the group consisting of 1-dethia-2-thia-cephalosporanic acid derivatives of the formula

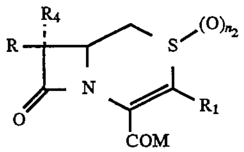

wherein R is selected from the group consisting of

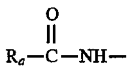 and 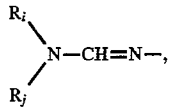

Ra is an organic radical, $R_i$ and $R_j$ are individual selected from the group consisting of hydrogen, aliphatic, aromatic and heterocycle or taken together with the nitrogen atom to which they are attached form an optionally substituted cycle or, $R_b$NH— $R_b$ is optionally substituted carbocyclic or heterocyclic aryl, $R_1$ is selected from the group consisting of a) —Z—$R_2$ wherein $R_2$ is selected from the group consisting of alkyl, alkenyl and alkynyl optionally interrupted by a heteroatom and optionally substituted and Z is selected from the group consisting of optionally oxidized sulfur, —O—, —NH— and —Se—, b) —$Z_a$—$R_3$ wherein $Z_a$ is selected from the group consisting of —$CH_2$—, —S—, —Se—, —O—, —NH—$CH_2$—S— and a simple bond and $R_3$ is selected from the group consisting of optionally substituted carbocycle or arylheterocycle and optionally substituted quaternary ammonium, c) optionally substituted alkyl, alkenyl and alkynyl of 2 to 8 carbon atoms optionally interrupted with a heteroatom, d) halogen, —CN, optionally esterified or salified carboxy, azido, thiocyanato and isothiocyanato and e) azidomethyl, aminomethyl, di- and mono-substituted aminomethyl, thiocyana methyl, isothiocyanatomethyl, carbamoyloxymethyl, semicarbazonomethine, optionally substituted aryl hydrazonomethine, nitromethyl di- and trihalomethyl, $-CH_2-ONO_2$, $-CH_2-\overset{\oplus}{P}-(Alk)_3$ and

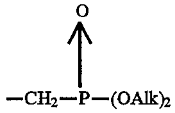

and AlK is alkyl of 1 to 4 carbon atoms, $R_4$ is selected from the group consisting of hydrogen and methoxy, —COM is —$COO^-$ or —COOA or an optionally substituted carbamoyl wherein A is selected from the group consisting of hydrogen, alkali metal, alkaline earth equivalent, magnesium equivalent, —$NH_4$, an organic amine and ester or $R_1$ and —COOA together with the carbon atoms to which they are attached form

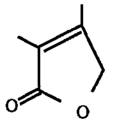 or 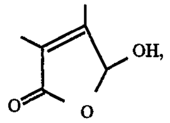

$n_2$ is 0, 1 or 2 and their non-toxic, pharmaceutically acceptable acid addition salts in racemic or optically active forms.

A preferred group of compounds of the invention are selected from the group consisting of 1-dethia-2-thia-cephalosporanic acid derivatives of the formula

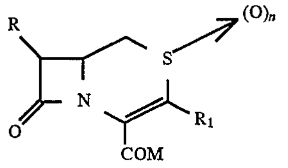

I wherein R is

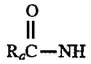

and $R_a$ is selected from the group consisting of ArO-$CH_2$, ArS-$CH_2$,

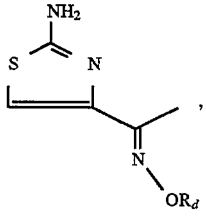
,
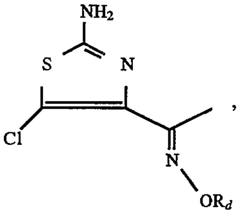
,

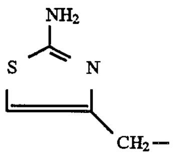
and
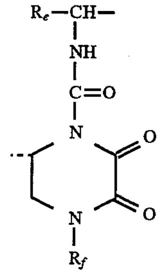

Ar and $R_e$ are individually selected from the the group consisting of phenyl and phenyl substituted with at least one member of the group consisting of halogen, alkyl and alkoxy and alkylthio of 1 to 4 carbon atoms, alkylsulfinyl and alkylsulfonyl of 1 to 4 alkyl carbon atoms, —$NH_2$, nitro, —OH, aminoalkyl of 1 to 4 carbon atoms, —CN, and —$CF_3$, $R_f$ is alkyl of 1 to 4 carbon atoms, $R_d$ is selected from the group consisting of a) hydrogen, b) alkyl of 1 to 6 carbon atoms, c) alkenyl and alkynyl of 2 to 6 carbon atoms, d) cycloalkyl of 3 to 8 carbon atoms, said alkyl, alkenyl, alkynyl and cycloa-alkyl being optionally substituted with a member of the group consisting of halogen acyl of 1 to 7 carbon atoms, —CN, carbamoyl, amino, —OH, —SH, alkylthio and alkoxy of 1 to 4 carbon atoms, oxo and carboxyl optionally salified or esterified, e) phenyl optionally substituted with carboxy, f)

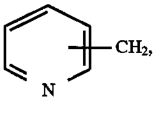

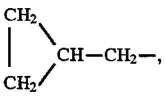

and h)

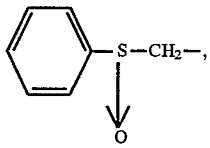

$R_1$ is selected from the group consisting of a) —Z—$R_2$, b) —$Z_a$—$R_3$, c) alkyl of 2 to 4 carbon atoms and alkenyl and alkynyl of 2 to 4 carbon atoms, all optionally interrupted with —0— or —S— optionally oxidized and optionally substituted with phenyl or phenyl substituted with at least one member of the group consisting of —$NO_2$, —CN, halogen, acetyl and carboxy optionally esterified or salified and d) a member of the group consisting of carboxy, esterified and salified carboxy, azidomethyl, aminomethyl, thiocyanato, carbamoyloxymethyl, semicarbazonomethine, phenylhydrozonomethine optionally substituted with —$NO_2$ and carbamoyloxymethyl, $R_2$ is selected from the group consisting of alkyl of 1 to 4 carbon atoms and alkenyl and alkynyl of 2 to 4 carbon atoms, all optionally substituted with at least one member of the group consisting of a) halogen, —$NH_2$, —CN, carboxy, esterified or salified carboxy, carbamoyl, methyltetrazolylcarbamoyl and acyl and b) aryl and arylthio selected from the group consisting of phenyl, diphenyl, naphthyl, thienyl, furyl, pyrrolyl, imidazolyl, pyrazolyl, thiazolyl, isothiazolyl, oxazolyl, isoxazolyl, triazolyl, thiadiazolyl, pyrannyl, oxadiazolyl, tetrazolyl, pyridinyl, pyrimidinyl, pyrazinyl, pyridazinyl, thiazinyl, oxazinyl, triazinyl, thiadiazinyl, oxadiazinyl, tetrazinyl, imidazolinyl, benzimidazolyl, benzothiazolyl and benzoxazol, all optionally substituted with at least one member of the group consisting of —$NO_2$, —CN, carboxy, esterified or salified carboxy, —$NH_2$, —OH, azido, sulfo, free or salified carboxy and halogen and c) quaternary ammonium selected from the group consisting of pyridinium, methylpyridinium, trialkyammonium of 1 to 4 alkyl carbon atoms and

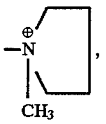

Z is selected from the group consisting of —NH—, selenium, —0—, —S— and oxidized sulfur, $R_3$ is selected from the group consisting of a) carbocyclic or heterocyclic aryl selected from the group consisting of phenyl, diphenyl, naphthyl, thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridinyl, pyrimidinyl, pyrazinyl, pyridazinyl, thiazinyl, oxazinyl, triazinyl, thiadiazinyl, oxadiazinyl, tetrazinyl,imidazolinyl, benzimidazolyl, benzothiazolyl and benzoxazole, all optionally substituted with at least one member of the group consisting of i) alkyl of 1 to 6 carbon atoms, ii) alkyl of 1 to 6 carbon atoms substituted with a member selected from the group consisting of phenyl, thienyl, phenoxy, alkoxy of 1 to 6 carbon atoms, alkoxycarbonyl of 2 to 7 carbon atoms, halogen, —OH, protected —OH, carboxy, free or esterified carboxy, aminoalkyl of 1 to 7 carbon atoms, dialkylamino of 1 to 4 carbon atoms and acylamino of an organic carboxylic acid of 1 to 7 carbon atoms, iii) alkenyl and alkynyl of 2 to 6 carbon atoms, phenyl, tolyl, halogen, —$NH_2$, —$NO_2$, alkylthio and alkoxy of 1 to 4 carbon atoms, —OH, —SH, carboxy, esterified or salified carboxy, carbamoyl, phenoxy, phenylthio, cyclopentyl and cyclohexyl, b) pyridinium, quinolinium, isoquinolinium, 2,3-cyclopentenopyridinium, cyclohexenopyridinium, thienopyridinium, imidazolinium pyrazinium and thiazolinium, all optionally substituted with at least one member of the group consisting of a) alkyl of 1 to 6 carbon atoms, b) alkyl of 1 to 6 carbon atoms substituted with at least one member of the group consisting of phenyl, thienyl, phenoxy, alkoxy of 1 to 6 carbon atoms, alkoxycarbonyl of 2 to 7 carbon atoms, halogen, —OH, protected —OH, carboxy, esterified or salified carboxy, aminoalkyl of 1 to 7 carbon atoms, dialkylamino of 1 to 6 alkyl carbon atoms and acylamino of an organic carboxylic acid of 1 to 7 carbon atoms, c) alkenyl and alkynyl of 2 to 6 carbon atoms, phenyl, tolyl, halogen, amino, dialkylamino of 1 to 6 carbon atoms, —$NO_2$ alkylthio and alkoxy of 1 to 4 carbon atoms, —OH, —CN, —SH, carboxy, salified or esterified carboxy, phenoxy, phenylthio, cyclopropyl, —$CF_3$, acetyl, thiocyanato and benzoyl, c) a member of the group consisting of

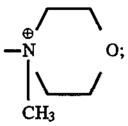 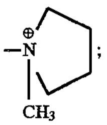 ; 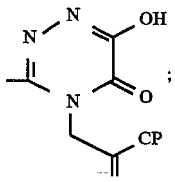 ;

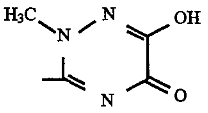 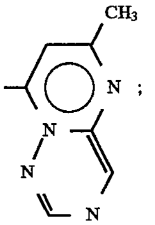 ;

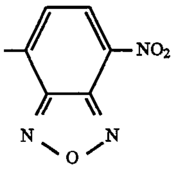 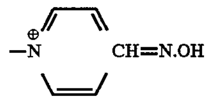

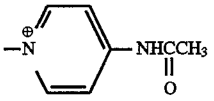 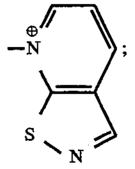 ;

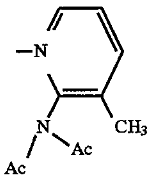 and 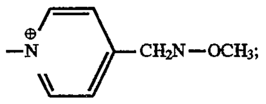

and d) is selected from the group consisting of di or trialkylammonium of 1 to 6 alkyl carbon atoms and

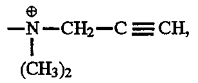

$Z_a$ is selected from the group consisting of —$CH_2$—, —S—, —Se—, —O—, —NH—, —$CH_2S$— and a simple bond, —COM is selected from the group consisting of optionally substituted carbamoyl, —$COO^-$ and —COOA, A is selected from the group consisting of hydrogen, an alkali metal, an alkaline earth metal, magnesium, —$NH_4$ and an organic amine base or $R_1$ and COOA together with the carbon atoms to which they are attached form

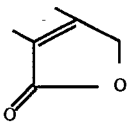 or 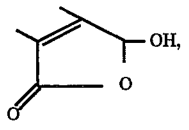

n is 0, 1 or 2 and their non-toxic, pharmaceutically acceptable acid addition salts.

A preferred group of compounds of formula I are those wherein R is

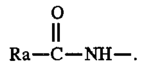

Examples of Ra are a) Ar—$(CH_2)_n$—;

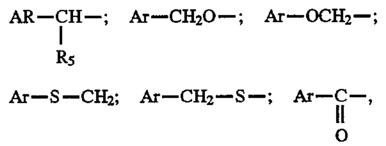

wherein Ar is selected from the group consisting of phenyl, optionally mono- or poly-substituted and aromatic heterocyclic having 5,6 or 7 links containing from 1 to 4 heteroatoms selected from sulfur, oxygen or nitrogen, n is an integer from 0 to 4, and $R_5$ is selected from the group consisting of amino, hydroxyl, azido, hydrazino, free or esterified or salified carboxyl, free or salified sulfo, sulfoamino, halogen, alkylhydrazino, phenylhydrazino and formyloxy.

Examples of the substituents of the phenyl or heterocyclic radicals are halogen, alkyl and alkoxy of 1 to 4 carbon atoms, alkylthio, alkylsulphinyl, alkylsulphonyl, aminoalkyl of 1 to 4 carbon atoms, preferably amino methyl, hydroxyl, nitro, amino, trifluoromethyl and cyano.

Examples of aromatic heterocyclic radicals are thiazolyl, furyl, thienyl, pyrrolyl, pyridinyl, pyrazinyl, pyrimidinyl, imidazolyl, pyrazolyl and tetrazolyl. The furyl, amino thiazolyl, amino halo thiazolyl, amino thiadiazolyl and amino pyrimidinyl radicals are preferred. b) Ra also is selected from the group consisting of alkyl, cycloalkyl, alkoxyl, alkenyl and cycloalkenyl, each of which can be optionally mono- or pol substituted by at least one alkylthio or cyanoalkylthio, mercapto, nitro, cyano or amino. c) Ra can also be

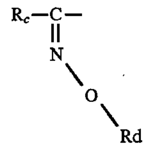

wherein Rc can have the same definition as Ar. Among the preferred values of Rc are particularly, 2-amino 4-thiazolyl; 2-amino 5-nitro, 5-chloro, 5-fluoro or 5-bromo thiazolyl and 5-amino-1,2,4-thiadiazolyl, 4-thiazolyl, 2-thienyl or 2-furyl; is selected from the group consisting of hydrogen, acyl, aryl, heteroaryl, arylalkyl, heteroarylalkyl, alkyl, cycloalkyl, alkenyl, cycloalkenyl and alkynyl optionally substituted and optionally interrupted by an oxygen or optionally oxidized sulfur, or Rd is an optionally substituted carbamoyl radical.

Examples of Rd are alkyl, halogen, acyl, cyano, carbamoyl, nitro, amino, hydroxy, mercapto, alkylthio, oxo, alkoxy and a free, esterified or salified carboxyl radical.

Examples of Ra are hydrogen, alkyl, optionally cyclic alkenyl, alkynylene aryl and mono- or poly-cyclic heteroaryl and especially the $-CH_3$, $-CH_2-CH_3$, $-CHF_2$, $-CH_2-CF_3$, $-CH_2O-CH_3$,

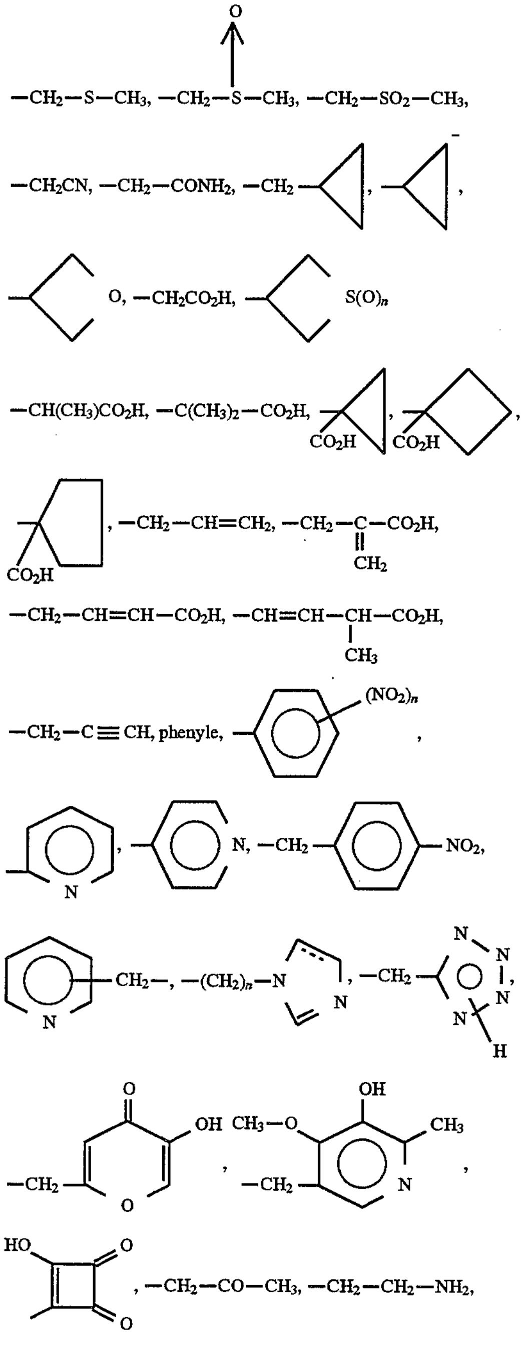

$-CH_2-CF_2-CO_2H$.

Among the preferred values of Rd are methyl, hydrogen ethyl, allyl, 1-methyl-1-carboxyethyl, carboxymethyl and difluoro methyl.

d) Ra can also be:

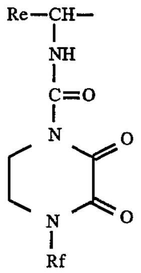

wherein Re has the same values as Ar and unsubstituted phenyl or phenyl substituted by one or more hydroxy are preferred. Rf can be an optionally substituted alkyl or —N=CH—Rg in which Rg is aryl as defined above for Ra. For Rf, ethyl, phenyl or furyl are preferred.

e) Ra can also be:

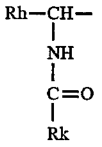

wherein Rh has the values indicated for Ar; Rk can be:

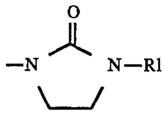

in which R1 is hydrogen or alkylsulfonyl, or —N=CH—Rm in which Rm has the same value as At, in particular furyl; Rk is an optionally substituted aryl, for example imidazolyl substituted by a carboxyl, or a substituted amino for example an acylamido such as N-methyl-benzoylamido or furylcarbonyl amido or amino substituted by an optionally substituted heterocycle or an optionally substituted and condensed aryl or an optionally substituted aralkyl.

Among this first group of compounds, Ra is preferably one of the following:

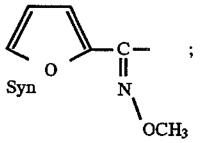

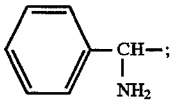

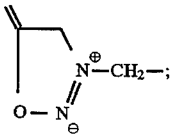

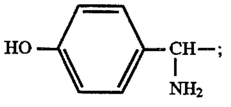

-continued
$N \equiv C-CH_2-$;
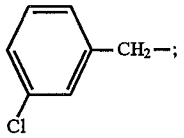
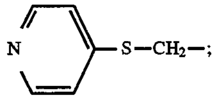
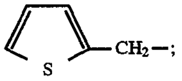
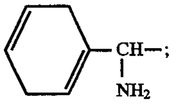
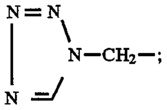
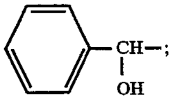
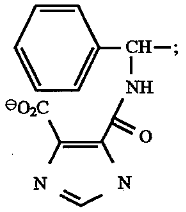
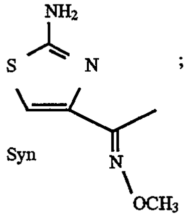
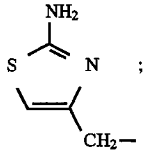
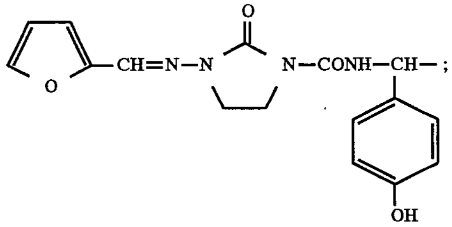
-continued
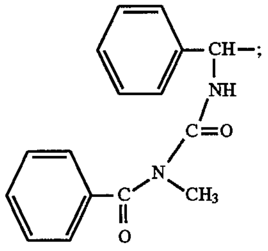
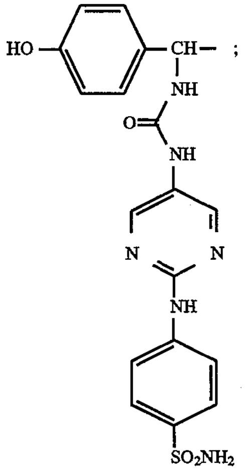
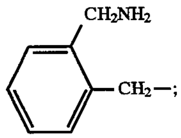
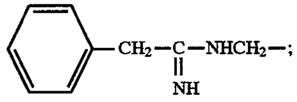
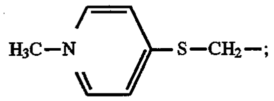
$HOOC-CH_2-S-CH_2-$;
$NC-CH=CH-S-CH_2-$;
$HO_2C-CH=CH-S-CH_2-$;
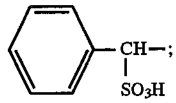
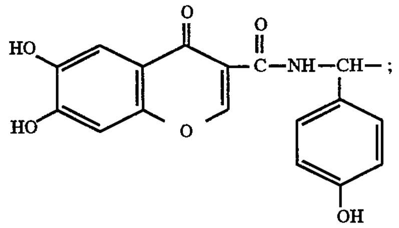

-continued
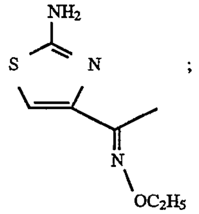
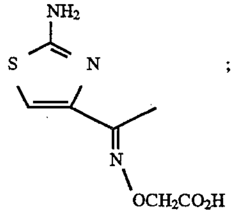
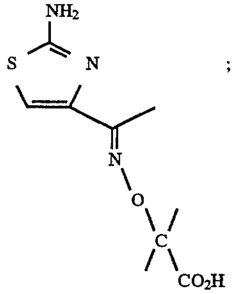
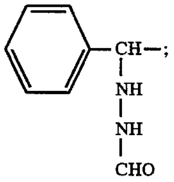
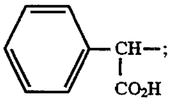
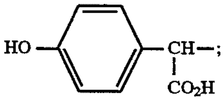
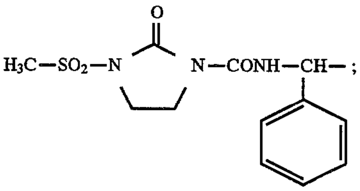
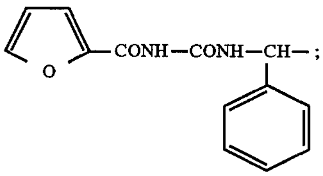
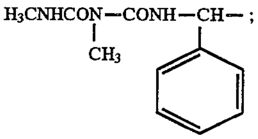
-continued
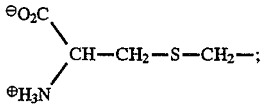
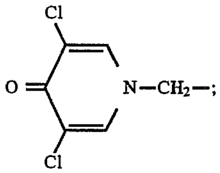
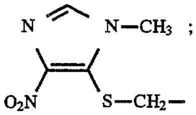
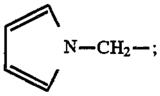
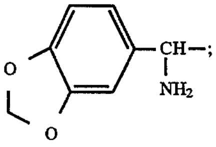
$NCCH_2-S-CH_2-$;
$F_3C-S-CH_2-$;
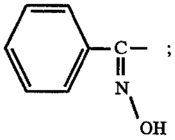
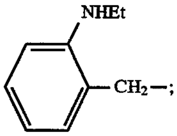
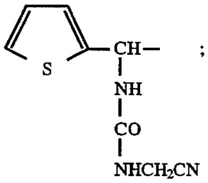
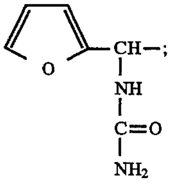

-continued
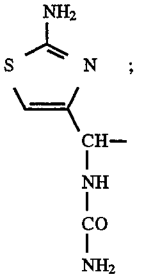
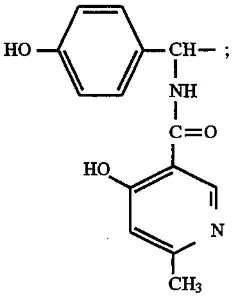
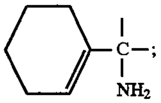
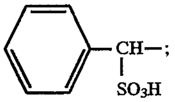
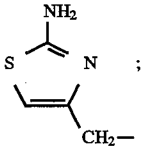
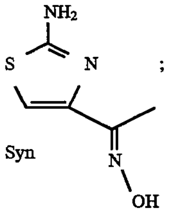
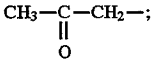
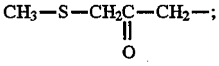
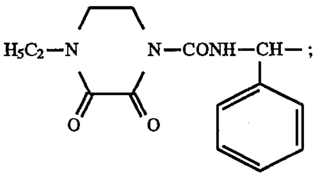
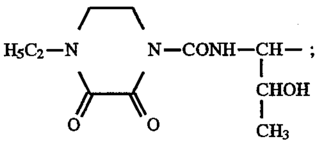
-continued
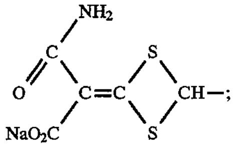
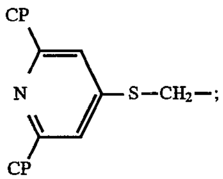
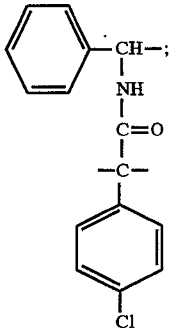
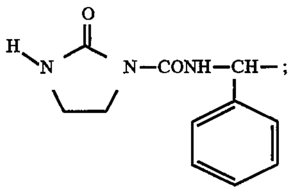
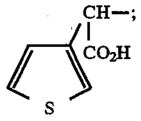
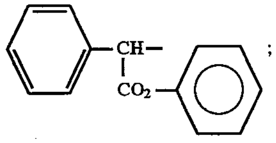
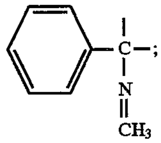
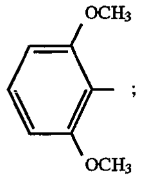
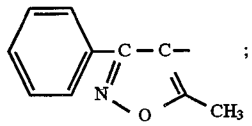

-continued

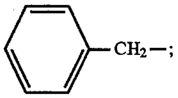

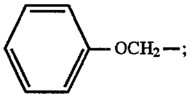

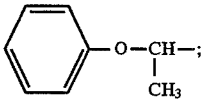

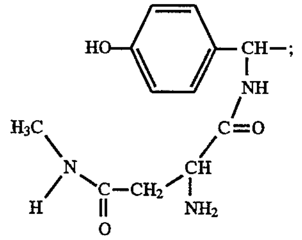

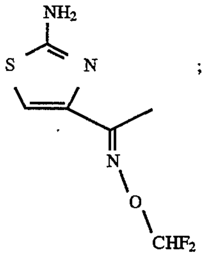
;

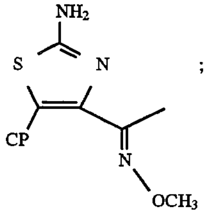
;

Another preferred group of compounds of formula I are those wherein R is

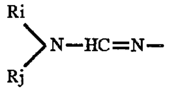

in which Ri and Rj are individually selected from the group consisting of hydrogen and alkyl of 1 to 8 carbon atoms, or Ri and Rj form, with the nitrogen atom to which they are bonded, an optionally substituted cyclic amine. Preferably,

is

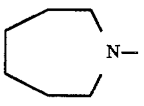 or 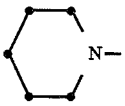 or

-continued

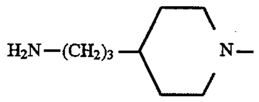

R can also be Rb—NH— in which Rb is an optionally substituted carbocyclic or heterocyclic aryl. Among such preferred values are

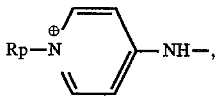

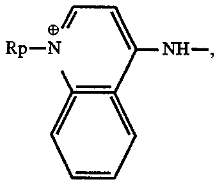

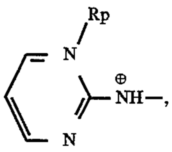

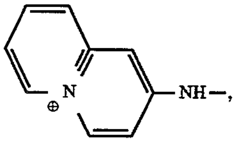

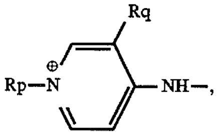

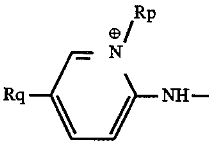 or

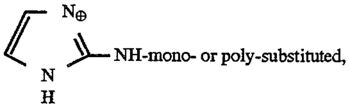

in which Rp is alkyl of 1 to 4 carbon atoms, preferably methyl, ethyl, isopropyl optionally interrupted by a heteroatom such as methoxy methyl optionally substituted by at least one halogen, such as trichloroethoxymethyl or trifluoroethoxy-methyl; or alkoxy such as ethoxy. Rp can also be arylalkyl such as benzyl or phenethyl optionally substituted by alkyl such as methyl, alkoxy such as methoxy, cyano or halogen such as fluoro. Rp can also be furfuryl or an optionally substituted phenyl methoxy methyl.

Rq can be hydrogen or alkyl of 1 to 4 carbon atoms such as methyl, or alkoxycarbonyl such as methoxy-carbonyl or tert-butoxycarbonyl.

Among the said preferred values of this category is

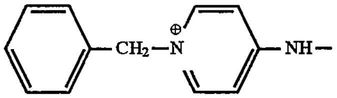

Among the values of $R_1$ are methylthio, ethylthio, propylthio, isopropylthio, butylthio, isobutylthio, tert-butylthio, sec-butylthio, pentylthio and hexylthio. In $Z—R_2$, $R_2$ is preferably alkyl of 1 to 4 carbon atoms.

$R_1$ can also be alkenylthio such as vinylthio, allylthio, 1-propenylthio or butenylthio and alkenyls of 2 to 4 carbon atoms are preferred. Finally, $R_1$ can be alkynylthio such as ethynylthio or propargylthio.

Among the values of $R_1$, there may also be mentioned the radicals formed with a substituent Z representing a selenium or oxygen atom or NH, for example methyl selenyl, methoxy and methylamino.

Among the optional substitutents of $Z—R_2$ are nitro, cyano, free, esterified or salified carboxy, optionally substituted or protected amino, optionally acylated or protected hydroxy, azido, free or salified sulfo, halogen, optionally-substituted carbamoyl, optionally-substituted aryl, optionally-substituted quaternary ammonium or optionally substituted heterocycle. $R_2$ can be interrupted by a heteroatom such as oxygen or sulfur, NH or selenium.

Among the values of $R_3$ are phenyl, diphenyl, naphthyl, thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridinyl, pyrimidinyl, pyrazinyl, pyridazinyl, thiazinyl, oxazinyl, triazinyl, thiadiazinyl, oxadiazinyl, tetrazinyl, imidazolinyl, benzimidazolyl, benzothiazolyl and benzoxazole.

Among the different aryl radicals, thiazol-2-yl, 1,3,4-thiadiazol-5-yl and 1,2,4-thiadiazol-5-yl, imidazol-2-yl, 1,3,4-triazol-5-yl, 1,3,4-thiadiazol-2-yl, 1,2,3-thiadiazol-5-yl, 1H-tetrazol-5-yl, pyridin-2-yl, 1,3,4-triazin-2-yl, 1,3,5-triazin-4-yl, pyridinium, quinolinium, isoquinolinium, 2,3-cyclopenteno pyridinium and trimethylammonium are preferred.

$R_3$ can optionally be substituted by at least one member selected from alkyl such as methyl, ethyl, propyl, isopropyl and linear or branched butyl and the alkyls can be substituted by aryl such as phenyl or thienyl, aryloxy such as lower phenoxy, alkyloxy such as methoxy, alkoxycarbonyl such as ethoxycarbonyl, by halogen such as chloro or bromo, free or protected hydroxy, free, esterified or salified carboxy, amino, alkylamino or dialkylamino or acylamido.

$R_3$ can also be substituted by at least one alkenyl such as vinyl, allyl or butenyl, alkynyl such as ethynyl or propargyl, aryl such as phenyl or tolyl, halogen such as chloro, bromo, iodo or fluoro, amino or nitro, alkoxy of 1 to 4 carbon atoms such as methoxy, alkylthio such as methylthio or hydroxy, mercapto, amino, free, esterified or salified carboxyl or carbamoyl. $R_3$ can also be substituted by two substituents forming together a cyclic radical such as cyclopentyl or cyclohexyl.

Za can be methylene, ethylene or propylene, preferably methylene.

The alkyl, alkenyl or alkynyl of $R_1$ can also be selected from the values mentioned above with ethyl and isopropyl being preferred. The heteroatom with which $R_1$ can be interrupted is selected preferably from the possibly oxidized sulfur or oxygen or NH.

Another preferred class for $R_1$ are substituted alkenyls of the formula $—CH{=}CH—K$ with K being hydrogen, optionally substituted alkyl or alkenyl, halogen, cyano, $—CF_3$,

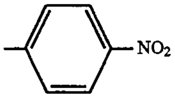

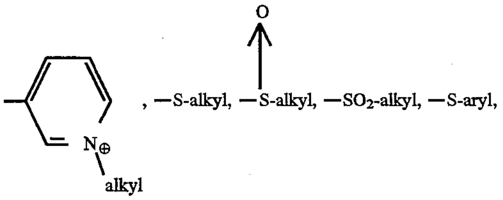

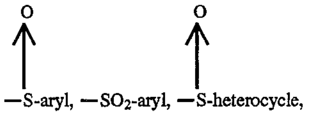

—S-heterocycle or $—SO_2$-heterocycle.

$R_1$ can also be alkyl interrupted by a heteroatom or substituted, for example:

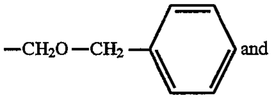 and $—CH_2—SO_2—CH_3$.

A particularly preferred group for $R_1$ are those containing a quaternary ammonium, in particular:

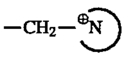 or 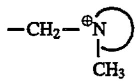

with the symbol

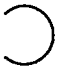

being the residue of a ring. The following $—CH_2$-quaternary ammonium members may be mentioned:

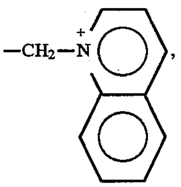,

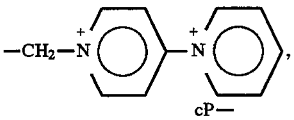, cP—

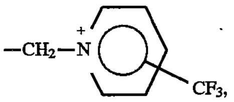 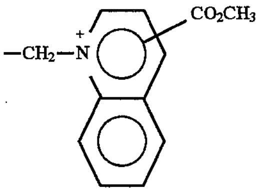

-continued
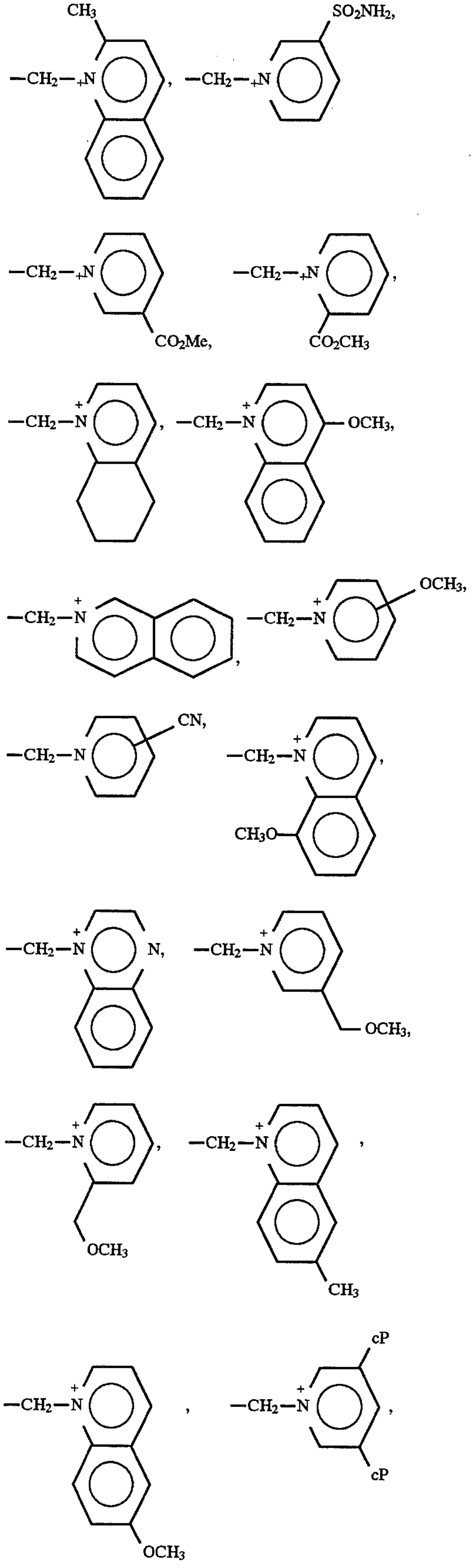
-continued
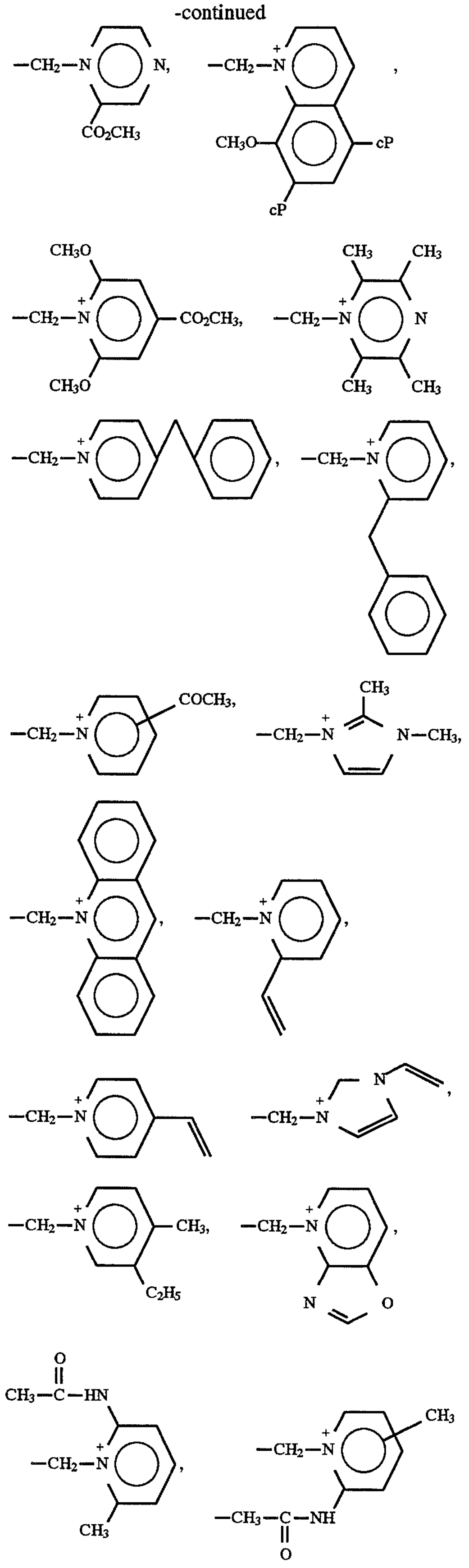

-continued
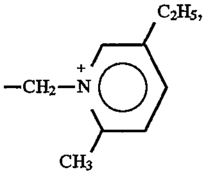
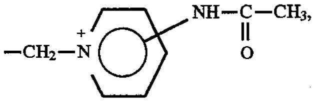
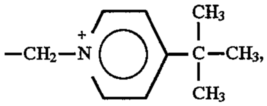
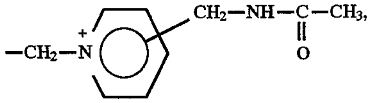
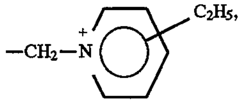
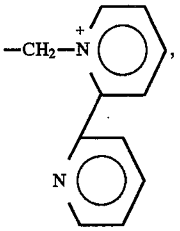
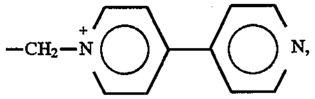
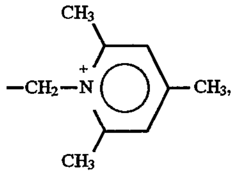
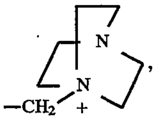
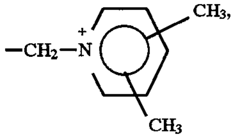
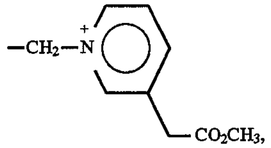
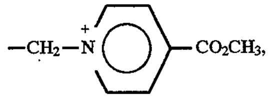
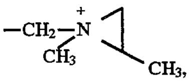
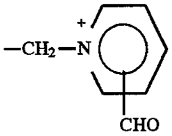
-continued
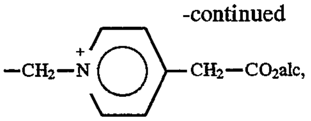
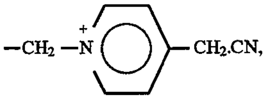
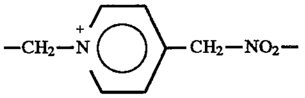
$R_1$ can also preferably be a non-cyclic quaternary ammonium. As values of $R_1$ are further mentioned:
$-CH_2-SO_2-CH_3$, $-CH_2NO_2$, $-CH_2-O-NO_2$,
$-CH_2-\overset{+}{P}(CH_3)_3$, 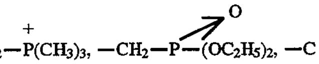 $-C\equiv CH$,
$-C\equiv C-CH_3$, $-C\equiv C-Cl$, $-C\equiv C-CO_2CH_3$,
$-C\equiv C-CF_3$, 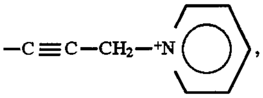
$-CH_2F$, $-CHF_2$, $-CF_3$, $-S-CF_3$,
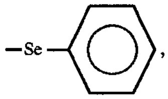 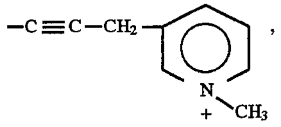
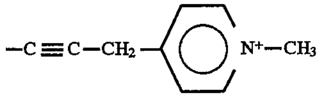
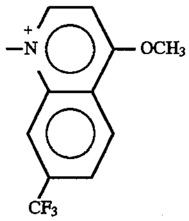 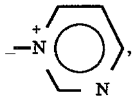 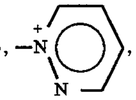
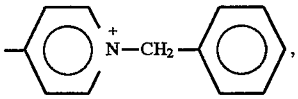 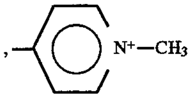
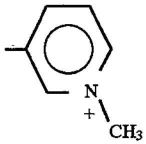 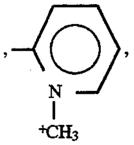
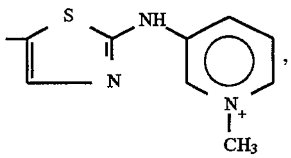

-continued

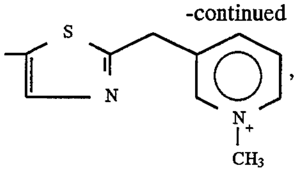
,
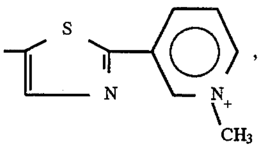
,
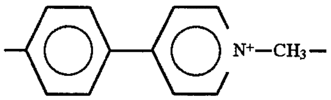

Among the values of A are an equivalent of sodium, of potassium, of lithium, of calcium, of magnesium or of ammonium. Among the organic bases are methylamine, propylamine, trimethylamine, diethylamine, triethylamine, N,N-dimethylethanolamine, tris(hydroxymethyl)amino methane, ethanolamine, pyridine, picoline, dicyclohexylamine, morpholine, benzylamine, procaine, lysine, arginine, histidine and N-methylglucamine.

Residues of easily-cleavable ester groups of A are methoxymethyl, ethoxymethyl, isopropyloxymethyl, α-methoxyethyl, α-ethoxyethyl, methylthiomethyl, ethylthiomethyl, isopropylthiomethyl, pivaloyloxymethyl, acetoxymethyl, propionyloxymethyl, butyryloxymethyl, isobutyryloxymethyl, valeryloxymethyl, isovaleryloxymethyl, tert-butylcarbonyloxymethyl, hexadecanoyloxymethyl, propionyloxyethyl, isovaleryloxyethyl, 1-acetyloxyethyl, 1-propionyloxyethyl, 1-butyryloxyethyl, 1-tert-butylcarbonyloxyethyl, 1-acetyloxypropyl, 1-hexadecanoyloxyethyl, 1-propionyloxypropyl, 1-methoxycarbonyloxyethyl, methoxycarbonyloxymethyl, 1-acetyloxybutyl, 1-acetyloxyhexyl, 1-acetyloxyheptyl, phthalidyl, 5,6-dimethoxyphthalidyl, tertbutylcarbonylmethyl, allyl, 2-chloroallyl, methoxycarbonylmethyl benzyl or tertbutyl.

Other residues of ester groups for A are methoxyethoxymethyl, dimethylaminoethyl, cyanomethyl, tertbutyloxycarbonylmethyl, 2,2-ethylenedioxyethyl, cyanoethyl, 2,2-dimethoxyethyl, 2-chloroethoxymethyl, 2-hydroxyethoxyethyl, 2,3-epoxypropyl, 3-dimethylamino, 2-hydroxypropyl, 2-hydroxyethyl 2-methylaminoethoxymethyl, 2-aminoethoxymethyl, 3-methoxy-2,4-thiadiazol-5-yl, 2-tetrahydropyranyl, 2-methoxyprop-2-yl, 1-hydroxyprop-2-yl, isopropyl, carbamoylmethyl, chloromethyl, 2-chloroethyl, acetylmethyl, 2-methylthioethyl or thiocyanatomethyl.

Further residues of ester groups for A are 2-chloro-1-acetyloxyethyl, 2-bromo -1-acetyloxyethyl, 2-fluoro-1-acetyloxyethyl, 2-methoxy-1-acetyloxyethyl, 2-methylacetyloxypropyl, 2-acetyloxyprop-2-yl, 1-methoxyacetyloxyethyl, 1-acetylcarbonyloxyethyl, 1-hydroxyacetyloxyethyl, 1-formylcarbonyloxyethyl, 1-(2-thienyl)carbonyloxyethyl, 1-(2-furyl)-carbonyloxyethyl, 1-(5-nitro-2-furyl)carbonyloxyethyl, 1-(2-pyrrolyl)-carbonyloxyethyl, 1-(propionyloxycarbonyloxy)ethyl, 1-(propyloxycarbonyloxyethyl, 1-(isopropyloxycarbonyloxy)ethyl, 1-(methoxyethoxycarbonyloxy)ethyl, 1-(allyloxycarbonyloxy)ethyl, 1-(2,3-epoxy)-propyloxycarbonyloxyethyl, 1-(2-furyl)methyloxycarbonyloxyethyl, 1-(2-fluoro)ethyloxycarbonyloxyethyl, 1-(methoxycarbonyloxy)propyl, (2-methoxycarbonyloxy)prop-2-yl, (methoxycarbonyloxy)chloromethyl, 1-(methoxycarbonyloxy)2-chloroethyl, 1-(methoxycarbonyloxy)2-methoxyethyl and 1-(methoxycarbonyloxy)1-allyl. A can also be:

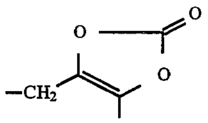

The products of formula I can also be presented in the form of salts of non-toxic, pharmaceutically acceptable organic or mineral acids. Among the acids with which it is possible to salify the amino group or groups of the compounds of formula I are organic acids such as acetic acid, trifluoroacetic acid, maleic acid, tartaric acid, methansulfonic acid, benzenesulfonic acid, p-toluenesulfonic, trifluoromethane sulfonic, formic acid, and inorganic acids such as phosphoric acid, sulfuric acid, hydrochloric acid, hydriodic acid and hydrobromic acid.

Among the values of A are especially the esters of the formula

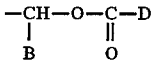

in which B is hydrogen or optionally substituted, linear or branched alkyl of 1 to 5 carbon atoms and D is an optionally substituted, linear or branched alkyl or alkoxy of 1 to 15 carbon atoms and especially of 1 to 5 carbon atoms and more particularly, the ester groups in which B is hydrogen or methyl or ethyl and D is methyl, ethyl, methoxy or ethoxy.

Among the further values of A are

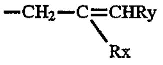

in which Rx is hydrogen, alkyl, especially methyl or ethyl, or halogen, especially chlorine, and Ry is hydrogen, halogen or aryl, especially phenyl, optionally substituted by methyl, methoxy or halogen, or Ry is alkyl optionally substituted by acyloxy, alkoxycarbonyl or halogen.

Among further values of A are

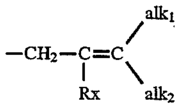

in which Rx is defined as above and $alk_1$ and $alk_2$ are individually alkyl of 1 to 4 carbon atoms.

When COM is substituted carbamoyl, $—CONH—(CH_2)_{n_a}$-aryl is preferred, $n_a$ being a number from 0 to 4 such as —CONH-phenyl optionally substituted by free esterified or salified carboxy.

Among the preferred compounds of formula I are the derivatives of formula

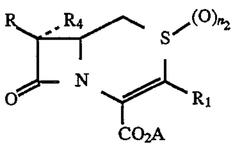

wherein $R_4$ is hydrogen, $n_2$ is 0, $CO_2A$ is selected from the group consisting of $CO_2H$ and $CO_2$— and R and $R_1$ are selected from the group consisting of:

1) R =

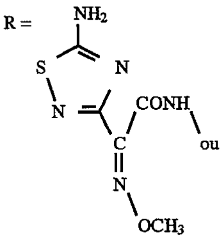

ou

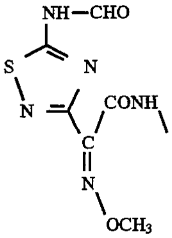

et $R_1$ =

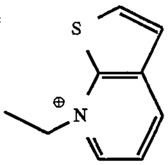

ou

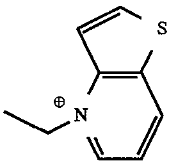

2) R =

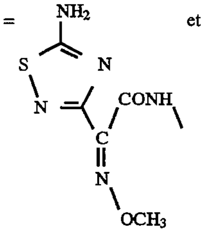

et $R_1$ =

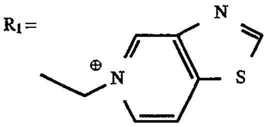

and their non toxic pharmaceutically acceptable acid addition salts in racemic or optically active form.

Among the preferred products of formula I of the invention are the syn isomers of the formula

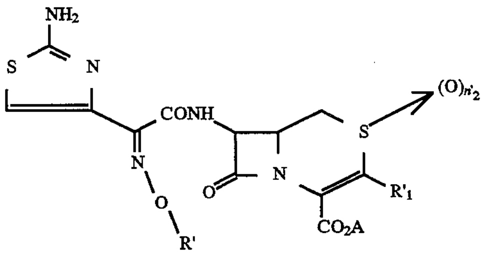

I' in which R' is hydrogen or an optionally substituted alkyl of alkenyl having at most 4 carbon atoms or an optionally substituted phenyl, $R_1'$ is: a) Z'—$R_2'$ in which $R'_2$ is alkyl or alkenyl of at most 4 carbon atoms optionally interrupted by a heteroatom and optionally substituted by halogen, amino, cyano or free, esterified or salified carboxy radical, by a carbamoyl radical optionally substituted by an aryl, by optionally substituted aryl, by optionally substituted quaternary ammonium or by optionally substituted heterocycle, and Z' is sulfur or oxygen: b) $Z'_a$—$R'_3$ in which $R'_3$is phenyl or optionally substituted heterocyclic aryl or an optionally substituted ammonium and $Z'_a$ is methylene or —$CH_2$—S— or sulfur, oxygen or selenium or a simple bond- c) alkyl or alkenyl of 2 to 4 carbon atoms, interrupted by oxygen or by sulfur optionally oxidized substituted, if applicable, by aryl, optionally esterified or salified carboxy, cyano, amino, acyl or halogen; d) azidomethyl, aminomethyl, thiocyanato, carbamoyloxymethyl, semicarbazonomethine or optionally substituted arylhydrazonomethine; $n'_2$ is 0 or 1 and A has the value indicated above.

Among the preferred values of R' are methyl, carboxymethyl and 1-methyl-1-carboxyethyl, the latter two radicals being optionally esterified or salified.

Among the preferred values of $R'_1$ are

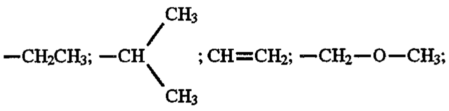

$-S-CH_2-CO_2H$; $S-CH_2-CO_2Et$; $-S-CH_2-CO_2tBu$;

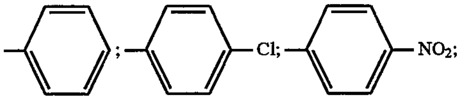

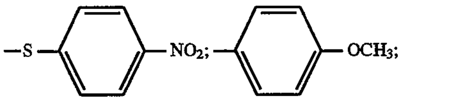

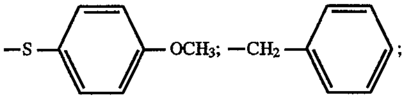

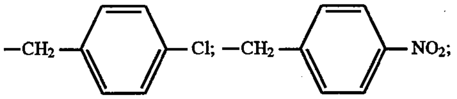

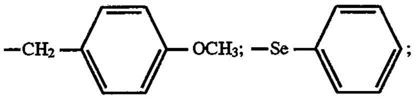

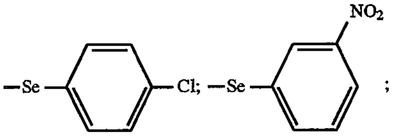

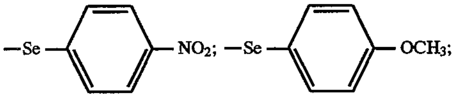

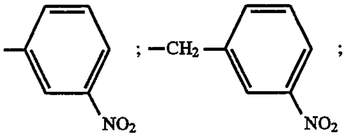

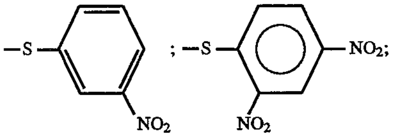

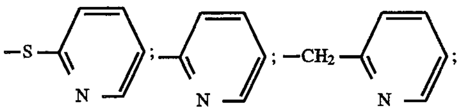

-continued
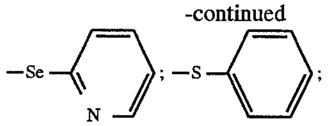
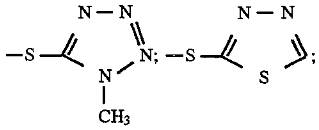
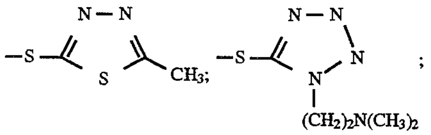
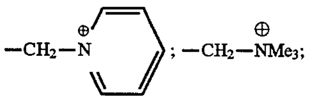
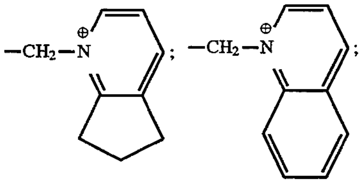
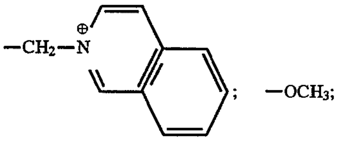
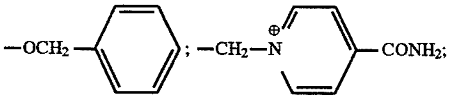
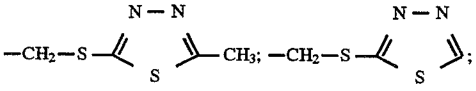
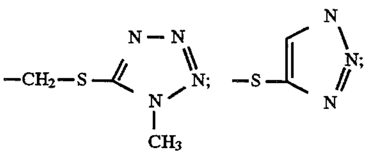
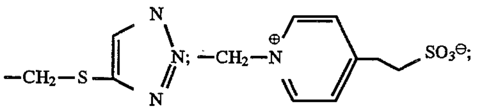
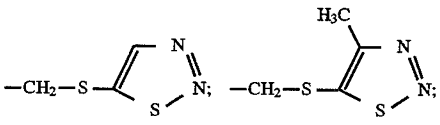
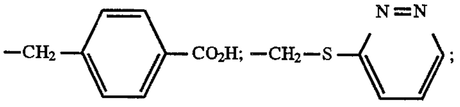
-continued
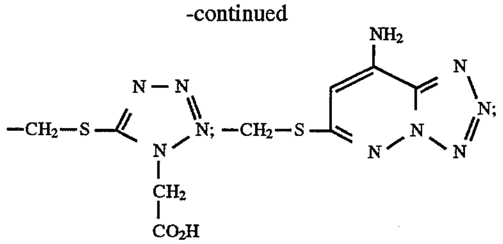
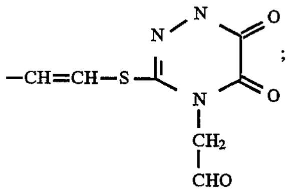
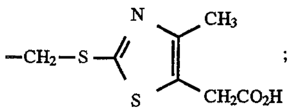
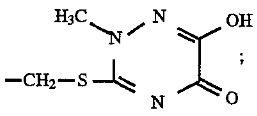
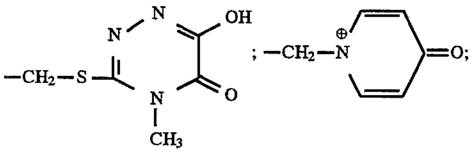
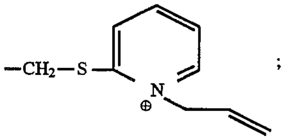
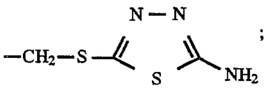
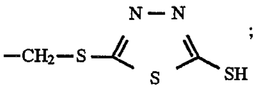
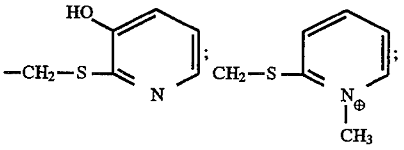
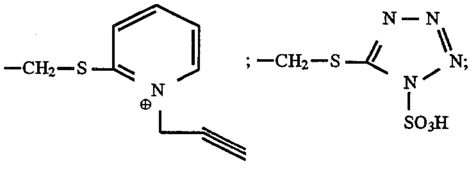
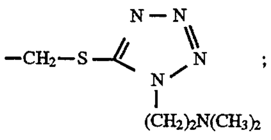

-continued
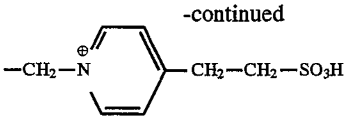
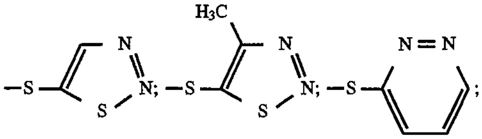
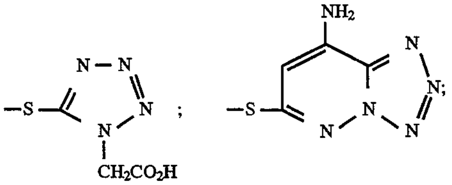
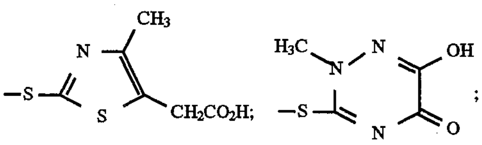
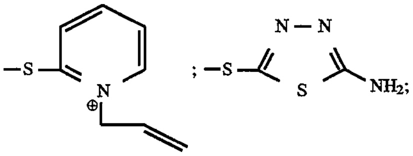
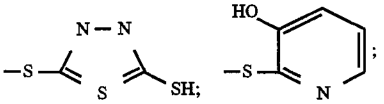
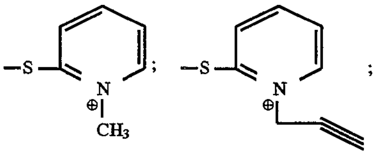
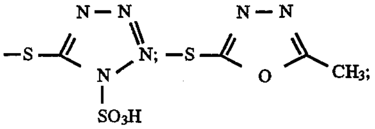
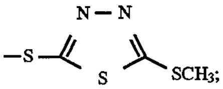
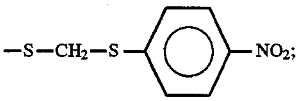
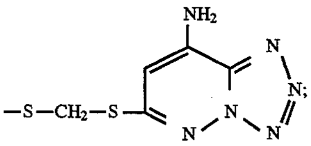
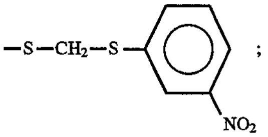
-continued
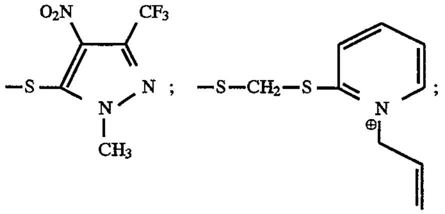
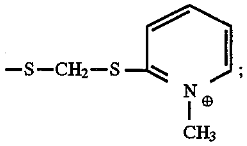
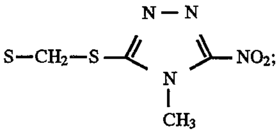
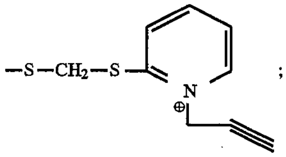
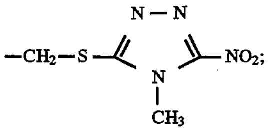
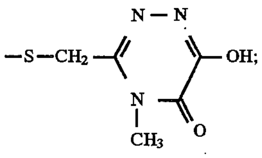
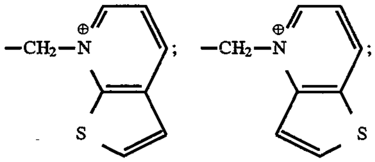
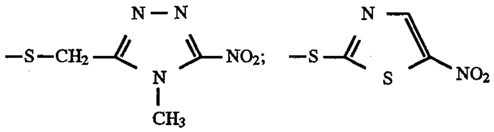
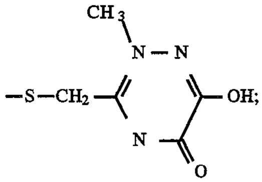
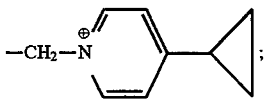

-continued

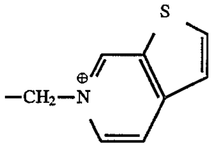 ; 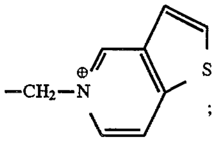 ;

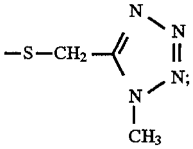 ; —CH$_2$N$_3$; 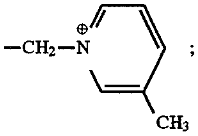 ;

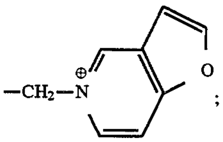 ; —CH$_2$—NH$_2$;

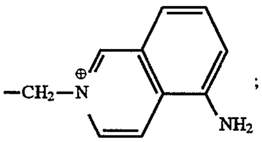 ; 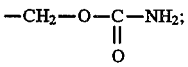

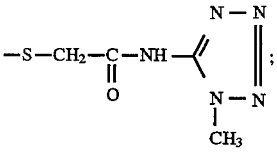 ; 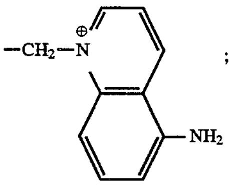 ;

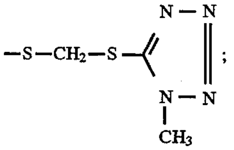

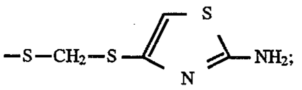

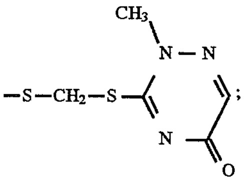

-continued

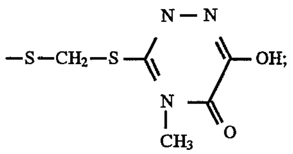

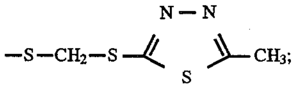

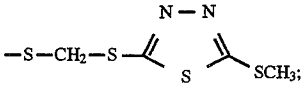

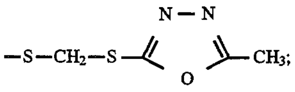

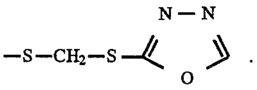

Among the preferred products of formula I' are those which R' is hydrogen or methyl or allyl and R'$_1$ is selected from the group consisting of methoxymethyl, pyridinylthio, pyridinyl, phenyl, phenylthio or thienopyridinium, all optionally substituted by methyl, cyclopropyl, nitro, chloro or methoxy radiophenylselenyl, methylthio or ethylthio optionally substituted by carboxy, ethoxycarbonyl or amino; ethyl, isopropyl, methyltetrazolythio, methyl or thiomethyl thiadiazolythio, methyloxadiazol; thio, trimethylammonium methyl, optionally substituted pyridinium or dihydropyridinium, as well as those in which R'$_1$ is Z'$_a$—R'$_3$ wherein Z'$_a$ is sulfur and R'$_3$ is heterocyclic aryl of 5 to 6 links and optionally substituted, or Z'$_a$ is methylene and R'$_3$ is an optionally substituted quaternary ammonium.

Among the preferred compounds of formula I' are those in which the substituents are selected from the group consisting of:

| R' | R'1 | R' | R'1 | R' | R'1 |
|---|---|---|---|---|---|
| 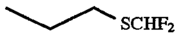 | 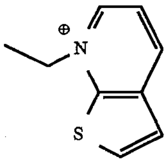 | $CHF_2$ | 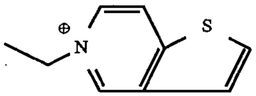 | $CH_2CH{=}CH{-}CH_3$ | 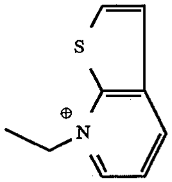 |
| 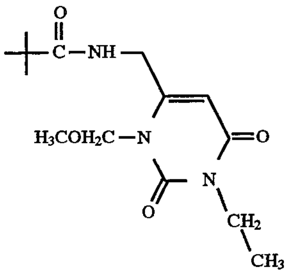 | 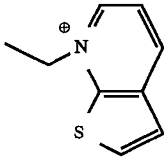 | 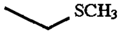 | 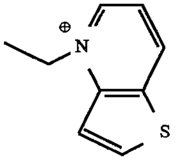 | 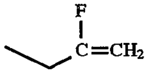 | 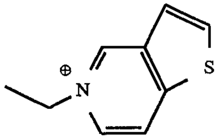 |
| 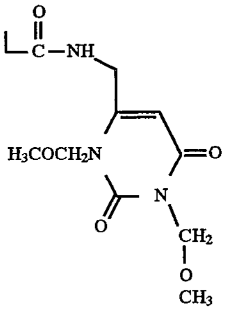 | 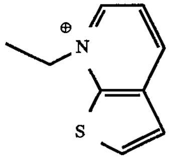 | 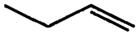 | 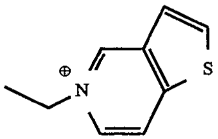 | $CH_3$ | 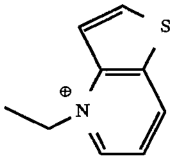 |
| $CH_2F$ | 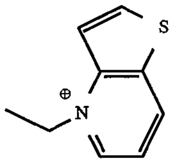 | $CHF_2$ | 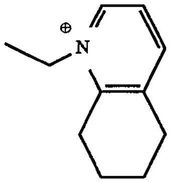 | $CH_3$ | 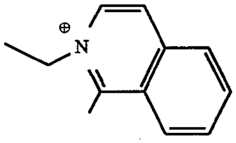 |

-continued
| R' | R'1 | R' | R'1 | R' | R'1 |
|---|---|---|---|---|---|
| $CH_2F$ | 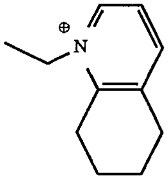 | 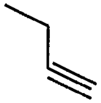 | 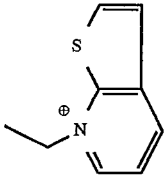 | $CH_3$ | 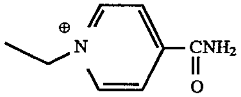 |
| $CH_2F$ | 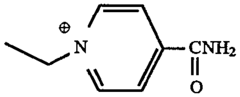 | 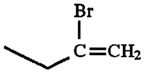 | 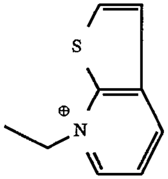 | $CH_3$ | 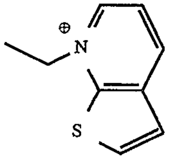 |
| 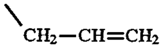 | 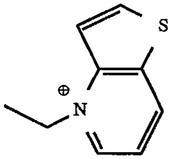 | $CH_3$ | 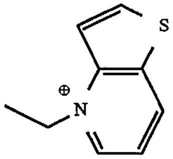 | $CH_2F$ | 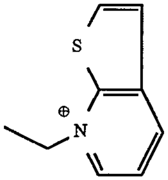 |
| $CHF_2$ | 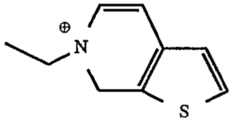 | 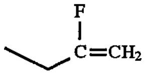 | 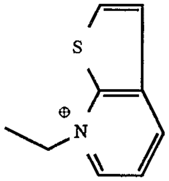 | $CH_3$ | 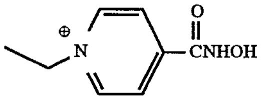 |
| $CH_3$ | 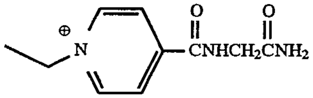 | $CH_2F$ | 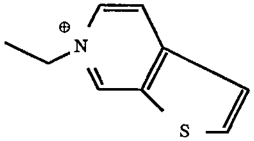 | 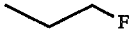 | 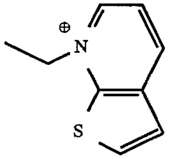 |
| $CH_3$ | 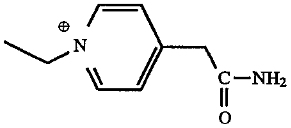 | $CH_2F$ | 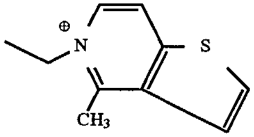 | $CH_3$ | 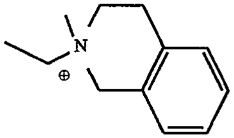 |

-continued
| R' | R'1 | R' | R'1 | R' | R'1 |
|---|---|---|---|---|---|
| $CH_3$ | 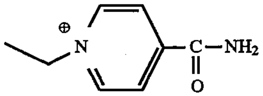 | $CHF_2$ | 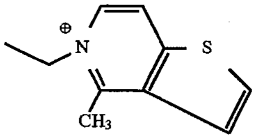 | | |
| $CH_2F$ | 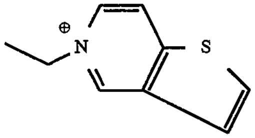 | $CH_3$ | 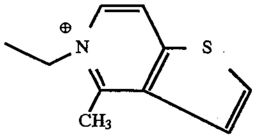 | | |
| $CH_3$ | 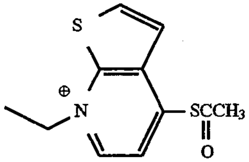 | 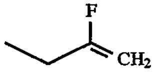 | 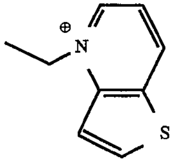 | | |
| $CH_3$ | 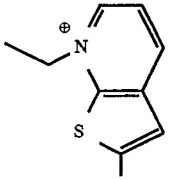 | $CH_3$ | 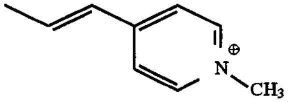 | | |

and their non toxic pharmaceutically acceptable acid addition salts in racemic or optically active form.

Particularly preferred compounds of the invention in racemic or optically-active form are: 7-[2-(2-aminothiazol-4-yl)-2-methoxyimino-acetamido]-3-(3-nitrophenylthio)-8-oxo-4-thia-1-azabicyclo[4,2,0]oct-2-ene-2-carboxylic acid, syn isomer; 7-[2-(2-aminothiazol-4-yl)-2-methoxyimino-acetamido]-3-(4-nitrophenyl)-8-oxo-4-thia-1-azabicyclo [4,2,0]oct-2-ene-2-carboxylic acid, syn isomer; 7-[2-(2-aminothiazol-4-yl)-2-methoxyimino-acetamido]-3- [(1-methyl-(1H) -tetrazol-5-yl) thio-]-8-oxo-4-thia-1-azabicyclo [4,2,0]oct-2-ene-2-carboxylic acid, syn isomer; 7-[2-(2-aminothiazol-4-yl)-2-methoxyimino-acetamido]-8-oxo-3-[(1-methyl-(1H)-tetrazol-5-yl)-thiomethyl]-4-thia-1-azabicyclo[4,2,0]oct-2-ene-2-carboxylic acid, syn isomer; 1-[7-[(2-aminothiazol-4-yl)-2-methoxyimino-acetamido]-2-carboxy-8-oxo-4-thia-1-azabicyclo[4,2,0]oct-2-en-3-yl]-methylpyridinium syn isomer; 1-[7-[(2-aminothiazol-4-yl)-2-methoxyimino-acetamido]-2-carboxy-8-oxo-4-thia-1-azabicyclo[4,2,0]oct-2-en-3-yl]methyl-(6,7-dihydro)-5H-1-pyrindinium, syn isomer;-6-(7-[2- (2-aminothiazol-4-yl)-2-methoxyimino-acetamido]-2-carboxy-8-oxo-4-thia-1-azabicyclo[4,2,0]oct-2-en-3-yl]-methyl-thieno[2,3-c]-pyridinium syn isomer; 7-[2-(2-aminothiazol-4-yl)-2-methoxyimino-acetamido]-8-oxo-2-carboxy-4-thia-1-azabicyclo[4,2,0]oct-2-en-3-yl)-methyl trimethyl ammonium, syn isomer; 7-[2-(2-aminothiazol-4-yl)-2-methoxyimino-acetamido]-8-oxo-4-thia-2-carboxy-1-azabicyclo[4,2,0]oct-2-en-3-yl)-methyl-4-cyclopropyl-pyridinium, syn isomer; 6-[7-[2-(2-aminothiazol-4-yl)-2-methoxyimino-acetamido]-8-oxo-4-thia-2-carboxy-1-azabicyclo[4,2,0]oct-2-en-3-yl]-methyl-7-methylthieno [2,3-c]pyridinium, syn isomer; 7-[7-[2-(2-aminothiazol-4-yl)-2-methoxyimino-acetamido]-8-oxo-4-thia-2-carboxy-1-azabicyclo[4,2,0]oct-2-en-3-yl]-methyl thieno[2,3-b] pyridinium, syn isomer; 7-[2-(2-aminothiazol-4-yl)-2-(2-propenyloxy)imino-acetamido]-2-carboxy-8-oxo-4-thia-1-azabicyclo[4,2,0]oct-2-en-3-yl]-methyl pyridinium, syn isomer; 1-[(7-[2-(2-aminothiazol-4-yl)-2-methoxyimino-acetamido]-2-carboxy-8-oxo-4-thia-1-azabicyclo[4,2,0]oct-2-en-3-yl)-methyl-(2-methylthio-pyridinium, syn isomer 7-[7-[2-(2-aminothiazol-4-yl)-[(difluoromethoxy) imino] acetamido]-2-carboxy-8-oxo-4-thia-1-azabicyclo [4,2,0] oct-2-ene-3-yl] methylthieno [2,3-b] pyridinium syn isomer; 4-7-[2-(2-aminothiazol-4-yl) [(difluoromethoxy) imino] acetamido-2-carboxy-8-oxo-4-thia-1-azabicyclo[4,2,0] oct-2-ene-3-yl] methylthieno [3,2-b] pyridinium syn isomer; internal salt of syn isomer 2-[7[2-(2-aminothiazol-4-yl)-2-(methoxyimino) acetamido 2-carboxy 8-oxo 4-thia 1-azabicyclo [4,2,0] oct-2-en-3-yl] methyl]isoquinolinium (6RS-7RS); 4-[7-[2-(2-aminothiazol-4-yl) 2-[methoxymethoxy) imino] acetamido-2-carboxy-8-oxo-4-thia-1-azabicyclo [4,2,0] oct-2-en-3-yl] methyl] thieno [3,2-b] pyridinium (6RS-7RS) syn isomer; 7-[7-[2-(2-aminothiazol-4-yl) 2-[(propenyloxy) imino] acetamido 2-carboxy-8-oxo-4- thia-1-azabicyclo [4,2,0] oct-2-en-3-yl] methyl] thieno [2,3-b] pyridinium (6RS,7RS) syn isomer 5-//7-//(2-amino 4-thiazolyl)/(difluoromethoxy) imino/ acetyl/amino/2-carboxy 8-oxo 4-thia 1-azabicyclo/4.2.0/oct-2-en 3-yl/methyl/thieno/3,2-c/pyridinium (6S) (7S) (Z), 4-//7-//2-(2-amino 4-thiazolyl) 2-(methoxyimino) acetyl/ amino/2-carboxy 8-oxo 4-thia 1-azabicyclo/4.2.0/oct-2-en 3-yl/methyl/thieno/3,2-b/pyridinium (6S) (7S) (Z), 4-//7-//(2-amino 4-thiazolyl) (methoxyimino) acetyl/ amino/2-carboxy 8-oxo 4-thia 1-azabicyclo/4.2.0/oct-2-en 3-yl/methyl/7-methyl thieno/3,2-b/pyridinium (6S) (7S) (Z), 5-//7-//(2-amino 4-thiazolyl)/(fluoromethoxy) imino/ acetyl/amino/2-carboxy 8-oxo 4-thia 1-azabicyclo/4.2.0/oct-2-en 3-yl/methyl/thieno/3,2-c/pyridinium 5-//7-//(2-amino 4-thiazolyl)/(fluoromethoxy) imino/ acetyl/amino/2-carboxy 8-oxo 4-thia 1-azabicyclo/4.2.0/oct-2-en 3-yl/methyl/4-methyl thieno/3,2-c/pyridinium (7S) (Z) and their non toxic pharmaceutically acceptable salts where applicable.

The novel process of the invention for preparing the compounds of formula I comprising reacting a compound of the formula

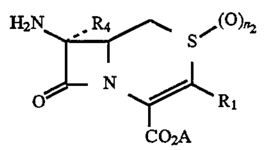

II wherein $R_1$, $R_4$, A and $n_2$ have the above definitions either with an acid of the formula $Ra—CO_2H$ $IV_a$ or a functional derivative thereof wherein Ra is an organic group or with a product of the formula

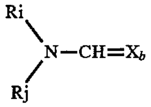

$IV_b$ in which Ri and Rj have the above definitions and $X_b$ is sulfur or oxygen, or with a product of the formula $R_b—X_c$ $IV_c$ in which $R_b$ is an optionally substituted carbocyclic or heterocyclic aryl and $X_c$ is halogen to obtain a product of formula I, which product is subjected, if necessary or if desired, to one or more of the following reactions in any order:

a) cleavage by hydrolysis, by hydrogenolysis or by action of thiourea of all or part of the protective group or groups;
b) esterification or salification of the carboxy or sulfo group or groups with a base,
c) salification of the amino group or groups with an acid;
d) resolution of the molecule to obtain an optically-active product; and/or
e) oxidation of the sulfur at position 2 of the isocephem ring.

The Ra can be one of the previously-mentioned radicals and when Ra contains functional groups such as amino, hydroxy, carboxy or sulfo, these groups can be protected.

In a preferred method of carrying out the process, the product of formula II is reacted with a functional derivative of a product of formula $IV_a$ which functional derivative can be, for example, a halide, a symmetrical or mixed anhydride, an amide or an activated ester. An example of a mixed anhydride is that formed with isobutyl chloroformate and that formed with pivaloyl chloride and the mixed carboxylic sulfonic anhydrides formed, for example, with p-toluenesulfonyl chloride. An example of an activated ester is the ester formed with 2,4-dinitrophenol and that formed with hydroxybenzothiazole. An example of a halide is the acid chloride or bromide. Also useful are the acid azide or the acid amide.

The anhydride can be formed in situ by the action of N,N-disubstituted carbodiimide, for example N,N-dicyclohexyl-carbodiimide. The acylation reaction is carried out preferably in an organic solvent such as methylene chloride but it is possible to use other solvents such as tetrahydrofuran, chloroform dimethylformamide, acetone or dimethylacetamide. When an acid halide is used generally when a molecule of hydrohalic acid is released during the reaction, the reaction is carried out preferably in the presence of a base such as sodium hydroxide, potassium hydroxide, the carbonates and bicarbonates of sodium or of potassium, sodium acetate, triethylamine, pyridine, morpholine or N-methyl-morpholine. The reaction temperature is generally lower than or equal to ambient temperature.

In a preferred method of carrying out the process, the products of formula $IV_b$ are converted into reactive derivatives such as chloro immonium halides, which can be prepared by reacting the products of formula $IV_b$ with halogenation agents such as phosgene, oxalyl chloride or thionyl chloride. It is also possible to prepare complexes with dialkyl sulfates, preferably dimethyl sulfate. The conditions of working for such reactions are known by the expert, for example, in French Patent No. 2,073,338.

In a preferred method of carrying out the process, the halogens used in the products of formula $IV_c$ are the chloride or the fluoride. Preferably a pyridinium derivative is used and the counter ion is then preferably an iodide, tosylate, bromide or BF4 ion.

The preparation of the products of formula $IV_c$ and the reaction of these products with the products of formula II are carried out under the conditions described, for example, in Journal of Medicinal Chemistry (1982) Vol. 25, No. 4, p. 457–469

The subsequent reactions of removing protecting functional groups, of esterification, of salification, of resolution and of oxidation are carried out under the usual conditions hereinafter for the products of formula I'

In a preferred mode of the process of the invention for preparing the products of formula I' a product of the formula

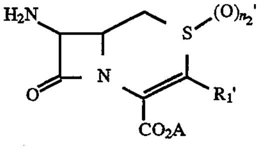

II' in which $R'_1$, A and $n'_2$ have the previous meaning is reacted with an acid of the formula

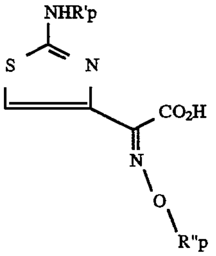

IV' or a functional derivative thereof wherein R'p is hydrogen or a group protecting the amino and R"p is a group protecting the hydroxyl or R"p is R' to obtain a product of the formula

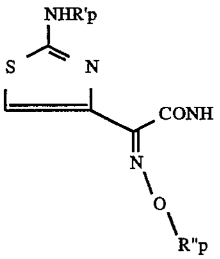

-continued

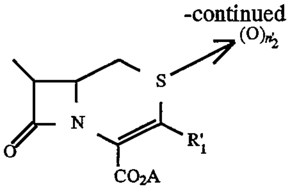

V' which product is subjected, if necessary or if desired, to one or more of the following reactions, in any order:

a) cleavage by hydrolysis, by hydrogenolysis or by action of thiourea of all or part of the protective group or groups;
b) esterification or salification of the carboxy group or groups with a base;
c) salification of the amino group or groups with an acid;
d) resolution of the molecule to obtain an optically-active product; and/or
e) oxidation of the sulfur atom at position 2 of the isocephem ring.

In addition to the groups mentioned above, the easily-removable ester group which A can be are for example, the ester formed with butyl, isobutyl, tert-butyl, pentyl, hexyl, acetoxymethyl, propionyloxymethyl, butyryloxymethyl, valeryloxymethyl, pivaloyloxymethyl, 2-acetoxyethyl, 2-propionyloxyethyl or 2-butyryloxyethyl. Also useful are 2-iodoethyl, βββ-trichloro-ethyl, vinyl, allyl, ethynyl, propynyl, benzyl, 4-methoxybenzyl, 4-nitrobenzyl, phenylethyl, trityl, diphenylmethyl 3,4-di-methoxyphenyl and 2-trimethyl silyl ethyl. There may also be mentioned phenyl, 4-chlorophenyl, tolyl and tert-butylphenyl.

The group protecting the amino radical which R'p can be are for example, alkyl of 1 to 6 carbon atoms such as, preferably tert-butyl or tert-amyl. R'p can also be aliphatic, aromatic or heterocyclic acyl or carbamoyl. There may be mentioned lower alkanoyl such as, for example, formyl, acetyl, propionyl, butyryl, isobutyryl, valeryl, isovaleryl, oxalyl, succinyl and pivaloyl. R'p can also be lower alkoxy or cycloalkoxycarbonyl such as, for example, methoxycarbonyl, ethoxycarbonyl, propoxycarbonyl, 1-cyclopropylethoxycarbonyl, isopropyloxycarbonyl, butyloxycarbonyl, tert-butyloxycarbonyl, pentyloxycarbonyl or hexyloxycarbonyl, benzoyl, toluolyl, naphthoyl, phthaloyl, mesyl, phenylacetyl or phenylpropionyl or an aralkoxycarbonyl such as benzyloxycarbonyl. The acyl groups can be substituted, for example, by chlorine, bromine, iodine or fluorine. The chloroacetyl, dichloroacetyl, trichloroacetyl, bromoacetyl or trifluoroacetyl are examples.

R'p can also be lower aralkyl such as benzyl, 4-methoxybenzyl, phenylbenzyl, trityl, 3,4-dimethoxybenzyl or benzhydryl and R'p can also be haloalkyl such as trichloroethyl. R'p can also be chlorobenzoyl, paranitrobenzoyl, para-tert-butyl-benzoyl, phenoxyacetyl, caprylyl, n-decanoyl, acryloyl or trichloroethoxycarbonyl or methylcarbamoyl, phenylcarbamoyl or naphthylcarbamoyl, as well as the corresponding thiocarbamoyls. The list above is not limiting and it is obvious that other groups for protecting amines known in particular in the chemistry of peptides, can also be used.

The group protecting the hydroxyl which R"p can represent can be selected from the list below: acyl such as for example, formyl, acetyl, chloroacetyl, bromoacetyl, dichloroacetyl, trichloroacetyl, trifluoroacetyl, methoxyacetyl, phenoxyacetyl, benzoyl, benzoylformyl or p-nitrobenzoyl, ethoxycarbonyl, methoxycarbonyl, propoxycarbonyl, βββ-trichloroethoxycarbonyl, benzyloxycarbonyl, tert-butoxycarbonyl, 1-cyclopropylethoxycarbonyl, tetrahydropyrannyl, tetrahydrothiopyrannyl, methoxytetra hydropyrannyl, trityl, benzyl, 4-methoxybenzyl, benzhydryl, trichloroethyl, 1-methyl-1-methoxyethyl and phthaloyl.

Other acyls may also be mentioned such as propionyl, butyryl, isobutyryl, valeryl, isovaleryl, oxalyl, succinyl and pivaloyl, phenylacetyl, phenylpropionyl, mesyl, chlorobenzoyl, para-nitrobenzoyl, para-tert-butylbenzoyl, capryl acryloyl, methylcarbamoyl, phenylcarbamoyl and naphthylcarbamoyl In a preferred method of the process, the product of formula II' is reacted with a functional derivative of a product of formula IV' which derivative can be selected from the derivatives mentioned above.

Depending upon R'p, R"p, and A, the products of formula IV' may or may not constitute products of formula I'. The products of formula IV' are products of formula I' when R'p is hydrogen, when R"p is not a group protecting the hydroxyl which one wishes to remove, for example 1-methoxyethyl, and when A is not among the easily-cleavable esters, one of those which one wishes to remove. In the other cases, the aim of the action on the product of formula IV' of one or more hydrolysis or hydrogenolysis agents or of thiourea is to remove R'p when this is a radical protecting the amino, to remove R"p when this is different from R' and/or to remove A when this is among the easily-cleavable ester groups, one of these which are one wishes to remove. However, it is, of course, possible to remove R'p without touching R"p and A when these must be kept. This applies, for example, when A is an ester which one wishes to keep such as propionyloxymethyl.

The nature of the reagents to be employed in all these cases is well known to the expert. Examples of such reactions are given further on in the experimental part. Hereinafter is given a non-exhaustive list of the means which can be employed to remove the different groups.

The removal of the group R'p can be carried out by acidic or basic hydrolysis, or using hydrazine. Preferably, acid hydrolysis is used to remove the optionally substituted alkoxy and cycloalkoxycarbonyl such as tert-pentyloxycarbonyl or tert-butyloxycarbonyl, optionally substituted aralkoxycarbonyl such as benzyloxycarbonyl and trityl, benzyhydryl, tert-butyl or 4-methoxybenzyl. The acid which is preferably used can be selected from the group constituted by hydrochloric acid benzene sulfonic acid or p-toluene sulfonic acid, formic acid or trifluoroacetic acid. However, other mineral or organic acids can be used.

Basic hydrolysis is preferably used to remove acyls such as trifluoroacetyl. The base which is preferably used is a mineral base such as sodium or potassium hydroxide. Magnesia, baryta or an alkali metal carbonate or bicarbonate such as the carbonates and bicarbonates of sodium or potassium or of other bases can also be used. Sodium acetate or potassium acetate can also be used. Hydrolysis using hydrazine is preferably used to remove groups such as phthaloyl.

The groups R'p can also be removed with zinc - acetic acid system for trichloroethyl and benzhydryl and benzyloxycarbonyl are preferably removed with hydrogen in the presence of a catalyst. Chloracetyl is removed by the action of thiourea in neutral or acidic medium according to the type of reaction described by MASAKI J.A.C.S., 90, 4508,, (1968). Other deprotection methods known in the literature can also be used.

Among the preferred groups, formyl, acetyl, ethoxycarbonyl, mesyl, trifluoroacetyl, chloracetyl and trityl may be mentioned with trityl and chloroacetyl being particularly preferred. The acid which is preferably used is trifluoroacetic acid.

The removal of A or R"p, when this is necessary, is carried out under conditions similar to those described previously for the removal of R'p. Among other means, acid hydrolysis can be used to remove the optionally substituted alkyl or aralkyl. Preferably an acid selected from the group formed by hydrochloric acid, formic acid, trifluorocacetic acid and p-toluene-sulfonic acid is used. The other values of A or R"p are, when this is desired, removed by processes known to the expert. Work is carried out preferably under moderate conditions, that is to say at ambient temperature or by heating slightly.

Of course, when, for example, R'p and A or R"p are removable groups belonging to different types, it is possible to use several agents considered in the previous lists to react with the products of formula IV'.

Salification of the products can be carried out according to the usual methods. Salification can, for example, be obtained by the action on a product in acid form or on a solvate, for example the ethanol solvate or a hydrate of this acid, of a mineral base such as sodium hydroxide or potassium hydroxide or the carbonate or bicarbonate of sodium or of potassium. The salts of mineral acids such as tri-sodium phosphate can also be used while salts of organic acids can also be called upon.

Examples of salts of organic acids are the sodium salts of straight or branched, saturated or unsaturated, aliphatic carboxylic acids of 1 to 18, preferably 2 to 10 carbon atoms which aliphatics can be interrupted by one or more heteroatoms such as oxygen or sulfur, or substituted by aryl radicals such as, for example, phenyl, thienyl or furyl or by one or more hydroxyls or by one or more halogens such as fluorine, chlorine or bromine, preferably chlorine, by one or more carboxylic or lower alkoxycarbonyls, preferably methoxycarbonyl, ethoxycarbonyl or propyloxycarbonyl or by one or more aryloxys, preferably phenoxy.

Moreover, there may be used as organic acids sufficiently soluble aromatic acids such as, for example, benzoic acids substituted preferably by lower alkyl radicals. Examples of such organic acids are formic acid, acetic acid, acrylic acid, butyric acid, adipic acid, isobutyric acid, n-caproic acid, isocaproic acid, chloropropionic acid, crotonic acid phenylacetic acid, 2-thienylacetic acid, 3-thienylacetic acid, 4-ethylphenylacetic acid and glutaric acid, the monoethyl ester of adipic acid, hexanoic acid, heptanoic acid, decanoic acid, oleic acid stearic acid, palmitic acid, 3-hydroxypropionic acid, 3-methoxypropionic acid, 3-methylthiobutyric acid, 4-chlorobutyric acid, 4-phenylbutyric acid, 3-phenoxybutyric acid, 4-ethylbenzote acid and 1-propylbenzoic acid. However, as sodium salt, sodium acetate, sodium 2-ethyl hexanoate or sodium diethyl acetate are preferred.

Salification can also be obtained by the action of an organic base such as triethylamine, diethylamine, trimethylamine, propylamine, N,N-dimethylethanolamine, tris(hydroxymethyl)amino methane, methylamine, ethanolamine, pyridine, picoline, dicyclohexylamine morophoiine and benzylamine. It can also be obtained by the action of arginine, lysine, procaine histidine and N-methyl glucamine. This salification is carried out preferably in a solvent or a mixture of solvents such as water, ethyl ether, methanol, ethanol or acetone.

The salts are obtained in amorphous or crystalline form according to the reaction conditions employed. The crystalline salts are prepared preferably by reacting free acids with one of the aliphatic carboxylic acid salts mentioned above, preferably with sodium acetate. Salification of the products with mineral or organic acids is carried out under the usual conditions.

Possible esterification of the products is carried out under standard conditions, generally by reacting the acid of formula I' with a derivative of the formula Z—$R_s$ in which Z, is hydroxyl or halogen such as chlorine, bromine or iodine and $R_s$ is the ester group to be, introduced, a group of which a non-exhaustive list appears above. In certain cases, it can be advantageous to carried out esterification on a product of which the amine is blocked before removing the group protecting the amine.

Possible resolution of the compounds of formula II' or of the compounds of formula V' can be carried out by an optical active organic carboxylic or sulfonic acid such as tartaric acid dibenzoyltartaric acid, camphosulphonic acid or glutamic acid, decomposition of the salt thus obtained being carried out with a mineral base such as sodium bicarbonate or of an organic base such as a tertiary amine such as triethylamine. Moreover, in optically-active base can be used.

Possible oxidation of the products of formula IV' can be carried out using oxygen, peroxides, hydroperoxides, peracids or hydrogen peroxide and the reaction is advantageously sensitized with light. These reagents can be in admixture with organic or mineral acids. Preferably m-chloro perbenzoic acid is used. The reaction conditions are known to the expert such as set out, for example, in French Patent No. 2,387,234.

The subject of the present application is also a process for preparing the products of the formula

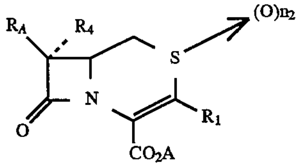

A in which $R_A$ is either a free amino or an amino protected by a mono or divalent protective group or $R_A$ is R, R having the meaning indicated above and $R_1$, $R_4$, A and $n_2$ have the meaning indicated above comprising reacting a product of the formula

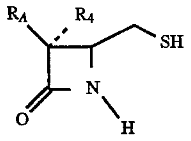

$II_A$ in which $R_A$ and $R_4$ have the above definitions with a product of the formula $$Hal—\underset{R_1}{CH}—CO—CO_2A \qquad III_A$$

in which Hal is halogen and $R_1$ and A have the above definitions to obtain a product of formula A which is subjected, if necessary or if desired, to any one or more of the following reactions, in any order:

a) cleavage by hydrolysis, by hydrogenolysis or by the action of thiourea of all or part of the protection group or groups;
b) esterification or salification of the carboxy group or groups with a base;
c) salification of the amine group or groups with an acid;
d) resolution of the molecule to obtain an optically-active product; and/or
e) oxidation of the sulfur atom at position 2 of the isocephem ring.

In a preferred method of the process above, the amino which $R_A$ can be is protected by a protective group such as trityl or phthalimide. Hal is preferably chlorine or bromine, preferably chlorine and A is preferably a alkyl, most preferably tert.-butyl. The action of the product of formula $III_A$ on the product of formula $II_A$ is preferably carried out in the presence of a base such as an amine base, preferably triethylamine or of a base such as lithium carbonate and can also be carried out in the presence of diazabicyclo-octane.

Intermediates of the invention are the products of the formula

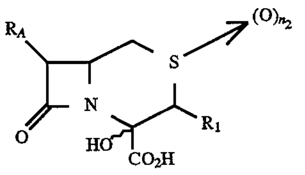

$A_1$ which may or may not be isolated. The final stage consists in dehydration which can be carried out, for example, using a reagent such as trifluoroacetic anhydride, phosphorus trichloride tribromide or tri-iodide, methanesulfonyl chloride, di-isopropyl carbodiimide, sulfuryl chloride, N,N-dimethylthiocarbamoyl chloride, phosphorus oxychloride or diphosphorus tetraiodide. The reaction is preferably carried out in the presence of a base such as pyridine.

Possibly, before obtaining the intermediate $A_i$, a precursor can be isolated of the formula

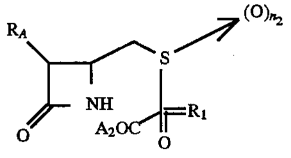

which is generally converted in situ into a product of formula $A_i$, itself leading to the product A. The process can also be carried out starting with optically-active products of formula $II_A$ prepared according to the process of Belgian Patent No. 887,428.

In a preferred process for preparing the products of the formula

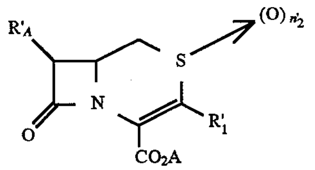

A' in which A, $R'_1$ and $n'_2$ have the above definitions and $R'_A$ is free amino or amino protected by mono or divalent protective group, or $R'_A$ is:

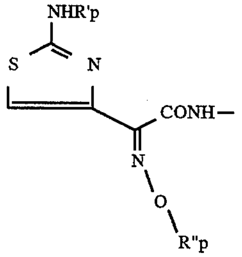

in which $R'_p$ and $R''_p$ have the above definitions comprises reacting a product of the formula $II_A$

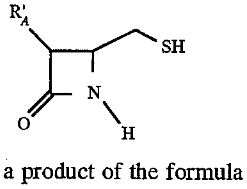

with a product of the formula $III_A$

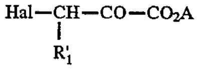

in which Hal is halogen and $R'_1$ and A have the above definitions obtain a product of formula A', which is subjected, if necessary or if desired, to any one or to several of the following reactions, in any order:

a) cleavage by hydrolysis, or hydrogenolysis or by the action of thiourea of all or part of the protective group or groups;
b) esterification or salification of the carboxy group or groups with a base;
c) salification of the amino group or groups with an acid;
d) resolution of the molecule to obtain an optically-active product; and/or
e) oxidation of the sulfur atom at position 2 of the isocephem ring.

A process for preparing the products of the formula $III'_{A_1}$

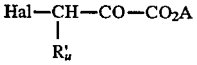

in which Hal is halogen and $R'_uR_1$ bonded by a carbon atom, $R_1$ and A having the above definitions comprises reacting a product of formula $R'_u$CHO with a product of formula $(Hal_1)_2CHCO_2A$ in the presence of a strong base to obtain a product of the formula $III'_{Ai}$

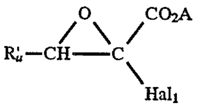

in which $Hal_1$ is halogen which product is treated with a halide to obtain the expected product of formula $III'_{A1}$.

$R'_u$ corresponding to $R_1$ bonded by a carbon atom are Za—$R_3$ in which Za is —$(CH_2)_a$—, a simple bond or —$CH_2$—S—, $R_3$ has the values indicated above or alkyl, alkenyl or alkynyl of 2 to 8 carbon atoms optionally substituted or interrupted by a hetero atom.

The strong base in the presence of which the products of formula $R'_u$CHO are reacted with the products of formula $(Hal_1)_2CH\ CO_2A$ can preferably be potassium tert-butylate. However, other bases can be used such as lithium diisopropylamine sodium hydride or butyl lithium and the reaction is carried out preferably in an apolar solvent such as tetrahydrofuran. Then a halide, preferably an alkali metal halide such as lithium bromide, is reacted with the product of formula $III'_{Ai}$.

A variation of this process which can also be used comprises reacting a product of the formula

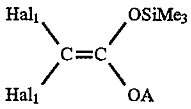

with the product of formula $R'_u$ CHO in the presence of a fluoride for example a trialkylammonium fluoride or an alkali metal fluoride. Then, as intermediate, a product of the formula

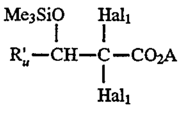

is obtained which gives again the product of formula $III'_{Ai}$.

The products of formula $III'_{Ai}$ can also be used directly in place of the products of formula $III_A$ in the reaction with the products of formula $II_A$. The action of the products of formula $III'_{Ai}$ with the products of formula $II_A$ is carried out preferably in the presence of an alkali metal carbonate, preferably lithium carbonate.

In a variation of the process for preparing the products of the formula

A'

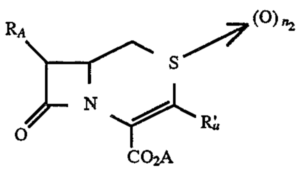

wherein $R_a$, $n_2$, A and A' have the above definitions, a product of formula $II_A$ is reacted with a product of formula $III'_{Ai}$ as described above. The subsequent operations described above of removing the protective groups, esterification, salification, resolution or oxidation are carried out as before.

The process of the present invention for preparing the products of the formula $III''_{A_1}$

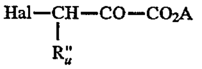

wherein Hal is halogen and $R''_u$ has the value of $R_1$ bonded by a heteroatom, $R_1$ and A having the above definitions comprises reacting a product of the formula $N_2$=CH—CO—$CO_2$A $III''_{Ai}$ with a product of the formula $R''_u$ Hal to obtain the expected product of formula $III''_{A_1}$. In a preferred method of carrying out the process, the action of the products of formula $III''_{Ai}$ with the products of formula $R''_u$ Hal is carried out in a solvent such as methylene chloride, carbon tetrachloride or benzene, preferably methylene chloride, at a temperature of the order of 0° C. to ambient temperature. Among the preferred products of formula $III''_{A_1}$ are those in which $R''_u$ has the values Z—$R_2$ and Za—$R_3$ in which Za is a heteroatom.

It should be noted that the products of formulae $III_A$, $III'_A$, $III'_{A_1}$ and $III''_{A_1}$ can be found in two different tautomeric forms. For example, $III_A$ can also be in the form:

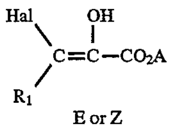

E or Z

The process of the invention for preparing the products of formula

IX

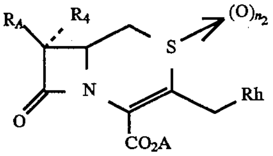

in which $R_A$, $R_4$, A and $n_2$ have the above definitions and Rh is an optionally substituted quaternary ammonium or S—R'h in which R'h is an optionally substituted carbocyclic or heterocyclic aryl corresponding to a product of formula I when $R_A$ is R comprises reacting either a product of formula R' h SH with a product of the formula

VI

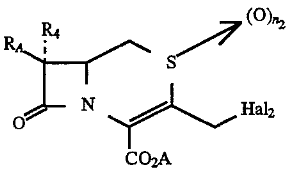

in which $R_A$, $R_4$, A and $n_2$ have the above definitions and $Hal_2$ is halogen, or an amine or an imine is reacted with a product of the formula

VII

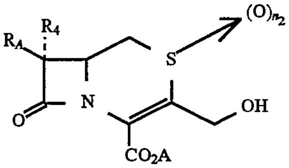

to obtain a product of formula IX which is subjected, if necessary or if desired, to any one or to several of the following reactions, in any order:

a) cleavage by hydrolysis, by hydrogenolysis or by the action of thiourea of all or part of the protective group or groups;
b) esterification or salification of the carboxy or sulfo group or groups with a base;
c) salification of the amino group or groups with an acid;
d) resolution of the molecule to obtain an optically-active product;
e) oxidation of the sulfur atom at position 2 of the isocephem ring;
f) deblocking of the amine function when $R_A$ is a protected amino;
g) treatment for a product with the formulae $IV_a$, $IV_b$ or $IV_c$ under the previously described conditions.

It is preferred to work with a sodium salt of the product of the formula $R'_nSH$. The amine or imine reacted with the product with the formula VII corresponds to the quaternary ammonium which it is wished to form. In particular, if it is desired to introduce a pyridinium radical, pyridine will be used and it is preferable to operate in the presence of an anhydride such as trifluoromethanesulfonic anhydride.

The process of the invention for the preparation of the products of formula VI comprises reacting a product of the formula $II_B$

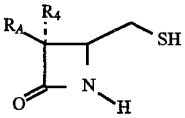

in which $R_A$ and $R_4$ have the above definitions with a product of the formula $III_B$

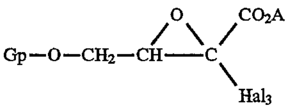

in which A has the above definition, $Hal_3$ is halogen and Gp is a protector group of the hydroxyl to obtain a product of the formula

VIII

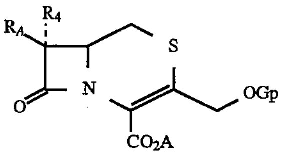

which product is submitted to a deprotection reaction to obtain the product of the formula

VII'

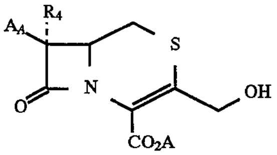

which product can first be submitted to an oxidation reagent, or which is submitted to a halogenation reaction to obtain a product of the formula

VI

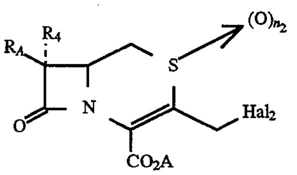

which product is optionally submitted to an oxidation reaction.

The preferred protector group for Gp is trimethylsilyl. $Hal_3$ preferably is chlorine atom and the protector group is preferably cleaved in an acid medium, for example, by dilute hydrochloric acid after the reaction of the products $II_B$ and $III_B$ has been carried out under the conditions previously described. The possible oxidation reactions are also carried out under the usual conditions and the halogenation reagent is preferably tosyl chloride in the presence of dimethylaminopyridine.

The process of the invention for the preparation of the products of the formula $I_H$

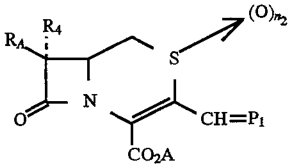

in which $R_A$, $R_4$, A and $n_2$ are defined as above and $P_1$ is a mono- or disubstituted carbon atom or a substituted nitrogen atom comprises reacting a product of the formula

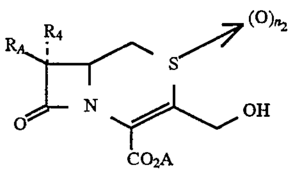

VII with an oxidation agent for the hydroxy function to obtain a product of the formula

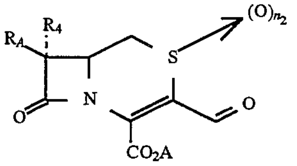

X which is treated either with an appropriate Wittig reagent to obtain a product of formula $I_H$ as previously defined, in which $P_1$ is a mono- or disubstituted carbon atom, or with a reagent including a free amine to obtain a product of formula $I_H$ in which $P_1$ is a substituted nitrogen atom.

The oxidation agent for the hydroxy function is preferably oxalyl chloride and the operation is done in dimethylsulfoxide in the presence of triethylamine. The reagent including a free amine is preferably a radical including the group $H_2N—NH—$ such as a hydrazine or a semi-carbazide.

The process of the invention for the preparation of products of the formula

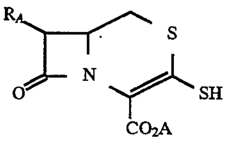

XI in which $R_A$ and $CO_2A$ have the above definitions comprises reacting a product of the formula

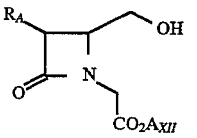

XII in which $R_A$ is defined as previously and $A_{XII}$ is hydrogen or an easily clearable ester group into a derivative which includes a reactive group for the hydroxy of the formula

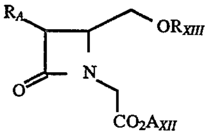

XIII in which $R_A$, $R_4$ and $A_{XII}$ are defined as above and $R_{XIII}$ is the residue of a reactive group and reacting the latter with carbon sulfide in the presence of a base to obtain the product of formula XI.

In a preferred operational method, the derivative including a reactive group for the hydroxy radical is tosyl chloride and the base in the presence of which the carbon sulfide is reacted is sodium, potassium or lithium bis trimethylsilyl amide. The invention is particularly directed to a process as previously defined wherein a product of formula XII is used as the starting material in which $R_A$ is an amino protected, notably by a tert-butoxycarbonyl.

The process as previously defined is preferably effected in that one or more of the following reactions are carried out on the product of formula XIII in any order: elimination of the protector group of the protected amino which Is $R_A$ to obtain a corresponding product in which $R_A$ is a free amine, which is converted by the previously described methods into products of formula XIII in which $R_A$ is R, R have the previously stated significance; cleavage of $A_{XXI}$ by the usual methods; and protection of the group $—CO_2H$.

The process of the invention for the preparation of the products of formula I in which $R_1$ is a radical attached to the ring of a sulfur atom comprises reacting a product of formula XI with a product of the formula $E—R''_1$ in which $R''_1$ has the above definitions for $R_2$ and $R_3$ or $R''_1$ is cyano and E is a reactive group.

The starting products of formula XII can be obtained by the reaction of a compound of the formula $$H_2N—CH_2—CO_2A_{XII}$$

with an aldehyde of the formula $OHC—CH═CH—G$ in which G is an alkyl, aryl or aralkyl having up to 8 carbon atoms and with a carboxylic acid halide of the formula

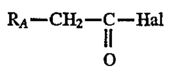

to obtain a product of the formula

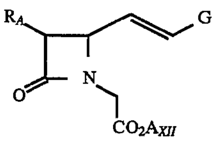

which is submitted to an ozonolysis in the presence of an alkanol to obtain a product of the formula

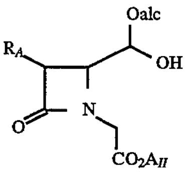

which is reduced to obtain the products of formula XII.

The novel antibiotic compositions of the invention are comprised of an antibiotically effective amount of at least one compound of formula I and their non-toxic, pharmaceutically acceptable acid addition salts and an inert pharmaceutical carrier or excipient. The compositions may be in the form of tablets, dragees, capsules, granules, suppositories, ointments, creams, gels and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions of the invention have a very good antibiotic activity on gram (+) bacteria such as staphylococci, streptococci and, in particular, on penicillin resistant staphylococci. Their activity on gram (−) bacteria, notably on coliform bacteria, klebsiella, salmonella and proteus is particularly remarkable.

These properties make the said compositions suitable for use as medicaments in the treatment of affections caused by sensitive germs and, in particular, in that of staphylococcia such as staphylococcal septicemia, malignant staphylococcia of the face or skin, pyodermatitis, septic or suppurating wounds, anthrax, phlegmons, erysipelas, acute primitive or post-influenza staphylococcia, bronchopneumonia, pulmonary suppuration. The compositions are also useful as medicaments in the treatment of colibacillosis and associated infections, in infections of proteus, klebsiella and salmonella and in other affections cause by gram (−) bacteria. The compositions may also be used to disinfect surgical instruments.

Among the preferred compounds of the invention are those wherein the active ingredient is the syn isomer of compounds of the formula

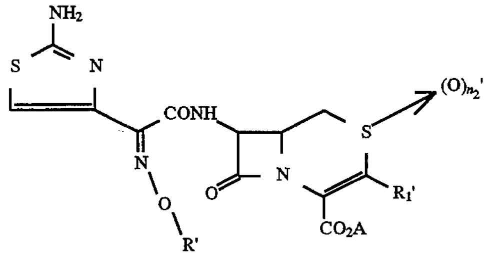

I' in which R' is hydrogen or alkyl or alkenyl having at the most 4 carbon atoms optionally substituted or optionally substituted phenyl, $R'_1$ is either:

a) Z'—$R'_2$ in which $R'_2$ is alkyl or alkenyl having at the most carbon atoms optionally interrupted by a heteroatom and optionally substituted by halogen, amino, cyano, free, esterified or salified carboxy, by a carbamoyl optionally substituted by an aryl, by optional substituted aryl, by optionally substituted quaternary ammonium, or by optionally substituted heterocycle, Z' is sulfur or oxygen;

b) $Z'_a$—$R'_3$ in which $R'_3$ is phenyl optionally substituted heterocyclic aryl or optionally substituted ammonium, and $Z'_a$ is methylene, —$CH_2$—S—, or a sulfur, oxygen or selenium or a simple bond;

c) alkyl or alkenyl of 2 to 4 carbon atoms optionally interrupted by an oxygen atom or optionally oxidized sulfur optionally substituted by aryl, carboxy possibly esterified or salified, cyano, amino, acyl or halogen;

d) azidomethyl, aminomethyl, thiocyanato, carbamoyloxy methyl, semicarbazonomethine, optionally substituted arylhydrazonomethine radical, $n'_2$ is 0 or 1 and A has the value indicated above.

Among the preferred products of formula I', as antibiotics are those wherein R' is hydrogen or methyl or allyl and $R'_1$ is chosen from the group consisting of methoxymethyl, pydidinylthio, pyridinyl, phenyl, phenylthio or thienopyridinium optionally substituted by methyl, cyclopropyl, nitro, chloro or methoxy; phenylselenyl, methylthio or ethylthio optionally substituted by carboxy, ethoxycarbnyl or amino; ethyl, isopropyl, methyltetrazolylthio, methyl- or thiomethyl-thiadiazolylthio, methyloxadiazolylthio, trimethylammonium methyl, or pyridinium optionally substituted or dihydropyridinium, as well as those in which $R'_1$ is $Z'_a$-$R'_3$ in which $Z'_a$ is sulfur and $R'_3$ is optionally substituted heterocyclic aryl with 5 or 6 links.

Especially preferred composition are those wherein the active compound is selected from the group consisting of 7-[2-(aminothiazol-4-yl)-2-methoxyimino-acetamido]-3-(3-nitro-phenythio)-8-oxo-4-thia-1-azabicyclo[4,2,0]oct-2-ene-2-carboxylic acid, syn isomer; 7-[2-(2-aminothiazol-4-yl) -2-methoxyimino-acetamido]-3-(4-nitro-phenyl) -8-oxo-4-thia-1-azabicyclo[4,2,0] oct-2-ene-2-carboxylic acid, syn isomer; 7-[2-(2-aminothiazol-4-yl)-2-methoxyimino-acetamido]-3[(1-methyl-(1H)-tetrazol-5-yl)-thio]-8-oxo-4-thia1-azabicyclo[4,2,0]oct-2-ene-2-carboxylic acid syn isomer; 7-[2-(2-aminothiazol-4-yl)-2-methoxyimino-acetamido-8-oxo-3- -[(1-methyl-(1H )-tetrazol-5-yl)-thiomethyl]-4-thia-1-azabicyclo[4,2,0]oct-2-ene-2-carboxylic acid, syn isomer; 1-[7-[(2-aminothiazol-4-yl)-2-methoxyimino-acetamido]-2-carboxy-8-oxo-4-thia-1-azabicyclo[4,2,0] oct-2-en-3-yl]-methylpyridinium, syn isomer; 1-[7-[(2-aminothiazol-4-yl)-2-methoxyimino-acetamido]-2-carboxy-8-oxo-4-thia-1-azabicyclo[4,2,0]oct-2-en-3-yl]-methyl-(6,7-dihydro)-5H-1-pyrindinium, syn. isomer; 6-(7-[2-(2-aminothiazol-4-yl)-2-methoxyimino-acetamido]-2-carboxy-8-oxo-4-thia-1-azabicyclo[4,2,0]oct-2-en-3-yl)-methylthieno[2,3-c]-pyridinium, syn isomer; 7-[2-(2-aminothioazol-4-yl)-2-methoxyimino-acetamido]-8-oxo-2-carboxy-4- thia-1-azabicyclo[4,2,0]oct-2-en-3-yl]-methyl trimethyl ammonium, syn isomer 7-[2-(2-aminothiazol-4-yl)-2-methoxyimino-acetamido]-8-oxo-4-thia-2-carboxy-1-azabicyclo[4,2,0]oct-2-en-3-yl)-methyl-4-cyclopropyl-pyridinium, syn isomer; 6-[7-[2-(2-aminothiazol-4-yl)-2-methoxyimino-acetamido]-8-oxo-4-thia-2-carboxy-1-azabicyclo [4,2,0]oct-2-en-3-yl]-methyl-7-methylthieno[2,3-c]pyridinium, syn isomer; 7-[7-(2-(2-aminothiazol-4-yl)-2-methoxyimino-acetamido]-8-oxo-4-thia-2-carboxy-1-azabicyclo[4,2,0]oct-2-en-3-yl]-methylthieno[2,3-b]pyridinium, syn isomer; 7-[2-(2-aminothiazol-4-yl)-2-(2-propenyloxy)-imino-acetamido]-2-carboxy-8-oxo-4-thia-1-azabicyclo [4,2,0]oct-2-en-3-yl]-methyl pyridinium, syn isomer; 1-[(7-[2-(2-aminothiazol-4-yl)-2-methoxyimino-acetamido]-2-carboxy-8-oxo-4-thia-1-azabicyclo[4,2,0]oct-2-en-3-yl)-methyl-(2-methylthio]-pyridinium, syn isomer 7-[7-2-(2-aminothiazol-4-yl)-[(difluoromethoxy)imino]acetamido]-2-carboxy-8-oxo-4-thia-1-azabicyclo [4,2,0] oct-2-ene-3-yl] methylthieno [2,3-b] pyridinium; 4-[7-[2-(2-aminothiazol-4-yl) [(difluoromethoxy) imino] acetamido-2-carboxy-8-oxo-4-thia-1-azabicyclo [4,2,0] oct-2-ene-3-yl] methylthieno [3,2-b] pyridinium internal salt of syn isomer 2-[7[2-(2-aminothiazol-4-yl)-2-(methoxyimino) acetamido 2-carboxy 8-oxo 4-thia 1-azabicyclo [4,2,0] oct-2-en-3-yl] methyl] isoquinolinium (6RS-7RS); 4-[7-[2-(2-aminothiazol-4-yl) 2-[(methoxymethoxy) imino] acetamido-2-carboxy-8-oxo-4-thia-1-azabicyclo [4,2,0] oct-2-en-3-yl] methyl] thieno [3,2-b] pyridinium (6RS-7RS);

7-[7-[2-(2-aminothiazol-4-yl) 2-[(propenyloxy) imino] acetamido 2-carboxy-8-oxo-4-thia-1-azabicyclo [4,2,0] oct-2-en-3-yl] methyl] thieno [2,3-b] pyridinium (6RS,7RS), 5-//7-//(2-amino 4-thiazolyl)/(difluoromethoxy) imino/ acetyl/amino/2-carboxy 8-oxo 4-thia 1-azabicyclo/4.2.0/oct-2-en 3-yl/methyl/thieno/3,2-c/pyridinium (6S) (7S) (Z), 4-//7-//2-(2-amino 4-thiazolyl) 2-(methoxyimino) acetyl/ amino/2-carboxy 8-oxo 4-thia 1-azabicyclo/4.2.0/oct-2-en 3-yl/methyl/thieno/3,2-b/pyridinium (6S) (7S) (Z), 4-//7-//(2-amino 4-thiazolyl) (methoxyimino) acetyl/ amino/2-carboxy 8-oxo 4-thia 1-azabicyclo/4.2.0/oct-2-en 3-yl/methyl/7-methyl thieno/3,2-b/pyridinium (6S) (7S) (Z), 5-//7-//(2-amino 4-thiazolyl)/(fluoromethoxy) imino/ acetyl/amino/2-carboxy 8-oxo 4-thia 1-azabicyclo/4.2.0/oct-2-en 3-yl/methyl/thieno/3,2-c/pyridinium, 5-//7-//(2-amino 4-thiazolyl)/(fluoromethoxy) imino/ acetyl/amino/2-carboxy 8-oxo 4-thia 1-azabicyclo/4.2.0/oct-2-en 3-yl/methyl/4-methyl thieno/3,2-c/pyridinium (6S) (7S) (Z) and their non toxic pharmaceutically acceptable salts.

The novel method of combatting bacterial infections in warm-blooded animals, including humans, comprises administering to warm-blooded animals an antibactericidally effective amount of at least one compound of formula I and their non-toxic, pharmaceutically acceptable acid addition salts. The compounds may be administered orally, rectally, parenterally, intramuscularly or topically on the skin and mucosa. The usual daily dose is depending on the condition treated, the specific compound and method of administration. For example, the compounds of Examples 23, 27, 28, 29, 33, 34 and 53 may be orally administered daily at a dose of 3.5 to 55 mg/kg or 7 to 14 mg/kg intramuscularly. The preferred compounds of formula are those wherein A is a cleavable ester such as propionyloxymethyl and it is administered orally.

The novel intermediates of the invention are those of the formulae

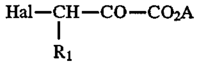

$III_A$ in which $R_1$, A and Hal have above definitions, the products of the formula

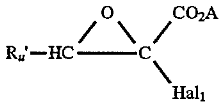

$III_{Ai}'$ in which $R'_u$, $Hal_1$ and A have above definitions, the products of the formula

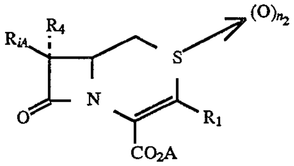

in which $R_4$, $R_1$, A and $n_2$ have above definitions and $R_{iA}$ is free amino or protected by a mono- or divalent protector group and the products of formula XI.

The products of formula $IV_b$ are described or can be prepared by the process of French Patent No. 2,073,338 and the products of formula $IV_c$ can be prepared or are described in J. of Med. Chem. (1982), Vol. 25, No. 4., p. 457. The products of formula $II_A$ are described or can be prepared by the method described in Belgian Patent No. 894,795. The products of formula $III'_A$ are described or can be prepared by the method described in J.O.C., Vol. 44, (25) 4741 (1983).

In addition to the products described in the examples to illustrate the invention without limiting it, the following products constitute products which can be obtained within the framework of the present application. These products respond to the formula

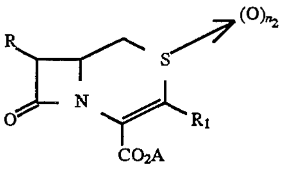

in which R, $R_1$, A and $n_2$ have the above definitions in the following tables.

| R | $R_1$ | $n_2$ | $CO_2A$ | R | $R_1$ | $n_2$ | $CO_2A$ |
|---|---|---|---|---|---|---|---|
| 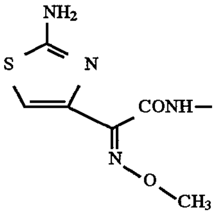 | 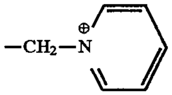 | 0 | $CO_2^{\ominus}$ | 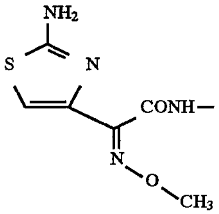 | 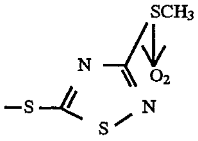 | 0 | $CO_2H$ |
| " | " | 1 | " | " | 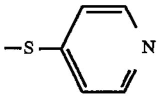 | " | " |
| " | $CH_2-{}^{\oplus}N(CH_3)_3$ | 0 | " | " | 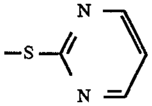 | " | " |
| " | " | 1 | " | " | $-S-CF_3$ | " | " |
| " | 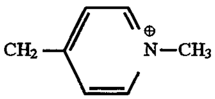 | 0 | " | " | 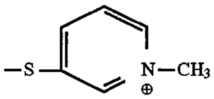 | " | " |
| " | " | 1 | " | | | | |
| " | 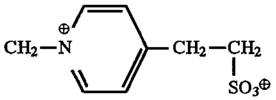 | 0 | $CO_2H$ | " | 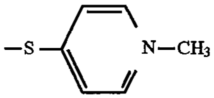 | " | " |
| " | " | 1 | " | | | | |
| " | 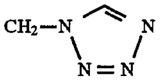 | 0 | " | " | 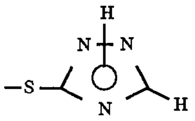 | " | " |

-continued
| R | $R_1$ | $n_2$ | $CO_2A$ | R | $R_1$ | $n_2$ | $CO_2A$ |
|---|---|---|---|---|---|---|---|
| " | 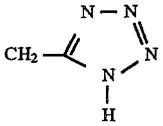 | 0 | " | " | 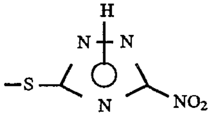 | " | " |
| " | 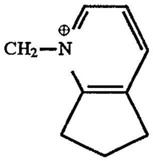 | 0 | $CO_2^{\ominus}$ | " | 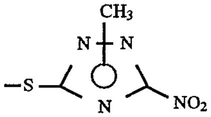 | " | " |
| " | " | 1 | " | " | 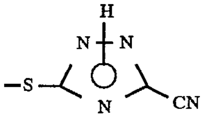 | " | " |
| 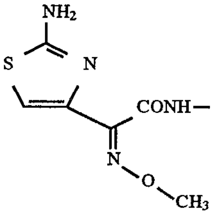 | 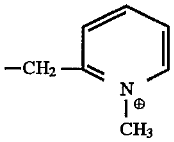 | 0 | $CO_2^{\ominus}$ | 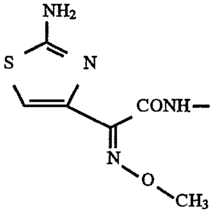 | 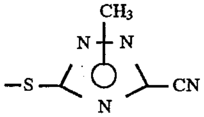 | 0 | $CO_2H$ |
| " | " | 1 | " | " | 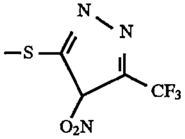 | " | " |
| " | 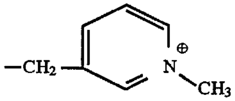 | 0 | " | " | 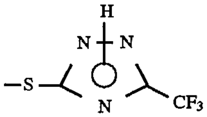 | " | " |
| " | " | 1 | " | " | 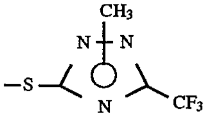 | " | " |

-continued
| R | $R_1$ | $n_2$ | $CO_2A$ | R | $R_1$ | $n_2$ | $CO_2A$ |
|---|---|---|---|---|---|---|---|
| " | 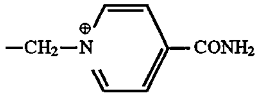 | 0 | " | " | 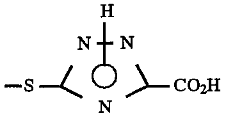 | " | " |
| " | " | 1 | " | " | 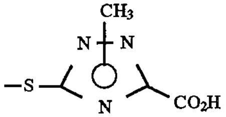 | " | " |
| " | 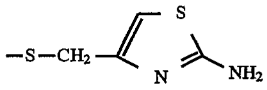 | 0 | $CO_2H$ | " | 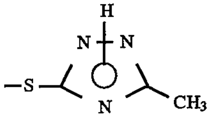 | " | " |
| " | 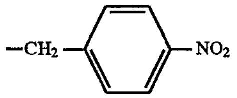 | 0 | " | " | 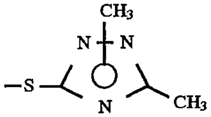 | " | " |
| " | 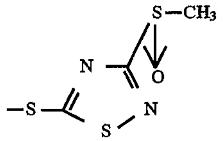 | " | " | " | 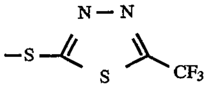 | " | " |
| " | 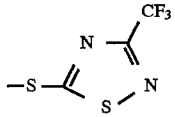 | " | " | " | 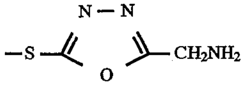 | " | " |
| " | 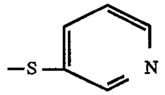 | " | " | " | 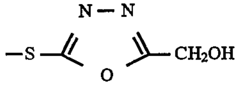 | " | " |
| " | SCN | " | " | " | 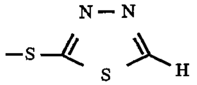 | " | " |

-continued
| R | $R_1$ | $n_2$ | $CO_2A$ | R | $R_1$ | $n_2$ | $CO_2A$ |
|---|---|---|---|---|---|---|---|
| " | $-S-CO_2Et$ | " | " | " | 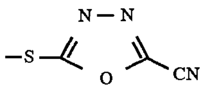 | " | " |
| 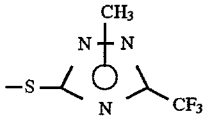 | 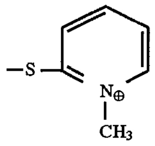 | 0 | $CO_2^{\ominus}$ | 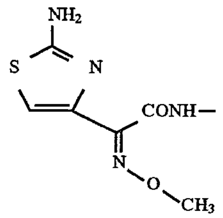 | 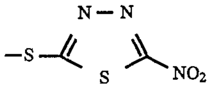 | 0 | $CO_2H$ |
| " | 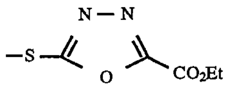 | " | $CO_2H$ | " | 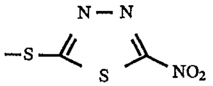 | " | " |
| " | 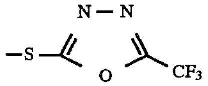 | " | " | " | 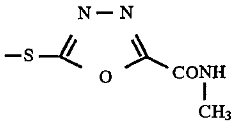 | " | " |
| " | 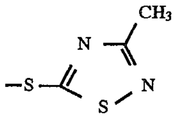 | " | " | " | 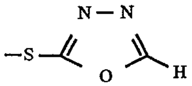 | " | " |
| " | 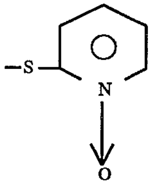 | " | " | " | 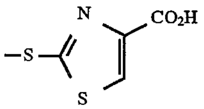 | " | " |
| " | 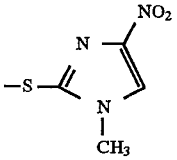 | " | " | " | 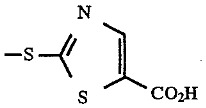 | " | " |

-continued
| R | $R_1$ | $n_2$ | $CO_2A$ | R | $R_1$ | $n_2$ | $CO_2A$ |
|---|---|---|---|---|---|---|---|
| " | $-S-CH_2-CH_2-SO_3^{\ominus}$ | " | " | " | 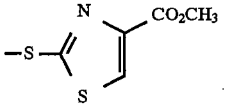 | " | " |
| " | 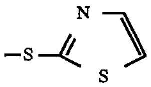 | " | " | " | 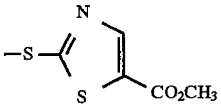 | " | " |
| " | 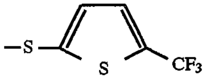 | " | " | " | 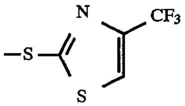 | " | " |
| " | 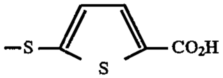 | " | " | " | 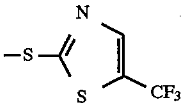 | " | " |
| " | 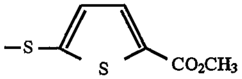 | " | " | " | 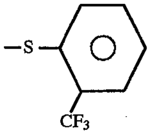 | " | " |
| | | | | " | 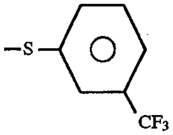 | " | " |
| 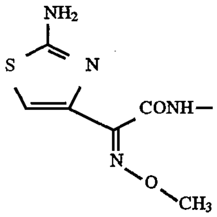 | 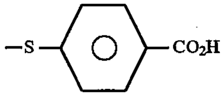 | 0 | $CO_2H$ | 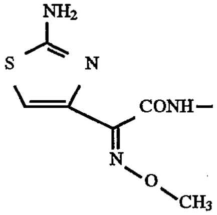 | 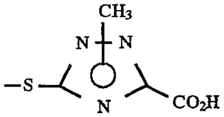 | 0 | $CO_2H$ |

-continued
| R | R₁ | n₂ | CO₂A | R | R₁ | n₂ | CO₂A |
|---|---|---|---|---|---|---|---|
| " | 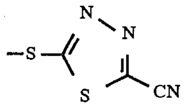 | " | " | " | 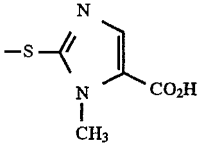 | " | " |
| " | 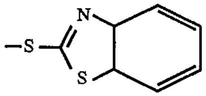 | " | " | " | 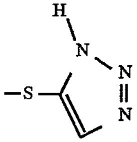 | " | " |
| " | 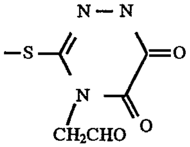 | " | " | " | 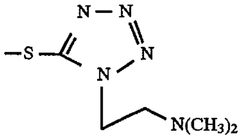 | " | " |
| " | 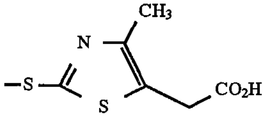 | " | " | " | 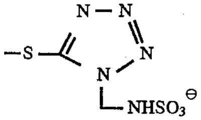 | " | " |
| " | 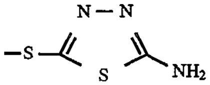 | " | " | " | 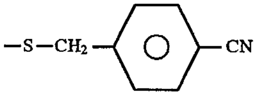 | " | " |
| " | 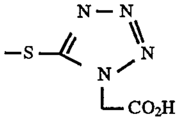 | " | " | " | 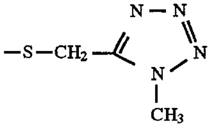 | " | " |
| " | 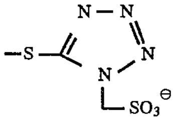 | " | " | " | 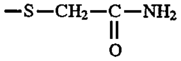 | " | " |

-continued
| R | $R_1$ | $n_2$ $CO_2A$ | R | $R_1$ | $n_2$ $CO_2A$ |
| --- | --- | --- | --- | --- | --- |
| " | 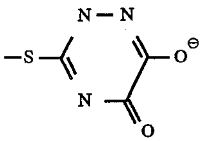 | " " | " | 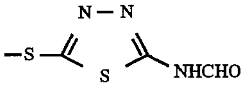 | " " |
| " | 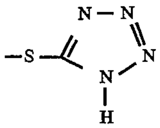 | " " | " | 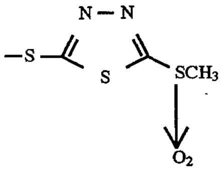 | " " |
| 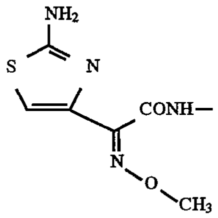 | 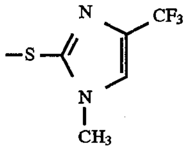 | 0 $CO_2H$ | 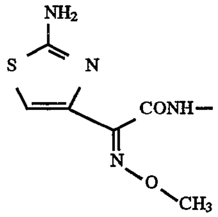 | 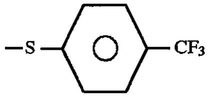 | 0 $CO_2H$ |
| " | 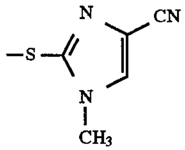 | " " | " | 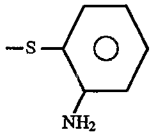 | " " |
| " | $-S-CH_2-CH_2-{}_{\oplus}N(CH_3)_3$ | " $CO_2^{\ominus}$ | " | 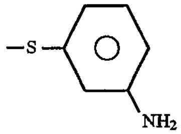 | " " |
| " | 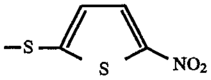 | " $CO_2H$ | " | 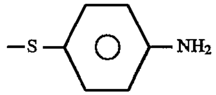 | " " |
| " | 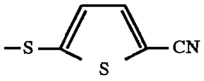 | " " | " | $-S-CH=CH-CONH_2$ | " " |

-continued
| R | $R_1$ | $n_2$ | $CO_2A$ | R | $R_1$ | $n_2$ | $CO_2A$ |
|---|---|---|---|---|---|---|---|
| " | 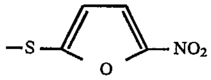 | " | " | " | 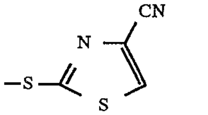 | " | " |
| " | 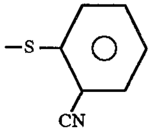 | " | " | " | 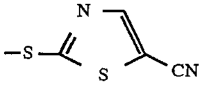 | " | " |
| " | 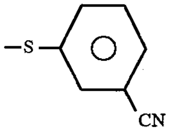 | " | " | " | 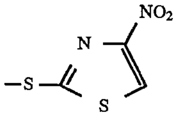 | " | " |
| " | 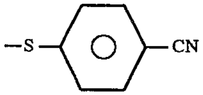 | " | " | " | 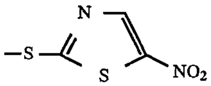 | " | " |
| " | 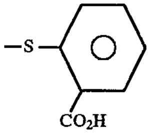 | " | " | " | 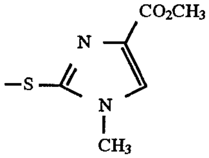 | " | " |
| " | 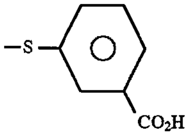 | " | " | " | 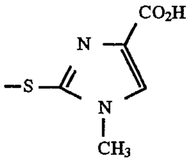 | " | " |

-continued
| R | $R_1$ | $n_2$ | $CO_2A$ | R | $R_1$ | $n_2$ | $CO_2A$ |
|---|---|---|---|---|---|---|---|
| 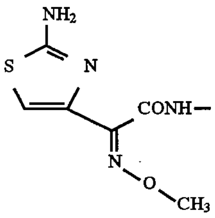 | 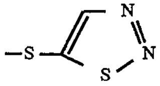 | 0 | $CO_2H$ | 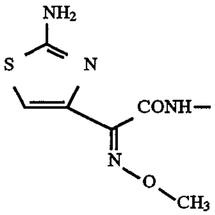 | 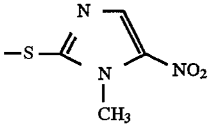 | 0 | $CO_2H$ |
| " | 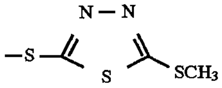 | " | " | " | 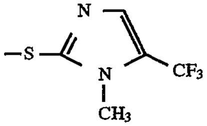 | " | " |
| " | 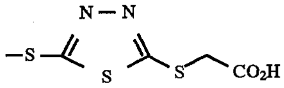 | " | " | " | 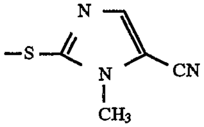 | " | " |
| " | 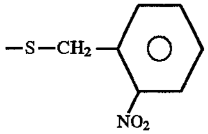 | " | " | | | | |
| " | 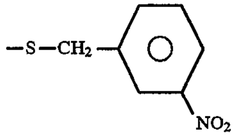 | " | " | | | | |
| " | 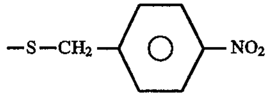 | " | " | 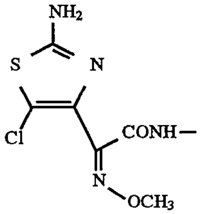 | 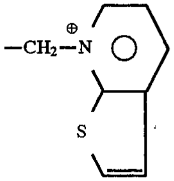 | " | " |

-continued
| R | $R_1$ | $n_2$ | $CO_2A$ | R | $R_1$ | $n_2$ | $CO_2A$ |
|---|---|---|---|---|---|---|---|
| " | 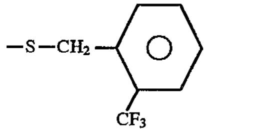 | " | " | | | | |
| " | 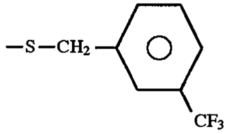 | " | " | | | | |
| " | 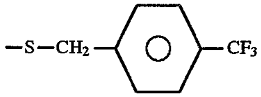 | " | " | | | | |
| " | 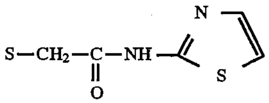 | " | " | | | | |
| " | $-S-CH_2-CN$ | " | " | | | | |
| " | 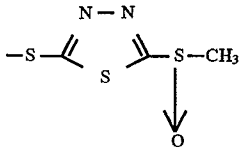 | " | " | | | | |
| 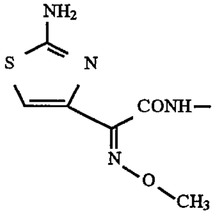 | 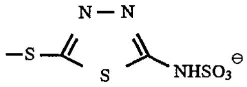 | 0 | $CO_2H$ | | | | |
| " | 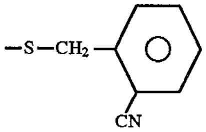 | " | " | | | | |

-continued
| R | $R_1$ | $n_2$ $CO_2A$ | R | $R_1$ | $n_2$ $CO_2A$ |
|---|---|---|---|---|---|
| " | 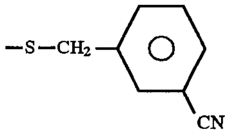 | " " | | | |
| " | 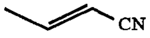 | " 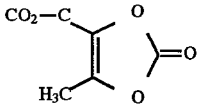 | | | |
| " | 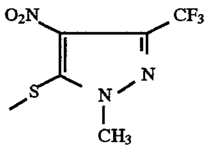 | " $CO_2H$ | | | |
| " | 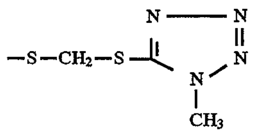 | " " | | | |
| 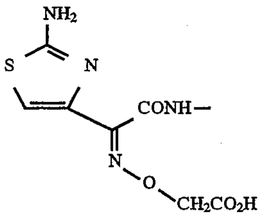 | 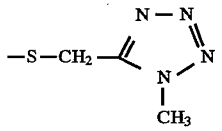 | 0 $CO_2H$ | 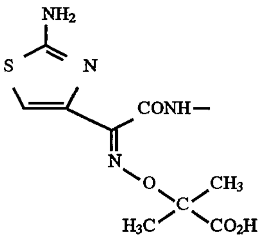 | 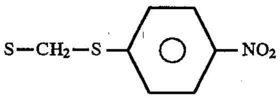 | 0 $CO_2H$ |
| " | 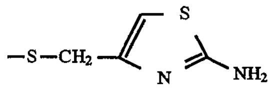 | " " | | | |
| " | 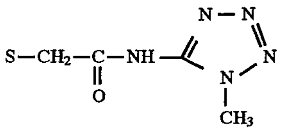 | " " | " | 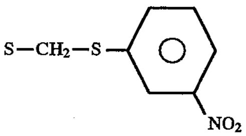 | " " |

-continued
| R | $R_1$ | $n_2$ | $CO_2A$ | R | $R_1$ | $n_2$ | $CO_2A$ |
|---|---|---|---|---|---|---|---|
| " | 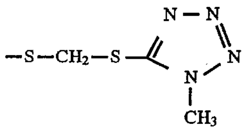 | " | " | " | 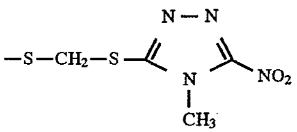 | " | " |
| " | 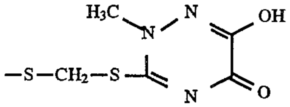 | " | " | " | 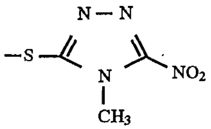 | " | " |
| " | 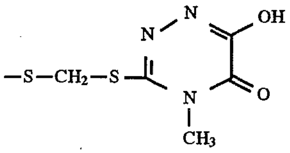 | " | " | " | 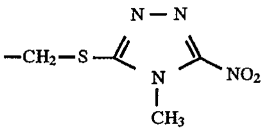 | " | " |
| " | 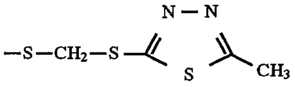 | " | " | " | 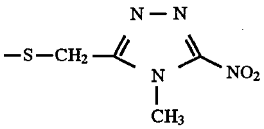 | " | " |
| " | 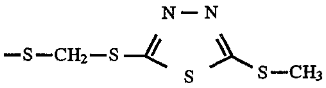 | " | " | " | 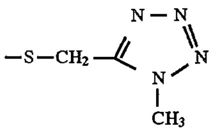 | " | " |
| " | 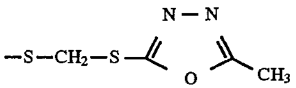 | " | " | " | 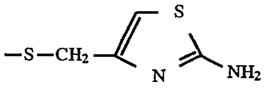 | " | " |
| 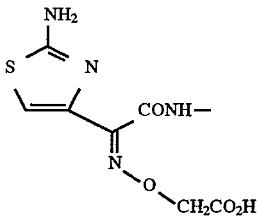 | 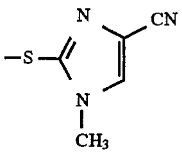 | 0 | $CO_2H$ | 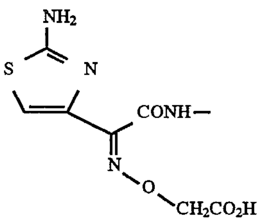 | $-S-CH=CH-CONH_2$ | 0 | $CO_2H$ |

-continued
| R | $R_1$ | $n_2$ | $CO_2A$ | R | $R_1$ | $n_2$ | $CO_2A$ |
|---|---|---|---|---|---|---|---|
| " | $-S-CH_2-CH_2-N(CH_3)_3$ | " | $CO_2^{\ominus}$ | " | 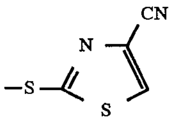 | " | " |
| " | 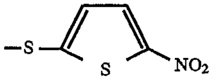 | " | $CO_2H$ | " | 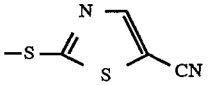 | " | " |
| " | 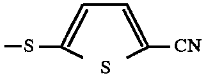 | " | " | " | 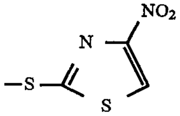 | " | " |
| " | 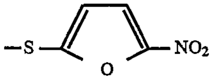 | " | " | " | 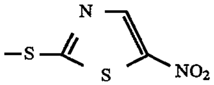 | " | " |
| " | 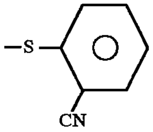 | " | " | " | 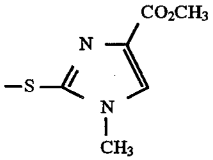 | " | " |
| " | 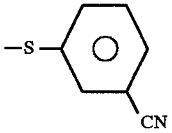 | " | " | " | 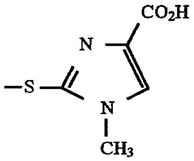 | " | " |
| " | 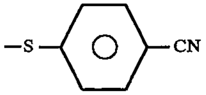 | " | " | " | 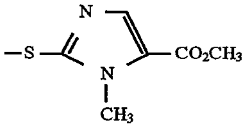 | " | " |
| " | 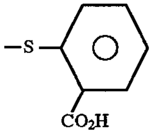 | " | " | | | | |

-continued
| R | $R_1$ | $n_2$ | $CO_2A$ | R | $R_1$ | $n_2$ | $CO_2A$ |
|---|---|---|---|---|---|---|---|
| " | 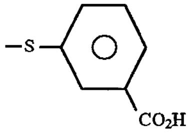 | " | " | " | 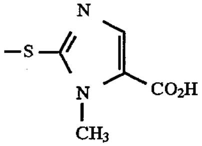 | " | " |
| " | 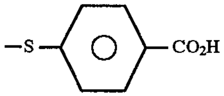 | " | " | " | 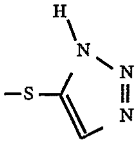 | " | " |
| 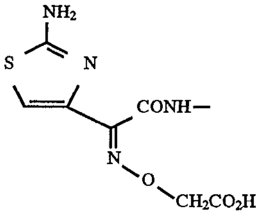 | 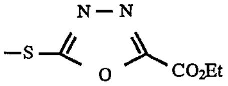 | 0 | $CO_2H$ | 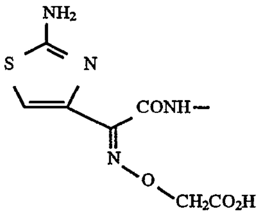 | 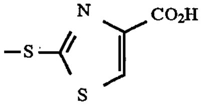 | 0 | $CO_2H$ |
| " | 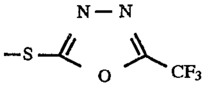 | " | " | " | 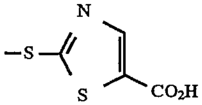 | " | " |
| " | 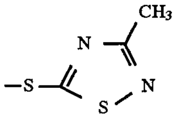 | " | " | " | 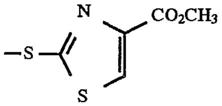 | " | " |
| " | 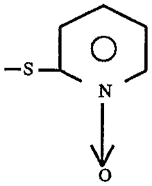 | " | " | " | 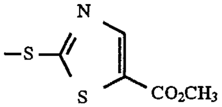 | " | " |

-continued
| R | $R_1$ | $n_2$ | $CO_2A$ | R | $R_1$ | $n_2$ | $CO_2A$ |
|---|---|---|---|---|---|---|---|
| " | 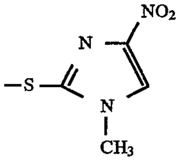 | " | " | " | 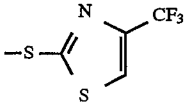 | " | " |
| " | $-S-CH_2-CH_2-SO_3^{\ominus}$ | " | " | " | 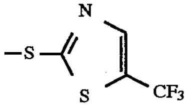 | " | " |
| " | 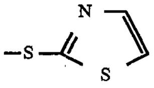 | " | " | " | 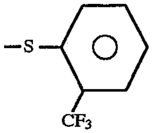 | " | " |
| | | | | " | 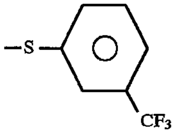 | " | " |
| " | 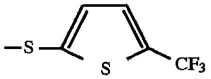 | " | " | " | 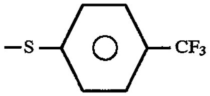 | " | " |
| " | 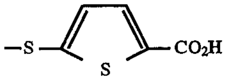 | " | " | " | 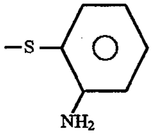 | " | " |
| " | 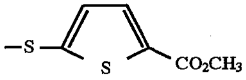 | " | " | " | 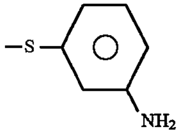 | " | " |

-continued
| R | $R_1$ | $n_2$ | $CO_2A$ | R | $R_1$ | $n_2$ | $CO_2A$ |
|---|---|---|---|---|---|---|---|
| " | 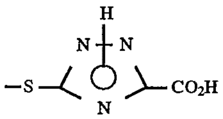 | " | " | " | 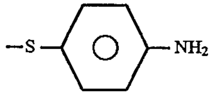 | " | " |
| 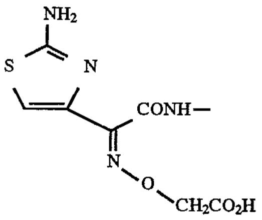 | 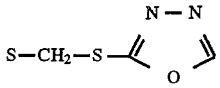 | 0 | $CO_2H$ | 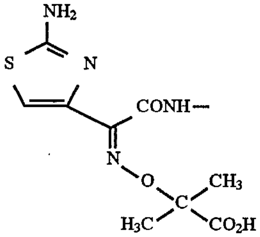 | 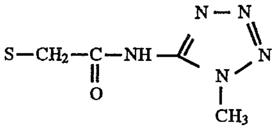 | 0 | $CO_2H$ |
| " | 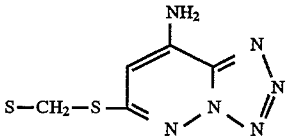 | " | " | | | | |
| " | 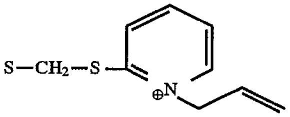 | " | " | " | 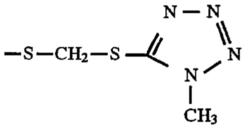 | " | " |
| " | 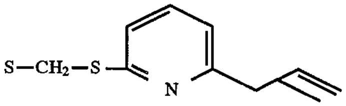 | " | " | " | 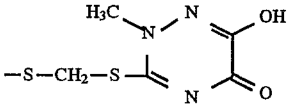 | " | " |
| " | 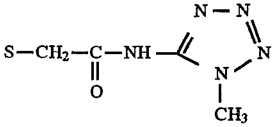 | " | " | " | 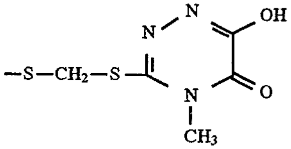 | " | " |

-continued
| R | $R_1$ | $n_2$ | $CO_2A$ | R | $R_1$ | $n_2$ | $CO_2A$ |
|---|---|---|---|---|---|---|---|
| " | 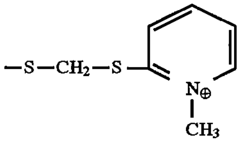 | " | " | " | 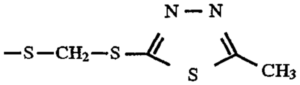 | " | " |
| " | 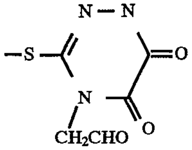 | " | " | " | 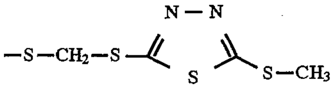 | " | " |
| " | 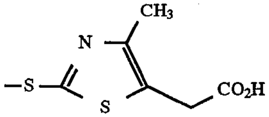 | " | " | " | 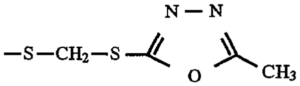 | " | " |
| " | 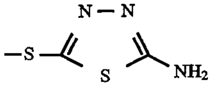 | " | " | " | 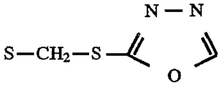 | " | " |
| 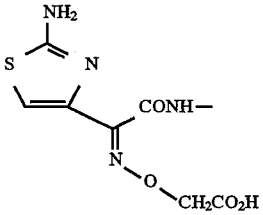 | 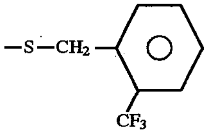 | 0 | $CO_2H$ | 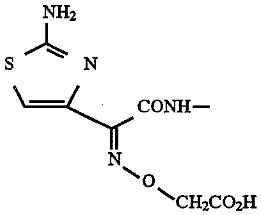 | 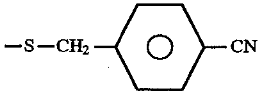 | 0 | $CO_2H$ |
| " | 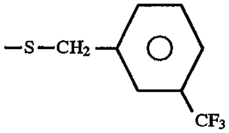 | " | " | " | 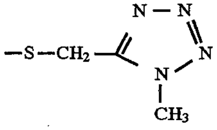 | " | " |
| " | 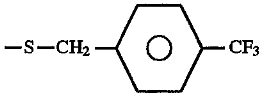 | " | " | " | 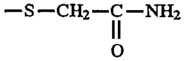 | " | " |

-continued
| R | $R_1$ | $n_2$ | $CO_2A$ | R | $R_1$ | $n_2$ | $CO_2A$ |
|---|---|---|---|---|---|---|---|
| " | 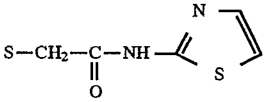 | " | " | " | 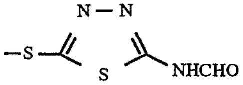 | " | " |
| " | $-S-CH_2-CN$ | " | " | | | | |
| " | 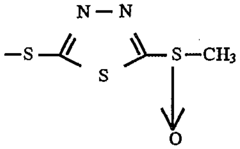 | " | " | " | 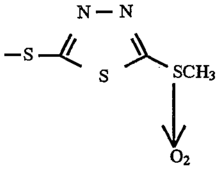 | " | " |
| " | 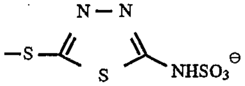 | " | " | " | 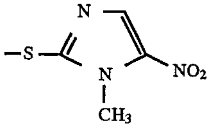 | " | " |
| " | 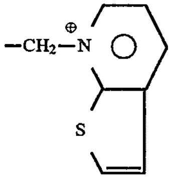 | " | " | " | 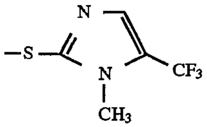 | " | " |
| " | 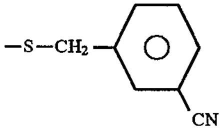 | " | " | " | 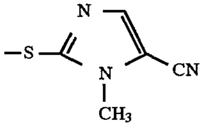 | " | " |
| 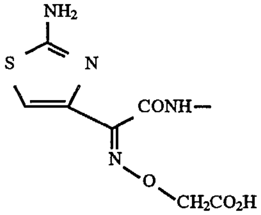 | 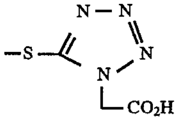 | 0 | $CO_2H$ | 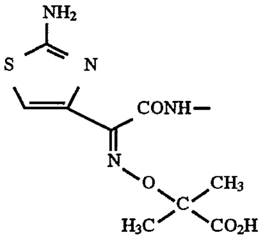 | | 0 | $CO_2H$ |

-continued
| R | $R_1$ | $n_2$ $CO_2A$ | R | $R_1$ | $n_2$ $CO_2A$ |
|---|---|---|---|---|---|
| " | 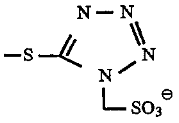 | " " | " | 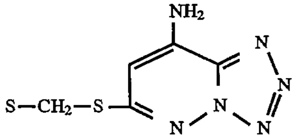 | " " |
| " | 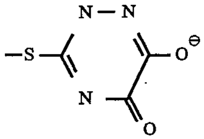 | " " | " | 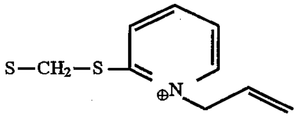 | " " |
| " | 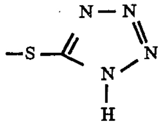 | " " | " | 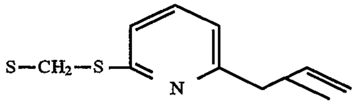 | " " |
| " | 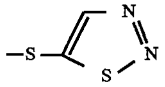 | " " | " | 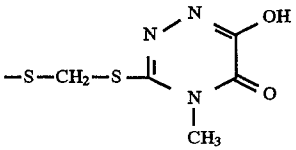 | " " |
| " | 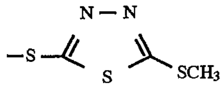 | " " | " | 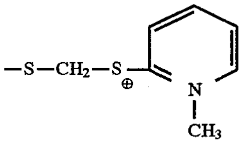 | " " |
| " | 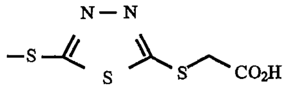 | " " | | | |
| " | 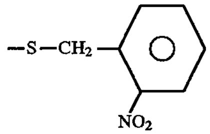 | " " | | | |

-continued
| R | $R_1$ | $n_2$ | $CO_2A$ | R | $R_1$ | $n_2$ | $CO_2A$ |
|---|---|---|---|---|---|---|---|
| " | 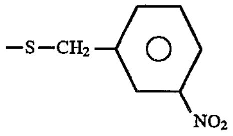 | " | " | | | | |
| " | 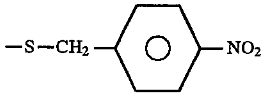 | " | " | | | | |
| 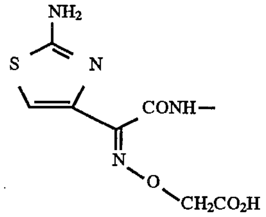 | 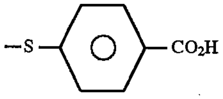 | 0 | $CO_2H$ | 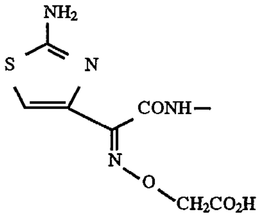 | 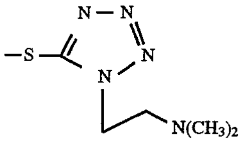 | 0 | $CO_2H$ |
| " | 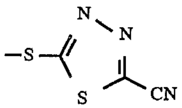 | " | " | " | 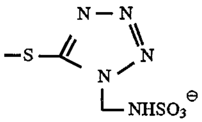 | " | " |
| " | 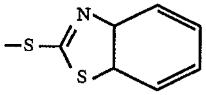 | " | " | | | | |
| " | 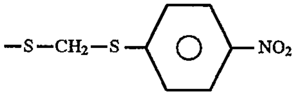 | " | " | | | | |
| " | 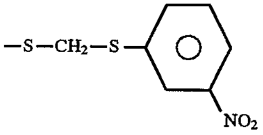 | " | " | | | | |

-continued
| R | $R_1$ | $n_2$ | $CO_2A$ | R | $R_1$ | $n_2$ | $CO_2A$ |
|---|---|---|---|---|---|---|---|
| " | 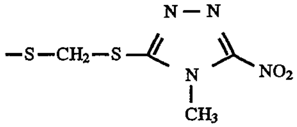 | " | " | | | | |
| " | 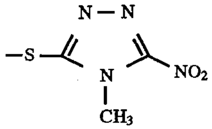 | " | " | | | | |
| " | 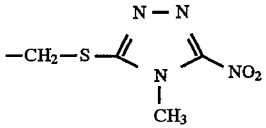 | " | " | | | | |
| " | 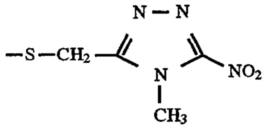 | " | " | | | | |
| 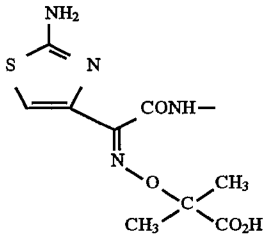 | 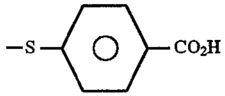 | 0 | $CO_2H$ | 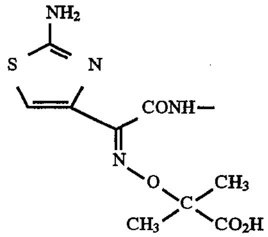 | 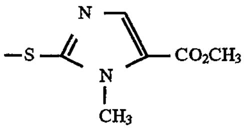 | 0 | $CO_2H$ |
| " | 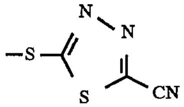 | " | " | " | 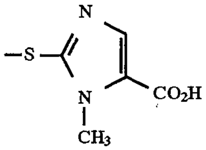 | " | " |

-continued
| R | $R_1$ | $n_2$ | $CO_2A$ | R | $R_1$ | $n_2$ | $CO_2A$ |
|---|---|---|---|---|---|---|---|
| " | 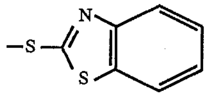 | " | " | " | 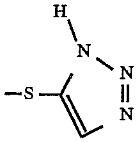 | " | " |
| " | 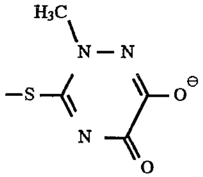 | " | " | " | 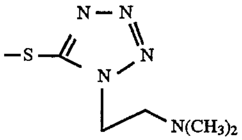 | " | " |
| " | 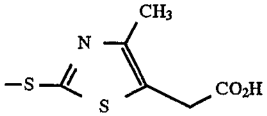 | " | " | " | 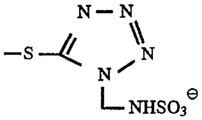 | " | " |
| " | 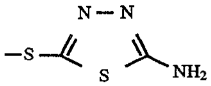 | " | " | " | 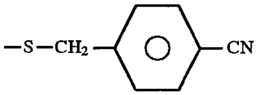 | " | " |
| " | 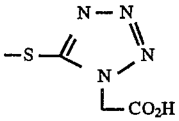 | " | " | " | 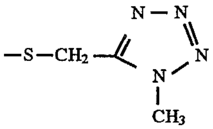 | " | " |
| " | 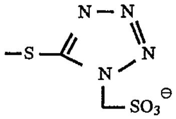 | " | " | " | 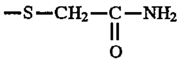 | " | " |
| " | 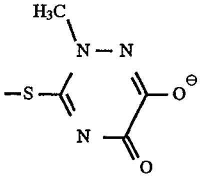 | " | " | " | 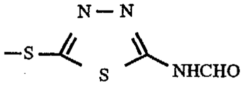 | " | " |

-continued
| R | $R_1$ | $n_2$ | $CO_2A$ | R | $R_1$ | $n_2$ | $CO_2A$ |
|---|---|---|---|---|---|---|---|
| " | 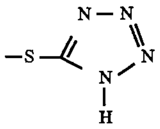 | " | " | " | 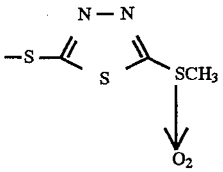 | " | " |
| 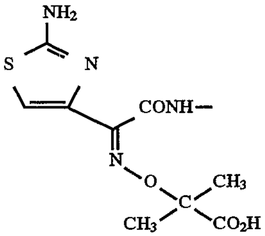 | 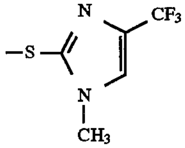 | 0 | $CO_2H$ | 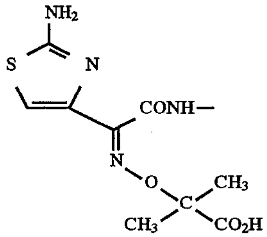 | 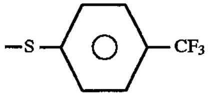 | 0 | $CO_2H$ |
| " | 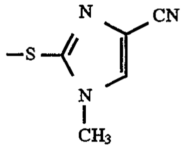 | " | " | " | 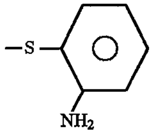 | " | " |
| " | $-S-CH_2-CH_2-{}^{\oplus}N(CH_3)_3$ | " | $CO_2^{\ominus}$ | " | 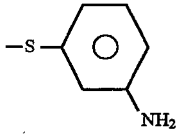 | " | " |
| " | 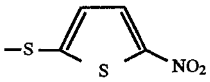 | " | $CO_2H$ | " | 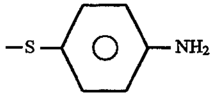 | " | " |
| " | 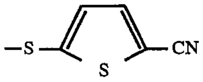 | " | " | " | $-S-CH=CH-CONH_2$ | " | " |
| " | 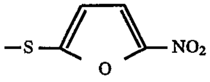 | " | " | " | 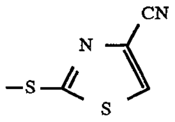 | " | " |

-continued
| R | $R_1$ | $n_2$ | $CO_2A$ | R | $R_1$ | $n_2$ | $CO_2A$ |
|---|---|---|---|---|---|---|---|
| " | 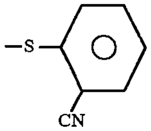 | " | " | " | 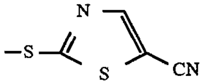 | " | " |
| " | 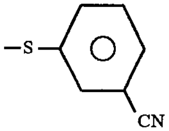 | " | " | " | 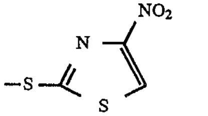 | " | " |
| " | 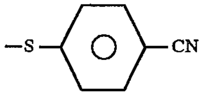 | " | " | " | 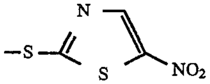 | " | " |
| " | 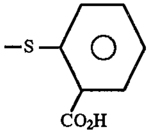 | " | " | " | 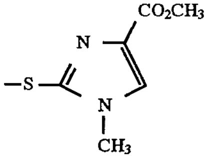 | " | " |
| " | 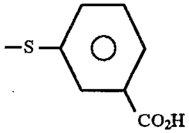 | " | " | " | 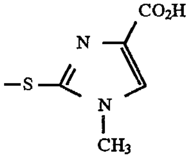 | " | " |
| 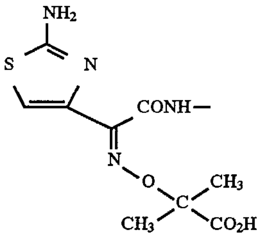 | 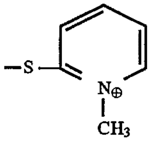 | 0 | $CO_2^{\ominus}$ | 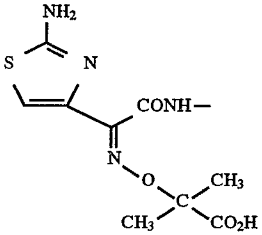 | 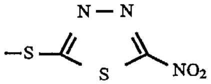 | 0 | $CO_2H$ |
| " | 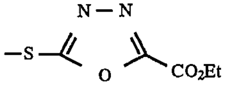 | " | $CO_2H$ | " | 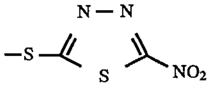 | " | " |

-continued
| R | $R_1$ | $n_2$ | $CO_2A$ | R | $R_1$ | $n_2$ | $CO_2A$ |
|---|---|---|---|---|---|---|---|
| " | 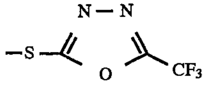 | " | " | " | 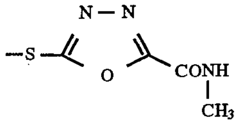 | " | " |
| " | 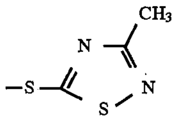 | " | " | " | 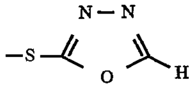 | " | " |
| " | 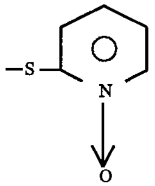 | " | " | " | 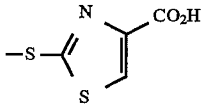 | " | " |
| " | 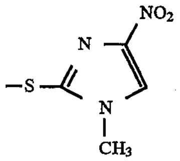 | " | " | " | 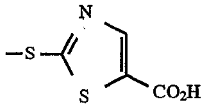 | " | " |
| " | $-S-CH_2-CH_2-SO_3^{\ominus}$ | " | " | " | 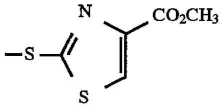 | " | " |
| " | 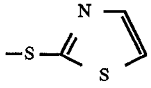 | " | " | " | 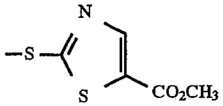 | " | " |
| " | 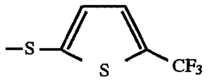 | " | " | " | 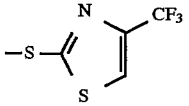 | " | " |

-continued
| R | $R_1$ | $n_2$ | $CO_2A$ | R | $R_1$ | $n_2$ | $CO_2A$ |
|---|---|---|---|---|---|---|---|
| " | 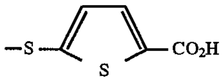 | " | " | " | 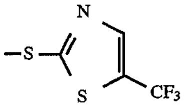 | " | " |
| " | 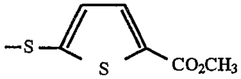 | " | " | " | 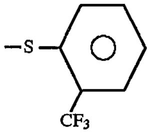 | " | " |
| | | | " | 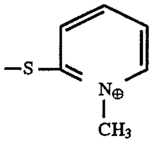 | " | | " |
| 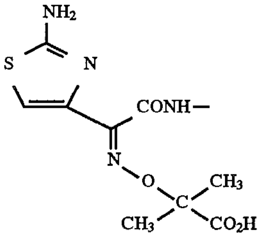 | 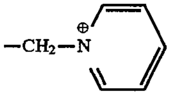 | 0 | $CO_2^{\ominus}$ | 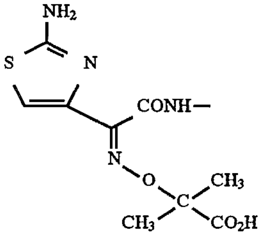 | 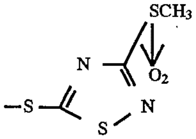 | 0 | $CO_2H$ |
| " | " | 1 | " | " | 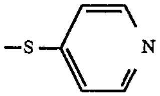 | " | " |
| " | $CH_2-^{\oplus}N(CH_3)_3$ | 0 | " | " | 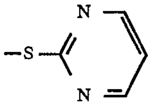 | " | " |
| " | " | 1 | " | " | $-S-CF_3$ | " | " |
| " | 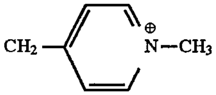 | 0 | " | " | 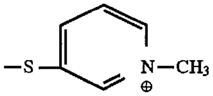 | " | " |
| " | " | 1 | " | | | | |

-continued
| R | $R_1$ | $n_2$ $CO_2A$ | R | $R_1$ | $n_2$ $CO_2A$ |
|---|---|---|---|---|---|
| " | 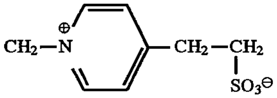 | 0 $CO_2H$ | " | 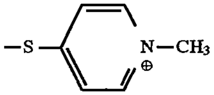 | " " |
| " | " | 1 " | " | 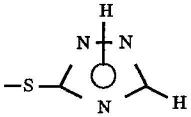 | " " |
| " | 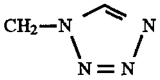 | 0 " | " | 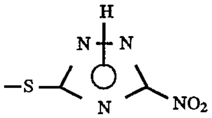 | " " |
| " | 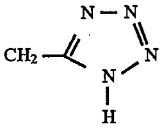 | 0 " | | | |
| " | 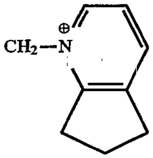 | 0 $CO_2^{\ominus}$ | " | 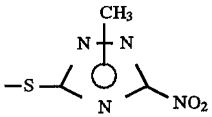 | " " |
| " | " | 1 " | " | 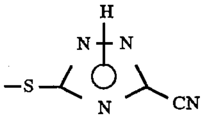 | " " |

-continued
| R | $R_1$ | $n_2$ $CO_2A$ | R | $R_1$ | $n_2$ $CO_2A$ |
|---|---|---|---|---|---|
| 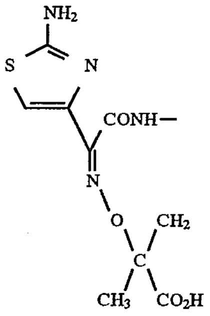 | 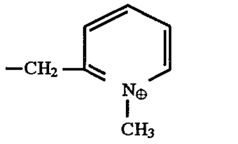 | 0 $CO_2^{\ominus}$ | 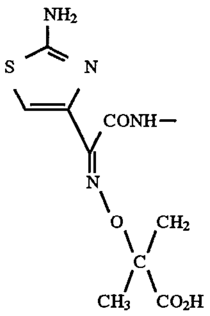 | 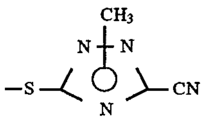 | 0 $CO_2H$ |
| " | " | 1 " | " | 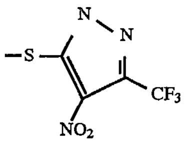 | " " |
| " | 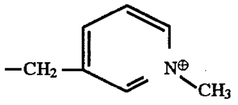 | 0 " | " | 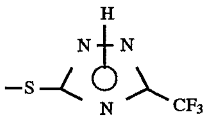 | " " |
| " | " | 1 " | " | 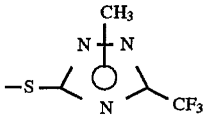 | " " |
| " | 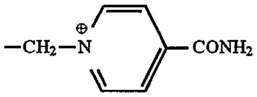 | 0 " | " | 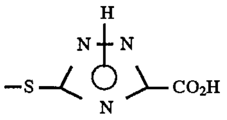 | " " |
| " | " | 1 " | " | 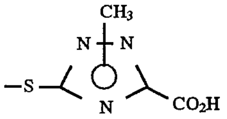 | " " |

-continued
| R | $R_1$ | $n_2$ | $CO_2A$ | R | $R_1$ | $n_2$ | $CO_2A$ |
|---|---|---|---|---|---|---|---|
| " | 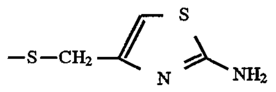 | 0 | $CO_2H$ | " | 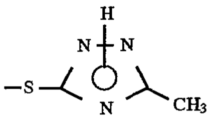 | " | " |
| " | 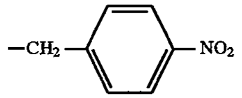 | 0 | " | " | 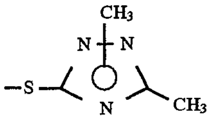 | " | " |
| " | 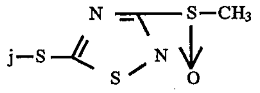 | " | " | " | 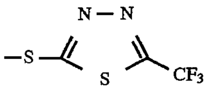 | " | " |
| " | 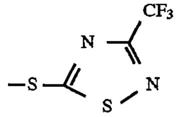 | " | " | " | 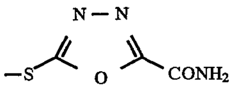 | " | " |
| " | 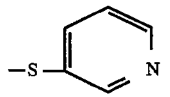 | " | " | " | 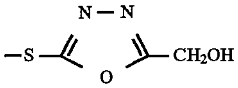 | " | " |
| " | SCN | " | " | " | 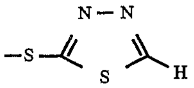 | " | " |
| " | $-S-CO_2Et$ | " | " | " | 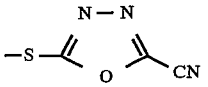 | " | " |

-continued
| R | $R_1$ | $n_2$ | $CO_2A$ | R | $R_1$ | $n_2$ | $CO_2A$ |
|---|---|---|---|---|---|---|---|
| 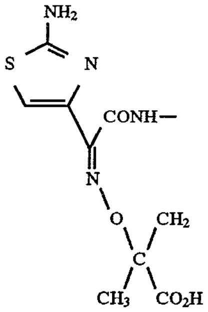 | 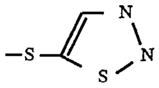 | 0 | $CO_2H$ | 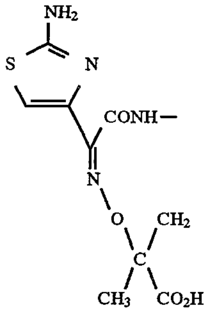 | 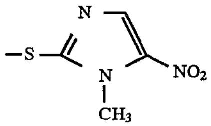 | 0 | $CO_2H$ |
| " | 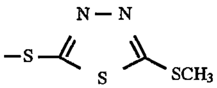 | " | " | " | 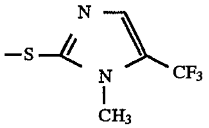 | " | " |
| " | 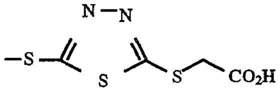 | " | " | " | 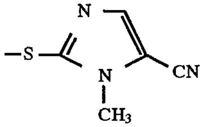 | " | " |
| " | 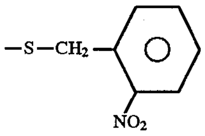 | " | " | | | | |
| " | 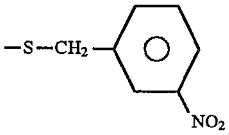 | " | " | | | | |
| " | 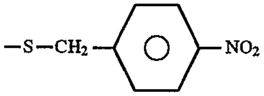 | " | " | | | | |

-continued
| R | $R_1$ | $n_2$ | $CO_2A$ | R | $R_1$ | $n_2$ | $CO_2A$ |
|---|---|---|---|---|---|---|---|
| " | 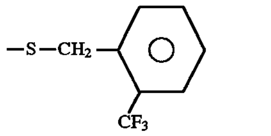 | " | " | | | | |
| " | 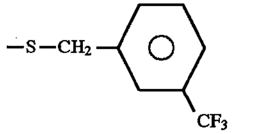 | " | " | | | | |
| " | 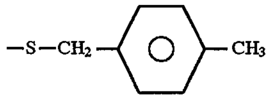 | " | " | | | | |
| " | 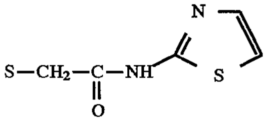 | " | " | | | | |
| " | $-S-CH_2-CN$ | " | " | | | | |
| " | 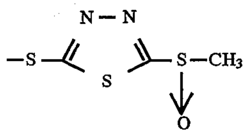 | " | " | | | | |
| 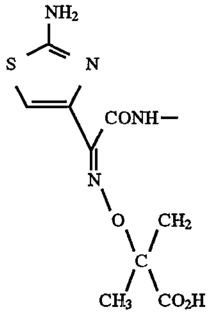 | 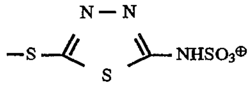 | 0 | $CO_2H$ | | | | |

-continued
| R | $R_1$ | $n_2$ | $CO_2A$ | R | $R_1$ | $n_2$ | $CO_2A$ |
| --- | --- | --- | --- | --- | --- | --- | --- |
| " | 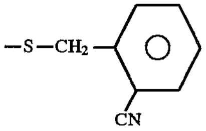 | " | " | | | | |
| " | 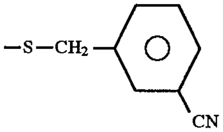 | " | " | | | | |
| 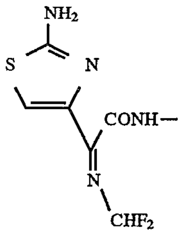 | 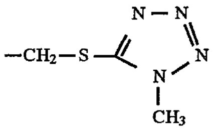 | 0 | $CO_2H$ | 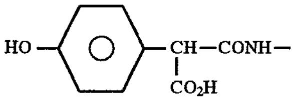 | 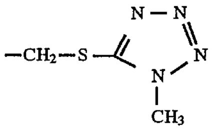 | 0 | $CO_2H$ |
| " | 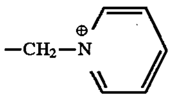 | " | $CO_2^{\ominus}$ | " | 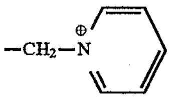 | " | $CO_2^{\ominus}$ |
| " | 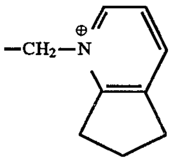 | " | " | " | 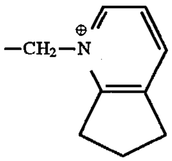 | " | " |
| " | 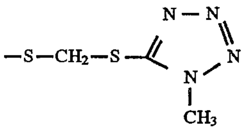 | " | $CO_2H$ | " | 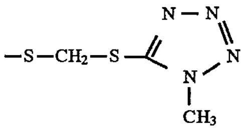 | " | $CO_2H$ |

-continued
| R | $R_1$ | $n_2$ $CO_2A$ | R | $R_1$ | $n_2$ $CO_2A$ |
|---|---|---|---|---|---|
| " | 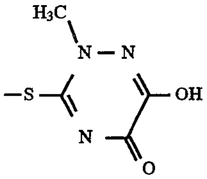 | " " | " | 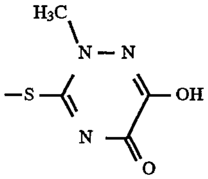 | " " |
| " | 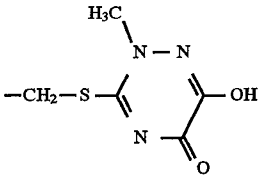 | " " | " | 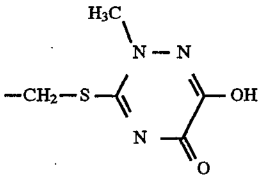 | " " |
| " | 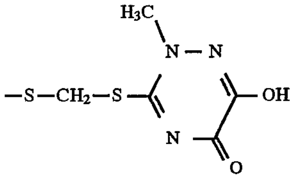 | " " | " | 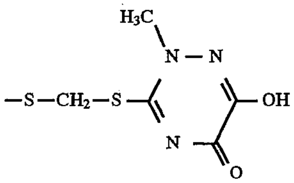 | " " |
| 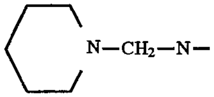 | 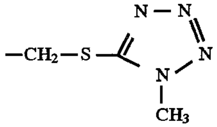 | " " | 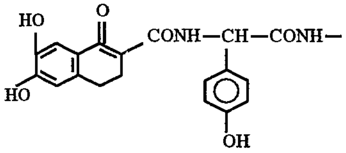 | 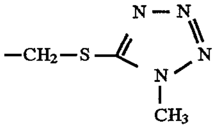 | " " |
| " | 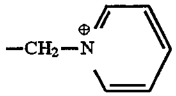 | " $CO_2^{\ominus}$ | " | 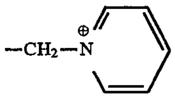 | " $CO_2^{\ominus}$ |

-continued
| R | $R_1$ | $n_2$ | $CO_2A$ | R | $R_1$ | $n_2$ | $CO_2A$ |
|---|---|---|---|---|---|---|---|
| 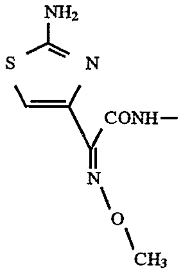 | 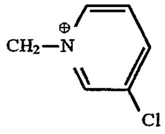 | 0 | $CO_2^{\ominus}$ | 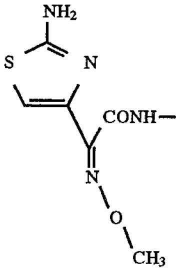 | 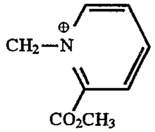 | 0 | $CO_2^{\ominus}$ |
| " | 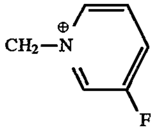 | " | " | " | 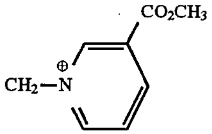 | " | " |
| " | 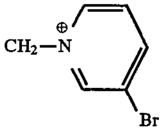 | " | " | " | 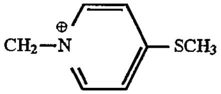 | " | " |
| " | 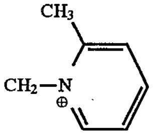 | " | " | " | 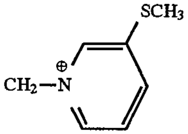 | " | " |
| " | 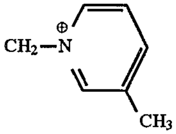 | " | " | " | 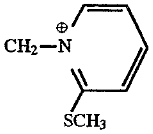 | " | " |
| " | 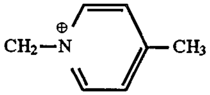 | " | " | " | 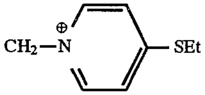 | " | " |

-continued
| R | $R_1$ | $n_2$ | $CO_2A$ | R | $R_1$ | $n_2$ | $CO_2A$ |
|---|---|---|---|---|---|---|---|
| " | 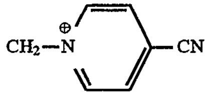 | " | " | " | 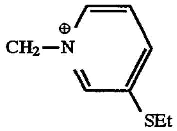 | " | " |
| " | 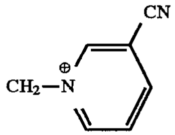 | " | " | " | 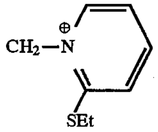 | " | " |
| " | 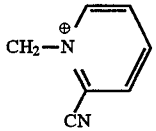 | " | " | " | 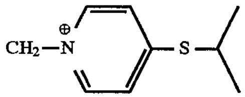 | " | " |
| " | 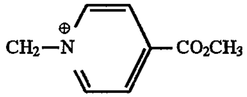 | " | " | " | 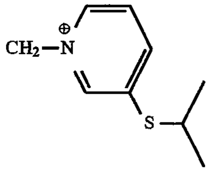 | " | " |
| 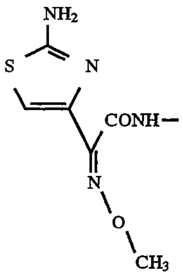 | 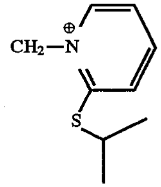 | 0 | $CO_2^{\ominus}$ | 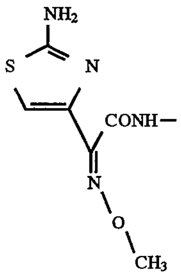 | 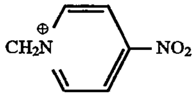 | 0 | $CO_2^{\ominus}$ |
| " | 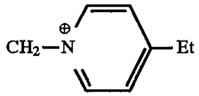 | " | " | " | 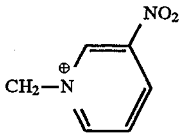 | " | " |

-continued
| R | $R_1$ | $n_2$ | $CO_2A$ | R | $R_1$ | $n_2$ | $CO_2A$ |
|---|---|---|---|---|---|---|---|
| " | 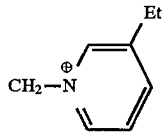 | " | " | " | 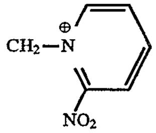 | " | " |
| " | 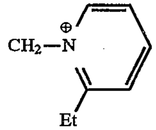 | " | " | " | 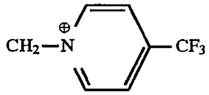 | " | " |
| " | 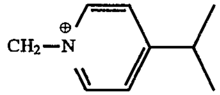 | " | " | " | 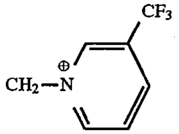 | " | " |
| " | 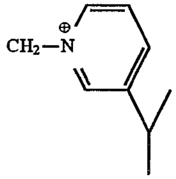 | " | " | " | 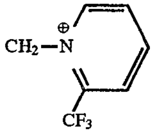 | " | " |
| " | 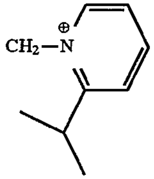 | " | " | " | 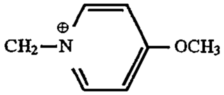 | " | " |
| " | 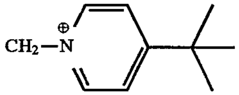 | " | " | " | 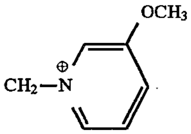 | " | " |

-continued
| R | $R_1$ | $n_2$ | $CO_2A$ | R | $R_1$ | $n_2$ | $CO_2A$ |
|---|---|---|---|---|---|---|---|
| " | 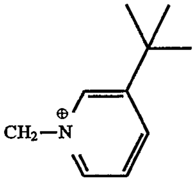 | " | " | " | 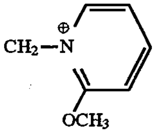 | " | " |
| " | 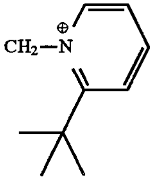 | " | " | " | 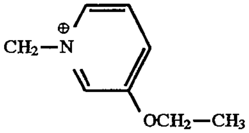 | " | " |
| 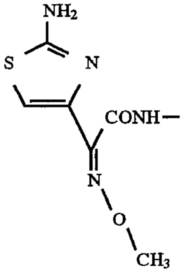 | 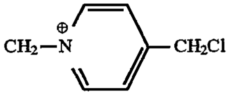 | 0 | $CO_2^{\ominus}$ | 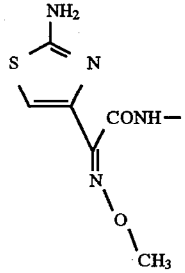 | 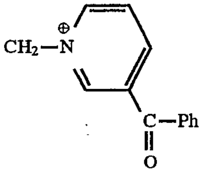 | 0 | $CO_2^{\ominus}$ |
| " | 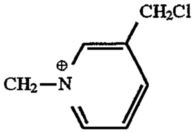 | " | " | " | 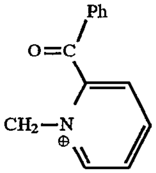 | " | " |
| " | 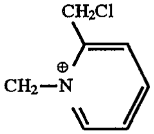 | " | " | " | 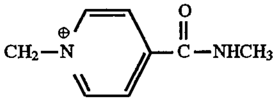 | " | " |

-continued
| R | R1 | n2 | CO2A | R | R1 | n2 | CO2A |
|---|---|---|---|---|---|---|---|
| " | 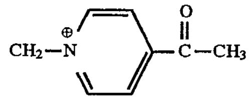 | " | " | " | 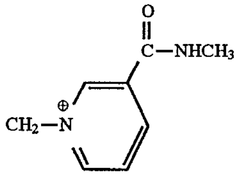 | " | " |
| " | 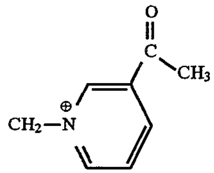 | " | " | " | 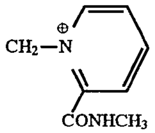 | " | " |
| " | 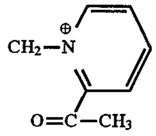 | " | " | " | 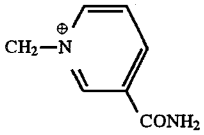 | " | " |
| " | 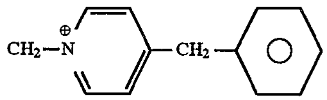 | " | " | " | 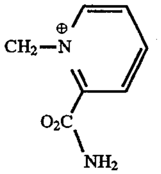 | " | " |
| " | 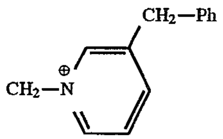 | " | " | " | 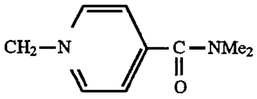 | " | " |
| " | 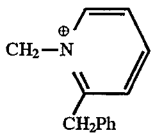 | " | " | " | 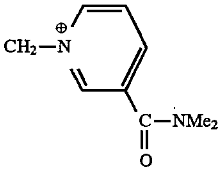 | " | " |

-continued
| R | R₁ | n₂ | CO₂A | R | R₁ | n₂ | CO₂A |
|---|---|---|---|---|---|---|---|
| " | 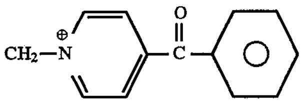 | " | " | " | 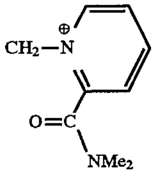 | " | " |
| 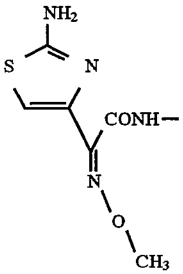 | 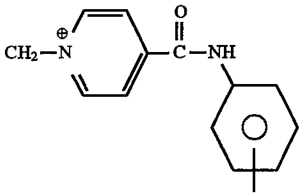 | 0 | $CO_2^{\ominus}$ | 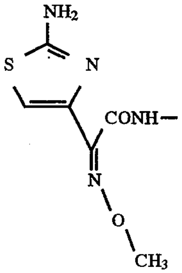 | 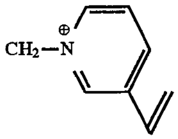 | 0 | $CO_2^{\ominus}$ |
| " | 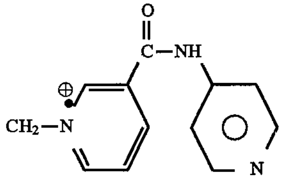 | " | " | " | 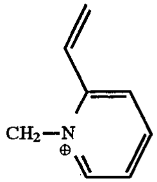 | " | " |
| " | 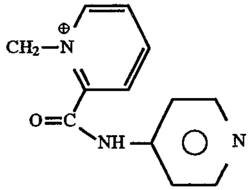 | " | " | " | 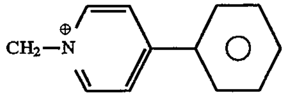 | " | " |
| " | 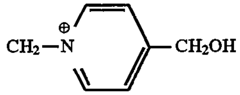 | " | " | " | 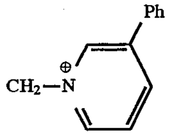 | " | " |

-continued
| R | $R_1$ | $n_2$ | $CO_2A$ | R | $R_1$ | $n_2$ | $CO_2A$ |
|---|---|---|---|---|---|---|---|
| " | 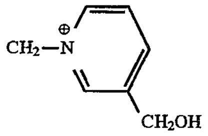 | " | " | " | 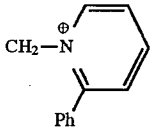 | " | " |
| " | 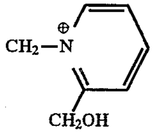 | " | " | " | 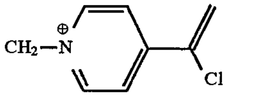 | " | " |
| " | 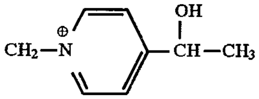 | " | " | " | 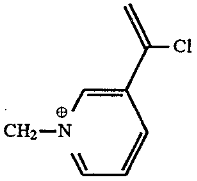 | " | " |
| " | 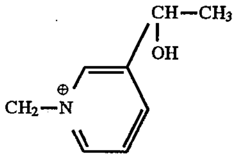 | " | " | " | 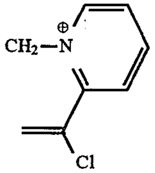 | " | " |
| " | 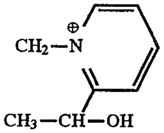 | " | " | " | 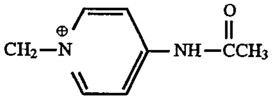 | " | " |
| " | 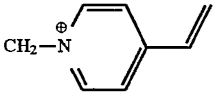 | " | " | " | 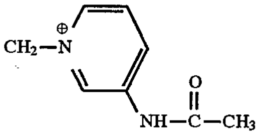 | " | " |

-continued
| R | R1 | n2 CO2A | R | R1 | n2 CO2A |
|---|---|---|---|---|---|
| 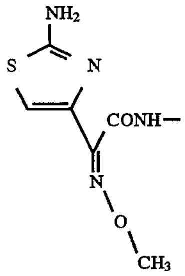 | 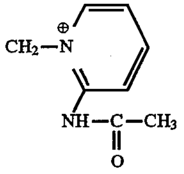 | 0 $CO_2^{\ominus}$ | 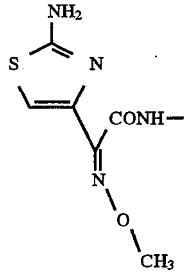 | 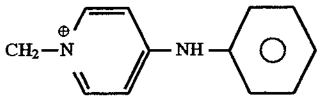 | 0 $CO_2^{\ominus}$ |
| " | 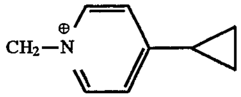 | " " | " | 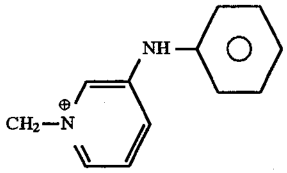 | " " |
| " | 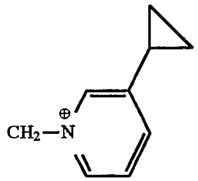 | " " | " | 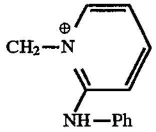 | " " |
| " | 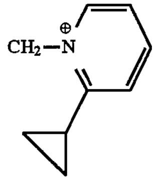 | " " | " | 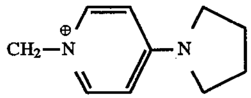 | " " |
| " | 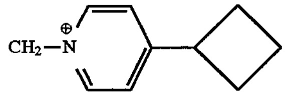 | " " | " | 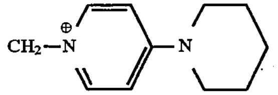 | " " |

-continued
| R | $R_1$ | $n_2$ | $CO_2A$ | R | $R_1$ | $n_2$ | $CO_2A$ |
|---|---|---|---|---|---|---|---|
| " | 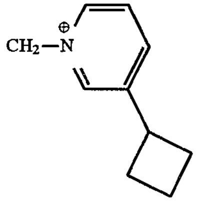 | " | " | " | 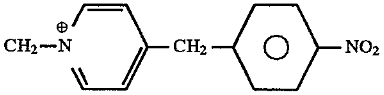 | " | " |
| " | 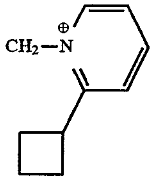 | " | " | " | 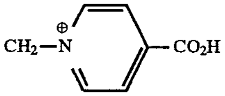 | " | " |
| " | 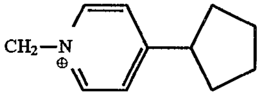 | " | " | " | 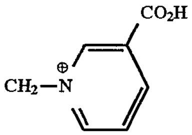 | " | " |
| " | 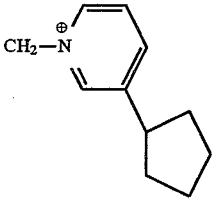 | " | " | " | 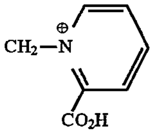 | " | " |
| " | 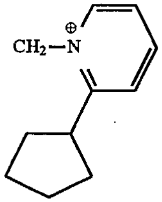 | " | " | " | 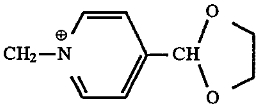 | " | " |

-continued
| R | $R_1$ | $n_2$ | $CO_2A$ | R | $R_1$ | $n_2$ | $CO_2A$ |
|---|---|---|---|---|---|---|---|
| 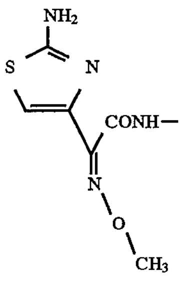 | 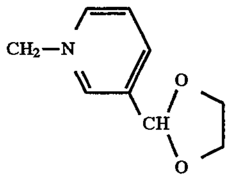 | 0 | $CO_2^{\ominus}$ | 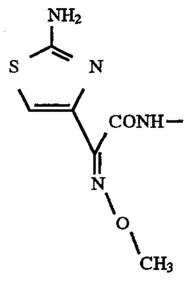 | 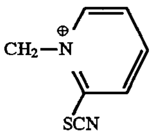 | 0 | $CO_2^{\ominus}$ |
| " | 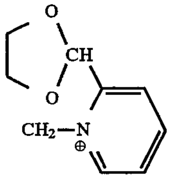 | " | " | " | 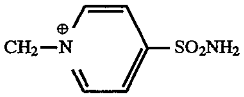 | " | " |
| " | 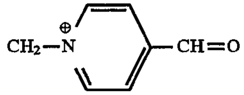 | " | " | " | 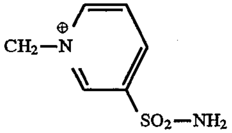 | " | " |
| " | 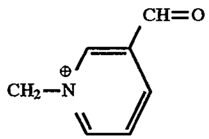 | " | " | " | 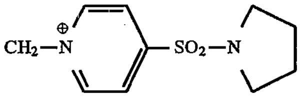 | " | " |
| " | 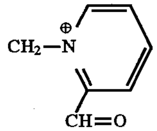 | " | " | " | 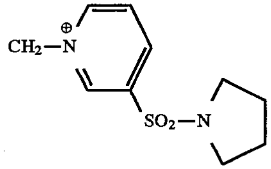 | " | " |
| " | 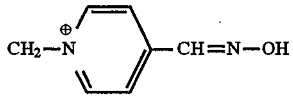 | " | " | " | 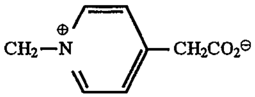 | " | " |

-continued
| R | $R_1$ | $n_2$ | $CO_2A$ | R | $R_1$ | $n_2$ | $CO_2A$ |
|---|---|---|---|---|---|---|---|
| " | 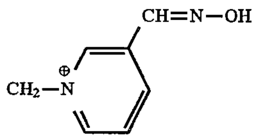 | " | " | " | 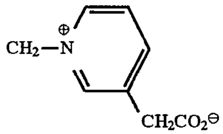 | " | " |
| " | 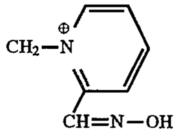 | " | " | " | 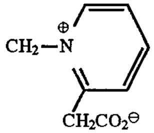 | " | " |
| " | 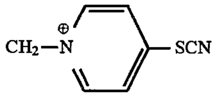 | " | " | " | 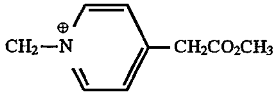 | " | " |
| " | 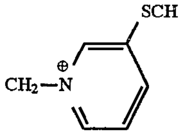 | " | " | " | 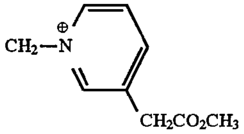 | " | " |
| 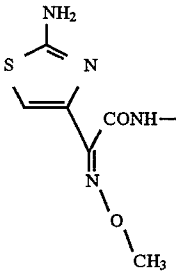 | 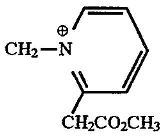 | 0 | $CO_2^{\ominus}$ | 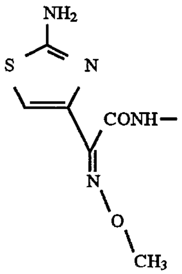 | 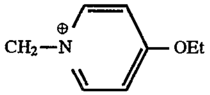 | 0 | $CO_2^{\ominus}$ |
| " | 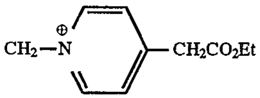 | " | " | " | 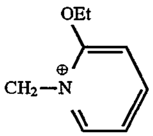 | " | " |

-continued
| R | $R_1$ | $n_2$ | $CO_2A$ | R | $R_1$ | $n_2$ | $CO_2A$ |
|---|---|---|---|---|---|---|---|
| " | 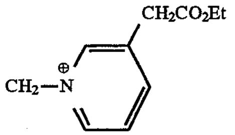 | " | " | " | 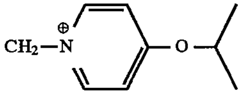 | " | " |
| " | 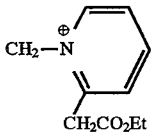 | " | " | " | 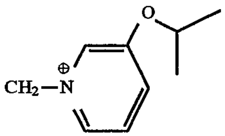 | " | " |
| " | 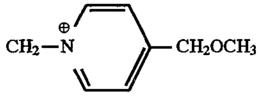 | " | " | " | 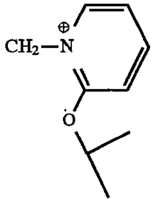 | " | " |
| " | 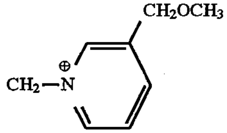 | " | " | " | 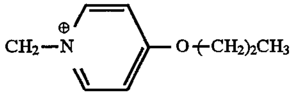 | " | " |
| " | 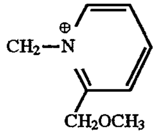 | " | " | " | 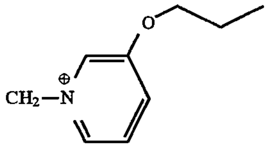 | " | " |
| " | 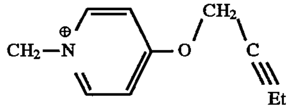 | " | " | " | 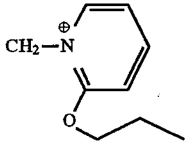 | " | " |

-continued
| R | $R_1$ | $n_2$ | $CO_2A$ | R | $R_1$ | $n_2$ | $CO_2A$ |
|---|---|---|---|---|---|---|---|
| " | 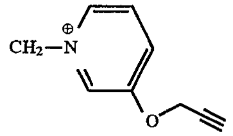 | " | " | " | 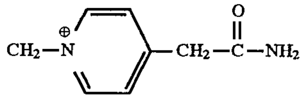 | " | " |
| " | 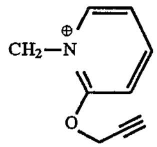 | " | " | " | 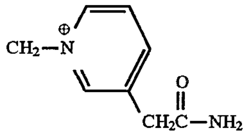 | " | " |
| 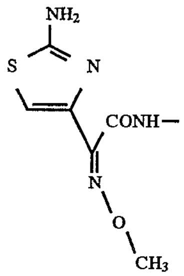 | 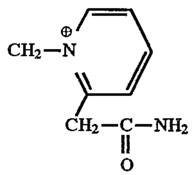 | 0 | $CO_2^{\ominus}$ | 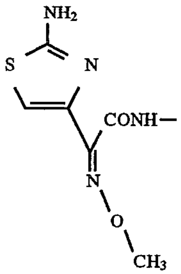 | 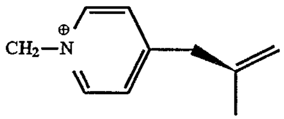 | 0 | $CO_2^{\ominus}$ |
| " | 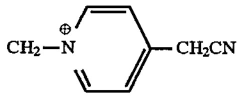 | " | " | " | 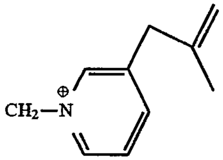 | " | " |
| " | 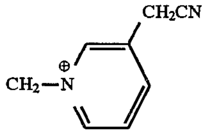 | " | " | " | 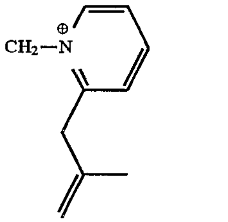 | " | " |

-continued
| R | $R_1$ | $n_2$ | $CO_2A$ | R | $R_1$ | $n_2$ | $CO_2A$ |
|---|---|---|---|---|---|---|---|
| " | 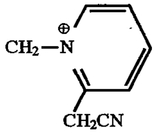 | " | " | " | 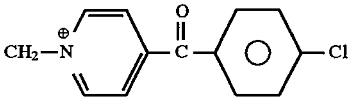 | " | " |
| " | 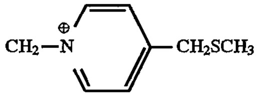 | " | " | " | 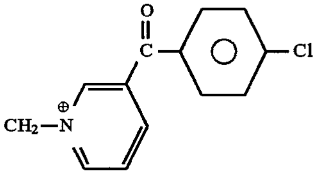 | " | " |
| " | 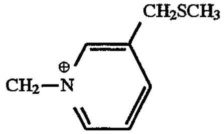 | " | " | " | 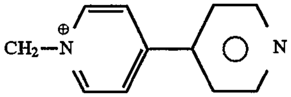 | " | " |
| " | 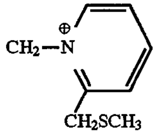 | " | " | " | 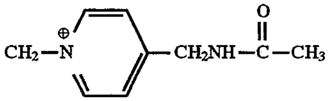 | " | " |
| " | 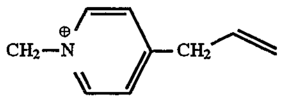 | " | " | " | 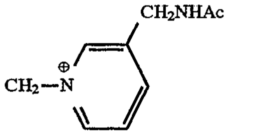 | " | " |
| " | 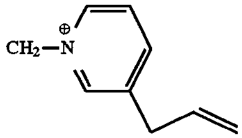 | " | " | " | 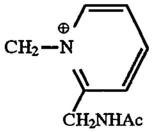 | " | " |

-continued
| R | $R_1$ | $n_2$ | $CO_2A$ | R | $R_1$ | $n_2$ | $CO_2A$ |
|---|---|---|---|---|---|---|---|
| " | 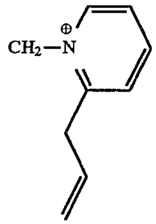 | " | " | " | 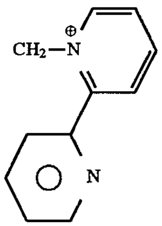 | " | " |
| 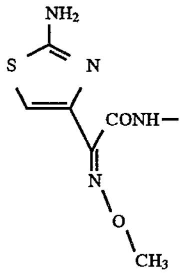 | 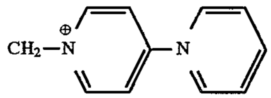 | 0 | $CO_2^{\ominus}$ | 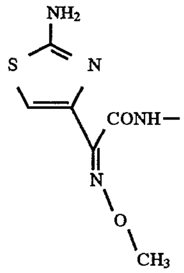 | 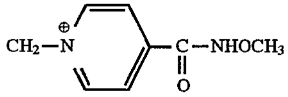 | 0 | $CO_2^{\ominus}$ |
| " | 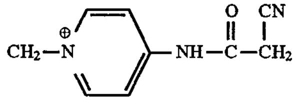 | " | " | " | 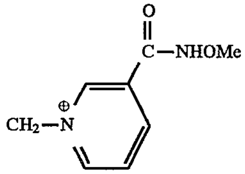 | " | " |
| " | 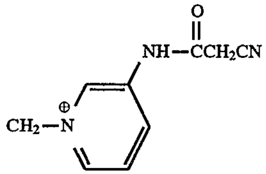 | " | " | " | 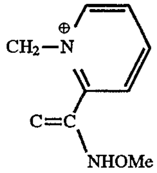 | " | " |
| " | 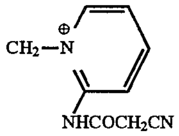 | " | " | " | 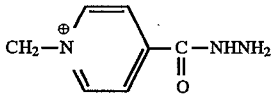 | " | " |

-continued
| R | $R_1$ | $n_2$ | $CO_2A$ | R | $R_1$ | $n_2$ | $CO_2A$ |
|---|---|---|---|---|---|---|---|
| " | 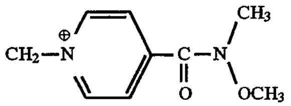 | " | " | " | 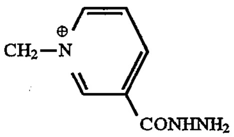 | " | " |
| " | 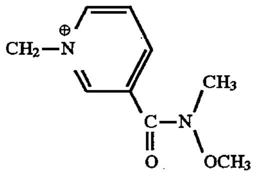 | " | " | " | 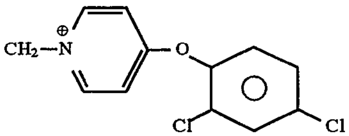 | " | " |
| " | 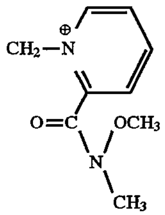 | " | " | " | 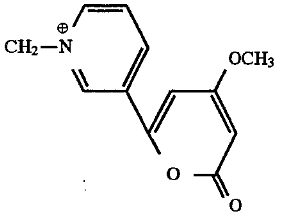 | " | " |
| " | 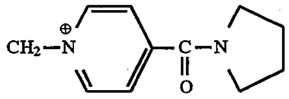 | " | " | " | 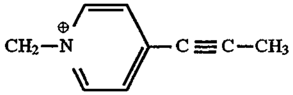 | " | " |
| " | 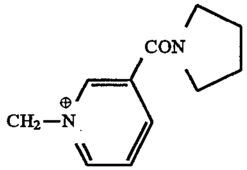 | " | " | " | 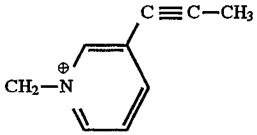 | " | " |
| " | 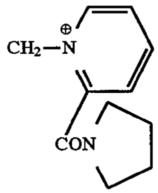 | " | " | " | 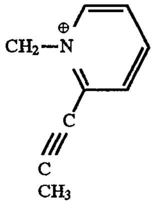 | " | " |

-continued
| R | $R_1$ | $n_2$ | $CO_2A$ | R | $R_1$ | $n_2$ | $CO_2A$ |
|---|---|---|---|---|---|---|---|
| 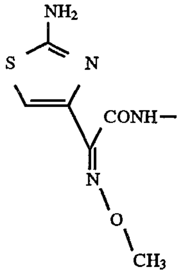 | 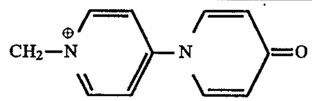 | 0 | $CO_2^{\ominus}$ | 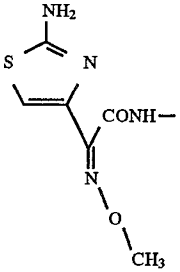 | 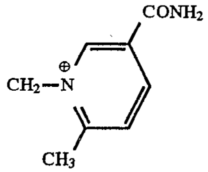 | 0 | $CO_2^{\ominus}$ |
| " | 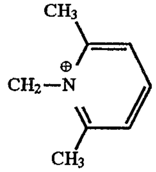 | " | " | " | 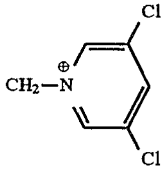 | " | " |
| " | 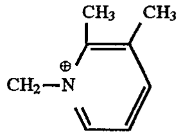 | " | " | " | 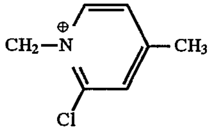 | " | " |
| " | 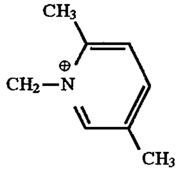 | " | " | " | 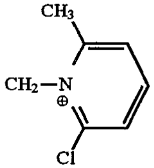 | " | " |
| " | 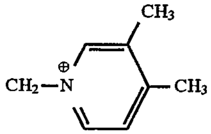 | " | " | " | 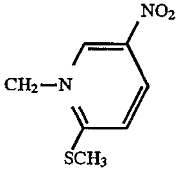 | " | " |

-continued
| R | $R_1$ | $n_2$ | $CO_2A$ | R | $R_1$ | $n_2$ | $CO_2A$ |
|---|---|---|---|---|---|---|---|
| " | 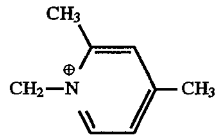 | " | " | " | 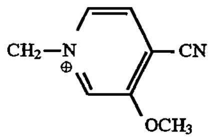 | " | " |
| " | 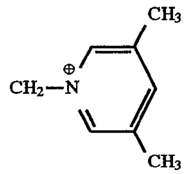 | " | " | " | 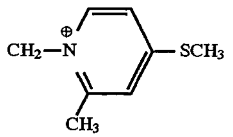 | " | " |
| " | 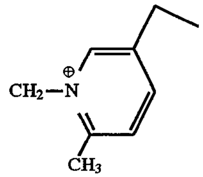 | " | " | " | 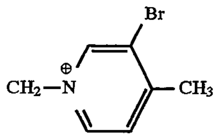 | " | " |
| " | 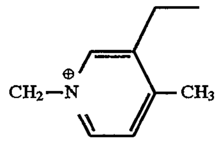 | " | " | " | 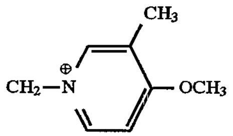 | " | " |
| " | 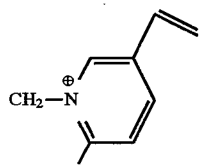 | " | " | " | 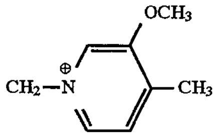 | " | " |

-continued
| R | $R_1$ | $n_2$ | $CO_2A$ | R | $R_1$ | $n_2$ | $CO_2A$ |
|---|---|---|---|---|---|---|---|
| 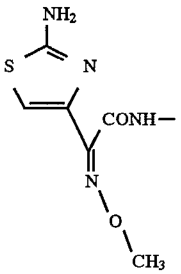 | 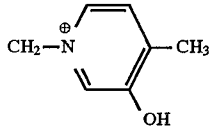 | 0 | $CO_2^{\ominus}$ | 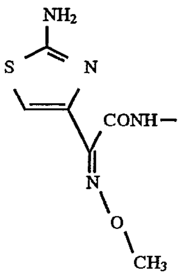 | 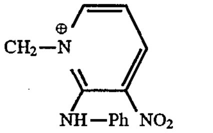 | 0 | $CO_2^{\ominus}$ |
| " | 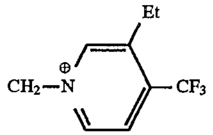 | " | " | " | 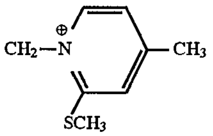 | " | " |
| " | 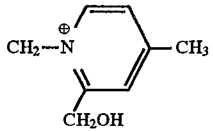 | " | " | " | 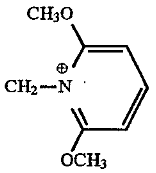 | " | " |
| " | 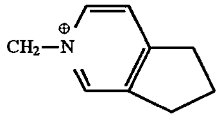 | " | " | " | 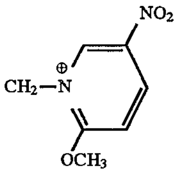 | " | " |
| " | 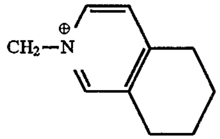 | " | " | " | 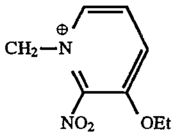 | " | " |

-continued
| R | $R_1$ | $n_2$ | $CO_2A$ | R | $R_1$ | $n_2$ | $CO_2A$ |
|---|---|---|---|---|---|---|---|
| " | 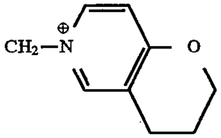 | " | " | " | 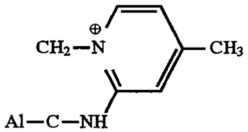 | " | " |
| " | 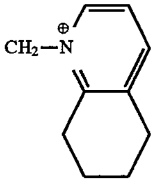 | " | " | " | 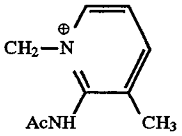 | " | " |
| " | 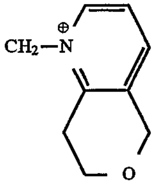 | " | " | " | 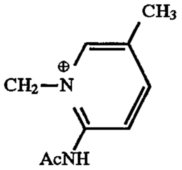 | " | " |
| " | 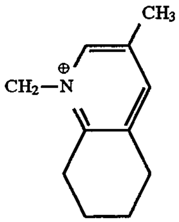 | " | " | " | 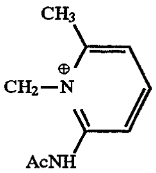 | " | " |
| " | 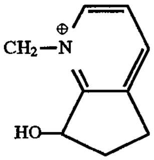 | " | " | " | 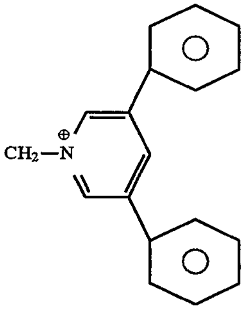 | " | " |

-continued
| R | $R_1$ | $n_2$ | $CO_2A$ | R | $R_1$ | $n_2$ | $CO_2A$ |
| --- | --- | --- | --- | --- | --- | --- | --- |
| 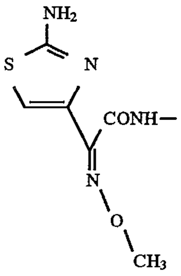 | 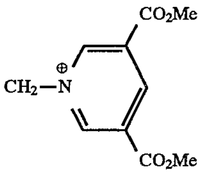 | 0 | $CO_2^{\ominus}$ | 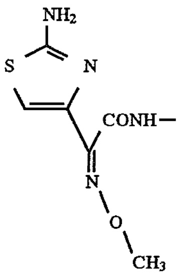 | 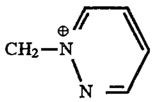 | 0 | $CO_2^{\ominus}$ |
| " | 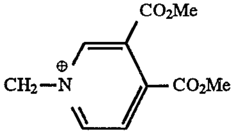 | " | " | " | 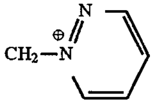 | " | " |
| " | 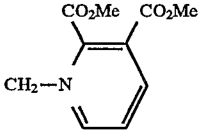 | " | " | " | 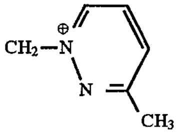 | " | " |
| " | 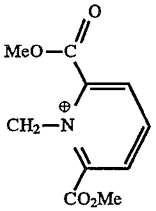 | " | " | " | 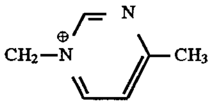 | " | " |
| " | 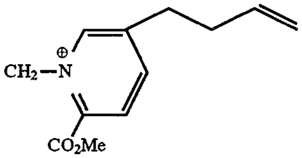 | " | " | " | 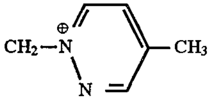 | " | " |

-continued
| R | $R_1$ | $n_2$ $CO_2A$ | R | $R_1$ | $n_2$ $CO_2A$ |
|---|---|---|---|---|---|
| " | 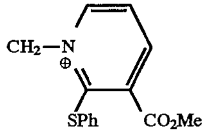 | " " | " | 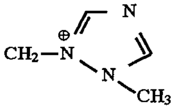 | " " |
| " | 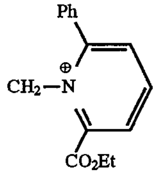 | " " | " | 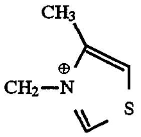 | " " |
| " | 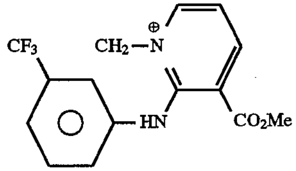 | " " | " | 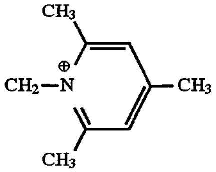 | " " |
| " | 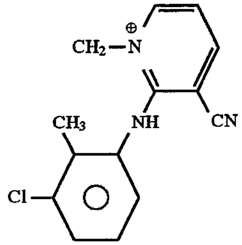 | " " | " | 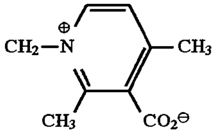 | " " |
| " | 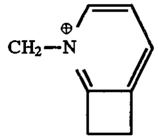 | " " | " | 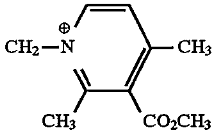 | " " |

-continued
| R | $R_1$ | $n_2$ | $CO_2A$ | R | $R_1$ | $n_2$ | $CO_2A$ |
|---|---|---|---|---|---|---|---|
| 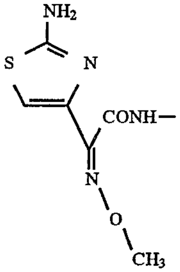 | 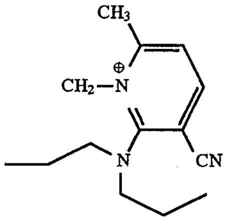 | 0 | $CO_2^{\ominus}$ | 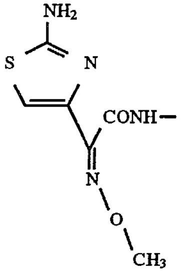 | 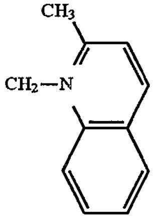 | 0 | $CO_2^{\ominus}$ |
| " | 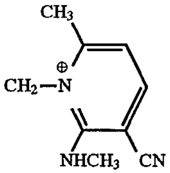 | " | " | " | 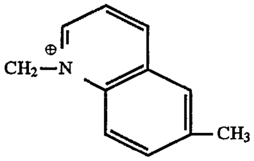 | " | " |
| " | 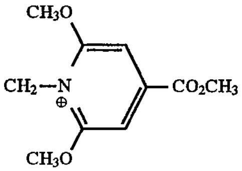 | " | " | " | 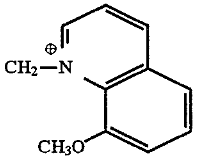 | " | " |
| " | 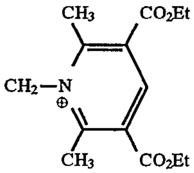 | " | " | " | 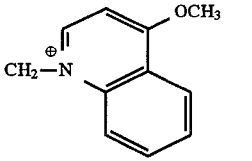 | " | " |
| " | 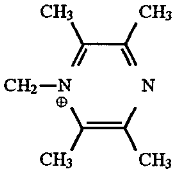 | " | " | " | 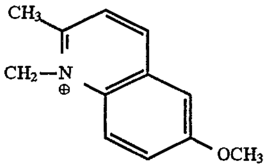 | " | " |

-continued
| R | $R_1$ | $n_2$ | $CO_2A$ | R | $R_1$ | $n_2$ | $CO_2A$ |
|---|---|---|---|---|---|---|---|
| " | 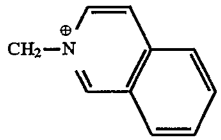 | " | " | " | 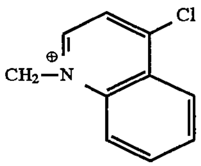 | " | " |
| " | 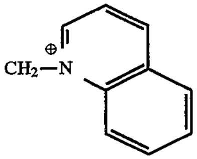 | " | " | " | 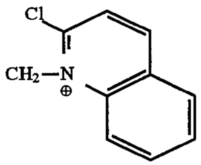 | " | " |
| " | 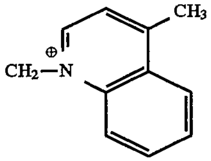 | " | " | " | 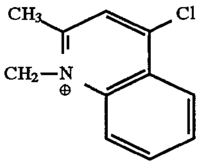 | " | " |
| " | 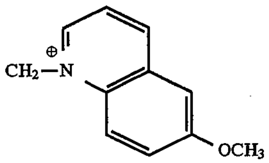 | " | " | " | 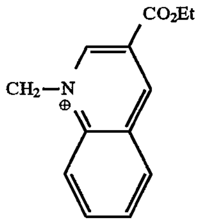 | " | " |
| " | 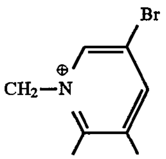 | " | " | " | 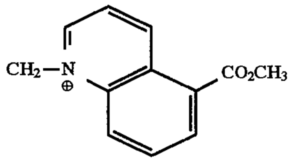 | " | " |

-continued
| R | $R_1$ | $n_2$ | $CO_2A$ | R | $R_1$ | $n_2$ | $CO_2A$ |
|---|---|---|---|---|---|---|---|
| 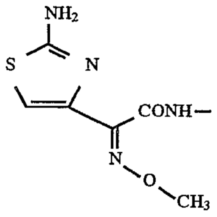 | 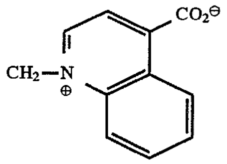 | 0 | $CO_2^{\ominus}$ | 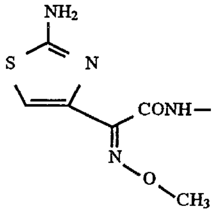 | 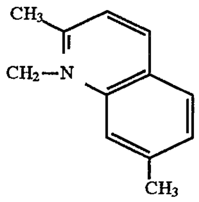 | 0 | $CO_2^{\ominus}$ |
| " | 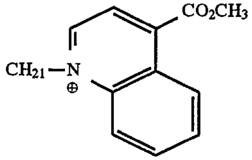 | " | " | " | 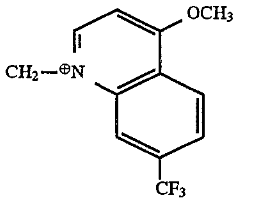 | " | " |
| " | 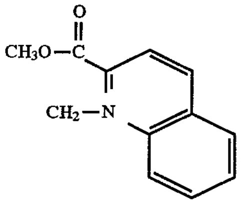 | " | " | " | 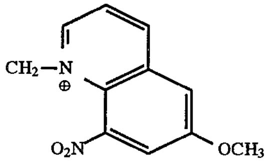 | " | " |
| " | 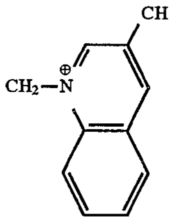 | " | " | " | 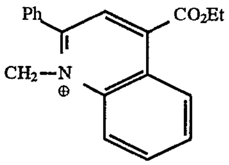 | " | " |
| " | 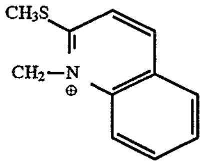 | " | " | " | 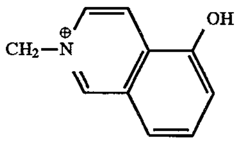 | " | " |

-continued
| R | $R_1$ | $n_2$ | $CO_2A$ | R | $R_1$ | $n_2$ | $CO_2A$ |
|---|---|---|---|---|---|---|---|
| " | 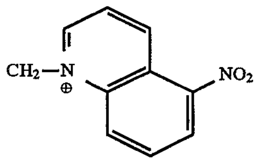 | " | " | " | 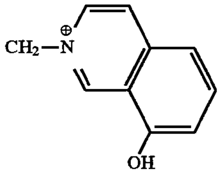 | " | " |
| " | 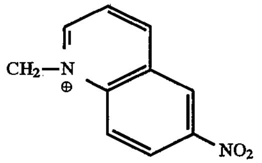 | " | " | " | 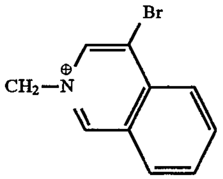 | " | " |
| " | 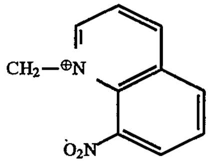 | " | " | " | 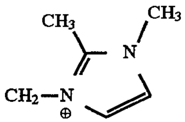 | " | " |
| " | 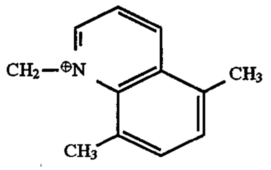 | " | " | " | 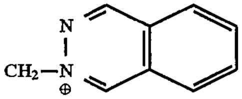 | " | " |
| " | 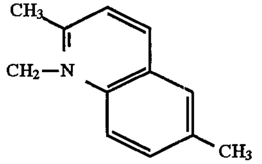 | " | " | " | 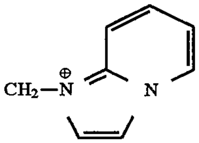 | " | " |

-continued
| R | $R_1$ | $n_2$ | $CO_2A$ | R | $R_1$ | $n_2$ | $CO_2A$ |
|---|---|---|---|---|---|---|---|
| 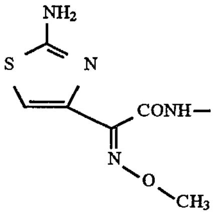 | 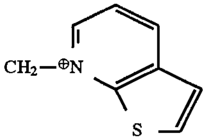 | 0 | $CO_2^{\ominus}$ | 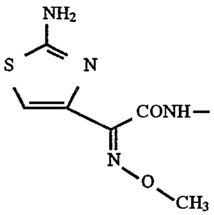 | 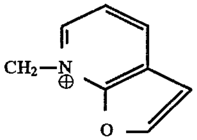 | 0 | $CO_2^{\ominus}$ |
| " | 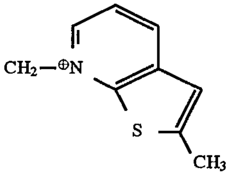 | " | " | " | 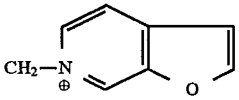 | " | " |
| " | 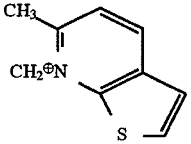 | " | " | " | 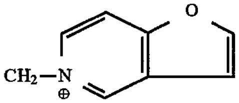 | " | " |
| " | 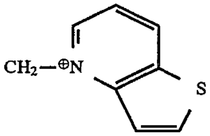 | " | " | " | 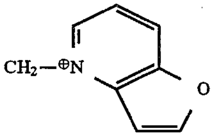 | " | " |
| " | 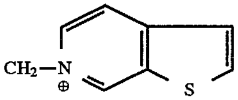 | " | " | " | 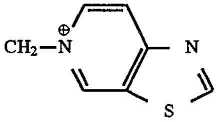 | " | " |
| " | 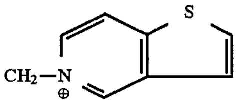 | " | " | " | 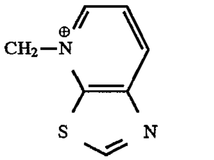 | " | " |

-continued
| R | $R_1$ | $n_2$ | $CO_2A$ | R | $R_1$ | $n_2$ | $CO_2A$ |
|---|---|---|---|---|---|---|---|
| " | 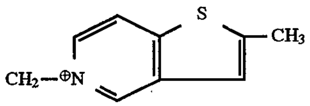 | " | " | " | 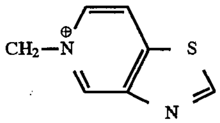 | " | " |
| " | 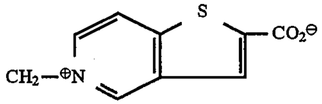 | " | " | " | 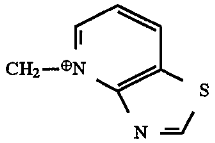 | " | " |
| " | 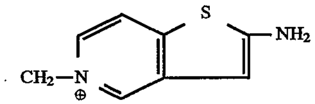 | " | " | " | 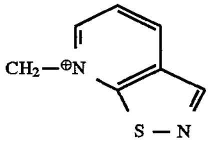 | " | " |
| " | 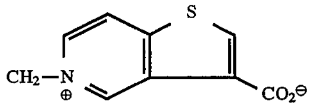 | " | " | " | 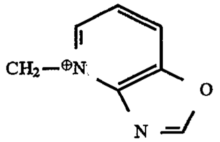 | " | " |
| 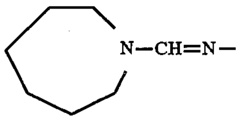 | 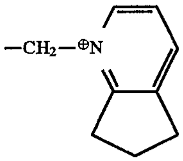 | 0 | $CO_2^{\ominus}$ | 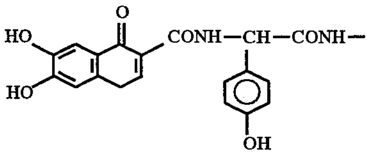 | 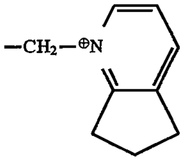 | 0 | $CO_2^{\ominus}$ |
| " | 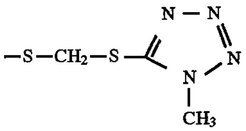 | " | $CO_2H$ | | 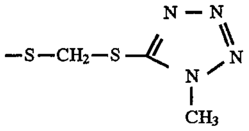 | " | $CO_2H$ |

-continued
| R | $R_1$ | $n_2$ | $CO_2A$ | R | $R_1$ | $n_2$ | $CO_2A$ |
|---|---|---|---|---|---|---|---|
| " | 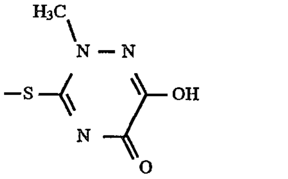 | " | " | | 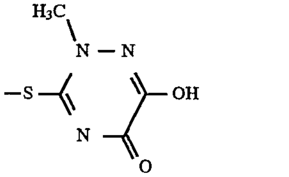 | " | " |
| " | 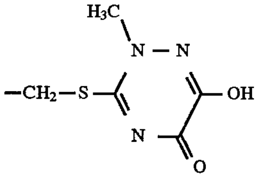 | " | " | | 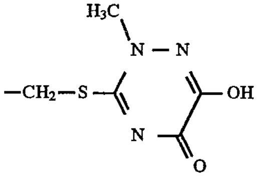 | " | " |
| " | 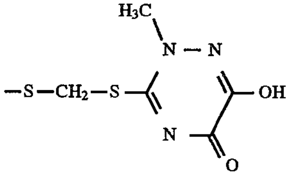 | " | " | | 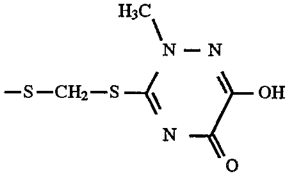 | " | " |
| 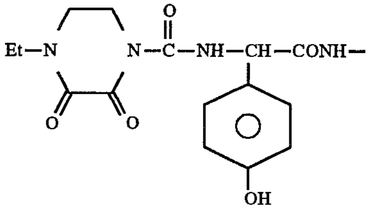 | 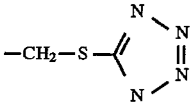 | " | " | 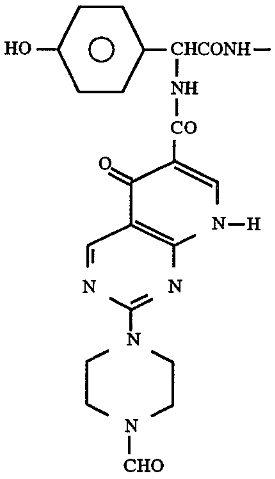 | 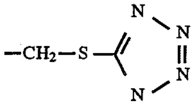 | " | " |

-continued
| R | $R_1$ | $n_2$ | $CO_2A$ | R | $R_1$ | $n_2$ | $CO_2A$ |
|---|---|---|---|---|---|---|---|
| " | 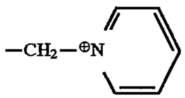 | " | $CO_2^{\ominus}$ | " | 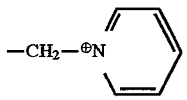 | " | $CO_2^{\ominus}$ |
| " | 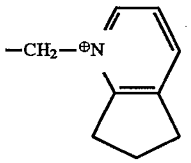 | " | " | " | 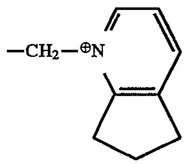 | " | " |
| " | 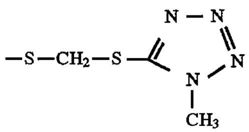 | " | $CO_2H$ | " | 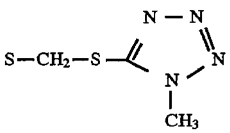 | " | $CO_2H$ |
| " | 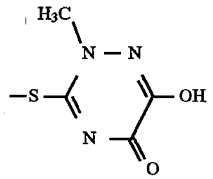 | " | " | " | 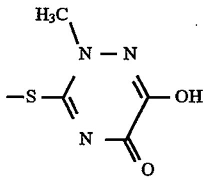 | " | " |
| 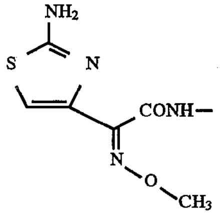 | 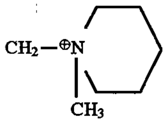 | 0 | $CO_2^{\ominus}$ | 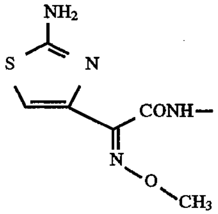 | $CH_2-ONO_2$ | 0 | $CO_2^{\ominus}$ |
| " | 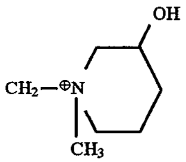 | " | " | " | $CH_2-NO_2$ | " | " |

-continued
| R | $R_1$ | $n_2$ | $CO_2A$ | R | $R_1$ | $n_2$ | $CO_2A$ |
|---|---|---|---|---|---|---|---|
| " | 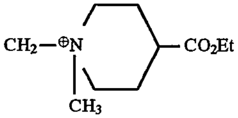 | " | " | " | $CH_2-SO_2CH_3$ | " | " |
| " | 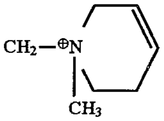 | " | " | " | 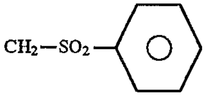 | " | " |
| " | 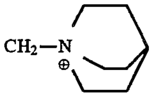 | " | " | " | 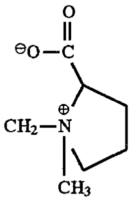 | " | " |
| " | 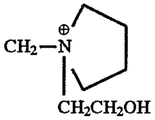 | " | " | " | 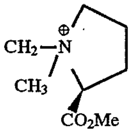 | " | " |
| " | 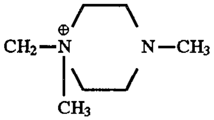 | " | " | " | 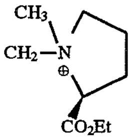 | " | " |
| " | 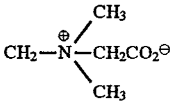 | " | " | " | 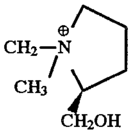 | " | " |
| " | 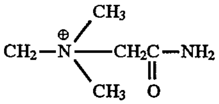 | " | " | " | 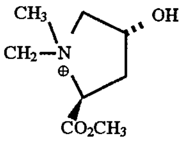 | " | " |

-continued
| R | $R_1$ | $n_2$ | $CO_2A$ | R | $R_1$ | $n_2$ | $CO_2A$ |
|---|---|---|---|---|---|---|---|
| " | 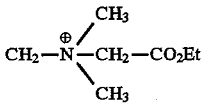 | " | " | " | 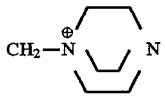 | " | " |
| 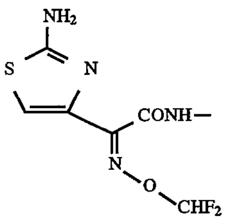 | 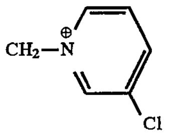 | 0 | $CO_2^{\ominus}$ | 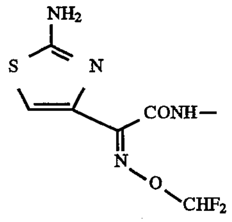 | 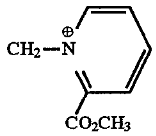 | 0 | $CO_2^{\ominus}$ |
| " | 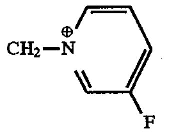 | " | " | " | 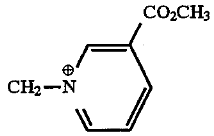 | " | " |
| " | 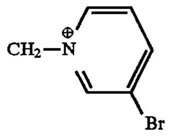 | " | " | " | 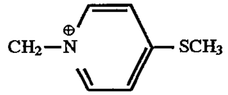 | " | " |
| " | 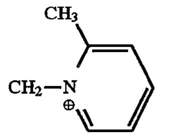 | " | " | " | 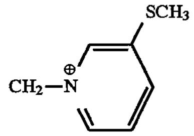 | " | " |
| " | 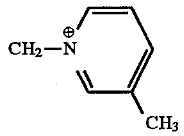 | " | " | " | 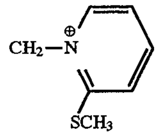 | " | " |
| " | 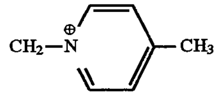 | " | " | " | 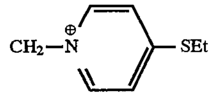 | " | " |

-continued
| R | $R_1$ | $n_2$ | $CO_2A$ | R | $R_1$ | $n_2$ | $CO_2A$ |
|---|---|---|---|---|---|---|---|
| " | 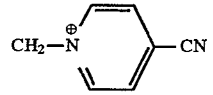 | " | " | " | 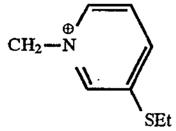 | " | " |
| " | 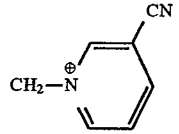 | " | " | " | 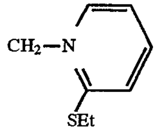 | " | " |
| " | 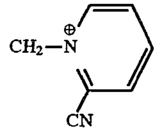 | " | " | " | 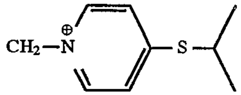 | " | " |
| " | 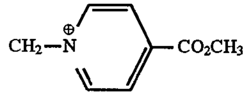 | " | " | " | 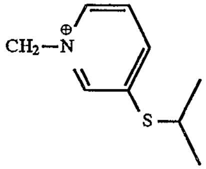 | " | " |
| 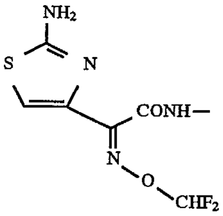 | 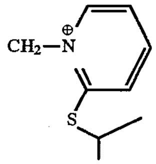 | 0 | $CO_2^{\ominus}$ | 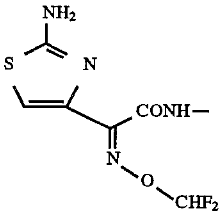 | 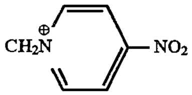 | 0 | $CO_2^{\ominus}$ |
| " | 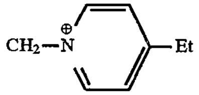 | " | " | " | 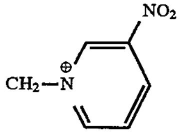 | " | " |

-continued
| R | $R_1$ | $n_2$ | $CO_2A$ | R | $R_1$ | $n_2$ | $CO_2A$ |
|---|---|---|---|---|---|---|---|
| " | 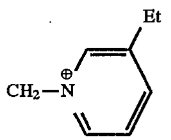 | " | " | " | 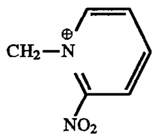 | " | " |
| " | 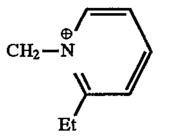 | " | " | " | 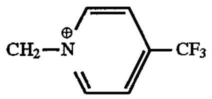 | " | " |
| " | 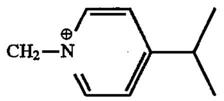 | " | " | " | 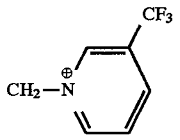 | " | " |
| " | 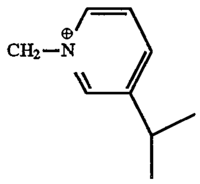 | " | " | " | 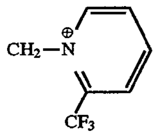 | " | " |
| " | 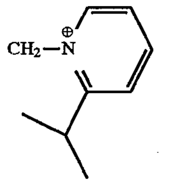 | " | " | " | 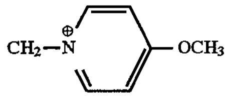 | " | " |
| " | 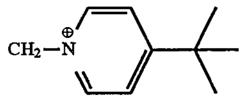 | " | " | " | 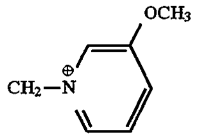 | " | " |

-continued
| R | $R_1$ | $n_2$ | $CO_2A$ | R | $R_1$ | $n_2$ | $CO_2A$ |
|---|---|---|---|---|---|---|---|
| " | 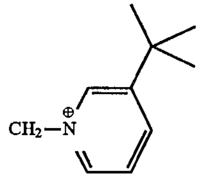 | " | " | " | 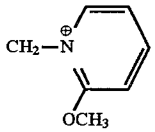 | " | " |
| " | 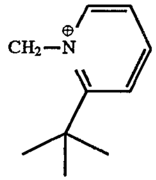 | " | " | " | 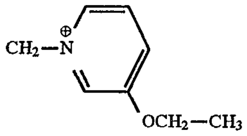 | " | " |
| 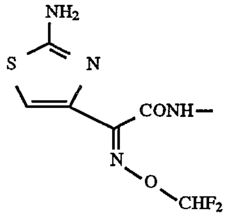 | 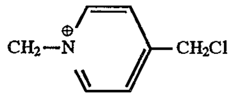 | 0 | $CO_2^{\ominus}$ | 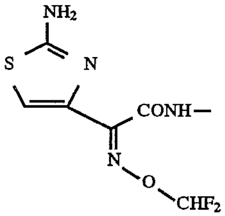 | 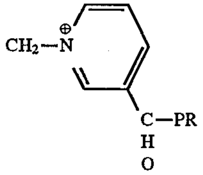 | 0 | $CO_2^{\ominus}$ |
| " | 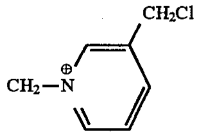 | " | " | " | 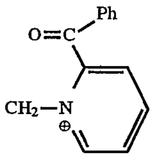 | " | " |
| " | 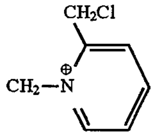 | " | " | " | 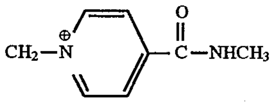 | " | " |

-continued
| R | $R_1$ | $n_2$ | $CO_2A$ | R | $R_1$ | $n_2$ | $CO_2A$ |
|---|---|---|---|---|---|---|---|
| " | 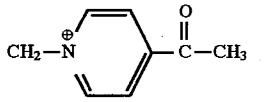 | " | " | " | 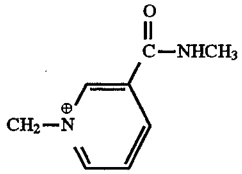 | " | " |
| " | 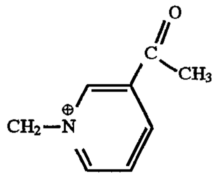 | " | " | " | 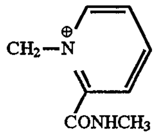 | " | " |
| " | 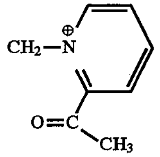 | " | " | " | 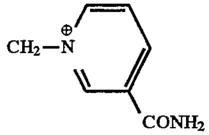 | " | " |
| " | 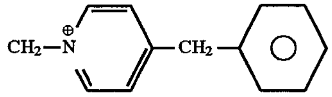 | " | " | " | 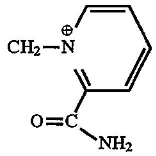 | " | " |
| " | 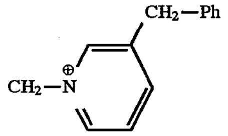 | " | " | " | 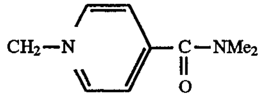 | " | " |
| " | 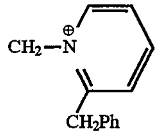 | " | " | " | 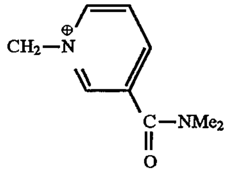 | " | " |

-continued
| R | $R_1$ | $n_2$ | $CO_2A$ | R | $R_1$ | $n_2$ | $CO_2A$ |
|---|---|---|---|---|---|---|---|
| " | 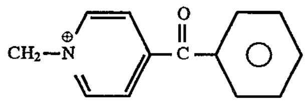 | " | " | " | 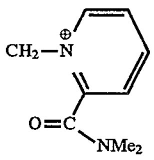 | " | " |
| 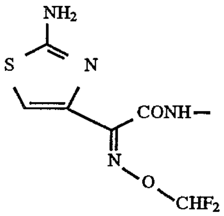 | 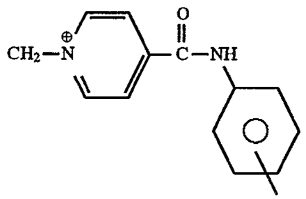 | 0 | $CO_2^{\ominus}$ | 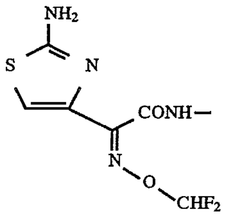 | 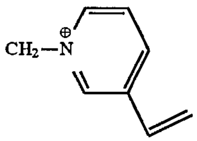 | 0 | $CO_2^{\ominus}$ |
| " | 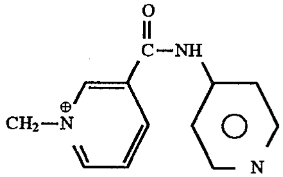 | " | " | " | 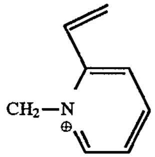 | " | " |
| " | 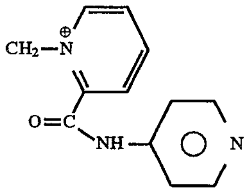 | " | " | " | 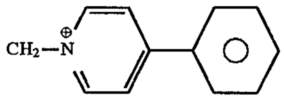 | " | " |
| " | 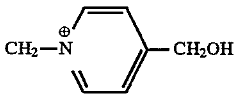 | " | " | " | 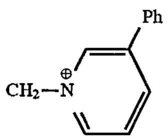 | " | " |
| " | 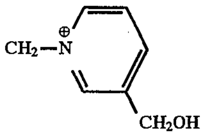 | " | " | " | 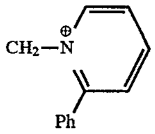 | " | " |

-continued
| R | $R_1$ | $n_2$ $CO_2A$ | R | $R_1$ | $n_2$ $CO_2A$ |
|---|---|---|---|---|---|
| " | 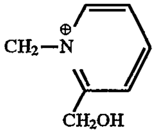 | " " | " | 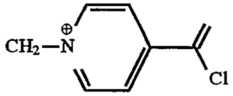 | " " |
| " | 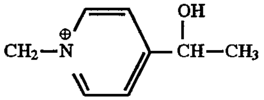 | " " | " | 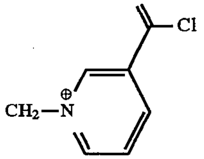 | " " |
| " | 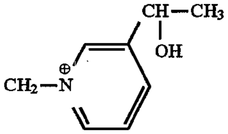 | " " | " | 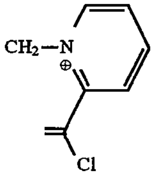 | " " |
| " | 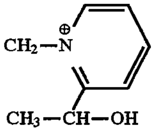 | " " | " | 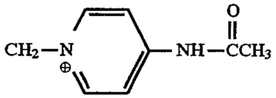 | " " |
| " | 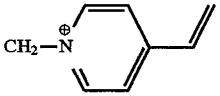 | " " | " | 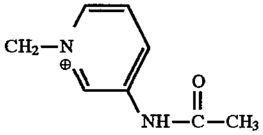 | " " |
| 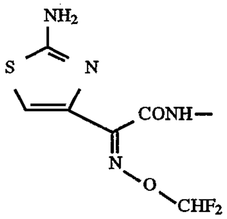 | 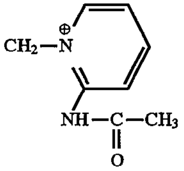 | 0 $CO_2^{\ominus}$ | 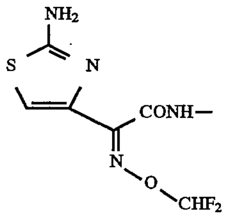 | 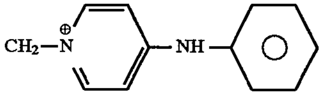 | 0 $CO_2^{\ominus}$ |

-continued
| R | $R_1$ | $n_2$ | $CO_2A$ | R | $R_1$ | $n_2$ | $CO_2A$ |
|---|---|---|---|---|---|---|---|
| " | 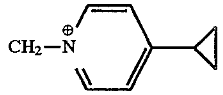 | " | " | " | 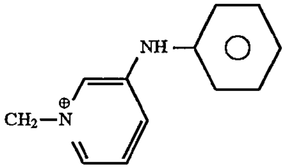 | " | " |
| " | 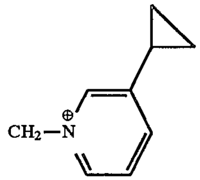 | " | " | " | 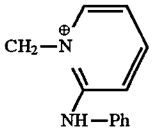 | " | " |
| " | 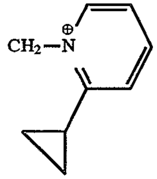 | " | " | " | 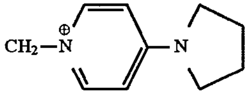 | " | " |
| " | 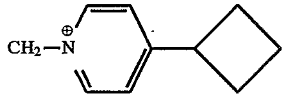 | " | " | " | 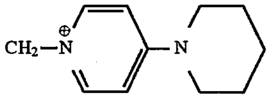 | " | " |
| " | 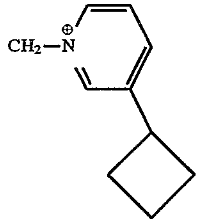 | " | " | " | 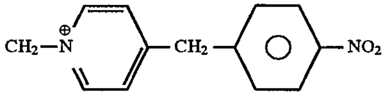 | " | " |

-continued
| R | $R_1$ | $n_2$ | $CO_2A$ | R | $R_1$ | $n_2$ | $CO_2A$ |
|---|---|---|---|---|---|---|---|
| " | 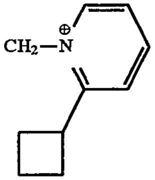 | " | " | " | 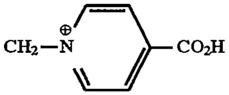 | " | " |
| " | 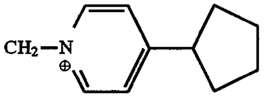 | " | " | " | 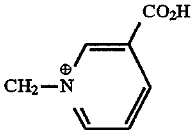 | " | " |
| " | 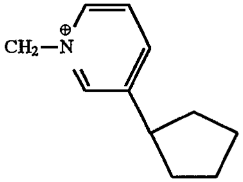 | " | " | " | 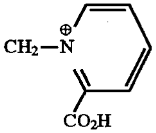 | " | " |
| " | 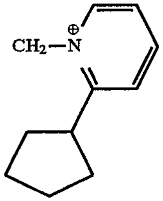 | " | " | " | 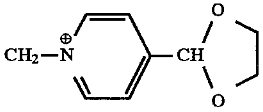 | " | " |
| 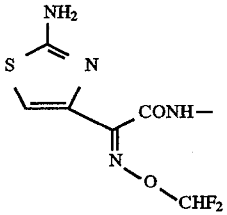 | 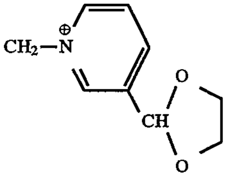 | 0 | $CO_2^{\ominus}$ | 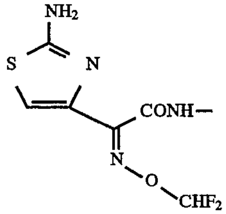 | 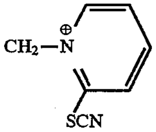 | 0 | $CO_2^{\ominus}$ |

-continued
| R | $R_1$ | $n_2$ | $CO_2A$ | R | $R_1$ | $n_2$ | $CO_2A$ |
|---|---|---|---|---|---|---|---|
| " | 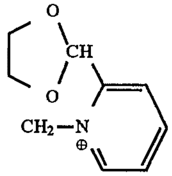 | " | " | " | 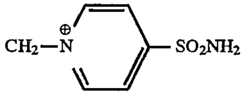 | " | " |
| " | 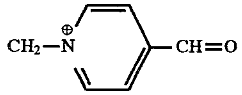 | " | " | " | 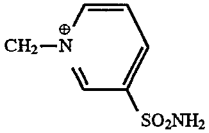 | " | " |
| " | 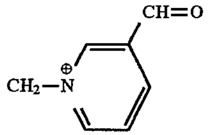 | " | " | " | 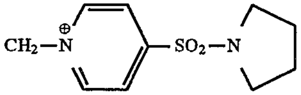 | " | " |
| " | 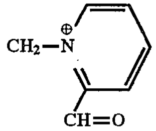 | " | " | " | 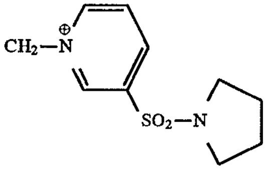 | " | " |
| " | 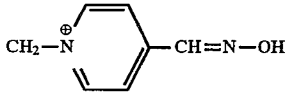 | " | " | " | 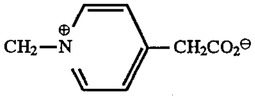 | " | " |
| " | 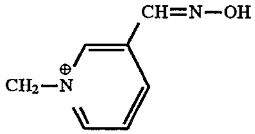 | " | " | " | 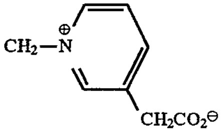 | " | " |
| " | 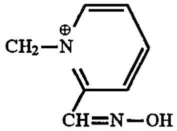 | " | " | " | 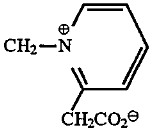 | " | " |

-continued
| R | $R_1$ | $n_2$ $CO_2A$ | R | $R_1$ | $n_2$ $CO_2A$ |
|---|---|---|---|---|---|
| " | 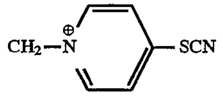 | " " | " | 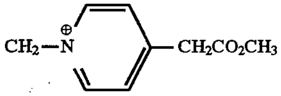 | " " |
| " | 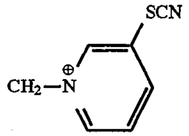 | " " | " | 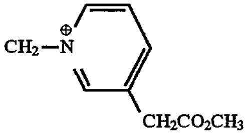 | " " |
| 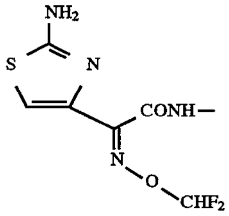 | 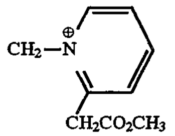 | 0 $CO_2^{\ominus}$ | 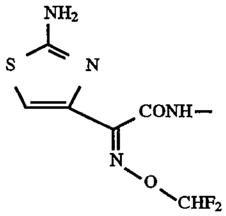 | 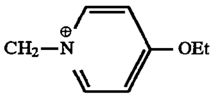 | 0 $CO_2^{\ominus}$ |
| " | 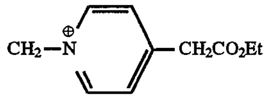 | " " | " | 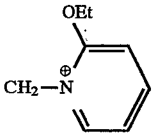 | " " |
| " | 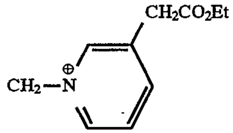 | " " | " | 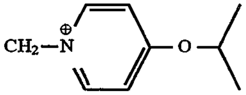 | " " |
| " | 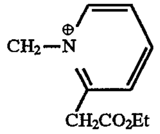 | " " | " | 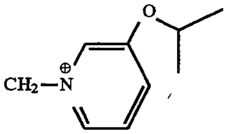 | " " |

-continued
| R | $R_1$ | $n_2$ | $CO_2A$ | R | $R_1$ | $n_2$ | $CO_2A$ |
|---|---|---|---|---|---|---|---|
| " | 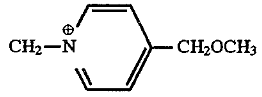 | " | " | " | 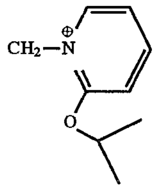 | " | " |
| " | 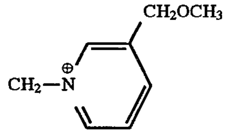 | " | " | " | 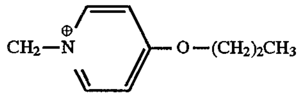 | " | " |
| " | 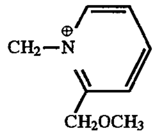 | " | " | " | 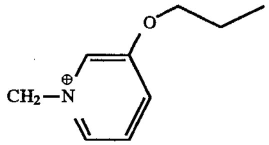 | " | " |
| " | 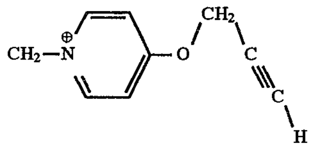 | " | " | " | 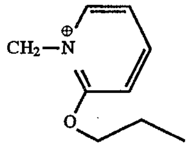 | " | " |
| " | 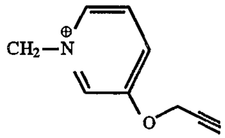 | " | " | " | 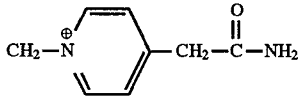 | " | " |
| " | 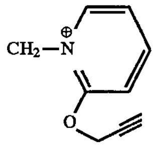 | " | " | " | 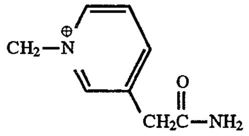 | " | " |

-continued
| R | $R_1$ | $n_2$ | $CO_2A$ | R | $R_1$ | $n_2$ | $CO_2A$ |
|---|---|---|---|---|---|---|---|
| 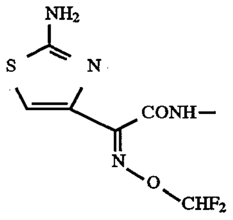 | 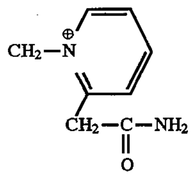 | 0 | $CO_2^{\ominus}$ | 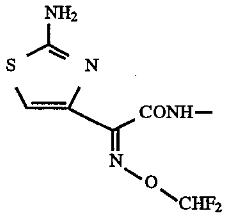 | 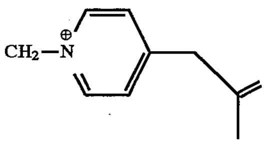 | 0 | $CO_2^{\ominus}$ |
| " | 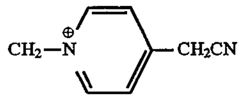 | " | " | " | 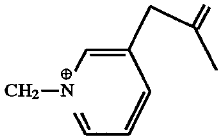 | " | " |
| " | 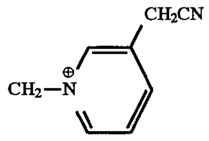 | " | " | " | 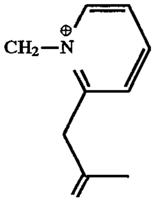 | " | " |
| " | 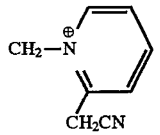 | " | " | " | 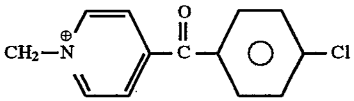 | " | " |
| " | 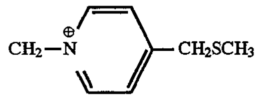 | " | " | " | 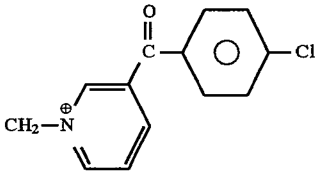 | " | " |
| " | 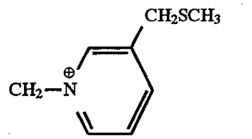 | " | " | " | 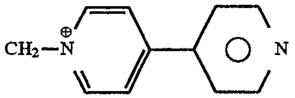 | " | " |

-continued
| R | $R_1$ | $n_2$ | $CO_2A$ | R | $R_1$ | $n_2$ | $CO_2A$ |
|---|---|---|---|---|---|---|---|
| " | 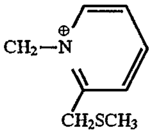 | " | " | " | 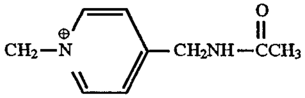 | " | " |
| " | 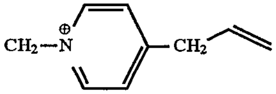 | " | " | " | 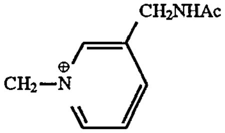 | " | " |
| " | 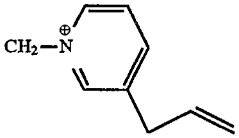 | " | " | " | 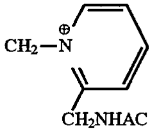 | " | " |
| " | 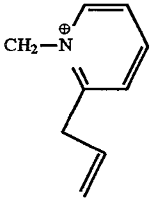 | " | " | " | 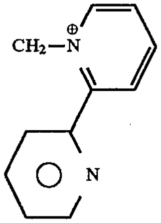 | " | " |
| 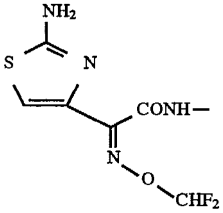 | 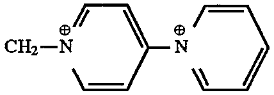 | 0 | $CO_2^{\ominus}$ | 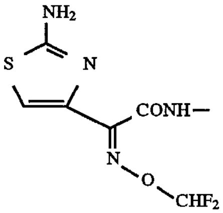 | 0 | | $CO_2^{\ominus}$ |
| " | 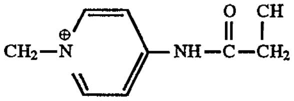 | " | " | " | 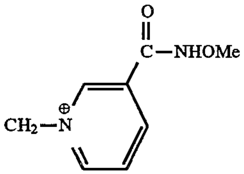 | " | " |

-continued
| R | $R_1$ | $n_2$ | $CO_2A$ | R | $R_1$ | $n_2$ | $CO_2A$ |
|---|---|---|---|---|---|---|---|
| " | 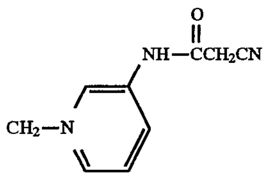 | " | " | " | 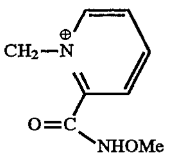 | " | " |
| " | 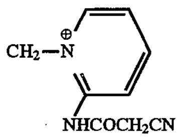 | " | " | " | 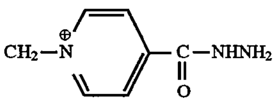 | " | " |
| " | 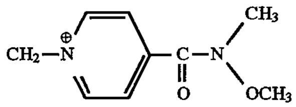 | " | " | " | 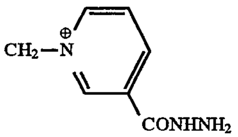 | " | " |
| " | 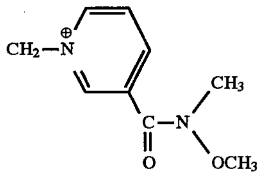 | " | " | " | 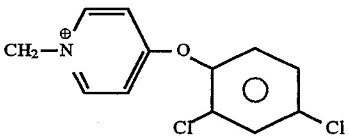 | " | " |
| " | 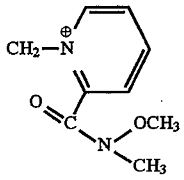 | " | " | " | 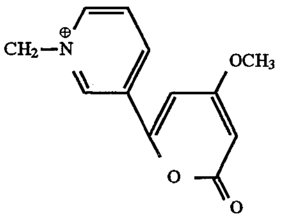 | " | " |
| " | 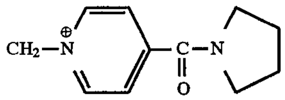 | " | " | " | 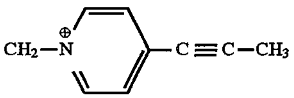 | " | " |

-continued
| R | $R_1$ | $n_2$ | $CO_2A$ | R | $R_1$ | $n_2$ | $CO_2A$ |
|---|---|---|---|---|---|---|---|
| " | 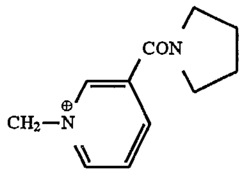 | " | " | " | 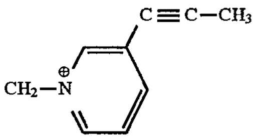 | " | " |
| " | 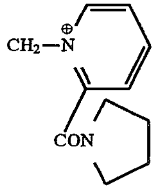 | " | " | " | 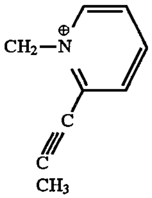 | " | " |
| 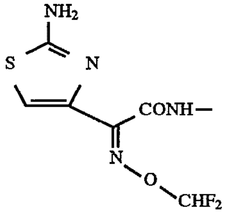 | 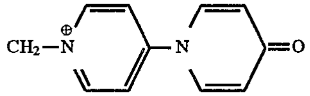 | 0 | $CO_2^{\ominus}$ | 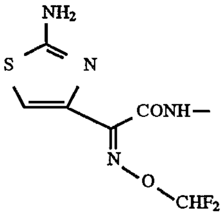 | 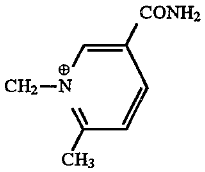 | 0 | $CO_2^{\ominus}$ |
| " | 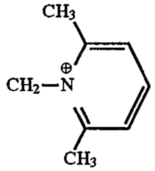 | " | " | " | 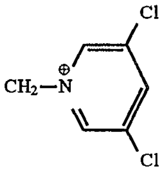 | " | " |
| " | 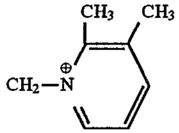 | " | " | " | 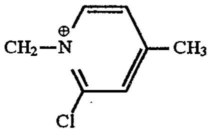 | " | " |

-continued
| R | $R_1$ | $n_2$ | $CO_2A$ | R | $R_1$ | $n_2$ | $CO_2A$ |
|---|---|---|---|---|---|---|---|
| " | 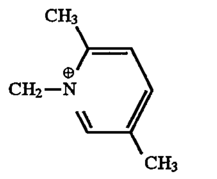 | " | " | " | 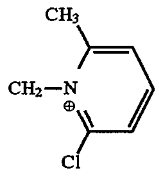 | " | " |
| " | 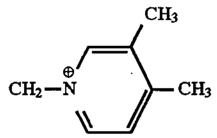 | " | " | " | 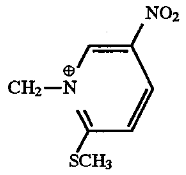 | " | " |
| " | 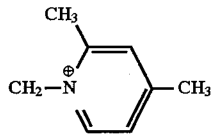 | " | " | " | 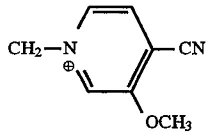 | " | " |
| " | 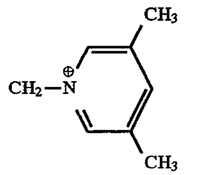 | " | " | " | 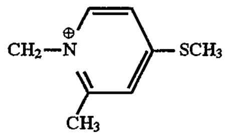 | " | " |
| " | 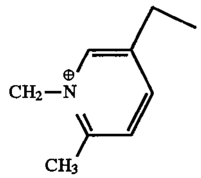 | " | " | " | 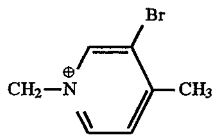 | " | " |
| " | 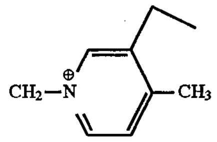 | " | " | " | 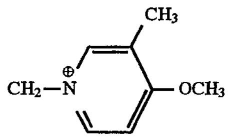 | " | " |

-continued
| R | $R_1$ | $n_2$ | $CO_2A$ | R | $R_1$ | $n_2$ | $CO_2A$ |
|---|---|---|---|---|---|---|---|
| " | 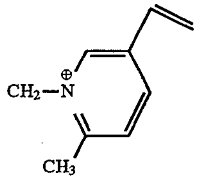 | " | " | " | 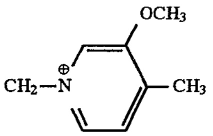 | " | " |
| 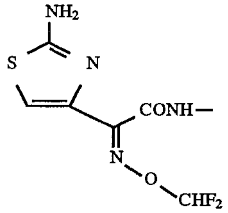 | 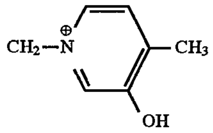 | 0 | $CO_2^\ominus$ | 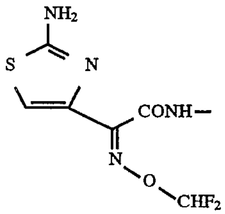 | 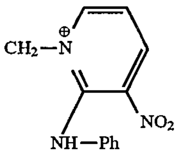 | 0 | $CO_2^\ominus$ |
| " | 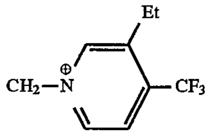 | " | " | " | 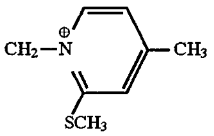 | " | " |
| " | 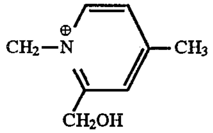 | " | " | " | 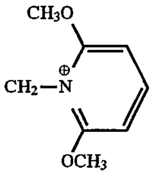 | " | " |
| " | 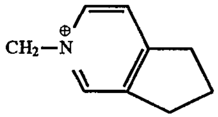 | " | " | " | 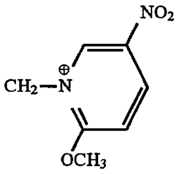 | " | " |
| " | 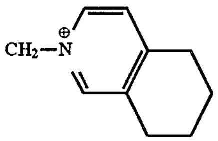 | " | " | " | 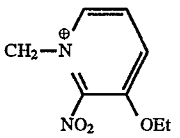 | " | " |

-continued
| R | $R_1$ | $n_2$ $CO_2A$ | R | $R_1$ | $n_2$ $CO_2A$ |
|---|---|---|---|---|---|
| " | 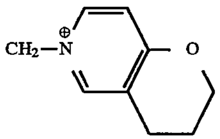 | " " | " | 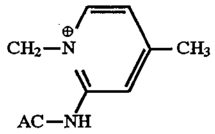 | " " |
| " | 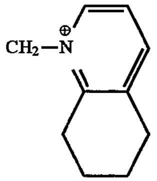 | " " | " | 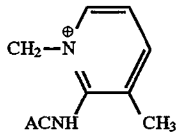 | " " |
| " | 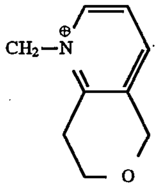 | " " | " | 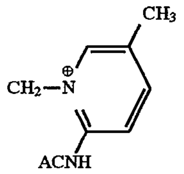 | " " |
| " | 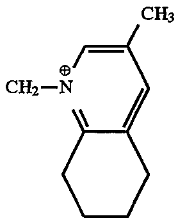 | " " | " | 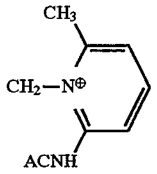 | " " |

-continued
| R | $R_1$ | $n_2$ | $CO_2A$ | R | $R_1$ | $n_2$ | $CO_2A$ |
|---|---|---|---|---|---|---|---|
| " | 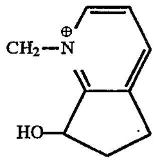 | " | " | " | 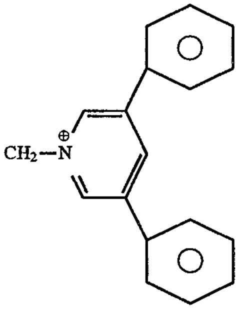 | " | " |
| 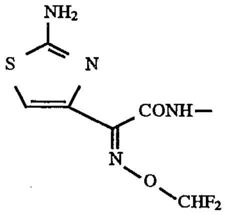 | 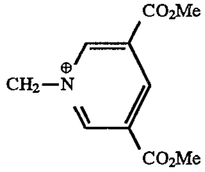 | 0 | $CO_2^{\ominus}$ | 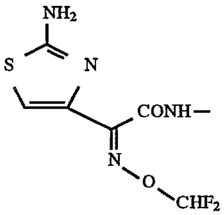 | 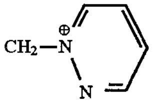 | 0 | $CO_2^{\ominus}$ |
| " | 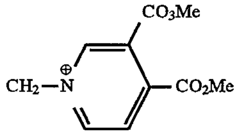 | " | " | " | 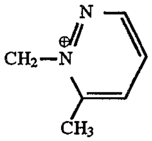 | " | " |
| " | 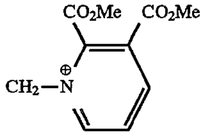 | " | " | " | 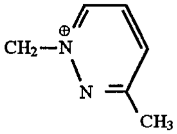 | " | " |
| " | 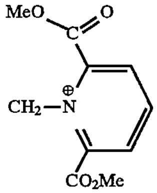 | " | " | " | 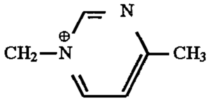 | " | " |

-continued
| R | $R_1$ | $n_2$ | $CO_2A$ | R | $R_1$ | $n_2$ | $CO_2A$ |
|---|---|---|---|---|---|---|---|
| " | 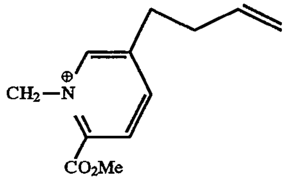 | " | " | " | 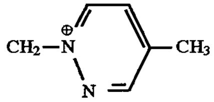 | " | " |
| " | 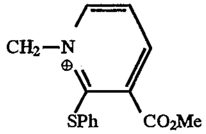 | " | " | " | 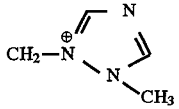 | " | " |
| " | 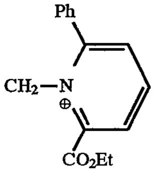 | " | " | " | 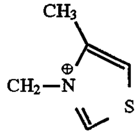 | " | " |
| " | 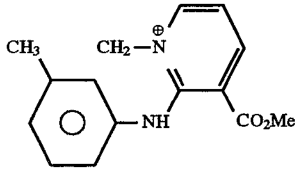 | " | " | " | 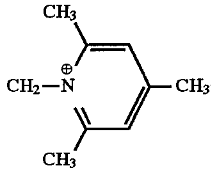 | " | " |
| " | 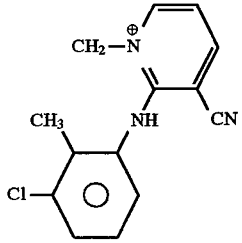 | " | " | " | 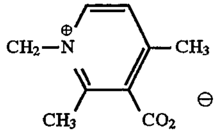 | " | " |

-continued
| R | $R_1$ | $n_2$ | $CO_2A$ | R | $R_1$ | $n_2$ | $CO_2A$ |
|---|---|---|---|---|---|---|---|
| " | 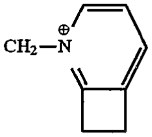 | " | " | " | 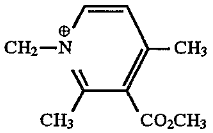 | " | " |
| 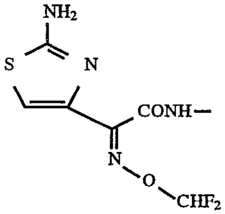 | 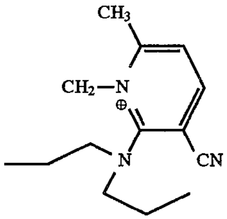 | 0 | $CO_2^{\ominus}$ | 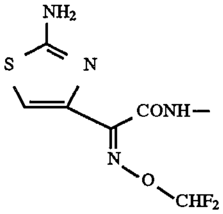 | 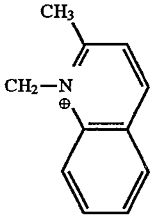 | 0 | $CO_2^{\ominus}$ |
| " | 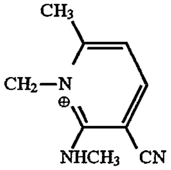 | " | " | " | 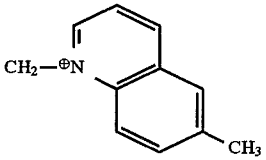 | " | " |
| " | 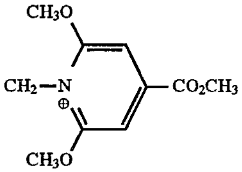 | " | " | " | 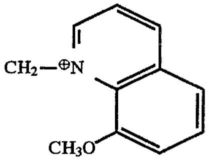 | " | " |
| " | 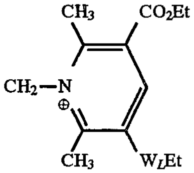 | " | " | " | 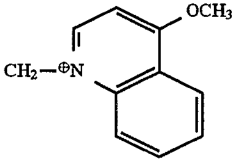 | " | " |

-continued
| R | $R_1$ | $n_2$ | $CO_2A$ | R | $R_1$ | $n_2$ | $CO_2A$ |
|---|---|---|---|---|---|---|---|
| " | 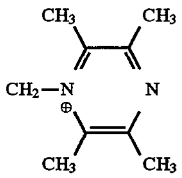 | " | " | " | 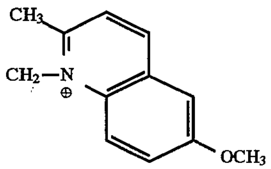 | " | " |
| " | 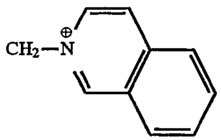 | " | " | " | 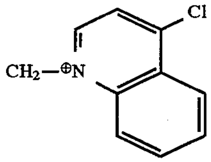 | " | " |
| " | 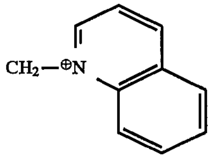 | " | " | " | 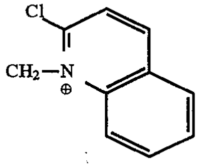 | " | " |
| " | 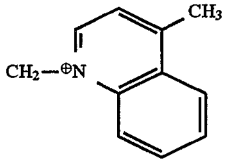 | " | " | " | 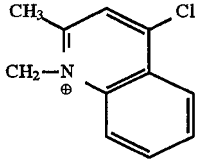 | " | " |
| " | 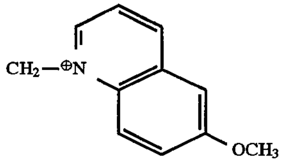 | " | " | " | 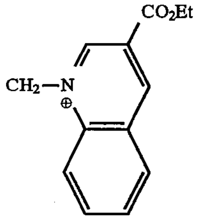 | " | " |

-continued
| R | $R_1$ | $n_2$ | $CO_2A$ | R | $R_1$ | $n_2$ | $CO_2A$ |
|---|---|---|---|---|---|---|---|
| " | 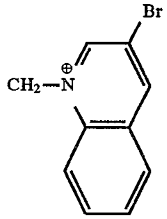 | " | " | " | 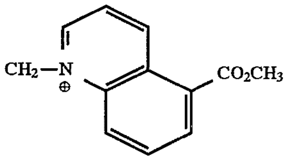 | " | " |
| 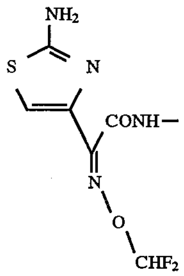 | 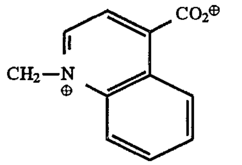 | 0 | $CO_2^{\ominus}$ | 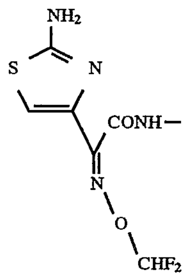 | 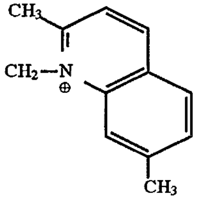 | 0 | $CO_2^{\ominus}$ |
| " | 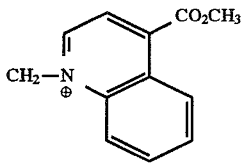 | " | " | " | 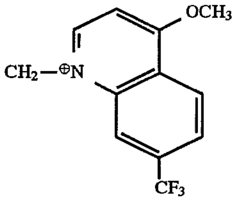 | " | " |
| " | 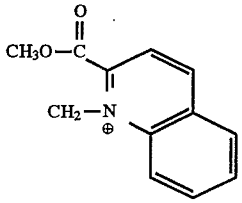 | " | " | " | 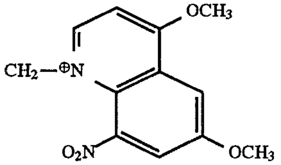 | " | " |

-continued
| R | $R_1$ | $n_2$ | $CO_2A$ | R | $R_1$ | $n_2$ | $CO_2A$ |
|---|---|---|---|---|---|---|---|
| " | 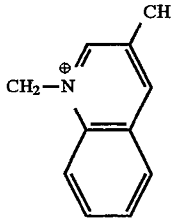 | " | " | " | 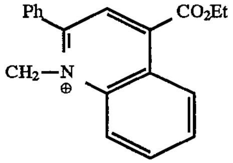 | " | " |
| " | 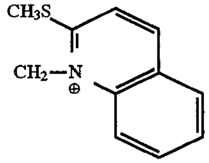 | " | " | " | 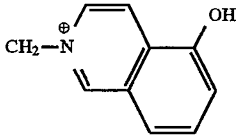 | " | " |
| " | 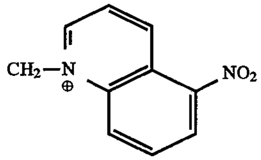 | " | " | " | 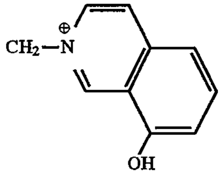 | " | " |
| " | 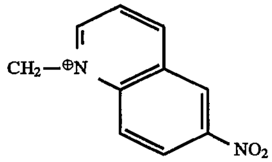 | " | " | " | 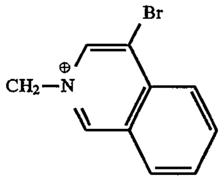 | " | " |
| " | 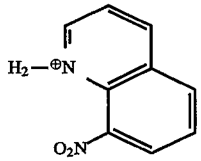 | " | " | " | 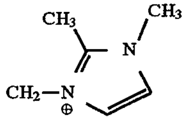 | " | " |

-continued
| R | $R_1$ | $n_2$ | $CO_2A$ | R | $R_1$ | $n_2$ | $CO_2A$ |
|---|---|---|---|---|---|---|---|
| " | 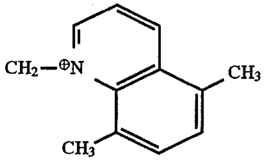 | " | " | " | 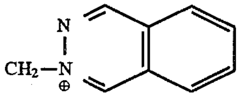 | " | " |
| " | 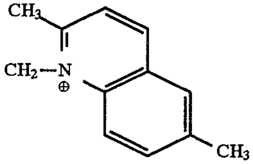 | " | " | " | 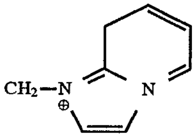 | " | " |
| 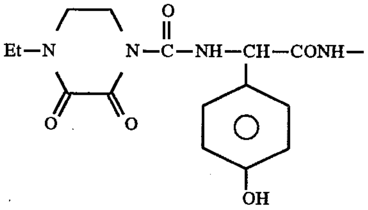 | 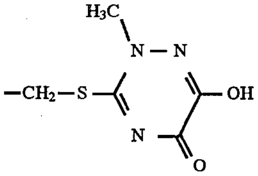 | 0 | $CO_2H$ | 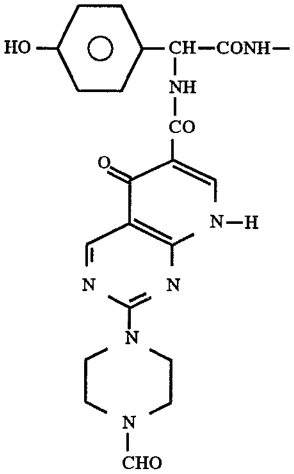 | 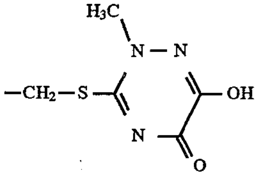 | 0 | $CO_2H$ |
| " | 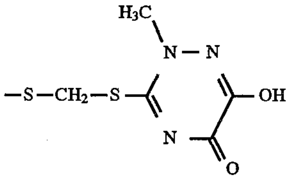 | " | " | " | 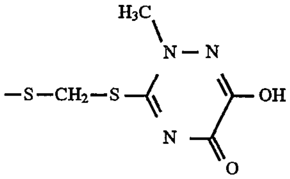 | " | " |

-continued
| R | $R_1$ | $n_2$ | $CO_2A$ | R | $R_1$ | $n_2$ | $CO_2A$ |
|---|---|---|---|---|---|---|---|
| 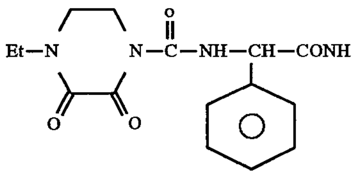 | 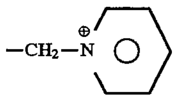 | " | " | 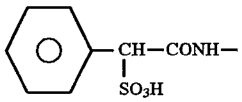 | 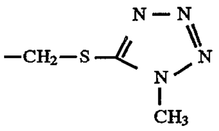 | " | " |
| 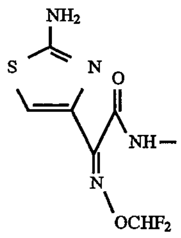 | $-CH=CH-CN$ | " | " | " | 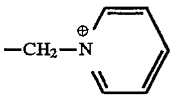 | " | $CO_2^{\ominus}$ |
| " | " | " | 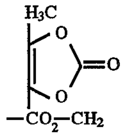 | " | 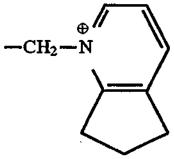 | " | " |
| | | | | " | 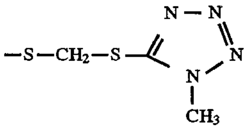 | " | $CO_2H$ |
| | | | | " | 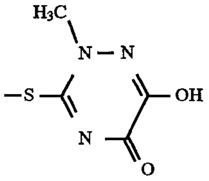 | " | " |

-continued
| R | $R_1$ | $n_2$ | $CO_2A$ | R | $R_1$ | $n_2$ | $CO_2A$ |
|---|---|---|---|---|---|---|---|
| 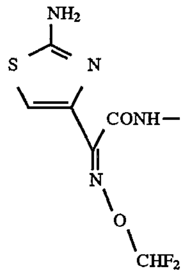 | 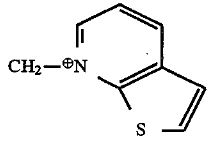 | 0 | $CO_2^{\ominus}$ | 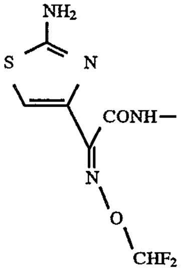 | 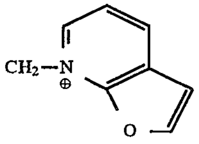 | 0 | $CO_2^{\ominus}$ |
| " | 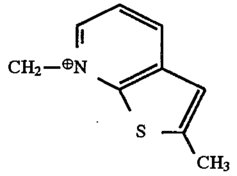 | " | " | " | 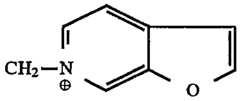 | " | " |
| " | 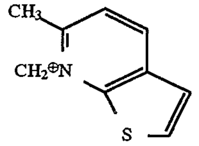 | " | " | " | 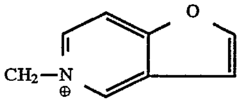 | " | " |
| " | 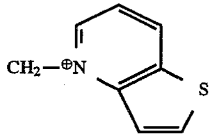 | " | " | " | 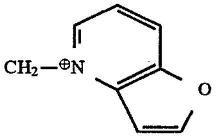 | " | " |
| " | 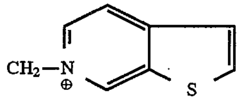 | " | " | " | 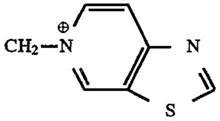 | " | " |
| " | 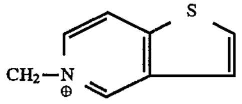 | " | " | " | 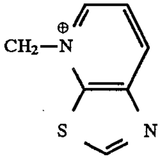 | " | " |

-continued
| R | $R_1$ | $n_2$ | $CO_2A$ | R | $R_1$ | $n_2$ | $CO_2A$ |
|---|---|---|---|---|---|---|---|
| " | 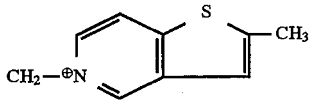 | " | " | " | 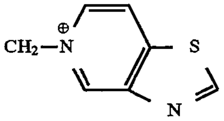 | " | " |
| " | 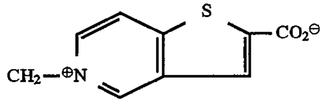 | " | " | " | 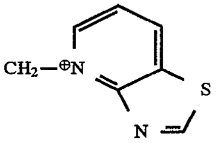 | " | " |
| " | 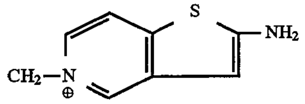 | " | " | " | 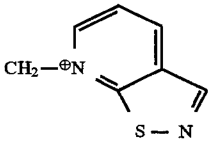 | " | " |
| " | 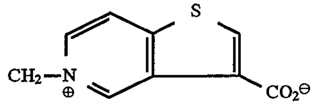 | " | " | 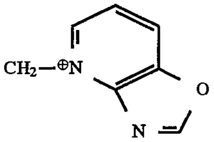 | " | " | |
| 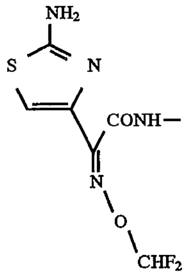 | 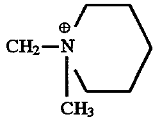 | 0 | $CO_2^{\ominus}$ | 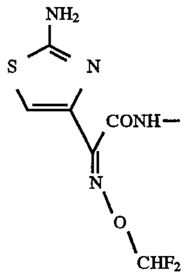 | $CH_2-ONO_2$ | 0 | $CO_2^{\ominus}$ |
| " | 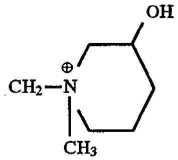 | " | " | " | $CH_2-NO_2$ | " | " |

-continued
| R | $R_1$ | $n_2$ | $CO_2A$ | R | $R_1$ | $n_2$ | $CO_2A$ |
|---|---|---|---|---|---|---|---|
| " | 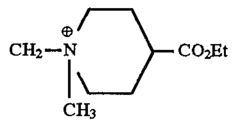 | " | " | " | $CH_2-SO_2CH_3$ | " | " |
| " | 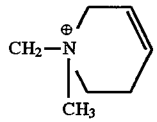 | " | " | " | 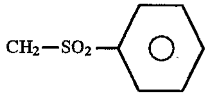 | " | " |
| " | 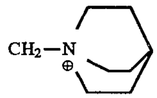 | " | " | " | 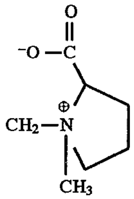 | " | " |
| " | 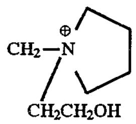 | " | " | " | 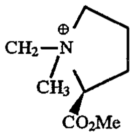 | " | " |
| " | 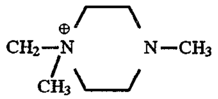 | " | " | " | 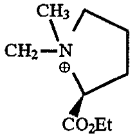 | " | " |
| " | 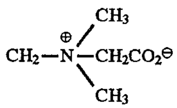 | " | " | " | 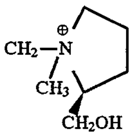 | " | " |
| " | 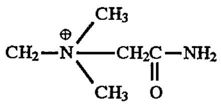 | " | " | " | 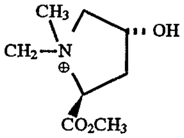 | " | " |

-continued
| R | $R_1$ | $n_2$ | $CO_2A$ | R | $R_1$ | $n_2$ | $CO_2A$ |
|---|---|---|---|---|---|---|---|
| " | 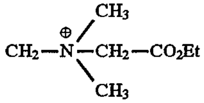 | " | " | " | 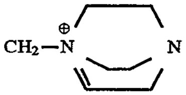 | " | " |
| 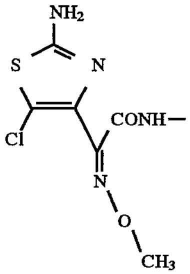 | 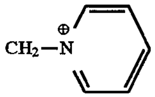 | 0 | $CO_2^{\ominus}$ | 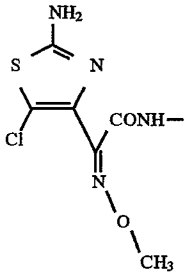 | 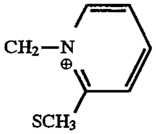 | 0 | $CO_2^{\ominus}$ |
| " | 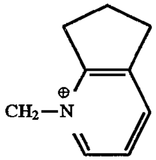 | " | " | " | 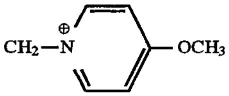 | " | " |
| " | 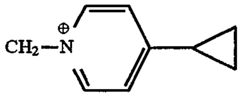 | " | " | " | 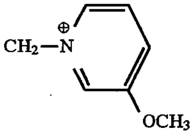 | " | " |
| " | 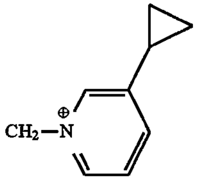 | " | " | " | 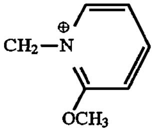 | " | " |

-continued
| R | $R_1$ | $n_2$ | $CO_2A$ | R | $R_1$ | $n_2$ | $CO_2A$ |
|---|---|---|---|---|---|---|---|
| " | 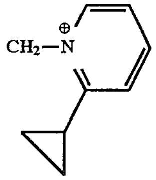 | " | " | " | 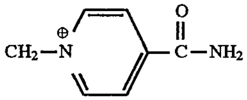 | " | " |
| " | 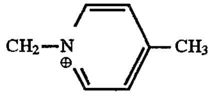 | " | " | " | 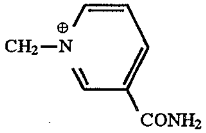 | " | " |
| " | 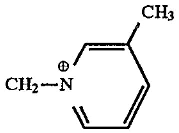 | " | " | " | 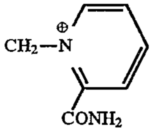 | " | " |
| " | 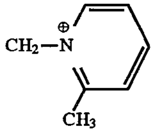 | " | " | " | 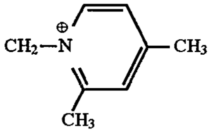 | " | " |
| " | 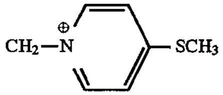 | " | " | " | 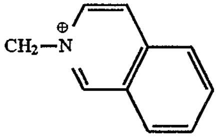 | " | " |
| " | 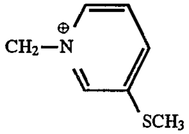 | " | " | " | 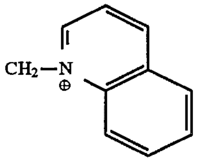 | " | " |

-continued
| R | R1 | n2 | CO2A | R | R1 | n2 | CO2A |
|---|---|---|---|---|---|---|---|
| 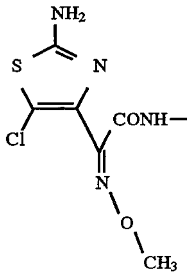 | 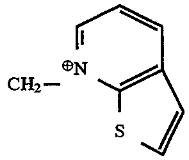 | 0 | $CO_2^{\ominus}$ | 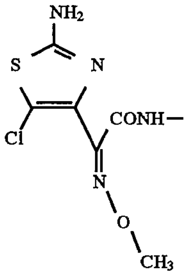 | 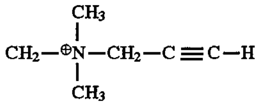 | 0 | $CO_2^{\ominus}$ |
| " | 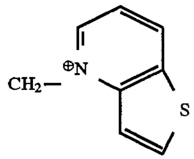 | " | " | " | 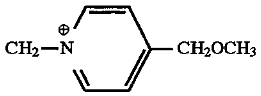 | " | " |
| " | 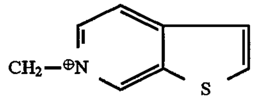 | " | " | " | 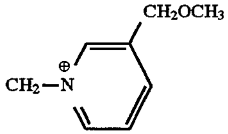 | " | " |
| " | 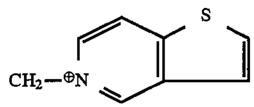 | " | " | " | 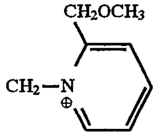 | " | " |
| " | 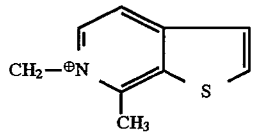 | " | " | " | 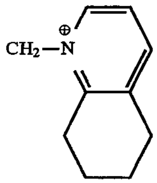 | " | " |
| " | 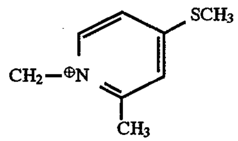 | " | " | " | $CH_2NO_2$ | " | " |

-continued
| R | $R_1$ | $n_2$ | $CO_2A$ | R | $R_1$ | $n_2$ | $CO_2A$ |
|---|---|---|---|---|---|---|---|
| " | 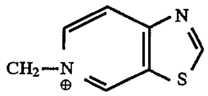 | " | " | | | | |
| " | $CH_2-\overset{\oplus}{N}(CH_3)_3$ | " | " | | | | |
| " | 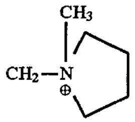 | " | " | | | | |
| " | 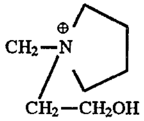 | " | " | | | | |
| 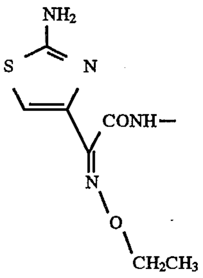 | 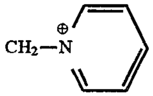 | 0 | $CO_2^{\ominus}$ | 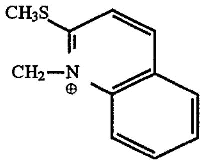 | 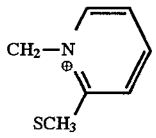 | 0 | $CO_2^{\ominus}$ |
| " | 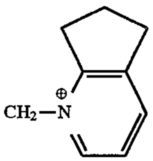 | " | " | " | 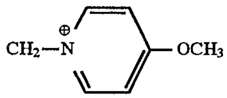 | " | " |
| " | 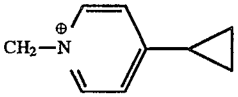 | " | " | " | 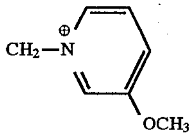 | " | " |

-continued
| R | $R_1$ | $n_2$ | $CO_2A$ | R | $R_1$ | $n_2$ | $CO_2A$ |
|---|---|---|---|---|---|---|---|
| " | 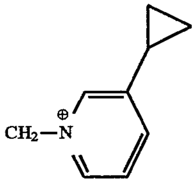 | " | " | " | 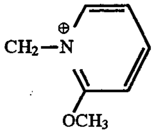 | " | " |
| " | 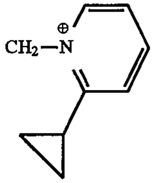 | " | " | " | 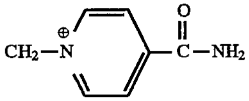 | " | " |
| " | 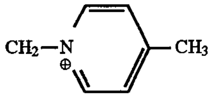 | " | " | " | 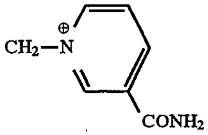 | " | " |
| " | 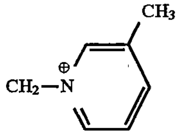 | " | " | " | 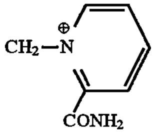 | " | " |
| " | 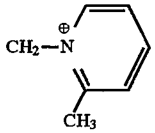 | " | " | " | 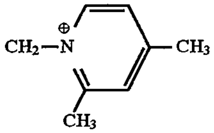 | " | " |
| " | 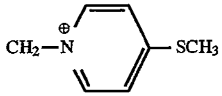 | " | " | " | 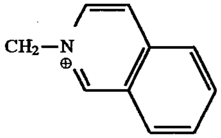 | " | " |

-continued
| R | $R_1$ | $n_2$ | $CO_2A$ | R | $R_1$ | $n_2$ | $CO_2A$ |
|---|---|---|---|---|---|---|---|
| " | 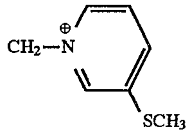 | " | " | " | 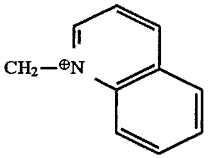 | " | " |
| 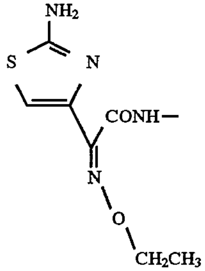 | 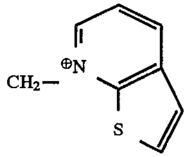 | 0 | $CO_2^{\ominus}$ | 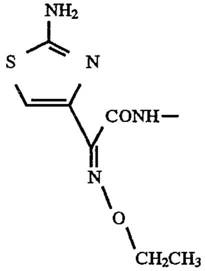 | 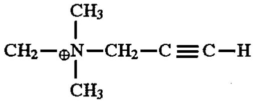 | 0 | $CO_2^{\ominus}$ |
| " | 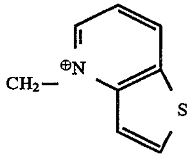 | " | " | " | 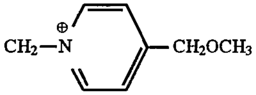 | " | " |
| " | 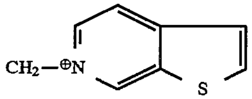 | " | " | " | 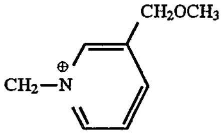 | " | " |
| " | 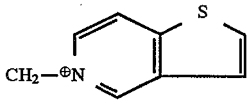 | " | " | " | 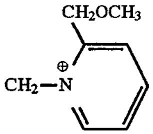 | " | " |

-continued
| R | $R_1$ | $n_2$ | $CO_2A$ | R | $R_1$ | $n_2$ | $CO_2A$ |
|---|---|---|---|---|---|---|---|
| " | 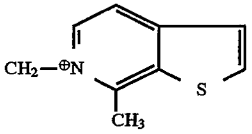 | " | " | " | 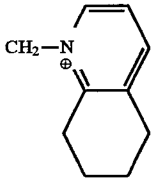 | " | " |
| " | 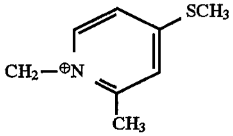 | " | " | " | $CH_2NO_2$ | " | " |
| " | 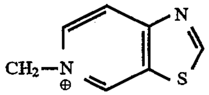 | " | " | | | | |
| " | $CH_2-\overset{\oplus}{N}(CH_3)_3$ | " | " | | | | |
| " | 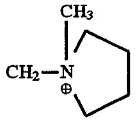 | " | " | | | | |
| " | 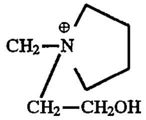 | " | " | | | | |
| 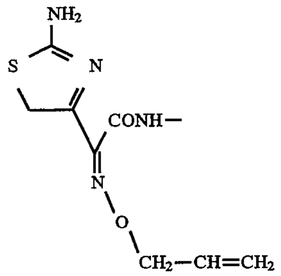 | 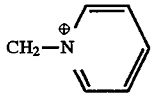 | 0 | $CO_2^{\ominus}$ | 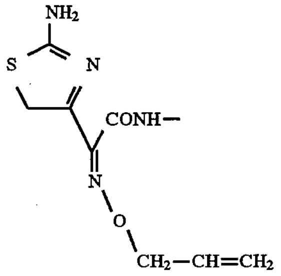 | 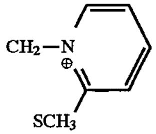 | 0 | $CO_2^{\ominus}$ |

-continued
| R | $R_1$ | $n_2$ | $CO_2A$ | R | $R_1$ | $n_2$ | $CO_2A$ |
|---|---|---|---|---|---|---|---|
| " | 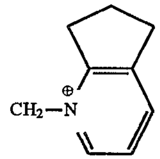 | " | " | " | 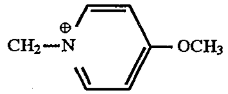 | " | " |
| " | 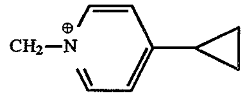 | " | " | " | 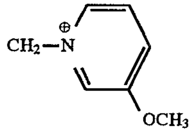 | " | " |
| " | 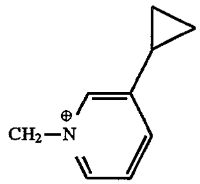 | " | " | " | 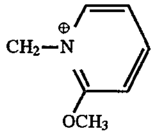 | " | " |
| " | 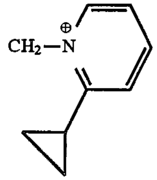 | " | " | " | 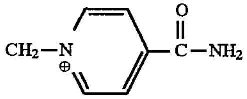 | " | " |
| " | 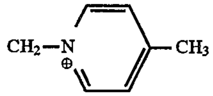 | " | " | " | 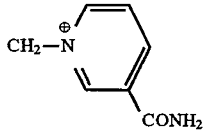 | " | " |
| " | 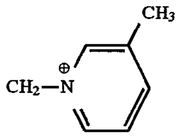 | " | " | " | 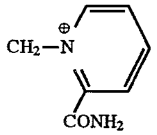 | " | " |

-continued
| R | $R_1$ | $n_2$ | $CO_2A$ | R | $R_1$ | $n_2$ | $CO_2A$ |
|---|---|---|---|---|---|---|---|
| " | 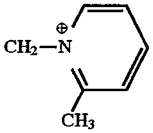 | " | " | " | 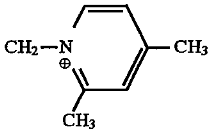 | " | " |
| " | 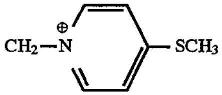 | " | " | " | 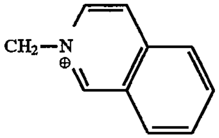 | " | " |
| " | 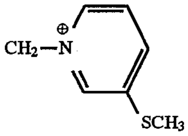 | " | " | " | 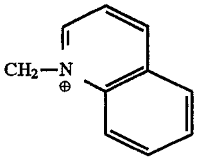 | " | " |
| 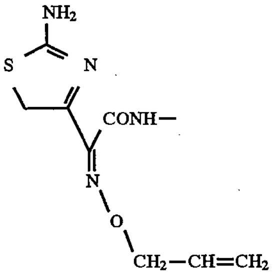 | 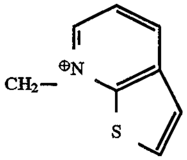 | 0 | $CO_2^{\ominus}$ | 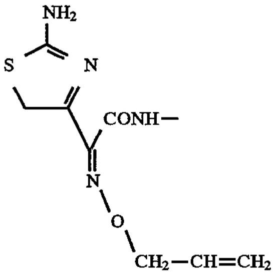 | 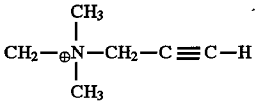 | 0 | $CO_2^{\ominus}$ |
| " | 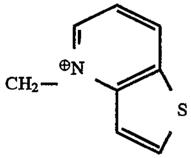 | " | " | " | 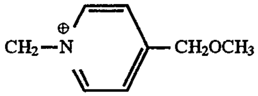 | " | " |
| " | 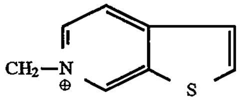 | " | " | " | 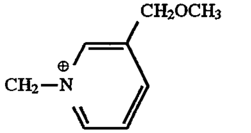 | " | " |

-continued
| R | $R_1$ | $n_2$ | $CO_2A$ | R | $R_1$ | $n_2$ | $CO_2A$ |
|---|---|---|---|---|---|---|---|
| " | 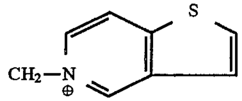 | " | " | " | 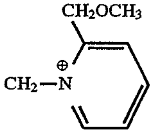 | " | " |
| " | 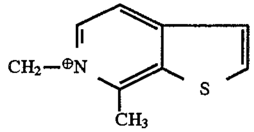 | " | " | " | 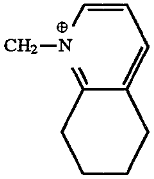 | " | " |
| " | 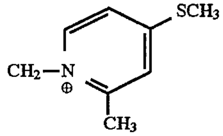 | " | " | " | $CH_2NO_2$ | " | " |
| " | 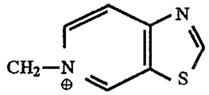 | " | " | | | | |
| " | $CH_2-\overset{\oplus}{N}(CH_3)_3$ | " | " | | | | |
| " | 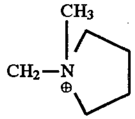 | " | " | | | | |
| " | 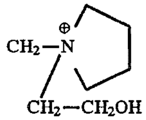 | " | " | | | | |

-continued
| R | $R_1$ | $n_2$ | $CO_2A$ | R | $R_1$ | $n_2$ | $CO_2A$ |
|---|---|---|---|---|---|---|---|
| 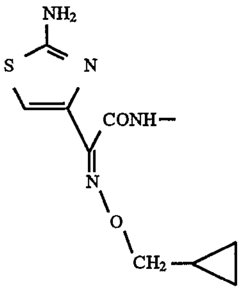 | 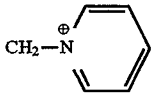 | 0 | $CO_2^{\ominus}$ | 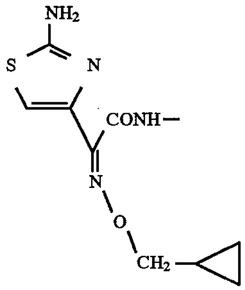 | 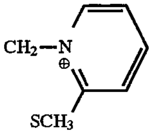 | 0 | $CO_2^{\ominus}$ |
| " | 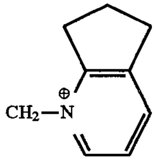 | " | " | " | 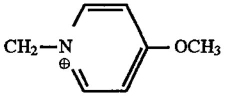 | " | " |
| " | 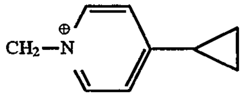 | " | " | " | 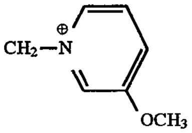 | " | " |
| " | 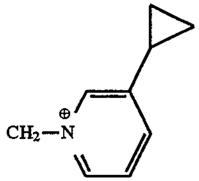 | " | " | " | 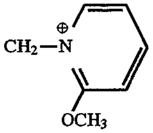 | " | " |
| " | 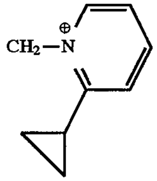 | " | " | " | 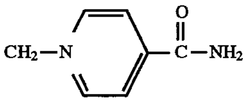 | " | " |

-continued
| R | $R_1$ | $n_2$ | $CO_2A$ | R | $R_1$ | $n_2$ | $CO_2A$ |
|---|---|---|---|---|---|---|---|
| " | 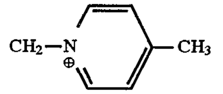 | " | " | " | 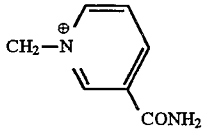 | " | " |
| " | 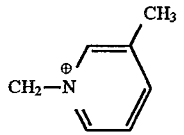 | " | " | " | 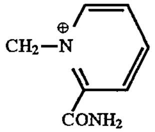 | " | " |
| " | 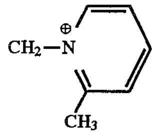 | " | " | " | 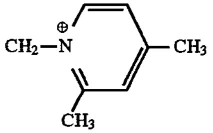 | " | " |
| " | 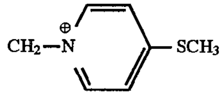 | " | " | " | 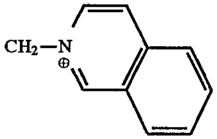 | " | " |
| " | 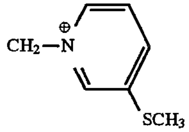 | " | " | " | 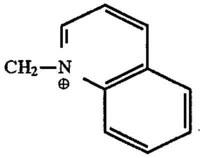 | " | " |
| 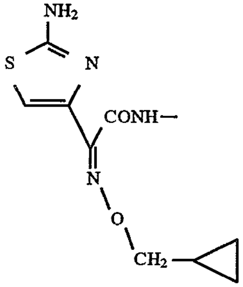 | 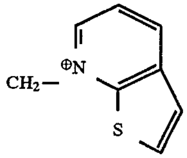 | 0 | $CO_2^{\ominus}$ | 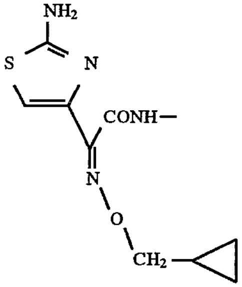 | 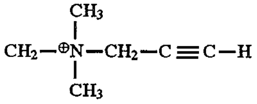 | 0 | $CO_2^{\ominus}$ |

-continued
| R | $R_1$ | $n_2$ | $CO_2A$ | R | $R_1$ | $n_2$ | $CO_2A$ |
|---|---|---|---|---|---|---|---|
| " | 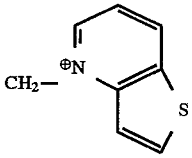 | " | " | " | 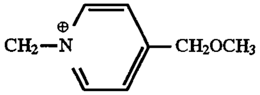 | " | " |
| " | 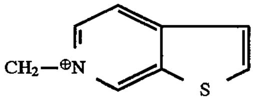 | " | " | " | 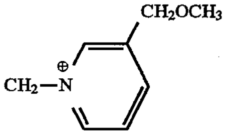 | " | " |
| " | 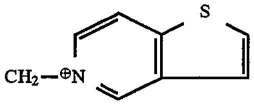 | " | " | " | 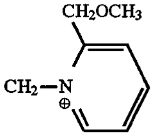 | " | " |
| " | 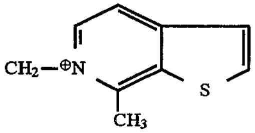 | " | " | " | 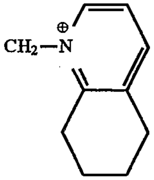 | " | " |
| " | 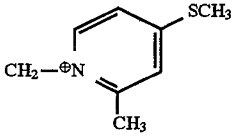 | " | " | " | $CH_2NO_2$ | " | " |
| " | 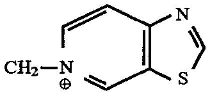 | " | " | | | | |
| " | $CH_2-\overset{\oplus}{N}(CH_3)_3$ | " | " | | | | |

-continued
| R | $R_1$ | $n_2$ | $CO_2A$ | R | $R_1$ | $n_2$ | $CO_2A$ |
|---|---|---|---|---|---|---|---|
| " | 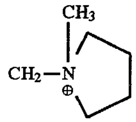 | " | " | | | | |
| " | 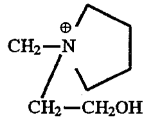 | " | " | | | | |
| 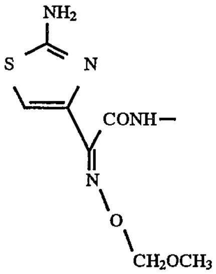 | 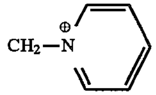 | 0 | $CO_2^\ominus$ | 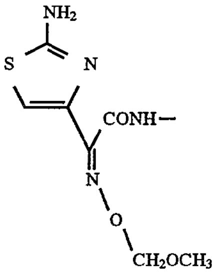 | 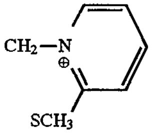 | 0 | $CO_2^\ominus$ |
| " | 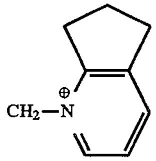 | " | " | " | 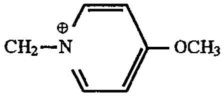 | " | " |
| " | 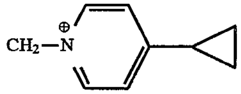 | " | " | " | 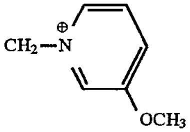 | " | " |
| " | 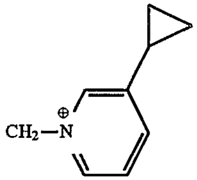 | " | " | " | 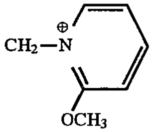 | " | " |

-continued
| R | $R_1$ | $n_2$ | $CO_2A$ | R | $R_1$ | $n_2$ | $CO_2A$ |
|---|---|---|---|---|---|---|---|
| " | 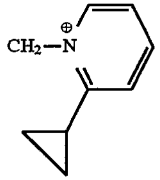 | " | " | " | 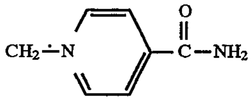 | " | " |
| " | 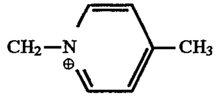 | " | " | " | 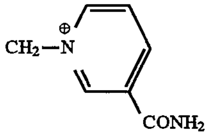 | " | " |
| " | 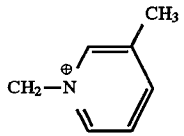 | " | " | " | 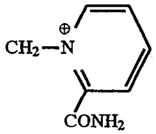 | " | " |
| " | 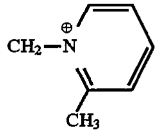 | " | " | " | 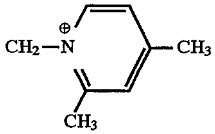 | " | " |
| " | 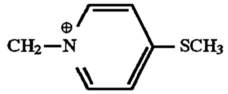 | " | " | " | 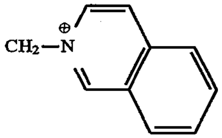 | " | " |
| " | 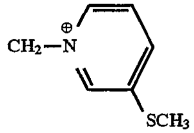 | " | " | " | 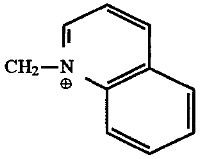 | " | " |

-continued
| R | $R_1$ | $n_2$ | $CO_2A$ | R | $R_1$ | $n_2$ | $CO_2A$ |
|---|---|---|---|---|---|---|---|
| 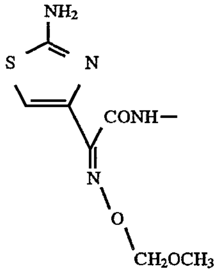 | 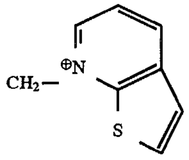 | 0 | $CO_2^{\ominus}$ | 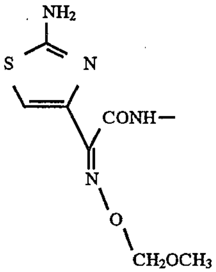 | 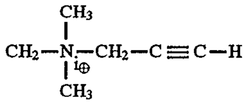 | 0 | $CO_2^{\ominus}$ |
| " | 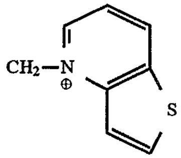 | " | " | " | 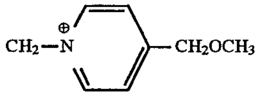 | " | " |
| " | 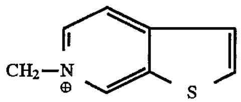 | " | " | " | 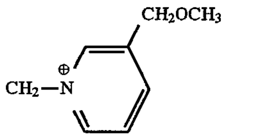 | " | " |
| " | 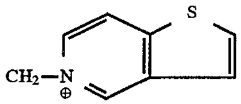 | " | " | " | 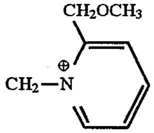 | " | " |
| " | 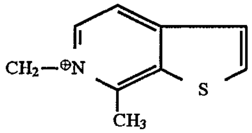 | " | " | " | 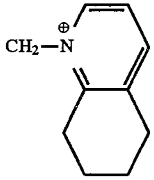 | " | " |
| " | 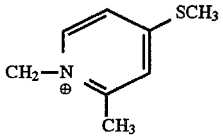 | " | " | " | $CH_2NO_2$ | " | " |

-continued
| R | $R_1$ | $n_2$ | $CO_2A$ | R | $R_1$ | $n_2$ | $CO_2A$ |
|---|---|---|---|---|---|---|---|
| " | 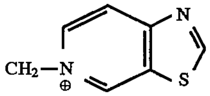 | " | " | | | | |
| " | $CH_2-\overset{\oplus}{N}(CH_3)_3$ | " | " | | | | |
| " | 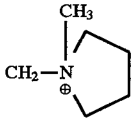 | " | " | | | | |
| " | 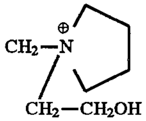 | " | " | | | | |
| 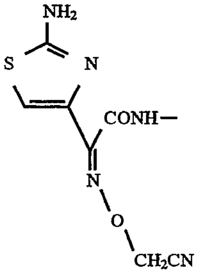 | 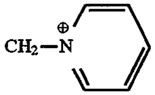 | 0 | $CO_2^{\ominus}$ | 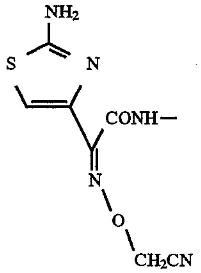 | 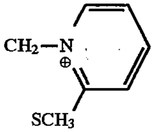 | 0 | $CO_2^{\ominus}$ |
| " | 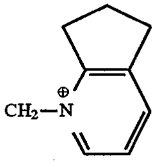 | " | " | " | 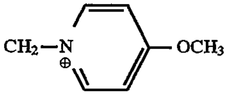 | " | " |
| " | 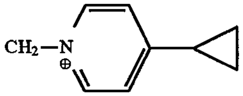 | " | " | " | 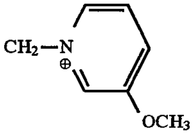 | " | " |

-continued
| R | $R_1$ | $n_2$ | $CO_2A$ | R | $R_1$ | $n_2$ | $CO_2A$ |
|---|---|---|---|---|---|---|---|
| " | 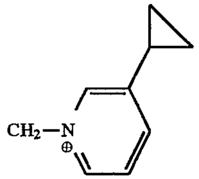 | " | " | " | 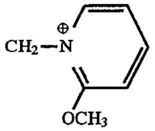 | " | " |
| " | 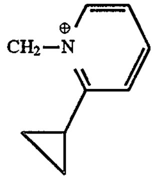 | " | " | " | 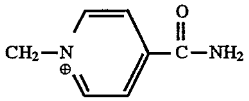 | " | " |
| " | 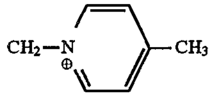 | " | " | " | 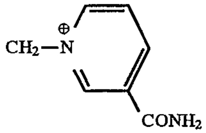 | " | " |
| " | 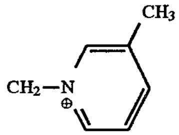 | " | " | " | 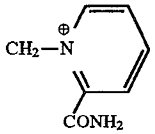 | " | " |
| " | 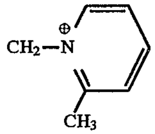 | " | " | " | 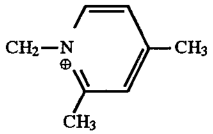 | " | " |
| " | 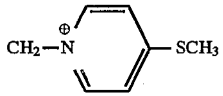 | " | " | " | 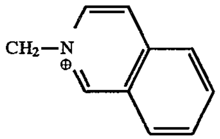 | " | " |

-continued
| R | $R_1$ | $n_2$ | $CO_2A$ | R | $R_1$ | $n_2$ | $CO_2A$ |
|---|---|---|---|---|---|---|---|
| " | 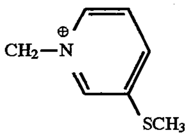 | " | " | " | 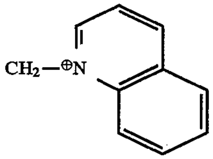 | " | " |
| 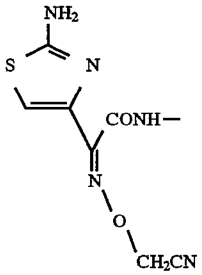 | 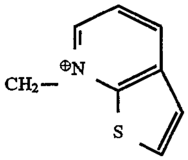 | 0 | $CO_2^{\ominus}$ | 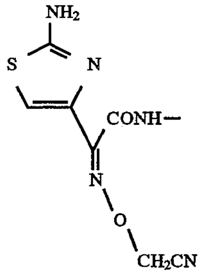 | 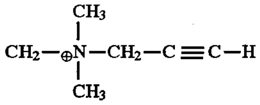 | 0 | $CO_2^{\ominus}$ |
| " | 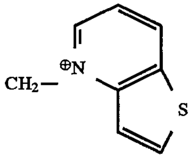 | " | " | " | 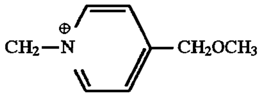 | " | " |
| " | 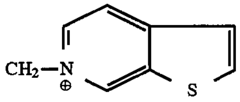 | " | " | " | 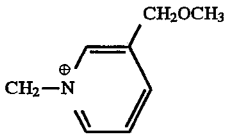 | " | " |
| " | 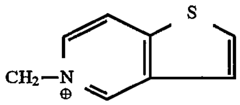 | " | " | " | 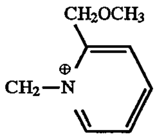 | " | " |

-continued
| R | $R_1$ | $n_2$ | $CO_2A$ | R | $R_1$ | $n_2$ | $CO_2A$ |
|---|---|---|---|---|---|---|---|
| " | 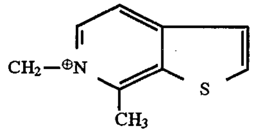 | " | " | " | 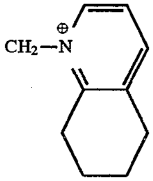 | " | " |
| " | 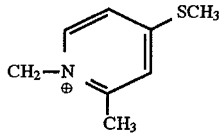 | " | " | " | $CH_2NO_2$ | " | " |
| " | 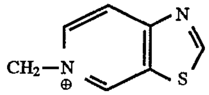 | " | " | | | | |
| " | $CH_2-\underset{\oplus}{N}(CH_3)_3$ | " | " | | | | |
| " | 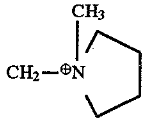 | " | " | | | | |
| " | 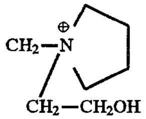 | " | " | | | | |
| 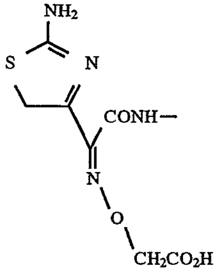 | 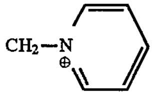 | 0 | $CO_2^{\ominus}$ | 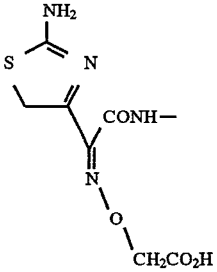 | 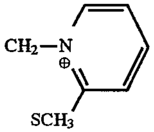 | 0 | $CO_2^{\ominus}$ |

-continued
| R | $R_1$ | $n_2$ | $CO_2A$ | R | $R_1$ | $n_2$ | $CO_2A$ |
|---|---|---|---|---|---|---|---|
| " | 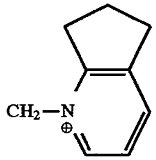 | " | " | " | 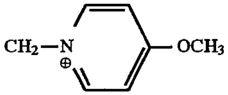 | " | " |
| " | 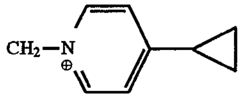 | " | " | " | 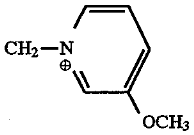 | " | " |
| " | 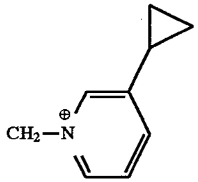 | " | " | " | 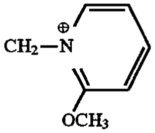 | " | " |
| " | 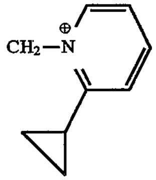 | " | " | " | 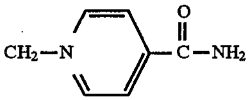 | " | " |
| " | 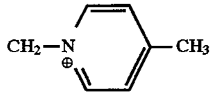 | " | " | " | 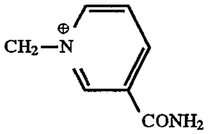 | " | " |
| " | 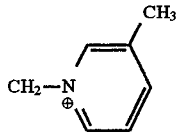 | " | " | " | 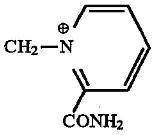 | " | " |

-continued
| R | $R_1$ | $n_2$ | $CO_2A$ | R | $R_1$ | $n_2$ | $CO_2A$ |
|---|---|---|---|---|---|---|---|
| " | 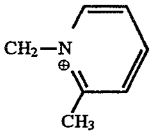 | " | " | " | 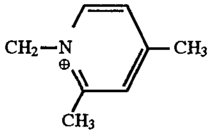 | " | " |
| " | 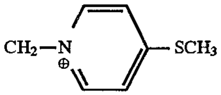 | " | " | " | 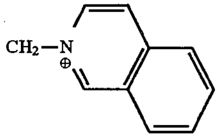 | " | " |
| " | 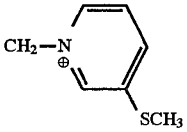 | " | " | " | 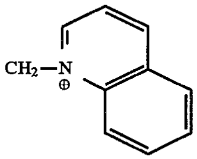 | " | " |
| 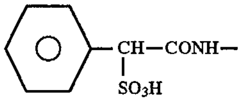 | 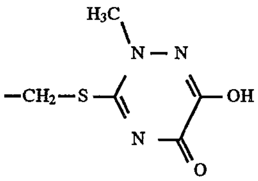 | 0 | $CO_2H$ | | | | |
| " | 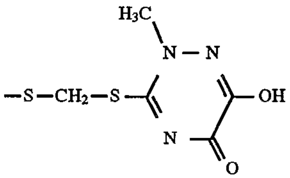 | " | " | | | | |

-continued
| R | $R_1$ | $n_2$ | $CO_2A$ | R | $R_1$ | $n_2$ | $CO_2A$ |
|---|---|---|---|---|---|---|---|
| 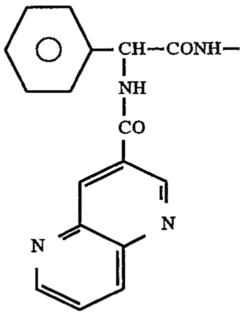 | 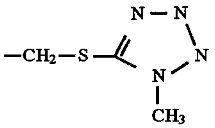 | " | " | | | | |
| " | 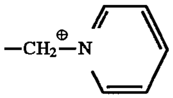 | " | $CO_2^{\ominus}$ | | | | |
| " | 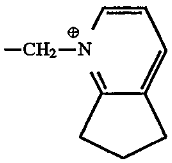 | " | " | | | | |
| " | 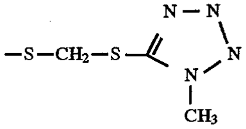 | " | $CO_2H$ | | | | |
| " | 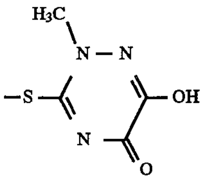 | " | " | | | | |

-continued
| R | $R_1$ | $n_2$ | $CO_2A$ | R | $R_1$ | $n_2$ | $CO_2A$ |
|---|---|---|---|---|---|---|---|
| " | 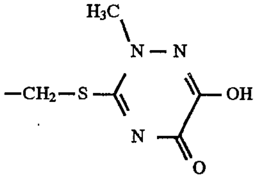 | " | " | | | | |
| " | 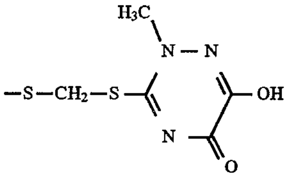 | " | " | | | | |
| 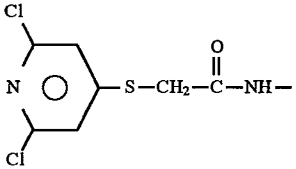 | 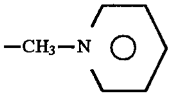 | " | " | | | | |
| 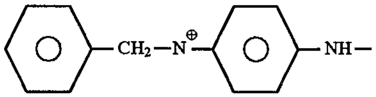 | 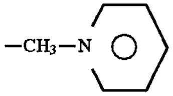 | 0 | $CO_2H$ | | | | |
| 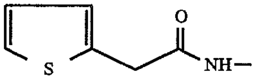 | " | " | " | | | | |
| 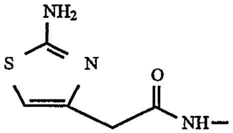 | " | " | " | | | | |

-continued
| R | $R_1$ | $n_2$ | $CO_2A$ | R | $R_1$ | $n_2$ | $CO_2A$ |
|---|---|---|---|---|---|---|---|
| 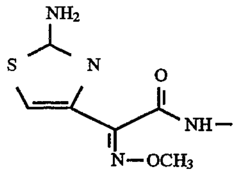 | 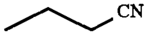 | " | 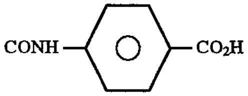 | | | | |
| 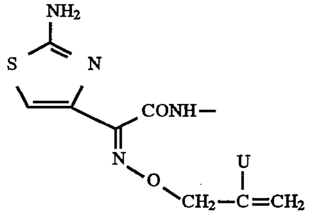 | 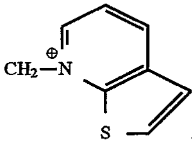 | 0 | $CO_2^{\ominus}$ | 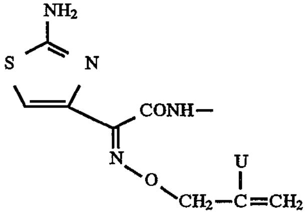 | 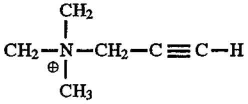 | 0 | $CO_2^{\ominus}$ |
| " | 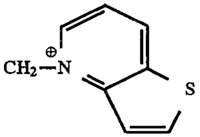 | " | " | " | 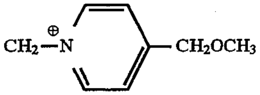 | " | " |
| " | 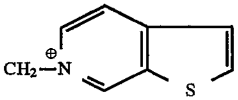 | " | " | " | 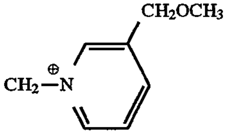 | " | " |
| " | 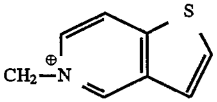 | " | " | " | 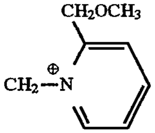 | " | " |
| " | 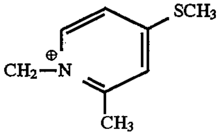 | " | " | " | $CH_2NO_2$ | " | " |

-continued
| R | $R_1$ | $n_2$ | $CO_2A$ | R | $R_1$ | $n_2$ | $CO_2A$ |
|---|---|---|---|---|---|---|---|
| " | 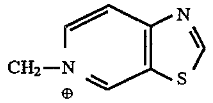 | " | " | | | | |
| " | $CH_2-\overset{\oplus}{N}(CH_3)_3$ | " | " | | | | |
| " | 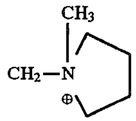 | " | " | | | | |
| " | 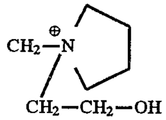 | " | " | | | | |
| 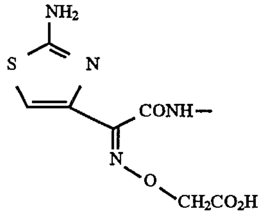 | 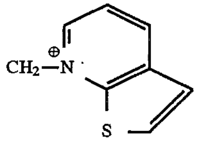 | 0 | $CO_2^{\ominus}$ | 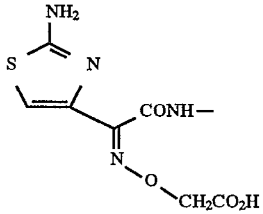 | 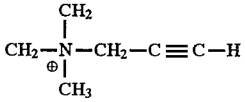 | 0 | $CO_2^{\ominus}$ |
| " | 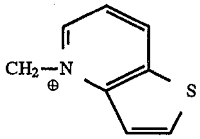 | " | " | " | 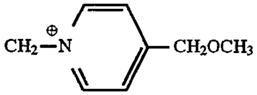 | " | " |
| " | 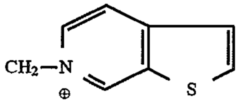 | " | " | " | 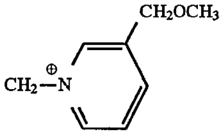 | " | " |

-continued
| R | $R_1$ | $n_2$ | $CO_2A$ | R | $R_1$ | $n_2$ | $CO_2A$ |
|---|---|---|---|---|---|---|---|
| " | 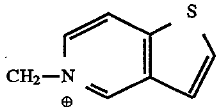 | " | " | " | 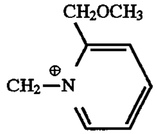 | " | " |
| " | 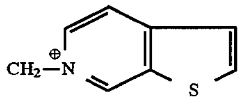 | " | " | " | 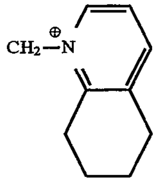 | " | " |
| " | 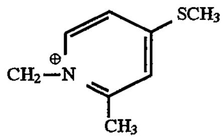 | " | " | " | $CH_2NO_2$ | " | " |
| " | 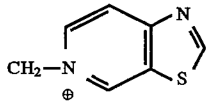 | " | " | | | | |
| " | $CH_2-\overset{\oplus}{N}(CH_3)_3$ | " | " | | | | |
| " | 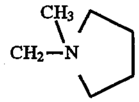 | " | " | | | | |
| " | 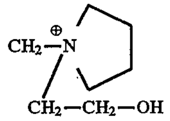 | " | " | | | | |

-continued
| R | $R_1$ | $n_2$ | $CO_2A$ | R | $R_1$ | $n_2$ | $CO_2A$ |
|---|---|---|---|---|---|---|---|
| 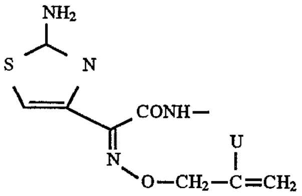 | 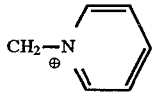 | 0 | $CO_2^{\ominus}$ | 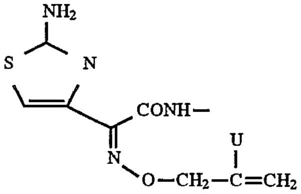 | 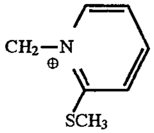 | 0 | $CO_2^{\ominus}$ |
| " | 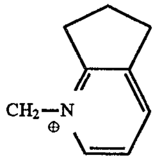 | " | " | " | 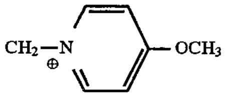 | " | " |
| " | 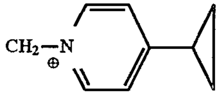 | " | " | " | 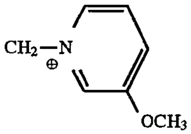 | " | " |
| " | 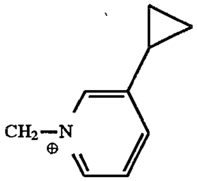 | " | " | " | 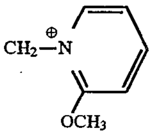 | " | " |
| " | 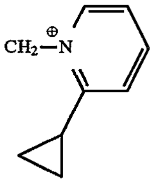 | " | " | " | 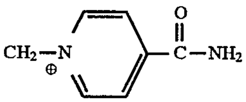 | " | " |
| " | 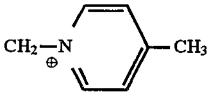 | " | " | " | 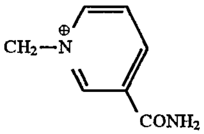 | " | " |

-continued
| R | $R_1$ | $n_2$ | $CO_2A$ | R | $R_1$ | $n_2$ | $CO_2A$ |
|---|---|---|---|---|---|---|---|
| " | 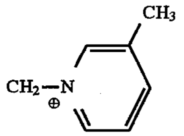 | " | " | " | 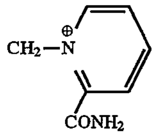 | " | " |
| " | 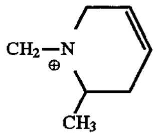 | " | " | " | 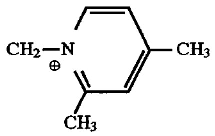 | " | " |
| " | 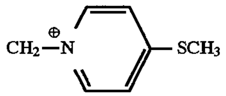 | " | " | " | 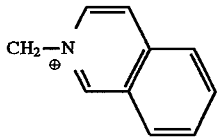 | " | " |
| " | 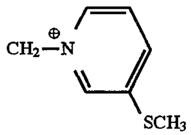 | " | " | " | 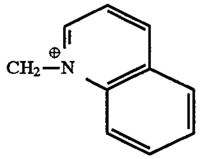 | " | " |
| 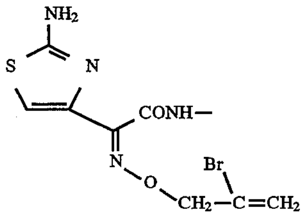 | 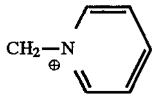 | 0 | $CO_2^{\ominus}$ | 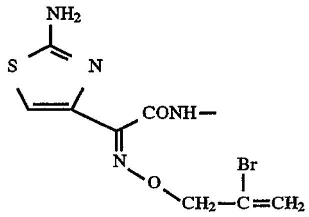 | 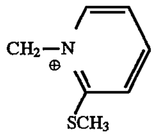 | 0 | $CO_2^{\ominus}$ |
| " | 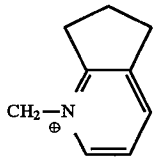 | " | " | " | 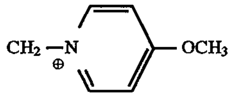 | " | " |

-continued
| R | $R_1$ | $n_2$ | $CO_2A$ | R | $R_1$ | $n_2$ | $CO_2A$ |
|---|---|---|---|---|---|---|---|
| " | 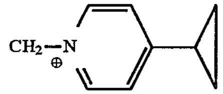 | " | " | " | 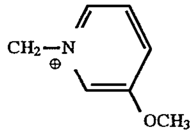 | " | " |
| " | 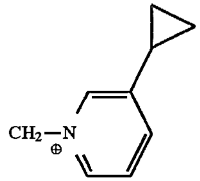 | " | " | " | 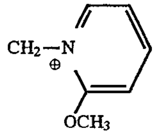 | " | " |
| " | 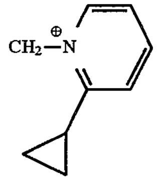 | " | " | " | 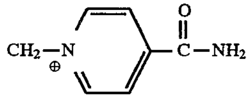 | " | " |
| " | 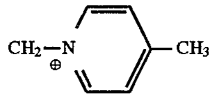 | " | " | " | 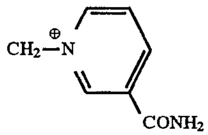 | " | " |
| " | 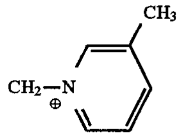 | " | " | " | 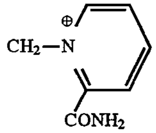 | " | " |
| " | 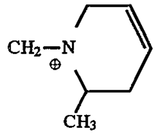 | " | " | " | 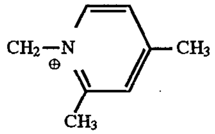 | " | " |

-continued
| R | $R_1$ | $n_2$ | $CO_2A$ | R | $R_1$ | $n_2$ | $CO_2A$ |
|---|---|---|---|---|---|---|---|
| " | 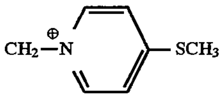 | " | " | " | 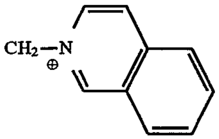 | " | " |
| " | 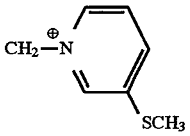 | " | " | " | 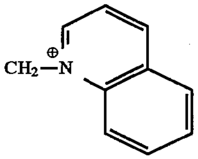 | " | " |
| 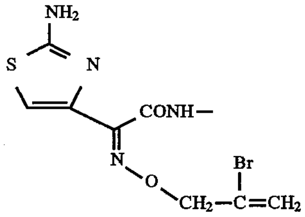 | 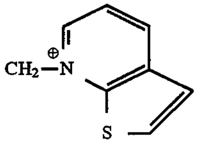 | 0 | $CO_2^{\ominus}$ | 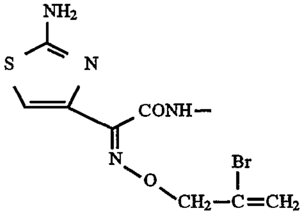 | 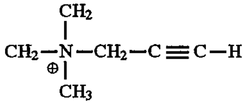 | 0 | $CO_2^{\ominus}$ |
| " | 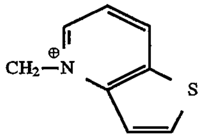 | " | " | " | 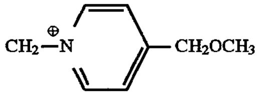 | " | " |
| " | 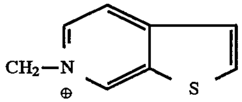 | " | " | " | 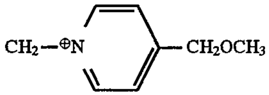 | " | " |
| " | 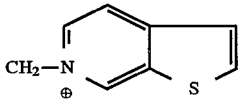 | " | " | " | 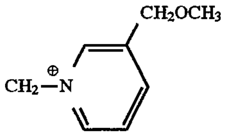 | " | " |

-continued
| R | $R_1$ | $n_2$ $CO_2A$ | R | $R_1$ | $n_2$ $CO_2A$ |
|---|---|---|---|---|---|
| " | 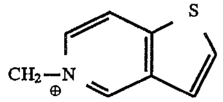 | " " | " | 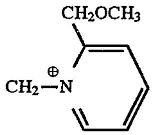 | " " |
| " | 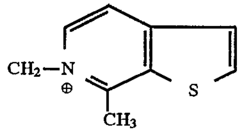 | " " | " | 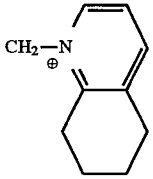 | " " |
| " | 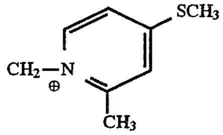 | " " | " | $CH_2NO_2$ | " " |
| " | 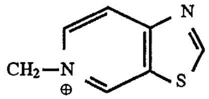 | " " | | | |
| " | $CH_2-\overset{\oplus}{N}(CH_3)_3$ | " " | | | |
| " | 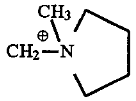 | " " | | | |
| " | 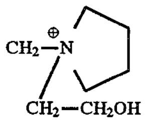 | " " | | | |

-continued
| R | $R_1$ | $n_2$ $CO_2A$ | R | $R_1$ | $n_2$ $CO_2A$ |
|---|---|---|---|---|---|
| 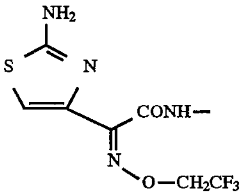 | 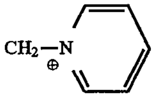 | 0 $CO_2^{\ominus}$ | 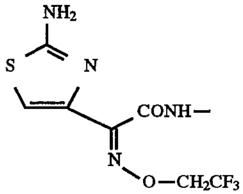 | 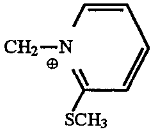 | 0 $CO_2^{\ominus}$ |
| " | 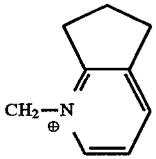 | " " | " | 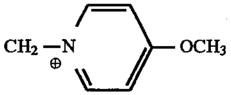 | " " |
| " | 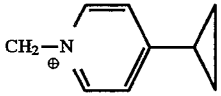 | " " | " | 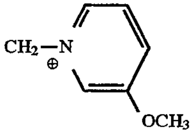 | " " |
| " | 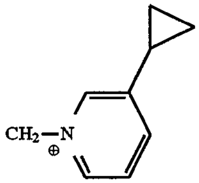 | " " | " | 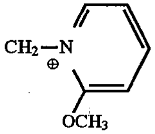 | " " |
| " | 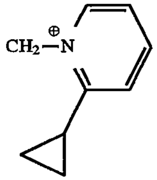 | " " | " | 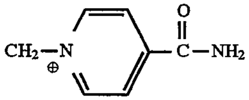 | " " |
| " | 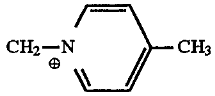 | " " | " | 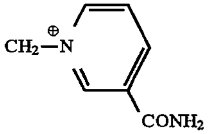 | " " |

-continued
| R | $R_1$ | $n_2$ $CO_2A$ | R | $R_1$ | $n_2$ $CO_2A$ |
| --- | --- | --- | --- | --- | --- |
| " | 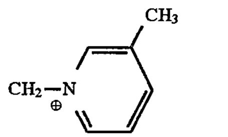 | " " | " | 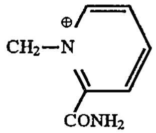 | " " |
| " | 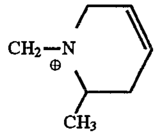 | " " | " | 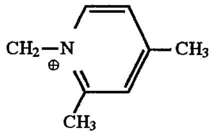 | " " |
| " | 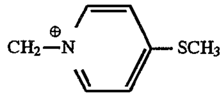 | " " | " | 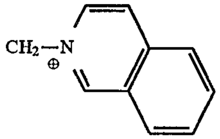 | " " |
| " | 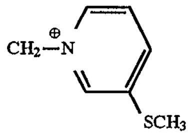 | " " | " | 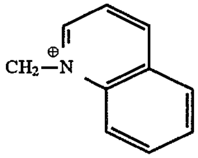 | " " |
| 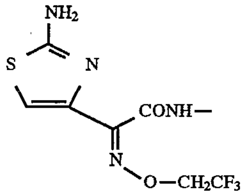 | 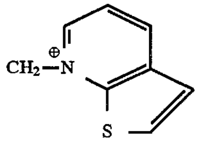 | 0 $CO_2^{\ominus}$ | 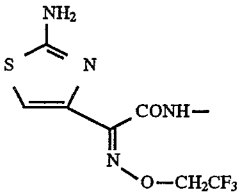 | 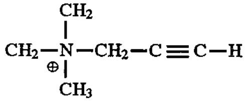 | 0 $CO_2^{\ominus}$ |
| " | 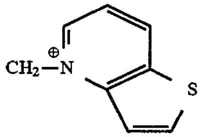 | " " | " | 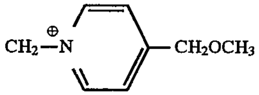 | " " |

-continued
| R | $R_1$ | $n_2$ | $CO_2A$ | R | $R_1$ | $n_2$ | $CO_2A$ |
|---|---|---|---|---|---|---|---|
| " | 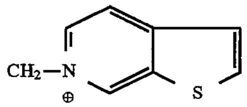 | " | " | " | 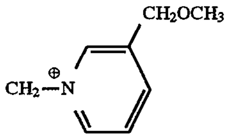 | " | " |
| " | 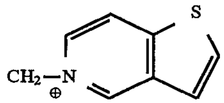 | " | " | " | 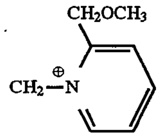 | " | " |
| " | 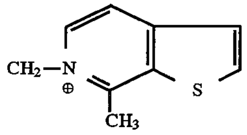 | " | " | " | 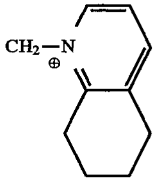 | " | " |
| " | 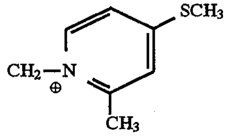 | " | " | " | $CH_2NO_2$ | " | " |
| " | 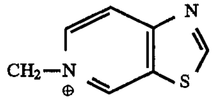 | " | " | | | | |
| " | $CH_2-\overset{\oplus}{N}(CH_3)_3$ | " | " | | | | |
| " | 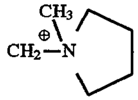 | " | " | | | | |
| " | 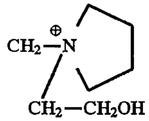 | " | " | | | | |

-continued
| R | $R_1$ | $n_2$ | $CO_2A$ | R | $R_1$ | $n_2$ | $CO_2A$ |
|---|---|---|---|---|---|---|---|
| 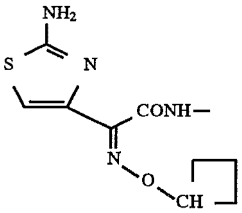 | 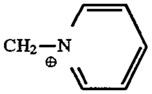 | 0 | $CO_2^{\ominus}$ | 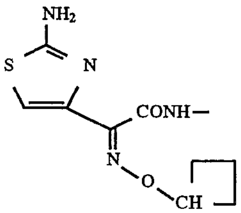 | 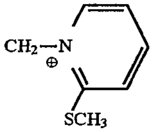 | 0 | $CO_2^{\ominus}$ |
| " | 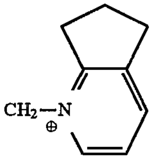 | " | " | " | 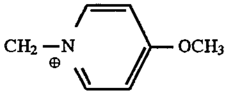 | " | " |
| " | 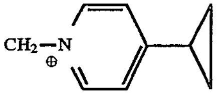 | " | " | " | 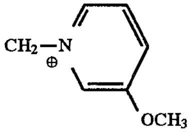 | " | " |
| " | 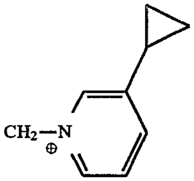 | " | " | " | 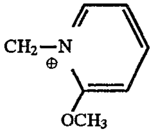 | " | " |
| " | 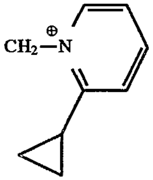 | " | " | " | 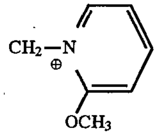 | " | " |
| " | 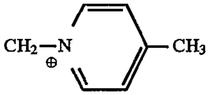 | " | " | " | 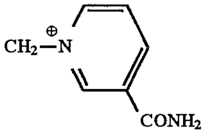 | " | " |

-continued
| R | R₁ | $n_2$ | $CO_2A$ | R | R₁ | $n_2$ | $CO_2A$ |
|---|---|---|---|---|---|---|---|
| " | 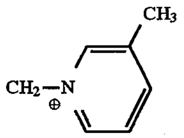 | " | " | " | 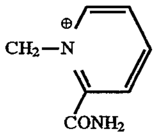 | " | " |
| " | 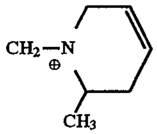 | " | " | " | 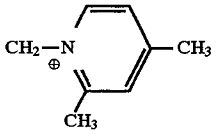 | " | " |
| " | 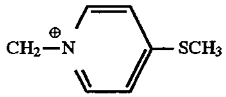 | " | " | " | 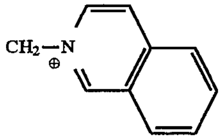 | " | " |
| " | 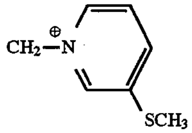 | " | " | " | 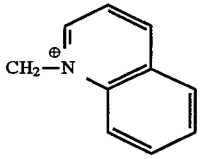 | " | " |
| 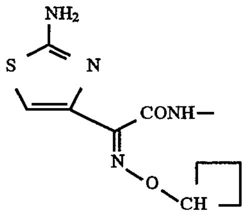 | 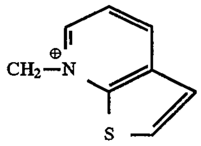 | 0 | $CO_2^{\ominus}$ | 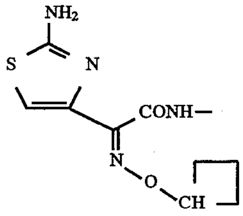 | 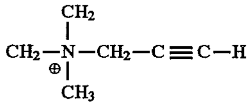 | 0 | $CO_2^{\ominus}$ |
| " | 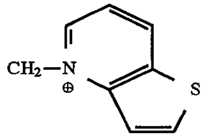 | " | " | " | 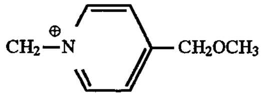 | " | " |

-continued
| R | $R_1$ | $n_2$ | $CO_2A$ | R | $R_1$ | $n_2$ | $CO_2A$ |
|---|---|---|---|---|---|---|---|
| " | 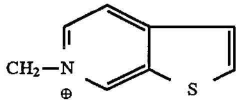 | " | " | " | 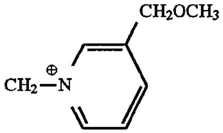 | " | " |
| " | 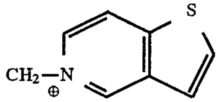 | " | " | " | 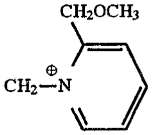 | " | " |
| " | 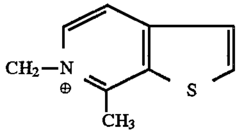 | " | " | " | 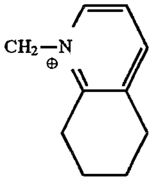 | " | " |
| " | 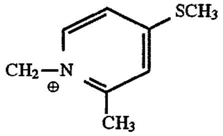 | " | " | " | $CH_2NO_2$ | " | " |
| " | 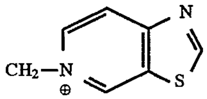 | " | " | | | | |
| " | $CH_2-\overset{\oplus}{N}(CH_3)_3$ | " | " | | | | |
| " | 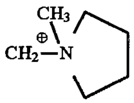 | " | " | | | | |
| " | 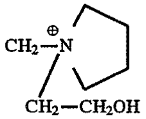 | " | " | | | | |

-continued
| R | $R_1$ | $n_2$ | $CO_2A$ | R | $R_1$ | $n_2$ | $CO_2A$ |
|---|---|---|---|---|---|---|---|
| 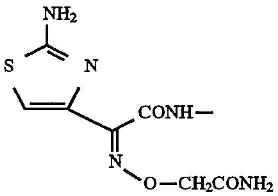 | 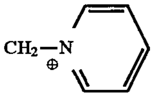 | 0 | $CO_2^{\ominus}$ | 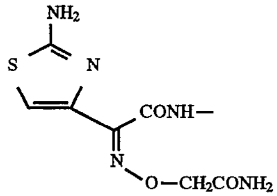 | 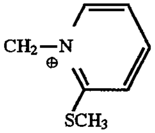 | 0 | $CO_2^{\ominus}$ |
| " | 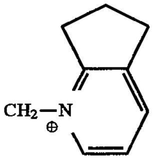 | " | " | " | 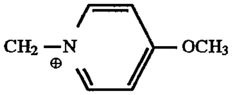 | " | " |
| " | 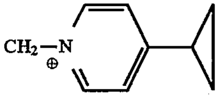 | " | " | " | 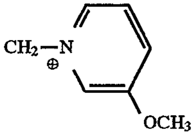 | " | " |
| " | 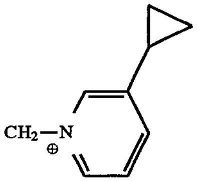 | " | " | " | 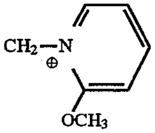 | " | " |
| " | 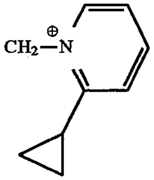 | " | " | " | 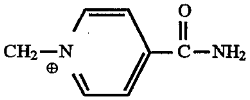 | " | " |
| " | 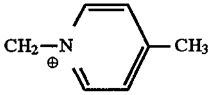 | " | " | " | 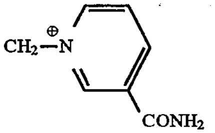 | " | " |

-continued
| R | $R_1$ | $n_2$ | $CO_2A$ | R | $R_1$ | $n_2$ | $CO_2A$ |
|---|---|---|---|---|---|---|---|
| " | 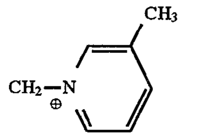 | " | " | " | 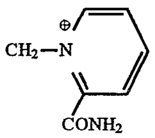 | " | " |
| " | 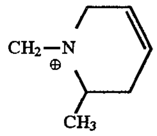 | " | " | " | 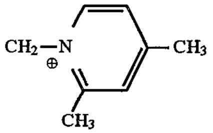 | " | " |
| " | 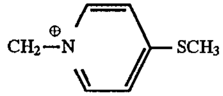 | " | " | " | 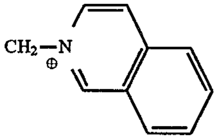 | " | " |
| " | 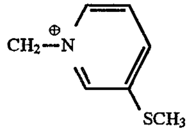 | " | " | " | 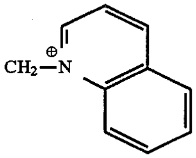 | " | " |
| 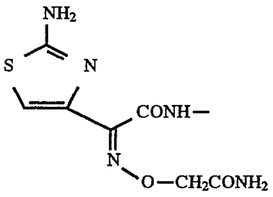 | 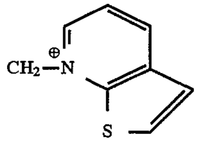 | 0 | $CO_2^{\ominus}$ | 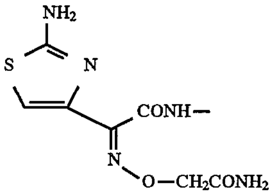 | 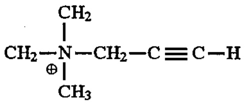 | 0 | $CO_2^{\ominus}$ |
| " | 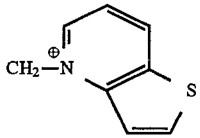 | " | " | " | 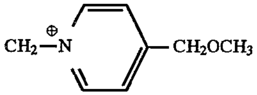 | " | " |

-continued
| R | $R_1$ | $n_2$ | $CO_2A$ | R | $R_1$ | $n_2$ | $CO_2A$ |
|---|---|---|---|---|---|---|---|
| " | 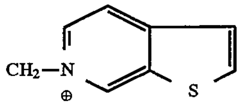 | " | " | " | 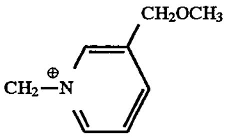 | " | " |
| " | 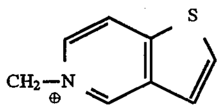 | " | " | " | 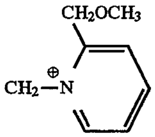 | " | " |
| " | 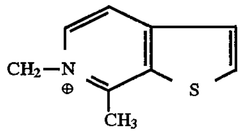 | " | " | " | 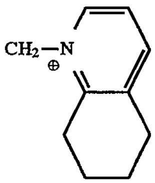 | " | " |
| " | 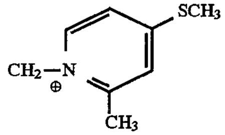 | " | " | " | $CH_2NO_2$ | " | " |
| " | 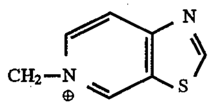 | " | " | | | | |
| " | $CH_2-N(CH_3)_3$ ⊕ | " | " | | | | |
| " | 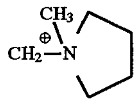 | " | " | | | | |
| " | 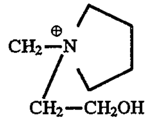 | " | " | | | | |

-continued
| R | $R_1$ | $n_2$ | $CO_2A$ | R | $R_1$ | $n_2$ | $CO_2A$ |
|---|---|---|---|---|---|---|---|
| 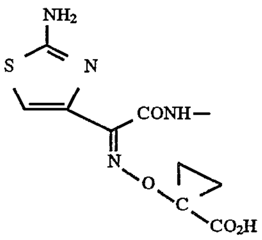 | 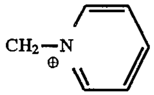 | 0 | $CO_2^{\ominus}$ | 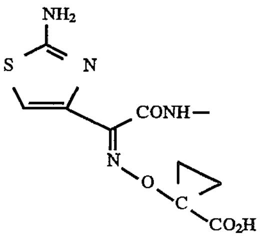 | 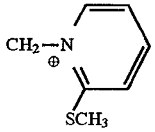 | 0 | $CO_2^{\ominus}$ |
| " | 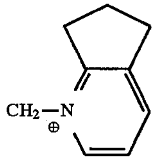 | " | " | " | 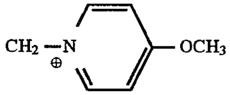 | " | " |
| " | 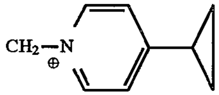 | " | " | " | 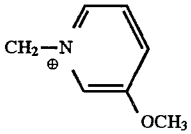 | " | " |
| " | 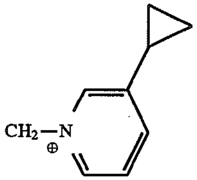 | " | " | " | 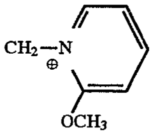 | " | " |
| " | 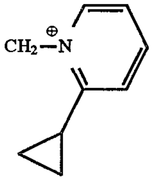 | " | " | " | 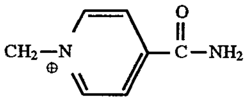 | " | " |
| " | 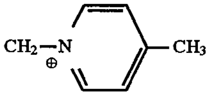 | " | " | " | 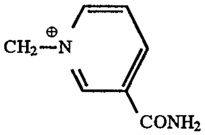 | " | " |

-continued
| R | $R_1$ | $n_2$ | $CO_2A$ | R | $R_1$ | $n_2$ | $CO_2A$ |
|---|---|---|---|---|---|---|---|
| " | 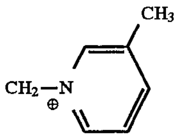 | " | " | " | 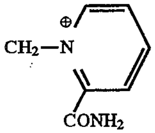 | " | " |
| " | 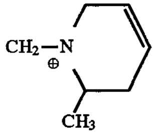 | " | " | " | 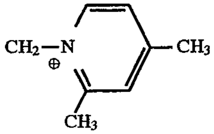 | " | " |
| " | 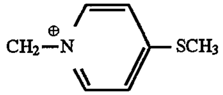 | " | " | " | 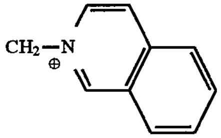 | " | " |
| " | 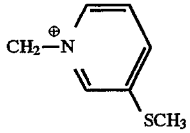 | " | " | " | 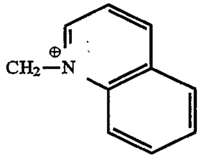 | " | " |
| 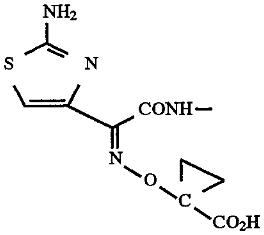 | 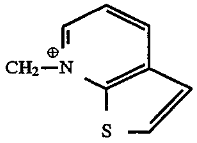 | 0 | $CO_2^{\ominus}$ | 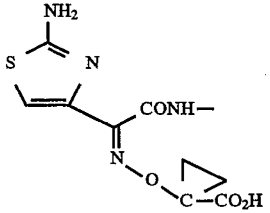 | 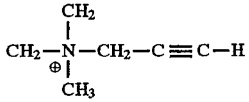 | 0 | $CO_2^{\ominus}$ |
| " | 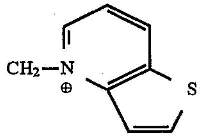 | " | " | " | 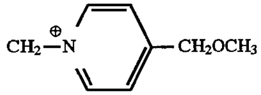 | " | " |

-continued
| R | $R_1$ | $n_2$ | $CO_2A$ | R | $R_1$ | $n_2$ | $CO_2A$ |
|---|---|---|---|---|---|---|---|
| " | 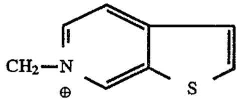 | " | " | " | 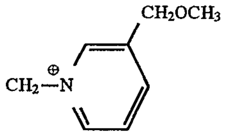 | " | " |
| " | 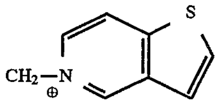 | " | " | " | 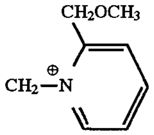 | " | " |
| " | 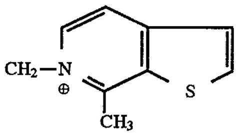 | " | " | " | 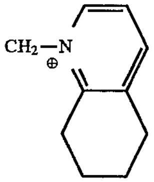 | " | " |
| " | 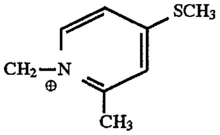 | " | " | " | $CH_2NO_2$ | " | " |
| " | 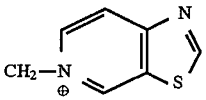 | " | " | | | | |
| " | $CH_2-\overset{\oplus}{N}(CH_3)_3$ | " | " | | | | |
| " | 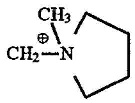 | " | " | | | | |
| " | 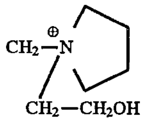 | " | " | | | | |

-continued
| R | $R_1$ | $n_2$ $CO_2A$ | R | $R_1$ | $n_2$ $CO_2A$ |
|---|---|---|---|---|---|
| 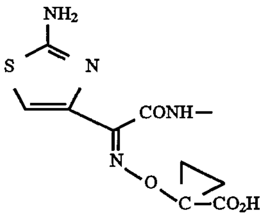 | 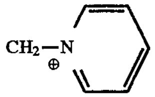 | 0 $CO_2^{\ominus}$ | 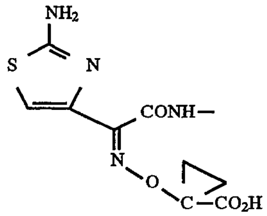 | 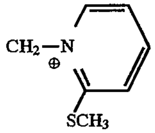 | 0 $CO_2^{\ominus}$ |
| " | 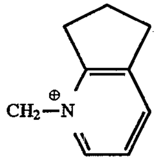 | " " | " | 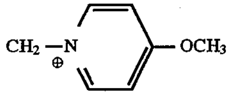 | " " |
| " | 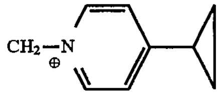 | " " | " | 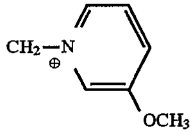 | " " |
| " | 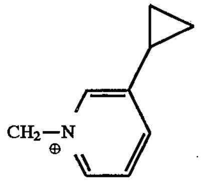 | " " | " | 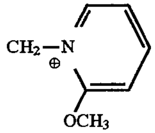 | " " |
| " | 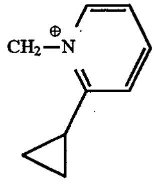 | " " | " | 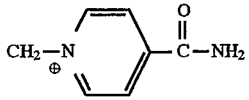 | " " |
| " | 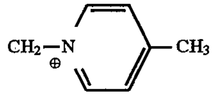 | " " | " | 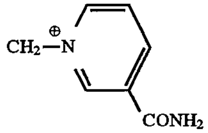 | " " |

-continued
| R | $R_1$ | $n_2$ | $CO_2A$ | R | $R_1$ | $n_2$ | $CO_2A$ |
|---|---|---|---|---|---|---|---|
| " | 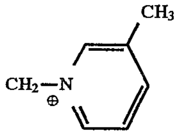 | " | " | " | 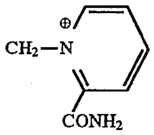 | " | " |
| " | 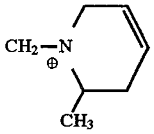 | " | " | " | 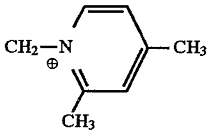 | " | " |
| " | 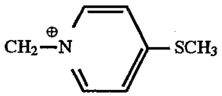 | " | " | " | 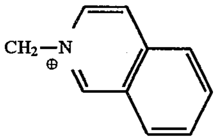 | " | " |
| " | 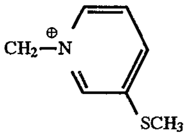 | " | " | " | 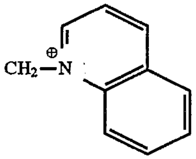 | " | " |
| 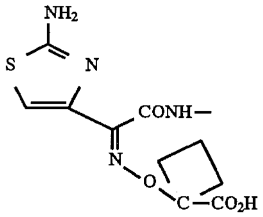 | 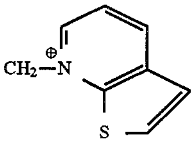 | 0 | $CO_2^{\ominus}$ | 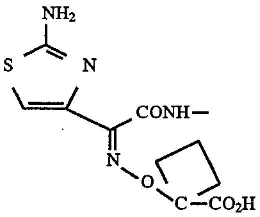 | 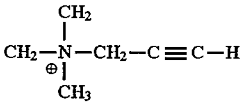 | 0 | $CO_2^{\ominus}$ |
| " | 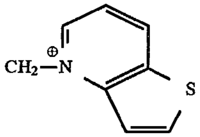 | " | " | " | 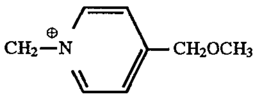 | " | " |

-continued
| R | $R_1$ | $n_2$ $CO_2A$ | R | $R_1$ | $n_2$ $CO_2A$ |
|---|---|---|---|---|---|
| " | 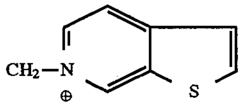 | " " | " | 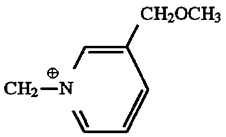 | " " |
| " | 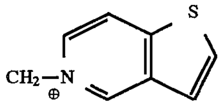 | " " | " | 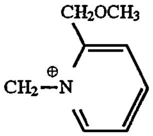 | " " |
| " | 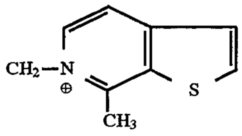 | " " | " | 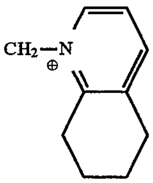 | " " |
| " | 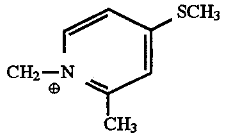 | " " | " | $CH_2NO_2$ | " " |
| " | 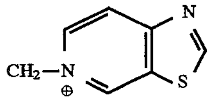 | " " | | | |
| " | $CH_2-\overset{\oplus}{N}(CH_3)_3$ | " " | | | |
| " | 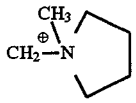 | " " | | | |
| " | 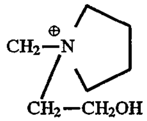 | " " | | | |

-continued
| R | $R_1$ | $n_2$ $CO_2A$ | R | $R_1$ | $n_2$ $CO_2A$ |
| --- | --- | --- | --- | --- | --- |
| 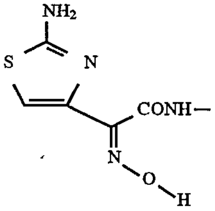 | 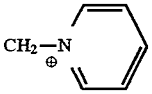 | 0 $CO_2^{\ominus}$ | 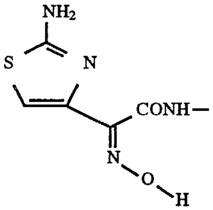 | 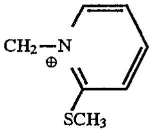 | 0 $CO_2^{\ominus}$ |
| " | 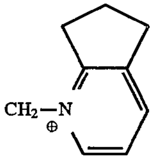 | " " | " | 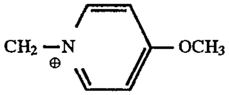 | " " |
| " | 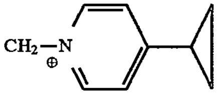 | " " | " | 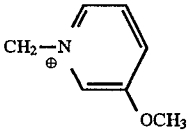 | " " |
| " | 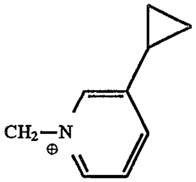 | " " | " | 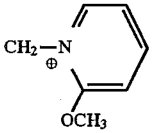 | " " |
| " | 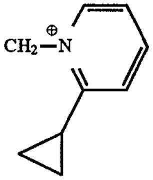 | " " | " | 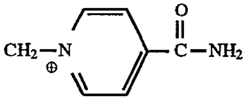 | " " |
| " | 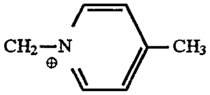 | " " | " | 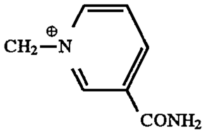 | " " |

-continued
| R | $R_1$ | $n_2$ | $CO_2A$ | R | $R_1$ | $n_2$ | $CO_2A$ |
|---|---|---|---|---|---|---|---|
| " | 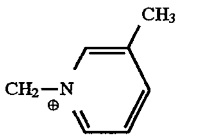 | " | " | " | 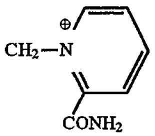 | " | " |
| " | 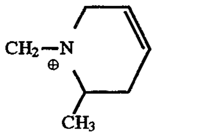 | " | " | " | 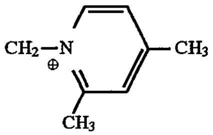 | " | " |
| " | 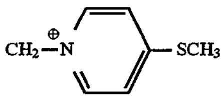 | " | " | " | 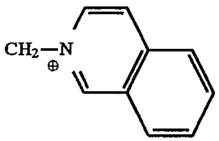 | " | " |
| " | 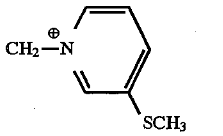 | " | " | " | 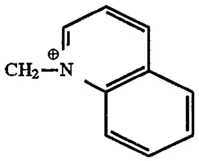 | " | " |
| 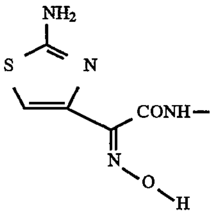 | 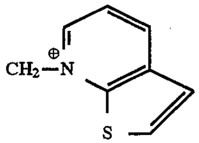 | 0 | $CO_2^{\ominus}$ | 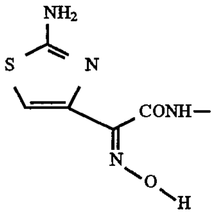 | 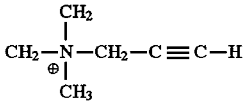 | 0 | $CO_2^{\ominus}$ |
| " | 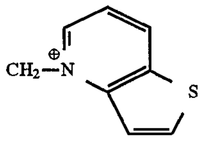 | " | " | " | 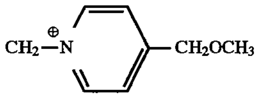 | " | " |

-continued
| R | $R_1$ | $n_2$ | $CO_2A$ | R | $R_1$ | $n_2$ | $CO_2A$ |
|---|---|---|---|---|---|---|---|
| " | 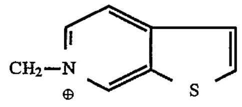 | " | " | " | 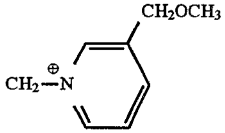 | " | " |
| " | 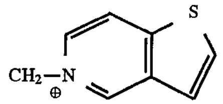 | " | " | " | 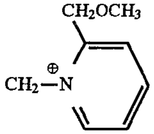 | " | " |
| " | 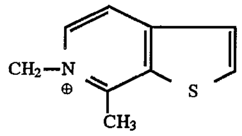 | " | " | " | 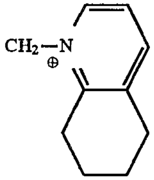 | " | " |
| " | 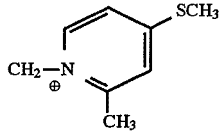 | " | " | " | $CH_2NO_2$ | " | " |
| " | 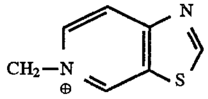 | " | " | | | | |
| " | $CH_2-\overset{\oplus}{N}(CH_3)_3$ | " | " | | | | |
| " | 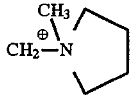 | " | " | | | | |
| " | 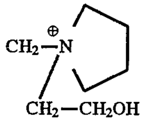 | " | " | | | | |

In the following examples there are described several preferred embodiments to illustrate the invention. However, it is to be understood that the invention is not intended to be limited to the specific embodiments.

EXAMPLE 1

Syn isomer of racemic cis 7-[2-(2-aminothiazol-4-yl)-2-methoxyimino-acetamido]-8-oxo-4-thia-3-methoxymethyl-1-azabicyclo [4,2,0]oct-2-ene-2-carboxylic acid STEP A: Methoxyacetaldehyde 100 ml of methoxyacetaldehyde dimethyketal, 100 ml of water and 3.2 ml of concentrated hydrochloric acid were refluxed and then several fractional distillations were carried out to obtain 8.7 g of the methoxyacetaldehyde.

STEP B: 1,1-dimethylethyl-2-chloro-3-methoxymethyloxirane carboxylate

A mixture composed of 2.106 g of methoxyacetaldehyde, 3.8 ml of tert.-butyl dichloroacetate and 25 ml of tetrahydrofuran was cooled to −20° C. and over 15 minutes, 29 ml of potassium tert.-butylate in tetrahydrofuran (0.9M/l) were introduced. The mixture stood for 1 hour 20 minutes after which 25 ml of ether and 25 ml of water were added. The mixture was extracted with ether and the organic phase was washed with water saturated with sodium chloride, then dried and concentrated to dryness under reduced pressure. The residue was chromatographed on silica and eluted with methylene chloride to obtain 1.44 g of 1,1-dimethylethyl-2-chloro-3-methoxymethyloxirane carboxylate.

STEP C: 1,1-dimethylethyl 7-[2- (2-tritylaminothiazol-4-yl) -2-methoxyimino-acetamido]-8-oxo-2-hydroxy-3-methoxymethyl-4-thia-1-azabicyclo[4,2,0]octane-2-carboxylate 1.38 g of 1,1-dimethylethyl-2-chloro-3-methoxymethyloxirane-carboxylate 2.736 g of the syn isomer of racemic cis 4-mercaptomethyl-3-[2-(2-tritylaminothiazol-4-yl)-2-methoxyimino-acetamido]-2-oxo-1-azetidine [prepared by the process described in Belgian patent No. 894,795] and 12 ml of dimethylformamide were mixed together and after 10 minutes of contact, 458 mg of lithium carbonate were added. The mixture was stirred for 2 hours 50 minutes and was then poured into 100 ml of water and 60 ml of ethyl acetate. After extraction with ethyl acetate, the organic phase was washed with water, dried and concentrated to dryness under reduced pressure and the residue was taken up in ether to obtain 3.058 g of 1,1-dimethylethyl 7-[2-(2-tritylaminothiazol-4-yl)-2-methoxyimino-acetamido]-8-oxo-2-hydroxy-3-methoxymethyl-4-thia-1-azabicyclo[4,2,0]octane-2-carboxylate.

Analysis: $C_{38}H_{41}O_7N_5S_2$; molecular weight=743.91 Calculated: % C 61.35 % H 5.56 % N 9.41 % S 8.62 Found: 61.1 5.7 8.9 8.4

STEP D: 1,1-dimethylethyl 7-[2-(2-tritylaminothiazol-4-yl)-2-methoxyimino-acetamido]-8-oxo-3-methoxymethyl-4-thia-1-azabicyclo[4,2,0]oct-2-ene-2-carboxylate 4,44 g of diphosphorus tetraiodide suspended in 35 ml of pyridine was stirred for 5 minutes and then 3.058 g of 1,1-dimethylethyl 7-[2-(2-tritylaminothiazol-4-yl)-2-methoxyimino-acetamido]-8-oxo-2-hydroxy-3-methoxymethyl-4-thia-1-azabicyclo[4,2,0]octane-2-carboxylate were added all at once and the mixture was stirred for 2 hours 40 minutes. The pyridine was distilled off and the residue was taken up in 50 ml of ethyl acetate. The mixture was filtered, and 50 ml of N hydrochloric acid were added to the liltrate which was vigorously stirred. The organic phase was decanted, washed with water, dried and concentrated to dryness under reduced pressure. The residue was chromatographed on silica with a methylene chloride-ethyl acetate mixture (85–15) and the recovered fractions were concentrated to dryness and crystallized from methanol to obtain 703 mg of 1,1-dimethylethyl 7-[2-(2-tritylaminothiazol-4-yl)-2-methoxyimino-acetamido]-8-oxo-3-methoxymethyl-4-thia-1-azabicyclo[4,2,0]oct-2-ene-2-carboxylate.

Analysis: $C_{38}H_{39}O_6N_5S_2$; molecular weight=725.89 Calculated: % C 62.88 % H 5.41 % N 9.65 % S 8.83 Found: 62.7 5.4 9.6 8.8

STEP E: Syn isomer of racemic cis 7-[2-(2-aminothiazol-4-yl)-2-methoxyimino-acetamido]-8-oxo-4-thia-3-methoxymethyl-1-azabicyclo [4,2,0]oct-2-ene-2-carboxylic acid 246 mg of 1,1-dimethylethyl 7-[2-(2-tritylaminothiazol-4-yl)-2-methoxyimino-acetamido-8-oxo-3-methoxymethyl-4-thia-1-azabicyclo[4,2,0]oct-2-ene-2-carboxylate dissolved in 1 ml of trifluoroacetic acid were left in contact for 50 minutes at ambient temperature and 12 ml of isopropyl ether were added. The precipitate formed was filtered to obtain 176 mg of crude trifluoroacetate which were dissolved in ethanol. 2 drops of pyridine were added and then crystallization was allowed for one hour to obtain 88 mg of syn isomer of racemic cis 7-[2-(2-aminothiazol-4-yl)-2-methoxyimino-acetamido]-8-oxo-4-thia-3-methoxymethyl-1-azabicyclo[4,2,0]oct-2-ene-1-carboxylic acid.

Analysis: $C_{15}H_{17}O_6N_5S_2$; molecular weight=427.46 Calculated: % C 42.15 % H 4.01 % N 16.38 % S 15.00 Found: 42.2 4.0 16.2 15.0

EXAMPLE 2

4-oxide of the syn isomer of racemic cis 7-[2-(2-aminothiazol-4-yl)-2-methoxyimino-acetamido]-8-oxo-4-thia-3-methoxymethyl-1-azabicyclo[4,2,0]oct-2-ene-2-carboxylic acid STEP A: 4-oxide of 1,1-dimethylethyl 7-[2-(2-tritylaminothiazol-4-yl)-2-methoxyimino-acetamido]-8-oxo-3-methoxymethyl-4-thia-1-azabicyclo[4,2,0]oct-2-ene-2-carboxylate.

660 mg of 1,1-dimethylethyl 7-[2-(2-tritylaminothiazol-4-yl)-2-methoxyimino-acetamido-8-oxo-3-methoxymethyl-4-thia-1azabicyclo[4,2,0]oct-2-ene-2-carboxylate and 257 mg of 85% m-chloroperbenzoic acid were dissolved in 9 ml of methylene chloride and agitated for 1 hour. Water was added followed by 2 ml of a saturated solution of sodium bicarbonate. Extraction was with methylene chloride and the organic phase was dried and concentrated to dryness under reduced pressure. The residue was chromatographed on silica and eluted with a mixture of methylene chloride and ethyl acetate (1—1) to obtain 515 mg of 4-oxide of 1,1-dimethylethyl 7-[2-(2-tritylaminothiazol-4-yl)-2-methoxyimino-acetamido]-8-oxo-3-methoxymethyl-4-thia-1-azabicyclo[4,2,0]oct-2-ene-2-carboxylate (α-isomer)

STEP B: 4-oxide of the syn isomer of racemic cis 7-[2-(2-aminothiazol-4-yl)-2-methoxyimino-acetamido]-8-oxo-4-thia-3-methoxymethyl-1-azabicyclo[4,2,0]oct-2-ene-2-carboxylic acid By operating as in Step E of Example 1, 515 mg of the said α-isomer and 2.1 ml of trifluoroacetic acid were reacted to obtain 168 mg of 4-oxide of the syn isomer of racemic cis 7-[2-(2-aminothiazol-4-yl)-2-methoxyimino-acetamido]-8-oxo-4-thia-3-methoxymethyl-1-azabicyclo[4,2,0]oct-2-ene-2-carboxylic acid.

Analysis: $C_{15}H_{17}O_7N_5S_2$; molecular weight=443.46 Calculated: % C 40.63 % H 3.86 % N 15.79 % S 14.46 Found: 40.7 3.9 15.5 14.2

EXAMPLE 3

Syn isomer of racemic cis 7-[2-(2aminothiazol-4yl)-2-methoxyimino-acetamido]-8-oxo-3-[(2-pyridyl) thio]-4-thia-1-azabicyclo[4,2,0]oct-2-ene-2-carboxylic acid STEP A: 1,1-dimethylethyl 7-[2-(2-tritylaminothiazol-4-yl)-2-methoxyimino-acetamido]-8-oxo-3-[(2-pyridyl)thio]-4-thia-1-azabicyclo[4,2,0]octane-2-carboxylate Preparation of 2-pyridylsulfenyl chloride (Harp. et al., Synthesis 181 (1979).

A mixture of 2.31 g of 98% 2,2'-dipyridyl-disulfide in 25 ml of carbon tetrachloride and 2 drops of triethylamine was cooled to 0° C. with stirring and then over half-an-hour and at 0° C., 1.489 g of sulfuryl chloride in solution in 15 ml of carbon tetrachloride were introduced with stirring for a further half-an-hour at 0° C. The solution was decanted and the organic phase was evaporated to dryness under reduced pressure to obtain 2.85 g of crude unstable product. A solution of 1.60 g of 2-pyridyl-sulfenyl chloride in 25 ml of methylene chloride was added over 15 minutes to 1.70 g of 1,1-dimethylethyl 3-diazopyruvate in 50 ml of methylene chloride and the mixture was stirred for 45 minutes at ambient temperature under an inert atmosphere. A solution of 1,1-dimethylethyl 3-chloro-3-(2-pyridyl)-thio-pyruvate was obtained to which 5.18 g of 4-mercaptomethyl-3-[2-(2-tritylaminothiazol-4-yl)-2-methoxyimino-acetamido]-2-oxo-1-azetidine were added all at once followed by 1.5 ml of triethylamine. The mixture was stirred for 2 hours at ambient temperature and was filtered to remove the insoluble matter and the filtrate was poured into 350 ml of water and 10 ml of 2N hydrochloric acid. After decanting the organic phase was washed with water, treated with active charcoal and dried and concentrated to dryness under reduced pressure. The residue was chromatographed on silica with elution with a mixture of methylene chloride and ethyl acetate (75–25) to obtain 4.22 g of 1,1-dimethylethyl 7-[2-(2-tritylaminothiazol-4-yl)-2-methoxyimino-acetamido]-8-oxo-3-[(2-pyridyl)thio]-4-thia-1-azabicyclo [4,2,0]octane-2-hydroxy-2-carboxylate.

STEP B: 1,1-dimethylethyl 7-[2-(2-tritylaminothiazol-4-yl)-2-methoxyimino-acetamido]-8-oxo-3-[(2-pyridyl)thio]-4l-thia-1-azabicyclo[4,2,0]oct-2-ene-2-carboxylate To 395 mg of the product obtained above dissolved in 5 ml of pyridine, 556 mg of diphosphorous tetraiodide were added with stirring over 2 hours 30 minutes under an inert atmosphere. 5 ml of ethyl acetate were added and the insoluble matter was filtered off. The filtrate was evaporated to dryness under reduced pressure and the residue was taken up by 25 ml of methylene chloride. After washing with water, drying and concentrating to dryness under reduced pressure, the residue was chromatographed on silica with elution with a mixture of methylene chloride-ethyl acetate to obtain 106.5 g of 1,1-dimethlylethyl 7-[2-(2-tritylaminothiazol-4-yl)-2-methoxyimino-acetamido]-8-oxo-3-[(2-pyridyl)thio]-4-thia-1-azabicyclo [4,2,0]oct-2-ene-2-carboxylate melting at 160° C.

STEP C: Syn isomer of racemic cis 7-[2-(2-aminothiazol-4-yl)-2-methoxyimino-acetamido]-8-oxo-3-[(2-pyridyl) thio]-4-thia-1-azabicyclo[4,2,0]oct-2-ene-2-carboxylic acid 237.3 mg of the product of Step B and 3 ml of 66% formic acid were heated at 60° C. for 2 hours 30 minutes and after diluting with 3 ml of water, the insoluble matter was separated and the filtrate was concentrated to dryness at 60° C. under reduced pressure and the residue was taken up in 6 ml of water. The solution was evaporated again and treated twice with 6 ml of a mixture of acetonitrile-ethanol (1—1), evaporating on each occasion to eliminate the water to obtain 160 mg of product which were taken up in 7 ml of anhydrous ether and 0.3 ml of acetonitrile. The mixture was left to rest for 1 hour, after which it was filtered and washed with ether to obtain 120 mg of syn isomer of racemic cis 7-[2-(2-aminothiazol-4-yl)-2-methoxyimino-acetamido]-8-oxo-3-[(2-pyridyl)thio]-4-thia-1-azabicyclo[4,2,0]oct-2-ene-2-carboxylic acid melting at ≈230° C. (decomposed)

IR Spectrum Nujol

Absence of trityl Presence of lactam, C=0 1766 $cm^{-1}$ C=0 1663 $cm^{-1}$

UV Spectrum in EtOH max: 335 nm max: 299–300 nm in EtOH - HCl 0.1N infl: 310 nm.

EXAMPLE 4

Syn isomer of racemic cis 7-[2-(2-aminothiazol-4-yl)-2-methoxyimino-acetamido]-8-oxo-3-[(4-nitrophenyl)methylthio]-4-thia-1-azabicyclo[4,2,0] oct-2-ene-2-carboxylic acid STEP A: Syn isomer of racemic cis 1,1-dimethylethyl 7-[2-(2-tritylaminothiazol-4-yl)-2-methoxyimino-acetamido]-2-hydroxy-3-[(4-nitrophenyl)methylthio]-8-oxo-4-thia-1-azabicyclo[4,2,0]octane-2-carboxylate Using the procedure of Step A of Example 3, 925 mg of 4,4'-dinitrobenzyl disulfide [described in Chem. Ber., Vol. 88, 1995 (1955)], 2.75 mmole of chlorine, 1.12 g of 1,1-dimethylethyl diazopyruvate, 1.23 g of syn isomer of racemic cis 3-[2-(2-tritylaminothiazol-4-yl)-2-methoxyimino-acetamido]-2-oxo-1-azeetidine and 0.77 ml of triethylamine were reacted to obtain 1.07 g of syn isomer of racemic cis 1,1-dimethylethyl 7-[2- (2-tritylaminothiazol-4-yl)-2-methoxyimino-acetamido]-2-hydroxy-3-[(4-nitrophenyl) methylthio]-oxo-4-thia-1-azabicyclo[4,2,0]octane-2-carboxylate.

STEP B: Syn isomer of racemic cis 1,1-dimethylethyl 7-[2-(2-tritylaminothiazol-4-yl)-2-methoxyimino-acetamido]-3-[(4-nitrophenyl)methylthio]-8-oxo-4-thia-1-azabicyclo[4,2,0]oct-2-ene-2-carboxylate By operating as in Step B of Example 3, 922 mg of the product of Step A and 1.21 g of diphosphorous tetraiodide in 10 ml of pyridine were reacted and after chromatography, 339 mg of syn isomer of racemic cis 1,1-dimethylethyl 7-[2-(2-tritylaminothiazol-4-yl)-2-methoxyimino-acetamido-3-[(4-nitrophenyl) methylthio]-8-oxo-4-thia-1-azabicyclo[4,2,0]oct-2-ene-2-carboxylate were obtained.

STEP C: Syn isomer of racemic cis 7-[2-(2-aminothiazol-4-yl)-2-methoxyimino-acetamido]-8-oxo-3-[4-nitrophenyl) methylthio]-4-thia-1-azabicyclo[4,2,0]oct-2-ene-2-carboxylic acid 200 mg of the product of Step B in 4 ml of 66% aqueous formic acid were stirred for three hours, then cooled, filtered and evaporated under reduced pressure. The residue was re-dissolved in 10 ml of acetonitrile and 5 ml of methanol and the solution was evaporated, 5 ml of methylene chloride and 1 ml of methanol were added to the residue and suspension was stirred over night and then filtered. The product was dried under vacuum to obtain 103 mg of syn isomer of racemic cis 7-[2-(2-aminothiazol-4-yl)-2-methoxyimino-acetamido]-8-oxo-3-[4-nitrophenyl) methylthio]-4-thia-1-azabicyclo[4,2,0]oct-2-ene-2-carboxylic acid.

UV Spectrum: (ethanol)

infl: 233 nm $E_1^1$=434 infl: 257 nm $E_1^1$=356 ε=19600 max: 294 $E_1^1$=353 ε=19400

EXAMPLE 5

Syn isomer of racemic cis 7-[2-(2-aminothiazol-4-yl)-2-methoxyimino-acetamido]-8-oxo-3-(isopropyl)-4-thia-1-azabicyclo[4,2,0]oct-2-ene-2-carboxylic acid STEP A: 1,1-dimethylethyl 2-chloro-3-(isopropyl) oxirane carboxylate 9.25 g of tert.-butyl dichloroacetate and 5 ml of isobutyraldehyde were cooled to −20° C. and 50 ml of 1M/l of potassium tert.-butylate in tetrahydrofuran were added over 20 minutes. The temperature of the medium was allowed to rise over 1 hour 25 minutes and 50 ml of water and 50 ml of ether were added. After extraction with ether, the organic solution was washed with water saturated with sodium chloride, dried and concentrated to dryness under reduced pressure to obtain 10.7 g of 1,1-dimethylethyl 2-chloro-3-(isopropyl) oxirane carboxylate.

STEP B: 1,1-dimethylethyl 3-bromo-4-methyl-2-oxopentanoate 16.2 g of anhydrous lithium bromide were introduced into 20.5 ml of tetrahydrofuran. After dissolving and cooling to 27° C., 10.2 g of 1,1-dimethylethyl 2-chloro-3-(isopropyl) oxirane carboxylate were added and the mixture was left in contact for half-an-hour. The reaction mixture was then poured into 90 ml of a half-saturated aqueous solution of sodium chloride and the mixture was extracted with ether. The organic phase was dried and concentrated to dryness under reduced pressure to obtain 8.9 g of 1,1-dimethylethyl 3-bromo-4-methyl-2-oxopentanoate containing 12% of the chlorated homog.

STEP C: 1,1-dimethylethyl 7-[2-(2-tritylaminothiazol-4-yl)-2-methoxyimino-acetamido]-8-oxo-3-(isopropyl)-4-thia-1-azabicyclo[4,2,0]oct-2-ene-2-carboxylate 0.34 ml of triethylamine were added drop by drop to a stirred suspension of 1.2 g of syn isomer of racemic cis 4-mercaptomethyl-3-[2-(2-tritylaminothiazol-4-yl)-2-methoxyimino-acetamido]2-oxo-1-azetidine, 15 ml of dichloromethane and 636 mg of 1,1-dimethylethyl 3-bromo-4-methyl-2-oxo-pentanoate. After half-an-hour, 1.25 ml of pyridine were added, and then 2.67 ml of a solution of phosphorus tribromide in methylene chloride (0.48 ml $PBr_3$ diluted with 10 ml of $Cl_2CH_2$) was added dropwise and left in contact for 45 minutes. 18 ml of N hydrochloric acid were added, and the mixture was extracted with methylene chloride. The organic phase was dried and concentrated to dryness udder reduced pressure. After chromatographying the residue on silica and eluting with methylene chloride with 10% of ethyl acetate, 374 mg of product were obtained which were crystallized from an ether-isopropyl ether mixture to obtain 293 mg of 1,1-dimethylethyl 7-[2-(2-tritylaminothiazol-4-yl)-2-methoxyimino-acetamido]-8-oxo-3-(isopropyl)-4-thia-1-azabicyclo[4,2,0]oct-2-ene-2-carboxylate.

STEP D: Syn isomer of racemic cis 7-[2-(2-aminothiazol-4-yl)-2-methoxyimino-acetamido]-8-oxo-3-(isopropyl)-4-thia-1-azabicyclo[4,2,0]oct-2-ene-2-carboxylic acid 455 mg of the product of Step C and 1.82 ml of trifluoroacetic acid were mixed together and left to rest for 20 minutes. 25 ml of isopropyl ether were added the precipitate formed was separated, then dissolved in 2 ml of water containing 1 ml of sodium bicarbonate in saturated solution with stirring. The insoluble matter was filtered off and 2N hydrochloric acid was added to the filtrate to obtain a pH of 4. After 1 hour, the mixture was filtered and the product was rinsed with water and then with ether to obtain 73 mg of syn isomer of racemic cis 7-[2-(2-aminothiazol-4-yl)-2methoxyimino-acetamido]-81-oxo-3-(isopropyl)-4-thia-1-azabicyclo[4,2,0]oct-2-ene-2-carboxylic acid.

Analysis: $C_{16}H_{19}O_5N_5S_2$; molecular weight=425.49 Calculated: % C 45.17 % H. 4.50 % N 16.46 % S 15.07 Found: 44.6 4.4 16.1 14.2

UV Spectrum EtOH max: 225 nm $E_1^1$ : 465 ε=19800 max: 296 $E_1^1$ : 395 ε=16800

EXAMPLE 6

4-oxide of syn isomer of racemic cis 7-[2-(2-aminothiazol-4-yl) -2-methoxyimino-acetamido]-8-oxo-4-thia-3-(isopropyl)-1-azabicyclo[4,2,0]oct-2ene-2-carboxylic acid STEP A: 4-oxide of 1,1-dimethylethyl 7-[2-(2-tritylaminothiazol-4-yl)-2-methoxyimino-acetamido]-8oxo-4-thia-3-(isopropyl)-1-azabicyclo[4,2,0]oct-2-ene-2-carboxylate Using the procedure of Example 2, 602 mg of 1,1-dimethylethyl 7-[2-(2-tritylaminothiazol-4-yl)-2-methoxyimino-acetamido]-8-oxo-4-thia-3-(isopropyl)-1-azabicyclo[4,2,0]oct-2-ene-2-carboxylate and 235 mg of m-chloro perbenzoic acid were reacted to obtain 317 mg of 4-oxide of 1,1-dimethylethyl 7-[2-(2-tritylaminothiazol-4-yl)-2-methoxyimino-acetamido]-8-oxo-4-thia-3-(isopropyl)-1-azabicyclo[4,2,0]oct-2-ene-2-carboxylate.

STEP B: 4-oxide of syn isomer of racemic cis 7-[2-(2-aminothiazol-4-yl)-2-methoxyimino-acetamido]-8-oxo-4-thia-3-(isopropyl)-1-azabicyclo[4,2,0]oct-2-ene-2-carboxylic acid Using the procedure of Step E of Example 1, 307 mg of the product of Step A and 1.3 ml of trifluoroacetic acid were reacted to obtain 1 48 mg of 4-oxide of syn isomer of racemic cis 7-[2-(2-aminothiazol-4-yl)-2-methoxyimino-acetamido]-8-oxo-4-thia-3-(isopropyl)-1-azabicyclo[4,2,0]-oct-2-ene-2-carboxylic acid.

Analysis: $C_{16}H_{19}O_6N_5S_2$; molecular weight=441.49 Calculated: % C 43.53 % H 4.34 % N 15.86 % S 14.52 Found: 43.9 4.4 15.5 14.1

EXAMPLE 7

Syn isomer of racemic cis 7-[2-(2-aminothiazol-4-yl)-2-methoxyimino-acetamido]-8-oxo-4-thia-3-ethyl-1-azabicyclo[4,2,0]oct-2-ene-2-carboxylic acid STEP A: 1,1-dimethylethyl 2-chloro-3-ethyloxirane carboxylate 4 ml of tert.-butyl dichloroacetate and 2 ml of propanal diluted with 2 ml of tetrahydrofuran were mixed together and cooled to −20° C. 28 ml of 0.9M/l of potassium tert.-butylate in tetrahydrofuran were introduced over 12 minutes and at −20° C. followed by allowing the temperature to rise to 20° C. over 1 hour 20 minutes. 25 ml of ether and 25 ml of water were added, followed by stirring, decanting, and re-extracting with ether. The organic phase was washed with water saturated with sodium chloride, then dried and concentrated to dryness to obtain 4.7 g of 1,1-dimethylethyl 2-chloro-3-ethyloxirane carboxylate.

STEP B: 1,1-dimethylethyl 7-[2-(2-tritylaminothiazol-4-yl)-2-methoxyimino-acetamido]-8-oxo-3-ethyl-2-hydroxy-4-thia-1-azabicyclo[4,2,0]octane-2-carboxylate 1.157 g of 1,1-dimethylethyl 2-chloro-3-ethyloxirane carboxylate and 2.39 g of syn isomer of racemic cis 4-mercaptomethyl-3-[2-(2-tritylaminoethiazol-4-yl)-2-methoxyimino-acetamido]-2-oxo-1-azetidine in 10 ml of dimethylformamide were stirred and 414 mg of lithium carbonate were added and the mixture was left in contact for 2 hours. The reaction mixture was poured into 100 ml of water and then was extracted with ethyl acetate. The organic phase was washed with water, dried and concentrated to dryness under reduced pressure. The residue was taken up in isopropyl ether and after several hours was filtered to obtain 3.197 g of 1,1-dimethylethyl 7-[2-(2-tritylaminothiazol-4- yl)-2-methoxyimino-acetamido]-8-oxo-3-ethyl-2-hydroxy-4-thia-1-azabicyclo[4,2,0]octane-2-carboxylate.

Analysis: $C_{38}H_{41}O_6N_5S_2$; molecular weight=727.91 Calculated: % C 62.70 % H 5.68 % N 9.62 % S 8.81 Found: 62.2 5.7 9.3 8.6

STEP C: 1,1-dimethylethyl 7-[2-(2-tritylaminothiazol-4-yl)-2-methoxyimino-acetamido]-8-oxo-31-ethyl-4-thia-1-azabicyclo[4,2,0]oct-2-ene-2-carboxylate.

Using the procedure of Example 1, 560 mg of diphosphorous tetraiodide, 4.5 ml of pyridine and 394 mg of the product of Step B were reacted to obtain 125 mg of 1,1-dimethylethyl 7-[2-(2-tritylaminothiazol-4-yl)-2-methoxyimino-acetamido]-8-oxo-3-ethyl-4-thia-1-azabicyclo[4,2,0]oct-2-ene-2-carboxylate.

Analysis: $C_{38}H_{39}O_5N_5S_2$; molecular weight=709.89 Calculated: % C 64.29 % H 5.54 % N 9.86 % S 9.03 Found: 63.9 5.6 9.7 8.8

STEP D: Syn isomer of racemic cis 7-[2-(2-aminothiazol-4-yl)-2-methoxyimino-acetamido]-8-oxo-4-thia-3-ethyl-1-azabicyclo[4,2,0]oct-2-ene-2-carboxylic acid 155 mg of syn isomer of racemic cis 7-[2-(2-aminothiazol-4-yl)-2-methoxyimino-acetamido]-8-oxo-4-thia-3-ethyl-1-azabicyclo[4,2,0]oct-2-ene-2-carboxylic acid were obtained by using the procedure of Step E of Example 1 starting with 489 mg of the product of Step C and 1.95 ml of trifluoroacetic acid.

EXAMPLE 8

4-oxide of syn isomer of racemic cis 7-[2-(2-aminothiazol-4-yl)-2-methoxyimino-acetamido]-3-ethyl-8-oxo-4-thia-1-azabicyclo[4,2,0]oct-2-ene-2-carboxylic acid STEP A: 4-oxide of 1,1-dimethylethyl 7-[2-(2-tritylaminothiazol-4-yl)-2-methoxyimino-acetamido]-3-ethyl-8-oxo-4-thia-1-azabicyclo[4,2,0]oct-2-ene-2-carboxylate Using the procedure of Example 2, 517 mg of 1,1-dimethylethyl 7-[2-(2-tritylaminothiazol-4-yl)-2-methoxyimino-acetamido]-8-oxo-3-ethyl-4-thia-1-azabicyclo[4,2,0]oct-2-ene-2-carboxylate were reacted to obtain 387 mg of 4-oxide of 1,1-dimethylethyl 7-[2-(2-tritylaminothiazol-4-yl)-2-methoxyimino-acetamido]-3-ethyl-8-oxo-4-thia-1-azabicyclo[4,2,0]oct-2-ene-2-carboxylate.

STEP B: 4-oxide of syn isomer of racemic cis 7-[2-(2-aminothiazol-4-yl)-2-methoxyimino-acetamido]-3-ethyl-8-oxo-4-thia-1-azabicyclo[4,2,0]oct-2-ene-2-carboxylic acid Starting with 366 mg of the product of Step A using the procedure of Step E of Example 1, 86 mg of 4-oxide of syn isomer of racemic cis 7-[2-(2-aminothiazol-4-yl)-2-methoxyimino-acetamido]-3-ethyl-8-oxo-4-thia-1-azabicyclo[4,2,0]oct-2-ene-2-carboxylic acid were obtained.

Analysis: $C_{15}H_{17}O_6N_5S_2$; molecular weight=427.46 Calculated: % C 42.15 % H 4.01 % N 16.38 % S 15.00 Found: 42.6 4.2 16 14.1

UV Spectrum - 0.1N in EtOH/HCl
max: 272 nm, $E_1^1$: 527 ε=22500.

EXAMPLE 9

Syn isomer of racemic cis 7-[2-(2-aminothiazol-4-yl)-2-methoxyimino-acetamido]-8-oxo-3-(2-pyridyl)-4-thia-1-azabicyclo[4,2,0]oct-2-ene-2-carboxylic acid STEP A: 1,1-dimethylethyl 2-chloro-3-(2-pyridyl)oxirane carboxylate 4 ml of tert.-butyl dichloroacetate in 15 ml of tetrahydrofuran and 2.6 ml of picolinaldehyde were mixed together and cooled to −20° C. to −25° C. Over 15 minutes at this temperature, 28 ml of potassium tert.-butylate in tetrahydrofuran at 0.9M/l were introduced and the mixture was allowed to warm up to ambient temperature. After 1 hour and 25 minutes, 25 ml of water were added, and extraction was effected with tetrahydrofuran. The organic phase was washed with water saturated with sodium chloride and then dried. The resulting solution containing 1,1-dimethylethyl 2-chloro-3-(2-pyridyl)oxirane carboxylate was held at −25° C. and used for the following step of the synthesis.

STEPB: 1,1-dimethylethyl 3-[3-[(2-tritylaminothiazol-4-yl)-2-methoxyimino-acetamido]-2-oxo-4-azetidinylmethylthio]-3-(1,2-dihydro-2-pyridinylidene) pyruvate 2.39 g of syn isomer of racemic cis 4-mercaptomethyl-3-[2-(2-tritylaminothiazol-4-yl)-2-methoxyimino-acetamido]-2-oxo-1-azetidine were dissolved in 22 ml of dimethylformamide and 12.8 ml of the solution obtained above were added, followed by 480 ml of lithium carbonate with stirring for 2 hours. The solvent was distilled off and 100 ml of water were added. The mixture was extracted with ethyl acetate and the organic phase was washed with water, dried and concentrated to dryness under reduced pressure. The residue was taken up in ethanol and allowed to crystallize over 2 hours to obtain 2.357 g of 1,1-dimethylethyl 3-[3-[(2-tritylaminothiazol-4-yl)-2-methoxyiminoacetamido]-2-oxo-4-azetidinylmethylthio]-3-(1,2-dihydro-2-pyridinylidene)pyruvate.

Analysis: $C_{41}H_{40}O_6N_6S_2$; molecular weight=776.94 Calculated: % C 63.47 % H 5.07 % N 10.83 % S 8.26 Found: 63.3 5.2 10.7 8.0

STEP C: 1,1-dimethylethyl 7-[2-(2-tritylaminothiazol-4-yl)-2-methoxyimino-acetamido]-8-oxo-2-hydroxy-3-(2-pyridyl)-4-thia-1-azabicyclo[4,2,0]octane-2-carboxylate 3.053 g of the product of Step B and 1.3 g of triethylene diamine were dissolved in 30 ml of methylene chloride and the mixture was stirred for 1 hour and 30 minutes. Then 28 ml of N hydrochloric acid were added and extraction was effected with methylene chloride. The organic phase was dried and concentrated to dryness under reduced pressure. The residue was chromatographed on silica and eluted with a mixture of methylene chloride and ethyl acetate. The fraction rich in the expected product were recovered, the solvents were expelled and the crystals formed were taken up in ether to obtain 1.885 g of 1,1-dimethylethyl 7-[2-(2-tritylaminothiazol-4-yl)-2-methoxyimino-acetamido]-8-oxo-2-hydroxy-3-(2-pyridyl)-4-thia-1-azabicyclo[4,2,0]octane-2-carboxylate.

STEP D: 1,1-dimethylethyl 7-[2-(2-tritylaminothiazol-4-yl)-2-methoxyimino-acetamido]-8-oxo-3-(2-pyridyl)-4-thia-1-azabicyclo[4,2,0]oct-2-ene-2-carboxylate Using the procedure of Step D of Example 1, 743 mg of the product of Step E were reacted and after recrystallizing the crude product obtained from ethyl acetate, 284 mg of 1,1-dimethylethyl 7-[2-(2-tritylaminothiazol-4-yl)-2-methoxyimino-acetamido]-8-oxo-3-(2-pyridyl)-4-thia-1-azabicyclo[4,2,0]oct-2-ene-2-carboxylate were obtained.

Analysis: $C_{41}H_{38}O_5N_6S_2$; molecular weight=758.92 Calculated: % C 64.88 % H 5.05 % N 11.07 % S 8.45 Found: 64.5 5.1 10.9 8.2

STEP E: 7-[2-(2-aminothiazol-4-yl)-2-methoxyimino-acetamido]-8-oxo-3-(2-pyridyl)-4-thia-1-azabicyclo[4,2,0]oct-2-ene-2-carboxylic acid Using the procedure of Step E of Example 1, 413 mg of the product of Step D were reacted to obtain 343 mg of trifluoroacetate which were then dissolved in 1.5 ml of a saturated aqueous solution of sodium bicarbonate. After filtering and acidifying to a pH of 4 with 2N hydrochloric acid, a part of the water was distilled off, and the solution was allowed to crystallized for 1 hour. The crystals were filtered and rinsed with water to obtain 131 mg of 7-[2-(2-aminothiazol-4-yl)-2-methoxyimino-acetamido]-8-oxo-3-(2-pyridyl)-4-thia-1-azabicyclo[4,2,0]oct-2-ene-2-carboxylate acid.

Analysis: $C_{18}H_{16}O_5N_6S_2$; molecular weight=460.49 Calculated: % C 46.95 % H 3.50 % N 18.25 % S 13.93 Found: 46.4 3,4 17.9 13.5

EXAMPLE 10

4-oxide of syn isomer of racemic cis 7-[2-(2-aminothiazol-4-yl)-2-methoxyimino-acetamido]-8-oxo-3-(2-pyridyl)-4-thia-1-azabicyclo[4,2,0]oct-2-ene-2-carboxylic acid STEP A: 4-oxide of 1,1-dimethylethyl 7-[2-(2-tritylaminothiazol-4-yl)-2-methoxyimino-acetamido]-8-oxo-3-pyridyl-4-thia-1-azabicyclo[4,2,0]oct-2-ene-2-carboxylate Using the procedure of Example 2, 537 mg of the product of Example 9 were reacted to obtain 243 mg of 4-oxide of 1,1-dimethylethyl 7-[2-(2-tritylaminothiazol-4-yl)-2-methoxyimino-acetamido]-8-oxo-3-pyridyl-4-thia-1-azabicyclo[4,2,0]oct-2-ene-2-carboxylate corresponding to the α-isomer.

STEP B: 4-oxide of syn isomer of racemic cis 7-[2-(2-aminothiazol-4-yl)-2-methoxyimino-acetamido]-8-oxo-3-(2-pyridyl)-4-thia-1-azabicyclo[4,2,0]oct-2-ene-2-carboxylic acid Using the procedure of Step E of Example 1, dissolving the trifuloroacetate obtained in methanol, adding triethylamine to pH 4, and allowing crystallize for 15 minutes, 92 mg of 4-oxide of syn isomer of racemic cis 7-[2-(2-aminothiazol-4-yl)-2-methoxyimino-acetamido]-8-oxo-3-(2-pyridyl)-4-thia-1-azabicyclo[4,2,0]oct-2-ene-2-carboxylic acid were obtained.

Analysis: $C_{18}H_{16}O_6N_6S_2$; molecular weight=476.49 Calculated: % C 45.37 % H 3.38 % N 17.64 % S 13.46 Found: 45.3 3.6 16.9 12/9

EXAMPLE 11

Syn isomer of racemic cis 7-[2-(2-aminothiazol-4-yl)-2-methoxyimino-acetamido]-3-phenyl-8-oxo-4-thia-1-azabicyclo[4,2,0]oct-2-ene-2-carboxylic acid STEP A: 3-bromo-3-phenyl-pyruvic acid 12.31 g of phenyl-pyruvic acid and 50 ml of acetic acid were mixed together and then a solution of 12.34 g of bromine in 4 ml of acetic acid was added drop by drop over 1 hour. After the introduction was finished, stirring was continued for 15 minutes, followed by concentration to dryness under reduced pressure. The residue was taken up in 40 ml of dichloroethane and concentrated to dryness under reduced pressure, 30 ml of dichloroethane were added, and crystallization was allowed for 2 hours at 20° C. to obtain 12.6 g of 3-bromo-3-phenyl-pyruvic acid melting at 110° C.

STEP B: 1,1-dimethylethyl 3-bromo-3-phenyl pyruvate

A mixture of 12.05 g of 3-bromo-3-phenyl-pyruvic acid in 120 ml of ethyl acetate was cooled to 0° to +5° C. over 20 minutes and after 14.9 g of O-tert-butyl isourea in 10 ml of ethyl acetate were introduced, the mixture was stirred for 1 hour at 0° to +5° C., then for 3 hours at 20° C. The urea formed was filtered off, and the ethyl acetate solution was washed with a saturated aqueous solution of sodium bicarbonate, then with water. The residue, after drying and concentrating to dryness under reduced pressure, was triturated with ether, taken to dryness and chromatographed over silica with elution with a mixture of methylene chloride and ethyl acetate (70–30) to obtain 3.14 g of 1,1-dimethylethyl 3-bromo-3-phenyl-pyruvate.

Analysis: $C_{13}H_{15}BrO_3$; molecular weight=299.172 Calculated: % C 52.15 % H 5.05 % Br 26.71 Found: 53.4 5.4 23.6

IR Spectrum

Presence of $CH_3$ C=0 1746 $cm^{-1}$ 1723 $cm^{-1}$ Tert-butyl ester, 1372 $cm^{-1}$ 1155 $cm^{-1}$ STEP C: 1,1-dimethylethyl 7-[2-(2-tritylaminothiazol-4-yl)-2-methoxyimino-acetamido]-3-phenyl-8-oxo-4-thia-1-azabicyclo[4,2,0]oct-2-ene-2-carboxylate 3.94 g of 1,1-dimethylethyl 3-bromo-3-phenyl-pyruvate and 1.93 ml of triethylamine were introduced into a solution of 6.13 g of syn isomer of racemic cis 4-mercaptomethyl-3-[2-(2-tritylaminothiazol-4-yl)-2-methoxyimino-acetamido]-2-oxo-1-azetidine and 120 ml of methylene chloride. After agitating for 20 minutes at 20° C., 7.5 ml of pure pyridine, and then over 15 minutes, 2.98 g of phosphorus tribromide in 20 ml of methylene chloride were added with stirring for a further 20 minutes. The reaction mixture was poured into 1 liter of water and ice, and the mixture was extracted with methylene chloride. The organic phase was washed with water, dried and concentrated to dryness under reduced pressure. The residue was purified by chromatography and elution with a mixture of methylene chloride and ethyl acetate (85–15) to obtain 1.14 g of 1,1-dimethylethyl 7-[2-(2-tritylaminothiazol-4-yl)-2-methoxyimino-acetamido]-3-phenyl-8-oxo-4-thia-azabicyclo[4,2,0]oct-2-ene-2-carboxylate.

UV Spectrum in ethanol (+2 ml DMSO for dissolving) max: 310 nm $E_1^1$: 203 ε=15300 in ethanol HCl 0.1N infl.: 284 nm $E_1^1$: 246 ε=18500 max.: 293 nm $E_1^1$: 256 ε=19200 infl.: 302 nm $E_1^1$: 246 ε=18500 infl.: 315 nm $E_1^1$: 187 ε=14000

STEP D: Syn isomer of racemic cis 7-[2-(2-aminothiazol-4-yl)-2-methoxyimino-acetamido]-3-phenyl-8-oxo-4-thia-1-azabicyclo[4,2,0]oct-2-ene-2-carboxylic acid 400 mg of the product of Step C and 2 ml of trifluoroacetic acid were stirred for 20 minutes at 20° C. and then over 10 minutes 20 ml of isopropyl ether were added dropwise. After stirring for a further 20 minutes, separating and drying, 297 mg of trifluoroacetate were obtained which were taken up in 2 ml of ethanol, 0.046 ml of pyridine and then 2 ml of ethanol were added with stirring for 30 minutes to obtain 138 mg of syn isomer of racemic cis 7-[2-(2-aminothiazol-4-yl)-2-methoxyimino-acetamido]-3-phenyl-8-oxo-4-thia-1-azabicyclo[4,2,0]oct-2-ene-2-carboxylic acid melting at 220° C. (with decomposition).

UV Spectrum 1) in ethanol (+1 ml of DMSO for dissolving) max: 308 nm $E_1^1$; 276 ε=14200
2) in ethanol HCl 0.1N max: 248 nm $E_1^1$: 378 ε=19500 infl.: 254 nm $E_1^1$: 370 max.: 283 nm $E_1^1$: 296 ε=15300 infl.: 309 nm $E_1^1$: 234 ε=12000

EXAMPLE 12

4-oxide of syn isomer of racemic cis 7-[2-(2-aminothiazol-4-yl)-2-methoxyimino-acetamido]-3-phenyl-8-oxo-4-thia-1-azabicyclo[4,2,0]oct-2-ene-2-carboxylic acid STEP A: 4-oxide of 1,1-dimethylethyl 7-[2-(2-tritylaminothiazol-4-yl)-2-methoxyimino-acetamido]-3-phenyl-8-oxo-4-thia-1-azabicyclo[4,2,0]oct-2-ene-2-carboxylate 600 mg of 1,1-dimethylethyl 7-[2-(2-tritylaminothiazol-4-yl)-2-methoxyimino-acetamido]-8-oxo-3-phenyl-4-thia-1-azabicyclo[4,2,0]oct-2-ene-2-carboxylate were dissolved in 20 ml of methylene chloride and then 193 mg of 85% m-chloroperbenzoic acid were added all at once. The mixture was stirred for 40 minutes and 10 ml of a 0.5M solution of sodium hyposulfite were added with stirring over 10 minutes. The organic phase was decanted and was washed with a saturated solution of sodium bicarbonate, then dried and concentrated to dryness under reduced pressure. The residue was chromatographed on silica and eluted with a mixture of methylene chloride and ethyl acetate (60–40) to obtain 59 mg of α isomer and 364 mg of β isomer of 4-oxide of 1,1-dimethylethyl 7-[2-(2-tritylaminothiazol-4-yl)-2-methoxyimino-acetamido]-3-phenyl-8-oxo-4-thia-1-azabicyclo[4,2,0]oct-2-ene-2-carboxylate melting at ≈200° C. (with decomposition).

Analysis: $C_{42}H_{39}N_5O_6S_2$; molecular weight=773.936 Calculated: % C 65.18 % H 5.08 % N 9.05 % S 8.29 Found: 64.6 5.2 8.6 8.1

UV Spectrum 1) in EtOH infl: 224 nm $E_1^1$: 403 ε=19200 max: 299 nm $E_1^1$: 322 ε=15300

2) in EtOH/HCl 0.1N. infl: 221 nm $E_1^1$: 310 max: 283 nm $E_1^1$: 370 ε=17600 infl: 309 nm $E_1^1$: 243 ε=11500

STEP B: 4-oxide of syn isomer of racemic cis 7-[2-(2-aminothiazol-4-yl)-2-methoxyimino-acetamido]-3-phenyl-8-oxo-4-thia-1-azabicyclo[4,2,0]oct-2-ene-2-carboxylic acid Using the procedure of Step D of Example 11, 325 mg of the product of Step A and 1.7 ml of trifluoroacetic acid were reacted. 15 ml of isopropyl ether were added with agitation 20 minutes at 15°–20° C. to precipitate 176 mg of crude product. The latter was triturated with ethyl acetate, chromatographed on silica and eluted with a mixture of methylene chloride and methanol (92–8). The useful fraction was concentrated to dryness and the residue was taken up in ethyl acetate, separated to obtain 55 mg of 4-oxide of syn isomer of racemic cis 7-[2-(2-aminothiazol-4-yl)-2-methoxyimino-acetamido]-3-phenyl-8-oxo-4-thia-1-azabicyclo[4,2,0]oct-2-ene-2-carboxylic acid.

UV Spectrum 1) in EtOH infl.: 224 nm $E_1^1$: 403 ε=19200 max: 299 nm $E_1^1$: 322 ε=15300

2) in EtOH/HCl 0.1N infl: 221 nm $E_1^1$: 310 max: 283 nm $E_1^1$: 370 ε=17600 infl: 309 nm $E_1^1$: 243 ε=11500

EXAMPLE 13

Syn isomer of racemic cis 7-[2-(2-aminothiazol-4-yl)-2-methoxyimino-acetamido]-3-(4-nitrophenyl)-8-oxo-4-thia-1-azabicyclo[4,2,0]oct-2-ene-2-carboxylic acid STEP A: 1,1-dimethylethyl 2-chloro-3-(4-nitrophenyl)-oxirane carboxylate 5.55 g of tert.-butyl dichloroacetate in 30 ml of tetrahydrofuran and 4.99 g of 4-nitrobenzaldehyde in 30 ml of tetrahydrofuran were cooled to −20° C. and, over 20 minutes, 30 ml of a molar solution of potassium tert.-butylate in tetrahydrofuran were added dropwise at −20° C. The reaction mixture was stirred while the temperature was allowed to rise to 20° C., and it was then poured into 100 ml of water and ice, and was extracted with ether. The organic phase was washed with water saturated with sodium chloride, then with water, dried, and concentrated to dryness under reduced pressure. The residue was chromatographed on silica and eluted with methylene chloride to obtain 6.44 g of 1,1-dimethylethyl 2-chloro-3-(4-nitrophenyl)oxirane carboxylate melting at 60° C.

STEP B: 1,1-dimethylethyl 7-[2-(2-tritylaminothiazol-4-yl)-2-methoxyimino-acetamido]-2-hydroxy-3-(4-nitrophenyl)-8-oxo-4-thia-1-azabicyclo[4,2,0]octane-2-carboxylate 4.32 g of the product of Step A were dissolved in 130 ml of dimethylformamide and 7.24 g of syn isomer of racemic cis 4-mercaptomethyl-3-[(2-tritylaminothiazol-4-yl)-2-methoxyimino-acetamido]-2-oxo-1-azetidine were added with stirring for five minutes. Then, 1.06 g of lithium carbonate were introduced all at once and after stirring for 1 hour, the reaction mixture was poured into 1.2 liters of water and ice followed by extraction with ethyl acetate. The extracts were washed with water, dried, and concentrated to dryness under reduced pressure. The residue was chromatographed on silica and eluted with a mixture of methylene chloride and ethyl acetate (85–15) to obtain 7.4 g of product. The latter was dissolved in a mixture of 30 ml of isopropyl ether and 15 ml of methylene chloride at reflux, and the methylene chloride was evaporated away. The product crystallized out hot and after 1hour at 20° C. 6.074 g of 1,1-dimethylethyl 7-[2-(2-tritylaminothiazol-4-yl)-2-methoxyimino-acetamido]-2-hydroxy-3-(4-nitrophenyl)-8-oxo-4-thia-1-azabicyclo[4,2,0]octane-2-carboxylate were separated and after crystallization melted at 265° C.

STEP C: 1,1-dimethylethyl 7-[2-(2-tritylaminothiazol-4-yl)-2-methoxyimino-acetamido]-3-(4-nitrophenyl)-8-oxo-4-thia-1-azabicyclo[4,2,0]oct-2-ene-2-carboxylate 7.41 g of product of Step B were dissolved in 74 ml of pyridine, then at 10 minute intervals and in 2 roughly equal fractions, 10.28 g of diphosphorus tetraiodide were added followed by cooling to 20° C. and stirring for 50 minutes. The reaction mixture was poured into 1 liter of water and ice and the pH was adjusted to 4 by slowly adding 260 ml of 2N hydrochloric acid. The mixture was extracted with ethyl acetate and the organic phase was washed with water, dried and concentrated to dryness under reduced pressure. The residue was chromatographed on silica and eluted with a mixture of methylene chloride and ethyl acetate (85–15). After isolating the product, it was taken up at reflux in a mixture of 30 ml of isopropyl ether and 20 ml of methylene chloride and the methylene chloride was distilled off. Crystallization was obtained from the hot solution and the temperature was allowed to return to ambient and after resting for one hour at 20° C., 3.97 g of 1,1-dimethylethyl 7-[2-(2-tritylaminothiazol-4-yl)-2-methoxyiminoacetamido-3-(4-nitrophenyl)-8-oxo-4-thia-1-azabicyclo[4,2,0]oct-2-ene-2-carboxylate melting at 197° C. were obtained.

STEP D: Syn isomer of racemic cis 7-[2-(2-aminothiazol-4-yl)-2-methoxyimino-acetamido]-3-(4-nitrophenyl)-8-oxo-4-thia-1-azabicyclo[4.2,0]oct-2-ene-2-carboxylic acid Under an inert atmosphere, 800 mg of the product of Step C were stirred for 50 minutes in 4 ml of trifluoroacetic acid and then 50 ml of isopropyl ether were added slowly. The precipitate formed was separated and then 3.5 ml of trifluoroacetic acid were added with stirring for 3 hours. A further 50 ml of isopropyl ether were added with stirring for 10 minutes. The trifluoroacetate was separated and taken up in 10 ml of ethanol. The mixture was stirred for 10 minutes and 0.2 ml of pyridine were added, and stirring was continued for a further 15 minutes. The product was separated, then dissolved in 15 ml of water saturated with sodium bicarbonate. The pH was adjusted to 2 by adding 2N hydrochloric acid and after 15 minutes, the product was separated and washed with water to obtain 200 mg of syn isomer of racemic cis 7-[2-(2-aminothiazol-4-yl)-2-methoxyimino-acetamido]-3-(4-nitrophenyl)-8-oxo-4-thia-1-azabicyclo[4,2,0 ]oct-2-ene-2-carboxylic acid melting at >260° C.

EXAMPLE 14

4-oxide of syn isomer of racemic cis 7-(2-(2-aminothiazol-4-yl)-2-methoxyimino-acetamido]-3-(4-nitrophenyl)-8-oxo-4-thia-1-azabicyclo[4,2,0]oct-2-ene-2-carboxylic acid STEP A: 4-oxide of 1,1-dimethylethyl 7-[2-(2-tritylaminothiazol-4-yl)2-methoxyimino-acetamido]-3-(4-nitrophenyl)-8-oxo-4-thia-1-azabicyclo[4,2,0]oct-2-ene-2-carboxylate A mixture of 1.9 g of 1,1-dimethylethyl 7-[2-(2-tritylaminothiazol-4-yl)-2-methoxyimino-acetamido]-3-(4-nitrophenyl)-8-oxo-4-thia-1-azabicyclo[4,2,0]oct-2-ene-2-carboxylate in 57 ml of methylene chloride and 750 mg of 85% m-chloroperbenzoic acid was stirred for 2 hours and after diluting with methylene chloride, 5 ml of a 0.5M/l of an aqueous solution of sodium hyposulfite were added with stirring for 5 minutes. Then, the decanted organic phase was washed with 15 ml of a saturated aqueous solution of sodium bicarbonate, then with water, dried and concentrated to dryness under reduced pressure. The residue was chromatographed on silica and eluted with a mixture of methylene chloride and ethyl acetate (75–25). Each of the 2 isomers was recrystallized from isopropyl ether to obtain 110 mg of β isomer of 4-oxide of 1,1-dimethylethyl 7-[2-(2-tritylaminothiazol-4-yl)-2-methoxyimino-acetamido]-3-(4-nitrophenyl)-8-oxo-4-thia-1-azabicyclo[4,2,0]oct-2-ene-2-carboxylate melting at 180° C. (pasty fusion) and 592 mg of the corresponding α isomer melting at 210° C. (with decomposition).

STEP B: Syn isomer of racemic cis 7-[2-(2-aminothiazol-4-yl)-methoxyimino-acetamido]-3-(4-nitrophenyl)-8-oxo-4-thia-1-azabicyclo[4,2,0]oct-2-ene-2-carboxylic acid 200 mg of the product of Step A (α isomer) with 1 ml of trifluoroacetic acid were stirred for 2 hours and then the trifluoroacetate was precipitated by slowly adding 20 ml of isopropyl ether. After 20 minutes, the trifluoroacetate was separated and taken up in 2 ml of ethanol and 8 ml of methanol. 0.04 ml of pyridine were added in 2 lots and after leaving to crystallize for 1 hour, 82 mg of syn isomer of racemic cis 7-[2-(2-aminothiazol-4-yl)-2-methoxyimino-acetamido]-3-(4-nitrophenyl)-8-oxo-4-thia-1-azabicyclo[4,2,0]oct-2-ene-2-carboxylic acid were obtained.

Analysis: $C_{19}H_{16}N_6O_8S_2$; molecular weight=520.503 Calculated: % C 43.84 % H 3.10 % N 16.15 % S 12.32 Found: 44.3 3.1 15.7 11.6

UV Spectrum 1) in EtOH max.: 234 nm $E_1^1$: 369 ε=19200 infl.: 308 nm $E_1^1$: 264 max.: 327 nm $E_1^1$: 283 ε=14700
2) in EtOH/HCl 0.1N max: 270 nm $E_1^1$: 361 ε=18800 infl.: 282 nm $E_1^1$: 352 ε=18300 max: 322 nm $E_1^1$: 279 ε=14500

EXAMPLE 15

Syn isomer of racemic cis 7-[2-(2-aminothiazol-4-yl)-2-methoxyimino-acetamido-]3-(4-chlorophenyl)-8-oxo-4-thia-1-azabicyclo[4,2,0]oct-2-ene-2-carboxylic acid STEP A: 1,1-dimethylethyl 2-chloro-3-(4-chlorophenyl)-oxirane carboxylate 5.55 g of tert.-butyl dichloroacetate in 30 ml of tetrahydrofuran were stirred while 4.64 g of 4-chlorobenzaldehyde were added, and after cooling to −20° C., 30 ml of an N solution of potassium tert.-butylate in tetrahydrofuran were added. The temperature was allowed to rise to 20° C. and after 20 minutes, 50 ml of ether and 40 ml of water saturated with sodium chloride were added, with stirring for 5 minutes. The decanted organic phase was washed with water saturated with sodium chloride, then dried and concentrated to dryness under reduced pressure. The residue was chromatographed on silica and eluted with methylene chloride to obtain 1.90 g of 1,1-dimethylethyl 2-chloro-3-(4-chlorophenyl)-oxirane carboxylate.

Analysis: $C_{13}H_{14}Cl_2O_3$ Calculated: % C 54.00 % H 4.88 % Cl 24.52 Found: 52.8 4.9 24.6

STEP B: 1,1-dimethylethyl 7-[2-(2-tritylaminothiazol-4-yl)-2-methoxyimino-acetamido]-2-hydroxy-3-(4-chlorophenyl)-8-oxo-4-thia-1-azabicyclo[4,2,0]octane-2-carboxylate Using the procedure of Step B of Example 13, 4.86 g of the product of Step A were reacted to obtain 8.37 g of 1,1-dimethylethyl 7-[2-(2-tritylaminothiazol-4-yl)-2-methoxyimino-acetamido]-2-hydroxy-3-(4-chlorophenyl)-8-oxo-4-thia-1-azabicyclo[4,2,0]octane-2-carboxylate which melted at 191° C., after purification by chromatography on silica and elution with $CH_2Cl_2$—ACOEt (85–15).

STEP C: Syn isomer of racemic cis 1,1-dimethylethyl 7-[2-(2-tritylaminothiazol-4-yl)-2-methoxyimino-acetamido]-3-(4-chlorophenyl)-8-oxo-4-thia-1-azabicyclo[4,2,0]oct-2-ene-2-carboxylate Using the procedure of Step C of Example 13, 8.060 g of the product of Step B were reacted to obtain 3.680 g of syn isomer of racemic cis 1,1-dimethylethyl 7-[2-(2-tritylaminothiazol-4-yl)-2-methoxyimino-acetamido]-3-(4-chlorophenyl)-8-oxo-4-thia-1-azabicyclo[4,2,0]oct-2-ene-2-carboxylate melting at 183° C.

STEP D: Syn isomer of racemic cis 7-[2-(2-aminothiazol-4-yl)-2-methoxyimino-acetamido]-3-(4-chlorophenyl)-8-oxo-4-thia-1-azabicyclo[4,2,0]oct-2-ene-2-carboxylate acid Using the procedure of Step D of Example 11, 238 mg of syn isomer of racemic cis 7-[2-(2-aminothiazol-4yl)-2-methoxyimino-acetamido]-3-(4-chlorophenyl)-8-oxo-4-thia-1-azabicyclo[4,2,0]oct-2-ene-2-carboxylic acid melting at >260° C. were obtained.

Analysis: $C_{19}H_{16}ClN_5O_5S_2$ Calculated: % C 46.20 % H 3.27 % N 14.18 % Cl 7.18 Found: 45.7 3.3 13.5 6.9

IR Spectrum C=0 1760 $cm^{-1}$ (βlactam) C=0 1706 $cm^{-1}$ (acid) C=0 1650 $cm^{-1}$ (amide) Amide II heterocycle 1525–1540 $cm^{-1}$ aromatic 1605 $cm^{-1}$ 1583 $cm^{-1}$ 1490 $cm^{-1}$

EXAMPLE 16

Syn isomer of racemic cis 4-oxide of 7-[2-(2-aminothiazol-4yl)-2-methoxyimino-acetamido]-3-(4-chlorophenyl)-8-oxo-4-thia-1-azabicyclo[4,2,0]oct-2-ene-2-carboxylic acid STEP A: 4oxide of 1,1-dimethylethyl 7-[2-(2-tritylaminothiazol-4-yl)-2-methoxyimino-acetamido]-3-(4-chlorophenyl)-8-oxo-4-thia-1-azabicyclo[4,2,0]oct-2-ene-2-carboxylate Using the procedure of Step A of Example 14, 2.4 g of 1,1-dimethylethyl 7-[2-(2-tritylaminothiazol-4-yl)2-methoxyimino-acetamido]-3-(4-chlorophenyl)-8-oxo-4-thia-1-azabicyclo[4,2,0]oct-2-ene-2-carboxylate were reacted to obtain after crystallization from isopropyl ether, 173 mg of β isomer of 4-oxide of 1,1-dimethylethyl 7-[2-(2-tritylaminothiazol-4-yl)-2-methoxyimino-acetamido]-3-(4-chlorophenyl)-8-oxo-4-thia-1-azabicyclo[4,2,0]oct-2-ene-2-carboxylate melting at 185°–190° C., and 1.27 g of the corresponding α isomer melting at 185°–190° C., after crystallization from ether.

STEP B: 4-oxide of syn isomer of racemic cis 7-[2-(2-aminothiazol-4-yl)-2-methoxyimino-acetamido]-3-(4-chlorophenyl)-8-oxo-4-thia-1-azabicyclo[4,2,0]oct-2-ene 2-carboxylic acid Using the procedure of Step B of Example 14, 300 mg of the product of Step A were reacted to obtain 119 mg of 4-oxide of syn isomer of racemic cis 7-[2-(2-aminothiazol-4-yl-2-methoxyimino-acetamido]-3-(4-chlorophenyl)-8-oxo-4-thia-1-azabicyclo[4,2,0]oct-2-ene 2-carboxylic acid melting at ≈260° C. (with decomposition).

EXAMPLE 17

Syn isomer of racemic cis 7-[2-(2-aminothiazol-4-yl)-2-methoxyimino-acetamido]-8-oxo-3-(phenylseleno)-4-thia-1-azabicyclo[4,2,0]oct-2-ene-2-carboxylic acid STEP A: Tert-butyloxalic acid chloride 84 ml of oxalyl chloride in 800 ml of ether was cooled to −60° C. and over half-an-hour, a solution of 94 ml of tert.-butanol, 80 ml of pyridine and 200 ml of ether was added. The temperature was allowed to rise to 0° C. with stirring for a further hour. After filtering and concentrating the filtrate dryness, the residue was distilled under reduced pressure to obtain 93 g of tert-butyloxalic acid chloride boiling at 13 mm Hg, 45°–46° C.

STEP B: Tert-butyl diazopyruvate 16 g of the product of Step A were cooled to 0° C.–5° C. in 400 ml of ether, and 350 ml of diazomethane in solution at 25.5 g/liter in methyl chloride were added. Stirring was continued for half-an-hour after the introduction, followed by concentration to dryness under reduced pressure. The residue was taken up in very little n-pentane, and, after separating, 11 g tert-butyl diazopyruvate were obtained melting at 100° C.

STEP C: Tert-butyl 7-[2-(2-tritylaminothiazol-4-yl)-2-methoxyimino-acetamido]8-oxo-4-thia-2-hydroxy-3-phenylseleno-1-azabicyclo[4,2,0]octan-2-carboxylate The solution of phenylseleno-pyruvate prepared below was added all at once to 557 mg of 4-mercaptomethyl-3-[2-(2-tritylaminothiazol-4-yl)-2-methoxyimino-acetamido]-2-oxo-1-azetidine suspended in 4 ml of methylene chloride, followed by 0.2 ml of triethylamine. After stirring for 1 hour at ambient temperature under an inert atmosphere, the reaction mixture was poured into 20 ml of a mixture of water and ice. The mixture was extracted with methylene chloride and the organic phase was washed with water, dried and concentrated to dryness under reduced pressure to obtain 950 mg of crude product. The residue was chromatographed on silica and eluted with a mixture of methylene chloride and ethyl acetate (70–30) to obtain 280 mg of tert-butyl 7-[2-(2-tritylaminothiazol-4-yl)-2-methoxyimino-acetamido]-8-oxo-4-thia-2-hydroxy-3-phenylseleno-1-azabicyclo[4,2,0]octan-2-carboxylate melting at ≈230° C. (decomposes).

Preparation of tert-butyl 3-chloro-3-phenylseleno-pyruvate 170 mg of tert-butyl diazopyruvate were dissolved in 2 ml of methylene chloride and then 191 mg of phenylselenyl chloride were added. The mixture was stirred at ambient temperature until the evolvement of gas ceases.

STEP D: Tert-butyl 7-[2-(2-tritylaminothiazol-4-yl)-2-methoxyimino-acetamido]-8-oxo-4-thia-3-(phenylseleno)-1-azabicyclo[4.2,0]oct-2-ene-2-carboxylate 4 g of the crude product of Step C and 40 ml of pyridine were stirred while 5.24 g of diphosphorus tetraiodide were added in two lots over 10 minutes and the mixture was left with stirring at ambient temperature for 1 hour. The mixture was poured into 500 ml of water, 200 ml of ethyl acetate and 200 ml of N hydrochloric acid, and after stirring for a quarter of an hour, the decanted aqueous phase was re-extracted with ethyl acetate. The combined organic phases were washed with water, dried and concentrated to dryness under reduced pressure. The residue was chromatographed on silica and eluted with a mixture of methylene chloride and ethyl acetate (9–1) to obtain 370 mg of product which was taken up in isopropyl ether to obtain 300 mg of tert-butyl 7-[2-(2-tritylaminothiazol-4-yl)-2-methoxyimino-acetamido]-8-oxo-4-thia-3-(phenylseleno)-1-azabicyclo[4,2,0]oct-2-ene-2-carboxylate melting at ≈150° C. (pasty).

STEP E: Syn isomer of racemic cis 7-[2-(2-aminothiazol-4-yl)-2-methoxyimino-acetamido]-8-oxo-3-(phenylseleno)-4-thia-1-azabicyclo[4,2,0]oct-2-ene-2-carboxylic acid 300 mg of the product of Step D in 6 ml of 66% formic acid were heated at 60° C. for one and a quarter hours and the triphenylcarbinol formed was separated. The filtrate was concentrated to dryness under reduced pressure and the residue was taken up with 15 ml of isopropyl ether to obtain 190 mg of syn isomer of racemic cis 7-[2-(2-aminothiazol-4-yl)-2-methoxyimino-acetamido]-8-oxo-3-(phenylseleno)-4-thia-1-azabicyclo[4,2,0]oct-2-ene-2-carboxylic acid melting at ≈190° C.

Analysis: $C_{18}H_{17}N_5O_5S_2Se$; molecular weight=538.46

Calculated: % C 42.38 % H 3.18 % N 13.00 % S 11.90

Found: 42.9 3.3 12.5 13.4

UV Spectrum 1) in EtOH Infl: 216 nm $E_1^1$: 505 Infl: 233 nm $E_1^1$: 399 ε=21500 max: 310 nm $E_1^1$: 244 ε=13100
2) in EtOH/HCl 0.1N infl: 216 nm $E^1$: 430 max: 276 nm $E_1^1$: 318 ε=17100 infl: 283 nm $E_1^1$: 315 max: 322 nm $E_1^1$: 212 ε11400

EXAMPLE 18

Racemic cis 7-[2-(2-aminothiazol-4-yl)-2-methoxyimino-acetamido]-3-(3-nitrophenylthio)-8-oxo-4-thia-1-azabicyclo[4,2,0]oct-2-ene-2-carboxylic acid STEP A: 1,1-dimethylethyl 7-[2-(2-tritylaminothiazol-4-yl)-2-methoxyimino-acetamido]-2-hydroxy-3-(3-nitrophenylthio)-8-oxo-4-thia-1-azabicyclo[4,2,0]octane-2-carboxylate A solution of 678 mg of di(3-nitrophenyl) disulfide in 5 ml of methylene chloride was cooled to 0° C. and then a solution of 142 mg of chlorine in 1.12 ml of carbon tetrachloride was added dropwise and agitated for 10 minutes at 0° C. and 20 minutes at ambient temperature. After cooling to 0° C., a solution of 681 mg of tert-butyl diazopyruvate in 5 ml of methylene chloride was added slowly and the mixture was stirred for 30 minutes at ambient temperature. Then, 1.6 g of 4-mercaptomethyl-3-[2-(2-tritylaminothiazol-4-yl)-2-methoxyimino-acetamido]-2-oxo-1-azetidine and 0.56 ml of triethyiamine were added and stirring was maintained for a further hour. After filtering, the filtrate was washed with 0.1N hydrochloric acid, dried and concentrated to dryness. The residue was chromatographed on silica and eluted with a chloroform-acetone mixture (9–1) to obtain 800 mg of 1,1-dimethylethyl 7-[2-(2-tritylaminothiazol-4-yl)-2-methoxyimino-acetamido]-2-hydroxy-3-(3-nitrophenylthio)-8-oxo-4-thia-1-azabicyclo[4,2,0]octane-2-carboxylate.

UV Spectrum 1) in EtOH max: 248 nm $E_1^1$: 373 ε=31800 infl: 295 nm $E_1^1$: 90 ε=7700
2) in EtOH/HCl 0.1N max: 252 nm $E_1^1$: 310 ε=26400 infl: 290 nm $E_1^1$: 189 ε=16100 infl: 300 nm $E_1^1$: 133 ε=11300

STEP B: Racemic 1,1-dimethylethyl 7-[2-(2-tritylaminothiazol-4-yl)-2-methoxyimino-acetamido]-3-(3-nitrophenylthio)-8-oxo-4-thia-1-azabicyclo[4,2,0]oct-2-ene-2carboxylate A suspension of 677 mg of diphosphorus tetraiodide in 7 ml of pyridine was stirred under an inert atmosphere for 5 minutes and then 780 mg of the product of Step A were added. The mixture was stirred for 2 hours and then a further 363 mg of diphosphorus tetraiodide were added. The stirring was maintained for 1 hour and the reaction mixture was poured into 50 ml of ethyl acetate and filtered. The filtrate was evaporated to dryness under reduced pressure and the residue was dissolved in methylene chloride. The organic phase was washed with 0.1N hydrochloric acid, then with water, dried and concentrated to dryness. The residue was chromatographed on silica and eluted with a mixture of chloroform and acetone (10–0.5) to obtain 348 mg of racemic 1,1-dimethylethyl 7-[2-(2-tritylaminothiazol-4-yl)-2-methoxyimino-acetamido]-3-(3-nitrophenylthio)-8-oxo-4-thia-1-azabicyclo[4,2,0]oct-2-ene-2-carboxylate which crystallized from ether.

UV Spectrum 1) in EtOH max: 241 nm $E_1^1$: 470 ϵ=39200 max: 309 nm $E_1^1$: 227 ϵ=19000

2) in EtOH/HCl 0.1N infl: 242 nm $E_1^1$: 425 ϵ=35500 max: 270 nm $E_1^1$: 309 ϵ=25800 infl: 291nm $E_1^1$: 290 infl: 303 nm $E_1^1$: 265 ϵ=22100 infl: 317 nm $E_1^1$: 203 ϵ=16900

STEP C: Racemic cis 7-[2-(2-aminothiazol-4-yl)-2-methoxyimino-acetamido]-3-(3-nitrophenylthio)-8-oxo-4-thia-1-azabicyclo[4,2,0]oct-2-ene-2-carboxylic acid 286 mg of the product of Step B dissolved in 3 ml of 66% formic acid were stirred for 4 hours and then filtered. The filtrate was concentrated to dryness and the residue was dissolve in an acetonitrile-ethanol mixture. The solvents were evaporated and the residue was crystallized from isopropanol to obtain 82 mg of racemic cis 7-[2-(2-aminothiazol-4-yl)-2-methoxyimino-acetamido]-3-(3-nitrophenylthio)-8-oxo-4-thia-1-azabicyclo[4,2,0]oct-2-ene-2-carboxylic acid. 65 mg of the same product were recovered from the mother liquors and melted at 180°–200° C. (with decomposition).

UV Spectrum in EtOH/HCl 0.1N infl.: 219 nm $E_1^1$: 439 max: 250 nm $E_1^1$: 495 ϵ=26500 infl: 280 nm $E_1^1$: 386 infl: 291 nm $E_1^1$: 352 infl: 310 nm $E_1^1$: 289 ϵ=15500

EXAMPLE 19

Syn isomer of racemic 7-[2-(2-aminothiazol-4-yl)-2-methoxyimino-acetamido]-8-oxo-3-(4-nitrophenylthio)-4-thia-1-azabicyclo[4,2,0]oct-2-ene-2-carboxylic acid STEP a: 1,1-dimethylethyl 7-[2-(2-tritylaminothiazol-4-yl)-2-methoxyimino-acetamido]-2-hydroxy-3-(4-nitrophenylthio)-8-oxo-4-thia-1-azabicyclo[4,2,0]octane-2-carboxylate 13.4.g of N-chlorosuccinimide in 80 ml of benzene were cooled to 5°–10° C. under an inert atmosphere and over 30 minutes 15.5 g of 4-nitro-thiophenol were introduced at less than 10° C. The mixture was stirred for 16 hours at ambient temperature and after filtering, the solvents were evaporated. The residue was dried under reduced pressure at ambient temperature to obtain 1.33 g of residue. The latter was taken up in 10 ml of methylene chloride and, over 15 minutes, this solution was added dropwise to a solution cooled to 0°–5° C. of 0.8 g of tert-butyl diazopyruvate in 15 ml of methylene chloride under an inert atmosphere. After stirring for 30 minutes, 2.62 g of 4-mercaptomethyl-3-[2-(2-tritylaminothiazol-4-yl)-2-methoxyimino-acetamido]-2-oxo-1-azetidine and 0.505 g of triethylamine were added. After stirring for 1 hour, washing with 0.1N hydrochloric acid, then with water, and concentrating to dryness, a residue was obtained which was chromatographed on silica and eluted with a chloroform-acetone mixture (9–1) to obtain 2.5 g of 1,1-dimethylethyl 7-[2-(2-tritylaminothiazol-4-yl)-2-methoxyimino-acetamido]-2-hydroxy-3-(4-nitrophenylthio)-8-oxo-4-thia-1-azabicyclo[4,2,0]octane-2-carboxylate.

UV Spectrum 1) in EtOH infl: 236 nm $E_1^1$: 317 ϵ=27000 infl: 259 nm $E_1^1$: 185 ϵ=15800

1) in EtOH infl: 266 nm $E_1^1$: 163 max: 316 nm $E_1^1$: 164 ϵ=14000

2) in EtOH/HCl 0.1N infl: 271 nm $E_1^1$: 194 max: 280 nm $E_1^1$: 206 ϵ=17600 infl: 289 nm $E_1^1$: 205 infl: 301 nm $E_1^1$: 190 ϵ=16200 infl: 321 nm $E_1^1$: 148 ϵ=12600

STEP B: 1,1-dimethylethyl 7-[2-(2-tritylaminothiazol-4-yl)-2-methoxyimino-acetamido]-3-(4-nitrophenylthio)-8-oxo-4-thia-1-azabicyclo[4,2,0-oct-2-ene-2-carboxylate Using the procedure of Step B of Example 18, 1.79 g of the product of Step A were reacted to obtain 500 mg of 1,1-dimethylethyl 7-[2-(2-tritylaminothiazol-4-yl)-2-methoxyimino-acetamido]-3-(4-nitrophenylthio)-8-oxo-4-thia-1-azabicyclo[4,2,0]oct-2-ene-2-carboxylate.

UV Spectrum in EtOH/HCl 0.1N max: 292 nm $E_1^1$: 280 ϵ=23400 infl: 319 nm $E_1^1$: 246 ϵ=20500

STEP C: Syn isomer of racemic 7-[2-(2-aminothiazol-4-yl)-2-methoxyimino-acetamido]-8-oxo-3-(4-nitrophenylthio)-4-thia-1-azabicyclo[4,2,0]oct-2-ene-2-carboxylic acid 200 mg of the product of Step B reacted as in Step C of Example 18, and the residue was taken up in acetonitrile. The solvent was evaporated and the product was crystallized from ether to obtain 80 mg of syn isomer of racemic 7-[2-(2-aminothiazol-4-yl-2-methoxyimino-acetamido]-8-oxo-3-(4-nitrophenylthio)-4-thia-1-azabicyclo[4,2,0]oct-2-ene-2-carboxylic acid melting at 190°–200° C. (with decomposition).

UV Spectrum

1) Ethanol max: 223 nm $E_1^1$: 481 max: 307 nm $E_1^1$: 363

2) in Ethanol/HCl 0.1N max: 222 nm $E_1^1$: 400 infl: 265–274 nm max: 290 nm $E_1^1$: 361 infl: 310 nm $E_1^1$: 331

EXAMPLE 20

Syn isomer of racemic 7-[2-(2-aminothiazol-4-yl)-2-methoxyimino-acetamido]-8-oxo-3-(4-methoxyphenylthio)-4-thia-1-azabicyclo[4,2,0]oct-2-ene-2carboxylic acid STEP A: 1,1-dimethylethyl 7-[2-(2-tritylaminothiazol-4-yl)-2-methoxyimino-acetamido]-2-hydroxy-3-(4-methoxyphenylthio)-8-oxo-4-thia-1-azabicyclo[4,2,0]octane-2-carboxylate Using the procedure of Step A of Example 19, 14.0 g of 4-methoxythiophenol were reacted to obtain after distillation of the residue, 5.16 g of 4-methoxyphenylsulfenyl chloride boiling at 78° C. at 0.12 mm Hg. 1 g of tert.-butyl diazopyruvate in 10 ml of methylene chloride was cooled to 0°–5° C. and then a solution of 1.12 g of 4-methoxyphenylsulfenyl chloride in 10 ml of methylene chloride was added dropwise, and the mixture was stirred.

After 30 minutes, 3.27 g of 4-mercaptomethyl-3-[2-(2-tritylaminothiazol-4-yl)-2-methoxyimino-acetamido]-2-oxo-1-azetidine and 0.82 ml of triethylamine were added, followed by stirring for one hour. The reaction mixture was washed with 0.1N hydrochloric acid then with water, dried and concentrated to dryness to obtain 3.7 g of 1,1-dimethylethyl 7-[2-(2-tritylaminothiazol-4-yl)-2-methoxyimino-acetamido]-2-hydroxy-3-(4-methoxyphenylthio)-8-oxo-4-thia-1-azabicyclo[4,2,0] octane-2-carboxylate after crystallization from ether.

UV Spectrum 1)in EtOH infl: 227 nm $E_1^1$: 430 ε=36000 infl: 241 nm $E_1^1$: 355 ε=29700 infl: 280 nm $E_1^1$: 124 infl: 296 nm $E_1^1$: 84 ε=7000

2) in EtOH/HCl 0.1N max : 252 nm $E_1^1$: 237 ε=19900 max: 273 nm $E_1^1$: 211 ε=17700 infl: 289 nm $E_1^1$: 187 ε=15700 infl: 301 nm $E_1^1$: 132

STEP B: 1,1-dimethylethyl 7-[2-(2-tritylaminothiazol-4-yl)-2-methoxyimino-acetamido]-3-(4-methoxyphenylthio)-8-oxo-4-thia-1-azabicyclo[4,2,0]oct-2-ene-2-carboxylate Using the procedure of Step B of Example 18, 2 g of the product of Step A were reacted, evaporating the pyridine under reduced pressure at less than 40° C., adding water, acidifying to pH 2 and extracting with ethyl acetate. The organic phases were dried, concentrated to dryness under reduced pressure and the residue was chromatographed on silica and eluted with a mixture of methylene chloride and acetone (10–0.5) to obtain 841 mg of 1,1-dimethylethyl 7-[2-(2-tritylaminothiazol-4-yl)-2-methoxy iminoacetamido]-3-(4-methoxyphenylthio)-8-oxo-4-thia-1-azabicyclo[4,2,0]oct-2-ene-2-carboxylate which after crystallization from ether melted at >215° C. (with decompositon).

UV Spectrum 1) in EtOH max: 238 nm $E_1^1$: 446 ε=36600 infl: 267 nm $E_1^1$: 227 max: 315 nm $E_1^1$: 215 ε=17600

2) in EtOH/HCl 0.1N infl: 235 nm $E_1^1$: 371 infl: 271 nm $E_1^1$: 250 max: 281 nm $E_1^1$: 255 ε=20900 max: 293 nm $E_1^1$: 253 ε=20700 infl: 303 nm $E_1^1$: 240 infl: 320 nm $E_1^1$: 198 ε=16200

STEP C: Racemic 1,1-dimethylethyl 7-[2-(2-aminothiazol-4-yl)-2-methoxyimino-acetamido]-3-(4-methoxyphenylthio)-8-oxo-4-thia-1-azabicyclo[4,2,0]oct-2-ene-2-carboxylate 810 mg of the product of Step B dissolved in 10 ml of 66% formic acid were stirred for one hour at ambient temperature and filtered. The filtrate was concentrated to dryness under reduced pressure at less than 30° C. and the residue was dissolved in a mixture of acetonitrile and methanol. The solvents were evaporated and the residue was crystallized from ether to obtain 516 mg of racemic 1,1-dimethylethyl 7-[2-(2-aminothiazol-4-yl)-2-methoxyimino-acetamido]-3-(4-methoxyphenylthio)-8-oxo-4-thia-1-azabicyclo[4,2,0]oct-2-ene-2-carboxylate.

UV Spectrum 1) in EtOH max: 236 nm $E_1^1$: 496 ε=28700 max: 310 nm $E_1^1$: 292 ε=16900

2) in EtOH/HCl 0.1N max: 240 nm $E_1^1$: 416 ε=24000 infl: 259 nm $E_1^1$: 352 infl: 281 nm $E_1^1$: 316 ε=18200 max: 317 nm $E_1^1$: 259 ε=15000

STEP D: Syn isomer of racemic 7-[2-(2-aminothiazol-4-yl)-2-methoxyimino-acetamido]-8-oxo-3-(4-methoxyphenylthio)-4-thia-1-azabicyclo[4,2,0]oct-2-ene-2-carboxylic acid 100 mg of the product of Step C dissolved in 2 ml of 66% formic acid were heated to 50° C. for 3 hours with stirring and was concentrated to dryness under reduced pressure. The residue was taken up in acetonitrile and the solvent was evaporated. The crude product was crystallized from ether and was then dissolved in methylene chloride with 10% of methanol. The solution was treated with active charcoal, then filtered and the filtrate was concentrated to dryness. The residue obtained was crystallized from ether to obtain 80 mg of syn isomer of racemic 7-[2-(2-aminothiazol-4-yl)-2-methoxyimino-acetamido]-8-oxo-3-(4-methoxyphenylthio)-4-thia-1-azabicyclo[4,2,0]oct-2-ene-2-carboxylic acid melting at 185°–190° C. (with decomposition).

UV Spectrum in EtOH/HCl 0.1N max: 242 nm $E_1^1$: 458 ε=23900 infl: 250 nm $E_1^1$: 358 infl: 282 nm $E_1^1$: 319 max: 316 nm $E_1^1$: 279 ε=14500

EXAMPLE 21

Syn isomer of racemic 7-[2-(2-aminothiazol-4-yl)-2-methoxyimino-acetamido]-8-oxo-3-phenylthio-4-thia-1-azabicyclo[4,2,0]oct-2-ene-2-carboxylic acid STEP A: 1,1-dimethylethyl 7-[2-(2-tritylaminothiazol-4-yl)-2-methoxyimino-acetamido]-2-hydroxy-8-oxo-3-phenylthio-4-thia-1-azabicyclo[4,2,0]octane-2-carboxylate Using the procedure of Step A of Example 19, 11 g of thiophenol were reacted and after distilling the residue under reduced pressure, 10.9 g of phenylsulfenyl chloride boiling at 68° C. at 4 mm Hg were obtained, 0.17 g of the said product were dissolved in 2 ml of methylene chloride and then 0.15 g of tert.-butyl diazopyruvate in 0.5 ml of methylene chloride were added with stirring for 15 minutes. Then, 5 ml of methylene chloride, 0.56 g of 4-mercaptomethyl-3-[2-(2-tritylaminothiazol-4-yl)-2-methoxyimino-acetamido]-2-oxo-1-azetidine and 0.1 g of triethylamine were added and the mixture was stirred for 30 minutes. The mixture was washed with water, dried and concentrated to dryness under reduced pressure. The residue was chromatographed on silica and eluted with a mixture of chloroform and acetone (8–2) to obtain 545 mg of 1,1-dimethylethyl 7-[2-(2-tritylaminothiazol-4-yl)-2-methoxyimino-acetamido]-2-hydroxy-8-oxo-3-phenylthio-4-thia-1-azabicyclo[4,2,0]octane-2-carboxylate.

UV Spectrum 1) in EtOH infl: 237 nm $E_1^1$: 310 ε=25000 infl: 246 nm $E_1^1$: 301 ε=24300 infl: 270 nm $E_1^1$: 151 infl: 295 nm $E_1^1$: 75 ε=6000

2) in EtOH/HCl 0.1N max: 252 nm $E_1^1$: 230 ε=18600 max: 274 nm $E_1^1$: 194 ε=15700 infl: 288 nm $E_1^1$: 170 ε=13700 infl: 300 nm $E_1^1$: 124

STEP B: 1,1-dimethylethyl 7-[2-(2-tritylaminothiazol-4-yl)-2-methoxyimino-acetamido]-8-oxo-3-phenylthio-4-thia-1-azabicyclo[4,2,0]oct-2-ene-2-carboxylate Using the procedure of Step B of Example 20, 1.5 g of the product of Step A were reacted to obtain 580 mg of 1,1-dimethylethyl 7-[2-(2-tritylaminothiazol-4-yl)-2-methoxyimino-acetamido]-8-oxo-3-phenylthio-4-thia-1-azabicyclo[4,2,0]oct-2-ene-2-carboxylate melting at 200°–202° C. (with decomposition).

UV Spectrum 1) in EtOH infl: 235 nm $E_1^1$: 410 infl: 273 nm $E_1^1$: 190 max.: 310 nm $E_1^1$: 216

2) in EtOH/HCl 0.1N max: 281–282 nm $E_1^1$: 266 max: 292 nm $E_1^1$: 274 infl: 304 nm $E_1^1$: 255 infl: 320 nm $E_1^1$: 191

STEP C: 1,1-dimethylethyl 7-[2-(2-aminothiazol-4-yl)-2-methoxyimino-acetamido]-8-oxo-3-phenylthio-4-thia-1-azabicyclo[4,2,0]oct-2-ene-2-carboxylate A mixture of 200 mg of the product of Step B dissolved in 5 ml of 66% formic acid was stirred for 1 hour at ambient temperature and then was concentrated to dryness under reduced pressure at less than 30° C. The residue was dissolved in a mixture of acetonitrile and methanol and the solvent was evaporated to obtain 110 mg of 1,1-dimethylethyl 7-[2-(2-aminothiazol-4-yl)-2-methoxyimino-acetamido]-8-oxo-3-phenylthio-4-thia-1-azabicyclo[4,2,0]oct-2-ene-2-carboxylate which after crystallization from ether had an Rf=0.42 ($CH_2C_2$-MeOH (9–1).

STEP D: Syn isomer of racemic 7-[2-(2-aminothiazol-4-yl)-2-methoxyimino-acetamido]-8-oxo-3-phenylthio-4-thia-1-azabicyclo[4,2,0]oct-2-ene-2-carboxylic acid 0.8 ml of trifluoroacetic acid and 0.2 ml of methylene chloride were cooled to −20° C. and 168 mg of the product of Step were added with stirring at −20° C. for one hour and then at 0° C. for 1 hour. The solvents were evaporated at 0° C. by a current at nigrogen and 5 ml of isopropyl ether were added with stirring at ambient temperature for 10 minutes. Then, the trifluoroacetate salt of the expected product was separated and dissolved in 1 ml of ethanol. Ethyl acetate and 3 drops of pyridine were added, and product crystallized which was purified by chromatography on silica and elution with an eluent mixture of methylene chloride and methanol (7–3). The recovered fractions were evaporated and the product was crystallized from methylene chloride containing a few drops of methanol to obtain 55 mg of syn isomer of racemic 7-[2-(2-amino-thiazol-4-yl)-2-methoxyimino-acetamido]-8-oxo-3-phenylthio-4-thia-1-azabicyclo[4,2,0]oct-2-ene-2-carboxylic acid UV Spectrum 1) in EtOH max: 304 nm $E_1^1$: 314 ε=15400 infl: 221 nm $E_1^1$: 457 infl: 231 nm $E_1^1$: 430
2) in EtOH/HCl 0.1N infl: 220 nm $E_1^1$: 381 ε=16500 infl: 225 nm $E_1^1$: 329 Max: 263 nm $E_1^1$: 336 infl: 280 nm $E_1^1$: 323 infl: 291 nm $E_1^1$: 308 infl: 331 nm $E_1^1$: 258

EXAMPLE 22

Racemic 7-[2-(2-aminothiazol-4-yl)-2-methoximino-acetamido]-3-(ethoxycarbonylmethylthio)-8-oxo-4-thia-1-azabicyclo[4,2,0]oct-2-ene-2-carboxylic acid STEP A: 1,1-dimethylethyl 7-[2-(2-tritylaminothiazol-4-yl)-2-methoxyimino-acetamido]-3-(ethoxycarbonylmethylthio)-2-hydroxy-8-oxo-4-thia-1-azabicyclo[4,2,0]octane-2-carboxylate 1.2 g of ethyl mercaptoacetate in 2 ml of carbon tetrachloride were added dropwise to 1.47 g of N-chlorosuccinimide suspended in 6 ml of carbon tetrachloride under an inert atmosphere and with strong stirring for 1 hour. After 10 minutes the solution of ethoxycarbonylmethylsulfenyl chloride obtained was filtered and added dropwise to a solution of 1.7 g of tert.-butyl diazopyruvate in 5 ml of carbon tetrachloride. The solvent were evaporated after stirring for 10 minutes and the residue was chromatographed on silica and eluted with a mixture of hexane and ethyl acetate (6–4) to obtain 1.48 g of tert.-butyl 3-chloro-3-(ethoxycarbonylmethylthio)-pyruvate. The latter was dissolved in 10 ml of methyl chloride and 2.23 g of 4-mercaptomethyl-3-[2-(2-tritylaminothiazol-4-yl)-2-methoxyimino-acetamido]-2-oxo-1-azetidine and 0.7 ml of triethylamine were added with stirring for 30 minutes followed by concentration to dryness. The residue was chromatographed on silica and eluted with a mixture of methylene chloride and acetone (8.5–1.5). After crystallization from ether 1.55 g of 1,1-dimethylethyl 7-[2-(2-tritylaminothiazol-4-yl)-2-methoxyimino-acetamido]-3-(ethoxycarbonylmethylthio)2-hydroxy-8-oxo-4-thia-1-azabicyclo[4,2,0]octane-2-carboxylate melting at 190°–195° C. (decomposition) were obtained.

UV Spectrum 1) in EtOH infl: 265 nm $E_1^1$: 155 ε=12700 infl: 271 nm $E_1^1$: 135 infl: 293 nm $E_1^1$: 82 ε=6700
2) in EtOH/HCl 0.1N max: 280 nm $E_1^1$: 201 ε=16400 infl: 290 nm $E_1^1$: 184

STEP B: Racemic 1,1-dimethylethyl 7-[2-(2-tritylaminothiazol-4-yl)-2-methoxyimino-acetamido]-3-(ethoxycarbonylmethylthio)-8-oxo-4-thia-1-azabicyclo[4,2,0]oct-2-ene-2-carboxylate 1.55 g of the product of Step A dissolved in 30 ml of pyridine and 1.4 g of diphosphorus tetraiodide were stirred under an inert atmosphere for 30 minutes and after a further 0.76 g of diphosphorus tetraiodide were added, the mixture was stirred for 1 hour. 100 ml of ethyl acetate were added followed by filtering and concentrating to dryness under reduced pressure at a temperature below 30° C. The residue was dissolved in ethyl acetate and the solution was filtered, washed first with 0.1N hydrochloric acid, then with a solution of sodium bicarbonate, and then with a sodium chloride solution, after which it was dried and concentrated to dryness. The residue was chromatographed on silica and eluted with a mixture of methylene chloride and acetone (10–0.75). After crystallization from ether, 675 mg of racemic 1,1-dimethylethyl 7-[2-(2-tritylaminothiazol-4-yl)-2-methoxyimino-acetamido]-3-(ethoxycarbonylmethylthio)-8-oxo-4-thia-1-azabicyclo[4,2,0]oct-2-ene-2-carboxylate melting at 212°–214° C. (decomposes) were obtained.

UV Spectrum 1) in EtOH infl: 227 nm $E_1^1$: 407 infl: 265 nm $E_1^1$: 195 ε=15600 max: 306 nm $E_1^1$: 203 ε=16200
2) in EtOH/HCl infl: 285 nm $E_1^1$: 260 max: 292 nm $E_1^1$: 270 ε=21600 infl: 300 nm $E_1^1$: 257 infl: 315 nm $E_1^1$: 180 ε=14400

STEP C: Racemic 7-[2-(2-aminothiazol-4-yl)-2-methoxyimino-acetamido]-3-(ethoxycarbonylmethylthio)-8-oxo-4-thia-1-azabicyclo[4,2,0]oct-2-ene-2-carboxylic acid A mixture of 200 mg of the product of Step B dissolved in 4 ml of 66% formic acid was stirred at 50° C. for 2 hours, after which the solution was cooled and filtered. The filtrate was concentrated to dryness under reduced pressure and the residue was re-dissolved in ethanol. The solvent was evaporated and 20 ml of ether were added with stirring for 30 minutes. Then, the crude products was separated and chromatographed on silica and eluted with a mixture of methylene chloride and methanol (8–2). After crystallization from ether, 70 mg of racemic 7-[2-(2-aminothiazol-4-yl)-2-methoxyimino-acetamido]-3-(ethoxycarbonylmethylthio)-8-oxo-4-thia-1-azabicyclo[4,2,0]oct-2-ene-2-carboxylic acid melting at >210° C. (decomposes) were obtained.

UV Spectrum 1) in EtOH max: 221–222 nm $E_1^1$: 327 ε=16400 max: 301 nm $E_1^1$: 251 ε=12600
2) in EtOH/HCl 0.1N max: 225 nm $E_1^1$: 246 ε=12500 max: 262 nm $E_1^1$: 264 ε=13200 infl: 290 nm $E_1^1$: 258 infl: 310 nm $E_1^1$: 190 ε=9800

EXAMPLE 23

Syn isomer of racemic cis 7-[2-(2-aminothiazol-4-yl)-2-methoxyimino-acetamido]-8-oxo-3-[(1-methyl-(1H)-tetrazol-5-yl)-thio]-4-thia-1-azabicyclo[4,2,0]oct-2-ene-2-carboxylic acid STEP A: 1,1-dimethylethyl 7-[2-(2-tritylaminothiazol-4-yl)-2-methoxyimino-acetamido]-8-oxo-3[(1-methyl-(1H)-tetrazol-5-yl)-thio-4-thia-1-azabicyclo[4,2,0]octane-2-hydroxy-2-carboxylate The bis(o-methyl-(1H)-tetrazol-5yl)-disulfide used was prepared as follows:

5 ml of 2N hydrochloric acid are added to 1.26 g of the sodium salt of 1-methyl-1,2-dihydro (5H) tetrazol-5-thione dissolved in 25 ml of water. Then, over 5 minutes and in small quantities, 2 ml of 30% hydrogen peroxide were introduced followed by heating to between 20° C. and 45° C. for a quarter of an hour. After cooling to 0° C. to 5° C., the crystals formed were separated and crystallized from 9 ml of ethanol to obtain 446 mg of bis(o-methyl-(1H)-tetrazol-5yl)-disulfide use melting at 114° C.

437 mg of bis (1-methyl-(1H)-tetrazol-5-yl)-disulfide suspended in 7.5 ml of methylene chloride cooled to −20° C. was admixed with stirring in an inert atmosphere with a solution of 124 mg of chlorine in 0.975 ml of carbon tetrachloride. The temperature was allowed to rise to 0° C. with stirring for 5 minutes at 0° C., 595 mg of tert-butyl diazopyruvate in solution in 5 ml of methylene chloride were added to the solution of 1-methyl-(1H)-tetrazol-5-yl sulfenyl chloride obtained over 10 minutes, with stirring for 15 minutes at 0° C. Then the temperature was allowed to rise to the ambient and the tert.-butyl 3-chloro-3-[1-methyl-(1H)-tetrazol-5-yl-thio]-pyruvate formed was added all at once to 2.16 g of 4-mercaptomethyl-3-[2-(2-tritylaminothiazol-4-yl)-2methoxyimino-acetamido]-2-oxo-1-azetidine, 0.61 ml of triethylamine and 10 ml of methylene chloride. After stirring for 3 hours, the insoluble matter was filtered off and the filtrate was washed with 50 ml of water to which was added 2 ml of 2N hydrochloric acid, and then with water, and dried and concentrated to dryness under reduced pressure. The residue was chromatographed on silica and eluted with a mixture of methylene chloride and ethyl acetate (75–25) to obtain 1.393 g. of 1,1-dimethylethyl 7-[2-(2-tritylaminothiazol-4-yl)-2-methoxyimino-acetamido]-8-oxo-3-[(1-methyl-(1H)-tetrazol-5-yl)-thio]-4-thia-1-azabicyclo[4,2,0]octane-2-hydroxy-2-carboxylate.

Analysis: $C_{38}H_{39}N_9O_6S_3$; molecular weight=813.983

| | % C | % H | % N | % S |
|---|---|---|---|---|
| Calculated: | 56.07 | 4.83 | 15.49 | 11.82 |
| Found: | 56.1 | 5.0 | 14.5 | 11.8 |

UV Spectrum 1) in EtOH infl: 240 nm infl: 265 nm infl: 278 nm infl: 298 nm 2) in EtOH/HCl 0.1N infl: 270 nm infl: 289 nm max: 278 nm STEP B: Syn isomer of racemic cis 1,1-dimethylethyl 7-[2-(2-tritylaminothiazol-4-yl)-2-methoxyimino-acetamido]-8-oxo-3-[(1-methyl-(1H)-tetrazol-5-yl)-thio]-4-thia-1-azabicyclo[4,2,0]oct-2-ene-2-carboxylate 1.19 g of diphosphorus tetraiodide were added to a solution of 1.135 g of the product of Step A in 14 ml of pyridine and then 30 minutes later, 0.4 g of the same was added followed by stirring for 3 hours. The reaction mixture was poured into 400 ml of water, 76 ml of 2N hydrochloric acid and 100 ml of ethyl acetate, and after decanting, the mixture was extracted with ethyl acetate. The combined organic phases were washed with water, dried and concentrated to dryness under reduced pressure. The residue was chromatographed on silica and eluted with a mixture of methylene chloride and ethyl acetate (85–15) to obtain 3.544 g of syn isomer of racemic cis 1,1-dimethylethyl 7-[2-(2-tritylaminothiazol-4-yl)-2-methoxyimino-acetamido]-8-oxo-3-[(1-methyl-(1H)-tetrazol-5-yl)-thio]-1-azabicyclo[4,2,0]oct-2-ene-2-carboxylate melting at 150° C.

UV Spectrum 1) in EtOH infl: 230 nm max: 310 nm 2) in EtOH/HCl 0.1N infl: 284 nm infl: 302 nm infl: 315 nm max: 292 nm STEP C: Syn isomer of racemic cis 7-[2-(2-aminothiazol-4-yl)-2-methoxyimino-acetamido]-8-oxo-3-[(1-methyl-(1H)-tetrazol-5-yl)-thio]-4-thia-1-azabicyclo[4,2,0]oct-2-ene-2-carboxylic acid 248 mg of the product of Step B dissolved in 3.5 ml of 66% formic acid were heated to 55° C. to 60° C. with stirring for 7 hours. After diluting with 3.5 ml of water, the insoluble matter was filtered off and the filtrate was concentrated to dryness under reduced pressure. The residue was taken up 3 times consecutively with 5 ml of ethanol with evaporation each time. The 152 mg of resin obtained were triturated in 10 ml of ether and separated after 16 hours to obtain 128 mg of syn isomer of racemic cis 7-[2-(2-aminothiazol-4-yl)-2-methoxyimino-acetamido]-8-oxo-3- [(1-methyl-(1H)-tetrazol-5-yl)-thio]-4-thia-1-azabicyclo[4,2,0]oct-2-ene-2-carboxylic acid melting at ≈210° C. (decomposes).

UV Spectrum 1) in EtOH max: 231 nm infl: 250 nm max: 305 nm 2) in EtOH/HCl 0.1N max: 229 nm max: 260 nm max: 284 nm infl: 291 nm infl: 311 nm.

EXAMPLE 24

Racemic 7-[2-(2-aminothiazol-4-yl)-2-methoxyimino-acetamido]-3-(carboxymethylthio)-8-oxo-4-thia-1-azabicyclo[4,2,0]oct-2-ene-2-carboxylic acid STEP A: 1,1-dimethylethyl 7-[2-(2-tritylaminothiazol-4-yl)-2-methoxyimino-acetamido]-3-[[2-(1,1-dimethylethoxy)-2-oxo-ethyl]-thio]-2-hydroxy-8-oxo-4-thia-1-azabicyclo[4,2,0]octane carboxylate.

Using the procedure of Step A of Example 23, 1.48 g of 1,1-dimethylethyl mercaptoacetate were reacted and the solution of 2-(1,1-dimethylethoxy)-2-oxo-ethyl sulfenyl chloride obtained was cooled to −10° C. 1.7 g of diazopyruvate in 5 ml of methylene chloride were added dropwise and the temperature was allowed to rise to about 20° C. Stirring was maintained for 20 minutes and then, after filtering, a solution of tert.-butyl 3-chloro-3-[2-(1,1-dimethylethoxy)-2-oxo-ethylthio]-pyruvate was obtained. To this 20 ml of methylene chloride, 2.78 g of 4-mercaptomethyl-3[2(2-tritylaminothiazol-4-yl)-2-methoxyimino-acetamido]-2-oxo-1-azetidine and 1.68 ml of triethylamine were added thereto and after stirring for one hour, the reaction mixture was filtered. To filtrate was washed with N hydrochloric acid with a sodium bicarbonate solution and then with water saturated with sodium chloride, dried and concentrated to dryness. The residue was chromatographed on silica and eluted with a mixture of methylene chloride and acetone (9–1) to obtain 1.07 g of the racemic 1,1-dimethylethyl 7-[2-(2-tritylaminothiazol-4-yl)-2-methoxyimino-acetamido]-3-[[2-(1,1-dimethylethoxy)-2-oxoethyl]-thio]-2-hydroxy-8-oxo-4-thia-1-azabicyclo[4,2,0] octane carboxylate.

UV Spectrum 1) in EtOH infl: 236 nm $E_1^1$: 273 ε=23000 infl: 258 nm $E_1^1$: 167 infl: 266 nm $E_1^1$: 144 ε=12200 infl: 296 nm $E_1^1$: 74 ε=6300

2) in EtOH/HCl 0.1N max: 279 nm $E_1^1$: 182 ε=15400 infl: 289 nm $E_1^1$: 164 ε=13900

The 1,1-dimethylethyl mercaptoacetate was prepared in the following way:

A mixture of 8.81 g of potassium O-ethyl dithiocarbonate in 20 ml of acetone was cooled to 0°–2° C. and then over 10 minutes and with stirring, 9.79 g of 1,1-dimethylethyl bromoacetate were added. After stirring for one hour at ambient temperature, the reaction mixture was poured into 200 ml of ether, then filtered and concentrated to dryness. The residue was taken up in 100 ml of ether, filtered and again evaporated to obtain 11.6 g of 1,1-dimethylethyl (ethoxythiocarbonyl)-thio acetate. The latter was cooled to 0° C. with stirring in an inert atmosphere and then 1.62 g of 1,2-diaminoethane were added dropwise with stirring for 2 hours at ambient temperature. 50 ml of hexane were then added with vigorous stirring for 10 minutes. The hexane phase was separated and the residue was extracted with hexane. The hexane soluti-n was washed with 0.1N hydrochloric acid, then with a sodium bicarbonate solution, dried and concentrated to dryness. The residue was distilled under reduced pressure in an inert atmosphere to obtain 4.5 g of 1,1-dimethylethyl mercapto-acetate melting at 72° C. under 21 mm Hg.

STEP B: 1,1-dimethylethyl 7-[2-(2-tritylaminothiazol-4-yl)-2-methoxyimino-acetamido]-3 [[2-(1,1-dimethylethoxy)-2-oxoethyl]-thio]-8-oxo-4-thia-1-azabicyclo[4,2,0]oct-2-ene-2-carboxylate 592 mg of diphosphorus tetraiodide were added with stirring over half-an-hour to 675 mg of the product of Step A dissolved in 13.5 ml of pyridine and under an inert atmosphere. Then a further 320 mg of this latter were added, and stirring was maintained for 2 hours. Then 50 ml of ethyl acetate was added, followed by filtering and concentrating to dryness under reduced pressure. The residue was dissolved in methylene chloride washed with N hydrochloric acid, with a sodium bicarbonate solution and then with water saturated with sodium chloride, dried and concentrated to dryness. The residue was chromatographed on silica and eluted with a mixture of methylene chloride and acetone (10–0.75), and, after crystallization from ether, 312 mg of 1,1-dimethylethyl 7-[2-(2-tritylaminothiazol-4-yl)-2-methoxyimino-acetamido]-3-[[2-(1,1-dimethylethoxy)-2-oxoethyl]-thio]-8-oxo-4-thia-1-azabicyclo[4,2,0]oct-2-ene-2-carboxylate were obtained.

UV Spectrum 1) in EtOH infl: 233 nm $E_1^1$: 351 infl: 263 nm $E_1^1$: 190 $\epsilon$=15500 infl: 271 nm $E_1^1$: 166 max: 308–309 nm $E_1^1$: 191 $\epsilon$=15600

2) in EtOH/HCl 0.1N max: 282 nm $E_1^1$: 240 max: 292 nm $E_1^1$: 246 $\epsilon$=20100 infl: 301 nm $E_1^1$: 232 infl: 312 nm $E_1^1$: 185 $\epsilon$=15100

STEP C: Racemic 7-[2-(2-aminothiazol-4-yl)-2-methoxyimino-acetamido]-3-(carboxymethylthio)-8 -oxo-4-thia-1-azabicyclo[4,2,0]oct-2-ene-2-carboxylic acid A solution of 200 mg of the product of Step B in 4 ml of 66% aqueous formic acid was stirred for two hours and a half at 50° C. The cooled solution was filtered and evaporated. The residue was re-dissolved in a mixture of methanol and acetonitrile which was evaporated and the treatment was repeated. The residue was again dissolved in 5 ml of methanol and after carbon black was added, the mixture was stirred for a further 2 hours, then filtered. 30 ml of ether were added dropwise with stirring for hour and the white precipitate was separated and dried at 50° C. to obtain 53 mg of racemic 7-[2-(2-aminothiazol-4-yl)-2-methoxyimino-acetamido]-3-(carboxymethylthio)-8-oxo-4-thia-1-azabicyclo[4,2,0]oct-2-ene-2-carboxylic acid melting at 190° to 200° C. (with decomposition)

UV Spectrum (in ethanol+HCl 0.1N) max: 266 nm $E_1^1$: 308 $\epsilon$=14600 max: 203 nm $E_1^1$: 308 $\epsilon$=14600 infl: 310 nm $E_1^1$: 230 $\epsilon$=10900

EXAMPLE 25

Syn isomer of racemic 7-[2-(2-aminothiazol-4-yl)-2-methoxyimino-acetamido]-3-[(2-aminoethyl)thio]-8-oxo-4-thia-1-azabicyclo[4,2,0]oct-2-ene-2-carboxylic acid STEP A: Syn isomer of racemic 1,1-dimethylethyl 7-[2-(2-tritylaminothiazol-4-yl)-2-methoxyimino-acetamido]3-[2[[(1,1-dimethylethoxy)-carbonyl]-amino]ethyl]-thio-2-hydroxy-8-oxo-4-thia-1-azabicyclo[4,2,0]octane-2-carboxylate A solution of 1.3 ml of chlorine in carbon tetrachloride titrating 127.5 mg was added at −20° C., under nitrogen and with stirring to a solution of 881.3 mg of bi[[(1,1-dimethylethoxy)-carbonyl]-amino]-ethyl disulfide in 15 ml of methylene chloride and the temperature was allowed to rise to 0° with stirring for 5 minutes.

b) A solution of 783 mg of tert.-butyl diazopyruvate in 10 ml of methylene chloride was added to this solution at +5° C. and the temperature was allowed to rise to ambient.

c) To this reaction mixture, there was added successively 2.85 g of 4-mercaptomethyl-3-[2-(2-tritylaminothiazol-4-yl)-2-methoxyimino-acetamido]-2-oxo-1-azetidine solvated with 11% of methylene chloride and 581.8 mg of triethylamine. Then using the procedure of Step A of Example 23, 3.857 g of crude product were isolated and chromatographed on silica (eluent: methylene chloride-ethyl acetate 75–25) to obtain 1.539 g of syn isomer of racemic 1,1-dimethylethyl 7-[2-(2-tritylaminothiazol-4-yl)-2-methoxyimino-acetamido]-3-[2-[[(1,1-dimethylethoxy)-carbonyl]-amino]-ethyl]-thio-2-hydroxy-8-oxo-4-thia-1-azabicyclo[4,2,0] octane-2-carboxylate melting at 210° C.

Analysis: $C_{43}H_{50}N_6O_8S_3$; molecular weight=875.1 Calculated: % C 59.02 % H 5.76 % N 9.60 % S 10.99 Found: 59.2 5.8 9.5 10.7

The bis [[(1,1-dimethylethoxy)-carbonyl]-amino]-ethyl disulfide used was prepared as follows:

3.04 g of triethylamine were added to a suspension of 3.38 g of crystamine dihydrochloride in 30 ml of methanol and then, over 5 minutes, a solution of 7.25 g of ditert-butyl carbonate in 10 ml of methanol was added. The mixture was stirred for 45 minutes at ambient temperature and evaporated to dryness. The residue was taken up in 75 ml of ethyl acetate, and the triethylamine hydrochloride was separated. The liltrate was evaporated under reduced pressure to obtain 5.64 g of a colorless solid melting at 104° to 106° C.

STEP B: Syn isomer of racemic 1,1-dimethylethyl 7-[2-(2-tritylaminothiazol-4-yl)-2-methoxyimino-acetamido]-8-oxo-3-[[2-[[(1,1-dimethylethoxy)-carbonyl]-amino]-ethyl]-thio]-4-thia-1-azabicyclo[4,2,0]oct-2-ene-2-carboxylate Using the procedure of Step B of Example 23, 1.321 g of the product of Step A in solution in 13 ml of pyridine and 1.719 g of diphosphorus tetraidodide were reacted to obtain 1.08 g of crude product. The latter was combined with 135 mg of product obtained in another action and chromatographed on silica and eluted with methylene chloride and ethyl acetate (85–15) to obtain 539 mg of syn isomer of racemic 1,1-dimethylethyl 7-[2-(2-tritylaminothiazol-4-yl)-2-methoxyimino-acetamido]-8-oxo-3-[[2-[[(1,1-dimethylethoxy)-carbonyl]-amino]-ethyl]-thio]-4-thia-1-azabicyclo[4,2,0]oct-2-ene-2-carboxylate Analysis: $C_{43}H_{48}N_6O_7S_3$; molecular weight=857.09 Calculated: % C 60.26% H 5.64 % N 9.8 Found: 59.9 5.6 9.3

STEP C: Syn isomer of racemic 7-(2-(2-aminothiazo-4-yl)-2-methoxyimino-acetamido]-3-[(2-aminoethyl)-thio]-8-oxo-4-thia-1-azabicyclo[4,2,0]oct-2-ene-2-carboxylic acid 428.5 mg of the product of Step B dissolved in 5 ml of 66% formic acid was placed in an oil bath at 50° to 55° C. and heated for 5 hours. Then, 5 ml of water were added and the isoluble matter was separated and washed with 0.2 ml of water (104 mg of triphenylcarbinol). After evaporating the filtrate to dryness, 277 mg of resin were obtained which was triturated in 5 ml of methanol. The mixture stood over night and the following day, 162 mg of an ochre-colored solid separated which melted at 270° C.

UV Spectrum.

1) in EtOH+dimethyl sulfoxide max.: 298 nm $E_1^1$: 345 $\epsilon$=15800

2) in EtOH/HCl 0.1N 2 infl: 275 nm $E_1^1$: 327 310 nm $E_1^1$: 256 $\epsilon$=11700 1 max: 285 nm $E_1^1$: 342 $\epsilon$=15700

EXAMPLE 26

Using the procedure of the examples previously described, the following products are obtained:

a) Syn isomer of racemic cis 7-[2-(2-aminothiazol-4-yl)-2-methoxyimino-acetamido]-3-[(5-methyl-1,3,4-thiadiazol-2-yl)-thio]-8-oxo-4-thia-1-azabicyclo[4,2,0]oct-2-ene-2-carboxylic acid UV Spectrum in EtOH =HCl 0.1N max: 228 nm $E_1^1$: 340 ε=17500 max: 262 nm $E_1^1$: 363 ε=18600 infl: 281 nm $E_1^1$: 336 ε=17300 infl: 291 nm $E_1^1$: 314 infl: 309 nm $E_1^1$: 250 ε=12800 b) Syn isomer of racemic cis 7-[2-(2-aminothiazol-4-yl)-2-methoxyimino-acetamido]-8-oxo-3-[(5-[methylthio]-1,3,4-thiadiazol-2-yl)thio]-4-thia-1-azabicyclo[4,2,0]oct-2-ene-2-carboxylic acid UV Spectrum 1) in EtOH max: 225 nm $E_1^1$: 331 ε=18000 max: 299–300 nm $E_1^1$: 305 ε=16600

2) in EtOH+HCL 0.1N max: 224 nm $E_1^1$: 245 ε=13400 infl: 264 nm $E_1^1$: 275 infl: 275 nm $E_1^1$: 305 max: 286 nm $E_1^1$: 333 ε=18200 Infl: 310 nm $E_1^1$: 254 ε=13900 c) Trifluoroacetate of syn isomer of racemic cis 7-[2-(2-aminothiazol-4-yl)-2-methoxyimino-acetamido]-3-[(5-methyl-1,3,4-oxadiazol-2-yl)-thio]-8-oxo-4-thia-1-azabicyclo[4,2,0]oct-2-ene-2-carboxylic acid UV Spectrum 1) in EtOH max: 228 nm $E_1^1$: 343 ε=21000 max: 306 nm $E_1^1$: 221 ε=13500

2) in EtOH +HCl 0.1N infl: 222 nm $E_1^1$: 274 max: 261–262 nm $E_1^1$: 245 ε=15000 max: 284 nm $E_1^1$: 238 ε=14500 infl: 310 nm $E_1^1$: 190 ε=11600

EXAMPLE 27

Syn isomer of racemic cis 7-[2-(2-aminothiazol-4-yl)-2-methoxyimino-acetamido]-8-oxo-3-[(1-methyl-(1H)-tetrazol-5-yl)-thiomethyl-4-thia-1-azabicyclo] 4,2,0]oct-2-ene-2-carboxylic acid STEP A: 2-[(1,1-dimethylethyl)-dimethylsilyloxy]-ethanol 18 g of methylsilyl tert.-butyl chloride, 150 ml of dichloro methane, 17.5 cm3 of dimethyl formamide and 33.6 ml of ethylene glycol were mixed at 20° C. and under nitrogen. After solution is complete, 20.1 ml of triethylamine were added and then 1.8 g of 4-dimethylaminopyridine. After 2 hours 45 minutes of stirring, the solution was poured into 120 ml of water and was neutralized with about 40 ml of hydrochloric acid to obtain a pH of 3. After decanting, the aqueous phase was re-extracted with 20 ml of pentane and the organic phase was washed with 60 ml of water. The water was re-extracted with 20 ml of pentane and the combined organic phases were dried and distilled under reduced pressure to obtain 13.9 g of 2[(1,1-dimethylethyl)-dimethylsilyloxy]-ethanol boiling at 82°–86° C. under 16 mm Hg.

STEP B: 2-[(1,1-dimethylethyl)-dimethylsilyloxy]-acetaldehyde 4.71 ml of oxalyl chloride dissolved in 120 ml of dichloromethane, with stirring under nitrogen were cooled to –70° C. and while maintaining the temperature at –65° C. there was introduced over 12 minutes a solution of 8.6 ml of dimethylsulfoxide and 26 ml of dichloromethane. After 10 minutes contact at this temperature, a solution of 8.81 g of 2-[(1,1-dimethylethyl)-dimethylsilyloxy]-ethanol of Step A, 50 ml of dichloromethane and 8.86 ml of pyridine were introduced over 12 minutes at –65° C. After 15 minutes of contact at this temperature, 35 m of triethylamine were added over 8 minutes at –65° C. and at 13° C., N hydrochloric acid was added to obtain a pH of 4. After decanting, the aqueous phase was re-extracted with 50 ml of dichloromethane and the organic phase was dried and distilled under reduced pressure to obtain crude product which was chromatographed on silica and eluted with dichloromethane to obtain 7.95 g of 2-[1,1-dimethylethyl)-dimethylsilyloxy]-acetaldehyde.

STEP C: 1,1-dimethylethyl 2-chloro-3-(tert-butyldimethylsilyloxymethyl)-oxirane carboxylate Using the procedure of Step B of Example 1, taking the precaution of introducing at the same time at –20° C. the solution of potassium tert-butylate and 7.95 g of the aldehyde of Step B in solution in 1,1-dimethylethyl dichloroacetate, after chromatography on silica and elution with hexane-dichloromethane (6–4), 9.4 g of 1,1-dimethylethyl 2-chloro-3-(tert-butyldimethylsilyloxymethyl)-oxirane carboxylate were obtained.

STEP D: 1,1-dimethylethyl 7-[2-(2-tritylaminothiazol-4-yl)-2-methoxyimino-acetamido]-8-oxo-2-hydroxy-3-[(1,1-dimethylethyl)-dimethylsilyloxymethyl]-4-thia-1-azabicyclo[4,2,0]octane-2-carboxylate Using the procedure of Step C of Example 1 and a reaction time of 16 hours. 8.31 g of the syn isomer of racemic cis 4-mercaptomethyl-3-[2-(2-tritylaminothiazol-4-yl)-2-methoxyimino-acetamido]-2-oxol-azetidine were reacted with the product of Step C. 9.09 g of 1,1-dimethylethyl 7-[2-(2-tritylaminothiazol-4-yl)-2-methoxyimino-acetamido]-8-oxo-2-hydroxy-3-[(1,1-dimethylethyl)-dimethylsilyloxymethyl]-4-thia-1-azabicyclo[4,2,0]octane-2-carboxylate were obtained after chromatography on silica and elution with dichloromethane-ethyl acetate (75–25).

STEP E: 1,1-dimethylethyl 7-[2-(2-tritylaminothiazol-4-yl)-2-methoxyimino-acetamido]-8-oxo-3-[(1,1-dimethylethyl)-dimethylsilyloxymethyl]-4-thia-1-azabicyclo[4,2,0]oct-2-ene-2-carboxylate Using the procedure of Step D of Example 1, the contact was reduced to 55 minutes and the reaction mixture was poured, into water, acidified with 2N hydrochloric acid to a pH of 1.4, and extracted with ethyl acetate. 9.09 g of the product of Step D after chromatography yield 4 g of 1,1-dimethylethyl 7-[2-(2-tritylaminothiazol-4-yl)-2-methoxyimino-acetamido]-8-oxo-3-[(1,1-dimethylethyl)-dimethylsilyloxymethyl]-4-thia-1-azabicyclo[4,2,0]oct-2-ene-2-carboxylate.

UV Spectrum in EtOH infl: 233 nm $E_1^1$: 364 infl: 265 nm $E_1^1$: 173 infl: 302 nm $E_1^1$: 229 ε=18900

STEP F: 1,1-dimethylethyl 7-[2-(2-tritylaminothiazol-4-yl)-2-methoxyimino-acetamido]-8-oxo-3-hydroxymethyl-4-thia-1-azabicyclo[4,2,0]oct-2-ene-2-carboxylate 2.595 g of silyl derivative of Step E were suspended in 30 ml of acetone and 4.7 ml of N hydrochloric acid and the solution cleared little by little. After 3 hours of stirring, 7.7 ml of water saturated with sodium bicarbonate were added, and the acetone was distilled under reduced pressure. 20 ml of dichloromethane were added, and after stirring the decanted organic phase was re-extracted, dried and distilled under reduced pressure. The gum residue was dissolved in 5.5 ml of ethyl acetate to which was added 43 ml of ether. After 3 hours 15 minutes of stirring, the crystals formed were filtered off, rinsed and dried to obtain 2.232 g of 1,1-dimethylethyl 7-[2-(2-tritylaminothiazol-4-yl)-2-methoxyimino-acetamido]-8-oxo-3-hydroxymethyl-4-thia-1-azabicyclo[4,2,0]oct-2-ene-2-carboxylate.

STEP G: 1,1-dimethylethyl 7-[2-(2-tritylaminothiazol-4-yl)-2-methoxyimino-acetamido]-8-oxo-3-chloromethyl-4-thia-1-azabicyclo[4,2,0]oct-2-ene-2-carboxylate 623 mg of the alcohol of Step F were dissolved in 8 ml of dichloromethane with 834 mg of tosyl chloride and a solution of 534 mg of 4-dimethylamino-pyridine and 5 ml of dichloromethane was introduced over 20 minutes. After 1 hour of stirring, 2.2 ml of N hydrochloric acid were added with stirring and the decanted organic phase was dried and distilled under reduced pressure. The residue was chromatographed on silica and eluted with dichloromethane ethyl acetate (9–1) and crystallized from ether to obtain 245 mg of 1,1-dimethylethyl 7-[2-(2-tritylaminothiazol-4-yl)-2-methoxyimino-acetamido]-8-oxo-3-chloromethyl-4-thia-1-azabicyclo[4,2,0]oct-2-ene-2-carboxylate.

UV Spectrum in EtOH infl: 224 nm $E_1^1$: 441 ϵ=38200 infl: 264 nm $E_1^1$: 179 infl: 271 nm $E_1^1$: 164 max: 306 nm $E_1^1$: 222 ϵ=19200

STEP H: 1,1-dimethylethyl 7-[2-(2-tritylaminothiazol-4-yl)-2-methoxyimino-acetamido]-8-oxo-3-[(1-methyl-1H-tetrazol-5-yl)-thio-methyl]-8-oxo-4-thia-1-azabicyclo[4,2,0]oct-2-ene-2-carboxylate 301 mg of the product of Step G and 114 mg of the sodium salt of 1-methyl-5-mercapto-1,2,3,4-tetrazole were dissolved in 3 ml of dimethylformamide and after stirring for 1 hour 40 minutes, the solution was poured into 30 ml of water and extracted with ethyl acetate. The organic phase was dried and distilled under reduced pressure. The gum obtained was dissolved in 2 ml of ethyl acetate and ether was added up to the limit of solubility. The crystals obtained after 45 minutes were filtered, rinsed with ether and dried to obtain 283 mg of 1,1-dimethylethyl 7-[2-(2-tritylaminothiazol-4-yl)-2-methoxyimino-acetamido]-8-oxo-3[(1-methyl-1H-tetrazol-5-yl)-thio-methyl]-8-oxo-4-thia-1-azabicyclo[4,2,0]-oct-2-ene-2-carboxylate in 2 lots.

STEP I: 7- [2-(2-aminothiazol-4-yl)-2-methoxyimino-acetamido]-8-oxo-3-[(1-methyl-1H-tetrazol-5-yl)-thiomethyl]-4-thia-1-azabicyclo[4,2,0]oct-2-ene-2-carboxylic acid Using the procedure of Step E of Example 1, the crude product was dissolved in water with sodium bicarbonate and acidified to a pH of 4, then filtered after the greater part of the water had been distilled off. 371 mg of the product of Step H yield 61 mg of 7-[2-(2-aminothiazol-4-yl)-2-methoxyimino-acetamido]-8-oxo-3-[(1-methyl-1H-tetrazol-5-yl)-thiomethyl]-4-thia-1-azabicyclo[4,2,0]oct-2-ene-2-carboxylic acid UV Spectrum 1) in EtOH max: 302 nm $E_1^1$: 295 ϵ=15100
2) in EtOH/HCl 0.1N infl: 273 nm $E_1^1$: 304 max: 285 nm $E_1^1$: 318 ϵ=16300 infl: 292 nm $E_1^1$: 312 ϵ=16000 infl: 309 nm $E_1$: 245 ϵ=12500

The corresponding optically active products and especially the syn 6S, 7S isomer of 1,1-dimethyl-ethyl 7-[2-(2-tritylaminothiazol-4-yl)-2-methoxyimino-acetamido]-8-oxo-3-hydroxymethyl-4-thia-1-azabicyclo[4,2,0]oct-2-ene-2-carboxylate with a melting point of 180° C. was prepared from the syn isomer of 3S, 4S 4-mercaptomethyl-[2-(2-tritylamino-thiazol-4-yl)-2-methoxyimino-acetamidol-2-oxo-1-azetidine (described in French Application No. 2,538, 389).

| | | | |
|---|---|---|---|
| U.V. Spectrum (ethanol): | | | |
| Inflex. | 222 nm | $E_1^1$ = 444 | |
| Inflex. | 237 nm | $E_1^1$ = 352 | |
| Max. | 302 nm | $E_1^1$ = 223 | ϵ = 15,900 |
| U.V. Spectrum (ethanol + 0.1 NHCl): | | | |
| Inflex. | 221 nm | $E_1^1$ = 464 | |
| Inflex. | 263 nm | $E_1^1$ = 204 | |
| Inflex. | 285 nm | $E_1^1$ = 294 | |
| Inflex. | 293 nm | $E_1^1$ = 310 | = 22,100 |
| Inflex. | 300 nm | $E_1^1$ = 299 | |
| Inflex. | 310 nm | $E_1^1$ = 230 | |

EXAMPLE 28

1-[[7-[2-(2-aminothiazol-4-yl)-2-methoxyimino-acetamido]-2-carboxy-8-oxo-4-thia-1-azabicyclo[4,2,0]oct-2-ene-3-yl]-methyl]-pyridinium trifluoromethane sulfonate STEP A: 1-[7-[2-(2-tritylaminothiazol-4-yl)-2-methoxyimino-acetamido]-2-(1,1-dimethylethyl carboxylate)-8-oxo-4-thia-1-azabicyclo[4,2,0]oct-2-ene-3-yl]-methyl]-pyridinium trifluoromethane sulfonate 356 mg of the alcohol of Step F of Example 27 dissolved in 4 ml of a solution containing 0.4 ml of pyridine diluted to 10 ml in dichloromethane cooled under nitrogen to −70° C. was admixed over 5 minutes with 2.6 ml of a solution of 0.84 ml of trifluoromethane sulfonic anhydride extended to 20 ml with 130% dichloromethane and the solution was left to warm up spontaneously for 1 hour and 5 minutes. The solvent was evaporated under vacuum and the residue was dissolved in ethanol and the salt was left to crystallize for 17 hours to obtain 215 mg of 1-[7-[2-(2-tritylaminothiazol-4-yl)-2-methoxyimino-acetamido]-2-(1,1-dimethylethyl carboxylate)-8-oxo-4-thia-1-azabicyclo[4,2,0]oct-2-ene-3-yl]-methyl]-pyridinium trifiluloromethane sulfonate after filtration, rinsing and drying.

STEP B: 1-[[7-[2-(2-aminothiazol-4-yl)-2-methoxyimino-acetamido]-2-carboxy-8-oxo-4-thia-1-azabicyclo[4,2,0]oct-2-ene-3yl]-methyl]-pyridinium trifluoromethane sulfonate 215 mg of tritylated ester of Step A dissolved in 0.9 ml of trifluoroacetic acid was left closed to the atmosphere for 50 minutes, after which it was diluted with 10 ml of isopropyl ether. The precipitate was filtered, rinsed and dried, then dissolved in ethanol to which 2 drops of pyridine were added. After 15 minutes, the crystals formed were filtered off, rinsed and dried to obtain 65 mg of 1-[[7-[2-(2-aminothiazol-4-yl)-2-methoxyimino-acetamido]-2-carboxy-8-oxo-4-thia-1-azabicyclo[4,2,0]oct-2-ene-3-yl]-methyl-pyridinium trifluoromethane sulfonate.

UV Spectrum in EtOH infl: 215 $E_1^1$: 410 infl: 256 nm $E_1^1$: 276 ϵ=17200 infl: 264 nm $E_1^1$: 251 max: 293 nm $E_1^1$: 279 ϵ=17400

EXAMPLE 29

1-[[7-[(2-aminothiazol-4-yl)-methoxyimino-acetamido]-2-carboxy-8-oxo-4-thia-1-azabicyclo[4,2,0]oct-2-ene-3-yl]-methyl]-(6,7-dihydro)-5H-1-pyrindinium trifluoromethane sulfonate STEP A: 1-[[7-[(2-triphenylmethylaminothiazol-4-yl)-methoxyimino-acetamido]-2-(1,1-dimethylethyl carboxylate)-8-oxo-4-thia-1-azabicyclo[4,2,0]oct-2-ene-3-yl]-methyl](6,7-dihydro)-5H-1-pyrindinium trifuloromethane sulfonate 356 mg of the alcohol of Step F of Example 27 dissolved in 2 ml of dichloromethane and 4 ml of a solution of 0.58 ml of 6,7-dihydro-5H-1-pyrindane adjusted to 10 ml in dichloromethane cooled to −70° C. was admixed with 3 ml of a solution of 0.84 ml of trifluoromethane sulfonic anhydride extended to 20 ml in dichloromethane over 2 minutes. After this, the solution was reheated to ambient temperature for 2 hours and distilled under reduced pressure. The residue was triturated in ether, filtered, and the insoluble matter was dissolved in ethanol. The crystals formed were filtered off after standing for one hour to obtain 281 mg of 1-[[7-[(2-triphenylmethylaminothiazol-4-yl-methoxyimino-acetamido]-2-(1,1-dimethylethyl carboxylate)-8-oxo-4-thia-1-azabicyclo[4,2,0]oct-2-ene-3-yl]-methyl](6,7-dihydro)-5H-1-pyrindinium trifluoromethane sulfonate.

STEP B: 1-[[7-[(2-aminothiazol-4-yl)-methoxyimino-acetamido]-2-carboxy-8-oxo-4-thia-1-azabicyclo[4,2,0]oct-2-ene-3yl]-methyl-(6,7-dihydro)-5H-1-pyrindinium trifluoromethane sulfonate Using the procedure of Example. 28, 281 mg of the product of Step A were reacted to obtain 93 mg of 1-[[7-[2-aminothiazol-4-yl)-methoxyimino-acetamido]-2-carboxy-8-oxo-4-thia-1-azabicyclo[4,2,0]oct-2-ene-3-yl]-methyl]-(6,7-dihydro)-5H-1-pyrindinium trifluoromethane sulfonate.

UV Spectrum in EtOH/HCl 0.1N max: 223 nm $E_1^1$: 315 $\epsilon$=20900 max: 282 nm $E_1^1$: 394 $\epsilon$=26200 infl: 310 nm $E_1^1$: 200 $\epsilon$=13300

EXAMPLE 30

Syn isomer of racemic cis 7-[2-(2-aminothiazol-4-yl)-2-methoxyimino-acetamido]-8-oxo-3-[(1-carboxymethyl-1H-tetrazol-5-yl)-thio]-4-thia-1-azabicyclo[4,2,0]oct-2-ene-2-carboxylic acid Using the procedure of Example 3 and starting with a product of which the carboxyl group was protected in the form of diphenylmethyl ester, syn isomer of racemic cis 7-[2-(2-aminothiazol-4-yl)-2-methoxyimino-acetamido]-8-oxo-3-[(1-carboxymethyl-1H-tetrazol-5-yl)-thio]-4-thia-1-azabicyclo[4,2,0]oct-2-ene-2-carboxylic acid was obtained.

UV Spectrum 1) in EtOH max: 229 nm $E_1^1$: 393 $\epsilon$=21300 max: 305 nm $E_1^1$: 261 $\epsilon$=14100

2) in EtOH HCl 0.1N infl: 220 nm $E_1^1$: 306 infl: 310 nm $E_1^1$: 228 $\epsilon$=12300 max: 263 nm $E_1^1$: 293 $\epsilon$=15900 max: 284 nm $E_1^1$: 287 $\epsilon$=15500

EXAMPLE 31

Syn isomer of racemic cis 7-[2-(2-aminothiazol-4-yl)-2-methoxyimino-acetamido]-8-oxo-3-[(phenylmethoxymethyl)]-4-thia-1-azabicyclo[4,2,0] oct-2-ene-2-carboxylic acid Syn isomer of racemic cis 7-[2-(2-aminothiazol-4-yl)-methoxyimino-acetamido]-8-oxo-3-[(phenylmethoxymethyl)[-4-thia-1-azabicyclo[4,2,0]oct-2-ene-2-carboxylic acid was obtained using the procedure of Example 2.

Analysis: Calculated: % C 50.09 % H 4.20 % N 13.91 % S 12.73 Found: 50.0 4.2 13.6 12.4

EXAMPLE 32

Lactone of 7-[2-(2-aminothiazol-4-yl)-2-methoxyimino-acetamido]-8-oxo-3-hydroxymethyl-4-thia-1-azabicyclo[4,2,0]oct-2-ene-2-carboxylic acid 356 mg of the product of Step F of Example 27 dissolved in 1.4 ml of trifluoroacetic acid stood for 50 minutes in a closed receptacle and after 15 ml of isopropyl ether were added, the trifluoroacetate formed was separated, and 246 mg of the crude product were obtained. This was dissolved in ethanol, stirred for half-an-hour, filtered and dried to obtain 151 mg of lactone of 7-[2-(2-aminothiazol-4-yl)-2-methoxyimino-acetamido]-8-oxo-3-hydroxymethyl-4-thia-1-azabicyclo[4,2,0]oct-2-ene-2-carboxylic acid.

Analysis: $C_{14}H_{13}O_5S_2$; molecular weight=395.42 Calculated: % C 42.52 % H 3.31 % N 17.71 % S 16.22 Found: 42.5 3.3 17.3 15.9

EXAMPLE 33

Syn isomer of racemic cis 6-(7-[2-(2-aminothiazol-4-yl)-2-methoxyimino-acetamido]-2-carboxy-8-oxo-4-thia-1-azabicyclo[4,2,0]oct-2-ene-3-yl)-methyl-thieno-[2,3-c]-pyridinium trifluoromethanesulfonate trifluoroacetate 0.214 g of the product of Step F of Example 27 was cooled to −70° C. with 4 ml of methylene chloride and 203 g of thieno [2,3-c] pyridine and 0.1 ml of trifluoromethane sulfonic anhydride was added and the temperature was allowed to return to ambient with stirring. The reaction mixture was poured into 40 ml of water, stirred, decanted, and extracted with methylene chloride. The organic phases were dried and concentrated to dryness under reduced pressure at about 35° C. The residue was chromatographed on silica and eluted with a mixture of methylene chloride and methanol (92–8). to obtain 0.104 g of product. This latter was dissolved in 0.45 ml of trifluoroacetic acid, and the mixture was stirred for 50 minutes at ambient temperature. 4.5 ml of ethyl ether were added and after stirring for 5 minutes, separating, and rinsing with ether, 75 mg of syn isomer of racemic cis 6-(7-[2-(2-aminothiol-4-yl)-2-methoxyimino-acetamido]-2-carboxy-8-oxo-4-thia-1-azabicyclo[4,2,0]oct-2-en-3-yl)-methyl-thieno-[2,3-c] pyridinium trifluoromethanesulfonate trifluoroacetate were obtained.

NMR Spectrum (DMSO)

6.82 ppm, $H_5$ of the thiazole 7.94–8.01 ppm, $H_2$ of thienyl 8.91–8.96 ppm, $H_3$ of thienyl 8.55–8.63 ppm, H at β of the $N^+$ 8.88 ppm, H at position 5 of the thieno pyridine 10.0 ppm, H at position 7 of the thieno pyridine.

EXAMPLE 34

Syn isomer of racemic cis (7-[2-]2-aminothiazol-4-yl)-2-methoxyimino-acetamidol-8-oxo-2-carboxy-4-thia-1-azabicyclo[4,2,0]oct-2-en-3-yl)-methyl trimethyl ammonium trifluoromethanesulfonate STEP A: Syn isomer of racemic cis [[7-[2-(2-tritylaminothiazol-4-yl)-2-methoxyimino-acetamido]-8-oxo-2-(1,1-dimethylethyloxy)-carbonyl-4-thia-1-azabicyclo [4,2,0]oct-2-en-3-yl]-methyl]-trimethyl ammonium trifluoromethane sulfonate 392 mg of the product of Step F of Example 27 dissolved in 8.8 ml of methylene chloride cooled to −70° C. was admixed with 2.75 ml of a freshly prepared 0.74M solution of trimethylamine in methylene chloride followed still at this temperature by 3.3 ml of a freshly prepared solution of trifluoromethane sulfonic anhydride in methylene chloride (0.42 ml q.s. for 10 ml) added dropwise over 5 minutes. After 15 minutes at −70° C., 2 drops of trimethylamine solution were added to bring the pH to 4, and the solvent was distilled off. Water was added to the residue, which was then extracted with ethyl acetate. The organic phase was dried and concentrated to dryness under reduced pressure..The residue was triturated in ether and filtered to obtain 481 mg of syn isomer of racemic cis [[7-[2-(2-tritylaminothiazol-4-yl)-2-methoxyimino-acetamido]-8-oxo-2-(1,1-dimethylethyloxy)-carbonyl-4-thia-1-azabicyclo[4,2,0]oct-2-en-3-yl]-methyl]trimethyl ammonium trifluoromethane sulfonate.

STEP B: Syn isomer of racemic cis (7-(2-(2-aminothiazo-4-yl)-2-methoxyimino-acetamido)-8-oxo-2-carboxy-4-thia-1-azabicyclo[4,2,0]oct-2-en-3-yl)-methyl ammonium trifluoromethansulfonate Using the procedure of Step E of Example 1, 481 mg of the product of Step A were reacted to obtain 84 mg of syn isomer of racemic cis (7-[2-(2-aminothiazo-4-yl)-2-methoxyimino-acetamido]-8-oxo-2-carboxy-4-thia-1-azabicyclo[4,2,0]oct-2-en-3-yl)-methyl trimethyl ammonium trifluoromethanesulfonate.

| NMR Spectrum (DMSO) | |
|---|---|
| 6.83 ppm, $H_5$ of the thiazole | |
| 4.61–4.77 ppm<br>4.2–4.36 ppm | H of the $CH_2$ in α of the N+ |
| 3.14 ppm, H of the trimethylamino. | |

EXAMPLE 35

Syn isomer of racemic cis [7-[2-(2-aminothiazol-4-yl)-2-methoxyimino-acetamido]-8-oxo-2-carboxy-4-thia-1-azabicyclo[4,2,0]oct-2-en-3-yl)-methyl triethylammonium trifluoromethanesulfonate Using the procedure of Step 34, triethylamine was reacted to obtain 61 mg of [7-[2-(2-aminothiazol-4-yl)-2-methoxyimino-acetamido]-8-oxo-2-carboxy-4-thia-1-azabicyclo[4,2,0]oct-2-en-3-yl)-methyl triethylammonium trifluoromethanesulfonate.

| NMR Spectrum (DMSO) | |
|---|---|
| 4.2–4.37 ppm<br>4.64–4.7 ppm, | H in α of the $N^+$ |
| 3.86 ppm, H of the methoxy | |
| 5.66 ppm, H at position 7. | |

EXAMPLE 36

Syn isomer of racemic cis [7-[2-(2-aminothiazol-4-yl)-2-methoxyimino-acetamido]-8-oxo-2-carboxy-4-thia-1-azabicyclo[4,2,0]oct-2-ene-3-yl)-methyldimethyl-2-propynyl ammonium trifluoromethanesulfonate Using the procedure of Example 34, 2-dimethylaminopropyne was reacted to obtain 90 mg of syn isomer of racemic cis [7-[2-(2-aminothiazol-4-yl)-2-methoxyimino-acetamido]-8-oxo-2-carboxy-4-thia-1-azabicyclo[4,2,0]oct-2-ene-3-ylmethyldimethyl-2-propynyl ammonium trifluoromethanesulfonate.

NMR Spectrum (DMSO)

6.81 ppm, $H_5$ of the thiazole 3.14 ppm, H of the dimethyl ammonium 2.84 ppm, H in position 3 of the propynyl.

EXAMPLE 37

Syn isomer of racemic cis [7-[2-(2-aminothiazol-4-yl)-2-methoxyimino-acetamido]-8-oxo-2-carboxy-4-thia-1-azabicyclo[4,2,0]oct-2-ene-3-yl]-methyl-4-methyl morpholinium trifluoromethane sulfonate Using the procedure of Example 34, 4-methylmorpholine was reacted to obtain 115 mg of syn isomer of racemic cis [7-[2-(2-aminothiazol-4-yl)-2-methoxyimino-acetamido]-8-oxo-2-carboxy-4-thia-1-azabicyclo[4,2,0]oct-2-ene-3-yl]-methyl-4-methyl morpholinium trifluoromethane sulfonate.

| NMR Spectrum (DMSO) | |
|---|---|
| 6.82 ppm, $H_5$ of the thiazole | |
| 3.22 ppm, H of the $CH_3$ in position 1 of the morpholinium | |
| 4.33–4.5 ppm<br>4.7–4.9 ppm, | H of the $CH_2$ in α of the morpholinium. |

EXAMPLE 38

Syn isomer of racemic cis 7-[2-(2-aminothiazol-4-yl)-2-methoxyimino-acetamido]-8-oxo-4-thia-3-(dimethylaminomethyl)-1-azabicyclo[4,2,0]oct-2-ene-2-carboxylic acid trifluoromethane sulfonate trifluoroacetate Using the procedure of Example 34, 3-dimethylamino-propion nitrile was reacted to obtain after treatment with trifluoroacetic acid, 289 mg of syn isomer of racemic cis 7-[2-(2-aminothiazol-4-yl)-2-methoxyimino-acetamido]-8-oxo-4-thia-3-(dimethylaminomethyl)-1-azabicyclo[4,2,0]oct-2-ene-2-carboxylic acid trifluoromethane sulfonate trifluoroacetate, NMR Spectrum (DMSO)

6.84 ppm, H at position 5 of the thiazole 2.81 ppm, H of the dimethylamino.

The following products have been prepared using the procedure of Example 38 starting with the corresponding products.

EXAMPLE 39

Syn isomer of racemic cis [7-[2-(2-aminothiazol-4-yl)-2-methoxyimino-acetamido]-8-oxo-4-thia-2-carboxy-1-azabicyclo[4,2,0]oct-2-en-3-yl]methyl-1-methyl pyrrolidinium trifluoromethane sulfonate trifluoroacetate NMR Spectrum (DMSO)

6.88 ppm, $H_5$ of the thiazole 3.03 ppm, H of the $CH_3$—$N^+$.

EXAMPLE 40

Syn isomer of racemic cis [7-[2-(2-aminothiazol-4-yl)-2-methoxyimino-acetamido]-8-oxo-4-thia-2-carboxy-1-azabicyclo[4,2,0]oct-2-en-3-yl]-methyl-4-dimethylamino pyridinium trifluoromethane sulfonate trifluoroacetate

| NMR Spectrum | |
|---|---|
| 6.81 ppm, $H_5$ of the thiazole, | |
| 3.2 ppm, H of $(CH_3)_2N$— | |
| 5–5.16 ppm<br>5.35–5.41 ppm | H of the —$CH_2$ in position 3. |

EXAMPLE 41

Syn isomer of racemic cis [7-[2-(2-aminothiazol-4-yl)-2-methoxyimino-acetamido]-8-oxo-4-thia-2-carboxy-1-azabicyclo[4,2,0]oct-2-en-3-yl]-methyl-5-ethyl-2-methyl pyridinium trifluoromethane sulfonate trifluoroacetate

| NMR Spectrum |
|---|
| 6.87 ppm, $H_5$ of the thiazole |
| 2.77 ppm, H of the $CH_3$— at position 2 of the pyridinium |
| 1.17–1.25–1.33 ppm ⎫ |
| 2.68–2.76–2.84–2.92 ppm ⎭ H of the ethyl at position 5 of the pyridinium. |

EXAMPLE 42

Syn isomer of racemic cis [7-[2-(2-aminothiazol-4-yl)-2-methoxyimino-acetamido]-8-oxo-4-thia-2-carboxy-1-azabicyclo[4,2,0]oct-2-en-3-yl]-methyl-3-methyl-1H-imidazolium trifluoromethane sulfonate trifluoroacetate NMR Spectrum 6.83 ppm, $H_5$ of the thiazole 3.85 and 3.51 ppm, H of the $CH_3$—N.

EXAMPLE 43

Syn isomer of racemic cis [7-[2-(2-aminothiazol-4-yl)-2-methoxyimino-acetamido]-8-oxo-4-thia-2-carboxy-1-azabicyclo[4,2,0]oct-2-en-3-yl]-methyl-2-(1-methylethyl)-pyridinium trifluoromethane sulfonate trifluoroacetate

| NMR Spectrum |
|---|
| 6.83 ppm, $H_5$ of the thiazole |
| 1.31–1.38 ⎫ |
| 1.35–1.42 ⎭ ppm, H of the paired methyls. |

EXAMPLE 44

Syn isomer of racemic cis [7-[2-(2-aminothiazol-4-yl)-2-methoxyimino-acetamido]-8-oxo-4-thia-2-carboxy-1-azabicyclo[4,2,0]oct-2-en-3-yl]-methyl-4-cyclopropyl pyridinium trifluoromethane sulfonate trifluoroacetate NMR Spectrum 6.81 ppm, $H_5$ of the thiazole 1.05–1.58 ppm, H of the —$CH_2$ of the cyclopropyl 2.27 ppm, angular H of the cyclopropyl.

EXAMPLE 45

Syn isomer of racemic cis [7-[2-(2-aminothiazol-4-yl)-2-methoxyimino-acetamido]-8-oxo-4-thia-2-carboxy-1-azabicyclo[4,2,0]oct-2-en-3-yl]-methyl-1-pyrazinium trifluoromethane sulfonate trifluoroacetate NMR Spectrum 6.82 ppm, $H_5$ of the thiazole 9.3 and 9.61 ppm, aromatic H's.

EXAMPLE 46

Syn isomer of racemic cis 6-[(7-[2-(2-aminothiazol-4-yl)-2-methoxyimino-acetamido]-8-oxo-4-thia-2-carboxy-1-azabicyclo[4,2,0]oct-2-en-3-yl]-methyl]-7-methyl-thieno[2,3,-c]pyridinium trifluoromethane sulfonate trifluoroacetate NMR Spectrum 6.82 ppm, $H_5$ of the thiazole, 5.93 ppm H of the —$CH_2$—$N^+$

EXAMPLE 47

Syn isomer of racemic cis [7-[2-(2-aminothiazol-4-yl)-2-methoxyimino-acetamido]-8-oxo-4-thia-2-carboxy-1-azabicyclo[4,2,0]oct-2-en-3-yl]-methyl-3-methoxy pyridinium trifluoromethane sulfonate trifluoroacetate.

| NMR Spectrum |
|---|
| 6.82 ppm, $H_5$ of the thiazole |
| 4.02 ppm, H of the methoxy |
| 5.4–5.56 ppm ⎫ |
| 5.77–5.94 ppm ⎭ H of the —$CH_2N^+$ |

EXAMPLE 48

Syn isomer of racemic cis [7-[2-(2-aminothiazol-4-yl)-2-methoxyimino-acetamido]-8-oxo-4-thia-2-carboxy-1-azabicyclo[4,2,0]oct-2-en-3yl]-methyl-4-ethoxy pyridinium trifluoromethane sulfonate trifluoroacetate NMR Spectrum 6.82 ppm, $H_5$ of the thiazole 1.34–1.42–1.51 4.31–4.39–4.48–4.56 ppm, H of the ethoxy.

EXAMPLE 49

Syn isomer of racemic cis [7-[2-(2-aminothiazol-4-yl)-2-methoxyimino-acetamido]8-oxo-4-thia-2-carboxy-1-azabicyclo[4,2,0]oct-2-en-3-yl]-methyl-4-methoxy-methyl pyridinium trifluoromethane sulfonate trifluoroacetate NMR Spectrum 6.83 ppm, $H_5$ of the thiazole 4.82–4.71 ppm, H of the O—$CH_2$— 3.44–3.42 ppm, H of the $CH_3$ of the $CH_3$—O—$CH_2$.

EXAMPLE 50

Syn isomer of racemic cis 7-[7-[2-(2-aminothiazol-4-yl)-2-methoxyimino-acetamido]-8-oxo-4-thia-2-carboxy-1-azabicyclo[4,2,0]oct-2-en-3-yl]-methyl thieno[2,3-b]pyridinium trifluoromethane sulfonate trifluoroacetate

| NMR Stectrum |
|---|
| 6.87 ppm, $H_5$ of the thiazole |
| 5.94–6.11 ⎫ |
| 6.17–6.34 ppm, ⎭ H of the —$CH_2N^+$ |

-continued

| NMR Stectrum | | |
|---|---|---|
| 7.91–7.97<br>8.3–8.35 ppm, | ) | aromatic H's of the thiophene. |

EXAMPLE 51

Syn isomer of racemic cis [7-[2-(2-aminothiazol-4-yl)-2-methoxyimino-acetamido]-8-oxo-4-thia-2-carboxy-1-azabicyclo[4,2,0]oct-2-en-3-yl]-methyl-3-(1-methylethyloxy) pyridinium trifluoromethane sulfonate trifluoroacetate NMR Spectrum 6.84 ppm, $H_5$ of the thiazole 4.91 ppm, H of the O—CH—$(CH_3)_2$ 1.34–1.41 ppm, H of the $CH_3$ of the O—CH—$(CH_3)_2$

EXAMPLE 52

Syn isomer of racemic cis 2-amino α-(methoxyimino)-N-(1,7-dioxo-1,3,5,5a,6,7-hexahydro-3-hydroxy azeto [1,21-d]furo [3,4-d]-[1,4-thiazin-6-yl)-4-thiazolacetamide trifluoroacetate STEP A: 1,1-dimethylethyl 7-[2-(2-tritylaminothiazol-4-yl)-2-methoxyimino-acetamido]-3-formyl-8-oxo-4-thia-1-azabicyclo[4,2,0]oct-2-en-2-carboxylate 8.2.ml of a solution of oxalyl chloride (1 ml q.s. for 100 ml of methylene chloride) were cooled to −70° C. and 8.2 ml of a solution of dimethyl-sulfoxide (1.7 ml q.s. for 100 ml of methylene chloride) were added with stirring for 5 minutes. Then, 356 mg of the product of Step F of Example 27 in 10 ml of methylene chloride were added dropwise while the stirring was maintained and over 2 minutes and at −70° C., 5 ml of a triethylamine solution (2 ml q.s. for 20 ml of methylene chloride) were added. The temperature was raised to −45° C., and after standing for 10 minutes, water and 2.5 ml of N hydrochloric acid were added with further stirring. After decanting, extraction was effected with methylene chloride and the extracts were dried and concentrated to dryness under reduced pressure. The residue was dissolved in ethyl acetate, ether was added, and after 15 minutes and filtering, 256 mg of 1,1-dimethylethyl 7-[2-(2-tritylaminothiazol-4-yl)-2-methoxyimino-acetamido]-3-formyl-8-oxo-4-thia-1-azabicyclo[4,2,0]oct-2-en-2-carboxylate were obtained.

STEP B: Syn isomer of racemic cis 2-amino α-(methoxyimino)-N-(1,7-dioxo-1,3,5,5a,6,7-hexahydro-3-hydroxy azeto[1,2-d]furo [3,4-b]-[1,4]-thiazin-6-yl)-4-thiazol-acetamide trifluoroacetate Using the procedure of Example 34, Step B, 85 mg of the product of Step A were reacted to obtain 50 mg of syn isomer of racemic cis 2-amino α-(methoxyimino)-N-(1,7-dioxo-1,3,5,5a,6,7-hexahydro-3-hydroxy azeto[1,2-d]furo [3,4-b]-[1,4]-thiazin-6-yl)-4-thiazolacetamide trifluoroacetate.

NMR Spectrum (DMSO)

6.9 ppm, $E_5$ of the thiazole 3.91 ppm, H of the N—O—$CH_3$ 6.28 ppm H of the —CH—OH.

EXAMPLE 53

Syn isomer of 6S,7S 7-[7-[2-(2-aminothiazol-4-yl)-2-methoxyimino-acetamido]-2-carboxy-8-oxo-4-thia-1-azabicyclo[4,2,0]oct-2-en-3-yl]-methyl thieno [2,3-b]pyridinium trifluoromethane sulfonate Using the procedure of Example 34, syn isomer of 6S,7S, 1,1-dimethylethyl7-[2-(2-tritylaminothiazol-4-yl)-2-methoxy-iminoacetamido]-8-oxo-3-hydroxymethyl-4-thia-1-azabicyclo[4,2,0]oct-2-en-2-carboxylate obtained by the process of Example 27, Step F, and thieno [2,3-b]pyridine were reacted to obtain syn isomer of 6S ,7S 7-[7-[2-(2-aminothiazol-4-yl)-2-methoxyimino-acetamido]-2-carboxy-8-oxo-4-thia-1-azabicyclo[4,2,0]oct-2-en-2-yl]-methyl thieno [2,3-b]pyridinium trifluoromethane sulfonate.

| NMR Spectrum (DMSO) | | |
|---|---|---|
| 6.8 ppm, $H_5$ of the thiazole | | |
| 7.87–7.94 ppm<br>8.25–8.33 ppm | ) | H of the thiophene |
| 5.68 ppm, $H_7$ | | |

EXAMPLE 54

Syn isomer of racemic cis 7-[2-(2-aminothiazol-4-yl)-2-ethoxyimino-acetamido]-8-oxo-4-thia-2-carboxy-1-azabicyclo[4,2,0]oct-2-en-3-yl]-methyl pyridinium trifluoromethane sulfonate trifluoroacetate STEP A: Cis 3-(1,3-dihydro-1,3-dioxo-2H-isoindol-2-yl)-4-oxo-2-mercaptomethylazetidine 10.6 g of cis 3-(1,3-dihydro-1,3-dioxo-2H-isoindol-2-yl)-4-oxo-2-chloromethyl azetidine, (Belgian Patent No. 894, 785) and 48 g of sodium iodide mixed in 125 ml of hot dimethylformamide were stirred for 6 hours and after cooling to ambient temperature, 520 ml of water were added. The mixture was extracted with ethyl acetate and the organic phases were dried and concentrated to dryness under reduced pressure. The crystallized residue was taken up in very little ethyl acetate and after separating, rinsing with ethyl acetate and triturating with ether, 9.75g of the iodated derivative were obtained.

8.9 g of the iodated derivative were added dropwise to a solution of 2.1 g of sodium hydrogen sulfide in 40 ml of dimethylformamide, cooled to 0°–5° C. under an inert atmospheres, with stirring for 10 minutes. After acidifying with 1.5 ml of acetic acid, 220 ml of water were added followed by extraction with ethyl acetate. The organic phases were dried and concentrated to dryness under reduced pressure. The residue was chromatographed on silica and eluted with ethyl acetate. The solvent was evaporated and the crystallized residue was taken up in ether to obtain 4 g of cis 3-(1,3-dihydro-1,3-dioxo-2H-isoindol-2-yl)-4-oxo-2-mercaptomethylazetidine.

STEP B: Racemic cis 1,1-dimethylethyl 7-(1,3-dihydro-1,3-dioxo-2H-isoindol-2-yl)-8-oxo-3-[1,1-dimethylethyl)-dimethylsilyloxymethyl]--4-thia-1-azabicyclo[4,2,0]oct-2-en-2-carboxylate Using the procedure of Steps D & E of Example 27, the product of Step A was reacted to obtain racemic cis 1,1-dimethylethyl 7-(1,3-dihydro-1,3-dioxo-2H-isoindol-2-yl)-8-oxo-3-[1,1-dimethylethyl)-dimethylsilyloxymethyl]-4-thia-1-azabicyclo[4,2,0]oct-2-en-2-carboxylate.

STEP C: Racemic cis 1,1-dimethylethyl 7-amino-3-hydroxymethyl-8-oxo-4-thia-1-azabicyclo[4,2,0]oct-2-en-2-carboxylate 1.592 g of the product of Step B was dissolved in 4 ml of dimethylformamide and, over 12 minutes, 3.3 ml of an M solution of hydrazine in dimethylformamide were added dropwise. The dimethylformamide was distilled off at 45° C. under reduced pressure and 10 ml of water and then 3.3 ml of N hydrochloric acid and 8 ml of ethanol were added with stirring for 2 hours. After filtering and distilling off the ethanol, ethyl acetate was added with stirring followed by alkalizing the decanted aqueous phase with sodium bicarbonate and extracting the precipitate with ethyl acetate. The organic phases were dried and concentrated to dryness under reduced pressure. The residue was taken up in ethyl acetate and ether was added, and after triturating and filtering, 604 mg of racemic cis 1,1-dimethylethyl 7-amino-3-hydroxymethyl-8-oxo-4-thia-1-azabicyclo[4,2,0]oct-2-en-2-carboxylate were obtained.

STEP D: Syn isomer of racemic cis 1,1-dimethylethyl 7-[2-(2tritylaminothiazol-4-yl)-2-ethoxyimino-acetamido]-3-hydroxymethyl--8-oxo-4-thia-1-azabicyclo[4,2,0]oct-2-en-2-carboxylate 549 mg of the syn isomer of 2-[2-tritylaminothiazol-4-yl]-2-ethoxyimino acetic acid were dissolved in 5.5 ml of acetone and 0.18 ml of triethylamine and 228 mg of tosyl chloride were added immediately with stirring for 45 minutes. A solution of 285 mg of the product of Step C in 1 ml of water, 1.5 ml of a 1M sodium bicarbonate solution and 2 ml of acetone was added to the reaction mixture with stirring for 35 minutes. The acetone was distilled off under reduced pressure, and extraction was effected with methylene chloride. The organic phases were dried and concentrated to dryness. The residue was chromatographed on silica under pressure and elution with a methylene chloride-ethyl acetate mixture (75–25) to obtain 602 mg of syn isomer of racemic cis 1,1-dimethylethyl 7-[2-(2-tritylaminothiazol-4-yl)-2-ethoxyimino-acetamido]-3-hydroxymethyl-8-oxo-4-thia-1-azabicyclo[4,2,0]oct-2-en-2-carboxylate.

STEP E: Syn isomer of racemic cis 7-[2-(2-tritylaminothiazol-4-yl)-2-ethoxyimino-acetamido]-8-oxo-4-thia-2[(1,1-dimethylethoxy)carbonyl]-1-azabicyclo[4,2,0]oct-2-en-3-yl)-methyl pyridinium trifluoromethane sulfonate Using the procedure of Example 34, 218 mg of 1,1-dimethyl-ethyl 7-[2-(2-tritylaminothiazol-4-yl)-2-ethoxyimino-acetamido]-3-hydroxymethyl-8-oxo-4-thia-1-azabicyclo[4,2,0]oct-2-en-2-carboxylate obtained above and 3.4 ml of a solution of pyridine at 0.4 ml for 10 ml of methylene chloride were reacted to obtain 158 mg of 7-[2-(2-tritylaminothiazol-4-yl)-2-ethoxyimino-acetamido]-8-oxo-4-thia-2-[(1,1-dimethylethoxy)-carbonyl]-1-azabicyclo[4,2,0]oct-2-en-3-yl)-methyl pyridinium trifluoromethane sulfonate.

STEP F: syn isomer of racemic cis 7-[2-(2-aminothiazol-4-yl)-2-ethoxyimino-acetamido]-8-oxo-4-thia-2-carboxy-1-azabicyclo[4,2,0]oct-2-en-3-yl methyl pyridinium trifluoromethane sulfonate trifluoroacetate Using the procedure of Example 37, Step B, 160 mg of syn isomer of racemic cis 7-[2-(2-aminothiazol-4-yl)-2-ethoxyimino-acetamido]-8-oxo-4-thia-2-carboxy-1-azabicyclo[4,2,0]oct-2-en-3-yl]methyl pyridinium trifluoromethane sulfonate trifluoroacetate were obtained.

NMR Spectrum (DMSO)

6.83 ppm, $H_5$ of the thiazole, 1.12–1.20–1.28 ppm, 4.01–4.09–4.17–4.26 ppm, H of the N-O-ethyl.

EXAMPLE 55

Syn isomer of racemic cis (7-[2-(2-aminothiazol-4-yl)-2-carboxymethoxyimino-acetamido]-2-carboxy-8-oxo-4-thia-1-azabicyclo[4.2,0]oct-2-en-3-yl) methyl pyridinium trifluoromethane sulfonate NMR Spectrum (DMSO)

6.83 ppm, $H_5$ of the thiazole 4.6 ppm, H of the

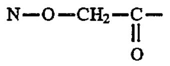

EXAMPLE 56

Syn isomer of racemic cis (7-[2-(2-aminothiazol-4-yl)-2-carboxymethoxyimino-acetamido]-2-carboxy-8-oxo-4-thia-1-azabicyclo[4,2,0]oct-2-en-3-yl)-methyl trimethylammonium trifluoromethane sulfonate trifluoroacetate NMR Spectrum (DMSO)

6.87 ppm, $H_5$ of the thiazole 3.15 ppm, H of the trimethyl $N^+$ 4.64 ppm, H of the

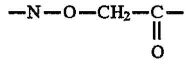

EXAMPLE 57

Syn isomer of racemic cis (7-[2-(2-aminothiazol-4-yl)-2-(1-carboxy-1-methylethoxy)-imino-acetamido]-2-carboxy-8-oxo-4-thia-1-azabicyclo[4,2,0]oct-2-en-3-yl)-methyl pyridinium trifluoromethane sulfonate trifluoroacetate NMR Spectrum (DMSO)

6.78 ppm, : $H_5$ of the thiazole 1.4 ppm, : H of the paired methyls.

EXAMPLE 58

Syn isomer of racemic cis (7-[2-(2-aminothiazol-4-yl)-2-(1-carboxy-1-methylethoxy)-imino-acetamido]-2-carboxy-8-oxo-4-thia-1-azabicyclo[4,2,0]oct-2-en-3-yl)-methyltrimethyl ammonium trifluoromethane sulfonate trifluoroacetate NMR Spectrum (DMSO)

6.78 ppm: $H_5$ of the thiazole 3.14 ppm: H of the trimethyl $N^+$ 144 ppm: H of the paired methyls.

EXAMPLE 59

Syn isomer of racemic cis (7-[2-(2-aminothiazol-4-yl)-2-phenoxyimino-acetamido]-2-carboxy-8-oxo-4-thia-1-azabicyclo[4,2,0]oct-2-en-3-yl)-methyl pyridinium trifluoromethane sulfonate trifluoroacetate NMR Spectrum (DMSO)

7.06 ppm: $H_5$ of the thiazole 7–7.44 ppm, H of the 0-0

EXAMPLE 60

Syn isomer of racemic cis (7-[2-(2-aminothiazol-4-yl)-2-difluoromethoxyimino-acetamido]-2-carboxy-8-oxo-4-thia-1-azabicyclo[4,2,0]oct-2-en-3-yl)-methyl pyridinium trifluoromethane sulfonate trifluoroacetate NMR Spectrum (DMSO)

7.08 ppm: $H_5$ of the thiazole 6.37–7.14–7.92 ppm: H of the —$CHF_2$

EXAMPLE 61

Syn isomer of racemic cis (7-[2-(2-aminothiazol-4-yl)-2-difluoromethoxyimino-acetamido]-2-carboxy-8-oxo-4-thia-1-azabicyclo[4,2,0]oct-2-en-3-yl) methyltrimethyl ammonium trifluoromethane sulfonate trifluoroacetate NMR Spectrum (DMSO)

7.11 ppm: $H_5$ of the thiazole 3.15 ppm: H of the trimethyl $N^+$

EXAMPLE 62

Syn isomer of racemic cis (7-[2-(2-aminothiazol-4-yl)-2-(2-propenyloxy)-imino-acetamido]-2-carboxy-8-oxo-4-thia-1-azabicyclo[4,2,0]oct-2-en-3-yl)-methyl pyridinium trifluoromethane sulfonate trifluoroacetate NMR Spectrum (DMSO)

6.8 ppm: $H_5$ of the thiazole 5.11–6 ppm: H of the $CH_2{=}CH$ and $H_7$ of $-CH_2O$

EXAMPLE 63

Syn isomer of racemic cis (7-[2-(2-aminothiazol-4-yl)-2-(2-propenyloxy)-imino-acetamido]2-carboxy-8-oxo-4-thia-1-azabicyclo[4,2,0]oct-2-en-3-yl)-methyl trimethyl ammonium trifluoromethane sulfonate trifluoroacetate NMR Spectrum (DMSO)

6.83 ppm: $H_5$ of the thiazole 3.14 ppm: H of the trimethyl $N^+$.

EXAMPLE 64

Syn isomer of racemic cis 1-(7-[2-(2-aminothiazol-4-yl)-2-cyano-methoxyimino-acetamido]-2-carboxy-8-oxo-4-thia-1-azabicyclo[4,2,0]oct-2-en-3yl)-methyl pyridinium trifluoromethane sulfonate trifluoroacetate STEP A: 1,1-dimethylethyl 7-[2-(2-tritylaminothiazol-4-yl)-2-cyano-methoxyimino-acetamido]-3-hydroxymethyl-8-oxo-4-thia-1-azabicyclo[4,2,0]oct-2-en 2-carboxylate Using the procedure of Step A of Example 54, 2-(2-tritylaminothiazol-4-yl)-2-cyanomethoxyimino acetic acid was reacted to obtain 1,1-dimethylethyl 7-[2-(2-tritylaminothiazol-4-yl)-2-cyanomethoxyimino-acetamido]-3-hydroxymethyl]-8-oxo-4-thia-1-azabicyclo[4,2,0]oct-2-en-2-carboxylate.

STEP B: 1-(7-[2-(2-tritylaminothiazol-4-yl)-2-cyanomethoxyimino-acetamido]-2-[1,1-dimethylethoxycarbonyl]-8-oxo-4-thia-1-azabicyclo[4,2,0]oct-2-en-3-yl)methyl pyridinium Using the procedure of Step A of Example 34 the product of Step A and pyridine were reacted to obtain 1-(7-[2-(2-tritylaminothiazol-4-yl)-2-cyanomethoxyimino-acetamido]-2-[1,1-dimethylethoxycarbonyl]-8-oxo-4-thia-1-azabicyclo[4,2,0]oct-2-en-3-yl)methyl pyridinium.

STEP C: 1-(7-[2-(2-aminothiazol-4-yl)-2-cyanomethoxyimino-acetamido]-2-carboxy-8-oxo-4-thia-1-azabicyclo[4,2,0]oct-2-en-3-yl)methyl pyridinium trifluoromethane sulfonate trifluoroacetate Using the procedure of Example 38, 116 mg of the product of Step B were reacted to obtain 91 mg of 1-(7-[2-(2-aminothiazol-4-yl)-2-cyanomethoxyimino-acetamido]-2-carboxy-8-oxo-4-thia-1-azabicyclo[4,2,0]oct-2-en-3-yl) methyl pyridinium trifluoromethane sulfonate trifluoroacetate.

| NMR Spectrum (DMSO) | |
|---|---|
| 6.91–6.94 ppm, $H_5$ of the thiazole | |
| 5.03 ppm, H of the acetonitrile, | |
| 8.14 to 8.31 ppm, H at β of $N^+$ | pyridine. |
| 8.61 to 8.77 ppm, H at γ of $N^+$ | pyridine. |
| 9.13 to 9.2 ppm, H at α of $N^+$ | pyridine. |

EXAMPLE 65

7-[2-(2-aminothiazol-4-yl)-2-methoxyimino-acetamido]-3-[[4-(2-chloro-2-propenyl)-1,4,5,6-tetrahydro-5,6-dioxo-1,2,4-triazin-3-yl]-thiomethyl]-8-oxo-4-thia-1-azabicyclo[4,2,0]oct-2-en-carboxylic acid trifluoroacetate STEP A: 1,1-dimethylethyl 7-[2-(2-tritylaminothiazol-4-yl)-2-methoxyimino-acetamido]-3-[[4-(2-chloro-2-propenyl)-1,4,5,6-tetrahydro-5,6-dioxo-1,2,4-triazin-3-yl]-thiomethyl]-8-oxo-4-thia-1-azabicyclo[4,2,0]oct-2-en-carboxylate 146 mg of syn isomer of racemic cis 1,1-dimethylethyl 7-[2-(2-tritylaminothiazol-4-yl)-2-methoxyimino-acetamido]-3-chloromethyl-8-oxo-4-thia-1-azabicyclo[4,2,0]oct-2-en-2-carboxylate of Example 27, Step G, 90 mg of 4-(2-chloro-2-propenyl)-1,4,5,6-tetrahydro-1,2,4-triazin-3-mercapto-5,6-dione, 83 mg of potassium carbonate, 60 mg of sodium iodide and 1.5 ml of dimethylflormamide were mixed together and stirred for three hours. 20 ml of water were added, and the pH was adjusted to 2 with N hydrochloric acid followed by extraction with ethyl acetate. The organic phase was washed with water, dried and concentrated to dryness under reduced pressure. The residue was chromatographed under pressure on silica and elution with a mixture of methylene chloride and ethyl acetate (1–1) to obtain 113 mg of 1,1-dimethylethyl 7-[2-(2-tritylaminothiazol-4-yl)-2-methoxyimino-acetamido]-3-[[4-(2-chloro-2-propenyl)-1,4,5,6-tetrahydro-5,6-dioxo-1,2,4-triazin-3-yl]-thiomethyl]-8-oxo-4-thia-1-azabicyclo[4,2,0]oct-2-en-carboxylate.

STEP B: Syn isomer of racemic cis 7-[2-(2-aminothiazol-4-yl)-2-methoxyimino-acetamidol-3-[(4-(2-chloro-2-propenyl)-1,4,5,6-tetrahydro-5,6-dioxo-1,2,4-triazin-3-yl]-thiomethyl]-8-oxo-4-thia-1-azabicyclo[4,2,0]oct-2-en-2-carboxylic acid trifluoracetate 113 mg of the product of Step A dissolved in 0.5 ml of trifluoroacetic acid stood for 50 minutes and then 5 ml of ether were added. After filtering, 70 mg of syn isomer of racemic cis 7-[2-(2-aminothiazol-4-yl)-2-methoxyimino-acetamido]-3-[[4–2-chloro-2-propenyl)-1,4,5,6-tetrahydro-5,6-dioxo-1,2,4-triazin-3-yl]-3-thiomethyl]-8-oxo-4-thia-1-azabicyclo[4,2,0]oct-2-en-2-carboxylic acid trifluoroacetate were obtained.

NMR Spectrum (DMSO)

6.83 ppm, $H_5$ of the thiazole 5.44 to 5.71 ppm, $H_7$ and the ethylene H's 11.25 ppm H of the hydroxyl.

EXAMPLE 66

Syn isomer of racemic cis 7-[2-(2-aminothiazol-4-yl)-2-methoxyimino-acetamido]-3-[(1,2,5,6-tetrahydro-2-methyl-5,6-dioxo-1,2,4-triazin-3-yl)-thiomethyl]-8-oxo-4-thia-1-azabicyclo[4,2,0]oct-2-en-2-carboxylic acid trifluoroacetate Using the procedure of Example 65, 3-mercapto-2-methyl-1,2,5,6-tetrahydro-1,2,4-triazin-5,6-dione were reacted to obtain 68 mg of syn isomer of racemic cis 7-[2-(2-aminothiazol-4-yl)-2-methoxyimino-acetamido]-3-[(1,2,5,6-tetrahydro-2-methyl-5,6-dioxo-1,2,4-triazin-3-yl)-thiomethyl]-8-oxo-4-thia-1-azabicyclo[4,2,0]oct-2-en-2-carboxylic acid trifluoroacetate.

NMR Spectrum (DMSO)

6.81 ppm, $H_5$ of the thiazole 7.3 ppm, H mobile, 3.99 ppm, $H_6$

EXAMPLE 67

Syn isomer of racemic cis 7-[2-(2-aminothiazol-4-yl)-2-methoxyimino-acetamido]-8-oxo-4-thia-3-[(4-nitrophenyl)-thiomethyl]-1-azabicyclo[4,2,0]oct-2-en-2-carboxylic acid trifluoroacetate Using the procedure of Example 65 and chromatography with elution with a mixture of methylene chloride and ether (82–18) 82 mg of syn isomer racemic cis 7-[2-(2-aminothiazol-4-yl)-2-methoxyimino-acetamido]-8-oxo-4-thia-3-[(4-nitrophenyl)-thiomethyl]-1-azabicyclo[4,2,0]oct-2-en-2-carboxylic acid trifluoroacetate were obtained.

NMR Spectrum (DMSO)

6.84 ppm, $H_5$ of the thiazole, 7.54–7.64 ppm, H at position β of the —$NO_2$ 8.21–8.11 ppm, H at position α of the —$NO_2$

EXAMPLE 68

(6RS) (7RS) (Z) 7-[2-(2-aminothiazol-4-yl)-2-methoxyimino-acetamido]-3-methylthio-8-oxo-4-thia-1-azabicyclo[4,2,0]oct-2-en-2-carboxylic acid STEP A: P-nitrobenzyl glycinate tosylate 190 g of monohydrated p-toluene sulfonic acid in 2 liters of toluene were refluxed for one and a half hours with water being eliminated by azeotropic distillation. After cooling, 75 g of glycine and 135 g of p-nitrobenzyl were added all at once and the mixture was refluxed for three hours with the water formed distilling off. After cooling, filtering, washing with toluene, triturating with methanol and drying under reduced pressure at 40° C., 294 g of p-nitrobenzyl glycinate tosylate were obtained melting at 210° C.

STEP B: P-nitrobenzyl glycinate

A mixture of one liter of methylene chloride, 500 ml of water and 100 g of p-nitrobenzyl glycinate tosylate was strongly stirred while 26 ml of 10N sodium hydroxide were added dropwise and stirring was continued for 5 minutes after the addition. The decanted aqueous phase was extracted with methylene chloride and the combined organic phases were washed with water, dried and concentrated to dryness under reduced pressure at less than 40° C. to obtain 52.3 g of p-nitrobenzyl glycinate melting at 45°–50° C.

STEP C: (4-nitrophenyl)-methyl-4-(2-phenyl)-ethenyl-31phthalimidoazetidin-2-one-1-acetate 105 g Of p-nitrobenzyl glycinate, 100 g of magnesium sulfate, 1000 ml of methylene chloride and 65 ml of triethylamine were mixed together, filtered, and cooled to −70° C. 70 ml of triethylamine were added, and then, over twenty minutes and at −70° C., a solution of 128 g of phthalimidoacetic acid chloride in 600 ml of methylene chloride was added. The mixture was refluxed for half-an-hour, and after cooling, the reaction mixture was poured into a mixture of 1000 ml of 0.1N hydrochloric acid and 1000 ml of iced water, and stirred for a quarter of an hour. After decanting and re-extracting with methylene chloride, the organic phases were filtered, washed with water, dried and concentrated to dryness under reduced pressure. The residue was taken up in 250 ml of ethyl acetate, the resins were broken up, and after twenty hours in the cold, filtered, washed with ethyl acetate and dried to obtain 154 g of (4-nitrophenyl)-methyl-4--(2-phenyl)-ethenyl-3-phthalimidoazetidin-2one-1-acetate melting at 150° C.

STEP D: (3RS) (4SR) (E) Nitrophenylmethyl-4-[2-phenylethenyl]-31-[(1,1-dimethylethyloxy)-carbonylamino]-azetidin-2-one-1-acetate 20 g of the product of Step C and 200 ml of dioxane were mixed together and 2.05 ml of hydrazine hydrate were added at 0° C. with stirring for one hour. 58.5 ml of N hydrochloric acid were added, and the mixture stood for 20 hours at ambient temperature. The insoluble matter was filtered off and the dioxane was evaporated under reduced pressure. The residue was taken up in 150 ml of water, 70 ml of methylene chloride and 70 ml of a molar solution of sodium bicarbonate and was stirred and decanted. The aqueous phase was extracted with methylene chloride and the combined organic phases were washed with water, dried and concentrated to dryness under reduced pressure to obtain 14.4 g of nitrophenylmethyl-3-amino-4-(2-phenyl-ethenyl)-azetidin-2-one-1-acetate. The 14.4 g of the product obtained in 150 ml of tetrahydrofuran with 13 ml of tert.-butyl dicarbonate were refluxed for one hour, after which the solvent was evaporated. The crystallized residue was taken up in ether, stirred for 15 minutes, filtered and dried under reduced pressure to obtain 14.1 g of (3RS) (4SR) (E) nitrophenylmethyl-4-[2-phenylethenyl]-3-[(1,1-dimethylethyloxyl)-carbonylamino]-azetidin-2-one-1-acetate melting at 160° C.

STEP E: (3RS) (4RS) 4-nitrophenylmethyl-4-[(hydroxy methyloxy)-methyl]-3-[(1,1-dimethylethyl)-oxycarbonylamino]-azetidin-2-one-1-acetate 18.5 g of (3RS) (4RS) (E) 4-nitrophenylmethyl-4-(2-phenylethenyl)-3-[(1,1-dimethylethyloxy)-carbonylamino]-azetidin-2-one-1-acetate dissolved in 185 ml of methylene chloride and 38 ml of methanol was cooled to −70° C. while a current of ozone was passed therethrough until saturation was reached and then, after 5 minutes, the excess ozones driven off. Finally, at −70° C., 5.57 ml of dimethyl sulfide were added, and the temperature was allowed to return to ambient. After one hour, the medium was poured into 350 ml of 0.1N hydrochloric acid and the mixture was extracted with methylene chloride. The organic phase was washed with water, dried and concentrated to dryness under reduced pressure. The residue was taken up in ether, cooled for one hour at 0°–5° C., filtered and dried to obtain 12.5 g of (3RS) 4RS) 4-nitrophenylmethyl-4-[(hydroxy methyloxy)-methyl] 3-[(1,1-dimethylethyl)-oxycarbonylamino]-azetidin-2-one-1-acetate melting at ≈125° C.

STEP F: (3RS) (4RS) 4-nitrophenylmethyl-4-hydroxymethyl-3-[(1,1-dimethylethyl)-oxycarbonyl-amino]-azetidine-2-one-1-acetate A mixture of 18 g of 4-nitrophenylmethyl-4-[(hydroxy methyl oxy)-methyl]-3-[(1,1-dimethylethyl)-oxycarbonylamino]-azetidin-2-one-1-acetate in 180 ml of tetrahydrofuran and 90 ml of acetic acid was cooled to −20° C. under agitation and 5.25 g of sodium cyanohydroboride were added in one lot. The temperature was allowed to return to ambient with the mixture stirred for one hour in an inert atmosphere. After concentrating to dryness under reduced pressure, 350 ml of water were added to the residue followed by extraction with methylene chloride. The organic phase was dried, and concentrated to dryness under reduced pressure. The residue was taken up with ether to obtain 15.3 g of (3RS)(4RS) 4-nitrophenylmethyl-4-hydroxymethyl-3-[(1,1-dimethylethyl)-oxy-carbonyl-amino]-azetidine-2-one-1-acetate.

STEP G: (3RS) (4RS) (4-nitrophenyl)-methyl-4-[(4-methylphenyl)-sulfonyloxy-methyl]-3-[(1,1-dimethylethyl)-oxycarbonyl-amino]-2-oxo-azetidin-1-yl-1-acetate 15.9 g of tosyl chloride in 170 ml of pyridine were cooled to 0° C. and 17 g of the product of Step F were added. The mixture stood with stirring at ambient temperature for twenty-four hours and the pyridine was evaporated under vacuum and 500 ml of water were added. After extracting with methylene chloride, the organic phase was washed with a mixture of 200 ml of water and 200 ml of 0.1N hydrochloric acid, dried, and concentrated to dryness under reduced pressure. The residue was taken up in 70 ml of ethanol, and after one hour at 0° to 5° C., then filtering, washing and drying, 16.6 g of (3RS) (4RS) (4-nitrophenyl) -methyl-4-[(4-methylphenyl)-sulfonyloxy-methyl]-3-[(1,1-dimethylethyl)-oxycarbonyl-amino]-2-oxo-azetidin-1-yl-1-acetate melting at 132° C. were obtained.

STEP H: (6RS) (7RS) (4-nitrophenyl)-methyl 7-[(1,1-dimethylethyl)-oxycarbonylamino]-3-mercapto-8-oxo-4-thia-1-azabicyclo[4,2,0] oct-2-en-2-carboxylate 0.112 g of (4-nitrophenyl)-methyl-4-[(4-methylphenyl)-sulfonyloxymethyl]-3-[(1,1-dimethylethyl)-oxycarbonylamino]-azetidin-2-one-1-acetate were dissolved in 2 ml of tetrahydrofuran cooled to −70° C. and then, while the temperature was maintained at equal to or below −65° C., 0.4 ml of a M solution of lithium bis trimethyl silyl amide in tetrahydrofuran was added dropwise. After stirring for 3 minutes, 0.2 ml of carbon were added in the same conditions. After allowing the temperature to rise to the ambient and pouring the medium into 10 ml of 0.1N hydrochloric acid, extraction was effected with methylene chloride. The organic phases were dried and concentrated to dryness under reduced pressure. The residue was taken up with ether and filtered to obtain 0.067 g of (6RS) (7RS) (4-nitrophenyl) -methyl 7 [(1,1-dimethylethyl)-oxycarbonylamino]-3-mercapto-8-oxo-4-thia-1-azabicyclo[4,2,0 ]oct-2-en 2-carboxylate melting at ≈170° C.

STEP I: (6RS) (7RS) (4-nitrophenyl)-methyl-7-[(1,1-dimethyl-ethyl)-oxycarbonyl amino]-3-methylthio-8-oxo-4-thia-1-azabicyclo [4,2,0]oct-2-en-2-carboxylate 1.7 g of (6RS) (7RS) (4-nitrophenyl)-methyl 7[(1,1-dimethylethyl)-oxycarbonylamino]-3-mercapto-8-oxo-4-thia-1-azabicyclo[4,2,0]oct-2-en 2-carboxylate and 25 ml of a 0.5M solution of diazomethane in methylene chloride were mixed together and after stirring for 5 minutes at ambient temperature, the solvent was expelled under reduced pressure. The residue was chromatographed on silica under pressure and eluted with a mixture of methylene chloride and ether (9-1) to obtain 1.45 g of (6RS)(7RS) (4-nitrophenyl)-methyl 7-[1,1-dimethylethyl)-oxycarbonyl amino]-3-methylthio-8-oxo-4-thia-1-azabicyclo[4,2,0]oct-2-en-2-carboxylate melting at 154° C.

STEP J: (6RS) (7RS) 7-[(1,1-dimethylethyl)-oxycarbonyl-amino]-methylthio-8-oxo-4-thia-1-azabicyclo[4,2,0]oct-2-en-2- carboxylic acid 1.45 g of (6RS) (7RS) (4-nitrophenyl)-methyl 7-[(1,1-dimethylethyl)-oxycarbonyl-amino]-3-methylthio-8-oxo-4-thia-1-azabicyclo[4,2,0]oct-2-en 2-carboxylate, 30 ml of tetrahydrofuran, 30 ml of methanol and 1.45 g of 10% palladized carbon were hydrogenated under a pressure of 2 atmospheres of hydrogen, while being vigorously stirred. After one hour, the pressure was taken up to ambient, and under an inert atmosphere, 4 ml of N hydrochloric acid were added. After separation, the solvent was expelled under reduced pressure at 35° C. and the residue was taken up in 100 ml of distilled water. The mixture was extracted with methylene chloride and the organic phase was dried, and evaporated to dryness under reduced pressure to obtain 1.3 g of (6RS) (7RS) 7-[(1,1-dimethylethyl)-oxycarbonyl-amino]-3-methylthio-8-oxo-4-thia-1-azabicyclo[4,2,0]oct-2-en-2-carboxylic acid.

STEP K: (6RS) (7RS) (Z) 7-[2-(2-aminothiazol-4-yl)-2-methoxyimino-acetamido]-3-methylthio-8-oxo-4-thia-1-azabicyclo[4,2,0]oct-2-en 2-carboxylic acid 1.3 g of (6RS) (7RS) 7-[(1,1-dimethylethyloxy)-carbonylamino]-3-methylthio-8-oxo-4-thia-1-azabicyclo[4,2,0]oct-2-en-2-carboxylic acid and 13 ml of nitromethane were stirred together cooled to 0° C., and a current of hydrochloric acid gas was passed through it for 15 minutes. 130 ml of ether were added, and after separating and rinsing with ether, 0.74 g of 7-amino-3-methylthio-8-oxo-4-thia-1-azabicyclo[4,2,0]oct-2-en-2-carboxylic acid hydrochloride were obtained.

1.33 g of 22 (2-tritylaminothiazol-4-yl)-2-methoxyimino acetic acid were dissolved in 13 ml of acetone and 0.44 ml of triethylamine and after complete solution, 0.6 g of tosyl chloride were added with stirring for one hour at ambient temperature.

After filtering off the insoluble matter, the 0.74 g of product obtained together with 7 ml of methylene chloride and 1.1 ml of triethylamine were added to the filtrate. The mixture was stirred for one hour at ambient temperature and then was poured into 100 mi of 0.1N hydrochloric acid and extracted with methylene chloride. The organic phase was dried and concentrated to dryness under reduced pressure at 35° C. to obtain 1.97 g of 7-[2-(2-tritylaminothiazol-4-yl)-2-methoxyimino-acetamido]-3-methylthio-8-oxo-4-thia-1-azabicyclo[4,2,0]oct-2-en-2-carboxylic acid.

The said 1.97 g were taken up in 10 ml of 66% formic acid and the mixture was stirred for 15 minutes at 50° C. and filtered. The solvent of the filtrate was evaporated under reduced pressure at 35° C. and the residue was taken up in ethanol. The solvent was expelled and the new residue was taken up with water, broken up, separated and dried to obtain 1.445 g of crude product. The latter was chromatographed on silica and eluted with a chloroform-acetone mixture (1-1). The residue was crystallized from ethanol, separated, rinsed and dried for 20 hours under reduced pressure at ambient temperature to obtain 0.046 g of (6RS)(7RS) (Z) 7-[2-(2-aminothiazol-4-yl)-2-methoxyimino-acetamido]-3-methylthio-8-oxo-4-thia-1-azabicyclo[4,2,0]oct-2-en-2-carboxylic acid.

Analysis: $C_{14}H_{15}N_{15}O_5S_3$: 429,5Calculated: C % 39,2 H % 3,5 N % 16,3 S % 22,4Found: 42,7 3,0 15,9 22

EXAMPLE 69

Syn isomer of racemic cis 1-[2-(7-[2-(2-aminothiazol-4-yl)-2-methoxyimino-acetamido]-2-carboxy-8-oxo-4-thia-1-azabicyclo [4,2,0]oct-2-en-3-yl)-2-thioethyl-1-methyl-pyrrolidium iodide STEP A: Syn isomer of racemic cis (4-nitrophenyl)methyl-3-[2-(2-tritylaminothiazol-4-yl)-1-methoxyimino-acetamido]-4-[4-methylphenyl sulfonyloxymethyl]-2-oxo-azetidin-1-yl-1-acetate 2.818 g of (3RS) (4RS) (4-nitrophenyl)-methyl-4-[(4-methylphenyl)-sulfonyloxymethyl]-3-[(1,1-dimethylethyloxy)-carbonylamino]-2-oxo-azetidin-1-yl-1-acetate in 20 ml of methylene chloride was cooled to 0° to +5° C. and 0.968 ml of triethylsilyl trifluoromethyl sulfonate was added with stirring for 5 minutes at 0° C. to +5° C. Then the temperature was allowed to rise to 20° C. and 10 ml of methanol were added followed by concentrating to dryness under reduced pressure at 30° C. maximum to obtain 4-(nitrophenyl)-methyl-4-[(4-methylphenyl)-sulfonylmethyl]-2-oxo-azetidin-1-yl-1-acetate trifluoromethyl sulfonate. (solution A).

2.88 g of 2- (2-tritylaminothiazol-4-yl) -2-methoxyimino acetic acid, 28.8 ml of acetone, 0.9 ml of triethylamine and 12.36 g of tosyl chloride were stirred together for one hour and after cooling to +10° C., solution (A) was introduced in 15 ml of methylene chloride with 1.68 ml of triethylamine and left at 20° C. for 40 minutes. The mixture was poured into a mixture of 150 ml of water, 100 ml of methylene chloride and 15 ml of a saturated aqueous solution of sodium bicarbonate. After decanting and re-extracting with methylene chloride,. the organic phases were dried and evaporated to dryness under reduced pressure. The residue was chromatographed on silica and eluted with a mixture of methylene chloride and acetone (9-1) to obtain 3.46 g of syn isomer of (4-nitrophenyl)-methyl-3-[2-(2-tritylaminothiazol-4-yl) -1-methoxyimino-acetamido]-4-[4-methylphenyl sulfonyloxymethyl]-2-oxo-azetidin-1-yl-1-acetate.

STEP B: Syn isomer of racemic cis diphenylmethyl-3-[2-(2-tritylaminothiazol-4-yl)-2-methoxyimine-acetamide]-4-[4-(-methylphenyl)-sulfonyloxymethyl]-2-oxo-azetidin-1-yl-1-acetate A mixture of 7.210 g of the product of Step A in 72 ml of a mixture of tetrahydrofuran and methanol (1-1) and 720 mg of 9.5% palladium on active carbon was hydrogenolysed and after filtering, the solvents were evaporated under reduced pressure. The residue was taken up in 30 ml of water and 12 ml of N hydrochloric acid and was extracted with methylene chloride. The organic phase was dried and concentrated to dryness under reduced pressure to obtain 7.58 g of the N-acetic derivative. 9.813 g of benzophenone hydrazone, 150 ml of ether, 11.27 g of dry sodium sulfate and 26.3 g of mercuric oxide were stirred together for 40 minutes. After filtering, the insoluble matter was rinsed with ether and 45 ml of the filtrate containing diphenyl diazomethane were poured onto the 7.58 g of the product obtained above dissolved in 70 ml of dioxane. After 40 minutes of stirring at 20° C., a further 22.5 ml of diphenyl diazomethane in solution in ether were added. After a further contact for 40 minutes at 20° C. 1 ml of acetic acid was added and the solvents were evaporated under reduced pressure at 30° C. maximum. The residue was chromatographed on silica and eluted with a methylene chloride-acetone mixture (9-1) to obtain 7.462, g of syn isomer of racemic cis diphenylmethyl- 3-[2-(2-tritylaminothiazol-4-yl)-2-methoxyimino-acetamido]-4-[4-(methylphenyl)-sulfonyloxymethyl]-2-oxo-azetidin-1-yl-1-acetate.

STEP C: Diphenylmethyl 7-[2-(2-tritylamino-thiazol-4-yl)-2-methoxyimino-acetamido]-3 -mercapto-8-oxo-4-thia-1-azabicyclo [4,2,0]oct-2-en-2-carboxylate 1.840 g of the product of Step B in 18.4 ml of tetrahydrofuran was cooled to −70° C., then 4 ml of a molar solution of lithium bis(trimethylsilyl)amide were added with stirring for 15 minutes at −70° C. under an inert atmosphere. 2 ml of carbon sulfide were added, and after standing for 40 minutes at 20° C., 113 μl of acetic acid were added. The solvents were evaporated under reduced pressure and the residue was taken up in water and extracted with ethyl acetate. The organic phases were washed with water, dried and evaporated to dryness under reduced pressure. The residue was taken up in 10 ml of isopropyl ether and separated to obtain 1.270 g of diphenylmethyl 7-[2-(2-tritylaminothiazol-4-yl)-2-methoxyimino-acetamido]-3-mercapto-8-oxo-4-thia-1-azabicyclo [4,2,0]oct-2-en-2-carboxylate.

NMR Spectrum ($CDCl_3$) 6.67 ppm: $H_5$ of the thiazole 6.76 ppm: H of the methyl of the diphenyl, 7.28 ppm: H of the diphenyl and of the trityl.

STEP D: Syn isomer of racemic cis diphenylmethyl 7-[2-(2-trityl-aminothiazol-4-yl)-2-methoxyimino-acetamido]-3-[(2-(1-pyrrolidinyl)-ethyl)-thio]-8-oxo-4-thia-1-azabicyclo [4,2,0]oct-2-en-2-carboxylate 85 mg of N-chloroethyl pyrrolidine hydrochloride, 2 ml of methylene chloride and 210 μl of triethylamine were mixed together and 412 mg of diphenylmethyl 7-[2-(2-tritylaminothiazol-4-yl)-2-methoxyimino-acetamido]-3-mercapto-8-oxo-4-thia-1-azabicyclo[4,2,0]oct-2-en-2-carboxylate in 3 ml of methylene choride was added. The mixture was refluxed for 3 hours and after cooling to 20° C., the reaction mixture was poured into 10 ml of iced water. The mixture was stirred for 5 minutes, decanted and re-extracted with methylene chloride. The combined organic phases were dried and concentrated to dryness under reduced pressure. The residue was chromatographed on silica and eluted with a mixture of methylene chloride and acetone (1-1). After taking up again in isopropyl ether, 157 mg of syn isomer of racemic cis diphenylmethyl 7-[2-(2-tritylaminothiazol-4-yl)-2-methoxyimino-acetamido]-3-[(2-(1-pyrrolidinyl)-ethyl)-thio]-8-oxo-4-thia-1-azabicyclo [4,2,0]oct-2-en-2-carboxylate were obtained.

STEP E: Syn isomer of racemic cis 1-[2-(7-[2-(2-tritylamino-thiazol-4-y1)-2-methoxyimino-acetamido]-2-diphenylmethyloxyy carbonyl-8-oxo-4-thia-1-azabicyclo[4,2,0]oct-2-en-3-yl)-thioethyl]-1-methyl pyrrolidinium iodide 0.1 ml of methyl iodide was added to 122 mg of the product of step D in 2.4 ml of acetonitrile and the mixture stood for 30 minutes at 20° C. By concentrating to dryness under reduced pressure, 143 mg of syn isomer of racemic cis 1-[2-(7-[2-(2-tritylaminothiazol-4-yl)-2-methoxyimino-acetamido]2-diphenyl methyloxy carbonyl-8-oxo-4-thia-1-azabicyclo[4,2,0]oct-2-en 3-yl)thioethyl]-1-methyl pyrrolidinium iodide were obtained.

STEP F: Syn isomer of racemic cis 1-[2-(7-[2-(2-aminothiazol-4-yl)-2-methoxyimino-acetamido]-2-carboxy-8-oxo-4-thia-1-azabicyclo [4,2,0]oct-2-en-3-yl)-2-thioethyl]-1-methyl pyrrolidinium iodide 245 mg of the product of Step E were heated for 2 hours to 60° C. with stirring in 2.5 ml of formic acid with 50% of water. After concentrating under reduced pressure, the residue was crystallized from 100% ethanol. The mixture was stirred for 1 hour at 20° C., filtered, rinsed with very little ethanol, then triturated twice with 1 ml of isopropylether to obtain 110 mg of syn isomer of racemic cis 1-[2-(7-[2-(2-aminothiazol-4-yl)-2-methoxyiminoacetamido]-2-carboxy-8-oxo-4-thia-1-azabicyclo[4,2,0]oct-2-en-3-yl)-2-thioethyl]-1-methyl pyrrolidinium iodide.

NMR Spectrum (DMSO) 6.83 ppm: H in position 3 of the thiazole, 2.11 ppm: H in positions 3 and 4 of the pyrrolidinyl, 3.05 ppm: H of the methyl at position I of the pyrrolidinyl.

Using the procedure of Example 69, the following products were prepared.

EXAMPLE 70

Syn isomer of racemic cis of 4-(7-[2-(2-aminothiazol-4-yl) -2-methoxyimino-acetamido]-2-carboxy-8-oxo-4-thia-1-azabicyclo[4,2,0]oct-2-en-3-yl)-thiomethyl-1-methyl pyridinium iodide starting with 4-chloromethyl pyridine hydrochloride NMR Spectrum (DMSO) 6.85 ppm: H at position 5 of the thiazole 7.95–8.05 ppm: H at positions 3 and 5 of the pyridyl 8.85–8.95 ppm: H at positions 2 and 6 of the pyridyl 4.28 ppm: S of the methyl at position 1 of the pyridyl.

EXAMPLE 71

Syn isomer of racemic cis 2-(7-[2-(2-aminothiazol-4-yl) -2-methoxyimino-acetamido]-2-carboxy-8-oxo-4-thia-1-azabicyclo[4,2,0]oct-2-en-3-yl) -thiomethyl-1-methyl pyridinium iodide, starting with 2-chloromethyl pyridine hydrochloride

| NMR Spectrum (DMSO) | |
|---|---|
| 6.85 ppm | H at position 5 of the thiazole |
| 7.73–7.81 ppm | H at position 3 of the thiazole |
| 7.96–8.1 ppm } | |
| 8.37–8.54 ppm } | H at positions 4 and 5 of the pyridyl |
| 9.02–9.1 ppm | H at position 6 of the pyridyl. |

EXAMPLE 72

Syn isomer of racemic cis 7-[2-(2-aminothiazol-4-yl)-2-methoxyimino-acetamido]-3-[(dihydro-(4H)5-hydroxy-4-oxo-pyran-2-yl-methyl thio]-8-oxo-4-thia-1-azabicyclo[4,2,0]oct-2-en- 2-carboxylic acid trifluoroacetate STEP A: Syn isomer of racemic cis diphenylmethyl 7-[2-(2-tritylamino thiazol-4-yl)-2-methoxyimino-acetamido]-3-[(dihydro-(4H) 5-hydroxy-4-oxo-pyran-2-yl)-methylthio]-8-oxo-4-thia-1-azabicyclo [4,2,0]oct-2-en-2-carboxylate Using the product of Step A of Example 69, 81.5 mg of 2-chloromethyl(dihydro-(4H)5-hydroxy-4-oxo-pyran-2-yl) were reacted to obtain 225 mg of the expected product.

STEP B: 7-[2-(2-aminothiazol-4-yl)-2-methoxyimino-acetamido]-3-[(dihydro-(4H)5-hydroxy-4-oxo-pyran-2-yl) methylthio]-8-oxo-4-thia-1-azabicyclo[4,2,0]oct-2-en-2-carboxylic acid trifluoroacetate 150 mg of the product of Step A and 2.5 ml of methylene chloride with 10% of trifluoroacetic acid were stirred together for 2 hours 45 minutes at 0° C.–+5° C. and then 25 ml of isopropyl ether were added with stirring for 10 minutes. The insoluble matter was separated by centrifuging, and after drying, 90 mg of the expected product were obtained.

NMR Spectrum (DMSO) 6.88 ppm: H at position 5 of the thiazole 8.04 ppm: H at position 6 of the pyranyl 6.37 ppm: H at position 3 of the pyranyl 4.0 ppm: H at α of the pyranyl.

EXAMPLE 73

Syn isomer of racemic cis 7-[2-(2-aminothiazol-4-yl)-2-methoxyimino-acetamido]-3-cyanomethylthio-8-oxo-4-thia-1-azabicyclo[4,2,0]oct-2-en-2-carboxylic acid Using the procedure of Example 72, acetonitrile bromide was reacted and the trifluoroacetate obtained was dissolved in 100% ethanol. A trace of pyridine was added, and crystallization was initiated. After stirring for 1 hour at 20° C., separating, rinsing with a minimum of ethanol and triturating twice with isopropyl ether, syn isomer of racemic cis 7-[2-(2-aminothiazol-4-yl)-2-methoxyimino-acetamido]-3-cyanomethylthio-8-oxo-4-thia-1-azabicyclo[4,2,0]oct-2-en-2-carboxylic acid was obtained.

NMR Spectrum (DMSO) 6.85 ppm: H at position 5 of the thiazole 4.07 ppm: H of the acetonitrile.

EXAMPLE 74

Syn isomer of racemic cis 7-[2-(2-aminothiazol-4-yl)-2-methoxyimino-acetamido]-3-[(5-methyl-1,2,4-triazol[1,5-a] pyrimidin-7-yl) thio]-8-oxo-4-thia-1-azabicyclo[4,2,0]oct-2-en-2-carboxylic acid Using the procedure of Example 73, 7-chloro-5-methyl-1,2,4-triazolo[1,5-a]pyrimidine was reacted to obtain the expected product.

NMR Spectrum (DMSO) 6.9 ppm: H at position 5 of the thiazole 8.67 ppm: H at position 3 of the triazole 7.03 ppm: E at position 5 of the pyrimidine 2.65 ppm: H of the $CH_3$

EXAMPLE 75

Syn isomer of racemic cis 7-[2-(2-aminothiazol-4-yl)-2-methoxyimino-acetamido]-3-chloromethylthio-oxo-4-thia-1-azabicyclo [4,2,0]oct-2-en-2-carboxylic acid trifluoroacetate STEP A: Diphenylmethyl 7-[2-(2-tritylamino-thiazol-4-yl)-2-methoxyimino-acetamido]-3-chloromethylthio-8-oxo-4-thia-1-aza-bicyclo[4,2,0]oct-2-en-2-carboxylate To 412 mg of diphenylmethyl 7-[2-(2-tritylamino-thiazol-4-yl)-2-methoxyimino-acetamido]-3-mercapto-8-oxo-4-thia-1-aza-bicyclo[4,2,0]oct-2-en-2-carboxylate in 3 ml of dimethylformamide, 97 mg of iodochloromethane and 75.9 mg of triethylamine were successively added. After standing for half-an-hour, the reaction mixture was poured in to 80 ml of water and 0.7 ml of N hydrochloric acid. The mixture was extracted with methylene chloride and the organic phases were washed with water, dried, and concentrated to dryness under reduced pressure. After chromatographing the residue on silica and elution with a mixture of methylene chloride and ethyl acetate (95-5), 199 mg of diphenylmethyl 7-[2-(2-tritylamino-thiazol-4-yl)-2-methoxyimino-acetamido]-3-chloromethylthio-8-oxo-4-thia-1-azabicyclo[4,2,01oct-2-en-2-carboxylate were obtained.

STEP B: Syn isomer of racemic cis 7-[2-(2-aminothiazol-4-yl)-2-methoxyimino-acetamido]-3-chloromethylthio-8-oxo-4-thia-1-aza-bicyclo[4,2,01oct-2-en-2-carboxylic acid trifluoroacetate 162 mg of the product of step A in 1.5 ml of trifluoroacetic acid was stirred at 0° C. in an inert atmosphere for 5 minutes and the solution obtained was poured into 25 ml of isopropy ether. The mixture was cooled to 0° C. stirred for several minutes. and then centrifuged. The residue was suspended in 25 ml of ether and this was centrifuged again and the operation was repeated. The trifluoracetate was dried under reduced pressure to obtain 88 mg of syn isomer of racemic cis 7-[2-(2-aminothiazol-4-yl)-2-methoxyimino-acetamido]-3-chloromethylthio-8-oxo-4-thia-1-azabicyclo[4,2,0]oct-2-en-2-carboxylic acid trifluoroacetate.

NMR Spectrum (DMSO) 6.91 ppm: H at position 5 of the thiazole 5.21 ppm: H of the chloromethyl

EXAMPLE 76

Syn isomer of racemic cis 7-[2-(2-aminothiazol-4-yl)-2-methoxy-imino-acetamido]-3[(3-ethoxy-3-oxo-1-(E)-propenyl)thio]-8-oxo-4-thia-1-azabicyclo[4,2,0]oct-2-en-2-carboxylic acid STEP A: Diphenylmethyl 7-[2-(2-tritylamino-thiazol-4-yl)-2-methoxyimino-acetamido]-3-[(3-ethoxy-3-oxo-1-(E)-propenyl)thio]-8-oxo-4-thia-1-azabicyclo[4,2,0]oct-2-en-2-carboxylate Using the procedure of Step A of Example 72, ethyl β-bromoacrylate was reacted to obtain the expected product.

STEP B: Syn isomer of racemic cis 7-[2-(2-aminothiazol-4-yl)-2-methoxyimino-acetamido]-3-13 - ethoxy-3-oxo-1-(E)-propenyl)thio]-8-oxo-4-thia-1-azabicyclo[4,2,0]oct-2-en-2-carboxylic acid Using the procedure of Step B of Example 69, the product of Step A was reacted with formic acid with 33% of water to obtain the expected product.

| NMR Spectrum (DMSO) | |
|---|---|
| 6.84 ppm | H in position of 5 of the thiazole |
| 5.83–6 ppm | H of the propenyl |
| 1.14–1.22–1.3 ppm } | |
| 4.0–4.05–4.17–4.25 ppm } | H of the ethyl |

Using the procedure of Example 76, the following products were prepared.

EXAMPLE 77

Syn isomer of racemic cis 7-[2-(2-aminothiazol-4-yl)-2-methoxyimino-acetamido]-3-[(3-cyano-2-(E)-propenyl)- thio]-8-oxo-4-thia1-azabicyclo[4,2,0]oct-2-en-carboxylic acid starting with 4-bromocrotonitrile NMR Spectrum (DMSO) 6.83 ppm: H at position 5.of the thiazole 3.78 ppm: H at position 1 of the propenyl 6.13 ppm: H of the ethylene of the propenyl

EXAMPLE 78

Syn isomer of racemic cis 7-[2-(2-aminothiazol-4-y1)-2-methoxyimino-acetamido]-3-thiocyanate-8-oxo-4-thia-1-azabicyclo[4,2,0]oct-2-en-2-carboxylic acid starting with tosyl cyanide NMR Spectrum (DMSO) 6.82 ppm: H at position 5 of the thiazole 5.55 ppm: H at position 7 of the isocepheme 3 ppm: H at position 8 of the isocepheme 3.8 ppm: H of the methoxyl.

EXAMPLE 79

Syn isomer of racemic cis 7-[2-(2-aminothiazol-4-yl)-2-methoxyimino-acetamido]-2-carboxy-8-oxo-4-thia-1-azabicyclo[4,2,01oct-2-en-3-y1) thiomethyltrimethylammoniunm iodide STEP A: Syn isomer of racemic cis diphenylmethyl 7-[2-(2-tritylaminothiazol-4-yl)-2-methoxyimino-acetamido]-3-iodomethylthio-8-oxo-4-thia-1-azabicyclo[4,2,0]oct-2-en-2-carboxylate 225 mg of solid sodium iodide were added to a solution of 873 mg of the chlorated derivative obtained in Example 75 dissolved in 6 ml of acetonitrile and after stirring for a few minutes, the solution was refluxed for 15 minutes. The reaction mixture was poured into 150 ml of water and extracted with methylene chloride. The organic phase were washed with water, dried, and concentrated to dryness under reduced pressure. The residue was chromatographed on silica and eluted with a mixture of methylene chloride and ethyl acetate (95-5) to obtain 385 mg of syn isomer of racemic cis diphenylmethyl 7-[2-(2-tritylaminothiazol-4-yl)-2-methoxyimino-acetamido]-3-iodomethylthio-8-oxo-4-thia-1-azabicyclo [4,2,0]oct-2-en-2-carboxylate.

STEP B: Syn isomer of racemic cis 7-[2-(2-tritylaminothiazol-4-yl)-2-methoxyimino-acetamido]-2-diphenylmethyloxy carbonyl-8-oxo-4-thia-1-azabicyclo[4,2,0]oct-2-en-3-yl)-thiomethyl-trimethylammonium iodide 144.6 mg of the 2-iodo derivative of Step A were dissolved in 1ml of tetrahydrofuran, and 0.6 ml of a 2.5M soluton of trimethylamine in ether was added. After 16 hours of contract, the reaction mixture was poured dropwise with stirring into 10 ml of ether. Stirring was continued for 15 minutes after the addition then by separating and drying, 131 mg of syn isomer of racemic cis 7-[2-(2-tritylaminothiazol-4-yl)-2-methoxyimino-acetamido]-2-diphenylmethyloxy carbonyl-8-oxo-4-thia-1-azabicyclo[4,2,01oct-2-en-3-yl)-thiomethyl-trimethylammonium iodide were obtained.

STEP C: Syn isomer of racemic cis 7-[2-(2-aminothiazol-4-yl)-2-methoxyimino-acetamido]-2-carboxy-8-oxo-4-thia-1-azabicyclo[4,2,0]oct-2-en-3-yl)-thiomethyl-trimethylammonium iodide 109 mg of the product of Step B were suspended in 2.2 ml of 66% formic acid under an inert atmosphere, and stirred until the end of the reaction. After concentrating at 40° C. under reduced pressure (1 mm Hg), the residue was taken up in water, then twice with 100% ethanol, evaporating each time in the same conditions. The residue was triturated in 15 ml of ether, and after separating, washing with ether and drying, 52 mg of syn isomer of racemic cis 7-[2-(2-aminothiazol-4-yl)-2-methoxyimino-acetamido]-2-carboxy-8-oxo-4-thia-1-azabicyclo[4,2,0]oct-2-en-3-yl)-thiomethyl-trimethylammonium iodide were obtained.

| NMR Spectrum (DMSO) | |
| --- | --- |
| 6.84 ppm, H in position 5 of the thiazole | |
| 4.71–4.86 ppm | H of the thiomethyl. |
| 5.04–5.2 ppm | |

EXAMPLE 80

Syn isomer of racemic cis 7-[2-(2-aminothiazol-4-yl)-2-methoxyimino-acetamido]-2-carboxy-8-oxo-thia-1-azabicyclo[4,2,0]oct-2-en-3-yl)-thiomethyl-pyridinium iodide STEP A: Syn isomer of racemic cis 1-[2-(2-tritylaminothiazol-4-yl)-2-methoxyimino-acetamido]-2-diphenylmethyloxycarbonyl-8-oxo-4-thia-1-azabicyclo[4,2,0]oct-2-en-3-yl)-thiomethyl pyridinium iodide 144.6 mg of the 2-iodo derivative of Step A of Example 79 and 1.5 ml of pyridine were mixed together and after 16 hours of standing at ambient temperature, the pyridine was evaporated under inert atmosphere. The residue was taken up in 10 ml of ether, triturated, and 135 mg of product were separated. This latter was dissolved in 1 ml of tetrahydrofuran, and 10 ml of ether were added dropwise with stirring. The precipitate formed was separated and dried to obtain 106.5 mg of syn isomer of racemic cis 7-[2-(2-tritylaminothiazol-4-yl)-2-methoxyimino-acetamido]-2-diphenylmethyloxycarbonyl-8-oxo-4-thia-1-azabicyclo[4,2,0]oct-2-en-3-yl)-thiomethyl pyridinium iodide STEP B: Syn isomer of racemic cis 7-[2-(2-aminothiazol-4-yl)-2-methoxyimino-acetamido]-2-carboxy-8-oxo-4-thia-1-azabicyclo[4,2,0]oct-2-en-3-yl) thiomethyl pyridinium iodide Using the procedure of Step B of Example 79, 90 mg of the product of Step A were reacted to obtain 48.5 mg of syn isomer of racemic cis 7-[2-(2-aminothiazol-4-yl)-2-methoxyimino-acetamido]-2-carboxy-8-oxo-4-thia-1-azabicyclo[4,2,0]oct-2-en-3-yl ) thiomethyl pyridinium iodide.

NMR Spectrum (DMSO) 6.85 ppm , H in position 5of the thiazole 6.01 ppm, H of the thiomethyl NMR Spectrum (DMSO) (Cont'd) 8.94–8.97 ppm, H at positions 2 and 6 of the pyridyl 8.16 ppm, H at positions 3 and 5 of the pyridyl 8.7 ppm, H at position 4 of the pyridyl.

EXAMPLE 81

Syn isomer of racemic cis 7-[2-(2-aminothiazol-4-yl)-2-methoxyimino-acetamido]-3[[(1-methyl-1H-tetrazol-5-yl)-aminocarbonylmethyl]-thio]-8-oxo-4-thia-1-azabicyclo[4,2,0]oct-2-en-2-carboxylic acid Using the procedure of Example 76, chloroacetylamino-1-methyl-1H-tetrazol-5-yl was reacted to obtain the expected product.

NMR Spectrum ($CDCl_3$ ) 6.82 ppm, $H_5$ of the thiazole, 3.86 and 3.88 ppm, H of the 1-methyl tetrazole.

EXAMPLE 82

Syn isomer of racemic cis 7-[2-(2-aminothiazol-4-yl)-2-methoxyimino-acetamido]-3-[[(2-methyl-2H-tetrazol-5-yl)-aminocarbonylmethyl]-thio]-8-oxo-4-thia-1-azabicyclo[4,2,0]oct-2-en-2-carboxylic acid Using the procedure of Example 74, chloroacetylamine-2-methyl-2H-tetrazol-5-yl was reacted to obtain the expected product.

NMR spectrum (DMSO) 6.84 ppm, H5 of the thiazole 4.3 ppm H of the 2-methyl tetrazole.

EXAMPLE 83

Syn isomer of racemic cis 7-[2-(2-aminothiazol-4-yl)-2-methoxyimino-acetamido]-3-[(2-cyano(Z)-ethen-1yl)-thio]-8-oxo-4-thia-1-azabicyclo[4,2,0]oct-2-en-2-carboxylic acid Using the procedure of Example 76, cyanoethynyl was reacted to obtain the expected product.

NMR Spectrum (DMSO) 6.83 ppm $H_5$ of the thiazole 7.6–7.72 ppm H in position 1 of the ethenyl 5.88–6 ppm H in position 2 of the ethenyl.

EXAMPLE 84

Syn isomer of racemic cis 7-[2-(2-aminothiazol-4-yl)-2-methoxyimino-acetamido]-3-[(7-nitro-4-benzofurazanyl)-thio]-8-oxo-4-thia-1-azabicyclo[4,2,0]oct-2-en-2-carboxylic acid trifluoroacetate Using the procedure of Example 72, 4-chloro-7-nitrofurazane was reacted to obtain the expected product.

NMR Spectrum (DMSO) 6.9 ppm: $H_5$ of the thiazole 7.47–7.55 ppm: H in position 5 of the benzofurazanyl 8.63–8.72 ppm : H in position 6 of the benzofurazanyl.

EXAMPLE 85

Syn isomer of racemic cis-7-[2-(2-aminothiazol-4-yl)-2-methoxyimino-acetamidol-8-oxo-4-thia-1-azabicyclo[4,2,0]oct-2-en-2,3-dicarboxylic acid STEP A: 1,1-dimethyl -ethyl 7-[2- (2-tritylamino-thiazol-4-yl)-2-methoxyimino-acetamido]-3-hydroxyiminomethyl-8-oxo-4-thia-1-azabicyclo[4,2,0]oct-2-en-2-carboxylate Under an inert atmosphere, 142 mg of (1,1-dimethyl)ethyl 7-[2-(2-tritylamino-thiazol-4-yl)-2-methoxyimino-acetamido]-3-formyl-8-oxo-4-thia-1-azabicyclo[4,2,0]oct-2-en-2-carboxylate, (prepared in Step A of Example 52) and 42 mg of hydroxylamine hydrochloride were dissolved in 0.4 ml of pyridine and the solution was stirred for 50 minutes and diluted with ether and with ethyl acetate. The mixture was washed with 6 ml of N hydrochloric acid and after extracting the aqueous phase with ethyl acetate, the organic phases were dried and concentrated to dryness. The residue was chromatographed under pressure on silica and eluted with a mixture of ethyl acetate and methylene chloride (25–75) to obtain 91 mg of 1,1-dimethy]-ethyl 7-[2-(2-tritylamino-thiazol-4-yl)-2-methoxyimino-acetamido]-3-hydroxyiminomethyl-8-oxo-4-thia-1-azabicyclo[4,2,0]oct-2-en-2-carboxylate.

STEP B: 1,1-dimethyl ethyl 7-[2-(2-tritylamino-thiazol-4-yl)-2-methoxyimino-acetamido]-3-cyano-8-oxo-4-thia-1-azabicyclo[4,2,0]oct-2-en-2-carboxylate Under an inert atmosphere, 151 mg of the product of Step A and 80 mg of tosyl chloride were dissolved in 6 ml of methylene chloride and then 120 ul of triethylamine were added dropwise with stirring for 25 minutes. The mixture was washed with lightly acidic water, then decanted and re-extracted with methylene chloride. The organic phases were dried and the solvent was distilled off. The residue was chromatographed under pressure on silica and eluted with a mixture of methylene chloride and acetone (93-7) to obtain 97 mg of 1,1-dimethyl -ethyl 7-[2-(2-tritylaminothiazol-4-yl)-2-methoxyimino-acetamido]-3-cyano-8-oxo-4-thia-1-azabicyclo[4,2,0]oct-2-en-2-carboxylate.

STEP C: Syn isomer of racemic cis 7-[2-(2-aminothiazol-4-yl)-2-methoxyimino-acetamido]-8-oxo-4-thia-1-azabicyclo[4,2,0]oct-2-en-2,3-dicarboxylic acid A suspension of 83 mg of the product of Step B and 0.9 ml of 66% formic acid was heated externally to 65° C., then the solvent was distilled off and the residue was taken up with ethanol to obtain 27 mg of syn isomer of racemic cis 7-[2-(2-aminothiazol-4-yl)-2-methoxyimino-acetamido]-8-oxo-4-thia-1-aza-bicyclo[4,2,0]oct-2-en-2,3-dicarboxylic acid.

NMR Spectrum (DMSO) 6.85 ppm: $H_5$ of the thiazole 5.59–5.73 ppm: $H_7$

EXAMPLE 86

Syn isomer of racemic cis 7-[2-(2-aminothiazol-4-yl)-2-methoxyimino-acetamido]-3-[(aminocarbonyl)-hydrazonomethyl]-8-oxo-4-thia-1-azabicyclo[4,2,0]oct-2-en-2-carboxylic acid trifluoroacetate STEP A: 1,1-dimethylethyl-7-[2-(2-tritylamino-thiazol-4-yl)-2-methoxyimino-acetamido]-3-[(aminocarbonyl)-hydrazonomethyl]-8-oxo-4-thia-1-azabicyclo[4,2,01oct-2-en-2-carboxylate 142 mg of 1,1-dimethylethyl-7-[2-(2-tritylamino thiazol-4-yl)-2-methoxyimino-acetamido]-3-formyl-8-oxo-4-thia-1-aza-bicyclo[4,2,0]oct-2-en-2-carboxylate, 60 mg of semicarbazide hydrochloride and 0.8 ml of dimethylformamide were mixed together and after one hour and thirty minutes, 10 ml of Water were added followed by extraction with ethyl acetate. The organic phases were dried, and concentrated to dryness. The residue was dissolved in ethanol and after allowing crystallization for 45 minutes and separating, 113 mg of 1,1-dimethylethyl 7-[2-(2-tritylamino-thiazol-4-yl)-2-methoxyimino-acetamido]-3-[(aminocarbonyl)-hydrazonomethyl]4-oxo-4-thia-1-azabicyclo[4,2,0]oct-2-en-2-carboxylate were obtained.

STEP B: Syn isomer of racemic cis 7-[2-(2-aminothiazol-4-yl)-2-methoxyimino-acetamido]-3-[(aminocarbonyl)-hydrazonomethyl]-8-oxo-4-thia-1-azabicyclo[4,2,01oct-2-en-2-carboxylic acid trifluoroacetate Using the procedure of Example 84, the product of Step A was reacted to obtain the expected product.

NMR Spectrum (DMSO) 6.9 ppm: $H_5$ of the thiazole 5.62–5.77 ppm: $H_7$

Syn isomer of racemic cis 7-[2-(2-aminothiazol-4-yl)-2-methoxyimino-acetamido]-3-[(4-nitrophenyl)-hydrazonomethyl]-8-oxo-4-thia-1-azabicyclo[4,2,0]oct-2-en-2-carboxylic acid STEP A: 1,1-dimethyl-ethyl7-[2-(2-tritylamino-thiazol-4-yl)-2-methoxyimino-acetamido]-3-[(4-nitrophenyl) rhydrazonomethyl]-8-oxo-4-thia-1-azabicyclo[4,2,0]oct-2-en-2-carboxylate Using the procedure of Step A of Example 86, p-nitrophenyl-hydrazine was reacted to obtain the expected product after crystallization from ethyl acetate.

STEP B: Syn isomer of racemic cis 7-[2-(2-aminothiazol-4-yl)-2-methoxyimino-acetamido]-3-[4-nitrophenyl)-hydrazonomethyl]-8-oxo-4-thia-1-azabicyclo[4,2,01oct-2-en-2-carboxylic acid Using the procedure of Example 85, Step C, the product of Step A was reacted and distilling the solvent azeotropically with the ethanol. The residue was triturated in methanol, filtered and dried to obtain the expected product.

NMR Spectrum (DMSO) 6.85 ppm : $H_5$ of the thiazole 8.13–8.23 ppm: H in the ortho position of the aromatic $NO_2$ 7.07–7.17 ppm: H in the ortho position of the aromatic

EXAMPLE 88

Syn isomer of racemic cis 7-[2-(2-aminothiazol-4-yl)-2-methoxyimino-acetamido]-3-[(ethoxycarbonyl)ethen-1-yl]-

8-oxo-4-thia-1-azabicyclo[4,2,0]oct-2-en-2-carboxylic acid trifluoroacetate

STEP A: 1,1-dimethyl-ethyl 7-[2-(2-tritylaminothiazol-4-yl) -2-methoxyimino-acetamido]3-[(ethoxycarbonyl)-ethen-1-yl]-8-oxo-4-thia-1-azabicyclo[4,2,0]oct-2-en-2-carboxylate 142 mg of 1,1-dimethyl-ethyl 7-[(2-tritylaminothiazol-4-yl)2-methoxyimino-acetamido]-3-formyl-8-oxo-4-thia-1-azabicyclo[4,2,0]oct-2-en-2-carboxylate and 139 mg of carbethoxymethylene-triphenyl phosphorane were dissolved in 4 ml of methylene chloride and after stirring for 48 hours, the solvent was expelled. The residue was chromatographed on silica and eluted with a mixture of methylene chloride and ethyl actate (9-1) to obtain 86 mg of 1,1-dimethyl-ethyl 7-[(2-(2-tritylaminothiazol-4-yl)-2-methoxyimino-acetamido]-3-[(ethoxycarbonyl)-ethen-1-yl)-8-oxo-4-thia-1-azabicyclo[4,2,0]oct-2-en-2-carboxylate.

STEP B: Syn isomer of racemic cis 7-[2-(2-aminothiazol-4-yl)-2-methoxyimino-acetamido]-3-(ethoxycarbonyl)-ethen-1-yl]-8-oxo-4-thia-1-azabicyclo[4,2,01oct-2-en-2-carboxylic acid trifluoroacetate Using the procedure of Step B of Example.84, the product of Step A was reacted to obtain the expected product.

| NMR Spectrum (DMSO) | |
|---|---|
| 6.88 ppm | $H_5$ of the thiazole |
| 6.07–6.24 ppm | ethylene H at α of the $CO_2$ |
| 7.74–7.92 ppm | ethylene H at β of the $CO_2$ |
| 1.67–1.24–1.32 ppm<br>4.04–4.12–4.21–4.28 ppm | H of the ethoxy |

EXAMPLE 89

Syn isomer of racemic cis 7-[2-(2-aminothiazol-4-yl)-2-methoxyimino-acetamido]-3-(3-oxo-1-buten-1-yl)-8-oxo-4-thia-1-azabicyclo[4,2,0]oct-2-en-2-carboxylic acid Using the procedure of Example 88, triphenyl phosphoranylidene-2-propanone was reacted to obtain the trifluoroacetate which was dissolved in water with an excess of sodium bicarbonate. The solution was filtered and the filtrate was acidified with 2 drops of formic acid. After 15 minutes, the crystals formed were filtered off, rinsed with water and then with ether to obtain the expected product.

NMR Spectrum (DMSO) 6.83 ppm: $H_5$ of the thiazole 6.32–6.48 ppm: ethylene H at position α of the C=0 7.63–7.80 ppm: ethylene H at position β of the C=0

EXAMPLE 90

Syn isomer of racemic cis 7-[2-(2-aminothiazol-4-71)-2-methoxyimino-acetamido]-3-(3-cyanoethen-1-yl)-8-oxo-4-thia-1-azbicyclo[4,2,0]oct-2-en-2-carboxylic acid Using the procedure of Example 88, cyanomethylene triphenyl phosphorane was reacted to obtain the expected product.

NMR Spectrum (DMSO) 6.88 ppm: $H_5$ of the thiazole 5.81–5.94 ppm: ethylene H at position α of the CN 7.24–7.38 ppm: ethylene H at position β of the CN

EXAMPLE 91

Syn isomer of racemic cis 7-[2-(2-aminothiazol-4-yl)-2-methoxyimino-acetamido]-3-[(4-nitrophenyl)-methylthio]-8-oxo-4-thia-1-azabicyclo[4,2,0]oct-2-en-2-carboxylic acid STEP A: p-nitrobenzyl disulfide 1.0 g of p-nitrobenzylmercaptan was dissolved in 30 of methylene chloride and 0.83 ml of triethylamine and 750 mg of iodine were added while maintaining the temperature at 25° C. and stirring for 10 minutes. After washing with N hydrochloric acid, the organic phase was dried and the solvent was evaporated. 20 ml of ether were added to the residue, and after stirring for 10 minutes, separating and drying, 839 mg of p-nitrobenzyl disulfide melting at 126° C. were obtained.

STEP B: 1,1-dimethylethyl 7-[2-(2-tritylamino thiazol-4-yl)-2-methoxyimino-acetamido]-2-hydroxy-3-[(4-nitrophenyl)-methylthio]-8-oxo-4-thia-1-azabicyclo[4,2,0]octane-2-carboxylate 925 mg of the disulfide of Step A were suspended in 10 ml of methylene chloride, and then, dropwise and with stirring 1.75 mmole of chlorine in 2.5 ml of methylene chloride were added. After stirring for 10 minutes, the reaction mixture was poured dropwise into a solution of 1.12 g of tert-.butyl diazopyruvate dissolved in 5 ml of methylene chloride. In parallel, this solution was added to a solution of 0.77 ml of triethylamine diluted in 4 ml of methylene chloride in suspension of 1.23 g of 4-mercaptomethyl-3-[2-(2-tritylamino-thiazol-4-yl)-2-methoxyimino-acetamido]-2-oxo-1-azetidine in 10 ml of methylene chloride. The mixture was stirred for 30 minutes, thin washed with 0.1N hydrochloric acid and with a sodium bicarbonate solution, dried and concentrated to dryness. The residue was chromatographed on silica and eluted with a mixture of methylene chloride and aceton (9-1) to obtain 960 mg of 1,1-dimethylethyl 7-[2-(2-tritylamino thiazol-4-yl )-2-methoxyimino-acetamido]-2-hydroxy-3-[(4-nitrophenyl)-methylthio]-8-oxo-4-thia-1-azabicyclo[4,2,0]octane-2-carboxylate (mixture of diastereo-isomers).

STEP C: 1,1-dimethylethyl 7-[2-(2-tritylamino-thiazol-4-yl)-2-methoxyimino-acetamido]-2-hydroxy-3-[(4-nitrophenyl)-methylthio]-8-oxo-4-thia-1-azabicyclo[4,2,0]oct-2-en-2-carboxylate.

Using the procedure of Example 1, Step D, the product of Step B was reacted to obtain the expected product.

STEP D: Syn isomer of racemic cis 7-[2-(2-aminothiazol-4-yl)-2-methoxyimino-acetamido]-3-[(4-nitrophenyl)-methylthio]-8-oxo-4-thia-1-azabicyclo[4,2,0]oct-2-en-2-carboxylic acid A mixture of 200 mg of the product of Step C in 4 ml of 66% formic acid was heated to 50° C. for three hours, after which it was cooled and filtered. The insoluble matter was washed with 66% formic acid, and the filtrate was evaporated under reduced pressure at 40° C. The residue was taken up in 10 ml of acetonitrile and 5 ml of methanol. After evaporating the solvent, 5 ml of methylene chloride and 1 ml of methanol were added with stirring for 16 hours. After filtering and drying, 103 mg of the expected product melting at 185°–190° C. (with decomposition) were obtained.

NMR Spectrum (DMSO) 6.82 ppm: $H_5$ of the thiazole 8.15–8.24 ppm: H in ortho position of the $NO_2$ 7.54–7.63 ppm : H in meta position of the $NO_2$

EXAMPLE 92

Syn isomer of racemic cis 7-[2-(2-aminothiazol-4-yl)-2-methoxyimino-acetamido]-3-[(5-methyl-1,3,4-thiadiazol-2-yl)-thio]-8-oxo-4-thia-1-azabicyclo[4,2,01oct-2-en-2-carboxylic acid STEP A: 1,1-dimethylethyl 3-chloro-2-hydroxy-(3-5-methyl-1,3,4-thiadiazol-2-yl)-thio propenoate, and 1,1-dimethylethyl 3-chloro-3-(5-methyl-1,3,4-thiadiazol-2-yl)-thio-2-oxo-propanoate.

1.34 g of N-chlorosuccinimide in 25 ml of benzene was cooled to 10° C. and over 10 minutes, 1.32 g of 5-methyl- 4-mercapto 1,3,4-thiadiazole were added. After stirring at 7° C. for 15 minutes, a solution of 1.72g of tert.-butyl diazopyruvate dissolved in 5 ml of methyle chloride was added over 10 minutes at 7°–8° C. The temperature was allowed to return to ambient .over one hour and the insoluble matter was filtered off and the filtrate was evaporated. The residue was taken up in ether and the solution was filtered. The filtrate was evaporated and the residue was chromatographed on silica and eluted with a mixture of methylene chloride and acetone (8.7–1.3) to obtain 820 mg of 1,1-dimethylethyl 3-chloro-2-hydroxy-3- (5-methyl-1,3,4-thiadiazol-2-yl)-thio propenoate, and 1,1-dimethylethyl 3-chloro-3-(5-methyl-1,3,4-thiadiazol-2-yl)-thio-2-oxo-propanoate in the form of a mixture of the two tautomers STEP B: Syn isomer of racemic cis 1,1-dimethylethyl 7-[2-(2-tritylamino thiazol-4-yl)-2-methoxyimino-acetamido]-2-hydroxy-3-[(5-methyl-1,3,4-thiadiazol-2-yl)-thio-8-oxo-4-thia-1-azabicyclo [4,2,0]octan-2-carboxylate.

493 mg of the product of Step B, 685 mg of syn isomer of racemic cis 4-mercaptomethyl-3-[2-(2-tritylamino thiazol-4-yl)-2-methoxyimino-acetamido]-2-oxo-1-azetidine, and 0.26 ml of triethylamine were stirred at ambient temperature for two hours in 10 ml of methylene chloride. After filtering, the solution was washed with 4 ml of N hydrochloric acid and then with 4 ml of a sodium bicarbonate solution, and dried and concentrated to dryness under reduced pressure. The residue was chromatographed on silica and eluted with a mixture of methylene chloride and acetone (8.5–1.5) to obtain 664 mg of syn isomer of racemic cis 1-1-dimethylethyl 7-[2-(2-tritylamino thiazol-4-yl)-2-methoxyimino-acetamido]-2-hydroxy-3-[[5-methyl-1,3,4-thiadiazol-2-yl)-thio-8-oxo-4-thia-1-azabicyclo [4,2,0] octan-2-carboxylate in the form of a mixture of stereoisomers.

STEP C: 1,1-dimethylethyl 7-[2-(2-tritylamino thiazol-4-yl)-2-methoxyimino-acetamido]-3-[(5-methyl-1,3,4-thiadiazol-2-yl)-thio]-8-oxo-4-thia-1-azabicyclo[4,2,01oct-2-en-2-carboxylate Using the procedure of Step 1, 895 mg of the product of Step C were reacted to obtain 234 mg of the expected product.

STEP D: Syn isomer of racemic cis 7-[2-(2-aminothiazo-4-yl)-2-methoxy-imino-acetamido]-3-[(5-methyl-1,3,4-thiadiazol-2-yl) thio]-8-oxo-4-thia-1-azabicyclo[4,2,0]oct-2-en-2-carboxylic acid 192 mg of the product of Step C were dissolved in 4 ml of 66% aqueous formic acid and the solution was stirred for 3 hours 50 minutes at 50° C. After cooling and filtering, the filtrate was concentrated to dryness under reduced pressure. The residue was dried at 50° C. for 30 minutes and then 5 ml of methanol were added with stirring for 16 hours at ambient temperature. After separating, rinsing with methanol, and drying under reduced presure at 50° C., 94 mg of the expected product were obtained.

NMR Spectrum (DMSO) 6.81 ppm, $H_5$ of the thiazole 2.72 ppm, H of the 5-methyl thiadiazole.

EXAMPLE 93

Syn isomer of racemic cis 1-[(7-[2-(2-aminothiazol-4-yl)-2-methoxy-imino-acetamido]-2-carboxy-8-oxo-4-thia-1-azabicyclo[4,2,0]oct-2-en-3-yl)-methyl-(2-methylthio)]-pyridinium trifluoromethane sulfonate trifluoroacetate Using the procedure of Example 38, 2-methylthio-pyridine was reacted to obtain the expected product.

| NMR Spectrum (DMSO) | |
|---|---|
| 6.83 ppm, $H_5$ of the thiazole | |
| 8.0–8.14 pp, $H_3$ of the pyridinium | |
| 8.97–9.06 ppm, $H_6$ of the pyridinium | |
| 7.8–7.96 ppm | ) |
| 8.4–8.56 ppm | ) $H_4$ and $H_5$ of the pyridinium. |

EXAMPLE 94

Syn isomer of racemic cis 1-[(7-[2-(2-aminothiazol-4-yl)-2-methoxy-imino-acetamido]-2-carboxy-8-oxo-4-thia-1-azabicyclo[4,2,0]oct-2-en-3-yl) -methyl-4-methyl]-pyridinium trifluoromethane sulfonate trifluoroacetate Using the procedure of Example 38, 4-picoline was reacted to obtain the expected product.

NMR Spectrum (DMSO) 6.83 ppm, $H_5$ of the thiazole 8.93–9 ppm, $H_2$ and $H_6$ of the pyridinium 8.01–8.08 ppm, $H_3$ and $H_5$ of the pyridinium.

EXAMPLE 95

Preparations for injections were prepared containing 500 mg of the syn isomer 7-[2-(2-aminothiazol-4-yl)-2-methoxyimino-acetamido]-8-oxo-3-[(1-methyl-(1H)-tetrazol-5-yl)-thio]-4-thia-1-azabicyclo[4,2,0]oct-2-ene-2-carboxylic acid or the syn isomer of 7-[2-(2-aminothiazol-4-yl)-2-methoxyimino-acetamido]-8-oxo-3-(4-nitrophenylthio)-4-thia-1-azabicyclo[4,2,0]oct-2-ene-2-carboxylic acid or the syn isomer of 1-(7-[(2-amino-4-thiazolyl) (methoxyimino) acetamido]-2-carboxy-8-oxo-4-thia-1-azabicyclo[4,2,0]oct-2-ene-3-yl)-methyl pyridinium trifluoromethane sulfonate and sufficient sterile aqueous excipient, q.s. for a final volume of 5 ml.

EXAMPLE 96

Trifluoroacetate and trifluoromethane sulfonate of 5-[{7-[2-(2-aminothiazol-4-yl)-2-methoxyimino-acetamido]-2-carboxy-8-oxo-4-thia-1-aza-bicyclo[4,2,0]-oct-2-ene-3-yl}-methyl]-thieno[3,2-c] pyridinium STEP A: Trifluoromethane sulfonate of 5-[{7-[{2-(2-triphenylmethyl amino-thiazol-4-yl)-2-methoxyimino-acetamido]-2-tert.-butoxycarbonyl-8-oxo-4-thia-1-azabicyclo[4-2-0]oct-2-en-3-yl}-methyl]-thieno [3,2-c] pyridinium 0.174 g of thieno[3,2-c]pyridine were added at −70° C. to a solution of 0.178 g of 5-[{7-[2-(2-triphenylmethylamino-thiazol-4-yl)-2-methoxyimino-acetamido]-2-tert.-butoxycarbonyl-8-oxo-4-thia-1-aza-bicyclo[4-2-0]oct-2-ene-3-yl}-methyl] hydroxy in 4 ml of methylene chloride and then 4.4 ml of a 0.1 M/l of trifluoromethane sulfonic acid anhydride in methylene chloride were added. The mixture was stirred at 0° C. for 30 minutes and was then poured into water. The decanted aqueous phase was extracted with methylene chloride and the combined organic phases were evaporated to dryness under reduced pressure to obtain 0.350 g of residue. The latter was chromatographed over silica and was eluted with a 97-3, then 95-5 and 90-10 mixtures of methylene chloride-methanol to obtain 90 mg of trifluoromethane sulfonate of 5-[{7-[(2-(2-triphenylmethyl amino-thiazol-4-yl)-2-methoxyimino-acetamido]-2-tert.-butoxycarbonyl-8-oxo-4-thia-1-aza-bicyclo[4-2-0]oct-2-en-5-yl}-methyl]-thieno[3,2-c]pyridinium.

STEP B: (Z), (6-R,S) (7-R,S) isomer of trifluoroacetate and trifluoromethane sulfonate of 5- [(7-[2-(2-amino-thiazol-4-yl)-2-methoxyimino-acetamido]-2-carboxy-8-oxo-4-thia-1-azabicyclo[4-2-0]-oct-2-ene-3-yl}-methyl]-thieno[3,2-c] pyridinium A mixture of 60 mg of the product of Step A and 0.4 ml of trifluoroacetic acid was stirred at room temperature for 50 minutes and 4 ml of ether were added thereto. The mixture was vacuum filtered and the product was dried to obtain 36 mg of the trifluoromethane sulfonate of 5-[{7-[(2-(2-amino-thiazol-4-yl)-2-methoxyimino-acetamido]-2- carboxy-8-oxo-4-thia-1-aza-bicyclo[4-2-0]oct-2-en-3-yl}-methyl]-thieno[3,2-c]pyridinium (trifluoroacetate)

IR Spectrum (nujol): 1772 $cm^{-1}$ (β-lactam); 1672 $cm^{-1}$ and 1630 $cm^{-1}$ (C=0); 1585 $cm^{-1}$ and 1550 $cm^{-1}$ (—C=C and C=N— amide II)

NMR Spectrum (DMSO): ppm

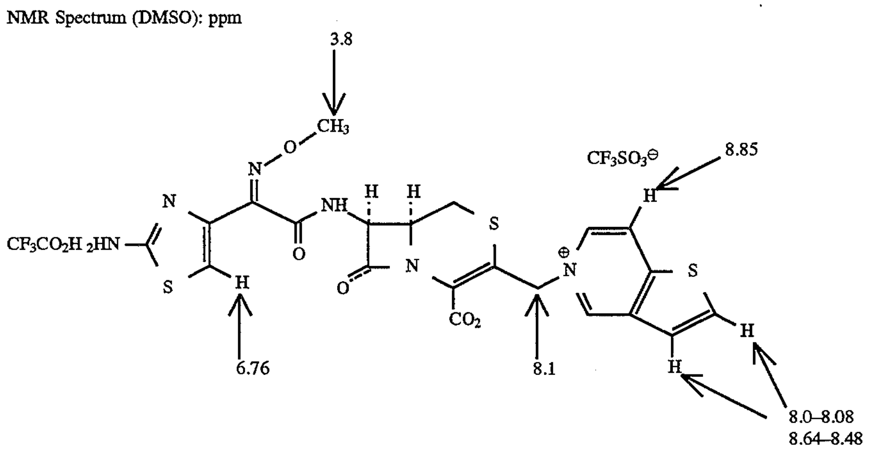

EXAMPLES 97 to 109

Using the procedure of Example 96 and the selection of the appropriate starting materials, the products of the following Table with the values set forth therein were prepared. The substituents refer to the compounds of formula I.

| | | | | | |
|---|---|---|---|---|---|
| EXAMPLE 97 | 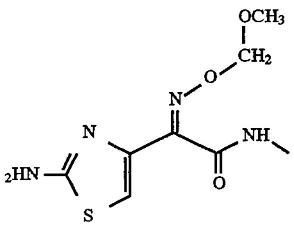<br>$CF_3CO_2H$ | 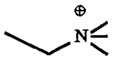<br>$CF_3SO_3^{\ominus}$ | O $-CO_2H$ | IR Spectrum (nujol) | UV Spectrum (ethanol) |
| | | | | 1779 $cm^{-1}$ β-lactam C=O | Max. 222 nm $E\frac{1}{1} = 306$ $\Sigma - 22\,900$ |
| | | | | 1670 $cm^{-1}$ amide C=O | Max. 298 nm $E\frac{1}{1} =$ $\Sigma - 14\,700$ |
| | | | | 1640 $cm^{-1}$ C=C | Max towards 410 nm $E\frac{1}{1} = 3.5$<br>(ethanol/HCl 0.1N) |
| | | | | 1574 $cm^{-1}$ C=N | |
| | | | | 1555 $cm^{-1}$ aromatic | Max. 222 nm $E\frac{1}{1} = 224$ |
| | | | | 1486 $cm^{-1}$ acid II | Infl. 265 nm $E\frac{1}{1} = 157$<br>$\Sigma = 14\,000$<br>Max. 288 nm $E\frac{1}{1} = 202$<br>$\Sigma = 15\,100$<br>Infl. 305 nm $E\frac{1}{1} = 172$<br>$\Sigma = 12\,900$ |

-continued

| | | | | | |
|---|---|---|---|---|---|
| EXAMPLE 98 | 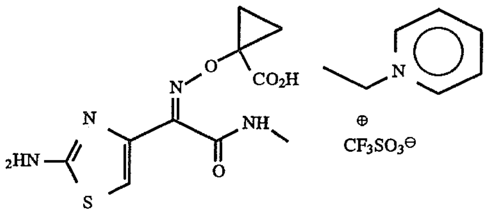<br>$CF_3CO_2H$ | O | $-CO_2H$ | m.p. = 170° C.<br><br>IR Spectrum (nujol)<br>1775 $^{cm-1}$ β-lactam C═O<br>1675 $^{cm-1}$ amide C═O<br>1707 $^{cm-1}$ other C═O<br>3120–1635 $^{cm-2}$ 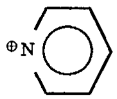<br>1580 $^{cm-1}$ aromatic<br>1560 $^{cm-1}$ conjugated system<br>1499 $^{cm-1}$ heterocycle<br>1487 $^{cm-1}$ amide II | <br><br>UV Specturm (ethanol)<br>Infl. 218 nm<br>$E\frac{1}{1} = 285$ $\Sigma = 23\ 000$<br>Infl. 255 nm<br>$E\frac{1}{1} = 173$ $\Sigma = 14\ 000$<br>Infl. 263 nm<br>$E\frac{1}{1} = 154$<br><br>Max. 296 nm $E\frac{1}{1} = 170$ $\Sigma = 13\ 700$<br>(ethanol, HCl 0.1N)<br>Max. 260 nm $E\frac{1}{1} = 214$ $\Sigma = 17\ 300$<br>Max. 290 nm $E\frac{1}{1} = 199$ $\Sigma = 16\ 100$<br>Infl. 310 nm $E\frac{1}{1} = 138$ $\Sigma = 11\ 200$ |

-continued

EXAMPLE 99

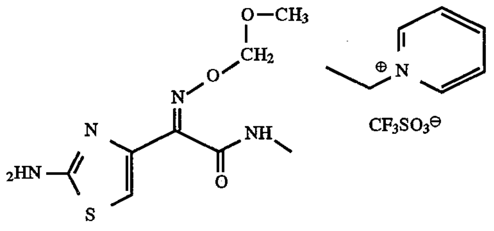

$CF_3CO_2H$

O —COOH m.p. = 170° C. (decomposition)

| IR Spectrum | UV Spectrum (ethanol) |
| --- | --- |
| 1776 $cm^{-1}$ β-lactam C=O | Max. 200 nm |
| 1670 $cm^{-1}$ amide C=O | $E\frac{1}{1} = 331$  Σ = 25 400 |
| 1633 $cm^{-1}$ aromatic | Infl. 256 nm $E\frac{1}{1} = 183$ |
| 1580 $cm^{-1}$ amide II | Infl. 265 nm $E\frac{1}{1} = 160$ |
| 1555 $cm^{-1}$ shoulder | Max. 294 nm |
| thiazole | $E\frac{1}{1} = 188$  Σ = 14 500 |
| | Max. 415 nm $E\frac{1}{1} = 21$ |
| | (ethanol, HCl 0.1N) |
| | Infl. 219 nm $E\frac{1}{1} = 260$ |
| | Max. 260 nm |
| | $E\frac{1}{1} = 235$  Σ 18 000 |
| | Max. 284 nm |
| | $E\frac{1}{1} = 216$  Σ = 16 600 |
| | Infl. 305 nm |
| | $E\frac{1}{1} = 162$  Σ = 12 500 |
| | Max. 420 nm $E\frac{1}{1} = 19$ |

EXAMPLE 100

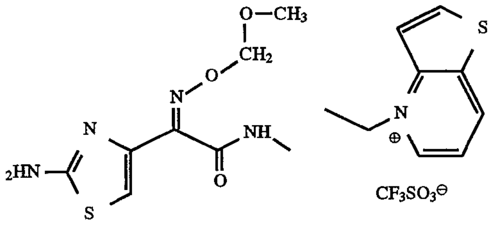

$CF_3CO_2H$

O —COOH NMR Spectrum (DMSO)

| | |
| --- | --- |
| peak at 3,3 ppm | $OCH_3$ |
| peak at 4,82 ppm | $OCH_2O$ |
| peak at 4,82 ppm | $OCH_2O$ |
| peak at 5,69 ppm | $H_7$ (β, lactam cis) |
| peak at 6,07–6,17 pp - $CH_2$—$N^{\oplus}$ | |
| peak at 6,84 ppm | $H_5$ thiazole "syn" |
| peak at 7,2–6,2 ppm les H mobiles | |

-continued

EXAMPLE 101

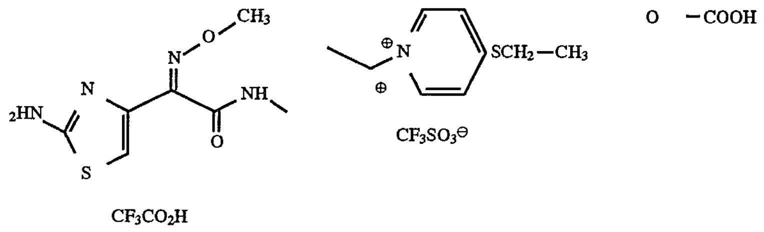

m.p. = 180° C.

| IR Spectrum | | UV Spectrum (ethanol) | |
|---|---|---|---|
| 1780 $^{cm-1}$ | β lactam c=o | Max. 230 nm $E\frac{1}{1} = 336$ | Σ = 26 800 |
| 1710 $^{cm-1}$ 1680 $^{cm-1}$ 1655 $^{cm-1}$ | other carbamyls | Max. 309 nm $E\frac{1}{1} = 451$ | Σ = 36 000 |
| | | (ethanol, HCl 0.1N) | |
| 1632 $^{cm-1}$ | region C=C | Max. 231 nm $E\frac{1}{1} = 294$ | Σ = 22 700 |
| 1602 $^{cm-1}$ | C=N | Infl. 270 nm $E\frac{1}{1} = 214$ | |
| 1545 $^{cm-1}$ 1440 $^{cm-1}$ | amide II —$NH_2$ | Max. 310 nm $E\frac{1}{1} = 438$ Σ = 35 000 | |

EXAMPLE 102

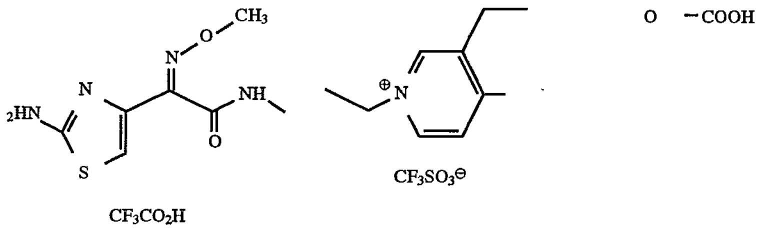

m.p. = 170–175° C. (decomposition)

| IR Spectrum (nujol) | | UV Spectrum (ethanol) | |
|---|---|---|---|
| 1775 $^{cm-1}$ | β-lactam C O | Max. 227 nm | |
| 1665 $^{cm-1}$ | amide CO | $E\frac{1}{1} = 332$ | Σ = 25 900 |
| 1637 $^{cm-1}$ | 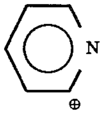 N typical amide | Infl. 258 nm $E\frac{1}{1} = 891$ | |
| | | Infl. 266 nm $E\frac{1}{1} = 883$ | |
| 1585 $^{cm-1}$ | amide II | Max 293 nm | |
| 1540 $^{cm-1}$ | thiazole | $E\frac{1}{1} = 191$ | Σ 14 900 |
| 1510 $^{cm-1}$ | conjugated system | (ethanol HCl 0.1N) | |

-continued
| | | |
|---|---|---|
| | | Max. 228 nm |
| | | $E\frac{1}{1} = 282$ $\Sigma = 22\ 000$ |
| | | Max. 267 nm |
| | | $E\frac{1}{1} = 246$ $\Sigma = 19\ 200$ |
| | | Max. 284 nm |
| | | $E\frac{1}{1} = 224$ $\Sigma = 17\ 500$ |
| | | Infl. 304 nm $E\frac{1}{1} = 872$ |
| | | Infl. 312 nm $E\frac{1}{1} = 142$ |
| | | Infl. 300 nm $E\frac{1}{1} = 105$ |
| EXAMPLE 103 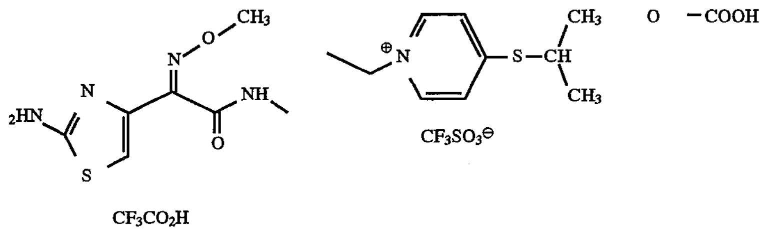 | m.p. = 180° C. | |
| | IR Spectrum (nujol) | UV Spectrum (ethanol) |
| | 1879 $cm^{-1}$ β-lactam 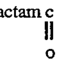 | Max. 231 nm |
| | | $E\frac{1}{1} = 3100$ $\Sigma = 25\ 200$ |
| | 1670 $cm^{-1}$ amide  | Infl. 270 nm $E\frac{1}{1} = 163$ |
| | 3120 $cm^{-1}$ | Infl. 278 nm $E\frac{1}{1} = 171$ |
| | 1430 $cm^{-1}$ 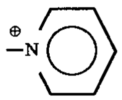 | Max. 309 nm |
| | | $E\frac{1}{1} = 425$ $\Sigma = 34\ 500$ |

-continued

| | | | |
|---|---|---|---|
| $1610^{cm^{-1}}$ | aromatic | (ethanol, HCl 0.1N) | |
| $1588^{cm^{-1}}$ | conjugated system | Max. 231 nm | |
| $1544^{cm^{-1}}$ | $COO^{\ominus}$ | $E\frac{1}{1} = 265$ | $\Sigma = 21\ 500$ |
| $1530^{cm^{-1}}$ | amide II | | |
| $1490^{cm^{-1}}$ | thiazole | Infl. 271 nm $E\frac{1}{1} = 216$ | |
| | | Infl. 277 nm $E\frac{1}{1} = 224$ | |
| | | Infl. 292 nm $E\frac{1}{1} = 289$ | |
| | | Max. 310 nm | |
| | | $E\frac{1}{1} = 410$ | $\Sigma = 35\ 300$ |

EXAMPLE 104

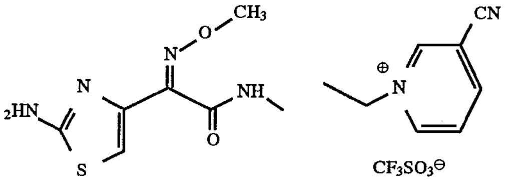

$CF_3CO_2H$ $CF_3SO_3^{\ominus}$

O —COOH m. p. = 160° C. (decomposition)

| | | | |
|---|---|---|---|
| IR Spectrum (nujol) | | UV Spectrum (ethanol) | |
| $1775^{cm^{-1}}$ | β-lactam 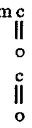 | Infl. 216 nm $E\frac{1}{1} = 351$ | |
| $1675^{cm^{-1}}$ | amide | Infl. 230 nm $E\frac{1}{1} = 291$ | |
| | | Infl. 270 nm $E\frac{1}{1} = 182$ | |
| $1640^{cm^{-1}}$ | | | |
| | | Max. 275 nm | |
| $3140^{cm^{-1}}$ | 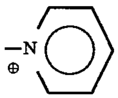 | $E\frac{1}{1} = 184$ | $\Sigma = 14\ 100$ |
| $1640^{cm^{-1}}$ | —C=CH | Max. 290 nm | |

-continued

| | | | |
|---|---|---|---|
| 1575 cm-1 | aromatic | $E\frac{1}{1} = 185$ | $\Sigma = 14\ 200$ |
| 1555 cm-1 | conjugated | (ethanol, HCl 0.1N) | |
| 1500 | system | Infl. 218 nm $E\frac{1}{1} = 307$ | |
| | amide II | | |
| | thiazole | | |
| | $COO^{\oplus}$ | | |
| 2255 cm-1 | C═H | Max. 270 nm | |
| | | $E\frac{1}{1} = 250$ | $\Sigma = 19\ 100$ |
| | | Infl. 288 nm $E\frac{1}{1} = 225$ | |
| | | Infl. 310 nm $E\frac{1}{1} = 149$ | |

EXAMPLE 105

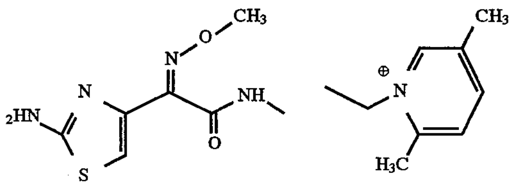

$CF_3CO_2H$ $CF_3SO_3^{\ominus}$

O —COOH m.p. = 180° C.

| IR Spectrum (nujol) | | UV Spectrum (ethanol) | |
|---|---|---|---|
| 1775 cm-1 | β lactam | Infl. 218 nm $E\frac{1}{1} = 291$ | |
| 1675 cm-1 | other carbonyl | Infl. 275 nm $E\frac{1}{1} = 217$ | |
| 1640 cm-1 | | Infl. 282 $E\frac{1}{1} = 218$ $\Sigma = 16\ 700$ | |
| 1578 cm-1 | region C═C | Infl. 295 $E\frac{1}{1} = 196$ | |
| 1528 cm-1 | C═H | (ethanol, HCl 0.1N) | |
| | amide II | Max. 220 nm $E\frac{1}{1} = 264$ | $\Sigma = 20\ 200$ |
| | | Max. 275 nm $E\frac{1}{1} = 294$ | $\Sigma = 22\ 300$ |
| | | Infl. 281 nm $E\frac{1}{1} = 285$ | |
| | | Infl. 293 nm $E\frac{1}{1} = 234$ | |
| | | Infl. 310 nm $E\frac{1}{1} = 165$ | $\Sigma = 12\ 500$ |

-continued

EXAMPLE 106

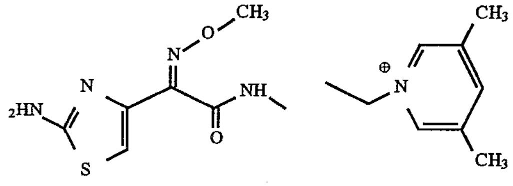

$CF_3CO_2H$ $CF_3SO_3^{\ominus}$

O —COOH m. p. = 200° C.

| IR Spectrum (nujol) | | UV Spectrum (ethanol) | |
|---|---|---|---|
| 1778 $cm^{-1}$ | β-lactam $C=O$ | Infl. 218 nm $E\frac{1}{1} = 332$ | |
| | | Infl. 273 nm $E\frac{1}{1} = 218$ | |
| 1670 $cm^{-1}$ | amide $C=O$ | Max. 279 nm $E\frac{1}{1} = 221$ | $\Sigma = 16\,900$ |
| 1640 $cm^{-1}$ | (shoulder) | Max. 292 nm $E\frac{1}{1} = 205$ | $\Sigma = 15\,700$ |
| series of CH—N 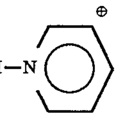 | | (ethanol HCl 0.1N) | |
| 1555 $cm^{-1}$ | aromatic | Max. 225 nm $E\frac{1}{1} = 272$ | $\Sigma = 20\,900$ |
| & | amide II | Max. 275 nm $E\frac{1}{1} = 282$ | $\Sigma = 22\,000$ |
| 1540 $cm^{-1}$ | thiazole | | |
| | $COO^{\oplus}$ II | Infl. 290 nm $E\frac{1}{1} = 233$ | |
| 1050 $cm^{-1}$ | —C=H—OR | Infl. 310 nm $E\frac{1}{1} = 156$ | $\Sigma = 12\,000$ |

-continued

EXAMPLE 107

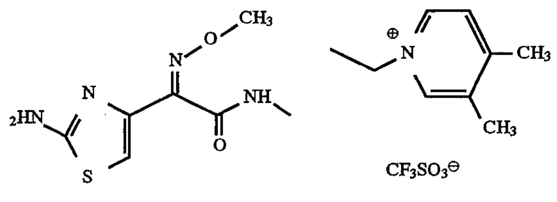

$CF_3CO_2H$ $CF_3SO_3^{\ominus}$

O —COOH m.p. = 170° C.

| IR Spectrum (nujol) | | UV Spectrum (ethanol) | |
|---|---|---|---|
| 1780 $cm^{-1}$ | β lactam c ‖ o | Max. 226 nm $E\frac{1}{1} = 326$ | $\Sigma = 25\,000$ |
| 1675 $cm^{-1}$ | amide c ‖ o | Infl. 256 nm $E\frac{1}{1} = 293$ | $\Sigma = 14\,800$ |
| | | Infl. 266 $E\frac{1}{1} = 280$ | |
| 1640 $cm^{-1}$, 1030 $cm^{-1}$, 1600 $cm^{-1}$ | 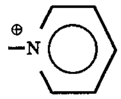 | Max. 292 $E\frac{1}{1} = 181$ (ethanol, HCl 0.1N) | $\Sigma = 14\,300$ |
| 1555, 1535, 1515 | aromatic conjugated system COO⊕ amide II thiazole | Max. 226 nm $E\frac{1}{1} = 277$ | $\Sigma = 21\,200$ |
| | | Max. 265 nm $E\frac{1}{1} = 840$ | $\Sigma = 18\,400$ |
| | | Max 284 nm $E\frac{1}{1} = 217$ | $\Sigma = 16\,600$ |
| | | Infl. 310 nm $E\frac{1}{1} = 144$ | $\Sigma = 11\,000$ |

-continued

EXAMPLE 108

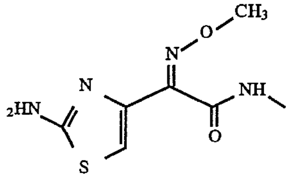

$CF_3CO_2H$

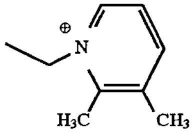

$CF_3SO_3^{\ominus}$

O —COOH m. p. 190° C.

IR Spectrum (nujol)

1780 $cm^{-1}$ β lactam C=O

1675 $cm^{-1}$ amide C=O 3120, 1640 (shoulder) 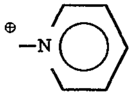

1575, 1550 conjugated system, amide II, thiazole, COO ⊕

UV Spectrum (ethanol)

Infl. 215 nm $E\frac{1}{1} = 332$

Infl. 226 nm $E\frac{1}{1} = 307$

Max. 276 nm $E\frac{1}{1} = 220$ $\Sigma = 16\,900$

Max. 294 nm $E\frac{1}{1} = 205$ $\Sigma = 15\,700$ (ethanol HCl 0.1N)

Max. 220 nm $E\frac{1}{1} = 263$ $\Sigma = 20\,200$

Max. 274 nm $E\frac{1}{1} = 292$ $\Sigma = 22\,400$

Infl. 292 nm $E\frac{1}{1} = 235$

Infl. 306 nm $E\frac{1}{1} = 183$ $\Sigma = 14\,000$

EXAMPLE 109

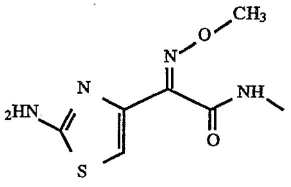

$CF_3CO_2H$

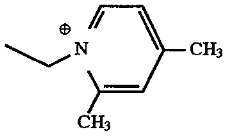

$CF_3SO_3^{\ominus}$

O $-CO_2H$ m.p. = 170° C.

IR Spectrum (nujol)

1175 $cm^{-1}$ β lactam C=O

1674 $cm^{-1}$ amide C=O

1640 $cm^{-1}$, 1030 $cm^{-1}$ 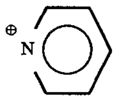

1570, 1555 $cm^{-1}$ conjugated system, heterocycle, amide II, COO ⊕

UV Spectrum (ethanol)

Max. 225 nm $E\frac{1}{1} = 352$ $\Sigma = 27\,000$

Max. 262 nm $E\frac{1}{1} = 206$ $\Sigma = 15\,800$

Max. 295 nm $E\frac{1}{1} = 203$ $\Sigma = 15\,000$ (ethanol, HCl 0.1N)

Max. 229 nm $E\frac{1}{1} = 295$ $\Sigma = 22\,600$

Max. 265 nm $E\frac{1}{1} = 254$ $\Sigma = 19\,900$

Max. 286 nm $E\frac{1}{1} = 230$ $\Sigma = 17\,000$

Infl. 303 nm $E\frac{1}{1} = 186$

-continued
EXAMPLE 110
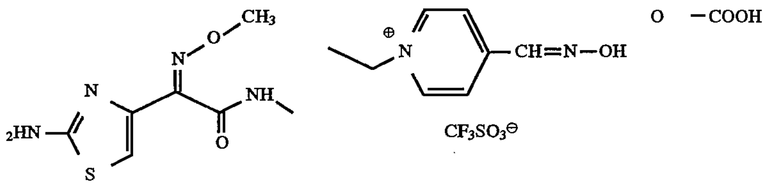
m.p. = 200–205° C. (decomposition)
| IR Spectrum (nujol) | | UV Spectrum (ethanol) | |
|---|---|---|---|
| 1770 $cm^{-1}$ | β lactam  | Infl. 217 nm $E\frac{1}{1} = 347$ | |
| 1670 $cm^{-1}$ | amide  | Max. 292 nm $E\frac{1}{1} = 400$ | Σ = 26 700 |
| 1610 $cm^{-1}$ | amide II | (ethanol, HCl 0.1N) | |
| 1580 $cm^{-1}$ | thiazole | Max 220 nm $E\frac{1}{1} = 287$ | Σ = 19 200 |
| 1550 $cm^{-1}$ | aromatic | | |
| 1520 $cm^{-1}$ | | Max. 286 nm $E\frac{1}{1} = 443$ | Σ = 29 600 |
| 3125 $cm^{-1}$ | 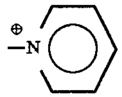 | | |
| 1640 $cm^{-1}$ | | | |
| 1030 $cm^{-1}$ | | | |

EXAMPLE 110

Trifluoromethane sulfonate (6R,S) (7R,S) (ΔZ) 1-[{7-[2-(2-aminothiazol-4-yl)-2-methoxyimino-acetamido]-2-carboxy-8-oxo-4- thia-1-azabicyclo[4-2-0]oct-2-ene-3-yl}-methyl]-4-[(hydroxyimino)-methyl]-pyridinium STEP A: 4-[(1-methoxy-1-methyl-ethoxyimino) -methyl]-pyridine 1.5 ml of 2-methoxy-propene were added all at once to a suspension of 610 mg of pyridine-4-aldoxime in 10 ml of methylene chloride and the mixture was stirred for 18 hours at 60° C. under reduced pressure. The mixture was cooled and evaporated to dryness under reduced pressure to obtain 950 mg of 4-[(1-methoxy-1-methyl-ethoxyimino)-methyl]-pyridine.

IR Spectrum (chloroform):

Absence of —OH and peaks at 2835 $cm^{-1}$ (u methyl); at 1599 $cm^{-1}$ (C═C) and at 1546 $cm^{-1}$ (C═N)

NMR Spectrum ($CDCH_3$): ppm

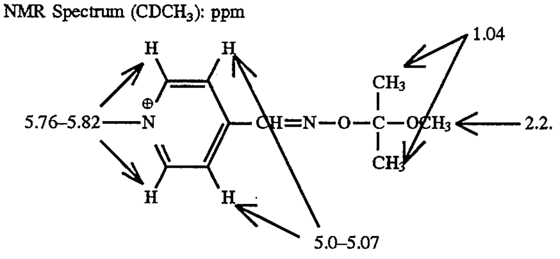

IR Spectrum (chloroform):

peak at 3400 $cm^{-1}$ (NH), at 1784 $cm^{-1}$ (β-lactam); at 1700 $cm^{-1}$ (CO ester); at 1678 $cm^{-1}$ (amide); at 1643, 1596, 1560 and 1525 $cm^{-1}$ (C═C, C═N, aromatic, amide, thiazole)

| U.V. Spectrum (ethanol): | | | |
|---|---|---|---|
| Inflex. | 224 nm | $E_1^1$ = 347 | ε = 36,000 |
| Inflex. | 240 nm | $E_1^1$ = 254 | ε = 26,400 |
| Inflex. | 288 nm | $E_1^1$ = 279 | |
| Max. | 297 nm | $E_1^1$ = 29 | |
| U.S. Spectrum (ethanol + 0.1 N HCl): | | | |
| Inflex. | 222 nm | $E_1^1$ = 336 | |
| Max. | 290 nm | $E_1^1$ = 347 | ε = 36,000 |
| Inflex. | 300 nm | $E_1^1$ = 314 | |

A mixture of 210 mg of the latter product and 1 ml of trifluoroacetic acid was stirred at 20° C. for one hour and then 10 ml of ether were added dropwise with stirring. The mixture was vacuum filtered and the product was washed and dried to obtain 150 mg of the above named product melting at 200°–210° C. (decomposition).

IR Spectrum (nujol):

peaks at 1776 $cm^{-1}$ (lactam CO); at 1672 $cm^{-1}$ (other carbonyls); at 1595, 1550, 1520 and 1490 $cm^{-1}$ (conjugated C═C system).

NMR Spectrum (DMSO): ppm

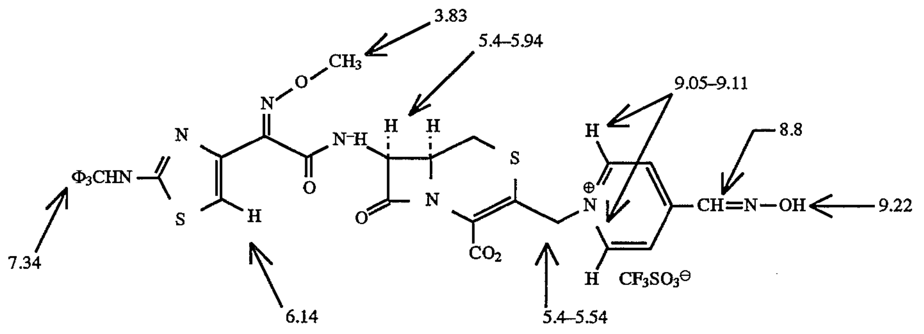

STEP B: Trifluoromethane sulfonate of (6RS, 7RS, ΔZ) 1-[{7-[(2-triphenylmethylamino-thiazol-4-yl)-2-methoxyimino-acetamido]-2-carboxy-8-oxo-4-thia-1-azabicyclo[4-2-O]oct-2-ene-3-yl)-methyl-4-(hydroxyiminomethyl)-pyridinium 7.2 ml of a 0.1N solution of trifluoromethane sulfonic acid anhydride in methylene chloride were added dropwise at −78° C. to a solution of 326 mg of the product of Step A and 300 mg of 5-[{7-[(2-triphenylamino-thiazol-4-yl)-2-methoxyimino-acetamido]-2-tert.-butoxy-carbonyl-8-oxo-4-thia-1-azabicyclo[4-2-0]-oct-2-ene-3-yl}-methylhydroxy in 20 ml of methylene chloride and after stirring at −70° C. for 30 minutes, the mixture was poured into iced water containing 4 ml of aqueous N hydrochloric acid with stirring. The decanted aqueous phase was extracted with methylene chloride and the combined organic phases were washed and evaporated to dryness under reduced pressure. The residue was chromatographed over silica and was eluted with a 95-5 methylene chloride-methanol mixture to obtain 235 mg of the tert.-butyl ester.

STEP C: Trifluoromethane sulfonate of (6RS, 7RS, ΔZ) 1-[{7-[{2-(2-amino-thiazol-4-yl)-2-methoxyimino-acetamido]-2-carboxy-8-oxo-4-thia-1-azabicyclo[4-2-0]oct-2-ene-3-yl}methyl]-4-(hydroxyimino)-methyl]-pyridinium A mixture of 120 mg of the product of Step B in 1 ml of 66% formic acid was stirred under nitrogen at 65° C. for 15 minutes and was then cooled to room temperature and vacuum filtered. The filtrate was washed with aqueous formic acid and with water and was evaporated to dryness. The residue was taken up in ethanol at 95° C. and the solution was evaporated to dryness again. The product was crystallized from a.1-1 isopropyl ether-ether mixture and then anhydrous ether to obtain 80 mg of the desired product melting at 200°–205° C. (decomposition).

| U.V. Spectrum (ethanol): | | |
|---|---|---|
| Max. 217 nm | $E_1^1 = 347$ | |
| Max. 292 nm | $E_1^1 = 400$ | $\epsilon = 26,700$ |
| **U.V. Spectrum (ethanol + 0.1 N HCl):** | | |
| Max. 220 nm | $E_1^1 = 287$ | $\epsilon = 19,200$ |
| Max. 286 nm | $E_1^1 = 443$ | $\epsilon = 29,600$ |

IR Spectrum (nujol):

1770 $cm^{-1}$ (CO of β-lactam); 1670 $cm^{-1}$ (amide CO}; 1610, 1580, 1550 and 1520 $cm^{-1}$ (amide II, thiazole, aromatic);. 3125, 1640 and 1030 $cm^{-1}$

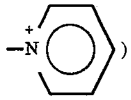

EXAMPLES 111 to 134

Using the procedure of Example 115 and the correct reactants, the compounds reported in the following Table were prepared.

| | | | | | | |
|---|---|---|---|---|---|---|
| EXAMPLE 111 | 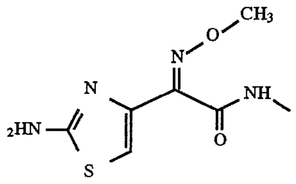<br>$CF_3CO_2H$ | 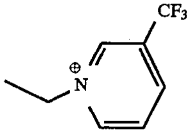<br>$CF_3SO_3^{\ominus}$ | O | $-CO_2H$ | m.p. = 190°-200° C. (decomposition)<br>IR Spectrum (nujol)<br>1715 $^{cm-1}$ β lactam $C{=}O$<br>1670 $^{cm-1}$, 1645 $^{cm-1}$ } C=O, C=Φ<br>1580 $^{cm-1}$, 1550 $^{cm-1}$, 1510 $^{cm-1}$ } C=C, C=N, amide II<br>1030 $^{cm-1}$ $F_3C-SO_3^{\ominus}$ | UV Spectrum (ethanol)<br>Infl. 220 nm $E\frac{1}{1}$ = 266<br>Infl. 232 nm $E\frac{1}{1}$ = 244<br>Infl. 257 nm $E\frac{1}{1}$ = 117<br>Infl. 264 nm $E\frac{1}{1}$ = 167<br>Max. 295 nm $E\frac{1}{1}$ = 172 Σ = 13 900<br>(ethanol, HCl 0.1N)<br>Infl. 220 nm $E\frac{1}{1}$ = 212<br>Infl. 263 nm $E\frac{1}{1}$ = 219<br>Max. 285 nm $E\frac{1}{1}$ = 203 Σ = 16 400<br>Infl. 290 nm $E\frac{1}{1}$ = 200<br>Max. 306 nm $E\frac{1}{1}$ = 152 Σ = 12 300 |
| EXAMPLE 112 | 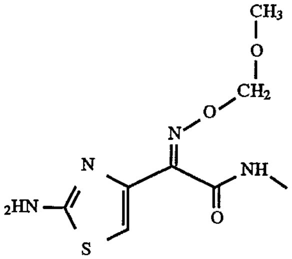<br>$CF_3CO_2H$, | 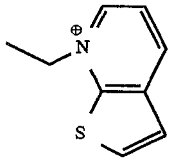<br>$CF_3SO_3^{\ominus}$ | O | $-COOH$ | IR Spectrum nujol<br>1775 $^{cm-1}$ β lactam $C{=}O$<br>1672 $^{cm-1}$ amide<br>1640 $^{cm-1}$, 1600, 1570, 1560 } aromatic, amide II, thiazole, $COO^{\ominus}$<br>1030 $^{cm-1}$ $F_3C-SO_3^{\ominus}$ | U.V. Spectrum (ethanol)<br>Max. 236 nm $E\frac{1}{1}$ = 410 Σ = 33 800<br>Max. 297 nm $E\frac{1}{1}$ = 202 Σ = 16 700<br>(ethanol HCl 0.1N)<br>Max. 239 nm $E\frac{1}{1}$ = 377 Σ = 32 100<br>Max. 294 nm $E\frac{1}{1}$ = 207 Σ = 17 100<br>Infl. 305 nm $E\frac{1}{1}$ = 202 |
| EXAMPLE 113<br>optically<br>active<br>(6S,7S) | 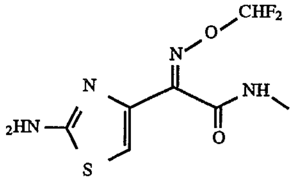 | 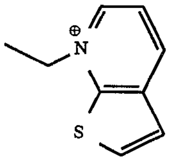 | O | 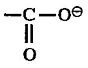 | U.V. Spectrum (ethanol)<br>Max. 235 nm $E\frac{1}{1}$ = 564 Σ = 32 500<br>Max. 296 nm $E\frac{1}{1}$ = 288 Σ = 16 600<br>(ethanol, HCl, 0, 1 N)<br>Max. 238 nm $E\frac{1}{1}$ = 519 Σ = 29 400<br>Max. 296 nm $E\frac{1}{1}$ = 301 Σ = 17 400 | |

-continued

| | | | | | | |
|---|---|---|---|---|---|---|
| EXAMPLE 114 | 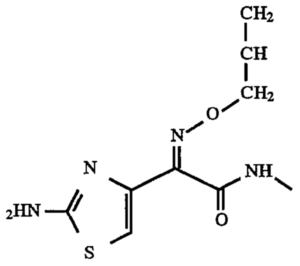<br>$CF_3CO_2H$, | 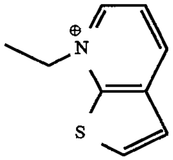<br>$CF_3SO_3^{\ominus}$ | O | $-COOH$ | IR Spectrum (nujol) | U.V. Spectrum (ethanol) |
| | | | | | 1775 $cm^{-1}$ β lactam c=o | Max. 239 nm $E\frac{1}{1}$ = 169 Σ = 38 200 |
| | | | | | 1670 $cm^{-1}$ amide c=o | Max. 295 nm $E\frac{1}{1}$ = 233 Σ = 19 100 |
| | | | | | 1640 $cm^{-1}$ 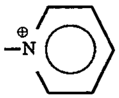 | (ethanol, HCl, 0.1N) |
| | | | | | 1030 $cm^{-1}$ $F_3C-SO_3^{\ominus}$ | Max. 239 nm $E\frac{1}{1}$ = 425 Σ = 34 400 |
| | | | | | 1530 $cm^{-1}$, 1560, 1520, 1510 } conjugated system, amide II, thiazole | Max. 293 nm $E\frac{1}{1}$ = 250 Σ = 20 500 |
| EXAMPLE 115 | 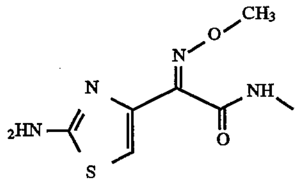<br>$CF_3CO_2H$, | 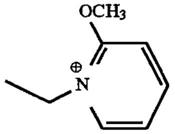<br>$CF_3SO_3^{\ominus}$ | O | $-CO_2H$ | m.p. = 190° C.<br>IR Spectrum (nujol) | U.V. Spectrum (ethanol) |
| | | | | | 1775 $cm^{-1}$ β lactam c=o | Infl. 226 nm $E\frac{1}{1}$ = 280 Σ = 21 500 |
| | | | | | 1675 $cm^{-1}$ β amide c=o | Max. 208 nm $E\frac{1}{1}$ = 299 Σ = 19 900 |
| | | | | | 1510 $cm^{-1}$ amide II | Infl. 304 nm $E\frac{1}{1}$ = 182 |
| | | | | | 1635 $cm^{-1}$ 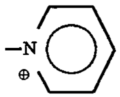 | (ethanol, HCl, 0.1N) |
| | | | | | | Infl. 224 nm $E\frac{1}{1}$ = 230 |
| | | | | | 1030 $cm^{-1}$ $CF_3SO_3^{\ominus}$ | Max. 285 nm $E\frac{1}{1}$ = 313 Σ = 24 000 |
| | | | | | 1580 $cm^{-1}$, 1515 $cm^{-1}$ } aromatic, thiazole, $-COO^{\ominus}$ | Infl. 304 nm $E\frac{1}{1}$ = 180 Σ = 13 800 |

-continued

| | | | | | | |
|---|---|---|---|---|---|---|
| EXAMPLE 116 | 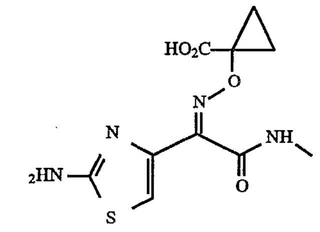<br>$CF_3CO_2H$ | 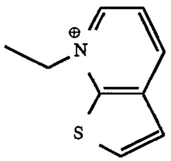<br>$CF_3SO_3^{\ominus}$ | O | $-CO_2H$ | NMR Spectrum<br>U.V. Spectrum (ethanol)<br>Max. 238 nm $E\frac{1}{1}$ = 401<br>Max. 299 nm $E\frac{1}{1}$ = 196<br>(ethanol, HCl 0.1N)<br>Max. 240 nm $E\frac{1}{1}$ = 369<br>Max. 295 nm $E\frac{1}{1}$ = 214 | |
| EXAMPLE 117 optically active (6S,7S) | 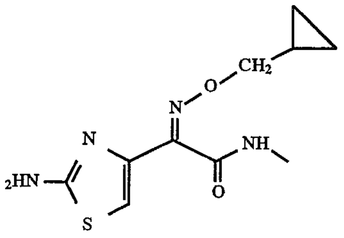<br>$CF_3CO_2H$, | 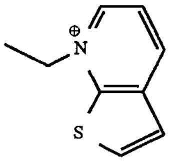<br>$CF_3SO_3^{\ominus}$ | O | $-CO_2H$ | IR Spectrum (nujol)<br>1980 $cm^{-1}$ β lactam C=O<br>1674 $cm^{-1}$ β amide C=O<br>1640 $cm^{-1}$, 1030 $cm^{-1}$ 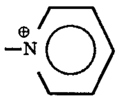 $CF_3SO_3^{\ominus}$<br>1600 $cm^{-1}$ aromatic<br>1580 $cm^{-1}$ conjugated system<br>1560 $cm^{-1}$ (shoulder) $COO^{\ominus}$<br>1500 $cm^{-1}$ heterocycle, amide II | U.V. Spectrum (ethanol)<br>Max. 238 nm $E\frac{1}{1}$ = 530 Σ = 44 200<br>Max. 295 nm $E\frac{1}{1}$ = 261 Σ = 21 800<br>Max. 240 nm $E\frac{1}{1}$ = 483 Σ = 40 300<br>Infl. 290 nm $E\frac{1}{1}$ = 282<br>Max. 294 nm $E\frac{1}{1}$ = 283 Σ = 21 600 |

-continued

| | | | | | | |
|---|---|---|---|---|---|---|
| EXAMPLE 118 | 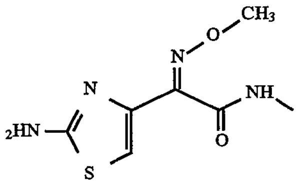 | $-SCG_3$ | O | $-CO_2H$ | IR Spectrum<br>1765 cm-1 β lactam C=O<br>1648 cm-1 β amide C=O<br>1630 cm-1 NH$_2$ of formation —C=C— , >C=N<br>1532 cm-1 amide II, thiazole, COO⊖<br>1160 cm-1, 1130 cm-1 CF$_3$<br>1025 cm-1 —C=N—OR | NMR Spectrum |
| EXAMPLE 121 | 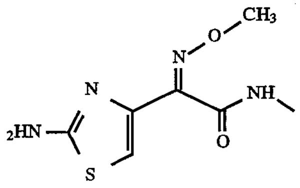<br>$CF_3CO_2H$, | 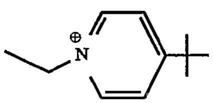<br>$CF_3SO_3^{\ominus}$ | O | $-CO_2H$ | IR Spectrum (nujol)<br>1788 cm-1 β lactam<br>1715 cm-1, 1682 cm-1, 1660 cm-1, 1645 cm-1 other C=O<br>1605 cm-1, 1569 cm-1, 1550 cm-1, 1538 cm-1, 1510 cm-1 region C=C, C=N<br>MP 200° C. | U.V. Spectrum (ethanol)<br>Max. 229 nm $E\frac{1}{1}$ = 366 Σ = 28 300<br>Infl. 255 nm $E\frac{1}{1}$ = 236<br>Infl. 261 nm $E\frac{1}{1}$ = 219<br>Max. 291 nm $E\frac{1}{1}$ = 198 Σ = 15 700<br>(ethanol, HCl 0.1N)<br>Max. 229 nm $E\frac{1}{1}$ = 319 Σ = 25 400<br>Infl. 260 nm $E\frac{1}{1}$ = 252<br>Max. 263 nm $E\frac{1}{1}$ = 254 Σ = 20 200<br>Max. 287 $E\frac{1}{1}$ = 263 Σ = 20 300<br>Inf. 310 $E\frac{1}{1}$ = 169 Σ = 13 400 |

-continued

| | | | | | | |
|---|---|---|---|---|---|---|
| EXAMPLE 122 | 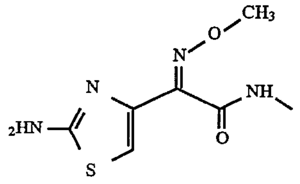<br>$CF_3CO_2H$ | 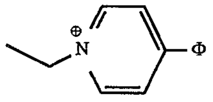<br>$CF_3SO_3^{\ominus}$ | O | $-CO_2H$ | IR Spectrum (nujol)<br>1775 $cm^{-1}$ β lactam c=o<br>1672 $cm^{-1}$ amide c=o<br>3125 $cm^{-1}$, 1639 $cm^{-1}$, 1490 $cm^{-1}$ } series of 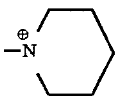<br>1595 $cm^{-1}$, 1558 $cm^{-1}$, 1525 $cm^{-1}$, 1490 $cm^{-1}$ } aromatic heterocycle amide II $COO^{\ominus}$<br>MP = 210° C. | U.V. Spectrum (ethanol HCl/N10)<br>Infl. 219 nm $E\frac{1}{1}$ = 286 Σ = 23 300<br>Max. 297 nm $E\frac{1}{1}$ = 415 Σ = 33 800<br>Max. 502 nm $E\frac{1}{1}$ = 16 |
| EXAMPLE 119 | 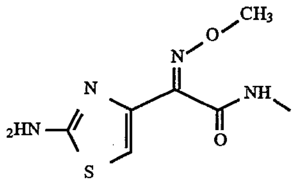<br>$CF_3CO_2H$, | 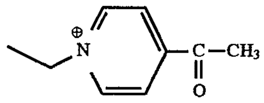<br>$CF_3SO_3^{\ominus}$ | O | $-CO_2H$ | IR Spectrum (nujol)<br>1775 $cm^{-1}$ β lactam C=O<br>1672 $cm^{-1}$ amide C=O<br>1705 $cm^{-1}$ cetone C=O<br>3120 $cm^{-1}$, 1640 $cm^{-1}$ } 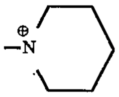<br>=CH<br>1570 $cm^{-1}$, 1530 $cm^{-1}$ aromatic amide thiazole $COO^{\ominus}$<br>m.p. = 185° C. | U.V. Spectrum (ethanol)<br>Max. 221 nm $E\frac{1}{1}$ = 368 Σ = 28 700<br>Max. 290 nm $E\frac{1}{1}$ = 221 Σ = 17 300<br>(ethanol, HCl 0.1N)<br>Max. 227 nm $E\frac{1}{1}$ = 310 Σ = 24 200<br>Infl. 270 nm $E\frac{1}{1}$ = 247<br>Max. 285 nm $E\frac{1}{1}$ = 263 Σ = 20 500<br>Infl. 304 nm $E\frac{1}{1}$ = 189 Σ = 14 800 |

-continued

| | | | | | | |
|---|---|---|---|---|---|---|
| EXAMPLE 120 | 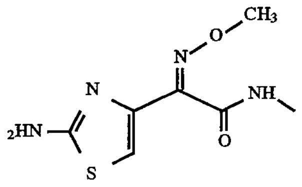<br>$CF_3CO_2H$ | 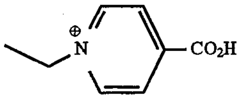<br>$CF_3SO_3^{\ominus}$ | O | $-CO_2H$ | IR Spectrum (nujol)<br>1785 $cm^{-1}$ β lactam<br>1745 $cm^{-1}$, 1709 $cm^{-1}$, 1681 $cm^{-1}$, 1650 $cm^{-1}$ } others C=O<br>1604 $cm^{-1}$, 1570 $cm^{-1}$, 1530 $cm^{-1}$ } region conjugated system amide II<br>MP = 220° C. | U.V. Spectrum (ethanol HCl N/10)<br>Max. 223 nm $E\frac{1}{1}$ = 314 Σ = 24 600<br>Max. 282 nm $E\frac{1}{1}$ = 275 Σ = 21 500<br>Infl. 290 nm $E\frac{1}{1}$ = 252 Σ = 19 700 |
| EXAMPLE 123 | 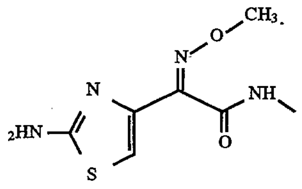<br>$CF_3CO_2H$, | 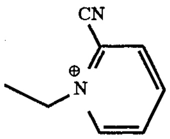<br>$CF_3SO_3^{\ominus}$ | O | $-CO_2H$ | IR Spectrum (nujol)<br>1775 $cm^{-1}$ β lactam C=O<br>1670 $cm^{-1}$ amide<br>1639 $cm^{-1}$ aromatic<br>1580 $cm^{-1}$ amide II<br>1517 $cm^{-1}$ thiazole<br>MP = 170 ° C. (decomposition) | U.V. Spectrum (ethanol)<br>Infl. 224 nm $E\frac{1}{1}$ = 296<br>Max. 287 $E\frac{1}{1}$ = 266 Σ = 20 000<br>Infl. 301 nm $E\frac{1}{1}$ = 204 Σ =<br>(ethanol, HCl, 0.1N)<br>Infl. 224 nm $E\frac{1}{1}$ = 245<br>Max. 284 nm $E\frac{1}{1}$ 318 Σ = 24 300<br>Infl. 306 nm $E\frac{1}{1}$ 177 Σ = 13 500 |

-continued

| | | | | | | |
|---|---|---|---|---|---|---|
| EXAMPLE 124 | 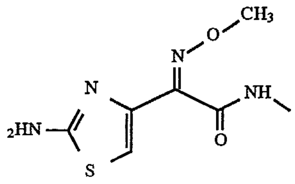<br>$CF_3CO_2H$ | 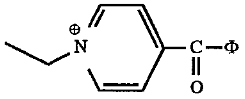<br>$CF_3SO_3^{\ominus}$ | O | $-CO_2H$ | IR Spectrum (nujol)<br>1776 $cm^{-1}$ β lactam C=O<br>1670 $cm^{-1}$ amide + 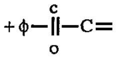<br>1520 $cm^{-1}$ amide II<br>3120 $cm^{-1}$ 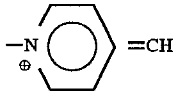<br>1640 $cm^{-1}$, 1595 $cm^{-1}$, 1580 $cm^{-1}$, 1567 $cm^{-1}$, 1550 $cm^{-1}$ } aromatic, $COO^{\ominus}$, C=C conjugated<br>1030 $cm^{-1}$ $^{\ominus}O_3S-CF_3$<br>MP = 180° C. | U.V. Spectrum (ethanol)<br>Infl. 220 nm $E\frac{1}{1}$ = 383 Σ = 32 200<br>Infl. 276 nm $E\frac{1}{1}$ = 241<br>Max. 284 nm $E\frac{1}{1}$ = 245 Σ = 20 600<br>(ethanol, HCl 0.1N)<br>Max. 225 nm $E\frac{1}{1}$ = 386 Σ = 27 500<br>Max. 275 nm $E\frac{1}{1}$ = 293 Σ = 24 700<br>Infl. 306 nm $E\frac{1}{1}$ = 93 Σ = 7 800 |
| EXAMPLE 125 | 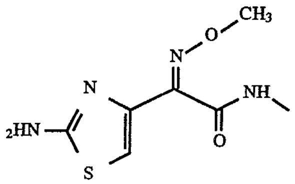<br>$CF_3CO_2H$ | 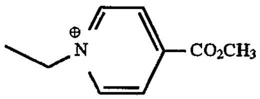<br>$CF_3SO_3^{\ominus}$ | O | $-CO_2H$ | IR Spectrum (nujol)<br>1775 $cm^{-1}$ β lactam<br>1740 $cm^{-1}$ ester<br>1675 $cm^{-1}$ amide<br>1640 $cm^{-1}$ + 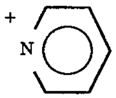<br>1579 $cm^{-1}$ $COO^{\ominus}$<br>1535 $cm^{-1}$ } amide II, thiazole<br>1047 $cm^{-1}$ C=N—OMe<br>MP = 190° C. | U.V. Spectrum (ethanol)<br>Max. 219 nm $E\frac{1}{1}$ = 480 Σ = 38 200<br>Max. 286 nm $E\frac{1}{1}$ = 273 Σ = 4 700<br>Infl. 294 nm $E\frac{1}{1}$ = 261<br>Infl. 380 nm $E\frac{1}{1}$ = 716<br>(ethanol, HCl 0.1N)<br>Max. 211 nm $E\frac{1}{1}$ = 398 Σ = 31 700<br>Infl. 278 nm $E\frac{1}{1}$ = 278<br>Max. 283 nm $E\frac{1}{1}$ = 330 Σ = 26 300<br>Infl. 304 nm $E\frac{1}{1}$ = 231 Σ = 18 400 |

-continued

| | | | | | | |
|---|---|---|---|---|---|---|
| EXAMPLE 126 | 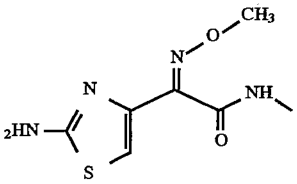 CF₃CO₂H | 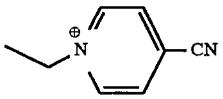 | O | $-CO_2H$ | IR Spectrum (nujol)<br>1176 $cm^{-1}$ β lactam c<br>1672 $cm^{-1}$ amide c<br>1515 $cm^{-1}$ } amide II<br>1530 $cm^{-1}$ } thiazole<br>1640 $cm^{-1}$ } aromatic<br>1588 $cm^{-1}$ }<br>1560 $cm^{-1}$ } C=C conjugated<br>3120 $cm^{-1}$ 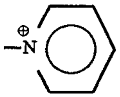<br>MP = 200° C. | U.V. Spectrum (ethanol)<br>Max. 239 nm E $\frac{1}{1}$ = 391 Σ = 29 900<br>Infl. 281 nm E $\frac{1}{1}$ = 281<br>Max. 286 nm E $\frac{1}{1}$ = 229 Σ = 17 500<br>Infl. 298 nm E $\frac{1}{1}$ = 206<br>(ethanol, HCl 0.1N)<br>Max. 226 nm E $\frac{1}{1}$ = 329 Σ = 25 000<br>Max 284 nm E $\frac{1}{1}$ = 276 Σ = 21 100<br>Infl. 305 nm E $\frac{1}{1}$ = 180 |
| EXAMPLE 127 | 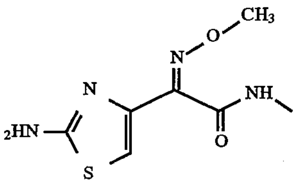 CF₃CO₂H | Cl⊖ 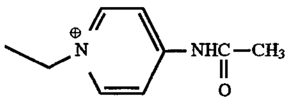 | O | $-CO_2H$ | IR Spectrum (nujol)<br>1770 $cm^{-1}$ β lactam c<br>1715 $cm^{-1}$ (é pauL.) } amide c<br>1670 $cm^{-1}$ (max) }<br>1640 $cm^{-1}$ } $NH_2$<br>1598 $cm^{-1}$ } C=C<br>1580 $cm^{-1}$ } C=N<br>1518 $cm^{-1}$ } COO⊖<br>aromatic<br>thiazole<br>amide II<br>1800 $cm^{-1}$ $CF_3$<br>MP = 220° C. | U.V. Spectrum (ethanol)<br>Max. 213 nm E $\frac{1}{1}$ = 300 Σ = 27 300<br>Infl. 235 nm E $\frac{1}{1}$ = 264<br>Max. 278 nm E $\frac{1}{1}$ = 481 Σ = 32 800<br>Infl. 300 E $\frac{1}{1}$ = 231 Σ = 15 800<br>(ethanol HCl 0.1N)<br>Infl. 228 nm E $\frac{1}{1}$ = 239<br>Max. 278 nm E $\frac{1}{1}$ = 561 Σ = 38 300<br>Infl. 310 nm E $\frac{1}{1}$ = 186 Σ = 12 700 |

-continued

| | | | | | | |
|---|---|---|---|---|---|---|
| EXAMPLE 128 | 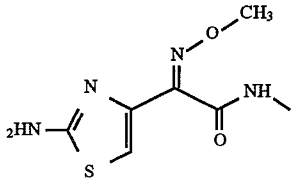<br>$CF_3CO_2H$ | 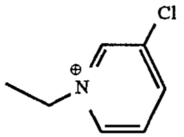<br>$CF_3SO_3^{\ominus}$ | O | $-CO_2H$ | IR Spectrum (nujol)<br>1790 $cm^{-1}$ β lactam<br>1708 $cm^{-1}$, 1681 $cm^{-1}$, 1659 $cm^{-1}$ } other C=O<br>1604 $cm^{-1}$, 1575 $cm^{-1}$, 1552 $cm^{-1}$, 1535 $cm^{-1}$, 1490 $cm^{-1}$, 1480 $cm^{-1}$ } region C=C aromatic heterocycle amide II<br>MP = 170°–180° C. (decomposition) | U.V. Spectrum (ethanol)<br>Infl. 215 nm $E\frac{1}{1}$ = 437 Σ = 33 800<br>Infl. 235 nm $E\frac{1}{1}$ = 321<br>Infl. 277 nm $E\frac{1}{1}$ = 259<br>Max. 281 nm $E\frac{1}{1}$ = 437 Σ = 33 800<br>Infl. 292 nm $E\frac{1}{1}$ = 246<br>(ethanol, HCl 0.1N)<br>Infl. 212 nm $E\frac{1}{1}$ = 320<br>Infl. 272 nm $E\frac{1}{1}$ = 335<br>Max. 280 nm $E\frac{1}{1}$ = 337 Σ = 26 100<br>Infl. 292 nm $E\frac{1}{1}$ = 281<br>Infl. 303 nm $E\frac{1}{1}$ = 281 Σ = 15 800 |
| EXAMPLE 129 | 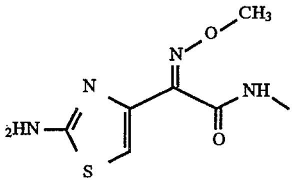<br>$CF_3CO_2H$ | 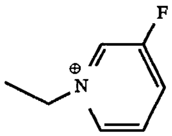<br>$CF_3SO_3^{\ominus}$ | O | $-CO_2H$ | IR Spectrum (nujol)<br>1769 $cm^{-1}$ β lactam C=O<br>1680 $cm^{-1}$ amide<br>1660 $cm^{-1}$ C=O C=C<br>1645 $cm^{-1}$ C(=O)—C=N<br>1595 $cm^{-1}$ aromatic<br>1502 $cm^{-1}$ C=C conjugated<br>MP = 180° C. (decompostion) | U.V. Spectrum (ethanol)<br>Infl. 200 nm $E\frac{1}{1}$ = 270<br>Max. 266 nm $E\frac{1}{1}$ = 205 Σ = 15 500<br>Max. 293 nm $E\frac{1}{1}$ = 208 Σ = 15 700<br>(ethanol, HCl, 0.1N)<br>Infl. 217 nm $E\frac{1}{1}$ = 250<br>Max. 268 nm $E\frac{1}{1}$ = 274 Σ = 20 700<br>Infl. 283 nm $E\frac{1}{1}$ = 240 Σ = 18 100<br>Infl. 303 nm $E\frac{1}{1}$ = 282 Σ = 13 800 |

-continued

| | | | | | | |
|---|---|---|---|---|---|---|
| EXAMPLE 130 | 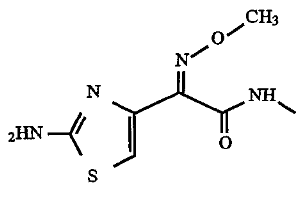<br>$CF_3CO_2H$ | 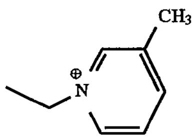<br>$CF_3SO_3^{\ominus}$ | O | $-CO_2H$ | IR Spectrum (nujol)<br>1773 $cm^{-1}$ β lactam c=O<br>1675 $cm^{-1}$ amide c=O<br>1535 $cm^{-1}$ amide II<br>1550 $cm^{-1}$ thiazole<br>1630 $cm^{-1}$ C=C<br>1580 $cm^{-1}$ C=N<br>1505 $cm^{-1}$ aromatic conjugated systems<br>MP = 200° C. (decomposition) | U.V. Spectrum (ethanol HCl N/10)<br>Infl. 218 nm $E\frac{1}{1}$ = 262<br>Max. 266 nm $E\frac{1}{1}$ = 264 Σ = 19 900<br>Infl. 283 nm $E\frac{1}{1}$ = 228<br>Infl. 310 nm $E\frac{1}{1}$ = 148 Σ = 11 100<br>(ethanol)<br>Infl. 215 nm $E\frac{1}{1}$ = 322 Σ = 24 000<br>Infl. 230 nm $E\frac{1}{1}$ = 284<br>Max. 264 nm $E\frac{1}{1}$ = 199 Σ = 15 000<br>Infl. 270 nm $E\frac{1}{1}$ = 192<br>Max. 293 nm $E\frac{1}{1}$ = 195 Σ = 14 700<br>Infl. 405 nm $E\frac{1}{1}$ = 4 |
| EXAMPLE 131 | 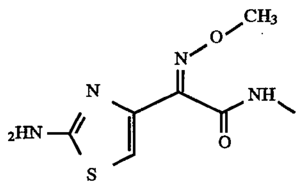<br>$CF_3CO_2H$ | 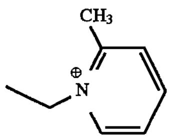<br>$CF_3SO_3^{\ominus}$ | O | $-CO_2H$ | IR Spectrum (nujol)<br>1775 $cm^{-1}$ β lactam<br>1673 $cm^{-1}$, 1630 $cm^{-1}$ } amide<br>1576 $cm^{-1}$ max, 1550 $cm^{-1}$ shoulder, 1515 $cm^{-1}$, 1495 $cm^{-1}$ } C=C, C=N, amide II<br>1030 $cm^{-1}$ $CF_3SO_3^{\ominus}$<br>MP = 160° C. (decomposition) | U.V. Spectrum (ethanol)<br>Infl. 220 nm $E\frac{1}{1}$ = 303<br>Max. 267 nm $E\frac{1}{1}$ = 208 Σ = 15 700<br>Infl. 278 nm $E\frac{1}{1}$ = 201<br>Max. 295 nm $E\frac{1}{1}$ = 209 Σ = 15 400<br>(ethanol, HCl 0.1N)<br>Infl. 220 nm $E\frac{1}{1}$ = 233<br>Max. 267 nm $E\frac{1}{1}$ = 273 Σ = 20 500<br>Infl. 284 nm $E\frac{1}{1}$ = 230<br>Infl. 291 nm $E\frac{1}{1}$ = 226<br>Infl. 310 nm $E\frac{1}{1}$ = 256 |

-continued

| | | | | | | |
|---|---|---|---|---|---|---|
| EXAMPLE 132 | 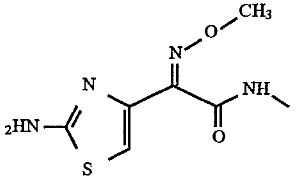<br>$CF_3CO_2H$ | 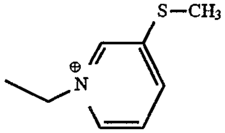<br>$CF_3SO_3^{\ominus}$ | O | $-CO_2H$ | IR Spectrum (nujol)<br>1775 $cm^{-1}$ β lactam<br>1670 $cm^{-1}$ } amide<br>1640 $cm^{-1}$ shoulder }<br>1570 $cm^{-1}$ max } region C=C<br>1540 $cm^{-1}$ shoulder } C=N<br>1495 $cm^{-1}$ max. } amide II<br>MP = 190° C. (decomposition) | U.V. Spectrum (ethanol)<br>Max. 230 nm $E\frac{1}{1}$ = 371 Σ = 29 100<br>Max. 272 nm $E\frac{1}{1}$ = 252 Σ = 29 800<br>Infl. 290 nm $E\frac{1}{1}$ = 221<br>Infl. 340 nm $E\frac{1}{1}$ = 48<br>(ethanol, HCl 0.1N)<br>Max. 231 nm $E\frac{1}{1}$ = 320 Σ = 25 100<br>Max. 274 nm $E\frac{1}{1}$ = 327 Σ = 25 700<br>Infl. 292 nm $E\frac{1}{1}$ = 248<br>Infl. 304 nm $E\frac{1}{1}$ = 198 |
| EXAMPLE 133 | 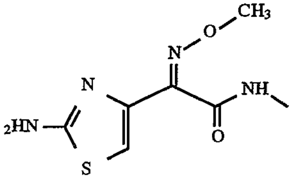<br>$CF_3CO_2H$ | 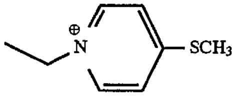<br>$CF_3SO_3^{\ominus}$ | O | $-CO_2H$ | IR Spectrum (nujol)<br>1775 $cm^{-1}$ β lactam<br>1672 $cm^{-1}$ amide<br>1545 $cm^{-1}$ } amide II<br>} thiazole<br>3120 $cm^{-1}$<br>1630 $cm^{-1}$<br>1545 $cm^{-1}$ 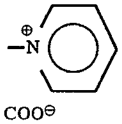<br>1492 $cm^{-1}$<br>MP = 160° C. (decomposition) | U.V. Spectrum (ethanol)<br>Max. 230 nm $E\frac{1}{1}$ = 347 Σ = 27 200<br>Max. 306 nm $E\frac{1}{1}$ = 460 Σ = 36 100<br>Max. 414 nm $E\frac{1}{1}$ = 67<br>(ethanol, HCl 0.1N)<br>Max. 230 nm $\frac{1}{1}$ = 296 Σ = 23 200<br>Infl. 272 nm $E\frac{1}{1}$ = 228<br>Max. 307 nm $E\frac{1}{1}$ = 446 Σ = 35 000 |

-continued

| | | | | | | | | |
|---|---|---|---|---|---|---|---|---|
| EXAMPLE 134 | 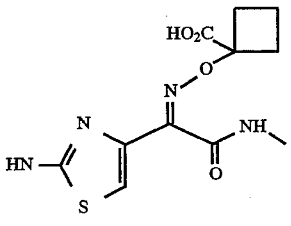 CF$_3$CO$_2$H | 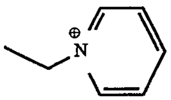 CF$_3$SO$_3^{\ominus}$ | O | $-CO_2H$ | IR Spectrum (nujol) | | U.V. Spectrum (ethanol) | |
| | | | | | 1775 cm-1 | β lactam | Infl. 236 nm $E\frac{1}{1}$ = 236 | |
| | | | | | 1710 cm-1 / 1667 cm-1 | others C=O | Infl. 253 nm $E\frac{1}{1}$ = 184 | Σ = 15 400 |
| | | | | | | | Infl. 259 nm $E\frac{1}{1}$ = 178 | |
| | | | | | 1630 cm-1 | COO$^{\ominus}$, NH$_2$, C=C, C=N | Infl. 295 nm $E\frac{1}{1}$ = 167 | Σ = 13 700 |
| | | | | | 1575 CM-1 | conjugated system | Infl. 410 nm $E\frac{1}{1}$ = 5 | |
| | | | | | 1550 cm-1 | aromatic | (ethanol, HCl 0.1N) | |
| | | | | | 1498 cm-1 | amide II | Infl. 223 nm $E\frac{1}{1}$ = 220 | |
| | | | | | 1485 cm-1 | thiazole | Max. 260 nm $E\frac{1}{1}$ = 214 | Σ = 17 600 |
| | | | | | | | Max. 290 nm $E\frac{1}{1}$ = 205 | Σ = 16 900 |
| | | | | | | | Infl. 315 nm $E\frac{1}{1}$ = 121 | Σ = 10 500 |
| | | | | | MP = 192° C. (decomposition) | | | |

EXAMPLE 136

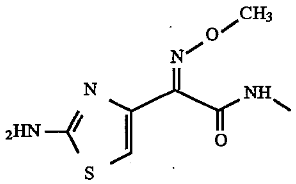

$CF_3CO_2H$

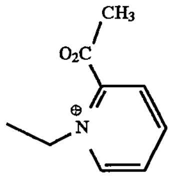

$CF_3SO_3^{\ominus}$

O $-CO_2H$ m.p. = 200° C. (decomposition)

IR Spectrum (nujol)

1780 $cm^{-1}$ β lactam c || o

1744 $cm^{-1}$ ester c || o

1675 $cm^{-1}$ amide c || o

1640 $cm^{-1}$
1620 $cm^{-1}$ }

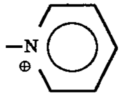

1580 $cm^{-1}$ $COO^{\ominus}$

1028 $cm^{-1}$ $CF_3SO_3^{\ominus}$

U.V. Spectrum (ethanol)

Max. 220 nm $E\frac{1}{1}=303$ $\Sigma = 24\,100$

Infl. 276 nm $E\frac{1}{1}=239$

Infl. 255 nm $E\frac{1}{1}=186$

Infl. 263 nm $E\frac{1}{1}=175$

Infl. 275 nm $E\frac{1}{1}=144$

Max. 247 nm $E\frac{1}{1}=148$ $\Sigma = 11\,800$

EXAMPLE 137

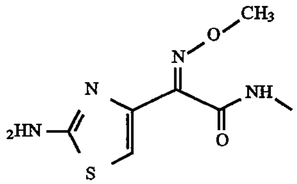

$CF_3CO_2H$

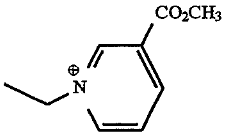

$CF_3SO_3^{\ominus}$

O $-CO_2H$ m.p. = 180° C.

IR Spectrum (nujol)

1775 $cm^{-1}$ c || o β lactam

1740 $cm^{-1}$ c || o

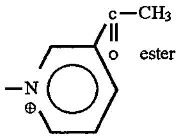

ester

1670 $cm^{-1}$ c || o amide

1640 $cm^{-1}$

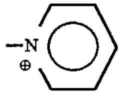

1575 $cm^{-1}$ $COO^{\ominus}$

1030 $cm^{-1}$ $CF_3SO_3^{\ominus}$

U.V. Spectrum (ethanol)

Infl. 218 nm $E\frac{1}{1}=335$

Infl. 234 nm $E\frac{1}{1}=272$

Max. 265 nm $E\frac{1}{1}=185$ $\Sigma = 14\,700$

Infl. 270 nm $E\frac{1}{1}=180$

Max. 294 nm $E\frac{1}{1}=184$ $\Sigma = 14\,700$ (ethanol, HCl 0.1N)

Infl. 219 nm $E\frac{1}{1}=272$

Max. 268 nm $E\frac{1}{1}=245$ $\Sigma = 19\,500$

Max. 284 nm $E\frac{1}{1}=220$ $\Sigma = 17\,500$

Inf. 310 nm $E\frac{1}{1}=146$

-continued

EXAMPLE 138

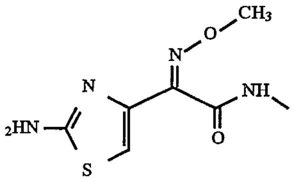

$CF_3CO_2H$,

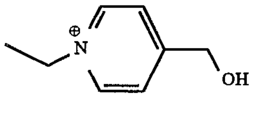

$CF_3SO_3^{\ominus}$

O —$CO_2H$ m.p. = 180° C.

IR Spectrum (nujol)

1775 $^{cm-1}$ β lactam c
‖
o

1670 $^{cm-1}$ amide c
‖
o

1640 $^{cm-1}$ 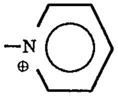

1030 $^{cm-1}$ $CF_3SO_3^{\ominus}$ 1600 to 1570 1550 $^{cm-1}$ } aromatic conjugated system $COO^{\ominus}$ U.V. Spectrum (ethanol)

Max. 225 nm $E\frac{1}{1}$ = 327 Σ = 25 100

Infl. 254 nm $E\frac{1}{1}$ = 212

Infl. 262 nm $E\frac{1}{1}$ = 185

Max. 295 nm $E\frac{1}{1}$ = 187 Σ = 14 400

(ethanol, HCl 0.1N)

Max. 228 nm $E\frac{1}{1}$ = 286 Σ = 22 000

Max. 257 nm $E\frac{1}{1}$ = 244 Σ = 18 800

Infl. 262 nm $E\frac{1}{1}$ = 241

Max. 285 nm $E\frac{1}{1}$ = 222 Σ = 17 100

Infl. 293 nm $E\frac{1}{1}$ = 213

Infl. 310 nm $E\frac{1}{1}$ = 150 Σ = 11 500

-continued

| | | | | | | |
|---|---|---|---|---|---|---|
| EXAMPLE 139 | 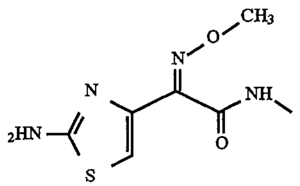<br>$CF_3CO_2H$ | 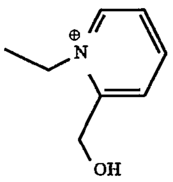<br>$CF_3SO_3^{\ominus}$ | O | $-CO_2H$ | m.p. = 180° C.<br>IR Spectrum (nujol)<br>1715 $cm^{-1}$ β lactam C=O<br>1675 $cm^{-1}$ amide C=O<br>1575 $cm^{-1}$, 1550 $cm^{-1}$, 1630 $cm^{-1}$: aromatic, C=C, C=N, amide II, $COO^{\ominus}$<br>1030 $cm^{-1}$ $CF_3SO_3$ | U.V. Spectrum (ethanol)<br>Infl. 220 nm $E\frac{1}{1}$ = 293<br>Infl. 230 nm $E\frac{1}{1}$ = 869<br>Infl. 262 nm $E\frac{1}{1}$ = 202<br>Max. 267 nm $E\frac{1}{1}$ = 207 Σ = 15 900<br>Infl. 272 nm $E\frac{1}{1}$ = 200<br>Max. 293 nm $E\frac{1}{1}$ = 194 Σ = 14 900<br>(ethanol, HCl, 0.1/N)<br>Max. 223 nm $E\frac{1}{1}$ = 241 Σ = 18 500<br>Max. 265 nm $E\frac{1}{1}$ = 268 Σ = 20 600<br>Infl. 284 nm $E\frac{1}{1}$ = 222<br>Infl. 292 nm $E\frac{1}{1}$ = 217<br>Infl. 310 nm $E\frac{1}{1}$ = 156 Σ = 12 200 |

EXAMPLE 140

Internal salt of 3-[{7-[(2-amino-thiazol-4-yl)-2-methoxyimino-acetamido]-2-carboxy-8-oxo-4-thia-1-azabicyclo[4-2-0-]oct-2-en-3-yl}methyl]pyridinium STEP A: 2-oxo-4-(pyridin-3-yl)-3-butenoic acid A solution of 4.7 ml of pyridine-3-carboxaldehyde and 3.49 ml of pyruvic acid in 15 ml of methanol was cooled to 5° C. and a solution of 6 g of potassium hydroxide in 15 ml of methanol was added dropwise over one minute with very strong stirring. Vigorous stirring was continued for 8 minutes and the mixture was vacuum filtered The product was washed with 10 ml of methanol at 0° C. then with ether and dried to obtain 4.2 g of the potassium salt. 3.07 g of the salt dissolved in 5 ml of water and 1.22 ml of hydrochloric acid was added dropwise at 0° C. with strong stirring. The mixture was stored at 20° C. for 20 minutes and was vacuum filtered. The product was washed and dried to obtain 1.95 g of 2-oxo-4-(pyridin-3-yl)-3-butenoic acid.

IR Spectrum (nujol):

General absorption region for NH/OH-bonds observed at 1720, 1692, 1610 and 1595 $cm^{-1}$.

| | | | |
|---|---|---|---|
| U.V. Spectrum (0.1 N HCl ethanol): | | | |
| Inflex. | 265 nm | $E_1^1 = 648$ | |
| U.V. Spectrum (ethanol): | | | |
| Inflex. | 280 nm | $E_1^1 = 791$ | |
| Max. | 296 nm | $E_1^1 = 933$ | ε = 16,500 |
| Inflex. | 375 nm | $E_1^1 = 8$ | |
| Inflex. | 274 nm | $E_1^1 = 703$ | |
| Max. | 283 nm | $E_1^1 = 754$ | ε = 13,400 |
| Max. | 289 nm | $E_1^1 = 751$ | ε = 13,300 |

STEP B: 1,1-dimethyl-ethyl 2-oxo-4-(pyridin-3-yl)-3-butenoate

A mixture of 1.41 g of the acid of Step A, 4.5 g of 0-tert.-butyl-N,N-diisopropyl-isourea and 32 ml of tetrahydrofuran was stirred at 20° C. under nitrogen for 15 hours and then 8 ml of aqueous N hydrochloric acid were added with stirring. 8 ml of aqueous N sodium hydroxide solution and 10 ml of ether were added with stirring and the mixture was filtered. The decanted aqueous phase was extracted with ether and the combined organic phases were washed and evaporated to dryness under reduced pressure. The residue was chromatographed over silica and was eluted with a 93-7 methylene chloride-acetone mixture to obtain 1.35 g of 1,1-dimethyl-ethyl 2-oxo-4-{pyridin-3-yl)-3-butenoate melting at 51°–52° C.

IR Spectrum (chloroform):

1740 and 1720 $cm^{-1}$ (C=0); 1695, 1668 and 1609 $cm^{-1}$ (C=C, pyridine).

| | | | |
|---|---|---|---|
| U.V. Spectrum (ethanol): | | | |
| Inflex. | 212 nm | $E_1^1 = 336$ | |
| Max. | 300 nm | $E_1^1 = 751$ | ε = 17,500 |
| Inflex. | 380 nm | $E_1^1 = 5.8$ | |
| U.V. Spectrum (0.1 NHCl-ethanol): | | | |
| Inflex. | 265 nm | $E_1^1 = 481$ | |
| Inflex. | 275 nm | $E_1^1 = 533$ | |
| Max. | 288 nm | $E_1^1 = 577$ | ε = 13,500 |

STEP C: 1,1-dimethyl-ethyl 4-(pyridin-3-yl)-2-(triethylsilyloxy)-2-butenoate 2.27 ml of triethylsilane and 44.4 mg of $(P\Phi_3)_3$ RhCl were added to a solution of 1.11 g of the product of Step B in 2 ml of toluene and the mixture was refluxed under nitrogen for 30 minutes and was cooled. The mixture was evaporated to dryness under reduced pressure and the residue was chromatographed over silica. Elution with a 95-5 methylene chloride-acetone mixture yielded 0.93 g of 1,1-dimethyl-ethyl 4-(pyridin-3-yl)-2-(triethylsilyloxy)-2-butenoate.

IR Spectrum (chloroform):

1661 $cm^{-1}$ (C=0-conjugated ester); 1370 $cm^{-1}$ (methyl of tert.-butyl); 1160 $cm^{-1}$ (C—O—C); 1641 $cm^{-1}$ (conjugated C=C); 1578 and 1480 $cm^{-1}$ (pyridine).

| | | | |
|---|---|---|---|
| U.V. Spectrum (ethanol): | | | |
| Max. | 236 nm | $E_1^1 = 333$ | ε = 11,600 |
| Inflex. | 259 nm | $E_1^1 = 175$ | |
| Inflex. | 267 nm | $E_1^1 = 108$ | ε = 3,800 |
| U.V. Spectrum (0.1 N HCl-ethanol): | | | |
| Max. | 239 nm | $E_1^1 = 282$ | ε = 9,850 |
| Inflex. | 254 nm | $E_1^1 = 248$ | |

STEP D: 1,1-dimethyl-ethyl 3-bromo-2-oxo-4-(pyridin-3-yl)-butanoate hydrochloride 6.3 ml of 0.95M of bromine in methylene chloride were added dropwise with strong stirring under nitrogen over 10 seconds to a solution of 1.05 g of the product of Step C in 10.5 ml of methylene chloride at −40° C. and after stirring at −20° C. for 30 seconds, 12 ml of a solution of aqueous 0.5N sodium thiosulfate containing 1 g of sodium bicarbonate suspended therein were added. The mixture was stirred at 0° C. until the coloration disappeared and the organic phase was rapidly separated and filtered. 0.96 ml of 3.13N hydrochloric acid in ether were added to the filtrate and the mixture was vacuum filtered. The product was dried to obtain 1 g of 1,1-dimethyl-ethyl 3-bromo-2-oxo-4- (pyridin-3-yl)-butanoate hydrochloride.

IR Spectrum (nujol): 1735 and 1752 $cm^{-1}$ (C=0); 1632, 1608 and 1553 $cm^{-1}$ (C=C, C=N)

| | | | |
|---|---|---|---|
| U.V. Spectrum (ethanol): | | | |
| Inflex. | 257 nm | $E_1^1 = 93$ | |
| Max. | 261 nm | $E_1^1 = 105$ | |
| Inflex. | 266 nm | $E_1^1 = 80$ | |
| Inflex. | 246,251 nm | | |
| U.V. Spectrum (0.1 N HCl-ethanol): | | | |
| Inflex. | 256 nm | $E_1^1 = 142$ | |
| Max. | 261 mn | $E_1^1 = 160$ | ε = 5,600 |
| Inflex. | 266 nm | $E_1^1 = 129$ | |

STEP E: 1,1-dimethyl-ethyl 7-[(2-(2-amino-thiazol-4-yl)-2-methoxyimino-acetamido]-8-oxo-3-(3-pyridylmethyl)-4-thia-1-azabicyclo(4,2-0)oct-2-ene-2-carboxylate 0.206 ml of triethylamine was added to a mixture of 356 mg of a thiol of the formula

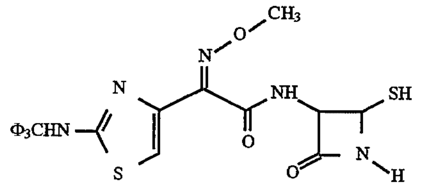

and 246 mg of 1,1-dimethyl-ethyl-3-bromo-3-oxo-4-(pyridin-3-yl)-butanoate and the mixture was stirred for 30 minutes, was washed with water, with aqueous saturated sodium chloride and evaporated to dryness under reduced pressure to obtain 489 mg of a raw product of the formula

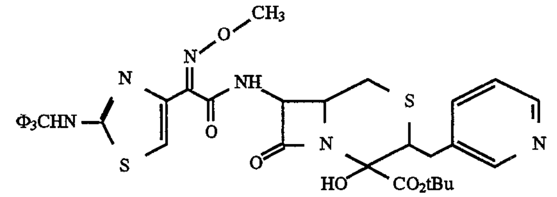

The said product was dissolved in 10 ml of pyridine and 545 mg of $P_2I_4$ were added thereto. The mixture was stirred for one hour at 20° C. and was then evaporated to dryness under reduced pressure. The residue was added to 30 ml of an aqueous 0.1N hydrochloric acid solution and ethyl acetate with stirring followed by the addition of 0.1N aqueous sodium hydroxide solution. The mixture was filtered and the decanted aqueous phase was extracted with ethyl acetate. The organic phase was washed with water and evaporated to dryness under reduced pressure. The residue was chromatographed over silica and was eluted with 97-3 methylene chloride-methanol mixture, The product was empasted with ether and dried to obtain the desired product.

-8-oxo-4-thia-1-azabicyclo[4-2-0]oct-2-ene-3-yl}-methyl]-1-methylpyrididinium iodide 0.068 ml of methyl iodide was added to a solution of 86 mg of the product of Step E in 1 ml of dimethylformamide and the mixture was stirred for 5 hours at 20° C. and was then evaporated to dryness under reduced pressure. The residue was dissolved in 1 nil of tetrahydrofuran and the solution was filtered. 10 ml of ether were added dropwise to the filtrate with stirring and the mixture was vacuum filtered. The product was dried to obtain 82 mg of the desired product, NMR Spectrum ($CDCl_3$): ppm

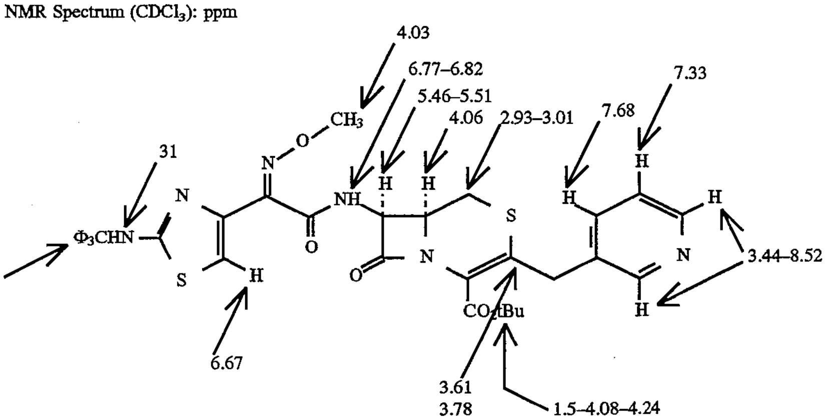

STEP F: Racemic cis 3-[{7-[2-(2-amino-thiazol-4-yl)-2-(Z) methoxyimino-acetamide]-2-(1,1-dimethylethoxycarbonyl)

NMR Spectrum ($CDCl_3$): ppm

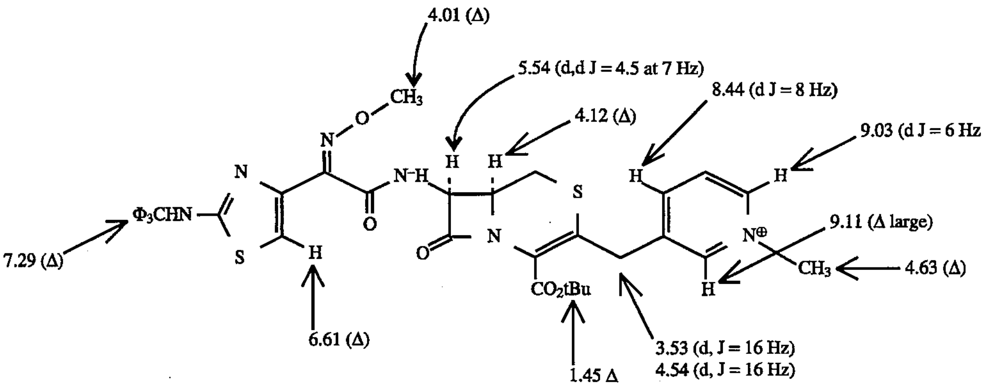

STEP G: Internal salt of 3-[{7-[2-(2-amino-thiazol-4-yl)-2-methoxyimino-acetamido]-2-carboxy-8-oxo-4-thia-1-azabicyclo[4-2-0]oct-2-ene-3-yl}methyl]-1-methyl-pyridinium A solution of 100 mg of the product of Step F in 2 ml of 66% aqueous formic acid was stirred at 60° C. for 30 minutes and was then cooled, diluted with 4 ml of water and filtered. The filtrate was washed with ether and the aqueous solution was evaporated to dryness under reduced pressure. The residue was subjected to high pressure liquid chromatography (1N $NH_4CO_3H$+14% of acetonitrile) and lyophilization to obtain 30 mg of the desired internal salt containing 1 mole of triethylamine and 1 mole of water.

IR Spectrum (nujol):

1760 $cm^{-1}$ (carbonyl of β-lactam) 1660 $cm^{-1}$ (C=0 of amide); 1585, 1535 and 1510 $cm^{-1}$ (aromatic, $COO^-$, amide II, thiazole); 1037 $cm^{-1}$ (C=N—OR).

| | | |
|---|---|---|
| U.V. Spectrum (ethanol): | | |
| Inflex. | 232 nm | $E_1^1 = 293$ |
| Max. | 266 nm | $E_1^1 = 251$ |
| Max. | 288 nm | $E_1^1 = 227$ |
| U.V. Spectrum (0.1 N HCl-ethanol): | | |
| Inflex. | 218 nm | $E_1^1 = 295$ |
| Max. | 268 nm | $E_1^1 = 311$ |
| Max. | 285 nm | $E_1^1 = 289$ |
| Inflex. | 310 nm | $E_1^1 = 176$ |

EXAMPLES 141 to 144

Using the procedure of Example 140, the compounds in the following Table were prepared.

| | | | | | | |
|---|---|---|---|---|---|---|
| EXAMPLE 141 | 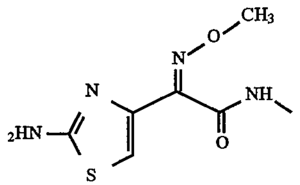<br>$CF_3CO_2H$ | 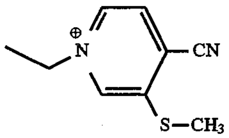<br>$CF_3SO_3^{\ominus}$ | O | $-CO_2H$ | IR Spectrum (nujol)<br>1775 cm−1 β lactam<br>1673 cm−1, 1640 cm−1 } other carbonyls<br>1580 cm−1, 1540 cm−1 } C=C, C=N, amide II<br><br>MP = 185° C. | U.V. Spectrum (ethanol)<br>Max. 222 nm $E\frac{1}{1}$ 386 Σ = 31 300<br>Max. 293 nm $E\frac{1}{1}$ = 359 Σ = 29 000<br>Max. 281 nm $E\frac{1}{1}$ 228 Σ = 18 500<br>Infl. 291 nm $E\frac{1}{1}$ = 215<br>Max. 377 nm $E\frac{1}{1}$ = 415 Σ = 3650<br>(ethanol, HCl, 0.1N)<br>Max. 226 nm $E\frac{1}{1}$ = 341 Σ = 27 600<br>Max. 245 nm $E\frac{1}{1}$ = 329 Σ = 26 600<br>Infl. 275 nm $E\frac{1}{1}$ = 270<br>Max. 280 nm $E\frac{1}{1}$ = 272 Σ = 22 000<br>Infl. 290 nm $E\frac{1}{1}$ = 241<br>Infl. 305 nm $E\frac{1}{1}$ = 179<br>Max. 376 nm $E\frac{1}{1}$ = 410 Σ = 3250 |
| EXAMPLE 142 | 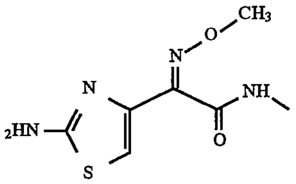<br>$CF_3CO_2H$ | 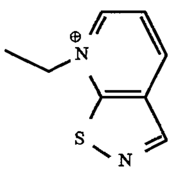<br>$CF_3SO_3^{\ominus}$ | O | $-CO_2H$ | IR Spectrum (nujol)<br>1776 cm−1 β lactam<br>1650 cm−1, 1710 cm−1 } absorption large et complexed other carbonyls<br>1640 cm−1, 1520 cm−1, 1590 cm−1 } region C=C, C=N, amide II | |

-continued

| | | | | | | |
|---|---|---|---|---|---|---|
| EXAMPLE 143 | 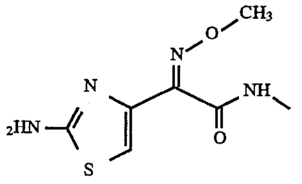<br>$CF_3CO_2H$ | 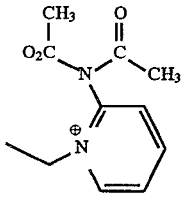<br>$CF_3SO_3^{\ominus}$ | O | $-CO_2H$ | IR Spectrum (nujol)<br>1780 $cm^{-1}$ β lactam C=O<br>1730 $cm^{-1}$ other carbonyls<br>1670 $cm^{-1}$ amide<br>1620 $cm^{-1}$, 1590 $cm^{-1}$, 1560 $cm^{-1}$, 1510 $cm^{-1}$, 1488 $cm^{-1}$ } aromatic, amide II, thiazole, $COO^{\ominus}$<br>1050 $cm^{-1}$ C=N—OR<br>MP = 200° C. | U.V. Spectrum (ethanol)<br>Infl. 220 nm $E\frac{1}{1}$ = 331 Σ = 27 000<br>Max. 289 nm $E\frac{1}{1}$ = 151 Σ = 20 500<br>(ethanol, HCl, 0.1N)<br>Infl. 222 nm $E\frac{1}{1}$ = 254<br>Max. 283 nm $E\frac{1}{1}$ = 292 Σ = 23 800<br>Infl. 305 nm $E\frac{1}{1}$ = 182 Σ = 14 800 |
| EXAMPLE 144 | 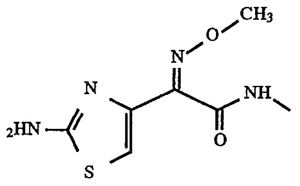<br>$CF_3CO_2H$ | 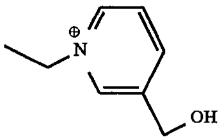<br>$CF_3SO_3^{\ominus}$ | O | $-CO_2H$ | IR Spectrum (nujol)<br>1773 $cm^{-1}$ β lactam<br>1673 $cm^{-1}$, 1637 $cm^{-1}$ } other C=O<br>1580 $cm^{-1}$, 1550 $cm^{-1}$, 1502 $cm^{-1}$ } C=C, C=N, amide II<br>MP = 180° C. | U.V. Spectrum (ethanol)<br>Infl. 220 nm $E\frac{1}{1}$ 307<br>Infl. 230 nm $E\frac{1}{1}$ = 281<br>Max. 265 nm $E\frac{1}{1}$ = 184 Σ = 14 100<br>Infl. 272 nm $E\frac{1}{1}$ = 178<br>Max. 294 nm $E\frac{1}{1}$ = 188 Σ = 14 500<br>(ethanol, HCl, 0.1N)<br>Infl. 220 nm $E\frac{1}{1}$ = 245<br>Max. 269 nm $E\frac{1}{1}$ = 248 Σ = 13 100<br>Infl. 283 nm $E\frac{1}{1}$ = 223<br>Infl. 291 nm $E\frac{1}{1}$ = 216<br>Infl. 306 nm $E\frac{1}{1}$ = 157 Σ = 12 100 |

EXAMPLE 145

3-(cyanomethylthio)-7-phenoxyacetamido-8-oxo-4-thia-1-azabicyclo [4-2-0]oct-2-ene-2-carboxylic acid STEP A: Diphenylmethyl racemic cis 4-([(4-methylphenyl)-sulfonyloxy]-methyl}-3-triphenylmethylamino-2-oxo-azetidin-1-yl-acetate A solution of 2.68 g of diphenyldiazomethane in 59 ml of ether was added to a solution of 6.55 g of 4-{[(4-methylphenyl)-sulfonyloxy]-methyl}-3-(triphenylmethylamino)-2-oxo-azetidin-1-yl-acetic acid in 70 ml of dioxane and after stirring for 3 hours at 20° C. 448 mg of diphenyldiazomethane were added. The mixture was stirred at 20° C. for 16 hours and was then evaporated to dryness under reduced pressure. The residue was chromatographed over silica and was eluted with a 10-0.5 methylene chloride-ether mixture to obtain 7.5 g of diphenylmethyl racemic cis 4-{[(4-methylphenyl)-sulfonyloxy]-methyl)-3-triphenylmethylamino-2-oxo-azetidin-1-yl-acetate.

IR Spectrum (chloroform):

3380 $cm^{-1}$ (NH); 1765 $cm^{-1}$ (CO of β-lactam)7 1745 $cm^{-1}$ (CO of ester); 1368, 1190 and 1178 $cm^{-1}$ (OTs).

NMR Spectrum ($CDCl_3$): ppm

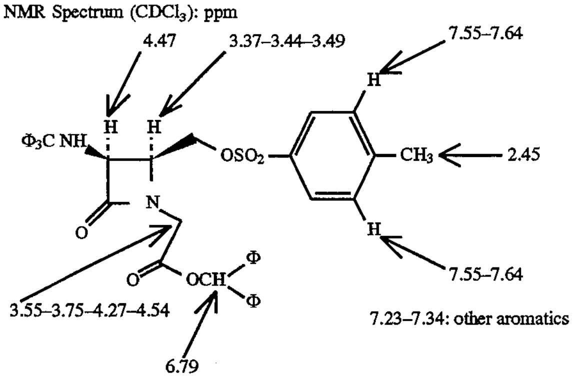

STEP B: Diphenylmethyl racemic cis 3-mercapto-7-(triphenylmethylamino)-8-oxo-4-thia-1-azabicyclo [4,2,0]-2-carboxylate 3.02 ml of carbon-sulfide were added to a solution of 3.68 g of the compound of Step A in 40 ml of tetrahydrofuran and the mixture was cooked to −78° C. 10 ml of a solution of 1M of lithium tris trimethylsilylamide in tetrahydrofuran were added dropwise to the solution at less than −60° C. and the mixture was stirred at −70° C. for 15 minutes and was poured into a monopotassium phosphate solution. The mixture was extracted with ethyl acetate and the organic phase was evaporated to dryness under reduced pressure. 50 ml of ether were added to the residue with stirring and the mixture was vacuum filtered. The product was dried to obtain 2.46 g of diphenylmethyl racemic cis 3-mercapto-7-(triphenylmethylamino)-8-oxo-4-thia-1-azabicyclo [4,2,01-2-carboxylate. Evaporation of the mother liquor yielded another 0.768 g of product.

IR Spectrum (chloroform):

1765 $cm^{-1}$ (C=0 of β-lactam); 1693 $cm^{-1}$ (conjugated ester); 1538 $cm^{-1}$ (C=C); 3340 $cm^{-1}$ (NH).

NMR Spectrum ($CDCl_3$): ppm

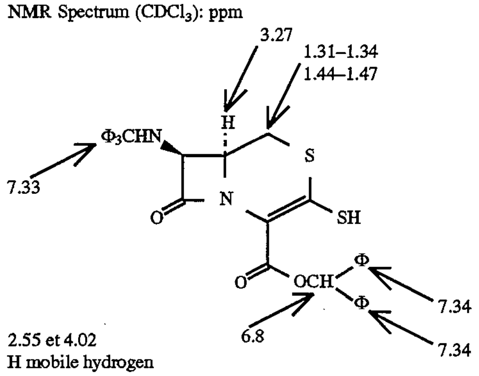

STEP C: Diphenylmethyl 7-amino-3-(cyanomethylthio)-8-oxo-4-thia-1-azabicyclo[4,2,0]oct-2-ene-2-carboxylate hydrochloride 0.2 ml of aqueous N hydrochloric acid were added to a solution of 135 mg of the compound of Step B in 1.4 ml of tetrahydrofuran and 0.7 ml of acetonitrile and the mixture was refluxed for 2 hours and evaporated to dryness under reduced pressure. 3 ml of ether were added to the residue and the mixture was vacuum filtered. The product was dried to obtain 92 mg of diphenylmethyl 7-amino-3-(cyanomethylthio)-8-oxo-4-thia-1-azabicyclo[4,2,01oct-2-ene-2-carboxylate hydrochloride.

STEP D: Diphenylmethyl racemic cis 3-(cyanomethylthio)-8-oxo-7-(triphenylmethylamino)-4-thia-1-azabicyclo[4,2,0] oct-2-ene-2-carboxylate 0.244 ml of bromoacetonitrile were added to a solution of 1.92 g of the product of Step C in 20 ml of tetrahydrofuran and after adding 0.504 ml of triethylamine, the mixture was stirred at 20° C. for 30 minutes and diluted with 60 ml of ethyl acetate. The mixture was filtered and the filtrate was evaporated to dryness under reduced pressure. The residue was added to 20 ml of ether and the mixture was stirred and vacuum filtered. The product was dried to obtain 1.66 g of diphenylmethyl racemic cis 3-(cyanomethylthio)-8-oxo-7-(triphenylmethylamino)-4-thia-1-azabicyclo[4,2,0]oct-2-ene-2-carboxylate.

NMR Spectrum ($CDCl_3$): ppm

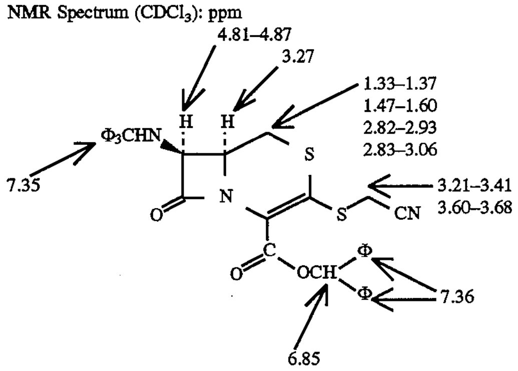

STEP E: Diphenylmethyl (6 R,S)(7 R,S) 3-cyanomethylthio-7-phenoxyacetamido-8-oxo-4-thia-1-azabicyclo[4,2,0 ]oct-2-ene-carboxylate 0.032 ml of phenoxyacetyl chloride were added to a mixture of 91 mg of the product of Step D, 2 ml of methylene chloride and 0.3 ml of pyridine and the mixture was stirred at 20° C. for 3 hours and was then diluted with 5 ml of methylene chloride. The mixture was washed and 5 ml of ether were added. The mixture was stirred and vacuum filtered to obtain 85 ml of diphenylmethyl (6 R,S) (7 R,S) 3-cyanomethyl thio-7-phenoxyacetamido-8-oxo-4-thia-1-azabicyclo[4,2.0]oct-2-ene-carboxylate.

IR Spectrum (chloroform):

3410 $cm^{-1}$ (secondary amide NH); 1690 $cm^{-1}$ (C=0); 1516 $cm^{-1}$ (amide II); 1598, 1589 and 1496 $cm^{-1}$ (O—O—C); 1781 $cm^{-1}$ (C=0 of β-lactam); 1720 $cm^{-1}$ (C=0 of ester); 2240 $cm^{-1}$ (C≡N)

| U.V. Spectrum (ethanol): | | | |
|---|---|---|---|
| Inflex. | 256 nm | $E_1^1 = 88$ | |
| Inflex. | 261 nm | $E_1^1 = 84$ | |
| Max. | 267 nm | $E_1^1 = 76$ | |
| Max. | 275 nm | $E_1^1 = 66$ | |
| Max. | 319 nm | $E_1^1 = 197$ | ε = 11,300 |

STEP F: (6 R,S) (7 R,S) 3-cyanomethylthio-7-phenoxyacetamido-8-oxo-4-thia-1-azabicyclo[4,2,01oct-2-ene-carboxylic acid 2 ml of 66% aqueous formic acid were added to a solution of 130 mg of the product of Step E in 3 ml of acetonitrile and the mixture was heated at 50° C. for 3 hours. The mixture was evaporated to dryness under reduced pressure and the residue was taken up in 2 ml of 66% aqueous formic acid. The solution was stirred for 30 minutes at 50° C. and the product was held at 50° C. under reduced pressure for 2 hours. The product was pasted with ether and vacuum filtered. The product was crystallized from methylene chloride and dried at 50° C. under vacuum to obtain 35 mg of (6 R,S) (7 R,S) 3-cyanomethylthin-7-phenoxyacetamido-8-oxo-4-thia-1-azabicyclo[4,2,01oct-2-ene-carboxylic acid.

Analysis: $C_{17}H_{15}N_3O_5S_2$; molecular weight=405.44 Calculated: % C 50.36 % H 3.73 % N 10.36 Found: 50.3 3.8 9.9

| U.V. Spectrum (ethanol): | | | |
|---|---|---|---|
| Inflex. | 220 nm | $E_1^1 = 378$ | ε = 15,300 |
| Inflex. | 233 nm | $E_1^1 = 165$ | |
| Max. | 262 nm | $E_1^1 = 92$ | ε = 3,750 |
| Max. | 268 nm | $E_1^1 = 101$ | ε = 4,100 |
| Max. | 275 nm | $E_1^1 = 111$ | ε = 4,500 |
| Max. | 309 nm | $E_1^1 = 275$ | ε = 11,100 |

EXAMPLE 146

3-[7-(2-{2-amino-thiazol-4-yl}-2-(Z)-methoxyimino-acetamido)-2-carboxy-8-oxo-4-thia-1-azabicyclo-4,2,0]-oct-2-en-3-yl}-1-methylpyridinium iodide STEP A: 1,1-dimethylethyl racemic cis 7-[2-(2-tritylamino-thiazol-4-yl)-2(Z)-methoxyimino-acetamido]-2-hydroxy-8-oxo-3-(3-pyridyl)-4-thia-1-azabicyclo[4,2,01octane-2-carboxylate 8.44 ml of a solution of 1.54M of potassium tert.-butylate in tetrahydrofuran were added dropwise over 15 minutes at −20° C. to a solution of 1.34 ml of pyridine-3-carboxaldehyde, 2 ml of tert.butyl dichloroacetate and 20 ml of tetrahydrofuran and the mixture was stirred at −20° C. for 45 minutes and returned to 20° C. The solution was washed with water and with aqueous saturated sodium chloride solution to obtain about 30 ml of a solution containing 12.6 mmoles of raw epoxide of the formula

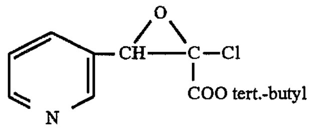

3.8 ml of the said freshly prepared epoxide solution were added to a mixture of 558 mg of a thiol of the formula

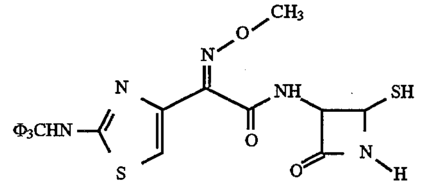

120 mg of lithium carbonate and 5.5 ml of dimethylformamide and the mixture was stirred for 2 hours at 20° C. and was poured into water. The mixture was extracted with ethyl acetate and the organic phase was evaporated to dryness under reduced pressure. The residue was chromatographed over silica and was eluted with a 97-3 methylene chloride-methanol mixture to obtain 540 mg of 1,1-dimethylethyl racemic cis 7-[2-(2- -2-hydroxy-8-oxo-3-(3-pyridyl)-4-thia-1-azabicyclo[4,2,01octane-2-carboxylate.

IR Spectrum (chloroform):

3496 $cm^{-1}$ (associated OH); 3408 $cm^{-1}$ (=C—NH, OH/NH associated); at 1772 $cm^{-1}$ (C=0 of β-lactam); 1680 $cm^{-1}$ (C=0); 3090, 3060 and 1493 $cm^{-1}$ (trityl); 1572 and 1517 $cm^{-1}$

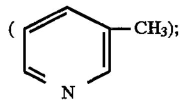

2820 $cm^{-1}$ (OMe); 1051 $cm^{-1}$ (C=N—OR); 17327, 1372 and 1153 $cm^{-1}$ (COO tert.-butyl, C=N).

| U.V. Spectrum (ethanol): | | | |
|---|---|---|---|
| Inflex. | 235 nm | $E_1^1 = 312$ | ε = 24,200 |
| Inflex. | 253 nm | $E_1^1 = 232$ | |
| Inflex. | 260 nm | $E_1^1 = 212$ | ε = 16,500 |
| Inflex. | 266 nm | $E_1^1 = 183$ | |
| Inflex. | 295 nm | $E_1^1 = 83$ | ε = 6,400 |
| U.V. Spectrum (0.1 NHCl-ethanol): | | | |
| Max. | 266 nm | $E_1^1 = 235$ | ε = 18,300 |
| Inflex. | 279 nm | $E_1^1 = 201$ | |
| Inflex. | 290 nm | $E_1^1 = 187$ | ε = 14,500 |
| Inflex. | 300 nm 140 | $E_1^1 = 140$ | |

STEP B: 1,1-dimethylethyl racemic cis 7-[(2-tritylamino-thiazol-4-yl]-2-(Z)-methoxyiminoacetamido)-8-oxo-3-(3-pyridyl)-4-thia-1-aza-bicyclo[4,2,01oct-2-ene-2-carboxylate 387 mg of $P_2I_4$ were added to a solution of 530 mg of the compound of Step A in 10 ml of pyridine and the mixture was stirred at 20° C. for 2 hours after which another 378 mg of $P_2I_4$ were added. The mixture was stirred for one hour followed by addition of another 194 mg of $P_2I_4$ and stirring for one hour. The mixture was evaporated to dryness under reduced pressure and the residue was stirred with 10 ml of ethyl acetate and filtered. The filtrate was concentrated to dryness under reduced pressure and the residue was chromatographed over silica. Elution with a 97-3 methylene chloride-methanol mixture yielded 227 mg of 1,1-dimethylethyl racemic cis 7-[(2-(2-tritlyamino-thiazol-4-yl-2-(Z)-methoxyiminoacetamido)-8-oxo-3-(3-pyridyl)-4-thia-1-aza-bicyclo[4,2,0]oct-2-ene-2-carboxylate.

IR Spectrum (chloroform):

3407 $cm^{-1}$ (NH amide); 1680 $cm^{-1}$ (C=0); 1550 $cm^{-1}$ (amide II); 1775 $cm^{-1}$ (C=0 of β-lactam); 1712, 1370 and 1157 $cm^{-1}$ (C=0, methyl of tert.butyl, COO); 1595 $cm^{-1}$ (aromatic); 1582 $cm^{-1}$ (conjugated C═C); 1495 $cm^{-1}$ (trityl); 1530 $cm^{-1}$ (thiazolyl); 1050 $cm^{-1}$ (C═N—OR); 2820 $cm^{-1}$ (OMe).

| | | | |
|---|---|---|---|
| U.V. Spectrum (ethanol): | | | |
| Inflex. | 234 nm | $E_1^1$ = 455 | ε = 34,500 |
| Inflex. | 258 nm | $E_1^1$ = 295 | |
| Max. | 309 nm | $E_1^1$ = 191 | ε = 14,500 |
| U.V. Spectrum (0.1 NHCl-ethanol): | | | |
| Max. | 266 nm | $E_1^1$ = 286 | ε = 21,700 |
| Inflex. | 290 nm | $E_1^1$ = 231 | ε = 17,500 |
| Inflex. | 300 nm | $E_1^1$ = 203 | |
| Inflex. | 324 nm | $E_1^1$ = 92 | ε = 7,000 |

STEP C: Racemic cis 3-[7-(2-{2-tritylamino-thiazol-4-yl}-2(Z)-methoxy-iminoacetamido)-2-(1,1-dimethylethoxycarbonyl)-8-oxo-4-thia-1-aza-bicyclo[4,2,0]-oct-2-en-3-yl]-1-methyl-pyridinium iodide 0.174 ml of methyl iodide were added to a solution of 213 mg of the compound of Step B in 2.6 ml of dimethylformamide and the mixture was stirred at 20° C. for 2 hours, 0.348 ml of methyl iodide were added thereto and the mixture was stirred at 20° C. for 2 hours and was evaporated to dryness under reduced pressure. The residue was dissolved in 1 ml of ethanol and the solution was added dropwise to 15 ml of ether. The mixture was vacuum filtered to obtain 221 mg of racemic cis 3-[7-(2-{2-tritylamino-thiazol-4-yl}-2-(Z)-methoxyiminoacetamido)-2-(1,1-dimethylethoxycarbonyl)-8-oxo-4-thia-1-azabicyclo [4,2,0]-oct-2-en-3-yl)-1-methyl-pyridinium iodide.

IR Spectrum (chloroform):

1781 $cm^{-1}$ (β-lactam); 1705 $cm^{-1}$ (ester); 3405 and 1673 $cm^{-1}$ (amide); 1575 and 1631 $cm^{-1}$ (C═C); 1595 $cm^{-1}$ (aromatic).

| | | | |
|---|---|---|---|
| U.V. Spectrum (ethanol): | | | |
| Inflex. | 218 nm | $E_1^1$ = 686 | |
| Inflex. | 258 nm | $E_1^1$ = 269 | ε = 24,200 |
| Inflex. | 266 nm | $E_1^1$ = 261 | |
| Max. | 306 nm | $E_1^1$ = 141 | ε = 12,700 |
| U.V. Spectrum (0.1 NHCl-ethanol): | | | |
| Inflex. | 216 nm | $E_1^1$ = 725 | |
| Inflex. | 270 nm | $E_1^1$ = 285 | ε = 25,700 |
| Inflex. | 290 nm | $E_1^1$ = 219 | ε = 19,700 |
| Inflex. | 300 nm | $E_1^1$ = 190 | |
| Inflex. | 316 nm | $E_1^1$ = 125 | ε = 11,300 |

STEP D: 3-[7-{2-(2-amino-thiazol-4-yl)-2-(Z)-methoxyimino-acetamido}-2-carboxy-8-oxo-4-thia-1-azabicyclo[4,2,0]-3-yl)-1-methylpyridinium iodide A solution of 100 mg of the product of Step C and 2 ml of aqueous 85% formic acid was heated at 55° C. for 90 minutes and was then cooled and diluted with 2 ml Of water. The mixture was filtered and the filtrate was evaporated to dryness. The residue was dissolved in 1 ml of methylene chloride and 0.5 ml of methanol and 2 ml of isopropanol were added to cause precipitation. The product was dried at 50° C. under reduced pressure to obtain 29 mg of 3-[7-{2-(2-aminothiazol-4-yl)-2-(Z)-methoxyimino-acetamido)-2-carboxy-8-oxo-4-thia-1-azabicyclo[4,2,0]-3-yl]-1-methylpyridinium iodide.

| | | | |
|---|---|---|---|
| U.V. Spectrum (ethanol): | | | |
| Max. | 220 nm | $E_1^1$ = 476 | |
| Inflex. | 160 nm | $E_1^1$ = 282 | |
| Inflex. | 300 nm | $E_1^1$ = 153 | |
| Inflex. | 330 nm | $E_1^1$ = 108 | |
| U.V. Spectrum (0.1 NHCl-ethanol): | | | |
| Max. | 219 nm | $E_1^1$ = 405 | |
| Max. | 265 nm | $E_1^1$ = 382 | ε = 23,000 |
| Inflex. | 290 nm | $E_1^1$ = 242 | ε = 14,600 |
| Inflex. | 320 nm | $E_1^1$ = 120 | ε = 7,200 |

EXAMPLES 147 and 148

Using the procedure of Example 146 and the appropriate reactants, the compounds in the following Table were prepared.

EXAMPLE 147

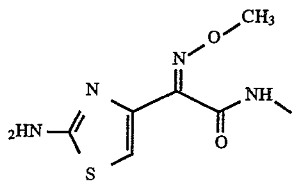

$CF_3CO_2H$

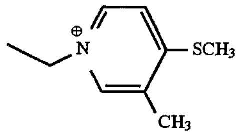

$CF_3SO_3^{\ominus}$

O $-CO_2H$

IR Spectrum (nujol)

1710 $cm^{-1}$ β lactam C=O

1680 $cm^{-1}$, 1665 $cm^{-1}$ } amide

1631 $cm^{-1}$, 1495 $cm^{-1}$ }

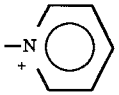

1030 $cm^{-1}$, 1580 $cm^{-1}$, 1555 $cm^{-1}$, 1536 $cm^{-1}$ } $CF_3SO_3^{\ominus}$, conjugated system, amide II, $COO^{\ominus}$, thiazole 1044 $cm^{-1}$ O=N—OMe U.V. Spectrum (ethanol)

Max. 231 nm $E\frac{1}{1}$ = 344 Σ = 27 500

Infl. 260 nm $E\frac{1}{1}$ = 159

Max. 303 nm $E\frac{1}{1}$ = 420 Σ = 23 500

(ethanol, HCl 0.1N)

Max. 231 nm $E\frac{1}{1}$ = 290 Σ = 23 200

Infl. 270 nm $E\frac{1}{1}$ = 220

Max. 303 nm $E\frac{1}{1}$ = 406 Σ = 32 400

EXAMPLE 148

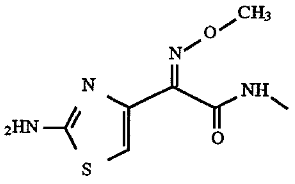

$CF_3CO_2H$

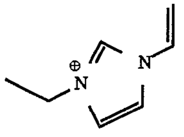

$CF_3SO_3^{\ominus}$

O $-CO_2H$

IR Spectrum (nujol)

1772 $cm^{-1}$ C=O β lactam

1710 $cm^{-1}$, 1670 $cm^{-1}$, 1640 $cm^{-1}$ } other carbonyls

1580 $cm^{-1}$, 1550 $cm^{-1}$, 1530 $cm^{-1}$ } C=C C=N, $NH_2$, amide I

U.V. Spectrum (ethanol)

Max. 225 nm $E\frac{1}{1}$ = 390 Σ = 29 400

Max. 297 nm $E\frac{1}{1}$ = 207 Σ = 15 600

Infl. 400 nm $E\frac{1}{1}$ = 303

(ethanol, HCl, 0.1N)

Max. 225 nm $E\frac{1}{1}$ = 332 Σ = 25 000

Infl. 276 nm $E\frac{1}{1}$ = 219

Max. 269 nm $E\frac{1}{1}$ = 235 Σ = 17 700

EXAMPLE 149

6R- (6α,7β)-3-[cyanomethylthio]-7- [{(4-ethyl-2,3-dioxo-1-piperazinyl-carbonyl}amino]-[3,4-dihydroxyphenylacetamido]-8-oxo-4-thia-1-azabicyclo[4,2,0]oct-2-ene-2-carboxylic acid STEP A: Diphenylmethyl 3-(cyanomethylthio)-7-[2-[(4-ethyl-2,3-dioxo-1-piperazinyl)-carbonyl}-amino)-2-(3,4-diacetoxyphenyl)-acetamido]-8-oxo-4-thia-1-azabicyclo[4,2,0]oct-2-ene-2-carboxylate 64.4 mg of diisopropylcarbodiimide were added to a mixture of 223 mg of an amine of the formula

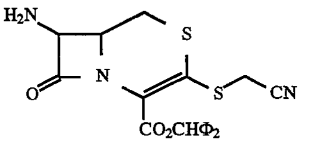

10 ml of methylene chloride, 3 ml of tetrahydrofuran and 0.5 ml of dimethylformamide and after cooling to 0° C., a solution of an acid of the formula

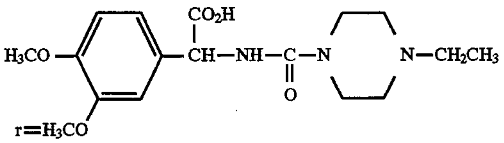

was added thereto over 10 minutes. The mixture was stirred at room temperature for 16 hours and was evaporated to dryness under reduced pressure. The residue was triturated with ether and was vacuum filtered and the product was dissolved in 4 ml of methylene chloride. The solution was filtered and 60 ml of ether were added to the filtrate. The mixture was stirred and vacuum filtered and the product was dried to obtain 308 mg of raw product. The latter was chromatographed over silica and eluted with a 95-5 ethyl acetate-acetone mixture. The product was triturated with 10 ml of ether and vacuum filtered and dried to obtain 172 mg of diphenylmethyl 3-(cyano-methylthio)-7-[2-{(4-ethyl-2,3-dioxo-1-piperazinyl)-carbonyl}amino]-2-(3,4-diacetoxyphenyl)-acetamido]-8-oxo-4-thia-1-azabicyclo[4,2,0]oct-2-ene-2-carboxylate.

IR Spectrum (chloroform):

3300 $cm^{-1}$ (NH); 1775 and 1715 $cm^{-1}$ (β-lactam+ phenolic acetate); 1687 $cm^{-1}$ (C=0); 3090 and 3060 $cm^{-1}$ (benzhydryl=CH); 1608, 1680 and 1505 $cm^{-1}$ (aromatic).

| U.V. Spectrum (ethanol): | | | |
|---|---|---|---|
| Inflex. | 254 nm | $E_1^1 = 107$ | |
| Max. | 319 nm | $E_1^1 = 129$ | ε = 11,000 |
| U.V. Spectrum (0.1 NHCl-ethanol): | | | |
| Inflex. | 256 nm | $E_1^1 = 150$ | |
| Inflex. | 269 nm | $E_1^1 = 229$ | ε = 18,600 |
| Inflex. | 302 nm | $E_1^1 = 218$ | ε = 18,600 |
| Inflex. | 370 nm | $E_1^1 = 55$ | |

STEP B: 6R (6α,7β) 3-cyanomethylthio-7-[{(4-ethyl-2,3-dioxo-1-piperazinyl)-carbonyl}amino]-3,4-dihydroxyphenylacetamido]-8-oxo-4-thia-1-azabicyclo[4,2,0]-oct-2-ene-2-carboxylic acid A mixture of 100 mg of the product of Step A and 2.4 ml of aqueous 66% formic acid was stirred at 50° C. for one hour and was then evaporated to dryness under reduced pressure. The residue was added to 5 ml of aqueous 5% sodium bicarbonate solution and the mixture was stirred at 20° C. for 2 hours and was filtered. The pH of the filtrate was adjusted to 1.5 by addition of 1.6 ml of aqueous 2N hydrochloric acid and the mixture was vacuum filtered. The product was washed with water and dissolved in 20 ml of ethyl acetate. The solution was evaporated to dryness under reduced pressure to obtain 21.5 mg of 6R (6α,7β) 3-cyanomethylthio-7-[{(4-ethyl-2,3-dioxo-1-piperazinyl)-carbonyl}amino)-3,4-dihydroxyphenylacetamido]-8-oxo-4-thia-1-azabicyclo[4,2,0]oct-2-ene-2-carboxylic acid. The mother liquor was saturated with sodium chloride and was extracted with ethyl acetate to obtain another 14 mg of the said product.

NMR Spectrum (DMSO): ppm

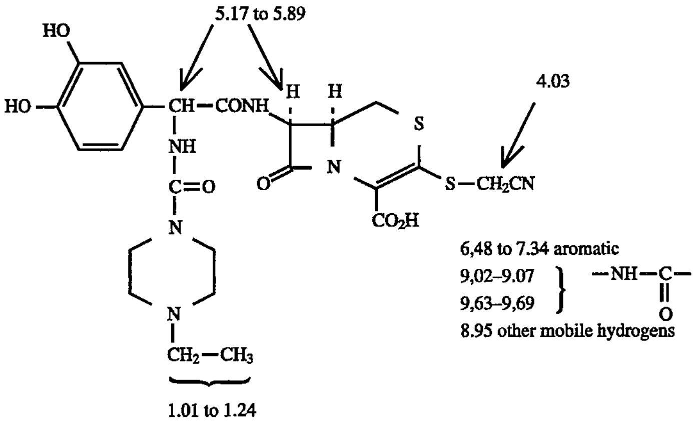

| U.V. Spectrum (ethanol): | | | |
|---|---|---|---|
| Inflex. | 230 nm | $E_1^1 = 295$ | |
| Max. | 289 nm | $E_1^1 = 143$ | ε = 8,650 |
| Max. | 314 nm | $E_1^1 = 168$ | ε = 10,200 |

-continued

| | U.V. Spectrum (0.1 NHCl-ethanol): | |
|---|---|---|
| Max. | 280 nm | $E_1^1 = 174$ |
| Inflex. | 317, 370, 410, 445 nm | |

EXAMPLE 150

Racemic syn cis 7-[(2-(2-aminothiazol-4-yl]-2(Z)-methoxyimino-acetamido)-3-(4-nitrophenyl)-ethenyl (E)]-8-oxo-4-thia-1-azabicyclo[4,2,0]oct-2-ene-2-carboxylic acid In a mixture of 149 mg of 7-[(2-(2-triphenylmethylaminothiazol-4-yl)-2(Z)-methoxyimino-acetamido]-8-oxo-4-thia-1-azabicyclo[4,2,0]oct-2-ene-3-yl]- methyl]-triphenyl phosphonium chloride and 34 mg of paranitro benzaldehyde in 3 ml of dichloromethane was added dropwise 1.2 ml of a solution of 0.28 ml of triethylamine in 10 ml of dichloromethane and after standing at 20° C. for 35 minutes, one drop of acetic acid was added. The mixture was evaporated to dryness under reduced pressure and the residue was chromatographed over silica. Elution with a 9-1 methylene chloride-ethyl acetate mixture and empasting with ether yielded 88 mg of compound. 67 mg of this product was empasted with 0.27 ml of trifluoro acetic acid for 35 minutes at ambient temperature, then 3 ml of ether was added and after triturating and filtering 35 mg of the desired compound was obtained.

EXAMPLE 151

Optically actif (6S,7S) 7-[(2-(2-amino-thiazol-4-yl)-2(Z)-methoxyimino-acetamido)-3-(2-(Z)cyanoethenyl)]-8-oxo-4-thia-1-azabicyclo [4,2,0]oct-2-ene-2-carboxylic acid STEP A: 1,1-dimethyl-ethyl (6S,7S) 7-[(2-(2-triphenylmethylaminothiazol-4-yl)-2(Z)-methoxyimino-acetamido]-3-formyl-8-oxo-4-thia-1-azabicyclo[4,2,0]oct-2-ene-2-carboxylate A solution of 1.275 mg of dimethylsulfoxide in 75 ml of dichloromethane was added over 15 minutes at −75° C. to 75 ml of a solution of 1 ml of oxalyl chloride per 100 ml of dichloromethane and after stirring for 5 minutes, 3.321 g of 1,1-dimethyl-ethyl (6S, 7S) 7- [(2-(2-triphenylmethylamino-thiazol-4-yl)-2(Z) methoxyaminoacetamido]-3-hydroxy-8-oxo-4-thia-1-azabicyclo[4,2,0]oct-2-ene-2-carboxylate were added thereto over 10 minutes at −67° C. Then, 4.66 ml of triethylamine were added at −72° C. over 2 minutes and after heating the mixture to −45° C., 24 ml of aqueous N hydrochloric acid and 93 ml of water were added. The decanted aqueous phase was extracted with dichloromethane and the organic phase was evaporated to dryness under reduced pressure. The residue was chromatographed over silica and was eluted with a 85-15 dichloromethane-ethylacetate mixture. The product was empasted with ether to obtain 2.65 g of 1,1-dimethyl-ethyl (6S, 7S) 7-[(2-(2-triphenylmethylamino-thiazol-4-yl)-2(Z)-methoxyimino-acetamido]-3-formyl-8-oxo-4-thia-1-azabicyclo [4,2,0]oct-2-ene-2-carboxylate melting at ≈180° C.

STEP B: 1,1-dimethyl-ethyl 7-[(2-(2-triphenylmethylamino-thiazol-4-yl)-2(Z) methoxyimino-acetamido]-3-[2-(Z)-cyanoethenyl)]-8-oxo-4-thia-1-azabicyclo[4,2,0]oct-2-ene-2-carboxylate A solution of 1.065 g of the product of Step A, 675 mg of cyanomethylene triphenylphosphorane and 27 ml of dichloromethane was stirred at 20° C. for 4¼ hours and was then evaporated to dryness under reduced pressure. The residue was chromatographed over silica and was eluted with a 1-1 dichloromethane-ether mixture. The product was dissolved in a 1-1 dichloromethane-ethanol mixture and the solution was evaporated to dryness under reduced pressure. The crystals were empasted with ethanol to obtain 563 mg of 1,1-dimethyl-ethyl 7-[(2-(2-triphenylmethylamino-thiazol-4-yl)-2(Z) methoxyiminoacetamido]-3-[2-(Z) cyanoethenyl) ]-8-oxo-4-thia-1-azabicyclo[4,2,0]oct-2-ene-2-carboxylate. The mother liquors were treated to obtain another 317 mg of product.

STEP C: 7[(2-(2-amino-thiazol-4-yl)-2(Z)-methoxyimino-acetamido)-3-(2(Z)cyanoethenyl)]-8-oxo-4-thia-1-acabicyclo[4,2,0]oct-2-ene-2-carboxylic acid A mixture of 366 mg of the product of Step B and 1.5 ml of trifluoroacetic acid stood for 45 minutes and was then diluted with ether and filtered. The filtrate was evaporated to dryness under reduced pressure and the residue was dissolved in ethanol. 3 drops of pyridine were added to the solution which was vacuum filtered to obtain 61 mg of the desired acid. The mother liquor yielded another 25 mg of the said acid.

EXAMPLE 152

Trifluoroacetate of 7-[(2-(2-amino-thiazol-4-yl)-2(Z)-methoxyimino-acetamido]-3-(3,3,3-trifluoropropenyl(Z)]-8-oxo-4-thia-1-azabicyclo [4,2,0]oct-2-ene-carboxylic acid STEP A: (6S,7S) 7-[(2-triphenylmethylamino-thiazol-4-yl)-2(Z)-methoxyimino-acetamido)-2-(1,1-dimethylethyloxycarbonyl)]-8-oxo-4-thia-1-azabicyclo[4,2,0]oct-2-ene-3-yl]-methyl triphenyl phosphonium chloride 14.1 g of silica were added to a solution of 2.182 g of 1,1-dimethylethyl (6S, 7S) 7[(2-(2-triphenylmethylamino-thiazol-4-yl)-2(Z)-methoxyimino-acetamido)-3-chloromethyl]-8-oxo-4-thia-1-azabicyclo 4,2,01oct-2-ene-2-carboxylate (prepared from a product described in French Patent No. 2,538,389 by the procedure of Step G of reference Example B], 1.679 g of triphenylphosphine and 24 ml of tetrahydrofuran and the tetrahydrofuran was distilled over 2 hours. The mixture was cooled and stirred at 20° C. for 26 hours. Chromatography over silica and elution with a 9-1 dichloromethane-methanol mixture yielded 1.89 g of (6S, 7S) 7-[(2-triphenylmethylamino-thiazol-4-yl)-2(Z)-methoxyimino-acetamido)-2-(1,1-dimethylethyloxy-carbonyl)]-8-oxo-4-thia-1-azabicyclo[4,2,01oct-2-ene-3-yl]-methyl triphenyl phosphonium chloride.

STEP B: 1,1-dimethyl-ethyl 7-[(2-(2-triphenylmethylamino-thiazol-4-yl)-2(Z)-methoxyimino-acetamido)-3-(3,3,3-trifluoro-1(Z)-propenyl)]-8-oxo-4-thia-1-azabicyclo[4,2,01oct-2-ene-2-carboxylate 9.14 ml of ethyl hemiacetal of trifluoroacetaldehyde were added to a solution of 343 mg of product of Step A in 6.9 ml of dichloromethane and after the addition of 9.12 ml of triethylamine, the mixture stood at 20° C. for 2 hours. Water was added thereto and the mixture was acidified with acetic acid. The decanted aqueous phase was extracted with dichloromethane and the organic phase was evaporated to dryness under reduced pressure. The residue was chromatographed over silica and eluted with a 9-1 dichloromethane-ethyl acetate to obtain 12 mg of isomer E and 44 mg of isomer Z of the above named compound.

NMR Spectrum ($CDCl_3$ at 90 MHZ): isomer E

Peaks at 1.55 ppm (s tert.-butyl); at 3.99 ppm (d,d J~10 and 13) and 3.15 ppm (d,d J~3.5 and 13)($SCH_2$); at 4.16 ppm (nm $H_6$); at 4.05 ppm (s $NOCH_3$); 5.48 ppm (d J~5 $H_7$ after exchange $D_2O$)] at 6.09 ppm (d,q) (J~16 and 1.5:17 ethylene in $MCF_3$); at 7.5 ppm (d,q)(J~16 and 1.5: ethylene H in C=C); at 6.66 ppm (s syn thiazole $H_5$); at 7.7 ppm ($CO_3$ ).

| NMR Spectrum ($CDCl_3$ at 90 MHZ); isomer Z |
|---|
| Peaks at 1.49 ppm (s tert.-butyl); 2.95 to 3.11 ppm ($CH_2$); 4.04 ppm (s noMe); 4.14 ppm (m $H_6$); 5.16 ppm (d, Jr5); after exchange $D_2$0:$H_7$ { 5.74 ppm (d,q) J = 12 and 8 ethylenic H in $CF_3$; 6.65 ppm (d) J = ethylenic H in C=C } at 6.63 ppm (s thiazole $H_5$); at 7.3 ppm ($CO_3$). |

STEP C: Trifluoracetate of 7-[(2- (2-amino-thiazol-4-yl)-2 (Z)-methoxyimino-acetamido)-3-(3,3,3-trifluoro-1(Z) propenyl)]-8-oxo-4-thia-1-azabicyclo[4,2,0]oct-2-ene-2-carboxylic acid A mixture of 41 mg of the Z isomer of Step C and 0.18 ml of trifluoroacetic acid stood at 20° C. for 45 minutes and after addition of ether, the mixture was vacuum filtered and dried to obtain the said product.

EXAMPLES 153 to 162

Using the procedure of Example 152, the compounds of the following Tables were prepared.

Example 153

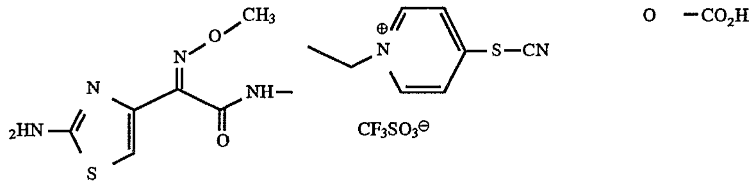

$CF_3CO_2H$

Spectre IR (nujol)

| | | |
|---|---|---|
| 1770 $cm^{-1}$ | β lactam c=o | |
| 1672 $cm^{-1}$ | amide c=o | |
| 1640 $cm^{-1}$ | aromatic | |
| 1570 $cm^{-1}$ | conjugated system | |
| 1525 $cm^{-1}$ | amide II | |
| 1490 $cm^{-1}$ | thiazole | |
| | —C-00 ⊖ | |

m.p. = 200° C.

Spectre UV (ethanol HCl 0.1/N)

| | | |
|---|---|---|
| Max. 248 nm | $E\frac{1}{1} = 270$ | Σ = 21 500 |
| Max. 283 nm | $E\frac{1}{1} = 247$ | Σ = 19 700 |
| Infl. 306 nm | $E\frac{1}{1} = 210$ | Σ = 16 700 |

Example 154

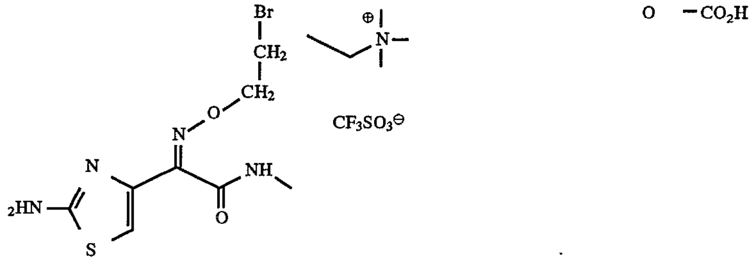

$CF_3CO_2H$

Spectre IR (nujol)

| | | |
|---|---|---|
| 1776 $cm^{-1}$ | β lactam C=O | |
| 1670 $cm^{-1}$ | amide C=O | |
| 1530 $cm^{-1}$ | amide II | |
| 1645 $cm^{-1}$ | thiazole | |
| 1605 $cm^{-1}$ | C=C | |
| 1584 $cm^{-1}$ | C=N | |
| 1560 $cm^{-1}$ | COO ⊖ | |
| 1030 $cm^{-1}$ | $CF_3SO_3$⊖ | |

m.p. = 162° C. (decomposition)

Spectre UV (ethanol)

| | | |
|---|---|---|
| Max. 221 nm | $E\frac{1}{1} = 245$ | Σ = 19 900 |
| Max. 299 nm | $E\frac{1}{1} = 181$ | Σ = 14 700 |

(ethanol, HCl 0.1N)

| | | |
|---|---|---|
| Max. 226 nm | $E\frac{1}{1} = 186$ | Σ = 15 100 |
| Infl. 270 nm | $E\frac{1}{1} = 169$ | |
| Max. 288 nm | $E\frac{1}{1} = 195$ | Σ = 15 800 |
| Infl. 307 nm | $E\frac{1}{1} = 154$ | |

-continued

| | | | | | | |
|---|---|---|---|---|---|---|
| Example 155 | 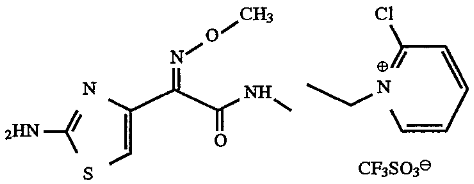 | O −$CO_2H$ | Spectre IR (nujol) | | Spectre UV (ethanol) | |
| $CF_3CO_2H$ | $CF_3SO_3^{\ominus}$ | | 1777 $^{cm-1}$ | β lactam 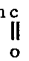 | Max. 229 nm $E\frac{1}{1}$ = 234 | Σ = 18 100 |
| | | | 1675 $^{cm-1}$ | amide 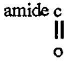 | Infl. 254 nm $E\frac{1}{1}$ = 167 | |
| | | | 3120 $^{cm-1}$ | | Infl. 260 nm $E\frac{1}{1}$ = 152 | |
| | | | 1639 $^{cm-1}$ | 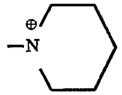 | Infl. 268 nm $E\frac{1}{1}$ = 131 | |
| | | | 1030 $^{cm-1}$ | $CF_3SO_3^{\ominus}$ | Max 297 nm $E\frac{1}{1}$ = 156 | Σ = 12 100 |
| | | | 1570 $^{cm-1}$ 1550 $^{cm-1}$ 1490 $^{cm-1}$ | aromatic conjugated system amide II thiazole COO ⊖ | (ethanol, Hcl 0.1N) | |
| | | | | | Infl. 223 nm $E\frac{1}{1}$ = 190 | |
| | | | | | Infl. 260 nm $E\frac{1}{1}$ = 199 | |
| | | | | | Max. 263 nm $E\frac{1}{1}$ = 206 | Σ = 15 900 |
| | | | 1050 $^{cm-1}$ | —C N—OR | Max 270 nm $E\frac{1}{1}$ = 199 | Σ = 15 600 |
| | | | | | Max 283 nm $E\frac{1}{1}$ = 190 | |
| | | | m.p. = 160° C. (decomposition) | | Infl. 302 nm $E\frac{1}{1}$ = 145 | |
| Example 156 | 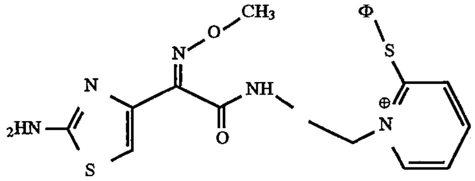 | O −$CO_2H$ | Spectre IR (nujol) | | Spectre UV (ethanol) | |
| $CF_3CO_2H$ | $CF_3SO_3^{\ominus}$ | | 1776 $^{cm-1}$ | β lactam | Infl. 232 nm $E\frac{1}{1}$ = 312 | |
| | | | 1673 $^{cm-1}$ | amide CO | Infl. 275 nm $E\frac{1}{1}$ = 144 | |
| | | | 1640 $^{cm-1}$ | pyridinium | Max. 304 nm $E\frac{1}{1}$ = 230 | Σ = 26 200 |
| | | | 1610 $^{cm-1}$ 1568 $^{cm-1}$ 1540 $^{cm-1}$ | aromatic COO⊖ amide II thiazole | (ethanol, HCl, 0.1N) | |
| | | | | | Infl. 232 nm $E\frac{1}{1}$ = 255 | |
| | | | | | Max. 258 nm $E\frac{1}{1}$ = 225 | Σ = 19 400 |
| | | | | | Infl. 264 nm $E\frac{1}{1}$ = 222 | |
| | | | 1045 $^{cm-1}$ | C=N—OR | Max. 273 nm $E\frac{1}{1}$ = 225 | Σ = 18 900 |
| | | | | | Infl. 290 nm $E\frac{1}{1}$ = 235 | |
| | | | | | Max. 236 nm $E\frac{1}{1}$ = 240 | Σ = 20 700 |
| | | | m.p. = 180–190° C. (decomposition) | | Infl. 310 nm $E\frac{1}{1}$ = 229 | Σ = 19 700 |

-continued

Example 157

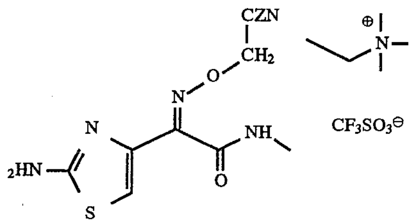

$CF_3SO_3^{\ominus}$ $CF_3CO_2H$

O —$CO_2H$

Spectre IR (nujol)

| | | |
|---|---|---|
| 1778 cm-1 | β lactam | |
| 1670 cm-1<br>1640 cm-1 | others C=O | |
| 1572 cm-1<br>1550 cm-1<br>1488 cm-1 | region C=C<br>C=N<br>$NH_2$<br>amide II | |

Spectre UV (ethanol)

| | |
|---|---|
| Max. 221 nm $E\frac{1}{1}$ = 258 | Σ = 19 200 |
| Infl. 230 nm $E\frac{1}{1}$ = 239 | |
| Max. 300 nm $E\frac{1}{1}$ = 180 | Σ = 13 400 |
| (ethanol, HCl 0.1N) | |
| Max. 221 nm $E\frac{1}{1}$ = 189 | Σ = 14 100 |
| Infl. 264 nm $E\frac{1}{1}$ = 148 | |
| Max. 292 nm $E\frac{1}{1}$ = 191 | Σ = 14 200 |
| Infl. 310 nm $E\frac{1}{1}$ = 152 | |

m.p. = 198° C. (decomposition)

Example 158

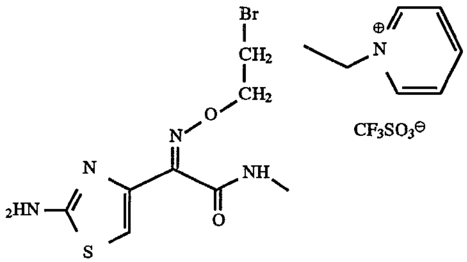

$CF_3SO_3^{\ominus}$ $CF_3CO_2H$

O —$CO_2H$

Spectre IR (nujol)

| | | |
|---|---|---|
| 1775 cm-1 | β lactam | |
| 1670 cm-1<br>1635 cm-1 | others C=O | |
| 1578 cm-1<br>1540 cm-1<br>1498 cm-1<br>1485 cm-1 | region C=C<br>C=N<br>amide II | |

Spectre UV (ethanol)

| | |
|---|---|
| Infl. 225 nm $E\frac{1}{1}$ = 262 | |
| Infl. 254 nm $E\frac{1}{1}$ = 188 | |
| Infl. 255 nm $E\frac{1}{1}$ = 175 | |
| Infl. 264 nm $E\frac{1}{1}$ = 152 | |
| Max. 296 nm $E\frac{1}{1}$ = 170 | Σ = 14 100 |
| Max 413 nm $E\frac{1}{1}$ = 4,7 | |
| (ethanol, HCl 0.1N) | |
| Infl. 220 nm $E\frac{1}{1}$ = 235 | |
| Infl. 226 nm $E\frac{1}{1}$ = 209 | |
| Max. 260 nm $E\frac{1}{1}$ = 209 | Σ = 17 400 |
| Infl. 266 nm $E\frac{1}{1}$ = 207 | |
| Max 286 nm $E\frac{1}{1}$ = 202 | Σ = 16 700 |
| Infl. 310 nm $E\frac{1}{1}$ = 136 | Σ = 11 300 |

m.p. = 160° C. (decomposition)

-continued

| | | | | | | |
|---|---|---|---|---|---|---|
| Example 159 | 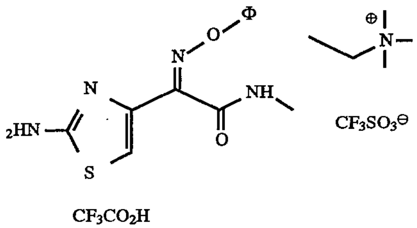 | O | $-CO_2H$ | Spectre IR (nujol) | Spectre UV (ethanol) | |
| | | | | 1778 $cm^{-1}$ β lactam | Max. 220 nm $E\frac{1}{1}$ = 356 | Σ = 27 800 |
| | | | | 1670 $cm^{-1}$ $\underset{O}{\underset{\|}{C}}$ complexed | Infl. 250 nm $E\frac{1}{1}$ = 170 | |
| | | | | | Infl. 266 nm $E\frac{1}{1}$ = 142 | |
| | | | | 1590 $cm^{-1}$, 1575 $cm^{-1}$, 1485 $cm^{-1}$ } $-C{=}C$, $-C{=}N$, amide II | Max. 301 nm $E\frac{1}{1}$ = 238 | Σ = 18 600 |
| | | | | | Max. 420 nm $E\frac{1}{1}$ = 3.5 | |
| | | | | | (ethanol, HCl, 0.1N) | |
| | | | | | Infl. 218 nm $E\frac{1}{1}$ = 283 | |
| | | | | | Infl. 268 nm $E\frac{1}{1}$ = 162 | |
| | | | | | Infl. 276 nm $E\frac{1}{1}$ = 270 | |
| | | | | m.p. = 186° C. (decomposition) | Max. 303 nm $E\frac{1}{1}$ = 284 | Σ = 22 200 |
| Example 160 | 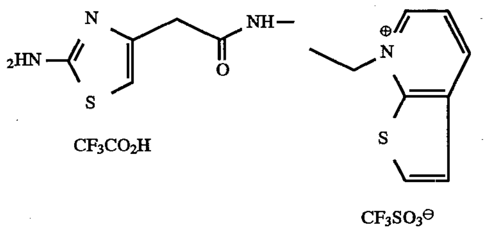 | O | $-CO_2H$ | Spectre de R.M.N. (DMSO) | Spectre UV (ethanol) | |
| | | | | peak at 3,2 ppm $CH_2S$ | Max. 289 nm $E\frac{1}{1}$ = 305 | Σ = 22 900 |
| | | | | peak at 3,4 ppm $CH_2-\overset{O}{\overset{\|}{C}}$ | Infl. 260 nm $E\frac{1}{1}$ = 119 | |
| | | | | peak at 5,48 ppm at 5,64 ppm $H_7$ | Max. 297 nm $E\frac{1}{1}$ = 155 | Σ = 11 650 |
| | | | | peak at 5,88–6,08 ppm, peak at 6,13–6,33 ppm } $CH-\overset{\ominus}{N}$ | (ethanol, HCl 0.1N) | |
| | | | | | Max. 240 nm $E\frac{1}{1}$ = 332 | Σ = 25 000 |
| | | | | peak at 6,43 ppm $H_5$ thiazol "syn" | Infl. 260 nm $E\frac{1}{1}$ = 277 | |
| | | | | peak at 7,87 a 8,3 ppm aromatic | Max 303 nm $E\frac{1}{1}$ = 148 | Σ = 11 900 |

-continued

Example 161

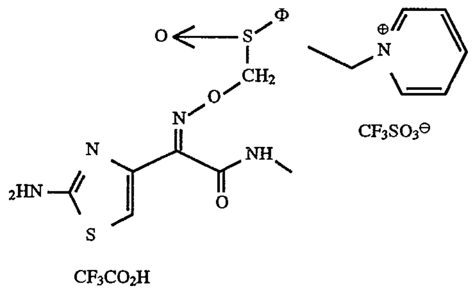

O —$CO_2H$

Spectre de RMN ($CDCl_3$)

peak at 5,07 ppm $OCH_2$ peak at 5,44–561 ppm
peak at 5,85–6,1 ppm } $N^{\ominus}CH_2$ peak at 5,66 ppm $H_7$ peak at 6,93 ppm $H_5$ thiazol "syn"
peak at 8,36 a 7,61 ppm H aromatic pyridine
peak at 7,61 ppm S—O
O Spectre UV (ethanol)

| | | |
|---|---|---|
| Max. 218 nm | $E\frac{1}{1}$ = 382 | Σ = 33 000 |
| Infl. 242 nm | $E\frac{1}{1}$ = 232 | |
| Infl. 256 nm | $E\frac{1}{1}$ = 215 | |
| Max. 297 nm | $E\frac{1}{1}$ = 185 | Σ = 16 000 |
| Max. 400 nm | $E\frac{1}{1}$ = 20 | |
| (ethanol, HCl 0.1N) | | |
| Max. 219 nm | $E\frac{1}{1}$ = 344 | Σ = 30 000 |
| Infl. 243 nm | $E\frac{1}{1}$ = 211 | Σ = 18 200 |
| Max. 250 nm | $E\frac{1}{1}$ = 204 | Σ = 17 600 |
| Max. 293 nm | $E\frac{1}{1}$ = 216 | Σ = 18 000 |
| Max 395 nm | $E\frac{1}{1}$ = 18 | |

Example 162

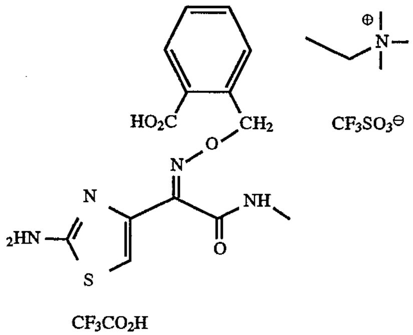

O —$CO_2H$

Spectre IR (nujol)

1775 $cm^{-1}$ β lactam

1670 $cm^{-1}$
1705 $cm^{-1}$
1645 $cm^{-1}$ } other c complexes ‖ o

1575 $cm^{-1}$
1540 $cm^{-1}$
1488 $cm^{-1}$ } region C═C, C═N aromatic, amide II Spectre UV (ethanol)

| | | |
|---|---|---|
| Max 226 nm | $E\frac{1}{1}$ = 312 | Σ = 26 200 |
| Infl. 293 nm | $E\frac{1}{1}$ = 172 | |
| Max. 297 nm | $E\frac{1}{1}$ = 176 | Σ = 14 800 |
| Max 417 nm | $E\frac{1}{1}$ = 5 | |
| (ethanol, HCl 0.1N) | | |
| Max. 226 nm | $E\frac{1}{1}$ = 262 | Σ = 22 000 |
| Infl. 266 nm | $E\frac{1}{1}$ = 173 | |
| Max. 286 nm | $E\frac{1}{1}$ = 212 | Σ = 17 800 |
| Infl. 290 nm | $E\frac{1}{1}$ = 207 | |
| Infl. 310 nm | $E\frac{1}{1}$ = 139 | Σ = 11 700 |

m.p. = 180° C. (decomposition)

EXAMPLE 163

Trifluoromethanesulfonate of trifluoroacetate of 1-[(7-{2-aminothiazol-4-yl)-2-carboxyphenylmethoxyimino-acetamido}-2-carboxy-8-oxo-4-thia-1-azabicyclo[4,2,0]oct-2-ene-3-yl]-methyl-pyridinium A mixture of 100 mg of the trifluoro-methane sulfonate of the trifluoroacetate of 1-[7-(2-triphenylmethylamino-thiazol-4-yl)-2-tert.-butoxycarbonylphenyl-methoxyimino-acetamido]-2-tert.-butoxy-carboxyl-8-oxo-4-thia-1-azabicyclo[4,2,01oct-2-ene-3-yl]methyl pyridinium and 0.6 ml of trifluoroacetic acid was stirred at room temperature for 50 minutes and. 5 ml of isoprepyl ether were added with stirring. The mixture was vacuum filtered and the product was dried to obtain 75 mg of the desired product melting at 190° C. (decomposition).

IR Spectrum (nujol):

1775 $cm^{-1}$ (C=0 of β-lactam); at 1675 $cm^{-1}$ ' (C=0 of amide); 1700 $cm^{-1}$ (other carbonyl); 1635 $cm^{-1}$ (C=C, C=N, band of

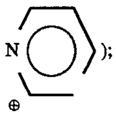);

1600 $cm^{-1}$ (aromatic); 1580 $cm^{-1}$ (conjugated system); $^{+}$1560 $cm^{-1}$ (amide II); 1495 $cm^{-1}$ (thiazole); 1487 $cm^{-1}$ ($COO^-$)

| | | | |
|---|---|---|---|
| U.V. Spectrum (ethanol): | | | |
| Max. | 226 nm | $E_1^1 = 336$ | ε = 28,900 |
| Max. | 292 nm | $E_1^1 = 168$ | ε = 14,400 |
| Inflex. | 250, 256, 263, 265, 417 nm | | |
| U.V. Spectrum (0.1 NHCl-ethanol): | | | |
| Max. | 224 nm | $E_1^1 = 299$ | ε = 25,700 |
| Max. | 250 nm | $E_1^1 = 218$ | ε = 18,700 |
| Inflex. | 264 nm | $E_1^1 = 216$ | |
| Max. | 286 nm | $E_1^1 = 224$ | ε = 19,200 |
| Inflex. | 314 nm | $E_1^1 = 115$ | ε = 9,900 |

EXAMPLES 164 to 172

Using the procedure of Example 163, the compounds of the following Tables were prepared.

Example 164

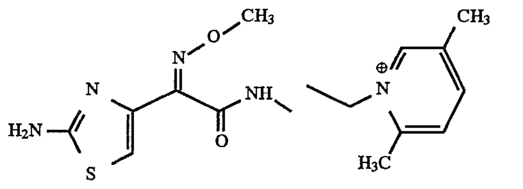

$CF_3CO_2H$ $CF_3SO_3^{\ominus}$

O $-CO_2H$

IR Spectrum (nujol)

- 1775 $cm^{-1}$ β lactam
- 1672 $cm^{-1}$, 1640 $cm^{-1}$ other carbonyls
- 1574 $cm^{-1}$, 1525 $cm^{-1}$ region C=C, C=N, amide II, $NH_2$ m.p. = 180° C.

UV Spectrum (ethanol)

- Infl. 225 nm $E\frac{1}{1}$ = 327 Σ = 25 600
- Max. 294 nm $E\frac{1}{1}$ = 265 Σ = 20 700

(ethanol, HCl 0.1N)

- Infl. 225 nm $E\frac{1}{1}$ = 281 Σ = 22 000
- Infl. 268 nm $E\frac{1}{1}$ = 201
- Max. 293 nm $E\frac{1}{1}$ = 289 Σ = 22 600

Example 165

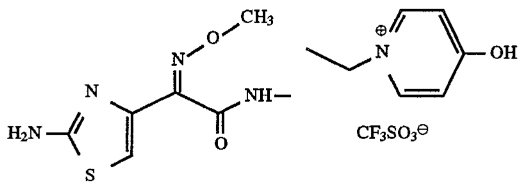

$CF_3CO_2H$ $CF_3SO_3^{\ominus}$

O $-CO_2H$

IR Spectrum (nujol)

- 1770 $cm^{-1}$ β lactam
- 1670 $cm^{-1}$ amide c=o
- 3140 $cm^{-1}$, 1640 $cm^{-1}$

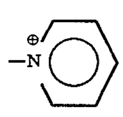

=CH

- 1588 $cm^{-1}$, 1530 $cm^{-1}$, 1495 $cm^{-1}$ conjugated system, aromatic, amide II, thiazole, $COO^{\ominus}$
- 1030 $cm^{-1}$ $CF_3SO_3^{\ominus}$ m.p. = 185° C.

UV Spectrum (ethanol)

- Max. 236 nm $E\frac{1}{1}$ = 311
- Max. 262 nm $E\frac{1}{1}$ = 334 Σ = 25 200
- Max 296 nm $E\frac{1}{1}$ = 245 Σ = 18 500

(ethanol, HCl, 0.1N)

- Max. 246 nm $E\frac{1}{1}$ = 365 Σ = 27 500
- Max 284 nm $E\frac{1}{1}$ = 250 Σ = 18 900
- Infl. 292 nm $E\frac{1}{1}$ = 245

-continued

| | | | | | |
|---|---|---|---|---|---|
| Example 166 | 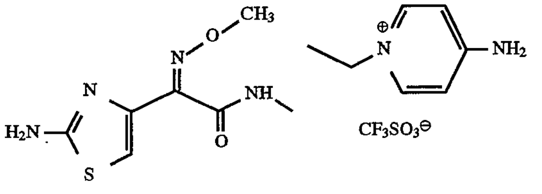<br>$CF_3CO_2H$ | O | $-CO_2H$ | IR Spectrum (nujol)<br>1770 $cm^{-1}$ β lactam c=o<br>1660 $cm^{-1}$ amide and others c=o<br>1580 $cm^{-1}$, 1560 $cm^{-1}$, 1540 $cm^{-1}$ } conjugated system aromatic thiazole amide II<br>1250 $cm^{-1}$, 1200 $cm^{-1}$, 1175 $cm^{-1}$ } $CF_3$ et $SO_2$<br>1030 $cm^{-1}$ $CF_3SO_3^{\ominus}$<br>m.p. = 200° C. | UV Spectrum (ethanol)<br>Infl. 228 nm $E\frac{1}{1}$ = 277<br>Infl. 237 nm $E\frac{1}{1}$ = 267<br>Max 273 nm $E\frac{1}{1}$ = 413 $\Sigma$ = 31 100<br>Infl. 296 nm $E\frac{1}{1}$ = 265 $\Sigma$ = 20 000<br>(ethanol, HCl 0.1N)<br>Infl. 227 nm $E\frac{1}{1}$ = 225<br>Max. 275 nm $E\frac{1}{1}$ = 491 $\Sigma$ = 37 000<br>Infl. 300 nm $E\frac{1}{1}$ = 254 $\Sigma$ = 29 100 |
| Example 167 | 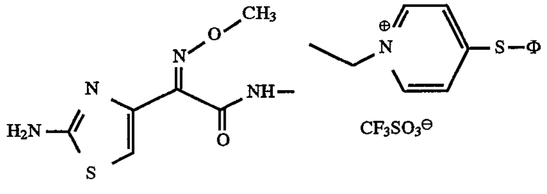<br>$CF_3CO_2H$ | O | $-CO_2H$ | IR Spectrum (nujol)<br>1788 $cm^{-1}$ β lactam c=o<br>1680 $cm^{-1}$ amide c=o<br>1540 $cm^{-1}$ amide II<br>3120 $cm^{-1}$, 1630 $cm^{-1}$ 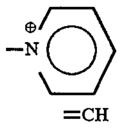 | UV Spectrum (ethanol)<br>Infl. 226 nm $E\frac{1}{1}$ = 317 $\Sigma$ = 26 800<br>Infl. 258 nm $E\frac{1}{1}$ = 162<br>Infl. 271 nm $E\frac{1}{1}$ = 171<br>Max. 303 nm $E\frac{1}{1}$ = 401 $\Sigma$ = 34 000<br>Max. 415 nm $E\frac{1}{1}$ = 5 |

-continued

Example 168

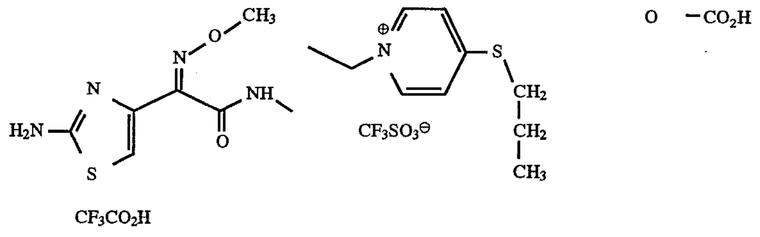

| | | | |
|---|---|---|---|
| | | (ethanol, HCl 0.1N) | |
| 1607 $cm^{-1}$ | aromatic | Infl. 228 nm $E\frac{1}{1}$ = 272 | Σ = 23 000 |
| 1550 $cm^{-1}$ | $COO^{\ominus}$ | Infl. 263 nm $E\frac{1}{1}$ = 203 | |
| 1490 $cm^{-1}$ | conjugated system | | |
| 1030 $cm^{-1}$ | $CF_3SO_3^{\ominus}$ | Infl. 268 nm $E\frac{1}{1}$ = 212 | |
| 1050 $cm^{-1}$ | $C{=}N{-}OCH_3$ | Infl. 275 nm $E\frac{1}{1}$ = 229 | |
| m.p. = 190° C. | | Max. 302 nm $E\frac{1}{1}$ = 991 | Σ = 33 100 |
| IR Spectrum (nujol) | | UV Spectrum (éthanol) | |
| 1782 $cm^{-1}$ | β lactam $C{=}O$ | Max. 230 nm $E\frac{1}{1}$ = 330 | Σ = 26 800 |
| 1710 $cm^{-1}$, 1680 $cm^{-1}$, 1555 $cm^{-1}$ | other carbonyls | Max 308 nm $E\frac{1}{1}$ = 453 | Σ = 36 800 |
| | | (ethanol, HCl 0,1/N) | |
| 1630 $cm^{-1}$ | region C=C | Max. 231 nm $E\frac{1}{1}$ = 271 | Σ = 22 300 |
| 1605 $cm^{-1}$ | region C=N | Infl. 270 nm $E\frac{1}{1}$ = 213 | |
| 1545 $cm^{-1}$ | amide II | | |
| 1532 $cm^{-1}$, 1490 $cm^{-1}$ | $NH_2$ | Max. 310 nm $E\frac{1}{1}$ = 430 | Σ = 34 300 |
| m.p. = 180° C. | | | |

Example 169

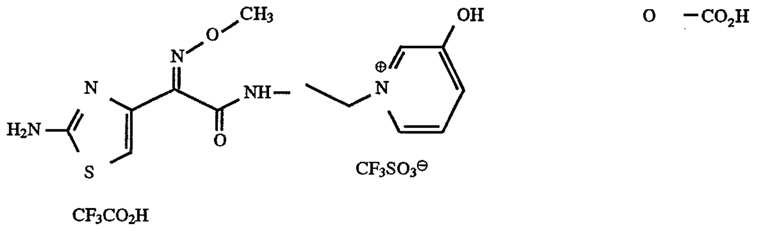

| | | | |
|---|---|---|---|
| IR Spectrum (nujol) | | UV Spectrum (éthanol) | |
| 1772 $cm^{-1}$ | β lactam | Infl. 223 nm $E\frac{1}{1}$ = 343 | Σ = 25 900 |
| 1670 $cm^{-1}$, 1645 $cm^{-1}$ | other carbonyls | Max 292 nm $E\frac{1}{1}$ = 276 | Σ = 20 800 |
| | | (ethanol, HCl 0.1/N) | |
| | | Infl. 223 nm $E\frac{1}{1}$ = 279 | |
| 1582 $cm^{-1}$, 1515 $cm^{-1}$, 1495 $cm^{-1}$ | region C=C, region C=N, amide II | Max. 290 nm $E\frac{1}{1}$ = 310 | Σ = 23 400 |
| | | Infl. 316 nm $E\frac{1}{1}$ = 132 | Σ = 10 000 |
| m.p. = 190–200° C. | | | |

-continued

| | | | | | | |
|---|---|---|---|---|---|---|
| Example 170 | 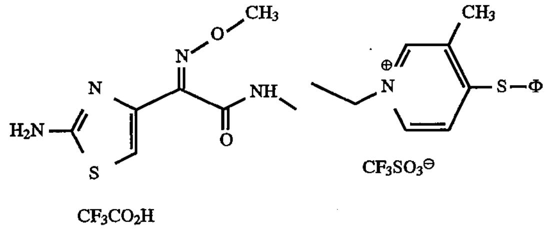 | O | −$CO_2H$ | IR Spectrum (nujol)<br>1788 $cm^{-1}$ β lactam<br>1716 $cm^{-1}$, 1690 $cm^{-1}$ } other carbonyls<br>1630 $cm^{-1}$, 1606 $cm^{-1}$, 1580 $cm^{-1}$, 1545 $cm^{-1}$, 1485 $cm^{-1}$ } region C═C, region C═N, amide II, aromatic, $NH_2$<br>m.p. = 190° C. | UV Spectrum (ethanol)<br>Infl. 219 nm $E\frac{1}{1}$ = 375<br>Max 230 nm $E\frac{1}{1}$ = 343<br>Max 300 nm $E\frac{1}{1}$ 402<br>(ethanol HCl 0.1N)<br>Infl. 221 nm $E\frac{1}{1}$ = 307<br>Max. 230 nm $E\frac{1}{1}$ = 295<br>Infl. 206 nm $E\frac{1}{1}$ = 217<br>Infl. 272 nm $E\frac{1}{1}$ = 236<br>Max. 299 nm $E\frac{1}{1}$ = 301 | <br><br>Σ = 29 500<br>Σ = 34 600<br><br><br>Σ = 25 400<br><br><br>Σ = 34 500 |
| Example 171 | 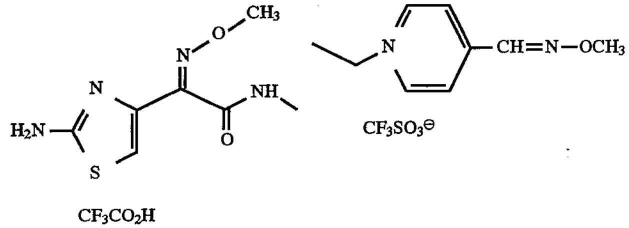 | O | −$CO_2H$ | IR Spectrum (nujol)<br>1775 $cm^{-1}$ β lactam c═o<br>1670 $cm^{-1}$ amide c═o<br>3120 $cm^{-1}$, 1030 $cm^{-1}$ } 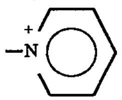<br>1590 $cm^{-1}$, 1555 $cm^{-1}$, 1535 $cm^{-1}$, 1510 $cm^{-1}$ } aromatic conjugated system, COO−, amide II, thiazole<br>m.p. = 185–190° C. (decomposition) | UV Spectrum (ethanol)<br>Infl. 217 nm $E\frac{1}{1}$ = 370<br>Max 299 nm $E\frac{1}{1}$ = 408<br>(ethanol HCl 0.1/N)<br>Infl. 219 nm $E\frac{1}{1}$ = 290<br>Max 294 nm $E\frac{1}{1}$ = 430 | <br><br>Σ = 32 500<br><br><br>Σ = 34 200 |

-continued
| Example 172 | | O | $-CO_2H$ | IR Spectrum (nujol) | | UV Spectrum (ethanol HCL N/10) | |
|---|---|---|---|---|---|---|---|
| | 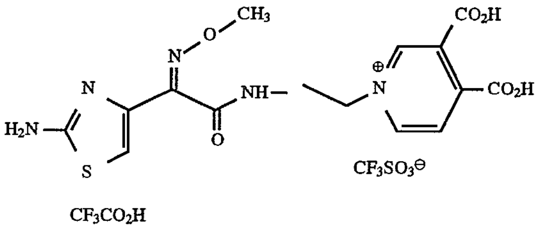 | | | $1772\ ^{cm-1}$ | β lactam c | Infl. 218 nm $E\frac{1}{1}$ = 310 | Σ = 25 600 |
| | | | | $1710\ ^{cm-1}$ | amide c o | Max 273 nm $E\frac{1}{1}$ = 272 | Σ = 22 500 |
| | | | | | | Infl. 281 nm $E\frac{1}{1}$ = 264 | |
| | | | | $1670\ ^{cm-1}$ | amide c | Infl. 304 nm $E\frac{1}{1}$ = 181 | Σ = 15 000 |
| | | | | $1640\ ^{cm-1}$ | 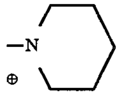 | | |
| | | | | $1575\ ^{cm-1}$ | amide II<br>thiazole<br>conjugated system<br>COO ⊖ | | |
| | | | | $1030\ ^{cm-1}$ | $CF_3SO_2^{\ominus}$ | | |
| | | | | m.p. = 220° C. (decomposition) | | | |

EXAMPLE 173

Trifluoromethanesulfonate of 1-[7-(2-(2-amino-thiazol-4-yl)-2[2-pyridinyl)-methoxyimino]-acetamido]-2-carboxy-8-oxo-4-thia-1-azabicyclo [4,2,0]oct-2-ene-3-yl]-methyl-pyridinium trifluoroacetate STEP A: 1,1-dimethyl-ethyl (6R,S) (7R,S) (Z) 3-hydroxymethyl-7-[(2-triphenylmethylamino-thiazol-4-yl)-2-(2-pyridinyl)-methoxyimino-acetamido]8-oxo-4-thia-1-azabicyclo[4,2,0]oct-2-ene-2-carboxylate A mixture of 440 mg of 2-(2-tritylamino-thiazol-4-yl)-2-(2-pyridinylmethoxyimino)-acetic acid, 4.5 ml of acetone, 0.130 ml of triethylamine and 0.160 g of tosyl chloride was stirred at 20° C. for 45 minutes and was poured all at once into a solution of 200 mg of 1,1-dimethyl-ethyl 3-hydroxyethyl-8-oxo-4-thia-1-azabicyclo[4,2,0]oct-2-ene-2-carboxylate in 1 ml of water, 1 ml of acetone and 1 ml of aqueous M sodium bicarbonate solution. The mixture was stirred at 20° C. for 35 minutes and was evaporated to dryness under reduced pressure. The residue was added to methylene chloride with stirring and was extracted with methylene chloride. The organic phase was evaporated to dryness under reduced pressure. The residue was chromatographed over silica and eluted with a 95-5 methylene chloride-methanol mixture to obtain 212 mg of the above compound.

NMR Spectrum ($CDCl_3$): 1.56 and 1.71 ppm (tert.-butyl); 3.05 ppm ($CH_2S$); 3.67 to 5.75 (absorption complexes $CH_2O$, $H_6$,$H_7$); 6.8 ppm ($H_5$ of syn thiazol); 7.33 ppm (trityl); 7.23 to 8.58 ppm (hydrogen of pyridine); 10.7–10.8 ppm (NHCO).

STEP B: Trifluoromethanesulfonate (6R,S) (7R,S) (Z) 1-[7-[{2-(2-triphenylmethylamino-thiazol-4-yl)-2-(2-pyridinylmethoxyimino)-acetamido}-8-oxo-4-thia-1-azabicyclo[4,2,0]oct-2-ene-3-yl]-methyl pyridinium A mixture of 200 mg of the product of Step A, 5 ml of methylene chloride and 2 ml of 4% pyridine in methylene chloride was stirred for 5 minutes and after cooling to –70° C., 1.7 ml of a 4% trifluoromethylsulfonic anhydride in methylene chloride was progressively added: The mixture was stirred at –70° C. for 10 minutes and the temperature slowly returned to 20° C. The mixture was evaporated to dryness under reduced pressure and the residue was added to ethyl acetate and aqueous N hydrochloric acid with stirring, The decanted aqueous phase was extracted with ethyl acetate and the organic phase was washed and evaporated under reduced pressure. The residue was chromatographed over silica and eluted with a 85-15 methylene chloride-methanol mixture to obtain 108 mg of the above compound.

IR Spectrum (nujol): 1781 $cm^{-1}$ (β-lactam); 17.25, 1700 and 1680 $cm^{-1}$ (other carbonyls); 1632, 1593 and 1580 $cm^{-1}$ (aromatic region-heterocycle); 1528, 1480 and 1500 $cm^{-1}$ (amide II).

| U.V. Spectrum (ethanol): | | | |
|---|---|---|---|
| Inflex. | 221 nm | $E_1^1$ = 349 | ε = 34,500 |
| Inflex. | 227 nm | $E_1^1$ = 328 | ε = 32,400 |
| Inflex. | 256 nm | $E_1^1$ = 203 | ε = 20,100 |
| Inflex. | 263 nm | $E_1^1$ = 179 | ε = 17,700 |
| Max. | 304 nm | $E_1^1$ = 147 | ε = 14,500 |
| U.V. Spectrum (0.1 NHCl-ethanol): | | | |
| Inflex. | 221 nm | $E_1^1$ = 337 | |
| Max. | 260 nm | $E_1^1$ = 200 | ε = 19,800 |
| Max. | 300 nm | $E_1^1$ = 171 | ε = 16,900 |

STEP C: Trifluoromethanesulfonate of 1-[7-(2-(2-amino-thiazol-4-yl)-2-[2-pyridinyl)-methoxyimino]-acetamido]-2-carboxy-8-oxo-4-thia-1-azabicyclo[4,2,0]oct-2-ene-3-yl]-methyl-pyridinium trifluoroacetate A mixture of 84 mg of the compound of Step B and 0.420 ml of trifluoroacetic acid was stirred at 20° C. for 50 minutes and 6 ml of isopropyl ether were added with stirring. The mixture was vacuum filtered and the product was dried to obtain 64 mg of the above compound melting at 180° C. (decomposition).

IR Spectrum (nujol): 1776 $cm^{-1}$ (β-lactam), 1675 $cm^{-1}$ (C═O); 1633 $cm^{-1}$ , 1570 $cm^1$, 1595 $cm^{-1}$, 1550 $cm^{-1}$, 1550 $cm^{-1}$ and 1483 $cm^{-1}$.

| U.V. Spectrum (ethanol): | | | |
|---|---|---|---|
| Inflex. | 217 nm | $E_1^1$ = 282 | ε = 22,700 |
| Inflex. | 226 nm | $E_1^1$ = 265 | |
| Max. | 255 nm | $E_1^1$ = 184 | ε = 14,800 |
| Max. | 204 nm | $E_1^1$ = 155 | ε = 12,500 |
| U.V. Spectrum (0.1 NHCl-ethanol): | | | |
| Max. | 220 nm | $E_1^1$ = 247 | ε = 19,900 |
| Max. | 258 nm | $E_1^1$ = 210 | ε = 16,500 |
| Max. | 293 nm | $E_1^1$ = 175 | ε = 14,100 |
| Inflex. | 320 nm | $E_1^1$ = 99 | ε = 8,000 |

EXAMPLE 174

Trifluoromethanesulfonate of (6R,S) (7R,S) 1-[7-[{2-(2-amino-thiazol-4-yl)-2-(3-pyridinylmethoxyimino)-acetamido}-2-carboxy-8-oxo-4-thia-1-azabicyclo[4,2,0]oct-2-ene-3-yl]-methyl-pyridinium trifluoroacetate STEP A: Ethyl 2-(2-tritylamino-thiazol-4-yl)-2-(3-pyridinyl-methoxyimino)-acetate A mixture of 4 g of a 50% sodium hydride suspension in vaseline oil, 400 ml of dimethylformamide and 18.3 g of ethyl 2-(2-tritylamino-thiazol-4-yl)-2-hydroxyimino-acetate was stirred at 20° C. for 20 minutes and then a solution of 6.6 g of 3-chloromethyl-pyridine hydrochloride in 600 ml of dimethylformamide was added dropwise. The mixture was stirred at 20° C. for 18 hours and was poured into water. The mixture was extracted with ether saturated with aqueous sodium chloride and the extract was evaporated to dryness under reduced pressure. Thr residue was chromatographed over silica and eluted with a 7-3 methylene chloride-ethyl acetate mixture to obtain 8.5 g of ethyl 2-(2-tritylamino-thiazol-4-yl)-2-(3-pyridinyl-methoxyiminoacetate.

IR Spectrum (chloroform): 1734 $cm^{-1}$ (C═O); 3405 $cm^{-1}$ (NH); 1528 $cm^{-1}$ (thiazole); 1580 $cm^{-1}$ and 1480 $cm^{-1}$

| U.V. Spectrum (ethanol): | | | |
|---|---|---|---|
| Max. | 223 nm | $E_1^1$ = 427 | ε = 23,400 |
| Inflex. | 251 nm | $E_1^1$ = 365 | |
| Inflex. | 262 nm | $E_1^1$ = 289 | ε = 15,800 |
| Max. | 301 nm | $E_1^1$ = 86 | ε = 4,700 |
| U.V. Spectrum (0.1 NHCl-ethanol): | | | |
| Max. | 259 nm | $E_1^1$ = 329 | ε = 18,000 |
| Inflex. | 279 nm | $E_1^1$ = 210 | |
| Inflex. | 291 nm | $E_1^1$ = 171 | |
| Inflex. | 300 nm | $E_1^1$ = 155 | ε = 8,500 |

The product was a mixture of 75% of the syn isomer and 25% of the anti isomer.

STEP B: 2-(2-tritylamino-thiazol-4-yl)-2-(3-pyridinylmethoxyimino)acetic acid

A mixture of 7 g of the product of Step A, 35 ml of dioxane, 35 ml of ethanol and 21 ml of aqueous N sodium hydroxide was stirred at 35°–40° C. for one hour and after cooling, the pH was adjusted to 2 by addition of aqueous N hydrochloric acid. 250 ml of water were added and the mixture was vacuum filtered. The product was washed and dried to obtain 4.9 g of 2-(2-tritylamino-thiazol-4-yl)-2-(3-pyridinylmethoxyimino)-acetic acid. mp=192° C.

| U.V. Spectrum (0.1 NHCl-ethanol): | | | |
|---|---|---|---|
| Max. | 263 nm | $E_1^1$ = 334 | =17,400 |
| Inflex. | 276 nm | $E_1^1$ = 273 | |
| Inflex. | 286 nm | $E_1^1$ = 253 | |

NMR Spectrum (DMSO): Possible mixture of 0.9 syn isomer and 0.1 anti isomer 5.16 and 5.28 ppm ($NOCH_2$); 6.86 ppm (syn) and 1.58 ppm (anti) ($H_5$ of thiazole); 7.67 to 7.76 ppm ($H_5$); 8.55 ppm ($H_2$ and $H_6$) [8.6 to 8.9 ppm (mobile hydrogens) 8.3 ppm ($H_4$+benzyl).

STEP C: 1,1-dimethyl-ethyl (6 R,S) (7 R,S) 3-hydroxymethyl-7[(2-{2-triphenylmethylamino-thiazol-4-yl}2-(3-pyridinylmethoxyimino-acetamido)-8-oxo-4-thia-1-azabicyclo[4,2,0]oct-2-ene-2-carboxylate A mixture of 437 mg of the product of Step B, 0.13 ml of triethylamine, 10 ml of tetrahydrofuran and 160 mg of tosyl chloride was stirred at 20° C. for 10 minutes and after adding another 160 mg of tosyl chloride and 0.130 ml of triethylamine, the mixture was stirred at 20° C. for 45 minutes. A mixture of 210 mg of 1,1-dimethyl-ethyl 3-hydroxymethyl-8-oxo-4-thia-1-azabicyclo[4,2,0]oct-2-ene-2-carboxylate, 2 ml of water, 1 ml of tetrahydrofuran and 1 ml of aqueous M sodium bicarbonate solution were added thereto all at once and the mixture was stirred at 20° C. for 25 minutes and was then evaporated to dryness under reduced pressure. The residue was added to methylene chloride and water with stirring and the decanted aqueous phase was extracted with methylene chloride. The combined organic phases were evaporated to dryness under reduced pressure and the residue was chromatographed over silica. Elution with ethyl acetate yielded mg of 1,1-dimethyl-ethyl (6 R,S) (7 R,S) 3-hydroxymethyl-7[(2-{2-triphenylmethylamino-thiazol-4-yl}2-(3-pyridinylmethoxyimino-acetamido)-8-oxo-4-thia-1-azabicyclo[4,2,0]oct-2-ene-2-carboxylate.

IR Spectrum (chloroform): $cm^{-1}$ (free and associated OH): 3406 $cm^{-1}$ (NH): 1775 $cm^{-1}$ (β-lactam); 1733 and 1625 $cm^{-1}$ (other C═Os).

| U.V. Spectrum (ethanol): | | | |
|---|---|---|---|
| Inflex. | 224 nm | $E_1^1$ = 414 | |
| Inflex. | 240 nm | $E_1^1$ = 336 | |
| Inflex. | 251 nm | $E_1^1$ = 268 | |
| Inflex. | 258 nm | $E_1^1$ = 235 | |
| Inflex. | 265 nm | $E_1^1$ = 207 | |
| Max. | 303 nm | $E_1^1$ = 220 | ε = 17,400 |
| U.V. Spectrum (0.1 NHCl-ethanol): | | | |
| Max. | 265 nm | $E_1^1$ = 237 | ε = 18,100 |
| Inflex. | 287 nm | $E_1^1$ = 262 | |
| Max. | 295 nm | $E_1^1$ = 282 | ε = 22,200 |
| Inflex. | 299 nm | $E_1^1$ = 277 | |
| Inflex. | 309 nm | $E_1^1$ = 226 | |

STEP D: Trifluoromethanesulfonate of (6 R,S) (7 R,S) 1-7-(2-{2-triphenylmethylamino-thiazol-4-yl}-2-(3-pyridinylmethoxyimino)-acetamido)-8-oxo-4-thia-1-azabicyclo[4,2,0]oct-2-ene-3-yl]-methyl-pyridinium 1.08 ml of a solution of 4.2% of trifluoromethylsulfonyl anhydride in methylene chloride were added dropwise at −70° C. to a mixture of 127 mg of the product of Step C, 5 ml of methylene chloride and 1.27 ml of a solution of 4% pyridine in methylene chloride and after stirring the mixture at −65° C. for 15 minutes, the temperature was allowed to rise to 20° C., The mixture was evaporated to dryness under reduced pressure and the residue was added to aqueous hydrochloric acid and ethyl acetate with stirring. The decanted aqueous phase was extracted with ethyl acetate and the combined organic phases were evaporated to dryness under reduced pressure. The residue was chromatographed over silica and was eluted with a 9-1 methylene chloride-methanol mixture to obtain 84 mg of the desired compound.

| U.V. Spectrum (ethanol): | | | |
|---|---|---|---|
| Inflex. | 224 nm | $E_1^1$ = 292 | |
| Inflex. | 235 nm | $E_1^1$ = 249 | |
| Inflex. | 251 nm | $E_1^1$ = 206 | |
| Inflex. | 256 nm | $E_1^1$ = 193 | |
| Inflex. | 264 nm | $E_1^1$ = 167 | |
| Max. | 303 nm | $E_1^1$ = 124 | ε = 12,300 |
| U.V. Spectrum (0.1 NHCl-ethanol): | | | |
| Max. | 260 nm | $E_1^1$ = 184 | ε = 18,200 |
| Inflex. | 264 nm | $E_1^1$ = 181 | |
| Inflex. | 285 nm | $E_1^1$ = 157 | |
| Max. | 294 nm | $E_1^1$ = 166 | ε = 16,400 |
| Inflex. | 300 nm | $E_1^1$ = 161 | |
| Inflex. | 320 nm | $E_1^1$ = 84 | |

NMR Spectrum ($CDCl_3$) 2.33 ppm ($SCH_2$); 3.45 ppm ($H_6$); 5.55 ppm ($H_7$); 5.24 ppm ($NOCH_2$); 4.96–514 and 5.86–6.01 ppm ($^{\oplus}CH_2$); 6.61 ppm ($H_5$ of thiazol); 7.69 ppm (triphenylmethyl); 7.67 to 8.60 ppm (pyridine hydrogens); 9.03–9.10 ppm (NHCO).

STEP E: Trifluoromethanesulfonate of 1-[7-(2-{-2-amino-thiazol-4-yl-2-(3-pyridinylmethoxyimino)-acetamido)-2-carboxy-8-oxo-4-thia-1-azabicyclo[4,2,0]oct-2-ene-3-yl]-methyl-pyridinium (trifluoroacetate)

A mixture of 74 mg of the product of Step D and 0.300 ml of trifluoroacetic acid was stirred at 20° C. for 50 minutes and then. 50 ml of isopropyl ether were added with stirring. The mixture was vacuum filtered and the product was dried to obtain 50 mg of the above named compound.

| U.V. Spectrum (ethanol): | | | |
|---|---|---|---|
| Inflex. | 222 nm | $E_1^1$ = 170 | |
| Inflex. | 253 nm | $E_1^1$ = 155 | |
| Inflex. | 255 nm | $E_1^1$ = 126 | |
| Inflex. | 265 nm | $E_1^1$ = 111 | |
| Inflex. | 297 nm | $E_1^1$ = 110 | ε = 8,900 |
| U.V. Spectrum (0.1 NHCl-ethanol): | | | |
| Inflex. | 220 nm | $E_1^1$ = 149 | |
| Max. | 260 nm | $E_1^1$ = 159 | ε = 12,800 |
| Inflex. | 266 nm | $E_1^1$ = 150 | |
| Max. | 290 nm | $E_1^1$ = 130 | ε = 10,500 |
| Inflex. | 310 nm | $E_1^1$ = 92 | |

NMR Spectrum (DMSO): 5.3 ppm ($OCH_2$); 5.47–5.64 ppm and 5.78–6.0 ppm ($^{\oplus}NCH_2$); 6.87 ppm ($H_5$ of syn thiazole): 5.7 ppm (cis $H_7$); 7.78 to 9.20 ppm (pyridine hydrogens); 9.34–9.43 ppm (NHCO).

EXAMPLE 175

6 (R,S),7 (R,S) 3-[(7-{2-(2-amino-thiazol-4-yl)-2(Z)-methoxyimino-acetamido}-2-carboxy-8-oxo-4-thia-1-azabicyclo[4,2,0]oct-2-ene-3-yl]methyl-thiazolinium iodide STEP A: 6 (R,S), 7 (R,S) 3-[7-{2-(2-triphenylmethylamino-thiazol-4-yl)-2-methoxyimino-acetamido}-2- tert.butoxycarbonyl-8-oxo-4-thia-1-azabicyclo[4,2,0]oct-2-ene-3-yl]-methyl-thiazolinium iodide A mixture of 117 mg of 2-[7-2-{2-triphenylmethylamino-thiazol-4-yl}-2-methoxyimino-acetamido)-2-tert.-butoxycarbonyl-8-oxo -4-thia-1-azabicyclo[4,2,0]oct-2-ene-3-yl]-methyl iodide and 0.35 ml of thiazole was stirred at 40° C. for 90 minutes and was then evaporated to dryness under reduced pressure. The residue was chromatographed over silica and eluted with a 92-8 methylene chloride-methanol mixture to obtain 76 mg of the above named compound.

IR Spectrum (chloroform): 1781 $cm^{-1}$ (C=O of β-lactam); 1699 and 1685 $cm^{-1}$ (conjugated ester and secondary amide); 3400 $cm^{-1}$ (NH); 1.520 $cm^{-1}$ (amide II); 1595 $cm^{-1}$; 1586 $cm^{-1}$.

| U.V. Spectrum (ethanol): | | | |
|---|---|---|---|
| Inflex. | 238 nm | $E_1^1 = 461$ | ε = 41,800 |
| Inflex. | 260 nm | $E_1^1 = 237$ | |
| Inflex. | 266 nm | $E_1^1 = 207$ | |
| Inflex. | 272 nm | $E_1^1 = 191$ | |
| Max. | 305 nm | $E_1^1 = 211$ | ε = 19,100 |
| U.V. Spectrum (0.1 NHCl-ethanol): | | | |
| Inflex. | 220 nm | $E_1^1 = 724$ | ε = 65,700 |
| Inflex. | 285 nm | $E_1^1 = 276$ | |
| Max. | 291 nm | $E_1^1 = 282$ | ε = 25,600 |
| Inflex. | 301 nm | $E_1^1 = 178$ | |

STEP B: (6 R,S) (7 R,S) 3-[7-(2-{-2-amino-thiazol-4-yl}-2 (Z)-methoxy-imino-acetamido)-2-carboxy-8-oxo-4-thia-1-azabicyclo[4,2,0]oct-2-ene -3-yl]-methyl-thiazolinium iodide A mixture of 70 mg of the product of Step A and 0.7 ml 33% aqueous formic acid was stirred at 60° C. for 90 minutes and was then cooled and added to a mixture of water and ethyl acetate with stirring. The decanted organic phase was evaporated to dryness under reduced pressure and extracted the two dry entrainments with 0.2 ml of ethanol for each. 0.2 ml of ethanol were added and the precipitate was recovered by centrifugation for 29 mg of the above named compound.

IR Spectrum (nujol): 1765 $cm^{-1}$ (C=O of β-lactam); 1665 $cm^{-1}$ (C=O); 1610, 1585 and 1530 $cm^{-1}$ (amide II, $NH_2$, C=C, C=N).

| U.V. Spectrum (0.1 NHCl-ethanol): | | | |
|---|---|---|---|
| Max. | 221 nm | $E_1^1 = 505$ | ε = 30,700 |
| Inflex. | 233 nm | $E_1^1 = 355$ | |
| Inflex. | 278 nm | $E_1^1 = 268$ | |
| Max. | 285 nm | $E_1^1 = 279$ | |
| Inflex. | 291 nm | $E_1^1 = 274$ | |
| Inflex. | 305 nm | $E_1^1 = 227$ | |

EXAMPLES 176 TO 177

Using the procedure of Example 175, the products of the following Table were prepared.

| | | | | | |
|---|---|---|---|---|---|
| EXAMPLE 176 | 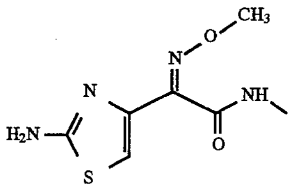 | 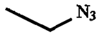 | O | $-CO_2H$ | IR SPECTRUM (nujol)<br>1760 $cm^{-1}$ β lactame<br>1660 $cm^{-1}$ autres carbonyles<br>1580 $cm^{-1}$ C=C<br>C=N<br>1530 $cm^{-1}$ amide<br>m.p. >250° C. |
| EXAMPLE 177 | 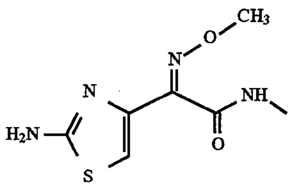<br>$CF_3CO_2H$ | 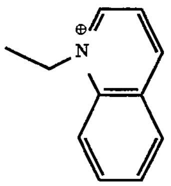 | O | $-CO_2^{\ominus}$ | IR Spectrum (nujol)<br>1770 $cm^{-1}$ lactame<br>1665 $cm^{-1}$ C=O amide<br>1605 $cm^{-1}$ $CO_2^{\ominus}$<br>1580 $cm^{-1}$ C=C; C=N<br>1550 $cm^{-1}$ amide II<br>1530 $cm^{-1}$<br>Ultra-violet<br>éthanol + DMSO Max. 297 nm Σ = 14700<br>éthanol HCl 0,1/N Max. 290 nm Σ = 16100<br>m.p. >260° C. (decomposition) |

EXAMPLE 178

Trifluoromethanesulfonate of (6R,S) (7R,S) (Z) 1-[7-(2-{2-amino-thiazol-4-yl}-2-methoxyimino-acetamido)-2-carboxy-8-oxo-4-thia-1-azabicyclo[4,2,0]oct-2-ene-3-yl]-2-methylthio-3-methylimidazolium (trifluoroacetate)

STEP A: 2-methylthio-1-methyl-imidazole 10 ml of a solution of 1.5% diazomethane in methylene chloride were added in 3 portions over 15 minutes at 0° C. to a solution of 1.14 g of 2-mercapto-1-methyl-imidazole in 5 ml of methylene chloride and after stirring at 0° C. for one hour, a second addition of 10 ml of the diazomethane in methylene chloride solution was made. The mixture was stirred at 20° C. for one hour and was then evaporated to dryness under reduced pressure. The residue was chromatographed over silica and was eluted with a 1-1 methylene chloride-ethyl acetate mixture to obtain 1 g of 2-methylthio-1-methyl-imidazole.

| | | | |
|---|---|---|---|
| U.V. Spectrum (ethanol): | | | |
| Max. | 221 nm | $E_1^1 = 583$ | $\epsilon = 7{,}500$ |
| Max. | 249 nm | $E_1^1 = 364$ | $\epsilon = 4{,}700$ |
| U.V. Spectrum (0.1 NHCl-ethanol): | | | |
| Max. | 222 nm | $E_1^1 = 453$ | $\epsilon = 5{,}800$ |
| Max. | 252 nm | $E_1^1 = 470$ | $\epsilon = 6{,}000$ |
| NMR Spectrum ($CDCl_3$-250 Mhz): ppm | | | |

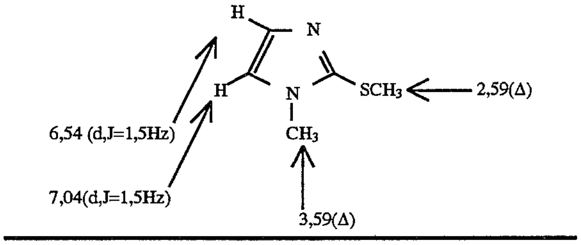

STEP B: Trifluoromethanesulfonate of (6R,S)(7,R,S)(Z) 1-[7-(2-{2-amino-thiazol-4-yl}-2-methoxyimino-acetamido)-2-carboxy-8-oxo-4-thia-1-azabicyclo[4,2,0]oct-2-ene-3-yl]-2-methylthio-3-methylimidazolium (trifluoroacetate)

0.125 of trifluoromethanesulfonic anhydride were added dropise at −70° C. to a mixture of 300 mg 5-[7-(2-{-2-trifluoromethylamino-thiazol-4-yl}-2-methoxyimino-acetamido)-2-tert.-butoxycarbonyl-8-oxo-4-thia-1-azabicyclo[4,2,0]oct-2-ene-yl]-methylhydroxy, 215 mg of the product of Step A and 20 ml of methylene chloride and the mixture was stirred at −70° C. for 10 minutes and then allowed to rise to −30° C. After stirring at −30° C. for one hour, the mixture was added to iced water. The decanted aqueous phase was extracted with methylene chloride and the combined organic phases were evaporated to drying under reduced pressure. The residue was chromatographed over silica and eluted with a 9-1 methylene chloride-methanol mixture to obtain 150 mg of a condensation product.

IR Spectrum (chloroform): 3400 $cm^{-1}$ (NH); 1784 $cm^{-1}$ (C=O of β-lactam); 1702 and 1680 $cm^{-1}$ (other $C{=}O_s$); 1670 $cm^{-1}$ (C=C); 1520 $cm^{-1}$ (C=N); 1486 $cm^{-1}$ (amide II); 1030 $cm^{-1}$ ($CF_3SO_3^{\ominus}$).

| | | | |
|---|---|---|---|
| U.V. Spectrum (ethanol): | | | |
| Inflex. | 225 nm | $E_1^1 = 441$ | |
| Inflex. | 302 nm | $E_1^1 = 192$ | $\epsilon = 18{,}700$ |
| Inflex. | 259–266–270 nm | | |
| U.V. Spectrum (0.1 NHCl-ethanol): | | | |
| Inflex. | 222 nm | $E_1^1 = 432$ | $\epsilon = 41{,}900$ |
| Inflex. | 276 nm | $E_1^1 = 224$ | |
| Max. | 292 nm | $E_1^1 = 246$ | $\epsilon = 23{,}900$ |
| Inflex. | 300 nm | $E_1^1 = 275$ | $\epsilon = 22{,}800$ |
| Inflex. | 310 nm | $E_1^1 = 182$ | $\epsilon = 17{,}700$ |

A mixture of 128 mg of the said product and 0.8 ml of trifluoroacetic acid containing 10% of water was stirred at 20° C. for one hour and then 5 ml of ether were added dropwise with stirring. The mixture was vacuum filtered and the product was dried to obtain 100 mg of the above named compound melting at 180° C.

EXAMPLES 179 to 190

Using the procedure of Example 178, the compounds of the following Tables were prepared.

| | | | | | |
|---|---|---|---|---|---|
| EXAMPLE 179 | 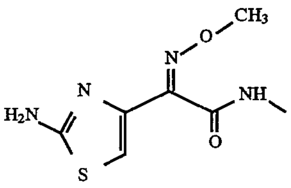<br>$CF_3CO_2H$ | 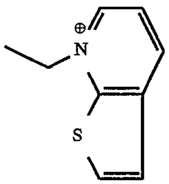<br>$CF_3SO_3^{\ominus}$ | O | $-CO_2H$ | U.V. Spectrum (éthanol)<br>Infl. 230 nm $E_1^1 = 492$<br>Max. 238 nm $E_1^1 = 553$ $\epsilon = 43200$<br>Max. 297 nm $E_1^1 = 244$ $\epsilon = 20000$<br>(éthanol HCl/N)<br>Inf. 230 nm E = 466<br>Max. 238 nm E = 534 $\epsilon = 43700$<br>Max. 299 nm E = 275 $\epsilon = 22500$ |
| EXAMPLE 180 | 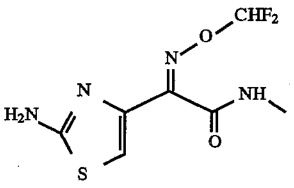<br>$CF_3CO_2H$ | 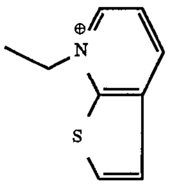<br>$CF_3SO_3^{\ominus}$ | O | $-CO_2H$ | NMR Spectrum (DMSO)<br>Pic de 5,56 à 5,81 ppm proton en $H_7$<br>Pic à 7,07 ppm proton en 5 duthiezole<br>Pic de 8,13 à 9,57 ppm protons aromatiques |
| EXAMPLE 181 | 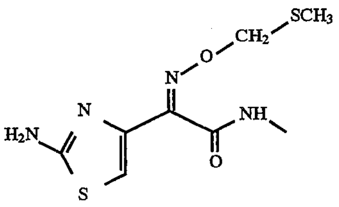<br>$CF_3CO_2H$ | 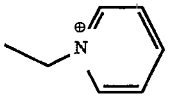<br>$CF_3SO_3^{\ominus}$ | O | $-CO_2H$ | IR Spectrum (nujol)<br>1775 $cm^{-1}$ β lactame<br>1675 $cm^{-1}$ amide<br>1630 $cm^{-1}$ aromatique<br>1585 $cm^{-1}$ $COO^{\ominus}$<br>1555 $cm^{-1}$ amide II<br>1500 $cm^{-1}$ thiazole |
| EXAMPLE 182 | 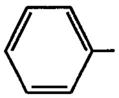 O—$CH_2$CONH— | 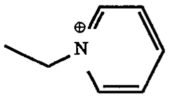<br>$CF_3SO_3^{\ominus}$ | O | $-CO_2H$ | NMR Spectrum (DMSO)<br>peak at 4,6 ppm $OCH_2$<br>peak at 5,43 to 6 ppm proton in position 7, and $CH_2-N^{\ominus}$<br>peak at 6,93 to 8,84 ppm aromatic protons<br>peak at 9,14 to 9,21 ppm protons in $H_4$ and $H_6$ pyridine |

-continued

| | | | | | |
|---|---|---|---|---|---|
| EXAMPLE 183 | 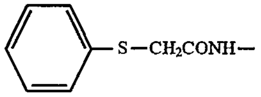 | 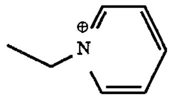<br>$CF_3SO_3^{\ominus}$ | O | $-CO_2H$ | NMR Spectrum (DMSO)<br>peak at 3,72 ppm 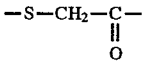<br>peak at 5,55 ppm protons in position 7<br>peak at 7,33 ppm phenyl<br>peak at 8,16 to 8,33 ppm proton in meta of N<br>peak at 8,63 to 8,76 ppm protons in para of N<br>peak at 9,12 to 9,18 ppm protons in ortho of N |
| EXAMPLE 184 | 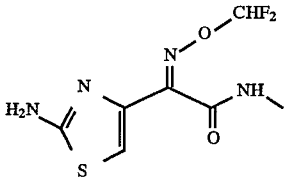<br>$CF_3CO_2H$ | 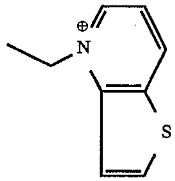<br>$CF_3SO_3^{\ominus}$ | O | $-CO_2H$ | U.V Spectrum (ethanol)<br>Max. 238 nm $E\frac{1}{1}$ = 471 $\Sigma$ = 39 100<br>Infl. 257 nm $E\frac{1}{1}$ = 148<br>Max. 245 nm $E\frac{1}{1}$ = 240 $\Sigma$ = 19 900<br>Infl. 320 nm $E\frac{1}{1}$ = 138<br>U.V. Spectrum (ethanol HCl 0.1/N)<br>Max. 839 nm $E\frac{1}{1}$ = 445 $\Sigma$ = 37 100<br>Infl. 261 nm $E\frac{1}{1}$ = 169<br>Max. 293 nm $E\frac{1}{1}$ = 272 $\Sigma$ = 22 600<br>Infl. 312 nm $E\frac{1}{1}$ = 291 |
| EXAMPLE 185 | 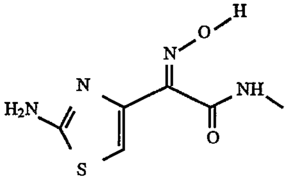<br>$CF_3CO_2H$ | 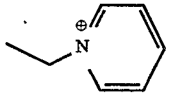<br>$CF_3SO_3^{\ominus}$ | O | $-CO_2H$ | NMR Spectrum (DMSO)<br>double centers on 5,52 and 5,91 ppm: $CH_2-\overset{\oplus}{N}$<br>peak at 5,66 ppm proton in 7<br>peak at 6,77 ppm protons in 5 of thiazole<br>peak at 11,66 ppm OH<br>m.p. = 170° C. (decomposition) |

-continued

EXAMPLE 186

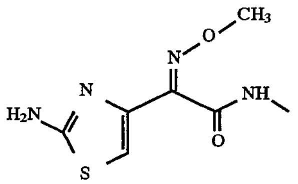

$CF_3CO_2H$

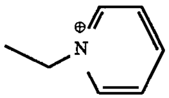

$CF_3SO_3^{\ominus}$

O $-CO_2H$

IR Spectrum (nujol)

1775 $^{cm-1}$ β lactam
1710 $^{cm-1}$, 1675 $^{cm-1}$ other carbonyls
1632 $^{cm-1}$, 1575 $^{cm-1}$, 1540 $^{cm-1}$ regions C═C, C═N
1498 $^{cm-1}$, 1485 $^{cm-1}$ $NH_2$ amide II
m.p. = 170° C. (decomposition)

EXAMPLE 187

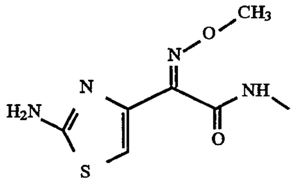

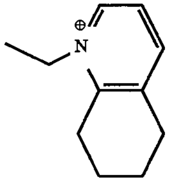

O $-CO_2^{\ominus}$

IR Spectrum red (nujol)

| | | | |
|---|---|---|---|
| 1767 $^{cm-1}$ | β lactam | C═N—OR | 1040 $^{cm-1}$ |
| 1665 $^{cm-1}$ | C═O amide | | |
| 1615 $^{cm-1}$ | $CO_2^{\ominus}$ | | |
| 1590 $^{cm-1}$ | aromatic | | |
| 1540 $^{cm-1}$ | amide II | | |
| 1480 $^{cm-1}$ | thiazole $NH_2$ | | |

Spectre ultra-violet

| | | |
|---|---|---|
| ethanol | Max. 283 nm | Σ = 16 300 |
| ethanol | Max. 225 nm | Σ = 16 700 |
| | Max. 277 nm | Σ = 20 000 |

m.p. >260° C. (decomposition)

EXAMPLE 188

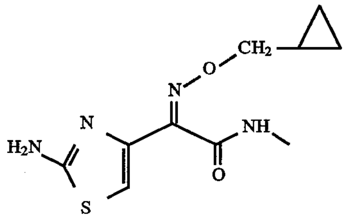

$CF_3CO_2H$

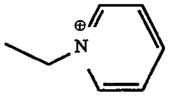

$CF_3SO_3^{\ominus}$

O $-CO_2H$

IR Spectrum (nujol)

| | |
|---|---|
| 1775 $^{cm-1}$ | β lactam |
| 1672 $^{cm-1}$ | amide C═O |
| 1635 $^{cm-1}$ | C═C C═N |

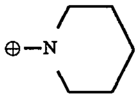

| | |
|---|---|
| 1580 $^{cm-1}$ | amide II |
| 1540 $^{cm-1}$ | thiazole |
| 1500 $^{cm-1}$ | aromatic |
| | $CO_2^{\ominus}$ |

-continued

EXAMPLE 189

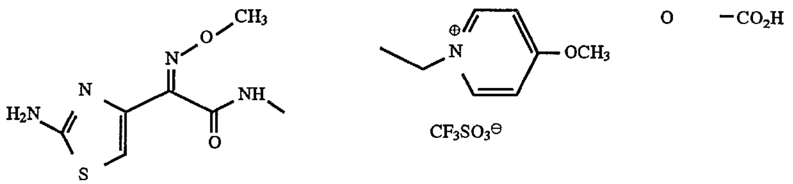

$CF_3CO_2H$ $CF_3SO_3^{\ominus}$

U.V. Spectrum (ethanol)

| | | |
|---|---|---|
| Infl. 256 nm | $E\frac{1}{1} = 194$ | $\Sigma = 15\,100$ |
| Max. 293 nm | $E\frac{1}{1} = 184$ | $\Sigma = 14\,300$ |
| Max. 412 nm | $E\frac{1}{1} = 6$ | |

U.V. Spectrum (ethanol HCl 0, 1/N)

| | | |
|---|---|---|
| Infl. 220 nm | $E\frac{1}{1} = 233$ | |
| Max. 260 nm | $E\frac{1}{1} = 232$ | $\Sigma = 28\,100$ |
| Max. 285 nm | $E\frac{1}{1} = 223$ | $\Sigma = 17\,400$ |
| Infl. 310 nm | $E\frac{1}{1} = 140$ | $\Sigma = 10\,900$ |

m.p. = 186° C. (decomposition)

IR Spectrum (nujol)

| | |
|---|---|
| 1773 $cm^{-1}$ | β lactam |
| 1673 $cm^{-1}$ | amide C=O |
| 1570 $cm^{-1}$ | amide II |
| 1525 $cm^{-1}$ | thiazole |

U.V. Spectrum (ethanol)

| | | |
|---|---|---|
| Max. 242 nm | $E\frac{1}{1} = 374$ | $\Sigma = 28\,700$ |
| Max. 295 nm | $E\frac{1}{1} = 194$ | $\Sigma = 14\,900$ |
| Max. 405 nm | $E\frac{1}{1} = 7$ | |

U.V. Spectrum (ethanol HCl 0, 1/N)

| | | |
|---|---|---|
| Max. 249 nm | $E\frac{1}{1} = 357$ | $\Sigma = 27\,400$ |
| Max. 286 nm | $E\frac{1}{1} = 215$ | $\Sigma = 16\,500$ |
| Infl. 306 nm | $E\frac{1}{1} = 177$ | $\Sigma = 13\,600$ |

m.p. = 170° C.

-continued

| | | | | | |
|---|---|---|---|---|---|
| EXAMPLE 190 | 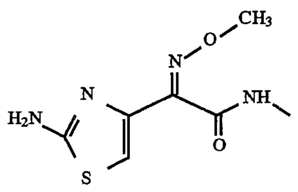<br>$CF_3CO_2H$ | 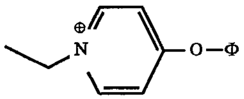<br>$CF_3SO_3^{\ominus}$ | O | $-CO_2H$ | IR Spectrum (nujol)<br>1798 $cm^{-1}$ β lactam<br>1680 $cm^{-1}$ amide C=O<br>3140 $cm^{-1}$, 1640 $cm^{-1}$ } ⊕ 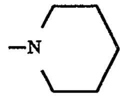<br>1605 $cm^{-1}$, 1530 $cm^{-1}$; 1590 $cm^{-1}$, 1510 $cm^{-1}$; 1550 $cm^{-1}$, 1485 $cm^{-1}$ } aromatic, conjugated system $COO^{\ominus}$, amide II, thiazole<br>U.V. Spectrum (ethanol)<br>Max. 232 nm $E\frac{1}{1} = 329$ $\Sigma = 27\ 300$<br>Max. 247 nm $E\frac{1}{1} = 190$ $\Sigma = 15\ 800$<br>Max. 413 nm $E\frac{1}{1} = 8$<br>U.V. Spectrum (ethanol HCl 0, 1/N)<br>Infl. 233 nm $E\frac{1}{1} = 278$<br>Max. 250 nm $E\frac{1}{1} = 288$ $\Sigma = 23\ 900$<br>Infl. 280 nm $E\frac{1}{1} = 227$<br>Infl. 308 nm $E\frac{1}{1} = 181$ $\Sigma = 13\ 400$<br>m.p. = 190° C. |
| EXAMPLE 191 optically active (6S, 7S) | 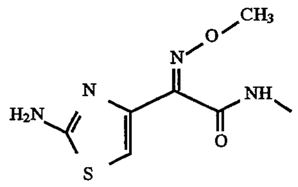<br>$CF_3CO_2H$ | 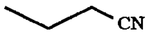 | O | 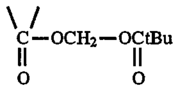 | Rf = 0,4 (eluant-acetate of ethyl) |

EXAMPLE 192

Trifluoromethane sulfonate of (6S,7S, ΔZ) 7-[[7-[[(2-amino-4-thiazolyl)-[[2-(difluoromethylthio)-ethoxyimino] acetamido]-2-carboxy-8-oxo-4-thia-1-azabicyclo[4,2,0]oct-2-en-3-yl]methyl]thieno][2,3-b]pyridinium (trifluoroacetate)

STEP A: p-toluene sulfonate of difluoromethyl thioethyl

Under an inert atmosphere, 3 g of lithium aluminum hydride and 20 ml of tetrahydrofuran were mixed together and then at 0° C. over about one hour, a solution of 6.3 g of difluoromethyl-thioacetic acid in 20 ml of tetrahydrofuran was added with stirring at 5° C. for one hour, and at 20° C. for two hours. At 0° C., a 2N aqueous solution of hydrochloric acid was introduced dropwise to destroy excess hydride and after water and methylene chloride were added with stirring, the decanted aqueous phase was extracted with methylene chloride. The extracts were washed with a saturated aqueous solution of sodium chloride, dried and evaporated to dryness b7 distilling under reduced pressure and dried under a good vacuum to obtain 2 g of (an alcohol product) which was used as is for the next step.

Under an inert atmosphere, 2 g of the said alcohol, and 8 ml of pyridine were mixed together and at 5° C., 3.1 g of tosyl chloride were added in small fractions. The mixture was stirred at +5° C. for one hour and was then poured into a 2M aqueous solution of hydrochloric acid (pH 1) and extracted with ethyl acetate. The extracts were washed with a 2N aqueous solution of hydrochloric acid, dried, and evaporated to dryness by distilling under reduced pressure. The residue was chromatographed over silica and eluted with methylene chloride to obtain 2.7 g of p-toluene sulfonate of difluoromethyl thioethyl which was used as is for alkylation of the oxime.

STEP B: 2-[(2-tritylamino-thiazol-4-yl)-2-(difluoromethylthio)-ethoxy]imino acetic acid (Z)

Under an inert atmosphere, 3.5 g of-an oxime of the formula

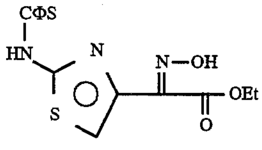

10 ml of dimethylformamide and 5 g of sodium hydride were stirred at +5° C. for ten minutes and then 2.7 g of the product of Step A were added with stirring for 90 minutes at 30° C. The reaction mixture was poured into a mixture of water and ice and adjusted to a pH of 6 by addition of 0.5 M aqueous solution of monosodium phosphate and extracted with ether. The extracts were washed with a saturated aqueous solution of sodium chloride, dried, and evaporated to dryness by distilling under reduced pressure. The 2.9 g of residue were chromatographed over silica under nitrogen pressure and eluted with methylene chloride to obtain 445 mg of the ethyl ester of the above acid.

Under an inert atmosphere, 400 mg of the ester, 10 ml of a mixture of dioxane and ethanol (8/2) and 1.4 ml of an N aqueous solution of sodium hydroxide were stirred at 20° C. for 16 hours. After bringing to 0° C., water and a N aqueous solution of hydrochloric acid were added and the precipitate formed was filtered off and dissolved in 50 ml of methylene chloride. After decanting, the methylene chloride solution was dried and evaporated to dryness. 10 ml of isopropyl ether were added slowly, and the precipitate formed was separated, washed, dried to obtain 324 mg of 2-[(2-tritylamino-thiazol-4-yl)-2-(difluoromethylthio)-ethoxy] imino acetic acid (Z).

| U.V. Spectrum (ethanol) | | | |
|---|---|---|---|
| Inflexion | 234 nm | $E_1^1 = 382$ | ε = 20,300 |
| Inflexion | 264 nm | $E_1^1 = 222$ | ε = 12,000 |
| Inflexion | 275 nm | $E_1^1 = 190$ | |
| U.V. Spectrum (ethanol + 0.1 N HCl) | | | |
| Inflexion | 270 nm | $E_1^1 = 225$ | |
| Max | 276 nm | $E_1^1 = 261$ | ε = 14,100 |
| Inflexion | 285 nm | $E_1^1 = 232$ | |
| NMR Spectrum ($CDCl_3$) in ppm | | | |
| H of $CH_2S$ | | 3.02–3.10–3.19 | |
| H of $OCH_2$ | | 4.40–4.48–4.57 | |
| H mobile | | 3.89 | |
| H of $CHF_2$ | | 6.33–6.97–7.59 | |
| $H_5$ thiazole syn | | 6.67 | |
| H of the trityl | | 7.33 | |

STEP C: 1,1-dimethylethyl 7-[[[(2-[(difluoromethyl)-thio] ethoxyimino]-2-[triphenylmethylamino]-4-thiazolyl]-acetamido-3-(hydroxymethyl)-8-oxo-4-thia-1-azabicyclo[4,2,0]oct-2-en-2-carboxylate Under an inert atmosphere, 360 mg of the product of Step B, 3 ml of acetone, 77 μl of triethylamine and 106 mg of tosyl chloride were stirred at 20° C. for 45 minutes. Then, a solution of 143 mg of 1,1-dimethylethyl (6S,7S) 7-amino-3-hydroxymethyl-8-oxo-4-thia-1-azabicyclo[4,2,0]oct-2-en 2-carboxylate in 1 ml of an M aqueous solution of sodium bicarbonate, 1 ml of water, and 1 ml of acetone was added all at once with stirring at 20° C. for 30 minutes. The acetone was eliminated by distillation and water and methylene chloride were added followed by stirring, decanting and extracting with methylene chloride. The extracts were washed with a saturated aqueous solution of sodium chloride, then dried and concentrated to dryness by distilling under reduced pressure. The 400 mg of residue were chromatographed over silica under nitrogen pressure and eluted with a mixture of methylene chloride and ethyl acetate (9/1) to obtain 259 mg of 1,1-dimethylethyl 7-[[[(2-[(difluoromethyl)thio]ethoxyimino]2-[triphenylmethylamino]-4-thiazolyl]-acetamido-3-(hydroxymethyl)-8-oxo-4-thia-1-azabicyclo[4,2,0]oct-2-en-2-carboxylate

| NMR Spectrum ($CDCl_3$) in ppm | |
|---|---|
| H of tBu | 1.47 |
| H of $CH_2S$ | 3.09–3.17–3.24 |
| H of $CH_2O$ | 4.43–4.5 |
| H of $CH_2OH$ | { 3.82–3.95<br>4.5–4.63 |
| $H_6$ | 4.04–4.09 |
| $H_7$ beta lactam cis | 5.43–5.5 |
| H of $SCHF_2$ | 6.28–6.89–7.50 |
| $H_5$ thiazole syn | 6.71 |
| H of NH $C\Phi_3$ | 7.04 |
| H of the trityl | 7.33 |

STEP D: Trifluoromethane sulfonate of (6S, 7S ΔZ) 7-[[7-[[(2-amino-4-thiazolyl)-[2-(difluoromethylthio)-ethoxy-imino]-acetamido]-2-carboxy-8-oxo,-,4-thia-1-azabicyclo [4,2,0]oct-2-en-3-yl]-methyl]-thieno] [2,3-b]pyridinium (trifluoroacetate)

Under an inert atmosphere, 121 mg of the product of Step C, 1.2 ml of methylene chloride and 80 mg of thieno[2,3-b]pyridine were mixed together and then, over about 10 minutes at −70° C., 1.06 ml of a 4.2% by volume of a solution of trifluoromethane sulfonic anhydride in methylene chloride was added with stirring at −70° C. for 30 minutes. After concentrating to dryness under reduced pressure at −40° C., the residue was chromatographed over silica under nitrogen pressure and eluded with, a mixture of methylene chloride and ethyl acetate (8/2), then with a mixture of methylene chloride and methanol (9/1) to obtain 107 mg of the product.

Under inert atmosphere, 107 mg of the said product and 440 ul of trifluoroacetic acid with 10% of water were mixed together, and stirred for two hours at 20° C. 8 ml of ether were added slowly with stirring and than the precipitate formed was separated, washed and dried to obtain 72 mg of trifluoromethane sulfonate of (6S, 7S, Z) 1,1-dimethylethyl 7-[[[(2-[(difluoromethyl)thio]-ethoxyimino]-2-[triphenylmethylamino]-4-thiazolyl]acetamido-3-(hydroxymethyl) -8-oxo-4-thia-1-azabicyclo[4,2,0]oct-2-en-2-carboxylate.

| UV Spectrum (ethanol + HCl 0.1N) | | |
|---|---|---|
| Max. | 240 nm $E_1^1$ = 435 | ε = 32,700 |
| Max. | 293 nm $E_1^1$ = 255 | ε = 22,700 |

| NMR Spectrum (dimethylsulfoxide) in ppm | |
|---|---|
| H of $CH_2S$, $CH_2O$ | 3.05–322 |
| $H_6$ | 4.03–4.18 |
| $H_7$ | 5.68 |
| H of $CH_2$— 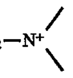 | 6.10 (d,d; J = 15 Hz) |
| $H_4$ | 7.91 (d; J = 6 Hz) |
| $H_6$ | 8.20 (m) |
| $H_3$ | 8.29 (m) |
| $H_5$ | 9.13 (d; J = 5 Hz) |
| $H_7$ | 9.25 (d; J = 5 Hz) |

EXAMPLE 193

Trifluoromethane sulfonate of (6S, 7S, ΔZ) 7-[[7-[[(2-amino-4-thiazolyl) [[2-(3-[[1,3-bis(methoxymethyl) 2,4-dioxo-1,2,3,4-tetrahydro-6-pyrimidinyl]methyl]amino]2-methyl 3-oxo-propoxyimino]acetamido]2-carboxy-8-oxo-4-thia 1-azabicyclo[4,2,0]oct-2-en-3-yl]methyl]thieno]2,3-b] pyridinium (trifluoroacetate)

STEP A: [(2,4-dioxo)-[1,3-bis(methoxymethyl-1,2,3,4-tetrahydro)-1,6-chloromethyl]-pyrimidine Under an inert atmosphere, 10 g of 6-chloro-methoxymethyl, 150 ml of dimethylformamide and 6.3 g of sodium hydride at 50% suspension in vaseline oil were stirred at +5° C. for twenty minutes and then over about five minutes, 40 ml of chloromethoxymethane were added with stirring at 20° C. for thirty minutes. Then, the reaction mixture was poured into a water and ice mixture, and the pH was adjusted to 7 by addition of a saturated aqueous solution of sodium bicarbonate. Extraction was effected with ether and the extracts were washed with a saturated aqueous solution of sodium bicarbonate, dried and concentrated to dryness by distilling under reduced pressure. The 8.3 g of residue were chromatographed over silica under nitrogen pressure and eluted with a mixture of methylene chloride and ethyl acetate (8/2) to obtain 3.7 g of [(2,4-dioxo)-[1,3-bis (methoxymethyl-1,2,3,4-tetrahydro)-1,6-chloromethyl]-pyrimidine.

| IR Spectrum (chloroform) in $cm^{-1}$ | |
|---|---|
| C=0 | 1720–1678 (F) |
| C=C | 1636 |
| Absence of NH | |
| Presence of methoxy. | |

STEP B: (6-phthalimidylmethyl) (2,4-dioxo) [1,3-bis (methoxymethyl)][1,2,3,4-tetrahydro]pyrimidine Under an inert atmosphere, 2 g of the product of Step A, 10 ml of dimethylformamide and 1.9 g of potassium phthalimide were stirred at 70° C. for 90 minutes and then was cooled. The reaction mixture was poured into a water and ice mixture and after stirring, extraction was done with methylene chloride. The extracts were washed by an N aqueous solution of sodium hydroxide, then by a saturated aqueous solution of sodium chloride, dried, and concentrated to dryness by distilling under reduced pressure, 60 ml of ether were added slowly with stirring and the precipitate formed was isolated, washed and dried to obtain 2 g of (6-phthalimidylmethyl)(2,4-dioxo) [1,3-bis (methoxymethyl)][1,2,3,4-tetrahydro]pyrimidine.

| U.V. Spectrum (ethanol) | | |
|---|---|---|
| Max. | 219 nm $E_1^1$ = 1,439 | ε = 51,700 |
| Inflexion | 230 nm $E_1^1$ = 528 | |
| Max. | 236 nm $E_1^1$ = 350 | ε = 12,600 |
| Max. | 262 nm $E_1^1$ = 261 | ε = 9,400 |
| Inflexion | 293 nm $E_1^1$ = 64 | |
| Inflexion | 300 nm $E_1^1$ = 55 | |

| NMR Spectrum ($CDCl_3$) in ppm | |
|---|---|
| H of $OCH_3$ | 2.31 and 2.34 |
| H of $CH_2$— 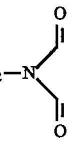 | 3.244–3.255 |
| H of $CH_2O$ | 3.60 and 3.69 |
| H of phthalimide | 5.16 to 5.42 |
| Other aromatic H | 3.73 |

STEP C [2,4-dioxo-1,3-bis-(methoxymethyl)-1,2,3,4-tetrahydro-6-aminomethyl]-pyrimidine Under an inert atmosphere, 2 g of the product of Step B and. 20 ml of methanol were mixed-together, and over about 35 minutes, 6.6 ml of an M solution of hydrazine hydrate in methanol were added dropwise followed by stirring at 20° C. for forty minutes followed by cooling to 5° C. The pH was brought to 2 with an N aqueous solution of hydrochlorice acid and stirring was continued at 20° C. for 150 minutes. Then, the precipitate formed was separated and washed with water. The filtrate was evaporated to dryness by distilling under reduced pressure and the pH was brought to 8 by adding a saturated aqueous solution of sodium bicarbonate, followed by concentrating to ¾ volume by distilling. The precipitate formed was separated, and the filtrate was evaporated to dryness by distilling under reduced pressure, then dried. Ethyl acetate was added with stirring, filtering, and concentrating the filutrate to dryness by distilling under reduced pressure. The dry extract was taken up for the last time with 30 ml of ether and stirred and the precipitate formed was separated and dried to obtain 800 mg of [2,4-dioxo-1,3-bis-(methoxymethyl)-1,2,3,4-tetrahydro-6-aminomethyl]-pyrimidine.

| NMR Spectrum ($CDCl_3$) in ppm | |
|---|---|
| H of $NH_2$ | 5.6 |
| H of the $OCH_3$ | 3.42 and 3.44 |
| H of $CH_2NH_2$ | 3.24 |
| H of $—CH_2O$ | 5.39 |
| H aromatics | 5.93 |

STEP D: [(2-tritylamino-4-thiazolyl][[2-[3-[[1,3-bis (methoxymethyl)-2,4-dioxo-1,2,3,4-tetrahydroxy-6-pyrimidinyl]methyl]amino]-2-methyl-3-oxo-propoxy]-imino acetic acid Under an inert atmosphere, 500 mg of acid of the formula

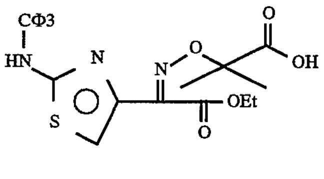

5 ml of tetrahydrofuran, and 144 mg of hydroxy benzotriazole were mixed together and then, at +5° C. 165 μl of diisopropylcarbodiimide were added all at once followed by stirring at +5° C.±10° for 70 minutes. All at once at +10° C., a solution of 240 mg of 1,3-bis(methoxymethyl) 2,4-dioxo 1,2,3,4-tetrahydropyrimidine in 5 ml of tetrahydrofurn was added with stirring at 20° C. for forty-five minutes. The solvent was eliminated by distilling under reduced pressure, then water and an M aqueous solution of sodium bicarbonate and ethyl acetate were added with stirring followed by decanting and extracting with ethyl acetate. The extracts were washed with a saturated aqueous solution of sodium chloride, then dried and concentrated to dryness by distilling under reduced pressure. The 900 mg of residue were chromatographed over silica under nitrogen pressure and eluted with a mixture of methylene chloride and ethyl acetate (75/25) to obtain 451 mg of the expected product Which was used as is for the saponification of the ethyl ester.

Under an inert atmosphere, the 451 mg of ethyl ester, 4 ml of tetrahydrofuran and 2 ml of ethanol were mixed together and then at +5° C. 1.2 ml of an N aqueous solution of sodium hydroxide were added dropwise followed by stirring between 32° and 42° C. for two hours, followed by cooling. An N aqueous solution of hydrochloric acid was added up to pH 3–4, and the solvents were eliminated by distilling under reduced pressure. Water, an N aqueous solution of hydrochloric acid and ethyl acetate were added to the residue with stirring followed by decanting and extracting with ethyl acetate. The extracts were washed with a saturated aqueous solution of sodium chloride, dried and concentrated to dryness by distilling under reduced pressure. 2 ml of ether were added slowly to the residue and the precipitate formed was isolated, washed, dried to obtain 350 mg of [(2-tritylamino-4-thiazolyl][[2-[3-[[1,3-bis(methoxymethyl)-2,4-dioxo-1,2,3,4-tetrahydro-6-pyrimidinyl]methyl]amino]-2-methyl-3-oxo-propoxy]-imino acetic acid.

| UV Spectrum (ethanol) | | | |
|---|---|---|---|
| Inflexion | 238 nm | $E_1^1 = 257$ | |
| Max. | 260 nm | $E_1^1 = 224$ | $\epsilon = 16{,}300$ |
| Inflexion | 267 nm | $E_1^1 = 218$ | |
| Inflexion | 297 nm | $E_1^1 = 87$ | |

-continued

| UV Spectrum (ethanol + 0.1 N HCl) | | | |
|---|---|---|---|
| Max. | 267 nm | $E_1^1 = 240$ | $\epsilon = 17{,}400$ |
| Inflexion | 287 nm | $E_1^1 = 171$ | |

STEP E: 1,1-dimethylethyl (6S,7S, ΔZ) 7-[[[[2-[[[1,3-bis (methoxymethyl) 2,4-dioxo 1,2,3,4-tetrahydro 6-pyrimidinyl]methyl]amino]2-methyl 3-oxo propoxy] imino][2-(triphenylmethyl)amino]8-oxo-4-thia 1-azabicyclo[4,2,0]oct-2-en 2-carboxylate Under an inert atmosphere, 350 mg of the product of Step D 3 ml of acetone, 66 μl of triethylamine and 191 mg of tosyl chloride were mixed together and stirred at 20° C. for 70 minutes. A solution of 1,1-dimethylethyl (6S, 7S, ΔZ) 7-amino-3-hydroxy-methyl-8-oxo-4-thia-1-azabicyclo[4,2,0]oct-2-en-2-carboxylate in 0.5 ml of an M aqueous solution of sodium bicarbonate, 0.5 ml of water and 0.5 ml of acetone were added all at once and stirred at 20° C. for 105 minutes. The acetone was eliminated by distilling under reduced pressure and water and methylene chloride were added with stirring, followed by decanting and extracting with methylene chloride. The extracts were washed with a saturated aqueous solution of sodium chloride, then dried and concentrated to dryness by distilling under reduced pressure. The 350 mg of residue were chromatographed over silica under nitrogen pressure and eluted with ethyl acetate to obtain 1,1-dimethylethyl (6S, 7S ΔZ) 7-[[[2-[[[1,3-bis (methoxymethyl) 2,4-dioxo 1,2,3,4-tetrahydro 6-pyrimidinyl]methyl]amino]2-methyl 3-oxo propoxy] imino][2-(triphenylmethyl)-amino]-8-oxo-4-thia-1-azabicyclo[4,2,0]oct-2-en-2-carboxylate.

| UV Spectrum (ethanol) | | | |
|---|---|---|---|
| Inflexion | 240 nm | $E_1^1 = 237$ | |
| Inflexion | 258 nm | $E_1^1 = 192$ | $\epsilon = 19{,}100$ |
| Max. | 302 nm | $E_1^1 = 153$ | $\epsilon = 15{,}200$ |
| UV Spectrum (ethanol + 0.1 N HCl) | | | |
| Max. | 268 nm | $E_1^1 = 189$ | $\epsilon = 18{,}800$ |
| Max. | 295 nm | $E_1^1 = 195$ | $\epsilon = 19{,}400$ |
| NMR Spectrum ($CDCl_3$) in ppm | | | |
| H of tBu | | | 1.52 |
| H of $OCH_3$ | | | 3.24 and 3.34 |
| H of $CH_2O$ | | | 5.18 and 5.28 |
| H of pyrimidine | | | 5.97 |
| $H_7$ lactam cis | | | 5.46 |
| $H_5$ thiazole "syn" | | | 6.74 |
| H of trityl | | | 7.38 |

STEP F: Trifluoromethane sulfonate of (6S, 7S, ΔZ) 7-[[7-[[(2-amino-4-thiazolyl) [[2-(3-[[1,3-bis-(methoxymethyl)-2,4-dioxo-1,2,3,4-tetrahydro-6-pyrimidinyl]-methyl]-amino]-2-methyl 3-oxo-propoxyimino]-acetamido]-2-carboxy-8-oxo-4-thia-1-azabicyclo[4,2,0]oct-2-en-3-yl]-methyl-thieno][2,3-b]pyridinium (trifluoroacetate)

Under an inert atmosphere, 150 mg of the product of E, 3 ml of methylene chloride and 81 mg of thieno[2,3-b] pyridine were mixed together and then at −70° C., over about ten minutes, 1 ml of a 5% by volume solution of trifluoromethane sulfonate in methylene chloride was introduced with stirring at −70° C. for fifteen minutes. After allowing the temperature to rise from −70° to +5° C. over about 20 minutes, the reaction mixture was concentratted to dryness under reduced pressure and the residue was chromatographed over silica under nitrogen pressure and eluted with a mixture of methylene chloride and methanol (9/1) to obtain 70 mg of the expected product.

Under an inert atmosphere, the said 70 mg and 280 μl of trifluoroacetic acid with 10% of water were mixed together and stirred at 20° C. for two hours. Then, 3 ml of ether were added slowly with stirring and the precipitate formed was separated, washed, dried to obtain 45 mg of an incompletely deblocked product.

The 45 mg of product and 600 ul of 66% aqueous formic acid were nixed together and stirred at 60° C. for two hours. 1 ml of ethanol was added, followed by concentrating to dryness by distilling under reduced pressure. After adding 1 ml of ethanol and stirring, the crystals formed were separated, washed, dried, and 12 mg of trifluoromethane sulfonate of (6S, 7S, ΔZ) 7-]]7-[[(2-amino-4-thiazolyl) [[2-(3-[[1,3-bis-(methoxymethyl)-2,4-dioxo-1,2,3,4-tetrahydro-6-pyrimidinyl]-methyl]-amino]-2-methyl-3-oxo-propoxyimino]-acetamido]-2-carboxy-8-oxo-4-1-azabicyclo[4,2,0]oct-2-en-3-yl]-methyl]-thieno]2,3-b]-pyridinium-(trifluoroacetate).

| | | |
|---|---|---|
| UV Spectrum (ethanol) | | |
| Max. | 239 nm $E_1^1$ = 406 | ε = 40,200 |
| Inflexion | 260 nm $E_1^1$ = 193 | ε = 19,100 |
| Max. | 295 nm $E_1^1$ = 193 | ε = 19,100 |
| UV Spectrum (ethanol + 0.1 N HCl) | | |
| Max. | 241 nm $E_1^1$ = 379 | ε = 36,700 |
| Inflexion | 260 nm $E_1^1$ = 225 | ε = 22,300 |
| Max. | 292 nm $E_1^1$ = 221 | ε = 21,900 |
| NMR Spectrum (dimethylsulfoxide) in ppm | | |
| No trityl, no tert-butyl | | |
| $H_7$ beta lactam | | 5.50 |
| H of $CH_2-N^{\oplus}$ | | 5.74 and 6.15 |
| $H_5$ thiazole | | 6.54 |
| H of $NH_2$ | | about 7.23 |

EXAMPLE 194

Trifluoromethane sulfonate of (6S,7S ΔZ) 7-[[2-[[(2-amino-4-thiazolyl) [[2-[[1,3-bis(methoxymethyl)-2,4-dioxo-1,2,3,4-tetrahydro-6-pyrimidinyl]-methyl]-amino]-2-oxo-ethoxyimino]-acetamido]-2-carboxy-8-oxo-4-thia-1-azabicyclo[4,2,0]oct-2-en-3-yl]-methyl]-thieno][2,3-b] pyridinium (trifluoroacetate)

STEP A: [(2-tritylamino-4-thiazolyl][[2-[(1,3-bis (methoxymethyl)-2,4-dioxo-1,2,3,4-tetrahydro-6-pyrimidyl)-methylamino)-2-oxo-ethoxy]-imino-acetic acid (Z)

Under an inert atmosphere, 500 mg of acid of the formula

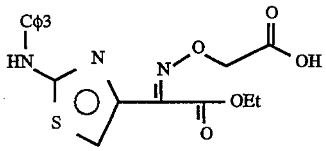

5 ml of tetrahydrofuran and 144 mg of hydroxy benzotriazole were mixed together, and at +5° C., 165 μl of diisopropylcarbodiimide were added all at once followed by stirring at +10° C. for 70 minutes. At +10° C., a solution of 240 mg of 1,3-methoxymethyl-2,4-dioxo-6-aminomethyl-1,2,3,4-tetrahydro-pyrimidine in 5 ml of tetrahydrofuran were added all at one followed by stirring at 20° C. for thirty minutes., followed by concentrating to dryness by distilling under reduced pressure. Water, an M aqueous solution of sodium bicarbonate and ethyl acetate were added with stirring followed by decanting and extracting with ethyl acetate. The extracts were washed with a saturated aqueous solution of sodium chloride, dried, and concentrated to dryness by distilling under reduced pressure. The 700 mg of residue were chromatographed over silica under nitrogen pressure, and eluted with a mixture of methylene chloride and ethyl acetate (7/3) to obtain 500 mg of the expected product which was used as is for the saponification of the ethyl ester.

Under an inert atmosphere, the 500 mg of product, 4 ml of tetrahydrofuran and 1.2 ml of N sodium hydroxide were mixed together and stirred at 40° C. for 45 minutes and cooled. An N aqueous solution of hydrochloric acid was added followed by concentrating to dryness by distilling under reduced pressure. Water, an N aqueous solution of hydrochloric acid and ethyl acetate were added with stirring followed by decanting and extracting with ethyl acetate. The extracts were washed with a saturated aqueous solution of sodium chloride, dried, and concentrated to dryness by distilling under reduced pressure. 2 ml of etcher were added slowly with stirring and the precipitate formed was separated, washed, dried to obtain 370 mg of [(2-tritylamino-4-thiazoly][[2-[(1,3-bis(methoxymethyl)-2,4-dioxo 1,2,3,4-tetrahydro-6-pyrimidyl)-methylamino)-2-oxo-ethoxy]-imino acetic acid (Z) which was used as is for the coupling reaction.

STEP B: 1,1-dimethylethyl (6S,7S ΔZ) 7-[[[[2-[[[1,3-bis (methoxymethyl-2,4-dioxo-1,2,3,4-tetrahydro-6-pyrimidinyl]-methylamino]2-oxo-ethoxyimino]-2-(triphenylmethyl)-amino]-4-thiazolyl]-acetamido]-3-hydroxymethyl]-8-oxo-4-thia-1-azabicyclo[4,2,0]oct-2-en-2-carboxylate Under an inert atmosphere, 570 mg of the product of Step A, 5 ml of acetone, 74 μl of triethylamine and 101 mg of tosyl chloride were mixed together and stirred at 20° C. for 45 minutes. A solution of 121 mg of 1,1-dimethylethyl (6S,7S ΔZ) 7-amino-3-hydroxymethyl-8-oxo-4-thia-1-azabicyclo[4,2,0]oct-2-en-2-carboxylate, 0.5 ml of an M aqueous solution of sodium bicarbonate, 0.5 ml of water and 0.5 ml of acetone were added all at once followed by stirring at 20° C. for 45 minutes. The acetone was eliminated by distilling under reduced pressure and then water and methylene chloride were added to the residue with stirring followed by decanting and extracting with methylene chloride. The extracts were washed with a saturated aqueous solution of sodium chloride, then dried and concentrated to dryness by distilling under reduced pressure. The 300 mg of residue were chromatographed over silica under nitrogen pressure and eluted with ethyl acetate to obtain 1.0 mg of 1,1-dimethylethyl (6S,7S ΔZ) 7-[[[[2-[[[1,3-bis (methoxymethyl) 2,4-dioxo-1,2,3,4-tetrahydro-6-pyrimidinyl]-methylamino]2-oxo-ethoxyimino]-2-(triphenylmethyl)-amino]-4-thiazolyl]-acetamido]-3-hydroxymethyl]-8-oxo-4-thia-1-azabicyclo[4,2,0]oct-2-en-2-carboxylate.

| | | | |
|---|---|---|---|
| UV Spectrum (ethanol) | | | |
| Inflexion | 242 nm | $E_1^1$ = 255 | |
| Max. | 304 nm | $E_1^1$ = 164 | ε = 15,700 |
| UV spectrum (ethanol + 0.1 N HCl) | | | |
| Max. | 267 nm | $E_1^1$ = 212 | ε = 20,200 |
| Max. | 294 nm | $El_1^1$ = 203 | ε = 19,400 |
| NMR Spectrum ($CDCl_3$) in ppm | | | |
| H of tBu | | | 1.5 |
| H of $CH_2S$ | | | 3.06 |

-continued

| | |
|---|---|
| H of $OCH_3$ | 3.33–3.38 |
| H of NH—CH and $CH_2OH$ | 3.78 to 4.6 |
| H of $OCH_2$ C=0 | 4.79 |
| H of $CH_2O$ | 5.26–5.31 |
| H of pyrimidine | 5.86 |
| $H_5$ thiazole | 6.71 |
| H of $C\emptyset_3$ | 7.27 |

STEP C: Trifluoromethane sulfonate of (6S,7S ΔZ) 7-[[7-[[(2-amino-4-thiazolyl) [[2-[[1,3-bis(methoxymethyl)-2,4-dioxo-1,2,3,4-tetrahydro-6-pyrimidinyl)-methyl]-amino]-2-oxo-ethoxyimino]-acetamido]-2-carboxy-8-oxo-4-thia 1-azabicyclo[4,2,0]oct-2-en-3-yl]-methyl]-thieno][2,3-b] pyridinium (trifluoroacetate)

Under an inert atmosphere, 130 mg of the product of Step B, 5 ml of methylene chloride and 74 mg of thieno[2,3-b] pyridine were mixed together, and then 1 ml of a 5% of volume solution of trifluoromethane sulfonic anhydride in methylene chloride was added at −70° C. over about fifteen minutes with stirring at −70° C. for ten minutes, and from −70° C. to +4° C. over fifteen minutes. After concentrating to dryness by distilling under reduced pressure, the residue was chromatographed over silica under nitrogen pressure and eluted with a mixture of methylene chloride and methanol (9/1) to obtain 100 mg of the expected product.

Under an inert atmosphere, the 100 mg of product and 0.5 ml of trifluoroacetic acid were mixed together and stirred at 20° C. for 150 minutes. 5 ml of ether were added slowly with stirring and the precipitate formed was separated, washed and dried to obtain 60 mg of product incompletely deblocked.

The 60 mg of product were taken up in 1 ml of a 66% aqueous solution of formic acid, and stirred at 20° C. for two hours. 1 ml of ethanol was added, followed by concentrating to dryness by distilling under reduced pressure. A further 1 ml of ethanol was added, and after stirring, the crystals formed were separated, washed and dried to obtain mg of trifluoromethane sulfonate of (6S, 7S ΔZ) 7-[[7-[[(2-amino-4-thiazolyl)[[2-[[1,3-bis(methoxymethyl)-2,4-dioxo-1,2,3,4-tetrahydro-6-pyrimidinyl)-methyl]-amino]-2-oxo-ethoxyimino]-acetamido]-2-carboxy-8-oxo-4-thia 1-azabicyclo[4,2,0]oct-2-en-3-yl]-methyl]-thieno][2,3-b] pyridinium (trifluoroacetate).

| UV Spectrum (ethanol) | | |
|---|---|---|
| Max. | 239 nm $E_1^1$ = 379 | ε 36,500 |
| Inflexion | 260 nm $E_1^1$ = 178 | |
| Max. | 297 nm $E_1^1$ = 182 | ε = 17,500 |
| UV Spectrum (ethanol + 0.1 N HCl) | | |
| Max. | 241 nm $E_1^1$ = 354 | ε = 34,000 |
| Inflexion | 260 nm $E_1^1$ = 211 | ε = 20,300 |
| Max. | 293 nm $E_1^1$ = 202 | ε 19,400 |
| NMR Spectrum (dimethylsulfoxide) in ppm Absence of tert-butyl and trityl | | |
| H of $CH_2S$ | 3.07 and 3.38 | |
| H of $OCH_3$ | 3.27 and 3.29 | |
| H of $N-CH_2-O$ | 5.0 and 5.19 | |
| H of $NH-CH_2$ | 4.38 | |
| H of $OCH_2-C(=O)$ | 4.57 and 4.69 | |
| $H_5$ pyrimidine | 5.63 | |
| $H_7$ | 5.73 | |
| H of $CH_2-N$ | 6.04 and 6.7 | |

-continued

| | |
|---|---|
| $H_5$ thiazole syn | 6.96 |
| H aromatics | 7.91–8.18–8.31–9.24–9.26. |

EXAMPLE 195

Trifluoromethane sulfonate of (6S,7S ΔZ) 4-[[7-[[(2-amino-4-thiazolyl) [(fluoromethoxy)imino]-acetamido]2-carboxy-8-oxo-4-thia-1-azabicyclo [4,2,0]oct-2-en-3-yl]methyl]-thieno][3,2-b]pyridinium (trifluoroacetate)

Under an inert atmosphere, 175 mg of 1,1-dimethylethyl (6S,7S ΔZ) 3-hydroxymethyl 7-[3-[7-[(2-triphenyl methylamino.-4-thiazolyl][(2-fluoromethyloxy)-acetamido]-amino]-8-oxo-4-thia 1-azabicyclo[4,2,0]oct-2-en-3-yl]-2-carboxylate, 3 ml of methylene chloride and 132 mg of thieno[3,2-b]pyridine were mixed together, and at −70° C. over about 10 minutes, 1.7 ml of a 5% by volume solution of trifluoromethane sulfonic anhydride in methylene chloride were added followed by stirring at −70° C. for 15 minutes, and from −70° C. to −40° C. for 15 minutes. The residue, after concentrating to dryness by distilling under reduced pressure finest at −40° C., then at +20° C. was chromatographed over silica under nitrogen pressure and eluted with a mixture of methylene chloride and methanol (9/1) to obtain 200 mg of the expected product.

Under an inert atmosphere, the 200 mg of product, 0.8 ml of trifluoroacetic acid, and 80 μl of water were mixed together and stirred at 20° C. for two hours. 10 ml of ether were added slowly with stirring and the precipitate formed was separated, washed and dried to obtain 28 mg of trifluoromethane sulfonate of (6S,7S (Z) 4-[[7-[[(2-amino-4-thiazolyl)-[(fluoromethoxy)-imino]-acetamido]2-carboxy-8-oxo-4-thia-1-azabicyclo[4,2,0]oct-2-en-3-yl]methyl]-thieno-[3,2-b]pyridinium (trifluoroacetate).

| UV Spectrum (ethanol) | | | |
|---|---|---|---|
| Max. | 236 nm | $E_1^1$ = 465 | ε = 36,300 |
| Max. | 297 nm | $E_1^1$ = 216 | ε = 16,900 |
| UV Spectrum (ethanol + 0.1 N HCl) | | | |
| Max. | 238 nm | $E_1^1$ = 452 | ε = 35,300 |
| Max. | 295 nm | $E_1^1$ = 236 | ε = 12,400 |
| Inflexion | 316 nm | $E_1^1$ = 165 | |
| NMR Spectrum (dimethylsulfoxide) in ppm | | | |
| H of $CH_2S$ cyclic | 3.02–3.27(m) | | |
| $H_6$ | 4.04(m) | | |
| $H_7$ | 5.65(m) | | |
| H of $CH_2F$ | 5.86 | | |
| H of $CH_2N^{\oplus}$ | 5.99 and 6.25 (J=14Hz) | | |
| $H_5$ thiazole | 6.96 | | |
| $H_6$ | 8.12(t; J=7Hz) | | |
| $H_3$ and $CH_2$ | 8.24(d; J=6Hz) 8.94(d; J=6Hz) | | |
| $H_5$ | 9.20(d; J=6Hz) | | |
| $H_7$ | 9.43(d; J=8Hz) | | |
| H of NH—C— | 9.38(d; J=8Hz) | | |
| H mobile | 7.24. | | |

EXAMPLE 196

Trifluoromethane sulfonate of (6S, 7S ΔZ) 1-[[7-[[(2-amino-4-thiazolyl) [(fluoromethoxy)imino]-acetamido [2-carboxy-8-oxo-4-thia-1-azabicyclo [4,2,0]oct-2-en-3-yl]methyl]-5,6,7,8-tetrahydro quinolinium (trifluoroacetate)

Under an inert atmosphere, 150 mg of 1,1-dimethylethyl (6S, 7S, ΔZ) 3-hydroxymethyl 7-[3-[7-(2-triphenyl methylamino-4-thiazolyl][(2-fluoromethyloxy)-imino]-acetamido]-8-oxo-4-1-azabicyclo[4,2,0]oct-2-en-3-yl]2-carboxylate, 3 ml of methylene chloride and 106 µl of cyclohexyl-pyridine-2,3 were mixed together, and at –70° C. over about 10 minutes, 1.4 ml of a 5% by volume solution of trifluoromethane sulfonic, anhydride in methylene chloride were introduced with stirring at –70° C. for 15 minutes. The residue, after concentrating to dryness by distilling under reduced pressure at –70° C. then at 0° C.)was chromatographed over silica and eluted with a mixture of methylene chloride and methanol (95/5) to obtain 125 mg of the expected product, Under inert atmosphere, 125 mg of the said product, 0.5 ml of trifluoroacetic acid and 50 µl of water were mixed together and stirred at 20° C. for two hours. 8 ml of ether were added slowly with stirring and the precipitate formed was separated, washed and dried to obtain 66 mg of trifluoromethane sulfonate of (6S, 7S ΔZ) 1-[[7-[[(2-amino-4-thiazolyl) [(fluoromethoxy)imino]-acetamido]2-carboxy-8-oxo-4-thia-1-azabicyclo[4,2,0]oct-2-en-3-yl]-methyl]5,6,7,8-tetrahydro quinolinium (trifluoroacetate).

| UV Spectrum (ethanol) | | | |
|---|---|---|---|
| Max. | 222 nm | $E_1^1 = 348$ | ε = 27,100 |
| Max. | 284 nm | $E_1^1 = 215$ | ε = 16,700 |
| Inflexion | 294 nm | $E_1^1 = 193$ | |
| **UV Spectrum (ethanol + 0.1 N HCl)** | | | |
| Inflexion | 210 nm | $E_1^1 = 258$ | |
| Max. | 281 nm | $E_1^1 = 263$ | ε = 20,500 |
| Inflexion | 300 nm | $E_1^1 = 192$ | |

| NMR Spectrum (dimethylsulfoxide) in ppm | |
|---|---|
| H of $CH_2$ at positions 3 and 4 | 1.75 to 1.95 |
| H of $CH_2$ at positions 2 and 5 and $CH_2$ cyclic | 2.99 to 3.32(m) |
| $H_6$ cis | 4.06 |
| $H_7$ H of $CH_2F$ and $CH_2N^{\oplus}$ | 5.63 to 5.86 |
| $H_5$ thiazole | 6.98 |
| $H_7$ | 7.97 |
| $H_6$ | 8.40 |
| $H_8$ | 8.88 |
| H of NMe | 9.39 |
| H mobile | 7.31–13.94 |

EXAMPLE 197

Trifluoroacetate of (6S, 7,S ΔZ) 4-(amino carbonyl) 1-[[7-[[<2-amino-4-thiazolyl) [(fluoromethoxy)imino]-acetamido]2-carboxy-8-oxo-4-thia-1-azabicyclo[4,2,0]oct-2-en 3-yl]methyl]pyridinium (trifluoroacetate)

Under an inert atmosphere, 150 mg of 1,1-dimethylethyl (6S, 7S ΔZ)3-iodomethyl-7-[3-[7-(2-triphenyl methylamino-4-thiazolyl) [(2-fluoromethyloxy)-imino]-acetamido]-8-oxo-4-thia-1-azabicyclo[4,2,0]oct-3-yl]-2-carboxylate, 0.3 ml of dimethylformamide and 87 mg of isonicotinamide were mixed together and stirred at 20° C. for 3 hours, then concentrated to dryness by distilling under reduced pressure. The residue was chromatographed over silica under nitrogen pressure and eluted with a mixture of methylene chloride and methanol (95/5) to obtain 126 mg of the expected product.

Under an inert atmosphere, the 126 mg of product, 0.5 ml of trifluoroacetic acid, and 50 µl of water were mixed together and stirred at 20° C. for two hours. Then, 5 ml of ether were added slowly with stirring and the precipitate formed was separated, washed and dried to obtain 76 mg of trifluoroacetate of (6S, 7S,ΔZ) 4-(amino carbonyl) 1-[[7-[[(2-amino-4-thiazolyl)[(fluoromethoxy)-imino]-acetamido]2-carboxy-8-oxo-4-thia-1-azabicyclo[4,2,0]oct-2-en-3-yl]-methyl]-pyridinium (trifluoroacetate).

| UV Spectrum (ethanol) | | |
|---|---|---|
| Max. | 220 nm $E_1^1 = 437$ | ε 33,300 |
| Inflexion | 260 nm $E_1^1 = 179$ | |
| Max. | 294 nm $E_1^1 = 195$ | ε 14,800 |
| Inflexion | 360 nm $E_1^1 = 15$ | |
| **UV Spectrum (ethanol + 0.1 N HCl)** | | |
| Max. | 220 nm $E_1^1 = 338$ | ε 25,700 |
| Max. | 264 nm $E_1^1 = 236$ | ε 18,000 |
| Inflexion | 280 nm $E_1^1 = 222$ | |
| Inflexion | 304 nm $E_1^1 = 175$ | ε 13,300 |

| NMR Spectrum (dimethylsulfoxide) in ppm | |
|---|---|
| H of $CH_2S$ cyclic | 3.04–3.34 (m) |
| $H_6$ | 4.12 (m) |
| $H_7$ | 5.72 (m) |
| H of $CH_2F$ and $CH_2N^{\oplus}$ | 5.58 to 5.90 (m) |
| $H_5$ thiazole | 6.97 (s) |
| $H^3$ and $H^5$ } pyridine | 8.48 (d; J = 6 Hz) |
| $H_2$ and $H_6$ } " | 9.29 (d; J = 6 Hz) |
| C(=O) $NH_2$ | 8.31 (s) |
| H of NHC | 8.70 (s) |
| | 9.37 (d; J = 8 Hz) |
| H mobiles | 7.30. |

EXAMPLE 198

Trifluoromethane sulfonate of (6S, 7S ΔZ) 4-[[7-[[(2-amino-4-thiazolyl) [(2-propenyloxy)-imino]-acetamido]-2-carboxy-8-oxo-4-thia-1-azabicyclo [4,2,0]oct-2-en-3-yl]-methyl]-thieno[3,2,-b]pyridinium trifluoroacetate STEP A: 1,1-dimethylethyl (6S, 7S ΔZ) 3-hydroxy-methyl-7-[3-[7-(2-triphenyl methylamino-4-thiazolyl][(2-propenyloxy)-imino]-acetamido]-8-oxo-4-thia-1-azabicyclo [4,2,0]oct-2-en-3-yl]2-carboxylate Under an inert atmosphere, 0.61 g of 2-(2-tritylamino-4-thiazolyl)-2-(propenyloxy)-imino acetic acid (syn), 0.190 ml of triethylamine, and 0.250 g of tosyl chloride were mixed together and stirred at 20° C. for 50 minutes. A mixture of 0.30 g of 1,1-dimethylethyl (6S, ΔZ) 7-amino-3-hydroxy-methyl-8-oxo-4-thia-1-azabicyclo[4,2,0]oct-2-en-2-carboxylate, 1.05 ml of water and 1.55 ml of an M aqueous solution of sodium bicarbonate were added all at once followed by stirring for 50 minutes at 20° C., followed by concentrating to dryness by distilling under reduced pressure. Methylene chloride and water were added with stirring and after decanting, extraction was done with methylene chloride. The extracts were washed with a saturated aqueous solution of sodium chloride and concentrated to dryness by distilling under reduced pressure. The residue was chromatographed over silica and eluted with a mixture of methylene chloride and ethyl acetate (85/15) to obtain 0.581 g of 1,1-dimethylethyl (6S, 7S ΔZ) 3-hydroxy methyl-7-[3-[7-(2-triphenylmethylamino-4-thiazolyl][(2-propenyloxy)-imino]-acetamido]-8-oxo-4-thia-1-azabicyclo[4,2,0]oct-2-en-3-yl]2-carboxylate with a Rf=0.45 in a mixture of methylene chloride and ethyl acetate (85/15). The product was used as is for the following step.

STEP B: Trifluoromethane sulfonate of (6S,7S ΔZ) 4-[[7-[[(2-triphenylmethylamino)-4-thiazolyl][2-(2-propenyloxy)-imino]-acetamido]-amino]2-[(1,1-dimethyl-ethoxy-carbonyl]-8-oxo-4-thia-1-azabicyclo[4,2,0]oct-en-3-yl]-methyl]-thieno[3,2-b]pyridinium Under an inert atmosphere, 0.3 g of the product of Step A of Example 7, 6 ml of methylene chloride and 3.2 ml of a solution of 268 mg of thienyl pyridine in 5 ml of methylene chloride were mixed together and stirred for 2 minutes at 20° C. At −70° C. 3 ml of a 4.2% by volume solution of trifluoromethane sulfonic acid anhydride in methylene chloride were added followed by stirring for 40 minutes while allowing the temperature to rise to −60° C. The trifluoromethane sulfonic anhydride was eliminated by distilling under a good vacuum, and the residual solution was chromatographed over silica and eluted with a mixture of methylene chloride and methanol (95/5). The residue was dissolved in methylene chloride, washed with an N aqueous solution of hydrochloric acid, dried and concentrated to dryness by distilling under reduced pressure to obtain 128 mg of trifluoromethane sulfonate of (6S, 7S ΔZ) 4-[[7-[[(2-triphenylmethylamino)-4-thiazolyl][2-(2-propenyloxy)-imino]-acetamido]-amino]2-((1,1-dimethyl-ethoxy-carbonyl]-8-oxo-4-thia-1-azabicyclo[4,2,0]oct-2-en-3-yl[-methyl]-thieno (3,2-b]pyridinium.

| IR Spectrum (chloroform) in $cm^{-1}$ | | | | |
|---|---|---|---|---|
| Beta lactam | C=O | 1788 | | |
| $CO_2tBu$ | C=O | 1702 | (F) | |
| | tBu Me | 1370 | | |
| | C—O—C | 1155 | | |
| Others C=O | | 1722 | Ep. | |
| Aromatics | | 1590 | | |
| Conjugated system | | 1570 | | |
| | | 1520 | (f) | |
| thiazole | | 1491 | (f) | |
| $TfO^{\ominus}$ | | 1030 | | |

| NMR Spectrum ($CDCl_3$) in ppm | | | | |
|---|---|---|---|---|
| H of $CO_2tBu$ | 1.48 | (s) | | |
| | 1.56 | (s) | | |
| H of $SCH_2$ | 3.01 | (m) | | |
| | and | | | |
| | 3.51 | | | |
| $H_6$ | 4.15 | | | |
| $H_7$ beta lactam cis | 5.65 | after exchange | | |
| H of $OCH_2$ | 4.74 | (d) | | |
| H of $CH_2N^{\ominus}$ | 5.43 | (d) | 6.19 | (d) |
| $H_7$ | 8.10 | (m) | | |
| H of $C\emptyset_3$ | 7.29 | | | |
| $H_5$ thiazole syn | 6.64 | (s) | | |
| H of $=CH_2$ | 5.13 | (d,d) | 11 and 2 | |
| | 5.28 | (d,m) | J about 16 | |
| H of $-CH=CH_2$ | 5.97 | (m) | | |
| $H_8$ | 9.41 | (d) | | |
| $H_6$ | 8.90 | (d) | | |
| $H_3$ and $H_4$ | 8.06 | (d) | | |
| | 8.48 | (d) | | |

STEP C: Trifluoromethane sulfonate of (6S, 7S ΔZ) 4-[[7-[[(2-amino-4-thiazolyl)-[(2-propenyloxy)-imino]-acetamido]2-carboxy-8-oxo-4-thia-1-azabicyclo[4,2,0]oct-2-en-3-yl]-methyl]-thieno[3,2-b]-pyridinium, trifluoroacetate Under an inert atmosphere, 100 mg of the product of Step B of Example 7, 0.5 ml of trifluoroacetic acid and 0.05 ml of water were mixed together and stirred at 20° C. for 2 hours. 3.5 ml of ether were added followed by stirring for 2 hours. The precipitate formed was separated, washed and dried to obtain 60 mg of trifluoromethane sulfonate of (6S,7S ΔZ) 4-[[7-[[(2-amino-4-thiazolyl)-[(2-propenyloxy)-imino]-acetamido]2-carboxy-8-oxo-4-thia-1-azabicyclo[4,2,0]oct-2-en-3-yl]-methyl]-thieno [3,2-b]-pyridininum.

| NMR Spectrum (dimethylsulfoxide) in ppm | | |
|---|---|---|
| H of $OCH_2$ | 4.6 | |
| H of $CH_2N^{\oplus}$ | 5.91–6.1 | |
| | 6.2–6.4 | |
| $H_7$ | 5.7 | |
| $H_5$ thiazole syn | 6.8 | |
| H thiophene | 8.2–8.3 | |
| | 8.9–9.0 | |
| $H_5$ | 8.2 | pyridine |
| $H_4$ and $H_6$ | 9.21–9.25 | pyridine |
| | 9.4–9.5 | pyridine |
| H of $=CH_2$ | 5.1–5.4 | |
| H of C H $=CH_2$ | 5.9 | |

| UV Spectrum (ethanol) | | |
|---|---|---|
| Inflexion | 229 nm $E_1^1$ = 443 | |
| Max. | 237 nm $E_1^1$ = 515 | ε = 42,300 |
| Max. | 295 nm $E_1^1$ = 255 | ε = 20,900 |
| Inflexion | 320 nm $E_1^1$ = 136 | |

| UV Spectrum (ethanol + 0.1N HCl) | | |
|---|---|---|
| Inflexion | 227 nm $E_1^1$ = 364 | |
| Max. | 238 nm $E_1^1$ = 480 | ε = 39,400 |
| Max. | 293 nm $E_1^1$ = 284 | ε = 23,300 |
| Inflexion | 314 nm $E_1^1$ = 182 | |

EXAMPLE 199

Iodide of (6S, 7S ΔZ) 6-[[7-[1[(2-amino-4-thiazolyl) [(difluoromethoxy)-imino]-acetamido]2-carboxy-8-oxo-4-thia-1-azabicyclo[4,2,0]oct-2-en-3-yl]-methyl]thieno[2,3-c] pyridinium, trifluoroacetate STEP A: 1,1-dimethylethyl of (6S, 7S ΔZ) 3-iodomethyl 7-[2-[2-triphenylmethylamino-4-thiazolyl]-[(difluoromethoxy)-imino]-acetamido]-8-oxo-4-thia-1-azabicyclo[4,2,0]oct-2-en-3-yl]2-carboxylate Under an inert atmosphere, 150 mg of 1,1-dimethyl ethyl of (6S, 7S ΔZ) 3-hydroxymethyl-7-[2-[2-triphenyl methylamino-4-thiazolyl](difluoromethoxy)-imino]-acetyl]-amino]-8-oxo-4-thia-1-azabicyclo[4,2,0]oct-2-en-3-yl]2-carboxylate, 2 ml of methylene chloride, 184 mg of $Bu_4N^{\oplus}I^{\ominus}$ and 0.094 ml of lutidine were mixed together and over about 20 minutes at −70° C., 1.6 ml of a 0.25 M solution in methylene chloride of trifluoromethane sulfonic anhydride were added dropwise and stirred for 30 minutes while allowing the temperature to rise from −70° to −35° C. A 0.1N aqueous solution of hydrochloric acid was added and after stirring and decanting, extraction was done with methylene chloride. The extracts were dried, concentrated to dryness by distilling under reduced pressure. The residue was chromatographed over silica under nitrogen pressure and eluted with a mixture of methylene chloride and ethyl acetate (95/5) to obtain 82 mg of the iodide derivative with a Rf=0.4 (methylene chloride, ethyl acetate (95/5)) which was used as is for the following step.

STEP B: Iodide of (6S, 7S, ΔZ) 1-[[7-[[2-triphenyl methyl amino-4-thiazolyl)-[(difluoromethoxy)-imino]-acetamido]-2-tertbutoxy-carbonyl-8-oxo-4-thia-1-azabicyclo[4,2,0]oct-2-en-3-yl]-methyl]-thieno[2,3-b]pyridinium Under an inert atmosphere, 130 mg of the iodine compound of Step A, 3 ml of methylene chloride, and 1.5 ml of metathienyl pyridine in 4% solution in methylene chloride were mixed together and stirred for 2 hours at 20° C. and concentrated to dryness by distilling under reduced pressure. The residue was chromatographed over silica and eluted with a mixture of methylene chloride and methanol (9/1) to obtain 85 mg of iodide of (6S, 7S) ΔZ) 1-[[7-[[2-triphenyl methyl amino-4-thiazolyl)-[(difluoromethoxy)-imino]-acetamido]-2tertbutyoxy-carbony-8-oxo-4-thia-1-azabicyclo[4,2,0]oct-2-en-3-yl]-methyl]-thieno][2,3-b] pyridinium which was used as is for the following step.

STEP C: Iodide of (6S, 7S ΔZ) 6-[[7-[[(2-amino-4-thiazolyl) [(difluoromethoxy)-imino]-acetamido]-2-carboxy-8-oxo-4-thia-1-azabicyclo oct-2-en-3-yl]-methyl]-thieno[2,3-c] pyridinium, trifluoroacetate Under an inert atmosphere, 75 mg of the compound of Step B, 1 ml of trifluoroacetic acid and 0.1 ml of water were mixed together and stirred for 1 hour at 20° C.1 ml of ether was added followed by separating, washing and drying under a vacuum to obtain 45 mg of iodide of (6S,7S,ΔZ) 6-[[7-[[(2-amino-4-thiazolyl) [(difluoromethoxy)-imino] acetamido]-2-carboxy-8-oxo-4-thia-1-azabicyclo[4,2,0]oct-2-en-3-yl]-methyl]-thieno[2,3-c]pyridinium, trifluoroacetate with a Rf=0.6 (acetone, water (2/1)).

| | | |
|---|---|---|
| UV Spectrum (ethanol) | | |
| Max. | 224 nm $E_1^1$ = 449 | ε = 36,300 |
| Max. | 240 nm $E_1^1$ = 471 | ε = 38,100 |
| Max. | 267 nm $E_1^1$ = 172 | ε = 13,900 |
| Max. | 277 nm $E_1^1$ = 169 | ε = 13,700 |
| Max. | 301 nm $E_1^1$ = 227 | ε = 18,400 |
| Inflexion | 318 nm $E_1^1$ = 192 | |
| Inflexion | 368 nm $E_1^1$ = 26 | |
| UV Spectrum (ethanol + 0.1N HCl) | | |
| Max. | 222 nm $E_1^1$ = 369 | ε = 29,200 |
| Max. | 243 nm $E_1^1$ = 469 | ε = 37,900 |
| Max. | 300 nm $E_1^1$ = 228 | ε = 18,400 |
| Inflexion | 314 nm $E_1^1$ = 219 | |
| Inflexion | 235–265–274 nm | |
| NMR Spectrum (dimethylsulfoxide) in ppm | | |
| $H_6$ | 4.1 | |
| H of $CH_2N^{\oplus}$ and $H_7$ | 5.7 | |
| $H_3$ thiazol syn | 7.1 | |
| H of $CHF_2$ | 6.3–7.2–8.0 | |
| $H_2$ | 10.0 | |
| H of the other aromatics | 8.0 to 9.0 | |
| H of NHCO | 9.5–9.6 | |
| H mobile | 7.4 | |

EXAMPLE 200

Iodide of (6S, 7S ΔZ) 5-[[7-[[(2-amino-4-thiazolyl])-[(difluoromethoxy)-imino]acetamido]2-carboxy-8-oxo-4-thia-1-azabicyclo[4,2,0]oct-2-en-3-yl]-methyl]-thieno[3,2-c]pyridinium (trifluoroacetate)

STEP A: Iodide of (6S, 7S ΔZ) 1-[[7-[(2-triphenylmethyl)-amino-4-thiazolyl)-[(difluoromethoxy)-imino]-acetamido]-2-tertbutoxycarbonyl-8-oxo-4-thia-1-azabicyclo[4,2,0]oct-2-en-3-yl]-methyl]-thieno[3,2-c]pyridinium Under an inert atmosphere, 150 mg of 1,1-dimethyl-ethyl (6S, 7S ΔZ) 3-iodomethyl 7-[-2[2-triphenylmethylamino-4-thiazolyl](difluoromethoxy)-imino]-acetamido]-8-oxo-4-thia-1-azabicyclo[4,2,0]oct-2-en-3-yl]2-carboxylate, 3 ml of methylene chloride and 1.75 ml of a 4.0% solution of thienopyridine in methylene chloride were mixed together and stirred at 20° C. for 16 hours, then concentrated to dryness by distilling under reduced pressure. The residue was chromatographed over silica under nitrogen pressure and eluted with a mixture of methylene chloride and methanol (9/1) to obtain 73 mg of iodide of (6S, 7S ΔZ) 1-[[7-[(2-triphenylmethyl)-amino-4-thiazolyl)-[(difluoromethoxy)imino]-acetamido]-2-tertbutoxycarbonyl-8-oxo-4-thia-1-azabicyclo[4,2,0]oct-2-en-3-yl]-methyl]-thieno[3,2-c] pyridinium.

STEP B: Iodide of (6S, 7S ΔZ) 5-[[7-[(,2-amino-4-thiazolyl) [(difluoromethoxy)imino]-acetamido]-2-carboxy-8-oxo-4-thia-1-azabicyclo[4,2,0]oct-2-en-3-yl]-methyl]-thieno][3,2-c]pyridinium (trifluoroacetate)

Under an inert atmosphere, 70 mg of the product of Step A, 1.4 ml of trifluoracetic acid and 0.14 ml of water were mixed together and stirred at 20° C. for one hour. The trifluoroacetic acid was eliminated by distilling under a good vacuum and 10 ml of ether were added to the residue with stirring. The precipitate formed was separated, washed and dried to obtain 37 mg of iodide of (6S, 7S ΔZ) 5-[[7-[[(2-amino-4-thiazol)[(difluoromethoxy)imino]-acetamido]-2-carboxy-8-oxo-4-thia-1-azabicyclo[4,2,0]oct-2-en-3-yl]-methyl]-thieno][3,2-c]-pyridinium (trifluoroacetate).

| | | |
|---|---|---|
| UV Spectrum (ethanol) | | |
| Max. | 239 nm $E_1^1$ = 690 | ε = 55,800 |
| Max. | 295 nm $E_1^1$ = 245 | ε = 19,800 |
| UV Spectrum (ethanol + 0.1N HCl) | | |
| Max. | 240 nm $E_1^1$ = 660 | ε = 53,400 |
| Max. | 295 nm $E_1^1$ = 261 | ε = 21,100 |
| NMR Spectrum (dimethylsulfoxide) in ppm | | |
| H of $CH_2S$ | | 3.06 and 3.16 |
| $H_6$ | | 4.15 |
| $H_7$ beta lactam cis | | 5.70 |
| H of $CH_2N^{\oplus}$ | | 5.59–5.98 |
| $H_5$ thiazole syn | | 7.06 |
| H of CH—$F_2$ | | 7.08(t; J about 70) |
| $H_3$ and $H_5$ | | 8.03(d; J about 5) 8.41(d; J about 5) |
| $H_6$ and $H_7$ | about | 8.85 |
| $H_2$ | | 9.77(s) |
| H of NHCO | | 9.57(s) |

EXAMPLE 201

Iodide of (6S, 7S ΔZ) 4-[[7-[[(2-amino-4-thiazolyl) [[(methylthio)-methoxy]-imino]-acetamido]2-carboxy-8-oxo-4-thia-1-azabicyclo[4,2,0]oct-2-en-3-yl]-methyl] thieno][3,2-b]pyridinium trifluoroacetate STEP A: Ethyl ester of syn isomer of 2-(2-tritylamino-4-thiazolyl) 2-[methyl-(thio)-methoxy]-imino acetic acid Under an inert atmosphere, 26 g of syn isomer of ethyl 2-(2-tritylamino-4-thiazolyl) (2-hydroxyimino) acetate, 1135 ml of dimethylformamide and 35.3 g of potassium carbonate were mixed together, and over 5 minutes at 0° C. 4.27 ml of methyl(thio)methyl chloride ($ClCH_2SCH_3$) were added with stirring for 20 minutes at 20° C. After filtering, 300 ml of water were added to the filtrate and the formation of a precipitate was observed, The precipitate was separated, dried, chromatographed over silica and eluted with methylene chloride to obtain 5.8 g of ethyl ester of syn isomer of 2-(2-tritylamino-4-thiazolyl) 2-[methyl(thio)methoxy]imino acetic acid STEP B: Syn isomer of 2-(2-tritylamino 4-thiazolyl) 2-[methyl(thio) methoxy]imino acetic acid Under an inert atmosphere, 1.5 g of the product of Step A, 10 ml of dioxane, 6 ml of ethanol, 2.5 ml of water and 0.240 g of sodium hydroxide were mixed together and stirred for 110 minutes at +55° C., then for 30 minutes at 20° C. The precipitate formed was separated and dissolved in a mixture of water, an N aqueous solution of hydrochloric acid and methylene chloride. After stirring and decanting, extraction was done with methylene chloride and the extracts were concentrated to dryness by distilling under reduced pressure to obtain 1 g of syn isomer of 2-(2-tritylamino-4-thiazolyl)

2-[methyl(thio)methoxy]imino acetic acid.

| | | |
|---|---|---|
| UV Spectrum (ethanol | | |
| Inflexion | 229 nm $E_1^1$ = 454 | |
| Inflexion | 237 nm $E_1^1$ = 409 | |
| Inflexion | 260 nm $E_1^1$ = 251 | |
| Inflexion | 267 nm $E_1^1$ = 231 | |
| Inflexion | 273 nm $E_1^1$ = 222 | |
| UV Spectrum (ethanol + 0.1N HCl) | | |
| Inflexion | 634 nm $E_1^1$ = 254 | |
| Max. | 277 nm $E_1^1$ = 285 | |
| Inflexion | 287 nm $E_1^1$ = 268 | ε = 13,900 |
| Inflexion | 298 nm $E_1^1$ = 208 | |
| IR Spectrum (Nujol) | | |
| C=O C=C C=N | | 1650 $cm^{-1}$ (Ep.) |
| COO⊖ aromatics conjugated system thiazol | | 1605 $cm^{-1}$ 1583 $cm^{-1}$ 1540 $cm^{-1}$ 1490 $cm^{-1}$ |
| | | 697 $cm^{-1}$ |
| strong band | | 995 $cm^{-1}$ |
| NMR Spectrum (dimethylsulfoxide) in ppm | | |
| H of $SCH_3$ | | 2.1 |
| H of $OCH_2S$ | | 5.0 |
| $H_5$ of thiazol | | 6.6 |
| H of CØ$_3$ | | 7.4 |
| H of COOH | | 8.6 |

STEP C: 1,1-dimethyl-ethyl (6S, 7S ΔZ) 3-hydroxy-methyl-7-[[2-(2-triphenylmethylamino)-4-thiazolyl][(2-methyl (thio)methoxy)-imino]-acetyl]3-amino]-8-oxo-4-thia-1-azabicyclo[4,2,0]oct-2-en-3-yl]2-carboxylate Under an inert atmosphere, 500 mg of the product of Step B, ml of acetone, 0.18 ml of triethylamine and 0.240 g of tosyl chloride were mixed together and stirred for 1 hour at 20° C. A mixture of 0.220 g of 1,1-dimethyl ethyl (6S, 7S ΔZ) 7-amino-3-hydroxy-methyl-8-oxo-4-thia-1-azabicyclo [4,2,0]oct-2-en-2-carboxylate, 1.1 g of sodium bicarbonate, ml of water and 1.2 ml of acetone were added-with stirring at 20° C. for minutes. The acetone was eliminated by distilling under reduced pressure and then methylene chloride was added. After stirring and decanting, extraction was done with methylene chloride. The extracts were washed with water, concentrated to dryness by distilling under reduced pressure, and the residue was chromatographed over silica and eluted with a mixture of methylene chloride and ethyl acetate (85/15) to obtain 387 mg of 1,1-dimethyl ethyl (6S, 7S ΔZ) 3-hydroxy 7-[[2-(2-triphenylmethylamino)-4-thiazolyl][(2-methyl(thio) methoxy)-imino]-acetyl]-3-amino]-8-oxo-4-thia-1-azabicyclo[4,2,0]oct-2-en-3-yl]2-carboxylate which was used as is for the following step.

STEP D: iodide of (6S, 7S ΔZ) 1-[[7-[[(2-triphenylmethylamino)-4-thiazolyl]-[methyl(thio)-methoxy]imino]-acetamido]2-[1-dimethylethoxy)-carbonyl]-8-oxo-4-thia-1-azabicyclo[4,2,0]oct-2-en-3-yl] methyl]-thieno[3,2-b]pyridinium Under inert atmosphere, 0.340 g of the product of Step C, 8 ml of methylene chloride, 0.33 g of $(Bu)_4N^{\oplus}I^{\ominus}$, and 0.21 ml of 2,6-lutidine are mixed together and 3.3 ml of a 4.2% by volume solution in methylene chloride of trifluoromethane sulfonic anhydride were added dropwise at 70° C. After allowing the temperature to rise to −48° C. and stirring at −40° C. for 25 minutes, the trifluoromethane sulfonic anhydride was eliminated by concentration under a good vacuum. The solution obtained was chromatographed over silica and eluted with a mixture of methylene chloride and ethyl acetate (9/1) to obtain 195 mg of 1,1-dimethylethyl 3-iodomethyl of (6S, 7S ΔZ) 7-[[[(2-triphenyl-methyl-amino)-4-thiazolyl][(2-methyl(thio)methoxy)-imino]-acetyl]3-amino]-8-oxo-4-thia-1-azabicyclo[4,2,0]oct-2-en-3-yl]2-carboxylate.

Under an inert atmosphere, 150 mg of the said product, 2 ml of methylene chloride, and 1.8 ml of a solution of thienyl pyridine (266 mg in 5 ml of methylene chloride) were mixed together and stirred at 20° C. for 26 hours. The reaction solution was chromatographed over silica and eluted with a mixture of methylene chloride and methanol (90/10) to obtain 45 mg of iodide of (6S,7S ΔZ) 1-[[7-[[(2-triphenyl methylamino)-4-thiazolyl][methyl(thio)methoxy]imino]-acetamido]2-[(1,1-dimethyl ethoxy)-carbonyl]-8-oxo-4-thia-1-azabicyclo[4,2,0]oct-2-en-3-yl]-methyl]-thieno[3,2-b]pyridinium.

| | | |
|---|---|---|
| UV Spectrum (ethanol) | | |
| Max. | 238 nm $E_1^1$ = 536 | ε = 53,800 |
| Max. | 299 nm $E_1^1$ = 222 | ε = 22,300 |
| UV Spectrum (ethanol + 0.1N HCl) | | |
| Max. | 235 nm $E_1^1$ = 490 | ε = 49,100 |
| Max. | 295 nm $E_1^1$ = 285 | ε = 28,600 |
| Inflexion | 314 nm $E_1^1$ = 190 | |
| Inflexion | 330 nm $E_1^1$ = 123 | |

STEP E: Iodide of (6S, 7S ΔZ) 4-[[7-[[(2-amino-4-thiazolyl) [[(methylthio)-methoxy]-imino]-acetamido]2-carboxy-8-oxo-4-thia 1-azabicyclo [4,2,0]oct-2-en-3-yl]-methyl]-thieno][3,2-b]pyridinium (trifluoroacetate)

0.040 g of the product of Step D, 0.3 ml of trifluoroacetic acid, and 0.03 ml of water were mixed together and stirred for 100 minutes at 20° C. 2.5 ml of ether were added, and after stirring, the precipitate formed was separated, washed and dried to obtain 25 mg of iodide of (6S, 7S ΔZ) 4-[[7-[[(2-amino-4-thiazolyl) [[(methylthio)-methoxy]-imino]-acetamido]2-carboxy-8-oxo-4-thia-1-azabicyclo[4,2,0]oct-2-en-3-yl]-methyl]-thieno][3,2-b]pyridinium (trifluoroacetate)

| | | |
|---|---|---|
| UV Spectrum (ethanol) | | |
| Max. | 237 nm $E_1^1$ = 539 | ε = 44,800 |
| Max. | 294 nm $E_1^1$ = 270 | ε = 22,400 |
| Inflexion | 320 nm $E_1^1$ = 193 | |
| Inflexion | 370 nm $E_1^1$ = 91 | |
| UV Spectrum (ethanol + 0.1N HCl) | | |
| Max. | 239 nm $E_1^1$ = 508 | ε = 42,200 |
| Inflexion | 260 nm $E_1^1$ = 222 | |
| Max. | 294 nm $E_1^1$ = 288 | ε = 23,900 |
| Inflexion | 314 nm $E_1^1$ = 200 | |
| NMR Spectrum (dimethylsulfoxide) in ppm | | |
| H of $SCH_3$ | 2.12(s) 2.21(s) | |
| $H_6$ | 4.06(m) | |
| H of $OCH_2S$ | 5.18 and 5.32 | |
| $H_7$ | 5.68(m) | |
| H of $N^{\oplus}CH_2$ | 5.98(d) and 6.23(d) | |
| $H_5$ thiazole syn | 6.76 and 6.14(s) | |
| $H_3$ | 8.11(d, d) | |
| $H_6$ and $H_7$ | 8.22(d) and 8.92(d) | |
| $H_4$ | 9.21(d) | |
| $H_2$ | 9.41(d) | |
| H of NHCO | 9.11-9.21(d) | |

EXAMPLE 202

Iodide of (6S, 7S ΔZ) 5-[[7-[[(2-amino-4-thiazolyl) [(2-propenyloxy)-imino]-acetamido]-2-carboxy-8-oxo-4-thia- 1-azabicyclo[4,2,0]oct-2-en-3-yl]-methyl]-thieno[3,2-c] pyridinium, trifluoroacetate STEP A: 1,1-dimethylethyl 3-iodomethyl 7-[2-(2-triphenyl-methylamino)-4-thiazolyl-[(2-propenyloxyimino)-acetamido]-8-oxo-4-thia-1-azabicyclo [4,2,0]oct-2-en-2-carboxylate Under an inert atmosphere, 500 mg of 1,1-dimethylethyl 3-hydroxymethyl 7-[2-(2-triphenyl methylamino)-4-thiazolyl][2-propenyloxyimino) acetamido]-8-oxo-4-thia-1-azabicyclo[4,2,0]oct-2-en-2-carboxylate, 8 ml of methylene chloride 500 mg of $(Bu)_4N^{\oplus}I^{\ominus}$ and 0 3 ml of 2 6-lutidine were mixed together and then 5 ml of a 4.2% by volume solution of trifluoromethane sulfonic anhydride in methylene chloride were added dropwise at −70° C. After stirring for 30 minutes while allowing the temperature to rise to −40° C., the mixture was concentrated to dryness by distilling under a good vacuum. The residue was chromatographed over silica and eluted with a mixture of methylene chloride and ethyl acetate (9/1) to obtain 334 mg of 1,1-dimethylethyl 3-iodomethyl 7-[2-(2-triphenyl-methyl-amino)-4-thiazolyl-[(2-propenyloxyimino)-acetamido]-8-oxo-4-thia-1-azabicyclo[4,2,0]oct-2-en-2-carboxylate with a Rf=0.8 (methylene chloride-ethyl acetate (9/1)).

| | | |
|---|---|---|
| UV Spectrum (ethanol) | | |
| Inflexion | 223 nm $E_1^1$ = 418 | |
| Inflexion | 234 nm $E_1^1$ = 346 | |
| Max. | 306 nm $E_1^1$ = 139 | ε = 11,800 |
| Inflexion | 266, 272, 280 nm | |
| UV Spectrum (ethanol + 0.1N HCl) | | |
| Inflexion | 220 nm $E_1^1$ = 440 | |
| Inflexion | 220 nm $E_1^1$ = 409 | |
| Max. | 280 nm $E_1^1$ = 194 | ε = 16,400 |
| Max. | 291 nm $E_1^1$ = 189 | ε = 16,000 |
| Inflexion | 302 nm $E_1^1$ = 167 | |
| Inflexion | 322 nm $E_1^1$ = 109 | |
| Inflexion | 263, 270, 275 nm. | |
| NMR Spectrum ($CDCl_3$) in ppm | | |
| H of tBu | 1.6 | |
| H of $SCH_2$ | 3.1 | |
| H of $CH_2I$ | 4.5 | |
| $H_6$ | 4.1 | |
| H of $OCH_2$ | 4.76–4.82 | |
| H of $=CH_2$ and $H_7$ | 5.3–5.4 | |
| H of C Ⓗ $=CH_2$ | 6.0 | |
| $H_5$ thiazol syn | 6.7 | |
| H of CØ$_3$ | 7.3 | |

STEP B: Iodide of (6S, 7S ΔZ) 1-[[7-[[2-triphenyl (methylamino)-4-thiazolyl]-[2-propenyloxy)-imino] acetamido]-2-[(1,1-dimethyl ethoxy)-carbonyl]-8-oxo-4-thia 1-azabicyclo[4,2,0]oct-2-en-3-yl]-methyl]-thieno [3,2-c]pyridinium 160 mg of the product of Step A, 2.2 ml of a solution of thienyl pyridine in methylene chloride (containing 266 mg in 5 ml of methylene chloride) and 2 ml of methylene chloride were mixed together and stirred at 20° C. for 24 hours. The reaction solution was chromatographed over silica and eluted with a mixture of methylene chloride and methanol (9/1) to obtain 60 mg of iodide of (6S, 7S ΔZ) 1-[[7-[[2-triphenyl (methylamino)-4-thiazolyl]-[[2-propenyloxy)-imino]-acetamido]2-[(1,1-dimethyl ethoxy)-carbonyl]-8-oxo-4-thia-1-azabicyclo[4,2,0]oct-2-en-3-yl]-methyl]-thieno[3,2-c]pyridinium with a Rf=0.2 (methylene chloride-methanol (9/1).

| | | |
|---|---|---|
| UV Spectrum (ethanol) | | |
| Max. | 240 nm $E_1^1$ = 657 | ε = 65,400 |
| Max. | 305 nm $E_1^1$ = 207 | ε = 20,600 |
| UV Spectrum (ethanol + 0.1N HCl) | | |
| Max. | 240 nm $E_1^1$ = 578 | ε = 57,500 |
| Max. | 292 nm $E_1^1$ = 252 | ε = 25,100 |
| Inflexion | 300 nm $E_1^1$ = 247 | |

STEP C: Iodide of (6S, 7S ΔZ) 5-[[7-[[(2-amino-4-thiazolyl)-[(2-propenyloxyimino]-acetamido]2-carboxy-8-oxo-4-thia-1-azabicyclo[4,2,0]oct-2-en-3-yl]-methyl]-thieno[3,2-c] pyridinium, trifluoroacetate 45 mg of the product of Step B, 0.30 ml of trifluoroacetic acid and 0.030 ml of water were mixed together and stirred at 20° C. for 3 hours, 3.5 ml of ether were added with stirring and the precipitate formed was separated, washed and dried to obtain 27 mg of iodide of (6S, 7S ΔZ) 5-[[7-[[(2-amino-4-thiazolyl)-[(2-propenyloxyimino]-acetamido]2-carboxy-8-oxo-4-thia-1-azabicyclo[4,2,0]oct-2-en-3-yl]-methyl] thieno[3,2-c]pyridinium, trifluoroacetate with a Rf=0.6 (acetone 2-water 1).

| | | |
|---|---|---|
| UV Spectrum (ethanol) | | |
| Max. | 239 nm $E_1^1$ = 592 | ε = 48,000 |
| Max. | 297 nm $E_1^1$ = 204 | ε = 16,500 |
| UV Spectrum (ethanol + 0.1N HCl) | | |
| Max. | 241 nm $E_1^1$ = 542 | ε = 43,900 |
| Inflexion | 278 nm $E_1^1$ = 198 | |
| Max. | 290 nm $E_1^1$ = 218 | ε = 17,700 |
| NMR Spectrum (dimethylsulfoxide) in ppm | | |
| H of $OCH_2$ | | 4.6 |
| H ethylene $H_7$ and $CH_2N^{\oplus}$ | | 5.1 to 6.1 |
| $H_5$ thiazol syn | | 6.8 |
| $H_2$ | | 9.8 |
| $H_7$ and $H_8$ | | 8.9 |
| $H_4$ and $H_5$ | | 8.06–8.11; 8.44–8.50 |
| H of NHCO | | 9.2–9.3 |

EXAMPLE 203

Trifluoromethane sulfonate of (6S, 7S ΔZ) 1-[[7-[[(2-amino-4-thiazolyl) [(difluoromethoxy)imino]-acetamido]-2-carboxy-8-oxo-4-thia-1-azabicyclo [4,2,0]oct-2-en-3-yl] methyl]-5,6,7,8-tetrahydro quinolinium, trifluoroacetate STEP A: Syn isomer of ethyl 2-(2-tritylamino thiazolyl)-2-hydroxyimino acetate hydrochloride 500 g of ethyl 2-(2-amino-4-thiazolyl)-2hydroxyimino acetate and 1.5 liter of dimethylformamide were mixed together and the suspension was stirred. Then, over about 5 minutes at −35° C., 355 ml of triethylamine and 670 g of trityl chloride were introduced and the temperature was allowed to return to 0° C. over 40 minutes. After stirring for 150 minutes at 0° C., the reaction mixture was poured into water and stirred for one hour, noting a crystallization. The precipitate formed was separated, washed with water and dried at 20° C. under a vacuum to obtain 1.1 kg of the trityl derivative sought. Checks: Protometric titre 94%.

1.1 kg of the said product and 5.3 liters of ethyl acetate were mixed together and stirred Then, at 0° C.°+5° C. 720 ml of a solution of hydrochloric gas at 137 g/liter in ethyl acetate were introduced. Crystallization was observed, and after stirring for 30 minutes at 0°–+5° C., the precipitate formed was separated, washed with ethyl acetate and dried to obtain 1.026 Kg of the hydrochloride product.

| | | |
|---|---|---|
| HCl by acidometry | 7.1% | (theoretical 7.38%) |
| HCl by argentimetry | 7.7% | (theoretical 7.38%) |
| Nitrogen motometric | 2.9% | (theoretical 2.83%) |

STEP B: Ethyl 2-triphenylmethylamino α-[(difluoromethoxy)imino]-4-thiazol acetate 3 g of the hydrochloride of Step A, 20 ml of a 2N aqueous solution of sodium hydroxide and 20 ml of ethanol were mixed together and stirred for 5 minutes. A dissolution was noted and then a precipitation of sodium salt which was dissolved by adding 60 ml of dioxane. Fregn 22 ($ClCHF_2$) was bubbled in for 30 minutes and 20 ml of a 2N aqueous solution of sodium hydroxide, 20 ml of ethanol and 60 ml of dioxane were added, and the bubbling in of Freon was continued for a further 30 minutes. Sodium bicarbonate was added to bring the pH to 9, and after stirring, the light insoluble matter formed was eliminated by filtering. The filtrate was concentrated by distilling under reduced pressure and chloroform was added followed by stirring, decanting, washing with water and with a saturated aqueous solution of sodium chloride, then drying. After concentrating by distilling under reduced pressure, the residue was chromatographed over silica and eluted with benzene to obtain 0.652 g of ethyl 2-triphenylmethylamino α-[(difluoromethoxy) amino]-4-thiazol acetate.

| | | |
|---|---|---|
| UV Spectrum (ethanol) | | |
| Max. | 308 nm $E_1^1 = 80$ | ε = 4,100 |
| I.R. Spectrum (chloroform) | | |
| C═N—OR | | 1141 $cm^{-1}$ |
| $CHF_2$ | | 1145, 1117 $cm^{-1}$ |
| Absence of OH | | |
| NMR Spectrum | | |
| In agreement, notably H of $CHF_2$ | | 5.5–6.7–7.9 ppm |
| $H_5$ thiazol syn | | 6.8 ppm |

STEP C: Syn isomer of 2-[2-triphenylmethylamino-thiazol-4-yl]2-difluoromethoxyimino-acetic acid 2.771 g of the product of Step B and 32 ml of ethanol were mixed together, then, dropwise, 6 ml of a normal aqueous solution of sodium hydroxide were added. This was seen to dissolve and then the sodium salt of the acid sought crystallized and the mixture stood in a closed receptacle for four hours. It was then concentrated to dryness by distilling under reduced pressure and water and ether were added to the residue. After filtering, 110 ml of methylene chloride, 27 ml of water and 2.05 ml of a 2N aqueous solution of hydrochloric acid (pH 2) were added to the crystallizate, followed by vigorous stirring. 20 ml of methanol were added to complete the dissolution, and after decanting into a flask, extraction was done with methylene chloride. The extracts were dried and concentrated to dryness by distilling under reduced pressure. The residue was dissolved in ethanol and the crystallization of the free acid was initiated. The ethanol was eliminated and ether was added with stirring. The precipitate was separated, washed and dried to obtain 1.534 g of syn isomer of 2-[2-triphenylmethylamino-thiazol-4-yl] -2-difluoromethoxyimino acetic acid.

| | | |
|---|---|---|
| UV Spectrum (ethanol) | | |
| Inflexion | 225 nm $E_1^1 = 610$ | |
| Inflexion | 258 nm $E_1^1 = 219$ | ε = 10,500 |
| Inflexion | 265 nm $E_1^1 = 210$ | |
| Inflexion | 271 nm $E_1^1 = 198$ | |
| Inflexion | 293 nm $E_1^1 = 108$ | ε = 5,200 |
| NMR Spectrum (dimethylsulfoxide) in ppm | | |
| H of $OCHF_2$ | | 6.0–7.2–8.4 |
| $H_5$ thiazol | | 7.2 |
| H of trityl | | 7.4 |

Analysis: $C_{25}H_{19}O_3SF_2$; molecular weight=479.51; Calculated: %C 62.62, %H 3.99, %N 8.76, %S 6.69, %F 7.92; Found: 62.6, 4.0, 8.6, 6.8, 7.7.

STEP D: 1,1-dimethylethyl (6S, 7S ΔZ) 3.,hydroxymethyl-7-[2-[2-triphenyl methyl amino 4-thiazolyl]-[(difluoromethoxy)-imino]-acetamido]-8-oxo-4-thia-1-azabicyclo[4,2,0]oct-2-en-3-yl]2-carboxylate Under an inert atmosphere, 0.905 g of the syn isomer of 2-[2-triphenylmethylamino thiazol-4-yl-]-2-difluoromethoxy-imino-acetic acid, 9 ml of acetone, 0.27 ml of triethylamine and 0.365 g of tosyl chloride were mixed together and stirred for 45 minutes at 20° C. 0.460 g of 1,1-dimethylethyl (6S, 7S ΔZ) 7-amino-3-hydroxymethyl-8-oxo-4-thia-1-azabicyclo[4,2,0]oct-2-en-2-carboxylate, 1.6 ml of a 1.57M aqueous solution of sodium bicarbonate, 2 ml of acetone and 2 ml of water were added all at once followed by stirring for 65 minutes at 20° C. The acetone was eliminated by distilling under reduced pressure and methylene chloride was added. After stirring and decanting, extraction was done with methylene chloride. The extracts were washed with water and concentrated to dryness by distilling under reduced pressure. The residue was chromatographed over silica and eluted with a mixture of methylene chloride and ethyl acetate (15/85) to obtain 530 mg of 1,1-dimethylethyl (6S, 7S ΔZ) 3-hydroxymethyl-7-[2-[2-triphenyl methyl amino-4-thiazolyl][difluoromethoxy) imino]-acetamido]-8-oxo-4-thia-1-azabicyclo[4,2,0]oct-2-en-3-yl]2-carboxylate.

STEP E: Trifluoromethane sulfonate of 4-[[7-((2-triphenylmethylamino]-4-thiazolyl [(difluoromethoxy)-imino]-acetamido]-2-[[1,1-dimethyl ethoxycarbonyl]-8-oxo-4-thia 1-azabicyclo[4,2,0]oct-2-en-3-yl]-methyl]-5,6,7,8-tetrahydro quinolinium Under an inert atmosphere, 200 mg of the product of Step D, 4 ml of methylene chloride and 0.17 ml of 2,3-cyclohexyl pyridine were mixed together and then, at −70° C. and over about 10 minutes, 0.160 ml of a 50% solution in methylene chloride of trifluoromethane sulfonic anhydride was added dropwise with stirring for 15 minutes at −70° C. The temperature was allowed to rise to −30° C. and excess trifluoromethane sulfonic anhydride was eliminated under a good vacuum. Water, methylene chloride and an N aqueous solution of hydrochloric acid were added followed by stirring, decanting and extracting with methylene chloride. The extracts were washed with a saturated aqueous solution of sodium chloride, then concentrated to dryness by distilling under reduced pressure. The residue was chromatographed over silica under nitrogen pressure and eluted with a mixture of methylene chloride and methanol (100/5) to obtain 109 mg of trifluoromethane sulfonate of 4-[[7-((2-triphenylmethyl-amino]-4-thiazolyl [(difluoromethoxy)-imino]-acetamido]-2-[[1,1-dimethylethoxy carbonyl]-8-oxo-4-thia-1-azabicyclo[4,2,0]oct-2-en-3-yl]-methyl]5,6,7,8-tetrahydroquinolinium with a Rf.=0.15 in a mixture of methylene chloride and methanol (95/5). The product was used as is for the following step.

STEP F: Trifluoromethane sulfonate of (6S, 7S, ΔZ) 1-[[7-[[(2-amino-4-thiazolyl) [(difluoromethoxyimino)] acetamido]-2-carboxy-8-oxo-4-thia-1-azabicyclo[4,2,0oct-2-en-3-yl]-methyl]-5,6,7,8-tetrahydro quinolinium, trifluoroacetate Under an inert atmosphere, 109 mg of the product of Step E, 0.44 ml of trifluoroacetic acid and 0.04 ml of water were mixed together and stirred for 2 hours at 20° C. 4 ml of ether were added, and after stirring, the precipitate formed was separated, washed with water and dried to obtain 74 mg of trifluoromethane sulfonate of (6S ,7S, ΔZ) 1-[[7-[[(2-amino-4-thiazolyl) [(difluoromethoxyimino]-acetamido]-2-carboxy-8-oxo-4-thia-1-azabicyclo[4,2,0]oct-2-en-3-yl]-methyl]-5,6,7,8-tetrahydro quinolinium, trifluoroacetate with a RF.=0.7 (acetone-water 2/1).

UV Spectrum (ethanol)

| | | |
|---|---|---|
| Max. | 220 nm $E_1^1$ = 341 | ε = 27,200 |
| Max. | 282 nm $E_1^1$ = 198 | ε = 15,800 |
| Inflexion | 292 nm $E_1^1$ = 178 | |

UV Spectrum (ethanol + 0.1 N HCl)

| | | |
|---|---|---|
| Max. | 220 nm $E_1^1$ = 267 | ε = 21,300 |
| Max. | 281 nm $E_1^1$ = 232 | ε = 18,500 |
| Inflexion | 295 nm $E_1^1$ = 198 | |

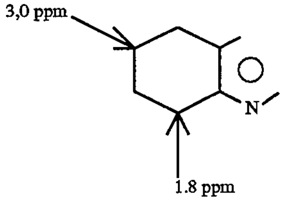

NMR Spectrum (dimethylsulfoxyde), in ppm

| | | | |
|---|---|---|---|
| H of $CH_2N^{\oplus}$ | 5.7 | pyridine | $H_2$ 8.77–8.81 |
| $H_7$ | 5.66 | | $H_4$ 8.36–8.44 |
| H of $CHF^2$ | 6.3–7.1–7.9 | | $H_3$ 7.89–8.02 |
| $H_5$ Thiazol syn | 7.1 | | |

EXAMPLE 204

Trifluoromethane sulfonate of (6S,7S ,ΔZ) 7-[[7-[[(2-amino-4-thiazolyl [(2-propynyloxy)-imino]-acetamido]2-carboxy-8-oxo-4-thia-1-azabicyclo [4,2,0]oct-2-en-3-yl]-methyl]-thieno[2,3-b]pyridinium STEP A: Syn isomer of 2-(2-tritylamino-4-thiazolyl)-2-(propynyloxy)-imino acetic acid Under an inert atmosphere, 1 g of ethyl 2-(2-tritylamino-4-thiazolyl)-[2-hydroxy]-imino acetate and 10 ml of dimethylformamide were mixed together, and at 0° C., 0.115 g of sodium hydride at 50% in vaseline oil were introduced with stirring for 5 minutes at 0° C. 0.235 ml of propargyl chloride was added dropwise with stirring for 30 minutes at 0° C. then for 16 hours at 20° C. Water was added and extraction was done with ether. The extracts were concentrated to dryness by distilling under reduced pressure to obtain 1 g of product which was used as is for the saponification.

1 g of the said ester, 7ml of dioxane, 7 ml of ethanol, 1.7 ml of water and 0.16 g of sodium hydroxide were mixed together and stirred for one hour and 15 minutes at 55° C. The reaction mixture was then poured into water and acidified to a pH of 2 by addition of an N aqueous solution of hydrochloric acid. After observing the formation of a precipitate, separating, dissolving the precipitate in methylene chloride, drying, and concentrating to dryness by distilling under reduced pressure, 503 mg of syn isomer of 2-(2-tritylamino-4-thiazolyl)-2-(propynyloxy)-imino acetic acid were obtained, IR Spectrum (chloroform)

| | | |
|---|---|---|
| =C—NH | | 3400 $cm^{-1}$ |
| —C≡CH | | 3308 $cm^{-1}$ |
| Region | C=O | 1731 $cm^{-1}$ |
| | C=C | 1624 $cm^{-1}$ |
| | C=N | 1592 $cm^{-1}$ |
| | | 1557 $cm^{-1}$ |
| | | 1529 $cm^{-1}$ |
| | | 1494 $cm^{-1}$ |

NMR Spectrum (dimethylsulfoxide) (ppm)

| | |
|---|---|
| H of ≡CH | 3.44–3.48–3.52 |
| H of $OCH_2$ | 4.66–4.70 |
| $H_5$ thiazol syn | 6.8 |
| H of $Ø_3$—C | 7.3 |
| H mobiles | 8.8 and 9.6 |

STEP B: 1,1-dimethyl-ethyl (6S, 7S, ΔZ) 3-hydroxymethyl-7-[3-[7-[[(2-triphenyl methyl)-amino-4-thiazolyl]][(2-propynyloxyimino]-acetamido]-8-oxo-4-thia-1-azabicyclo [4,2,0]oct-2-en-3-yl]2-carboxylate Under an inert atmosphere, 0.49 g of the product of Step A, 4.9 ml of acetone, 0.165 ml of triethylamine and 0.215 g of tosyl chloride were mixed together and stirred for one hour at 20° C. A mixture of 0.265 g of 1,1-dimethyl-ethyl (6S,7,ΔZ) 7-amino-3-hydroxy methyl-8-oxo-4-thia-1-azabicyclo[4,2,0]oct-2-en-2-carboxylate; 1.1 ml of water, 1.4 ml of 1M liter/aqueous solution of sodium bicarbonate and 2 ml of acetone was added together formed by stirring at 20° C. for two hours. After concentrating to eliminate the acetone, methylene chloride was added with stirring followed by decanting and washing the organic phase with a saturated aqueous solution of sodium chloride, and concentrating to dryness by distilling under reduced pressure. The residue was chromatographed over silica and eluted with a mixture of methylene chloride and ethyl acetate (85/15) to obtain 423 mg of 1,1-dimethyl-ethyl (6S, 7S, ΔZ) 3-hydroxymethyl-7-[3-[7-[[(2-triphenyl methyl)-amino-4-thiazolyl][(2-propynyloxy imino]-acetamido]-8-oxo-4-thia-1-azabicyclo[4,2,0]oct-2-en-3-yl]2-carboxylate with a Rf.= 0.4 in a mixture of methylene chloride and ethyl acetate (85/15).

I.R. Spectrum (Nujol)

General absorption region NH/OH

| | | |
|---|---|---|
| Beta lactam | C=O | 1760 $cm^{-1}$ |
| ester tBu | C=O | 1700 $cm^{-1}$ |
| tBuMe | | 1368 $cm^{-1}$, 1154 $cm^{-1}$ |
| Amide | C=O | 1677 $cm^{-1}$ |
| Conjugated system | | 1590 $cm^{-1}$ |
| Amide | | 1580 $cm^{-1}$ |
| Thiazol | | 1530 $cm^{-1}$ |
| Trityl | | 1490 $cm^{-1}$ |
| | | 800 $cm^{-1}$ |

U V Spectrum (ethanol)

| | | |
|---|---|---|
| Inflexion | 224 nm $E_1^1$ = 422 | |
| Inflexion | 237 nm $E_1^1$ = 346 | |
| Max. | 304 nm $E_1^1$ = 215 | ε = 16,100 |

U V Spectrum (ethanol + 0.1N HCl)

| | | |
|---|---|---|
| Inflexion | 223 nm $E_1^1$ = 399 | |
| Inflexion | 270 nm $E_1^1$ = 205 | |
| Inflexion | 285 nm $E_1^1$ = 253 | |
| Max. | 293 nm $E_1^1$ = 272 | ε = 2,000 |
| Inflexion | 268 nm $E_1^1$ = 264 | |

-continued

| NMR Spectrum ($CDCl_3$) (ppm) | |
|---|---|
| H of tBu | 1.5 |
| H of CH= | 2.55–2.58–2.61 |
| H of $CH_2$—O—N | 4.86–4.89 |
| H of $SCH_2$ | 3.11–3.17 |
| $H_6$ | 4.0 |
| $H_7$ beta lactam cis | 5.44–5.56 |
| H of $CH_2OH$ | 3.8–3.9 4.5–4.6 |
| H of hydroxyl | 3.77 |
| $H_5$ thiazol syn | 6.6 |
| H of NHCO | 6.9–7.0 |
| H of NH—CØ$_3$ | 7.2 |
| H of the trityl | 7.3 |

STEP C: 2-Trifluoromethane sulfonate of (6S, 7S, ΔZ) 7-[[7-[[(2-triphenylmethylamino-4-thiazolyl][(2-propynyloxy)-imino]-acetamido 2-[(1,1-dimethylethoxy) carbonyl-8-oxo-4-thia-1-azabicyclo[4,2,0]oct-2-en-3-yl]-methyl]thieno[2,3-b]pyridinium Under an inert atmosphere, 150 mg of the compound of Step B, 10 mg of thienyl pyridine and 3 ml of methylene chloride were mixed together and stirred for two minutes at 20° C., then cooled to –70° C. 0.236 ml of a solution of trifluoromethane sulfonic anhydride (1.75 equivalent) were added dropwise at –70° C. with stirring for one hour, while allowing the temperature to rise to –35° C. After concentrating to dryness under a good vacuum, adding methylene chloride, washing with an N aqueous solution of hydrochloric acid and concentrating to dryness by distilling under reduced pressure, the residue was chromatographed over silica and eluted with a mixture of methylene chloride and methanol (95/5) to, obtain 117 mg of 2-trifluoromethane sulfonate of (6S, 7S, ΔZ) 7-[[7-[[(2-triphenylmethylamino-4-thiazolyl][(2-propynyloxy)-imino]-acetamido 2-[(1,1-dimethyl ethoxy) carbonyl-8-oxo-4-thia-1-azabicyclo[4,2,0] oct-2-en-3-yl]methyl]-thieno[2,3-b]pyridinium.

| UV Spectrum (ethanol) | | |
|---|---|---|
| Max. | 239 nm $E_1^1$ = 580 | ε = 52,200 |
| Inflexion | 265 nm $E_1^1$ = 157 | |
| Max. | 303 nm $E_1^1$ = 228 | ε = 22,900 |
| UV Spectrum (ethanol + 0.1 N HCl) | | |
| Max. | 238 nm $E_1^1$ = 462 | ε = 46,300 |
| Inflexion | 287 nm $E_1^1$ = 250 | |
| Max | 293 nm $E_1^1$ = 271 | ε = 27,200 |

STEP D: Trifluoromethane sulfonate of 7-[[7-[[(2-amino-4-thiazolyl)-[(2-propynyloxy)-imino]-acetamido]2-carboxy-8-oxo-4-thia-1-azabicyclo[4,2,0]oct-2-en-3-yl]-methyl]-thieno[2,3-b]pyridinium Under an inert atmosphere, 112 mg of the Compound of Step C and 1.6 ml of a 66% aqueous solution of formic acid were mixed together and agitated for 2 hours at +65° C. After filtering, a little water and ethanol were added to the filtrate, which was then concentrated to dryness by distilling under reduced pressure. Again a little water and ethanol were added to the residue, which was again concentrated to dryness by distilling under reduced pressure. The residue was dissolved in methanol, and concentrated to dryness by distilling under reduced pressure. Ethyl acetate and ether were added to the residue, and after stirring, separating and drying, 67 mg of trifluoromethane sulfonate of 7-[[7-[[(2-amino-4-thiazolyl)-[(2-propynyloxy)-imino]-acetamido]2-carboxy-8-oxo-4-thia-1-azabicyclo[4,2,0]oct-2-en-3-yl]-methyl]-thieno[2,3-b]pyridinium were obtained with a Rf.= 0.55. (acetone 2-water 1).

| NMR Spectrum (dimethylsulfoxide) (ppm) | | |
|---|---|---|
| $H_5$ thiazol syn | 6.85 | |
| H of $NH_2$ | 7.3 | |
| H thiophene | 7.9–8.0 | |
| | 8.3–8.4 | |
| H pyridine | 8.2 (1H) | |
| | 9.1–9.2 (1H) | |
| | 9.30–9.33 (1H) | |
| 2H mobiles at | 4.7 | |
| $H_7$ | 5.6 | |
| H of $CH_2N^{\oplus}$ | 6.0–6.1 | |
| IR Spectrum (Nujol) | | |
| General absorption NH/OH | | |
| C≡CH | | 2120 $cm^{-1}$ |
| lactam C=O | | 1773 $cm^{-1}$ |
| aromatic | | 1600 $cm^{-1}$ |
| amide II | | 1578 $cm^{-1}$ |
| thiazol | | 1535 $cm^{-1}$ |
| Conjugated system | | |
| tfo$^{\ominus}$ | | 1030 $cm^{-1}$ |
| UV Spectrum (ethanol + 0.1 N HCl) | | |
| Max. | 241 nm $E_1^1$ = 527 | ε = 37,100 |
| Max. | 293 nm $E_1^1$ = 314 | ε = 22,100 |

EXAMPLE 205

Trifluoromethane sulfonate of (6S, 7S, ΔZ) 7-[[7-[(2-amino-4-thiazolyl-[(2-bromo-2-propenyloxy)-imino]-acetamido]-2-carboxy-8-oxo-4-thia-1-azabicyclo [4,2,0]oct-2-en-3-yl]-methyl]-thieno[2,3-b]pyridinium, trifluoroacetate STEP A: Syn isomer of 2-(2-tritylamino-4-thiazolyl)-2-[bromo-2-propenyloxy]-imino-acetic acid 1.5 g of the syn isomer of ethyl 2-(2-tritylamino-4-thiazol [2-hydroxy]-imino-acetate and 10 ml of dimethylformamide were mixed together and at 0° C., 0.174 g of sodium hydride at 50% in vaseline oil was added. After stirring for 5 minutes at 0° C. 0.64 ml of 2,3-dibromopropene was added dropwise followed by stirring for. 16 hours at 20° C. Water and then ether were added followed by decanting, extracting with ether, and concentrating the extracts to dryness by distilling under reduced pressure. The residue was chromatographed over silica and eluted with a mixture of methylene chloride and cyclohexane (95/5) to obtain 1.1 g of alkylated derivative with a Rf.=0.5 in the methylene chloride.

1.1 g of the said ester, 8 ml of dioxane, 7 ml of ethanol and 0.180 g of sodium hydroxide were mixed together and stirred for 90 minutes at +40° C. Precipitation was observed and the precipitate was separated and dissolved in methylene chloride in the presence of water. The solution was acidified to a pH of 2 by adding an N aqueous solution of hydrochloric acid, and after decanting, extraction was done with methylene chloride. The combined organic phases were concentrated to dryness by distilling under reduced pressure to obtain 670 mg of syn isomer of 2-(2-tritylamino-4-thiazolyl)-2-[bromo-2-propenyloxy]-imino-acetic acid with a Rf.=0.1 in a mixture of methylene chloride and methanol (9/1).

| IR Spectrum (chloroform) | | |
|---|---|---|
| =C—NH | | 3400 $cm^{-1}$ |
| General absorption region OH | | |
| Region | C=O | 1720, 1730 $cm^{-1}$ |
| | C=N | 1642 $cm^{-1}$ |
| | | 1616 $cm^{-1}$ |
| | | 1592 $cm^{-1}$ |

-continued

| | | |
|---|---|---|
| | | $1576\ cm^{-1}$ |
| | | $1529\ cm^{-1}$ |
| | | $1494\ cm^{-1}$ |
| NMR Spectrum (dimethylsulfoxide), (ppm) | | |
| | ( | 5.70–5.73 |
| H of $=CH_2$ | | 6.00–6.03 |
| $H_5$ thiazole syn | | 6.9 |
| H of $\phi_3$ | | 7.35 |
| H mobile | | 8.9 |
| H of $OCH_2$ | | 4.7 |

STEP B: Syn isomer of 1,1-dimethyl ethyl (6S, 7S, ΔZ) 3-hydroxymethyl-7[[[2-[(2-triphenyl methylamino)-4-thiazolyl]-[(2-bromo-2-propenyloxy-imino]-acetamido]-8-oxo-4-thia-1-azabicyclo[4,2,0]oct-2-en-2-carboxylate 575 mg of the syn isomer of 2-(2-tritylamino-4-thiazolyl)-2-[bromo-2-propenyloxy]-imino acetic acid, 5 ml of acetone, 0.165 ml of triethylamine and 0.215 g of tosyl chloride were mixed together and stirred for one hour at 20° C. Then, a mixture of 0.200 g of 7-amino-3-hydroxymethyl-8-oxo-4-thia-1-azabicyclo[4,2,0]oct-2-en-2-carboxylate of 1,1-dimethyl-ethyl (6S, 7S), ΔZ) 1 ml of water, 1.1 ml of an aqueous solution of sodium bicarbonate at 1M/liter, and 2 ml of acetone was added all at once and the mixture was stirred for one hour at 20° C. Then the acetone was eliminated by distilling under reduced pressure and methylene chloride was added. After stirring and decanting, the organic phase was washed with a saturated aqueous solution of sodium chloride, and concentrated to dryness by distilling under reduced pressure. The residue was chromatographed over silica and eluted with a mixture of methylene chloride and ethyl acetate (9/1) to obtain 388 mg of syn isomer of 1,1-dimethyl-ethyl (6S, 7S, ΔZ) 3-hydroxymethyl-7[[[2-[(2-triphenyl methyl amino)-4-thiazolyl]-[(2-bromo-2-propenyloxy imino]-acetamido]-8-oxo-4-thia-1-azabicyclo [4,2,0]oct-2-en-2-carboxylate.

| IR Spectrum (chloroform) | | |
|---|---|---|
| Amide | NH | $3404\ cm^{-1}$ |
| | C=O | $1684\ cm^{-1}$ |
| Amide II | | $1518\ cm^{-1}$ |
| Beta lactam C=O | | $1776\ cm^{-1}$ |
| Ester | tBu | |
| | tBu Me | $1369\ cm^{-1}$ |
| | C—O—C | $1155\ cm^{-1}$ |
| Aromatic | | $1633\ cm^{-1}$ |
| Conjugated system | | $1584\ cm^{-1}$ |
| Thiazol | | $1527\ cm^{-1}$ |
| C=C | | $1492\ cm^{-1}$ |

STEP C: Syn isomer of trifluoromethane sulfonate of 1,1-dimethyl ethyl]-methyl]-thieno[2,3-b]-pyridinium (6S, 7S, ΔZ) 1-[[7-((2-triphenylmethyl amino)-4-thiazolyl [[2-bromo-2-propenyloxy)-imino]-acetamido]-8-oxo-4-thia-1-azabicyclo[4,2,0]oct-2-en-3-yl]-2-carboxylate Under an inert atmosphere, 190 mg of the product of Step B, 5 ml of methylene chloride, and 0.126 g of thienyl pyridine were mixed together and stirred for 5 minutes. Then at −70° C., 0.140 ml of a solution of $(CF_3SO_2)_2O$ in methylene chloride was added dropwise followed by stirring for 50 minutes while allowing the temperature to rise to −50° C. After concentrating to dryness under a good vacuum, methylene chloride was added with stirring followed by washing with an N aqueous solution of hydrochloric acid, and again concentrating to dryness by distilling under reduced pressure. The residue was chromatographed over silica and eluted with a mixture of methylene chloride and methanol (9/1) to obtain 136 mg of syn isomer of trifluoromethane sulfonate of 1,1-dimethyl ethyl]-methyl]-thieno [2,3-b]pyridinium (6S, 7S ΔZ)1-[[7-((2-triphenylmethylamino)-4-thiazolyl [[2-bromo-2-propenyloxy)-imino]-acetamido]-8-oxo-4-thia-1-azabicyclo [4,2,0]oct-2-en-3-yl]-2-carboxylate

| | | |
|---|---|---|
| IR Spectrum (chloroform) | | |
| NH free combined (F) | $3400\ cm^{-1}$ (f) | |
| beta lactam | $1791\ cm^{-1}$ | |
| amine C=O amide | $1675\ cm^{-1}$ | |
| thiazol | $1525\ cm^{-1}$ | |
| aromatic | $1592\ cm^{-1}$ | |
| $NH_2$ def. | $1578\ cm^{-1}$ | |
| Conjugated system | $1496\ cm^{-1}$ | |
| $CO_2$tBu C=O | $1708\ cm^{-1}$ | |
| tBu Me | $1370\ cm^{-1}$ | |
| C=O—C | $1154\ cm^{-1}$ | |
| $TFO^{\ominus}$ | $1030\ cm^{-1}$ | |
| UV Spectrum (ethanol) | | |
| Max. | 258 nm $E_1^1 = 472$ | ε = 51,700 |
| Max. | 301 nm $E_1^1 = 197$ | ε = 21,600 |
| UV Spectrum (ethanol + 0.1 N HCl) | | |
| Max. | 237 nm $E_1^1 = 422$ | ε = 46,300 |
| Max. | 293 nm $E_1^1 = 241$ | ε = 26,400 |
| Inflexion | 285–314 nm | |

STEP D: Syn isomer of trifluoromethane sulfonate of (6S, 7S, ΔZ) 7-[[-[(2-amino-thiazolyl) [(2-bromo-2-propenyloxy)-imino]-acetamido]-2-carboxy-8-oxo-4-thia-1-azabicyclo[4,2,0]oct-2-en-3-yl]-methyl]-thieno[2,3-b] pyridinium trifluoroacetate Under an inert atmosphere, 125 mg of the product of Step C and 0.65 ml of trifluoroacetic acid were mixed together and stirred for 2 hours at 20° C. 3 ml of ether were added and after stirring, the precipitate formed was separated and dried to obtain 82 mg of syn isomer of trifluoromethane sulfonate of (6S, 7S, ΔZ) 7-[[7-[(2-amino-4-thiazolyl) [(2-bromo-2-propenyl-oxy)-imino]-acetamido]-2-carboxy-8-oxo-4-thia-1-azabicyclo[4,2,0]oct-2-en-3-yl]-methyl-thieno[2,3-b] pyridinium, trifluoroacetate.

| | | |
|---|---|---|
| UV Spectrum (ethanol) | | |
| Max. | 239 nm $E_1^1 = 512$ | ε = 46,100 |
| Max. | 298 nm $E_1^1 = 253$ | ε = 22,800 |
| UV Spectrum (ethanol + 0.1 N HCl) | | |
| Max. | 240 nm $E_1^1 = 457$ | ε = 41,100 |
| Max. | 293 nm $E_1^1 = 274$ | ε = 24,700 |
| NMR Spectrum (dimethylsulfoxide) (ppm) | | |
| H of $OCH_2$ | 4.7 | |
| H of $=CH_2$ | 5.7 and 6.0 | |
| $H_7$ beta lactam cis | 5.7 | |
| H of $CH_2N^{\oplus}$ | 6.2–6.4 | |
| | 6.0–6.1 | |
| $H_5$ thiazole syn | 6.9 | |
| $H_7$ and $H_8$ | 7.90–7.97 | |
| | 8.31–8.37 | |
| $H_5$ | 8.1 to 8.3 | |
| $H_6$ | 9.1–9.2 | |
| $H_4$ | 9.27–9.33 | |
| H of NHCO | 9.3–9.4 | |

EXAMPLE 206

Internal salt of (6S, 7S, ΔZ) 4-[[7-[[2-(2-amino-4-thiazolyl)-2-(methoxy-imino) acetamido]-2-carboxy-8-oxo-4-thia-1-azabicyclo[4,2,0]oct-2-en-3-yl]-methyl]thieno[3,2-b] pyridinium STEP A: Iodide and trifluoroacetate of (6S, 7S, ΔZ) 4-[[7-[[2-(2-amino-4-thiazolyl)-2-(methoxy imino)-acetamido]-2-carboxy-8-oxo-4-thia-1-azabicyclo [4,2,0]oct-2-en-3-yl]-methyl-thieno[3,2-b]pyridinium Under an inert atmosphere, 1.324 g of 1,1-dimethyl-ethyl 3-iodomethyl 7-[3-[7-[[(2-triphenylmethyl-amino-4-thiazolyl][2-(methoxy)-imino]-acetamido]-8-oxo-4-thia-1-azabicyclo[4,2,0]oct-2-en-3-yl]-2-carboxylate, 1.5 ml of acetonitrile and 0.3 g of thieno[3,2-b]pyridine were mixed together and stirred at 50° C. for 5 hours. Then, the solvent was eliminated by distilling under reduced pressure and methylene chloride and a 0.1N aqueous solution of hydrochloric acid were added. After stirring and decanting, extraction was done with methylene chloride. The extracts were concentrated to dryness by distilling under reduced pressure, and the 1.5 g of residue were chromatographed over silica and eluted with a mixture of methylene chloride and methanol (95/5) to obtain 0.976 g of the expected product.

IR Spectrum (chloroform) in $cm^{-1}$

| | | | |
|---|---|---|---|
| +C—NH | 3402 | C=C | 1598 |
| C=O | 1789 beta lactam | C=N | 1586 |
| C=O | 1703 | | 1571 |
| C=O | 1670 | | 1492 |
| amide II | 1526 | | |

NMR Spectrum ($CDCl_3$) in ppm

| | |
|---|---|
| H of tBu | 1.47 |
| H of 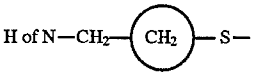 | 2.93 to 3.75 |
| H of N—$OCH_3$ | 4.0 |
| $H_7$ | 5.6 |
| H of 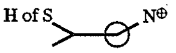 | 5.7 to 6.4 |
| $H_6$ | 6.3 |
| $H_5$ thiazol syn | 6.6 |
| H of $\phi_3C$ | 7.3 |
| H of pyridine | 7.9 to 9.8 |

Under an inert atmosphere, 0.28 g of the said product, and 2.8 ml of trifluoroacetic acid with 10% of water were mixed together and stirred at 20° C. for one hour. 30 ml of ether were added slowly with stirring at 20° C. for one hour until total concretion takes place. The precipitate formed was separated, washed and dried to obtain 0.219 g of iodide and trifluoroacetate of (6S, 7S, ΔZ) 4-[[7-[[2-(2-amino-4-thiazolyl)-2-(methoxyimino)-acetamido]-2-carboxy-8-oxo-4-thia-1-azabicyclo[4.2,0]oct-2-en-3-yl]-methyl]-thieno[3, 2-b]pyridinium.

IR Spectrum (Nujol) in $cm^{-1}$

| | |
|---|---|
| Absorption region | OH/NH |
| C=O beta lactam | 1775 |
| Others C=O | 1670–1640 |

UV Spectrum (ethanol + 0.1N HCl)

| | | |
|---|---|---|
| Max. | 239 nm | ε = 40,900 |
| Inflexion | 260 nm | |
| Max. | 293 nm | ε = 23,100 |
| Inflexion | 312 nm | |
| Inflexion | 440 nm | |

NMR Spectrum ($D_2O$ + DCl) in ppm

| | | |
|---|---|---|
| H of 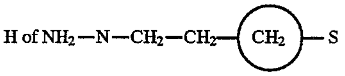 | 3.36 | isomer syn (Z) 80% |
| $H_6$ | 4.32 | |
| H of N—$OCH_3$ | 4.07 | |
| $H_7$ | 5.75 | |
| H of 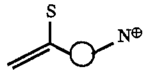 | 5.86–6.31 | |
| $H_5$ thiazol syn | 7.14 | |
| H of 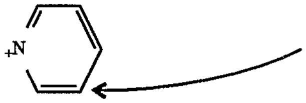 | 7.96 | |
| H of 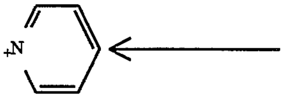 | 9.05 | |
| H of 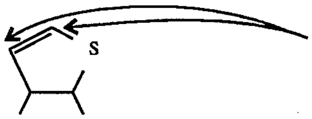 | 8.03–8.72 | |
| | | isomer anti (E) 20% |
| H of OMe | 4.24 | |
| $H_7$ | 5.69 | |
| $H_5$ thiazol | 7.85 | |

STEP B: Internal salt of (6S, 7S,ΔZ) 4-[[7-[[2-(2-amino-4-thiazolyl)-2-(methoxyimino)-acetamido]-2-carboxy-8-oxo-4-thia-1-azabicyclo[4,2,0]oct-2-en-3-yl]-methyl]-thieno[3, 2-b]pyridinium Under an inert atmosphere, 207 mg of the product of Step A, 1 ml of an M aqueous solution of triethylamine carbonate and 1 ml of acetic nitrile were mixed together and total dissolution was obtained. The solution was chromatographed on a 1 inch "inox" column filled with grafted RP 18 silica and eluted at a flow of 20 ml/minute with a gradient of distilled water containing from 5 to 20% of acetonitrile.

The interesting fractions were lyophilized to obtain 113 mg of internal salt of (6S, 7S, ΔZ) 4-[[7-[[2-(2-amino-4-thiazolyl)-2-(methoxyimino)-acetamido]-2-carboxy-8-oxo-4-thia-1-azabicyclo[4,2,0]oct-2-en-3-yl]-methyl]-thieno [3,2-b]pyridinium with a specific rotation of $[\alpha]_D$=−47° (c=0.5% in water) and melting about 200° C. with decomposition.

| | | |
|---|---|---|
| UV Spectrum (ethanol) | | |
| Max. | 238 nm | ε = 38,800 |
| Max. | 295 nm | ε = 19,700 |
| Inflexion | 320 nm | |
| UV Spectrum (ethanol + 0.1N HCl) | | |
| Max. | 238 nm | ε = 36,400 |
| Max. | 295 nm | ε = 21,900 |
| Inflexion | 314 nm | |
| NMR Spectrum ($D_2O$ + DCl) in ppm | | |
| 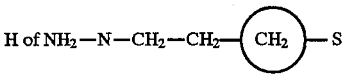 | | 3.29–336 |
| H of N—$OCH_3$ | | 4.08 |
| $H_6$ | | 4.23–4.37 |
| $H_7$ | | 5.71–5.77 |
| H of 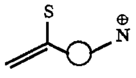 | | 5.80–6.0<br>6.3–6.5 |
| $H_5$ thiazol syn | | 7.2 |
| 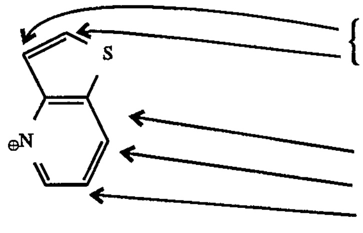 | | 8.03–8.1<br>8.7–8.8<br>9.18–9.27<br>7.9–8.1<br>9.04–9.11 |

EXAMPLE 207

Internal salt of (6S, 7S, ΔZ) 4-[[7-[[2-(2-amino-4-thiazolyl)-2-(methoxy-imino)-acetamido]-2-carboxy-8-oxo-4-thia-1-azabicyclo[4,2,0]oct-2-en-3-yl]-methyl]-thieno[3,2-b] pyridinium STEP A: Trifluoroacetate and trifluoromethane sulfonate of (6S, 7S, ΔZ) 4-[[7-[[2-(2-amino-4-thiazolyl)-2-(methoxyimino)-acetamido]-2-carboxy-8-oxo-4-thia-1-azabicyclo[4,2,0]oct-2-en-3-yl]-methyl]-thieno[3,2-b] pyridinium Under an inert atmosphere, 1 g of 1,1-dimethyl-ethyl 3-hydroxymethyl-7-[3-[7[[2-triphenylmethyl-amino-4-thiazolyl][2-methoxy)-imino]-acetamido]-8-oxo-4-thia-1-azabicyclo[4,2,0]oct-2-en-3-yl]-2-carboxylate, 10 ml of methylene chloride and 0.2 ml of thieno[3.2-b]pyridine were mixed together and at −70° C., 0.28 ml of trifluoromethane sulfonic acid anhydride was introduced with stirring at −20° C. for 15 minutes. Then, the mixture was poured into a 0.1N aqueous solution of hydrochloric acid, and after stirring and decanting, extraction was done with methylene chloride. The extracts were concentrated to dryness by distilling under reduced pressure, and the 1.57 g of residue were chromatographed over silica and eluted with a mixture of methylene chloride and methanol (90/10) to obtain 389 mg of trifluoroacetate and trifluoromethane sulfonate of (6S, 7S, ΔZ) 4-[[7-[[2-(2-amino-4-thiazolyl)-2-(methoxyimino)-acetamido]-2-carboxy-8-oxo-4-thia-1-azabicyclo[4,2,0]oct-2-en-3-yl]-methyl]thieno[3,2-b]pyridinium.

| | | | |
|---|---|---|---|
| IR Spectrum (chloroform) in $cm^{-1}$ | | | |
| Secondary amide NH | 3402<br>1526 | C=C<br>C=N | 1598<br>1586 |
| CO beta lactam | 1789 | | 1571 |
| C=O | 1703–1670 | | 1492 |
| NMR Spectrum ($CDCl_3$) in ppm. | | | |
| H of tBu | 1.47 | | |
| H of 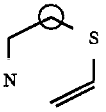 | 3.04–3.6 | | |
| H of N—OMe | 4.0 | | |
| $H_6$ | 4.2 | | |
| H of 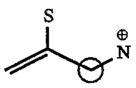 | 5.4–5.6–6.1–6.3 | | |
| $H_5$ thiazol syn | 6.6 | | |
| H of $\phi_3$C—NH | 7.2 | | |
| H of $\phi_3$C | 7.3 | | |
| 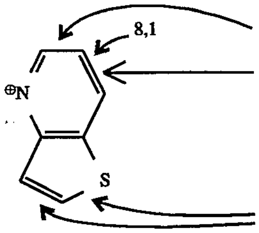 | 9.4–9.5<br>8.9–9.0<br>8.1–8.2–8.5–8.54 | | |

Under an inert atmosphere, 157 mg of the said product and 1.5 ml of trifluoroacetic acid with 10% of water were mixed together and stirred at 20° C. for one hour. 15 ml of ether were introduced slowly, with stirring at 20° C. for one hour until total concretion took place. The precipitate formed was separated, washed and concentrated to dryness by distilling under reduced pressure to obtain 116 mg of trifluoroacetate and trifluoromethane sulfonate of (6S, 7S, ΔZ) 4-[[7-[[2-(2-amino-4-thiazolyl)-2-(methoxyimino)-acetamido]-2-carboxy-8-oxo-4-thia-1-azabicyclo[4,2,0]oct-2-en-3-yl]-methyl]-thieno[2,3-b]pyridinium melting at about 200° C. with decomposition.

| | | |
|---|---|---|
| UV Spectrum (ethanol) | | |
| Max. | 238 nm | ε = 42,400 |
| Max. | 295 nm | ε = 21,200 |

-continued

| | | |
|---|---|---|
| UV Spectrum (ethanol + 0.1N HCl). | | |
| Max. | 230 nm | ε = 38,900 |
| Max. | 292 nm | ε = 23,600 |
| Inflexion | 314 nm | |
| NMR Spectrum ($D_2O$ + DCl) in ppm. | | |
| H of 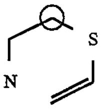 | 3.28–3.35 | |
| H of N—OMe | 4.06 | |
| $H_6$ | 4.23–4.26 | |
| $H_7$ | 5.75–5.71 | |
| H of 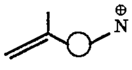 | 5.8–6.3<br>6.30–6.45 | |
| $H_5$ thiazole syn | 7.15 | |

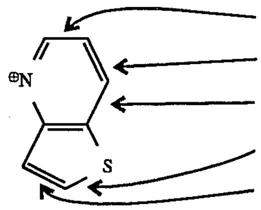

STEP B: Internal salt of (6S, 7S, ΔZ) 4-[[7-[[2-(2-amino-4-thiazolyl)-2-(methoxyimino)-acetamido]-2-carboxy-8-oxo-4-thia-1-azabicyclo[4,2,0]oct-2-en-3-yl]-methyl]-thieno[2,3-b]pyridinium Under an inert atmosphere, 159 mg of the product of Step A, 1.5 ml of an M aqueous solution of triethylamine carbonate and 1.5 ml of acetonitrile were mixed together to obtain total dissolution, chromatography was carried out on a 1-inch "inox" column filled with grafted RP 18 silica. Elution with a gradient of solvents (water 95-acetonitrile 5 to water 80-acetonitrile 20), at a rate of 20 ml per minute was effected and the interesting fraction was lyophilized to obtain 79 mg of internal salt of (6S, 7S, ΔZ) 4-[[7-[[2-(2-amino-4-thiazolyl)-2-(methoxyimino)-acetamido]-2-carboxy-8-oxo-4-thia-1-azabicyclo[4,2,0]oct-2-en-3-yl]-methyl]-thieno[2,3-b]pyridinium. The checks were identical to those of the product obtained at Step B of Example 206.

EXAMPLE 208

Trifluoromethane sulfonate of (6S, 7S, ΔZ) 7-[[7 [[(2-amino-4-thiazolyl)-[(2-fluoro-2-propenyloxy)-imino]-acetamido]-2-carboxy-8-oxo-4-thia-1-azabicyclo [4,2,0] oct-2-en-3-yl]-methyl]-thieno[2,3-b]pyridin-7-ium (trifluoroacetate)

Under an inert atmosphere, 140 mg of 1,1-dimethyl-ethyl (6S, 7S, ΔZ) 3-hydroxymethyl-7-[2-[2-triphenylmethylamino-4-thiazolyl)-2-fluoro-2-propenloxy)-imino]-acetamido]-8-oxo-4-thia-1-azabicyclo[4,2,0]oct-2-en-3-yl]-2-carboxylate, 4 ml of methylene chloride and 100 mg of thieno-pyridine were mixed together and at −70° C. and over 10 minutes, 0.220 ml of a 25% by volume solution of trifluoromethane sulfonic anhydride in methylene chloride were introduced with stirring from −70° C. to −30° C. over 60 minutes. After concentrating to dryness by distilling under reduced pressure at −20° C., the residue was chromatographed over silica under nitrogen pressure and eluted with a mixture of methylene chloride and ethyl acetate (85/15), then with methylene chloride and methanol (90/10) to obtain 130 mg of trifluoromethane sulfonate of (6S, 7S, ΔZ) 7-[[7-[[(2-amino-4-thiazolyl) [(2-fluoro-2-propenyloxy)-imino]-acetamido]-2-carboxy -8-oxo-4-thia 1-azabicyclo[4,2,0]oct-2-en-3-yl]-methyl]-thieno[2,3-b] pyridinium.

Under an inert atmosphere, 130 mg of the said product, 0.63 ml of trifluoroacetic acid and 0.04 ml of water were mixed together and stirred at 20° C. for two hours. 4 ml of ether were added slowly, and after stirring, the precipitate formed was separated, washed and dried to obtain 86 mg of trifluoromethyl sulfonate of (6S, 7S, ΔZ) 7-[[7-[[(2-amino-4-thiazolyl) [(2-fluoro-2-propenyloxy)-imino]-acetamido]-2-carboxy-8-oxo-4-thia-1-azabicyclo[4,2,0]oct-2-en-3-yl]-methyl]-thieno[2,3-b]pyridinium (trifluoroacetate).

| | | | |
|---|---|---|---|
| UV Spectrum (ethanol) | | | |
| Max. | 238 nm | $E^1_1$ = 515 | ε = 43,200 |
| Max. | 296 nm | $E^1_1$ = 249 | ε = 20,900 |
| UV Spectrum (ethanol + 0.1N HCl). | | | |
| Max. | 240 nm | $E^1_1$ = 950 | ε = 37,700 |
| Max. | 293 nm | $E^1_1$ = 265 | ε = 22,200 |
| NMR Spectrum (dimethyl sulphoxide) in ppm. | | | |
| H of 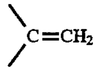 F and $=NOCH_2$ | 4.47–5.07 | | |
| $H_7$ beta lactam | 5.63–7.05 | | |
| H of $CH_2N^+$ | 5.94–6.24 | | |
| $H_5$ thiazol | 6.88 | | |
| H of CH=CH₂ thiophene | 7.90–7.98<br>8.30–8.37 | | |

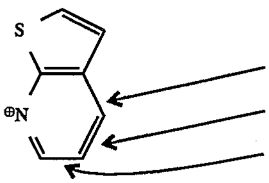

EXAMPLE 209

Trifluoromethane sulfonate of (6S, 7S, ΔZ) 7-[[7-[[(2-amino-4-thiazolyl) [(2-butenyloxy)-imino]-acetamido]-2-carboxy-8-oxo-4-thia-1-azabicyclo [4,2,0]oct-2-en-3-yl]-methyl-thieno[2,3-b]pyridinium (trifluoroacetate)

STEP A: 2-[(2-tritylamino-4-thiazolyl)-2-(2-butenyloxy)-imino acetic acid (⅔ E:⅓ Z)

Under an inert atmosphere, 1.8 g of 2-[(2-tritylamino-4-thiazolyl)-2-(hydroxy)-imino acetic acid, 18 ml of tetrahydrofuran and 450 mg of potassium tert-butylate were mixed together and stirred at +5° C. for 10 minutes. Then, 1 ml of crotyl chloride was added with stirring at 20° C. for one hour. The reaction mixture was poured into a mixture of water and ice, stirred and neutralized to a pH of 6 by a 0.5M aqueous solution of monosodium phosphate. Extraction was done with ether and the extracts were washed with a saturated aqueous solution of sodium chloride, dried, and concentrated to dryness by distilling under reduced pressure. The 1.8 g of residue was chromatographed over silica and eluted with methylene chloride to obtain 860 mg of the expected product.

Under an inert atmosphere, 0.134 g of the said ethyl ester, 0.5 ml of dioxane, 0.5 ml of 96° C. ethanol and 50 mg of solid sodium hydroxide were mixed together and stirred at 20° C. for 3 hours, then taken to 0° to +5° C. Water and an N aqueous solution of hydrochloric acid (pH 1) were added, and after stirring, the precipitate formed was separated and dried under vacuum in the presence of potassium hydroxide to obtain 111 mg of 2-[(2-tritylamino-4-thiazolyl)-2-(2-butenyloxy)-imino acetic acid (⅔ E:⅓ Z)

| NMR Spectrum (dimethylsulfoxide) in ppm | |
|---|---|
| H of $OCH_2$ (resolution ⅔, ⅓), | 4.52 to 4.61 |
| H of CH=CH ethylenes | 5.52 to 5.85 |
| H thiazol syn | 6.85 to 6.92 |
| Aromatic H's | 7.05 to 7.39 |
| H mobile | 9.01 |

STEP B: Trifluoromethane sulfonate of (6S, 7S, ΔZ) 7-[[7-[[(2-amino-4-thiazolyl)-[(2-butenyloxy) imino]-acetamido]-2-carboxy-8-oxo-4-thia-1-azabicyclo[4,2,0]oct-2-en-3-yl]-methyl]-thieno[2,3-b]pyridinium (trifluoroacetate)

Under an inert atmosphere, 0.340 g of 2-[(2-tritylamino-4-thiazolyl)-2-(2-butenyloxy)-imino acetic acid (⅔ E:⅓ Z), 3 ml of acetone, 0.104 ml of triethylamine and 0.136 g of tosyl chloride were mixed together and stirred at 20° C. for 45 minutes. A solution of 0.164 g of 1,1-dimethyl-ethyl (6S, 7S) 7-amino-3-hydroxymethyl-8-oxo-4-thia-1-azabicyclo [4,2,0]oct-2-en-2-carboxylate, 1 ml of an M aqueous solution of sodium bicarbonate, 1 ml of water and. 1 ml of acetone were added with stirring at 20° C. for one hour. The acetone was eliminated by distilling under reduced pressure and water and methylene chloride were added. After stirring and decanting, extraction was done with methylene chloride. The extracts were washed with a saturated aqueous solution of sodium chloride, dried and concentrated to dryness by distilling under reduced pressure. The 360 mg of residue were chromatographed over silica under nitrogen pressure and eluted with a mixture of methylene chloride and ethyl acetate (9/1) to obtain 260 mg of the expected product, Under an inert atmosphere, 160 mg of the said alcohol, 103 ml of methylene chloride, and 115 mg of thieno[2,3-b] pyridine were mixed together. Over about 10 minutes at −70° C., 1.5 ml of a 4.2% by volume solution of trifluoromethane sulfonic anhydride in methylene chloride were introduced with agitation at −70° C. for 30 minutes, and between −70° C. and −20° C. for 30 minutes. After concentrating to dryness by distilling under reduced pressure, the residue was chromatographed on silica eluting with a mixture of methylene chloride and methanol (90/10), and 50 mg of the expected product were obtained.

Under an inert atmosphere, 50 mg of the said product and 200 µl of trifluoroacetic acid were mixed together and stirred at 20° C. for two hours. 3 ml of ether were added slowly, and after stirring, the precipitate was separated, washed and dried to obtain 36 mg of trifluoromethane sulfonate of (6S, 7S, ΔZ) 7-[[7-[[(2-amino-4-thiazolyl)-[(2-butenyloxy)-imino]-acetamido]-2-carboxy-8-oxo-4-thia-1-azabicyclo[4,2,0]oct-2-en-3-yl]-methyl]-thieno[2,3-b]pyridinium (trifluoroacetate)

| UV Spectrum (ethanol) | | |
|---|---|---|
| Max. | 238 nm $E_1^1$ = 511 | ε = 42,700 |
| Max. | 296 nm $E_1^1$ = 258 | ε = 21,500 |
| UV Spectrum (ethanol + 0.1 N HCl) | | |
| Max. | 240 nm $E_1^1$ = 465 | ε = 38,800 |
| Max. | 294 nm $E_1^1$ = 283 | ε = 23,600 |

-continued

| NMR Spectrum (dimethylsulfoxide) in ppm | |
|---|---|
| E and Z isomers at the double bond (E ⅔, Z ⅓). | |
| H of $CH_3$—C | 1.60 |
| H of $CH_2$—S | 3.06 to 3.2 |
| $H_6$ | 4.02 |
| H of $OCH_2C$= | 4.49 (d) and 4.63 (d) |
| The ethylene H's and $H_7$ beta lactam | 5.51 to 5.78 |
| H of $CH_2N^+$ | 6.01 (d) to 6.20 (d) |
| $H_5$ thiazol | 6.78 to 6.79 |
| H in α and β of S | 791 (d) to 8.31 (d) |
| H in β of N | 8.20 (dd) |
| Other aromatic H's | 9.20 |

EXAMPLE 210

Iodide of (6S, 7S, ΔZ) 7-[[7-[[2-amino-4-thiazolyl)-[(2-fluoro-2-propenyloxy)-imino]-acetamido]-2-carboxy-8-oxo-4-thia-1-azabicyclo[4,2,0]oct-2-en-3-yl]-methyl]-thieno[3,2-c]pyridinium (trifluoroacetate)

Under an inert atmosphere, 250 mg of 1,1-dimethyl-ethyl (6S, 7S ΔZ) 3-hydroxymethyl-7-[2-[2-triphenylmethylamino-4-thiazolyl][(2-fluoro-2-propenyloxy)-imino]-acetamido]-8-oxo-4-thia-1-azabicyclo [4,2,0]oct-2-en-3-yl]-2-carboxylate, 5 ml of methylene chloride, 245 mg of tetrabutyl ammonium iodide and 0.146 ml of 2,6-lutidine were mixed together and over about 10 minutes at −70° C., 0.20 ml of a 50% solution of trifluoromethane sulfonic anhydride in methylene chloride were introduced with stirring at −70° C. to −50° C. for 60 minutes. After concentrating to dryness by distilling under reduced pressure at −10° C. the residue was chromatographed over silica under nitrogen pressure and eluted with a mixture of methylene chloride and ethyl acetate (95/5) to obtain 225 mg of the expected product.

Under an inert atmosphere, 120 mg of the said iodine derivative, 3 ml of acetonitrile and 56 mg of 7-methyl-thieno [3,2-b]pyridine were mixed together and stirred at 20° C. for 16 hours. After concentrating to dryness by distilling under reduced pressure, the residue was chromatographed over silica under nitrogen pressure and eluted with a mixture of methylene chloride and methanol (92/8) to obtain 0.88 g of the expected product.

Under an atmosphere of nitrogen, 88 mg of the said product, 0.50 ml of trifluoroacetic acid and 0.04 ml of water were mixed together and stirred at 20° C. for two hours. 3 ml of ether were added slowly, and after stirring, the precipitate formed was separated, washed and dried to obtain 42 mg of (6S, 7S, ΔZ) iodide of 5-[[7-[[(2-amino-4-thiazolyl)-[[(2-fluoro-2-propenyloxy)-imino]-acetamido]-2-carboxy-8-oxo-4-thia-1-azabicyclo[4,2,0]oct-2-en-3-yl]-methyl]-thieno (3,2-c]pyridinium (trifluoroacetate).

| UV Spectrum (ethanol) | | |
|---|---|---|
| Max. | 239 mn $E_1^1$ = 670 | ε = 54,700 |
| Max. | 295 nm $E_1^1$ = 235 | ε = 19,800 |
| Inflexion | 360 nm $E_1^1$ = 86 | |
| UV Spectrum (ethanol + 0.1 N HCl) | | |
| Max. | 241 nm $E_1^1$ = 651 | ε = 53,800 |
| Max. | 285 nm $E_1^1$ = 265 | ε = 21,600 |
| NMR Spectrum (dimethylsulfoxide) in ppm | | |
| $H_6$ and $CH_2S$ | | 3.07 to 4.09 |
| H of $CH_2O$ and CF=$CH_2$ | | 4.6 to 4.83 |

-continued

| | | |
|---|---|---|
| $H_7$ and H of $CH_2N^{\oplus}$ | | 5.64 to 5.97 |
| $H_5$ thiazol | | 6.81 |
| $H_5$ and $H_6$ | { | 8.05 |
| | | 8.44 |
| $H_6$ and $H_7$ | | 8.80 to 8.88 |
| $H_3$ | | 9.25 |
| H mobile | | 7.27 and 8.57 |

-continued

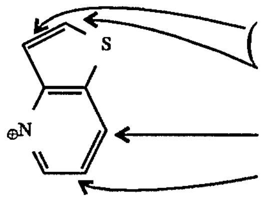

8.27–8.34
8.47–8.54
7.98–8.04
9.74–9.81

EXAMPLE 211

Internal salt of 4-[[7-[[(2-amino-4-thiazolyl) (methoxyimino)-acetamido]2-carboxy-8-oxo-4-thia-1-azabicyclo[4,2,0]oct-2-en-3-yl]-methyl]-thieno [3,2-b] pyridinium Under an inert atmosphere, 0.411 g of 1,1-dimethylethyl (6S, 7S, ΔZ) 3-iodomethyl-7-[3-[7-[(2-triphenylmethylamino]-8-oxo-thia-1-azabicyclo[4,2,0]oct-2-en-3-yl]2-carboxylate, 4 ml of acetonitrile, and 0.15 g of 7-methyl-thieno[3,2-b]pyridine were mixed together and stirred for 2 hours at 50° C., cooled, then concentrated to dryness by distilling under reduced pressure. Methylene chloride and a 0.1N aqueous solution of hydrochloric acid were added with stirring followed by decanting and extracting with methylene chloride. The extracts were concentrated to dryness by distilling under reduced pressure and the 0.56 g of residue were chromatographed over silica and eluted with a mixture of methylene chloride and methanol (95/5) to obtain 2.94 g of the expected product

| IR Spectrum (chloroform) in $cm^{-1}$ | | | |
|---|---|---|---|
| =C—NH | 3403 | C=C<br>C=N<br>amide II | 1596<br>1568<br>1525 |
| C=O beta lactam | 1784 | | |
| Other C=O | 1703 | | |
| | 1675 | Me of tBu | 1370 |

| NMR Spectrum ($CDCl_3$) in ppm. | |
|---|---|
| H of Me of TBu | 1.5 |
| H of Me of pyridine | 2.89 |
| H of 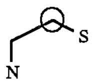 | 3.05–3.83 |
| $H_6$ | 4.15 |
| $H_7$ | 5.6 to 5.7 (J = 5) |
| H of 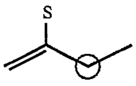 | 5.73–5.89<br>6.17–6.33 |
| $H_5$ thiazol | 6.64 |
| H of $\phi_3$-CN—H | 7.07 |
| H of $\phi_3$ | 7.32 |

Under an inert atmosphere, 0.275 g of the said product and 2.8 ml of trifluoroacetic acid with 10% of water were mixed together and stirred at 20° C. for one hour. 28 ml of ether were added slowly, and the precipitate formed after stirring was separated, washed and dried under vacuum to obtain 0.2 g of the crude product.

Under an inert atmosphere, 0.2 g of the said product, 1 ml of an M aqueous solution of triethylamine carbonate and 1 ml of acetonitrile were mixed together and when completely dissolved, the solution was chromatographed on a one inch "inox" column filled with grafted RP 18 silica and eluted at a flow of 20 ml/minute by a gradient of distilled water containing from 5% to 20% of acetonitrile. The interesting fractions were lyophilized and 0.072 g of internal salt of 4-[[7-[[(2-amino-4-thiazolyl) (methoxyimino)-acetamido]2-carboxy-8-oxo-4-thia-1-azabicyclo[4,2,0]oct-2-en-3-yl]-methyl]-thieno[3,2-b]pyridinium with a specific rotation of $[\alpha]_D$=−35° (c=0 2% in water).

| IR Spectrum (nujol) in $cm^{-1}$ | | | |
|---|---|---|---|
| Absorption OH/NH | | —C=C—<br>C=N | 1610<br>1590 |
| C=O beta lactam | 1765 | $CO_2$— | 1565 |
| other C=O | 1662 | amide II | 1545 |
| | | $NH_2$ def. | 1500 |

| UV Spectrum (ethanol) | | |
|---|---|---|
| Max. | 213 nm | ε = 31,300 |
| Max. | 236 nm | ε = 38,800 |
| Max. | 292 nm | ε = 19,900 |
| Inflexion | 306 nm | |

| UV Spectrum (ethanol + 0.1N HCl) | | |
|---|---|---|
| Max. | 238 nm | ε = 36 700 |
| Inflexion | 268 nm | |
| Max. | 291 nm | ε = 22,200 |
| Inflexion | 310 nm. | |

| NMR Spectrum ($D_2O$, DCl) in ppm. | |
|---|---|
| H of the $CH_3$ of pyridine | 2.92 |
| H of 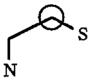 | 3.22 |
| H of N—$OCH_3$ | 4.05 |
| $H_6$ | 4.29 |
| $H_7$ | 5.70 |
| H of 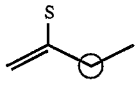 | 5.82 (J = 15)<br>6.84 (J = 15) |
| $H_5$ thiazol | 7.12 |

-continued

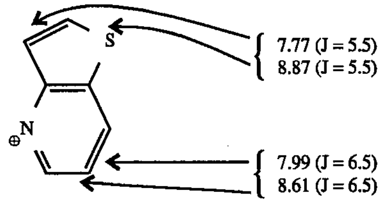

The 7-methyl thieno[3,2-b]pyridine used above was prepared as follows:

25 g of a mixture of 85% of 2-nitrothiophene and 15% of 3-nitrothiophene and 375 ml of a 37% aqueous solution of hydrochloric acid were mixed together and at 30° C. over about one hour, 50 g of granulated tin were introduced in small portions with stirring at 30° C. until the metal disappeared (in all, 4 hours). 50 ml of ethanol, 22 g of ferric chloride and 0.5 g of anhydrous zinc chloride were added and then at 60° C. 30 ml of methyl vinyl ketone and 60 ml of ethanol were introduced over about one hour and the mixture was maintained at 80° C. for two hours, and then at 20° C. for 16 hours. The reaction mixture was poured on to ice and carbon tetrachloride was added followed by concentrated ammonia until pH=9. The mixture was filtered on hyflosupercel, decanted, and extracted the aqueous phase with carbon tetrachloride. The organic phases were concentrated to dryness by distilling under reduced pressure, and the 9.8 g of residue were chromatographed over silica under nitrogen pressure. Elution with a gradient of 100% of methylene chloride to 100% of ethyl acetate yield 0.55 g of internal salt of 4-[[7-[[(2-amino-4-thiazolyl)-(methoxyimino)-acetamido]-2-carboxy-8-oxo-4-thia-1-azabicyclo[4,2,0]oct-2-en-3-yl]-methyl-thieno[3,2-b]pyridinium.

NMR Spectrum ($CDCl_3$) in ppm.

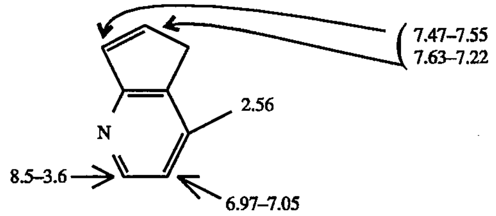

EXAMPLE 212

Internal salt of (6S, 7S, ΔZ) 2-[(7-[[(2-amino-4-thiazolyl)-(methoxyimino)acetamido]-2-carboxy-8-oxo-4-thia-1-azabicyclo[4,2,0]oct-2-en-3-yl]-methyl]-1-methyl isoquinolinium Under an inert atmosphere, 0.411 g of 1,1-dimethyl-ethyl (6S, 7S, ΔZ) 3-iodomethyl-7-[3-[7-[(2-triphenylmethylamino]-4-thiazolyl]2-(methoxy)-imino]-acetamido]-8-oxo-4-thia-1-azabicyclo[4,2,0]-oct-2-en-3-yl]-2-carboxylate and 0.15 g of 1-methyl-isoquinoline were mixed together and stirred at 50° C. for two hours, then concentrated to dryness by distilling under reduced pressure. Methylene chloride and 0.1N aqueous solution of hydrochloric acid were added followed by decanting and extracting with methylene chloride, The solvent was eliminated by distilling under reduced pressure and the 0.56 g of residue was chromatographed over silica and eluted with a mixture of methylene chloride and methanol (95/5) to obtain 0.332 g of the expected product.

Under an inert atmosphere, 0.332 g of the said product and 3 ml of trifluoroacetic acid with 10% of water were mixed together and stirred at 20° C. for one hour. 30 ml of ether were added slowly, and the precipitate formed after stirring was separated, washed and dried to obtain 0.209 g of the expected product.

Under an inert atmosphere, 0.209 g of the said product, 1 ml of an M aqueous solution of triethylamine carbonate and 1 ml of acetonitrile were mixed together, and when completely dissolved, the solution was chromatographed on a one-inch "inox" column filled with grafted RP 18 silica and eluted with a flow of 20 ml/minute by a gradient of distilled water containing from 5% to 20% of acetonitrile. The interesting fractions were lyophilized to obtain 0.060 g of internal salt of (6S, 7S, ΔZ) 2-[(7-[[(2-amino-4-thiazolyl)-(methoxyimino)-acetamido]-2-carboxy-8-oxo-4-thia-1-azabicyclo[4,2,0]oct-2-en-3-yl]-methyl]-1-methyl isoquinolinium.

IR Spectrum (Nujol) in $cm^{-1}$.

| | |
|---|---|
| Absorption region OH/NH | |
| C=O beta lactam | 1765 |
| other C=O | 1660 |
| $CO_2^{\ominus}$ | 1630 |
| C=O | 1610 |
| C=N | 1565 |
| Amide II | 1533 |

UV Spectrum (ethanol + 0.1N HCl)

| | | |
|---|---|---|
| Inflexion | 231 nm | |
| Max. | 235 nm | ε = 56,900 |
| Inflexion | 272 nm | |
| Max. | 281 nm | ε = 20,300 |
| Inflexion | 292 nm | |
| Inflexion | 310 nm | ε = 14,600 |
| Inflexion | 392 nm. | |

NMR Spectrum ($D_2O$ + DCl) in ppm.

| | |
|---|---|
| H of 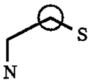 | 3.22–3.30 |
| H of the methyl of pyridine | 3.31 |
| H of N—$OCH_3$ | 4.04 |
| $H_6$ | 4.28 |
| H of 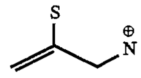 | 5.57 (J = 16 Hz) 6.14 (J = 16 Hz) |
| $H_7$ | 5.68 |
| $H_5$ thiazol syn | 7.10 |

-continued

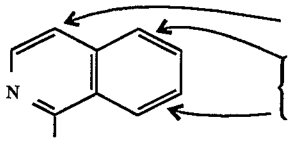

| | |
|---|---|
| | 8.65 (J = 8.5 Hz) |
| | 8.26 (J = 7 Hz) |
| | 8.50 (J = 7 Hz) |
| Other aromatic H's | 8.04 to 8.29 |

EXAMPLE 213

Iodide of (6S, 7S, ΔZ) 1-[[7-[[2-(2-amino-4-thiazolyl)-2-(methoxyimino)-acetamido]-2-carboxy-8-oxo-4-thia-1-azabicyclo[4,2,0]oct-2-en-3-yl]-methyl]-4-(amino carbonyl)-pyridinium STEP A: 1,1-dimethyl-ethyl 3-iodomethyl-7-[[2-(2-(triphenylmethyl)-amino-4-thiazolyl]-2-[methoxyimino]-acetamido]-8-oxo-4-thia-1-azabicyclo [4,2,0]oct-2-en-2-carboxylate Under an inert atmosphere, 2 g of 1,1-dimethylethyl (6S, 7S, ΔZ) 3-hydroxymethyl-7-[[2-(2-triphenylmethylamino-thiazol-4-yl)-2-(methoxy-imino)-acetamido]-8-oxo-4-thia-1-azabicyclo[4,2,0]oct-2-en-2-carboxylate, 20 ml of methylene chloride, 1.3 g of tetrabutylammonium iodide and 1.3 ml of 2,6-lutidine were mixed together and at −70° C. over about 15 minutes, 9 ml of a 10% solution of trifluoromethane sulfonic anhydride in methylene chloride were introduced with stirring at 0° C. for 15 minutes. A 0.1N aqueous solution of hydrochloric acid was added, and after stirring and decanting, extraction was done with methylene chloride. After concentrating to dryness by distilling under reduced pressure, the 4.36 g of residue were chromatographed over silica and eluted with a gradient of 1 to 10% of ethyl acetate in methylene chloride to obtain 1.324 g of 1,1-dimethylethyl 3-iodomethyl-7-[[2-(2-triphenylmethyl)-amino-4-thiazolyl]-2-[methoxy-imino]-acetamido]-8-oxo-4-thia-1-azabicyclo[4,2,0]oct-2-en-2-carboxylate melting at about 150° C. not very pure and having a specific rotation of $[\alpha]_D$=+13° (c=0.5% in chloroform)

| IR Spectrum (chloroform) in $cm^{-1}$. | |
|---|---|
| =C—NH | 3405–3255 |
| C=O beta lactam | 1775 |
| Other C=O | 1706–1680 |
| Amide II | 1528 |
| C=O, C=N | 1575–1496 |

UV Spectrum (ethanol) Inflex. 227 nm, inflex. 233 nm, inflex. 254 nm, inflex. 265 nm, inflex. 271 nm, max. 315 n, ε=13,000

UV Spectrum (ethanol +0.1N HCl) Inflex. 227 nm, inflex. 270 nm, max, 280 nm, ε=18,700, max, 291, nm, ε=17,800, inflex. 300 nm, inflex. 321 nm.

STEP B: Iodide of (6S, 7S, ΔZ) 1-[[7-[[2-(2-amino-4-thiazolyl)-2-(methoxy-imino)-acetamido]-2-carboxy-8-oxo-4-thia-1-azabicyclo[4,2,0]oct-2-en-3-yl]-methyl]-4-(aminocarbonyl)-pyridinium Under an inert atmosphere, 330 mg of the product of Step A, 33 ml of acetonitrile and 98 mg of isonicotinamide were mixed together and stirred at 50° C. for 5 hours. The acetonitrile was elminated by distilling under reduced pressure. Methylene chloride and a 0.1N aqueous solution of hydrochloric acid were added, and after stirring and decanting, extraction was done with methylene chloride. The extracts were washed with water and concentrated to dryness by distilling under reduced pressure. The 385 mg of residue were chromatographed over silica and eluted with a mixture of methylene chloride and methanol (9/1) to obtain 140 mg of the expected product at about 210° C. and having a specific rotation of $[\alpha]_D$=−82° (c=0.6% in chloroform).

| IR Spectrum (chloroform) in $cm^{-1}$. | |
|---|---|
| Absorption complex region NH/OH: 3505–3449–3401–3310 3255–3170 | |
| C=O beta lactam | 1782 |
| Other C=O | 1694 |
| Region C=C, CN; Amide II; $NH_2$ def. | 1642, 1596, 1586, 1566, 1598, 1492 |

Under an inert atmosphere, 200 mg of the said product and 2 ml of formic acid with 33% of water were mixed together and stirred at 50° C. for 5 hours, then was cooled, and the triphenylmethylcarbinol formed was eliminated by filtering, The filtrate was concentrated to dryness by distilling under reduced pressure and 2 ml of ethyl acetate were added. After stirring for one hour, the precipitate formed was separated to obtain 128 mg of iodide of (6S, 7S, ΔZ) 1-[[7-[[2-(2-amino-4-thiazolyl)-2-(methoxy-imino)-acetamido]-2-carboxy-8-oxo-4-thia-1-azabicyclo[4,2,0]oct-2-en-3-yl]-methyl]-4-(amino carbonyl)-pyridinium melting at 210° C. and having a specific rotation of $[\alpha]_D$=−55° (c=0.6% in dimethylformamide).

| IR Spectrum (Nujol) in $cm^{-1}$. | |
|---|---|
| Absorption complex region NH/OH | |
| C=O beta lactam | 1764 (F) |
| Other C=O | 1680 (complex) |
| Region C=C, CN; $NH_2$ def.; Amide II | 1625, 1565, 1542 |

| UV Spectrum (ethanol) | | | |
|---|---|---|---|
| Max. | 219 nm | $E^1_1$ = 532 | ε = 34,300 |
| Inflexion | 260 nm | $E^1_1$ = 209 | |
| Inflexion | 271 nm | $E^1_1$ = 209 | |
| Max. | 290 nm | $E^1_1$ = 213 | ε = 13,700 |
| **UV Spectrum (ethanol + 0.1N HCl).** | | | |
| Max. | 220 nm | $E^1_1$ = 470 | ε = 30,300 |

-continued

| | | | |
|---|---|---|---|
| Max. | 269 nm | $E^1_1 = 266$ | $\epsilon = 17{,}200$ |
| Inflexion | 283 nm | $E^1_1 = 249$ | |
| Inflexion | 293 nm | $E^1_1 = 226$ | |

EXAMPLE 214

Internal salt of (6S, 7S, ΔZ) 7-[[7-[(2-amino-4-thiazolyl)-(methoxyimino)-acetamido]-2-carboxy-8-oxo-4-thia-1-azabicyclo[4,2,0]oct-2-en-3-yl]-methyl]-4-methyl-thieno[2,3-b]pyridinium STEP A: 4-methyl-thieno[2,3-b]pyridine 25 g of a mixture of 85% of 2-nitrothiophene and 15% of 3-nitrothiophene and 375 ml of a 37% aqueous solution of hydrochloric acid were mixed together and then, at 30° C. over about one hour, 50 g of tin in granules were introduced in small portions. The mixture was stirred at 30° C. until the metal had disappeared (4 hours in all) and 50 ml of ethanol, 22 g of anhydrous ferric chloride and 0.5 g of anhydrous zinc chloride were added. Then at 60° C. over about one hour, 30 ml of methyl vinyl ketone and 60 ml of ethanol were introduced with stirring at 80° C. for two hours and at 20° C. for 16 hours. The reaction mixture was poured onto ice and carbon tetrachloride and concentrated ammonia were added to pH 9. After filtering on hyflosupercel and decanting, the aqueous phase was extracted with carbon tetrachloride, then dried and concentrated to dryness by distilling under reduced pressure. The 9.8 g of residue were chromatographed over silica under nitrogen pressure and eluted with a gradient of 100% of methylene chloride to 100% of ethyl acetate to obtain 7.55 g of 4-methyl thieno [2,3-b]pyridine.

STEP B: internal salt of (6S, 7S, ΔZ) 7-[[7-[(2-amino-4-thiazolyl)-(methoxyimino)-acetamido]-2-carboxy-8-oxo-4-thia-1-azabicyclo[4,2,0]oct-2-en-3-yl]-methyl]-4-methyl-thieno[2,3-b]pyridinium Under an inert atmosphere, 0.411 g of 1,1-dimethyl-ethyl (6S, 7S, ΔZ) 3-iodomethyl-7-[3-[7-[(2-triphenylmethylamino-4-thiazolyl][2-methoxyimino]-acetamido-8-oxo-4-thia-1-azabicyclo[4,2,0]oct-2-en-3-yl]-2-carboxylate) 4 ml of acetonitrile and 0.15 g of 4-methyl-thieno [2,3-b]pyridine were mixed together and stirred at 50° C. for two hours, then concentrated to dryness by distilling under reduced pressure. Methylene chloride and a 0.1N aqueous solution of hydrochloric acid were added and after stirring and decanting, extraction was done with methylene chloride. The solvent was eliminated by distilling under reduced pressure and the 0.55 g of residue were chromatographed over silica and eluted with a mixture of methylene chloride and methanol (95/5) to obtain 0.26 g of the expected product.

| I R Spectrum (chloroform) in $cm^{-1}$. | | | |
|---|---|---|---|
| =C—NH | 3403 | C=C | 1598 |
| C=O beta lactam | 1786 | C=N | 1375 |
| other C=O | 1705 | aromatic | 1525 |
| | 1674 | amide II | 1493 |

Under an inert atmosphere, 0.156 g of the said product, 1 ml of an M aqueous solution of triethylamine carbonate and 1 ml of acetonitrile were mixed together, and when completely dissolved, the solution was chromatographed on a one-inch "inox" column filled with grafted RP 18 silica and eluted at a flow of 20 ml/minute with a gradient of distilled water containing from 5% to 20% of acetonitrile. The interesting fractions were lyophilized to obtain 0.038 g of the expected internal salt melting at about 200° C. with decomposition.

| I R Spectrum (Nujol) in $cm^{-1}$ | | |
|---|---|---|
| Absorption region OH/NH | | |
| C=O beta lactam | | 1766 |
| other C=O | | 1660 |
| C=C | | |
| C=N | | 1609 |
| $CO_2^-$ | | 1570 |
| Amide II | | 1534 |
| U V Spectrum (ethanol) | | |
| Max. | 237 nm | $\epsilon = 35{,}500$ |
| Max. | 292 nm | $\epsilon = 17{,}700$ |
| Inflexion | 299 nm | |
| U V Spectrum (ethanol + 0.1 N HCl) | | |
| Max. | 240 nm | $\epsilon = 32{,}400$ |
| Max. | 290 nm | $\epsilon = 18{,}200$ |

EXAMPLE 215

Trifluoromethyl-sulfonate of (6S, 7S, ΔZ)7-[[7-[(2-amino-4-thiazolyl)-[fluoromethoxyimino]-acetamido]-2-carboxy-8-oxo-4-thia-1-azabicyclo [4,2,0]oct-2-en-3-yl]-methyl]-thieno[2,3-b]pyridinium (trifluoroacetate)

STEP A: 1,1-dimethyl-ethyl (6S, 7S, ΔZ) 3-hydroxymethyl-7-[3-[7-[(2-triphenylmethylamino-4-thiazolyl]-[(2-fluoromethoxyimino]-acetamido]-8-oxo-4-thia-1-azabicyclo[4,2,0]oct-2-en-3-yl]-2-carboxylate Under an inert atmosphere, 450 mg of the syn isomer of 2-(2-trifluoromethylamino-4-thiazolyl)-2-fluoromethoxy)-imino acetic acid, 6 ml of acetone, 13 μl of triethylamine and 168 mg of tosyl chloride were mixed together and stirred at 20° C. for 45 minutes. Then a solution of 1,1-dimethylethyl (6S, 7S) 7-amino-3-hydroxymethyl-8-oxo-4-thia-1-azabicyclo[4,2,0]oct-2-en-2-carboxylate, 1 ml of an M aqueous solution of sodium bicarbonate, 1 ml of water and 1 ml of acetone were added all at once with stirring at 20° C. for 30 minutes, The acetone was elminated by distilling under reduced pressure and water and methylene chloride were added. After stirring and decanting, extraction was done with methylene chloride. The extracts were washed with a saturated aqueous solution of sodium chloride and concentrated to dryness by distilling under reduced pressure. The 854 mg of residue were chromatographed over silica under nitrogen pressure and eluted with a mixture of methylene chloride and ethyl acetate (85/15) to obtain 451 mg of the expected product which was used as is for the following step.

STEP B: Trifluoromethane sulfonate of (6S, 7S, ΔZ) 4-[[7-((2-triphenyl-methylamino)-4-thiazolyl]-[(2-fluoromethoxy)-imino]-acetamido]-2-[(1,1-dimethyl ethoxy carbonyl]-8-oxo-4-thia-1-azabicyclo[4,2,0]oct-2-en-3-yl] methyl]-thieno[3,2-b]pyridinium Under an inert atmosphere, 150 mg of the alcohol of Step A) 2 ml of methylene chloride and 111 mg of thieno-pyridine were mixed together, and at −70° C., over about 10 minutes, 1.5 ml of a solution at 5% by volume of trifluoromethane sulfonic anhydride in methylene chloride were introduced with stirring at −70° C. for 10 minutes, and between −70° C. and 0° C. for 10 minutes. After concentrating to dryness by distilling under reduced pressure, the residue was chromatographed over silica under nitrogen pressure and eluted with a mixture of methylene chloride and methanol (9/1) to obtain 50 mg of trifluoromethane sulfonate of (6S, 7S, ΔZ) 4-[[7-((2-triphenyl-methylamino)-4-thiazolyl)-[(2-fluoromethoxy)-imino]-acetamido]-2-(1,1-dimethyl ethoxy carbonyl]-8-oxo-4-thia-1-azabicyclo[4,2,0] oct-2-en-3-yl]-methyl]-thieno[3,2,-b]pyridinium.

STEP C: Trifluoromethane sulfonate of (6S, 7S, ΔZ) 7-[[7-[(2-amino-4-thiazolyl)-[fluoromethoxyimino]-acetamido]-2-carboxy-8-oxo-4-thia-1-azabicyclo [4,2,0]oct72-en-3-yl]-methyl]-thieno[2,3-b]pyridinium (trifluoroacetate)

Under an inert atmosphere, 50 mg of the product of Step B and 0.300 ml of trifluoroacetic acid with 10% of water were mixed together and stirred at 20° C. for 90 minutes. 3 ml of ether were added slowly with stirring at 20° C. for 10 minutes and then the precipitate formed was separated, washed and dried under vacuum to obtain 27 g of trifluoromethane sulfonate of (6S, 7S, ΔZ) 7-[[7-[(2-amino-4-thiazolyl)-[fluoromethoxy-imino]-acetamido]-2-carboxy-8-oxo-4-thia-1-azabicyclo[4,2,0]oct-2-en-3-yl]-methyl]-thieno[2,3-b]pyridinium (trifluoroacetate).

| UV Spectrum (ethanol) | | |
|---|---|---|
| Max. | 241 nm $E_1^1$ = 445 | ε = 34,700 |
| Max. | 294 nm $E_1^1$ = 256 | ε = 20,000 |

By operating as at Example 197, the following products were obtained:

EXAMPLE 216

Iodide of (6S, 7S, ΔZ) 1-[[7-[[2-(2-amino-4-thiazolyl)-2-(methoxyimino)-acetamido]-2-carboxy-8-oxo-4-thia-1-azabicyclo[4,2,0]oct-2-en-3-yl]-methyl]-4-hydroxy amino carbonyl pyridinium melting at 210° C.

| I.R. Spectrum | | |
|---|---|---|
| 1778 $cm^{-1}$ | beta lactame | |
| 1672 $cm^{-1}$ | other carbonyls | |
| 1638 $cm^{-1}$ | Region | C=C |
| | | C=N |
| 1577 $cm^{-1}$ | | amide |
| | | $NH_2$ |
| 1560 $cm^{-1}$ | | |
| 1541 $cm^{-1}$ | | |

EXAMPLE 217

Iodide of (6S, 7S, ΔZ) 1-[[7-[[2-(2-amino-4-thiazolyl)-2-(methoxyimino)-acetamido]-2-carboxy-8-oxo-4-thia-1-azabicyclo[4,2,0]oct-2-en-3-yl]-methyl]-4-[[(2-amino-2-oxo-ethylamino]-carbonyl]-pyridinium melting at 210° C.

IR Spectrum: 1762 $cm^{-1}$ beta lactam, 1665 $cm^{-1}$ other carbonyls.

EXAMPLE 218

Chloride of (6S, 7S, ΔZ) 1-[[7-[[2-(2-amino-4-thiazolyl)-2-(methoxyimino)-acetamido]-2-carboxy-8-oxo-4-thia-1-azabicyclo[4,2,0]oct-2-en-3-yl]-methyl]-4-(2-amino-2-oxo-ethyl)-pyridinium melting at 200° C. and having a specific rotation of $[\alpha]_D$=−58°±2.5° (c=0.6% in DMSO)

IR Spectrum 1765 $cm^{-1}$ beta lactam, 1670 $cm^{-1}$ other C=O 1640 $cm^{-1}$

EXAMPLE 219

Iodide of (6S, 7S, ΔZ) 1-[[7-[[2-(2-amino-4-thiazolyl)-2-(methoxyimino) acetamido]-2-carboxy-8-oxo-4-thia-1-azabicyclo[4,2,0]oct-2-en-3-yl]-methyl]-4-(aminothiocarbonyl)-pyridinium melting at 210° C.

IR Spectrum 1767 $cm^{-1}$ beta lactam, 1669 $cm^{-1}$ other C=O, 1637 $cm^{-1}$ C=C, 1576 $cm^{-1}$ C=S, 1559 $cm^{-1}$ $NH_2$, 1530 $cm^{-1}$ amide Utilizing the process of Example 192 the following product was obtained:

EXAMPLE 220

Internal salt of (6S, 7S, ΔZ) 7-[[7-[[(5-amino-1,2,4-thiadiazol-3-yl) (methoxyimino)-acetamido]-2-carboxy-8-oxo-4-thia-1-azabicyclo[4,2,0]oct-2-en-3-yl]-methyl]-thieno[2,3-b]pyridinium

| IR Spectrum | |
|---|---|
| 1761 $cm^{-1}$ | beta lactam |
| 1660 $cm^{-1}$ | other C=O |
| 1610 $cm^{-1}$ | |
| 1574 $cm^{-1}$ | C=C |
| 1527 $cm^{-1}$ | C=N |
| | amide |
| | $NH_2$ |

Starting with the product protected on the amino radical of the amino thiadiazolyl by a trityl radical, the following product was obtained by the action of formic acid:

EXAMPLE 221

Internal salt of (6S, 7S, ΔZ) 7-[[7-[[(5-formylamino-1,2,4-thiadiazol-3-yl) (methoxyimino)-acetamido]-2-carboxy-8-oxo-4-thia-1-azabicyclo[4,2,0]oct-2-en-3-yl]-methyl]-thieno[2,3-b]pyridinium

| UV Spectrum (ethanol) | | |
|---|---|---|
| Max. | 239 nm $E_1^1$ = 795 | ε = 58,700 |
| Max. | 293 nm $E_1^1$ = 258 | ε = 19,000 |
| UV spectrum (ethanol + 0.1 N HCl) | | |
| Max. | 240 nm $E_1^1$ = 824 | ε = 60,800 |
| Max. | 301 nm $E_1^1$ = 251 | ε = 18,500 |

By operating as in Example 197, the following product was obtained:

EXAMPLE 222

Trifluoroacetate of (6S, 7S, ΔZ) 5-[[7-[[(2-amino-4-thiazolyl)-[(fluoromethoxy)-imino]-acetamido]-2-carboxy-8-oxo-4-thia-1-azabicyclo[4,2,0]oct-2-en-3-yl]-methyl]-thieno[3,2-c]pyridinium (trifluoroacetate)

| UV Spectrum (ethanol) | | |
|---|---|---|
| Max. | 239 nm $E_1^1$ = 706 | ε = 54,800 |
| Max. | 295 nm $E_1^1$ = 250 | ε = 19,400 |
| Inflexion | 368 nm $E_1^1$ = 19 | |
| UV Spectrum (ethanol + 0.1 N HCl) | | |
| Max. | 241 nm $E_1^1$ = 692 | ε = 53,700 |
| Inflexion | 263 nm $E_1^1$ = 244 | |
| Max. | 290 nm $E_1^1$ = 206 | ε = 20,700 |
| Inflexion | 298 nm $E_1^1$ = 254 | |

By operating as in Example 192, the following product was obtained:

EXAMPLE 223

Internal salt of (6S, 7S, ΔZ) 4-[[7-[[(5-formylamino-1,2,4-thiadiazol-3-yl) (methoxyimino)-acetamido]-2-carboxy-8-oxo-4-thia-1-azabicyclo[4,2,0]oct-2-en-3-yl]-methyl]-thieno[3,2-b]pyridinium

| UV Spectrum (ethanol) | | |
|---|---|---|
| Max. | 238 nm $E_1^1$ = 727 | ε = 38,700 |
| Max. | 294 nm $E_1^1$ = 239 | ε = 12,700 |
| Inflexion | 323 nm $E_1^1$ = 110 | |
| UV Spectrum (ethanol + 0.1 N HCl) | | |
| Max. | 238 nm, Max 298 nm, | Inflexion 309 nm. |

By operating as in Example 192, the following product was obtained:

EXAMPLE 224

Internal salt of (6S, 7S, ΔZ) 4-[[7-[[(5-amino-1,2,4-thiadiazol-3-yl) (methoxyimino)-acetamido]-2-carboxy-8-oxo-4-thia-1-azabicyclo[4,2,0]oct-2-en-3-yl]-methyl]-thieno[3,2-b]pyridinium.

| IR Spectrum | |
|---|---|
| 1765 $cm^{-1}$ | beta lactam |
| 1662 $cm^{-1}$ | other C=O |
| 1612 $cm^{-1}$ | C=C |
| | C=N |
| 1565 $cm^{-1}$ | $CO_2^-$ |
| 1530 $cm^{-1}$ | amide |
| 1510 $cm^{-1}$ | $NH_2$ |

EXAMPLE 225

Internal salt of (6S, 7S, ΔZ) 7-[[7-[[2-(2-amino-4-thiazolyl)-2-(methoxy-imino)-acetamido]-2-carboxy-8-oxo-4-thia-1-azabicyclo[4,2,0]oct-2-en-3-yl]-methyl]-4-(methylthio)-thieno[2,3-b]pyridinium

| IR Spectrum | |
|---|---|
| 1766 $cm^{-1}$ | beta lactam |
| 1664 $cm^{-1}$ | other C=O |
| 1612 $cm^{-1}$ | C=O |
| | C=N |
| 1582 $cm^{-1}$ | $CO_2^-$ |
| | amide |
| 1538 $cm^{-1}$ | $NH_2$ |

EXAMPLE 226

Internal salt of (6S, 7S,ΔZ) 7-[[7-[[(2-amino-4-thiazolyl) (methoxyimino) acetamido]-2-carboxy-8-oxo-4-thia-1-azabicyclo[4,2,0]oct-2-en-3-yl]-methyl]-2-methyl thieno[2,3-b]pyridinium $[\alpha]_D$=−10°±2° (c=0.4% $H_2O$),

| IR Spectrum | |
|---|---|
| 1768 $cm^{-1}$ | beta lactam |
| 1664 $cm^{-1}$ | other C=O |
| 1616 $cm^{-1}$ | C=O |
| | C=N |
| 1580 $cm^{-1}$ | $CO_2^-$ |
| 1534 $cm^{-1}$ | $NH_2$ |

EXAMPLE 227

Trifluoromethane sulfonate of (6S, 7S,ΔZ) 7-[[7-[[(2-amino-4-thiazolyl) [(fluoroethoxy)-imino]-acetamido]-2-carboxy-8-oxo-4-thia-1-azabicyclo [4,2,0]oct-2-en-3-yl]-methyl-thieno[2,3-b]pyridinium (trifluoroacetate)

| NMR Spectrum (DMSO) ppm | | |
|---|---|---|
| 3.14(m) | $CH_2S$ | 7.90–8.3–8.19–9.14–9.25–9.28 |
| 4.04(m) | $H_6$ | conjugated aromatic systems. |
| 5.67(d) | $H_7$ cis | |
| 4.28 to 4.62 | $CH_2CH_2$—F | |
| 6.10 | $CH_2N^+$ | |

EXAMPLE 228

Internal salt of (6S, 7S,ΔZ) 5-[[7-[[(5-amino-1,2,4-thiadiazol-3-yl)-(methoxyimino)-acetamido]-2-carboxy-8-oxo-4-thia-1-azabicyclo[4,2,0]oct-2-en-3-yl]-methyl]-thiazolo [4,5-c]pyridinium IR Spectrum 1763 $cm^{-1}$ beta lactam, 1663 $cm^{-1}$, 1627 $cm^{-1}$, 1609 $cm^{-1}$; other C=O, 1527 $cm^{-1}$, C=C; C=N; Amide; $NH_2$.

By operating as in Example 197, the following products were obtained:

EXAMPLE 229

Internal salt of (6S, 7S, ΔZ) 2-[[7-[[(2-amino-4-thiazolyl)-(methoxyimino) acetamido]-2-carboxy-8-oxo-4-thia-1-azabicyclo[4,2,0]oct-2-en-3-yl]-methyl]-2-methyl-1,3,4-trihydroisoquinolinium melting at 200° C.

| IR Spectrum | |
|---|---|
| 1763 $cm^{-1}$ | beta lactam |
| 1660 $cm^{-1}$ | 1615 $cm^{-1}$, other C=O |
| 1580 $cm^{-1}$ | C=C $NH_2$ |
| 1534 $cm^{-1}$ | C=N |
| 1500 $cm^{-1}$ | amide |

EXAMPLE 230

Trifluoroacetate of (6S, 7S, ΔZ) 6-[[7-[[(2-amino-4-thiazolyl)-[(fluoromethoxy)-imino]-acetamido]-2-carboxy-8-oxo-4-thia-1-azabicyclo[4,2,0]oct-2-en-3-yl]-methyl] thieno[2,3-c]pyridinium

| UV Spectrum, EtOH | | |
|---|---|---|
| Inflexion | 227 nm $E_1^1$ = 395 | |
| Max. | 240 nm $E_1^1$ = 443 | ε = 34,400 |
| Max. | 267 nm $E_1^1$ = 164 | ε = 12,700 |
| Max. | 279 nm $E_1^1$ = 166 | ε = 12,900 |
| Max. | 299 nm $E_1^1$ = 215 | ε = 16,700 |

By operating as in Example 192, the following products were obtained:

EXAMPLE 231

Trifluoromethane sulfonate of (6S, 7S, ΔZ) 5-[[7-[[(2-amino-4-thiazolyl) [(fluoromethoxyimino]-acetamido]-2-carboxy-8-oxo-4-thia-1-azabicyclo [4,2,0]oct-2-en-3-yl]-methyl]-4-methyl-thieno[3,2-c]pyridinium (trifluoroacetate)

| UV Spectrum 1) EtOH | | |
|---|---|---|
| Max. | 239 nm $E_1^1$ = 637 | ε = 52,700 |
| Max. | 298 nm $E_1^1$ = 225 | ε = 18,600 |

-continued

| UV Spectrum 2) EtOH, HCl 0.1N | | |
|---|---|---|
| Max. | 240 nm $E_1^1$ = 611 | ε = 50,500 |
| Max. | 290 nm $E_1^1$ = 240 | ε = 19,800 |

EXAMPLE 232

Trifluoromethane sulfonate of (6S, 7S,ΔZ) 5-[[7-[[(2-amino-4-thiazolyl) [(difluoromethoxyimino]-acetamido]-2-carboxy-8-oxo-4-thia-1-azabicyclo [4,2,0]oct-2-en-3-yl]-methyl]-4-methyl-thieno[3,2-c]pyridinium (trifluoroacetate)

| UV Spectrum 1) EtOH | | |
|---|---|---|
| Max. | 240 nm $E_1^1$ = 665 | ε = 56,200 |
| Max. | 299 nm $E_1^1$ = 232 | ε = 19,600 |
| UV Spectrum 2) EtOH, HCl 0.1N | | |
| Max. | 240 nm $E_1^1$ = 630 | ε = 53,200 |
| Max. | 291 nm $E_1^1$ = 258 | ε = 21,100 |

By operating as in Example 197, the following products are obtained:

EXAMPLE 233

Internal salt of (6S, 7S,ΔZ) 5-[[7-[[(2-amino-4-thiazolyl)-(methoxy-imino)-acetamido]-2-carboxy-8-oxo-9-thia-1-azabicyclo[4,2,0]oct-2-en-3-yl]-methyl]-4-methyl-thieno[3,2-c]pyridinium melting above 200° C.

| UV Spectrum 1) EtOH | | |
|---|---|---|
| Max. | 212 nm | ε = 33,600 |
| Max. | 240 nm | ε = 50,400 |
| Inflexion | 271 nm | |
| Max. | 292 nm | ε = 18,400 |
| UV Spectrum 2) EtOH + HCl 0.1N | | |
| Max. | 240 nm | ε = 48,000 |
| Inflexion | 273 nm | |
| Max. | 286 nm | ε = 20,500 |

EXAMPLE 234

Iodide of (6S, 7S, ΔZ) 4-[[7-[[(2-amino-4-thiazolyl)-[(2-fluoro-2-propenyloxy)imino)-acetamido]-2-carboxy-8-oxo-4-thia-1-azabicyclo[4,2,0]oct-2-en-3-yl]-methyl]-thieno[3,2-b]pyridinium (trifluoroacetate)

| UV Spectrum 1) in EtOH | | |
|---|---|---|
| Inflexion | 228 nm $E_1^1$ = 432 | |
| Max. | 236 nm $E_1^1$ = 478 | ε = 39,000 |
| Max. | 295 nm $E_1^1$ = 245 | ε = 20,000 |
| Inflexion | 315 nm $E_1^1$ = 160 | |
| UV Spectrum 2) in EtOH HCl 0.1N | | |
| Inflexion | 226 nm $E_1^1$ = 366 | |
| Max. | 238 nm $E_1^1$ = 453 | ε = 37,000 |
| Inflexion | 260 nm $E_1^1$ = 221 | |
| Max. | 292 nm $E_1^1$ = 273 | ε = 22,300 |
| Inflexion | 314 nm $E_1^1$ = 174 | |

EXAMPLE 235

Internal salt of (6S, 7S,ΔZ) 4-[2-[7-[[2-(2-amino-thiazolyl-4-yl)-2-(Methoxyimino)-acetamido]-2-carboxy-8-oxo-4-thia-1-azabicyclo[4,2,0]oct-2-en-3-yl]-ethenyl]-1-methyl pyridinium STEP A: Trifluoromethane sulfonate of 1,1-dimethyl-ethyl (6S, 7S) 7-[[2-(2-tritylamino-4-thiazolyl) 2(Z) (methoxyimino)-acetamido]-3-methyl triphenyl-phosphonium 8-oxo-4-thia-1-azabicyclo[4,2,0]oct-2-en-2-carboxylate 2,5 g of 1,1-dimethyl-ethyl 7-[[2-(2-tritylamino-thiazol-4-yl)-2-(methoxyimino)-acetamido]-3-hydroxymethyl-8-oxo-4-thia-1-azabicyclo [4,2,0]oct-2-en-2-carboxylate in 50 ml of methylene chloride and 2.75 g of triphenyl-phosphine were cooled to −70° C. Over 20 minutes, 0.865 ml of trifluoromethane sulfonic anhydride were added dropwise with stirring for one hour at −70° C. A solution of sodium bicarbonate and iced water was added slowly followed by extraction with methylene chloride. The organic phases were concentrated and the residue was chromatographed over silica. Elution with a mixture of methylene chloride and methanol (9/1) yield 2.7 g of the expected product melting at 170° C.

STEP B: 1,1-dimethylethyl (6S, 7S, ΔZ) 7-[[[2-(2-tritylamino-4-thiazolyl)-2-(methoxyimino)-acetamido]-3-(4-pyridyl)-ethenyl]-8-oxo-4-thia-1-azabicyclo [4,2,0]oct-2-en-2-carboxylate 650 mg of the product of Step A was stirred for a few minutes in 16 ml of methylene chloride and 5.5 ml of a saturated solution of potassium carbonate. 107 mg of 4-pyridine-carboxaldehyde (1M) in 1 ml of methylene chloride were added all at once. After 2 hours of vigorous stirring, the mixture was poured into 100 ml of water and ice, and extracted with methylene chloride. The extracts were washed with water, dried and concentrated to dryness under reduced pressure to obtain 660 mg of the expected product. The latter was chromatographed over silica and eluted with a mixture of methylene chloride and ethyl acetate (1/1), and the fractions of Rf 0.3 were isolated.

STEP C: Iodide of (6S, 7S, ΔZ, ΔE) 4-[2-[7-[[2-(2-tritylamino-4-thiazolyl)-2-(methoxyimino)-acetamido]-2-(1,1-dimethyl)-ethoxy carbony-8-oxo-4-thia-1-azabicyclo [4,2,0]oct-2-en-3-yl]ethenyl]-1-methyl-pyridinum 430 mg of the product of Step B were dissolved in 14 ml of acetonitrile and 3.5 ml of methyl iodide were added. The mixture was stirred for one hour at ambient temperature. After concentrating to dryness under reduced pressure, the residue was chromatographed over silica and eluted with a mixture of methylene chloride and methanol (9/1) to obtain 223.7mg of iodide of (6S, 7S, ΔZ, ΔE) 4-[2-[7-[[2-(2-tritylamino-4-thiazolyl)-2-(methoxyimino)-acetamido]-2-(1,1-dimethyl)-ethoxy carbonyl-8-oxo-4-thia-1-azabicyclo [4,2,0]oct-2-en-3-yl]ethenyl]-1-methyl-pyridinium,

| NMR Spectrum ($CDCl_3$), ppm | |
|---|---|
| $H_5$, thiazole | 6.44 |
| H of the $CH_3O$ | 4.01 |
| $H_7$ and $H_6$ of the cepheme | 5.56(m) and 4.14(m) |
| HC=CH delta E | 6.93(d J=16)<br>7.91 |
| H of the tBu | 1.54(s) |
| H of the $N^+$—$CH_3$ | 4.57(s) |

STEP D: Internal salt of (6S, 7S, ΔZ, ΔE) 4-[2-[7-[[2-(2-amino-thiazol-4-yl)-2-(methoxyimino)-acetamido]-2-carboxy-8-oxo-4-thia-1-azabicyclo [4,2,0]oct-2-en-3-yl]-ethenyl]-1-methyl-pyridinium 230 mg of the product of Step C were dissolved in 1.2, ml of trifluoroacetic acid with 10% of water, and stirred for one hour at ambient temperature under inert atmosphere. Dropwise, 12 ml of anhydrous ether were added, and stirring was continued for one hour. The precipitate was separated, washed abundantly with ether and dried to obtain 180 mg of the deblocked product. To 170 mg of this latter, 1 ml of triethylamine carbonate in aqueous solution and 1 ml of acetonitrile were added. The precipitate was separated and the filtrate was chromatographed on HPLC. The fraction of the eluate of water with 10% of acetonitrile was lyophilized and dried to obtain 28 mg of internal salt of (6S, 7S, ΔZ, ΔE) 4-[2-[7-[[2-(2-amino-thiazol-4-yl)-2-(methoxyimino)-acetamido]-2-carboxy-8-oxo-4-thia-1-azabicyclo[4,2,0]oct-2-en-3-yl]-ethenyl]-1-methyl-pyridinium melting above 260° C.

| NMR Spectrum ($D_2O$ + DC1) ppm | |
|---|---|
| $H_5$ of the thiazol syn | 7.15 |
| H of the $OCH_3$ | 4.10 |
| $H_7$ and $H_6$ of the cepheme cis | 5.70(d, J=5)<br>4.30(m) |
| HC═CH delta E | 7.24(d, J=16)<br>7.98(d, J=16) |
| $N^{\oplus}$—$CH_3$ | 4.32(s) |

EXAMPLE 236

Injectable solution was prepared containing 500 mg of one of the compounds selected from the group consisting of syn isomer of 7-[7-[2-(2aminothiazol-4-yl)-[(difluoromethoxy)-imino]acetamido]-2-carboxy-8-oxo-4-thia-1-azabicyclo[4,2,0]oct-2-ene-3-yl]-methylthieno[2,3-b]pyridinium trifluoromethane sulfonate trifluoroacetate; syn isomer of 4-[7-[2-(2-aminothiazo-4-yl) [(difluoromethoxy)-imino]-acetamido-2-carboxy-8-oxo-4-thia-1-azabicyclo[4,2,0]oct-2-ene-3-yl]-methylthieno[3,2-b]pyridinium trifluoromethane sulfonate trifluoroacetate, internal sale of syn isomer 2-[7-[2-(2-aminothiazol-4-yl)-2-(methoxyimino)-acetamido 2-carboxy-8-oxo-4-thia-1-azabicyclo[4,2,0]oct-2-en-3-yl]-methyl]-isoquinolinium (6RS-7RS); syn isomer of 4-[7-[2-(2-aminothiazol-4-yl)-2-[(methoxy-methoxy)-imino]-acetamido-2-carboxy-8-oxo-4-thia-1-azabicyclo[4,2,0]oct-2-en-3-yl]-methyl]-thieno[3,2-b]pyridinium (6RS-7RS); trifluoromethane sulfonate trifluoroacetate; syn isomer of 7-[7-[2-(2-aminothiazol-4-yl)-2-[(propenloxy)-imino]-acetamido-2-carboxy-8-oxo-4-thia-1-azabicyclo[4,2,0]oct-2-en-3-yl]-methyl]-thieno[2,3-b] pyridinium (6RS,7RS) trifluoromethane sulfonate trifluoroacetate; syn isomer of 1-[7-[2-(2-aminothiazol-4-yl)-2-(methoxyimino)-acetamido]-2-carboxy-8-oxo-4-thia-1-azabicyclo [4,2,0]oct-2-en-3-yl]-methyl 2,3-dimethyl pyridinium (6RS,7RS) trifluoromethane sulfonate trifluoroacetate or the product of Examples 200, 206, 207 or 222 and sufficient aqueous sterile excipient for a final volume of 5 ml.

PHARMACOLOGICAL STUDY

Activity In Vitro, Method of Dilution in Liquid Medium

A series of tubes was prepared in each of which the same quantity of a sterile nutritive medium was placed. Then, in each tube, increasing quantities of the product under study were distributed followed by inoculating each tube with a bacterial strain. After incubation in an oven at 37° C. for twenty-four or forty-eight hours, the inhibition of growth was determined by transillumination which enables the minimum inhibiting concentrations (M.I.C.) to be determined expressed in μg/ml. The following are the results obtained:

Using the above test procedure, certain of the compounds of the present invention were compared with cefazoline and the compounds of U.S. Pat. No. 4,476,124 for their antibacterial activity and the results are reported in Tables I and II. The results clearly show that the compounds of the invention are unexpectedly superior to the prior art compounds.

| STRAINS | 24 H | 48 H | 24 H | 48 H | 24 H | 48 H | 24 H | 48 H |
|---|---|---|---|---|---|---|---|---|
| | Prod. ex. 100 | | Prod. ex. 108 | | Prod. ex. 112 | | Prod. ex. 114 | |
| *Staphylococcus aureus* SG 511 | 1,2 | 2,5 | 1,2 | 5 | 1,2 | 2,5 | 1,2 | 2,5 |
| *Staphylococcus aureus* 285 | 1,2 | 5 | 5 | 10 | 2,5 | 2,5 | 1,2 | 2,5 |
| *Staphylococcus aureus* 54146 | 2,5 | 5 | — | — | 2,5 | 5 | 2,5 | 2,5 |
| *Streptococcus pyogenes* A 561 | <0,02 | <0,02 | 0,04 | 0,04 | 0,04 | 0,04 | <0,02 | 0,02 |
| *Streptococcus pyogenes* 77 A | <0,02 | <0,02 | <0,02 | <0,02 | 0,04 | 0,04 | <0,02 | <0,02 |
| *Escherichia Coli* 1894 | <0,02 | <0,02 | 0,04 | 0,04 | 0,04 | 0,04 | <0,02 | <0,02 |
| *Escherichia Coli* 078 | 0,04 | 0,08 | 0,08 | 0,08 | 0,08 | 0,08 | 0,08 | 0,08 |
| *Escherichia Coli* TEM | 0,15 | 0,15 | 0,3 | 0,3 | 0,15 | 0,15 | 0,3 | 0,3 |
| *Escherichia Coli* 1507 E | 0,04 | 0,04 | 0,08 | 0,08 | 0,08 | 0,08 | <0,02 | <0,02 |
| *Escherichia Coli* DCO | 0,15 | 0,15 | 0,15 | 0,15 | 0,3 | 0,3 | 0,3 | 0,3 |
| *Escherichia Coli* DC2 | 0,04 | 0,04 | 0,08 | 0,08 | 0,08 | 0,08 | <0,02 | <0,02 |
| *Salmonella typhimurium* MZ 11 | 0,15 | 0,3 | 0,3 | 0,3 | 0,15 | 0,15 | 0,3 | 0,3 |
| *Klebsiella pneumoniae* 52145 | 0,3 | 0,6 | 0,6 | 0,6 | 0,6 | 0,6 | 0,6 | 0,6 |
| *Klebsiella aerogenes* 1522 E | 1,2 | 1,2 | 0,3 | 0,3 | 0,6 | 0,6 | 0,6 | 0,6 |
| *Enterobacter cloacae* 1321 E | 0,08 | 0,08 | 0,08 | 0,08 | 0,08 | 0,08 | 0,08 | 0,08 |
| *Proteus mirabilis* A 235 | 0,3 | 0,6 | 0,3 | 0,3 | 0,3 | 1,2 | 0,3 | 0,3 |
| *Proteus vulgaris* A 232 | 0,6 | 2,5 | 0,15 | 0,15 | 0,6 | 2,5 | 0,3 | 0,6 |

-continued

| STRAINS | 24 H | 48 H | 24 H | 48 H | 24 H | 48 H | 24 H | 48 H |
|---|---|---|---|---|---|---|---|---|
| *Staphylococcus aureus* SG 511 | — | — | 2,5 | 2,5 | 2,5 | 5 | 1,2 | 1,2 |
| *Staphylococcus aureus* 285 | — | — | 2,5 | 5 | 5 | 5 | 2,5 | 10 |
| *Staphylococcus aureus* 54146 | — | — | 5 | 10 | 5 | 5 | 5 | 10 |
| *Streptococcus pyogenes* A 561 | — | — | <0,04 | <0,04 | <0,04 | <0,04 | <0,04 | <0,04 |
| *Streptococcus pyogenes* 77 A | — | — | <0,04 | <0,04 | <0,04 | <0,04 | <0,04 | <0,04 |
| *Escherichia Coli* 1894 | <0,02 | <0,02 | <0,04 | <0,04 | 0,08 | 0,08 | <0,04 | <0,04 |
| *Escherichia Coli* 078 | 0,08 | 0,08 | <0,04 | 0,08 | 0,08 | 0,08 | 0,15 | 0,15 |
| *Escherichia Coli* TEM | 0,3 | 0,3 | <0,04 | 0,08 | 0,15 | 0,15 | 0,15 | 0,15 |
| *Escherichia Coli* 1507 E | 0,04 | 0,04 | 0,08 | 0,08 | 0,15 | 0,15 | 0,15 | 0,15 |
| *Escherichia Coli* DC0 | 0.08 | 0.08 | 0.15 | 0,15 | 0,15 | 0,15 | 0,15 | 0,15 |
| *Escherichia Coli* DC2 | 0,04 | 0,04 | <0,04 | 0,08 | 0,08 | 0,15 | 0,08 | 0,08 |
| *Salmonella typhimurium* MZ 11 | 0,15 | 0,15 | 0,15 | 0,15 | 0,15 | 0,15 | 0,3 | 0,6 |
| *Klebsiella pneumoniae* 52145 | 0,15 | 0,15 | 0,3 | 0,3 | 0,3 | 0,3 | 0,6 | 0,6 |
| *Klebsiella aerogenes* 1522 E | 0,08 | 0,08 | 0,3 | 0,3 | 0,15 | 0,15 | 0,3 | 0,3 |
| *Enterobacter cloacae* 1321 E | 0,08 | 0,08 | 0,08 | 0,08 | 0,08 | 0,08 | 0,15 | 0,15 |
| *Proteus mirabilis* A 235 | 0,08 | 0,08 | 0,3 | 0,3 | 0,3 | 0,3 | 1,2 | 1,2 |
| *Proteus vulgaris* A 232 | 0,3 | 0,3 | 1,2 | 2,5 | 0,6 | 2,5 | 2,5 | 2,5 |
| *Staphylococcus aureus* SG 511 | 0,6 | 1,2 | 0,6 | 1,2 | — | — | 0,6 | 1,2 |
| *Staphylococcus aureus* 285 | 2,5 | 5 | 0,6 | 2,5 | — | — | 1,2 | 5 |
| *Staphylococcus aureus* 54146 | 5 | 5 | 1,2 | 5 | — | — | 2,5 | 5 |
| *Streptococcus pyogenes* A 561 | <0,04 | <0,04 | <0,02 | <0,02 | <0,02 | <0,02 | <0,02 | <0,02 |
| *Streptococcus pyogenes* 77 A | <0,04 | <0,04 | <0,02 | <0,02 | <0,02 | <0,02 | <0,02 | <0,02 |
| *Escherichia Coli* 1894 | <0,04 | <0,04 | <0,02 | <0,02 | <0,02 | <0,02 | 0,04 | 0,08 |
| *Escherichia Coli* 078 | <0,04 | <0,04 | <0,02 | <0,02 | 0,15 | 0,3 | 0,15 | 0,15 |
| *Escherichia Coli* TEM | 0,08 | 0,08 | 0,08 | 0,08 | 0,6 | 1,2 | 2,5 | 2,5 |
| *Escherichia Coli* 1507 E | <0,04 | <0,04 | <0,02 | <0,02 | 0,04 | 0,04 | <0,02 | 0,04 |
| *Escherichia Coli* DC0 | <0,04 | 0,08 | 0,08 | 0,08 | 0,6 | 0,6 | 2,5 | 2,5 |
| *Escherichia Coli* DC2 | <0,04 | <0,04 | <0,02 | <0,02 | 0,08 | 0,15 | <0,02 | 0,04 |
| *Salmonella typhimurium* MZ 11 | <0,04 | <0,04 | 0,08 | 0,08 | 0,3 | 0,3 | 0,6 | 0,6 |
| *Klebsiella pneumoniae* 52145 | 0,15 | 0,15 | 0,08 | 0,08 | 0,6 | 0,6 | 5 | 5 |
| *Klebsiella aerogenes* 1522 E | 0,08 | 0,08 | 0,3 | 0,3 | 0,6 | 0,6 | — | — |
| *Enterobacter cloacae* 1321 E | <0,04 | 0,08 | 0,04 | 0,04 | 0,15 | 0,15 | 0,6 | 0,6 |
| *Proteus mirabilis* A 235 | 0,15 | 0,15 | 0,15 | 0,15 | 0,04 | 0,08 | 1,2 | 1,2 |
| *Proteus vulgaris* A 232 | 0,3 | 0,3 | 1,2 | 2,5 | — | — | 1,2 | 1,2 |
| *Staphylococcus aureus* SG 511 | 0,3 | 0,6 | 1,2 | 1,2 | 0,6 | 1,2 | 1,2 | 2,5 |
| *Staphylococcus aureus* 285 | 0,3 | 0,6 | 1,2 | 2,5 | 0,6 | 1,2 | 2,5 | 5 |
| *Staphylococcus aureus* 54146 | 0,6 | 1,2 | 1,2 | 2,5 | 1,2 | 2,5 | — | — |
| *Streptococcus pyogenes* A 561 | <0,02 | <0,02 | <0,02 | <0,02 | <0,02 | <0,02 | <0,02 | <0,02 |
| *Streptococcus pyogenes* 77 A | <0,02 | <0,02 | <0,02 | <0,02 | <0,02 | <0,02 | <0,02 | <0,02 |
| *Escherichia Coli* 1894 | <0,02 | <0,02 | <0,02 | <0,02 | <0,02 | <0,02 | <0,02 | <0,02 |
| *Escherichia Coli* 078 | <0,02 | <0,02 | 0,08 | 0,08 | <0,02 | <0,02 | 0,15 | 0,15 |
| *Escherichia Coli* TEM | <0,02 | <0,02 | 0,3 | 0,3 | 0,08 | 0,15 | 0,15 | 0,3 |
| *Escherichia Coli* 1507 E | <0,02 | <0,02 | 0,04 | 0,04 | <0,02 | <0,02 | 0,08 | 0,08 |
| *Escherichia Coli* DC0 | 0,15 | 0,15 | 0,3 | 0,3 | 0,08 | 0,08 | 0,3 | 0,3 |
| *Escherichia Coli* DC2 | <0,02 | 0,02 | 0,04 | 0,04 | <0,02 | <0,02 | 0,04 | 0,08 |
| *Salmonella typhimurium* MZ 11 | <0,02 | 0,04 | 0,3 | 0,3 | 0,08 | 0,08 | 0,15 | 0,15 |
| *Klebsiella pneumoniae* 52145 | 0,04 | 0,08 | 0,6 | 0,6 | 0,08 | 0,15 | 0,3 | 1,2 |
| *Klebsiella aerogenes* 1522 E | 0,15 | 0,15 | 0,6 | 0,6 | 0,3 | 0,3 | 0,6 | 0,6 |

-continued

| STRAINS | 24 H | 48 H | 24 H | 48 H | 24 H | 48 H | 24 H | 48 H |
|---|---|---|---|---|---|---|---|---|
| *Enterobacter cloacae* 1321 E | <0,02 | <0,02 | 0,08 | 0,08 | 0,04 | 0,04 | 0,08 | 0,08 |
| *Proteus mirabilis* A 235 | 0,08 | 0,08 | 0,3 | 0,3 | 0,15 | 0,5 | 0,6 | 0,6 |
| *Proteus vulgaris* A 232 | 0,08 | 0,15 | 1,2 | 1,2 | 0,08 | 0,15 | 0,6 | 0,6 |
| *Staphylococcus aureus* SG 511 | 1,2 | 1,2 | 2,5 | 5 | | | | |
| *Staphylococcus aureus* 285 | 2,5 | 2,5 | 5 | 10 | | | | |
| *Staphylococcus aureus* 54146 | 2,5 | — | 5 | 10 | | | | |
| *Streptococcus pyogenes* A 561 | <0,04 | <0,04 | <0,04 | <0,04 | | | | |
| *Streptococcus pyogenes* 77 A | <0,04 | <0,04 | <0,04 | <0,04 | | | | |
| *Escherichia Coli* 1894 | <0,04 | <0,04 | <0,04 | 0,08 | | | | |
| *Escherichia Coli* 078 | 0,15 | 0,15 | 0,08 | 0,08 | | | | |
| *Escherichia Coli* TEM | 1,2 | 1,2 | 0,3 | 0,3 | | | | |
| *Escherichia Coli* 1507 E | <0,04 | <0,04 | 0,15 | 0,15 | | | | |
| *Escherichia Coli* DC0 | 0,6 | 0,6 | 0,15 | 0,15 | | | | |
| *Escherichia Coli* DC2 | <0,04 | <0,04 | 0,15 | 0,15 | | | | |
| *Salmonella typhimurium* MZ 11 | 0,3 | 0,3 | 0,3 | 0,3 | | | | |
| *Klebsiella pneumoniae* 52145 | 1,2 | 1,2 | 0,6 | 0,6 | | | | |
| *Klebsiella aerogenes* 1522 E | — | — | 1,2 | 1,2 | | | | |
| *Enterobacter cloacae* 1321 E | 0,3 | 0,3 | 0,08 | 0,15 | | | | |
| *Proteus mirabilis* A 235 | 0,3 | 0,6 | 0,3 | 0,3 | | | | |
| *Proteus vulgaris* A 232 | 0,6 | 0,6 | 0,6 | 2,5 | | | | |

TABLE I

Comparison of the products of the present application and Cefazoline.
Example of Application

| Tested Products | Product of Ex. 123 | | Product of Ex. 128 | | Product of Ex. 129 | | Product of Ex. 139 | | Product of Ex. 141 | | Product of Ex. 145 | |
|---|---|---|---|---|---|---|---|---|---|---|---|---|
| STRAINS | 24 h | 48 h | 24 h | 48 h | 24 h | 48 h | 24 h | 48 h | 24 h | 48 h | 24 h | 48 h |
| *Klebsiella pneumoniae* Exp. 52145 | 0,15 | 0,15 | 0,3 | 0,3 | 0,3 | 0,3 | 0,6 | 0,6 | 0,6 | 0,6 | 0,6 | 0.6 |
| *Proteus Mirabilis* (indol–) A 235 | 0,15 | 0,15 | 0,15 | 0,15 | 0.3 | 0,3 | 0,3 | 0,3 | 0,3 | 0,6 | 0,3 | 0,3 |
| *Proteus Vulgaris* (indol+) A 232 | 0,15 | 0,15 | 0,6 | 0,6 | 0,15 | 0,15 | 0,3 | 0,3 | 1,2 | 2,5 | 0,6 | 2,5 |
| Providencia Du 48 | 2,5 | 5 | 1,2 | 1,2 | 1,2 | 1,2 | 2,5 | 5 | 2,5 | 10 | 1,2 | 5 |
| Serratia Resistant Gentamicine 2532 | 1,6 | 0,6 | 1,2 | 1,2 | 1,2 | 1,2 | 2,5 | 2,5 | 1,2 | 1,2 | 1,2 | 1,2 |

| Tested Products | Product of Ex. 148 | | Product of Ex. 157 | | Product of Ex. 188 | | CEFAZOLINE | |
|---|---|---|---|---|---|---|---|---|
| STRAINS | 24 h | 48 h | 24 h | 48 h | 24 h | 48 h | 24 h | 48 h |
| *Klebsiella pneumoniae* Exp. 52145 | 0,15 | 0,3 | 0,6 | 1,2 | 0,6 | 0,6 | 1 | 1 |
| *Proteus Mirabilis* (indol–) A 235 | 0,15 | 0,15 | 0,3 | 0,3 | 0,3 | 0,3 | 8 | 10 |
| *Proteus Vulgaris* (indol+) A 232 | 0,15 | 0,3 | 0,3 | 0,3 | 0,6 | 0,6 | 740 | 740 |
| Providencia Du 48 | 0,6 | 1,2 | 5 | 5 | 2,5 | 2,5 | 740 | 740 |
| Serratia Resistant Gentamicine 2532 | 0,6 | 0,6 | 2,5 | 2,5 | 2.5 | 2,5 | 740 | 740 |

TABLE II

| Comparison of the products of the present application and the products of U.S. Pat. No. 4,476,124 | | | | | | | | | | | | |
|---|---|---|---|---|---|---|---|---|---|---|---|---|
| | Example of Application | | | | | | | | | | | |
| Tested Products | Product of Ex. 123 | | Product of Ex. 128 | | Product of Ex. 129 | | Product of Ex. 139 | | Product of Ex. 141 | | Product of Ex. 145 | |
| STRAINS | 24 h | 48 h | 24 h | 48 h | 24 h | 48 h | 24 h | 48 h | 24 h | 48 h | 24 h | 48 h |
| *Staphylococcus aureus* Exp. n°54146 | 5 | 10 | 2,5 | 5 | 20 | 40 | 5 | 5 | 5 | 10 | | 10 |
| *Streptococcus pyogenes* A561 | ≦0,04 | ≦0,04 | ≦0,04 | ≦0,04 | ≦0,04 | ≦0,04 | ≦0,04 | ≦0,04 | ≦0,04 | ≦0,04 | ≦0,04 | ≦0,04 |

| | | | | | | | Examples of USP 4,476,124 | | | | | |
|---|---|---|---|---|---|---|---|---|---|---|---|---|
| Tested Products | Product of Ex. 148 | | Product of Ex. 157 | | Product of Ex. 188 | | Product of Ex. 1 | | Product of Ex. 2 | | Product of Ex. 3 | |
| STRAINS | 24 h | 48 h | 24 h | 48 h | 24 h | 48 h | 24 h | 48 h | 24 h | 48 h | 24 h | 48 h |
| *Staphylococcus aureus* Exp. n°54146 | 1,2 | 2,5 | 5 | 5 | 5 | 10 | 740 | 740 | 20 | 20 | 720 | 720 |
| *Streptococcus pyogenes* A561 | ≦0,02 | ≦0,02 | ≦0,04 | ≦0,04 | ≦0,04 | ≦0,04 | 0,05 | 0,05 | 0,04 | 0,04 | 0,15 | 0,15 |

What we claim is:

1. A compound selected from the group consisting of a compound of the formula

I

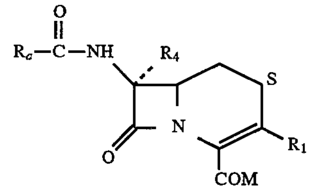

wherein $R_a$ is selected from the group consisting of

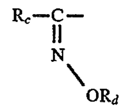

and

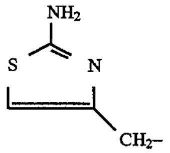

$R_c$ is selected from the group consisting of 2-amino-4-thiazolyl, 2-amino-5-chloro-thiazolyl, 5-amino-1,2,4-thiadiazolyl, 4-thiazolyl, 2-thienyl and 2-furyl, $R_d$ is selected from the group consisting of hydrogen, alkyl of 1 to 4 carbon atoms, alkenyl of 2 to 4 carbon atoms and phenyl, all optionally substituted with at least one member of the group consisting of halogen, —CN, carbamoyl, —$NO_2$, —$NH_2$, —OH, —SH, =O and carboxyl free, esterified or salified, $-CHF_2$, 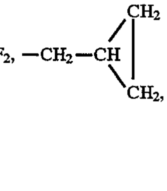 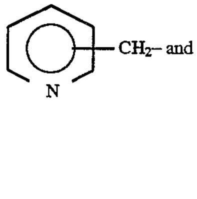 and -continued

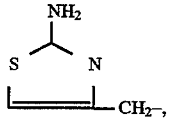

$R_1$ is selected from the group consisting $-Z-R_2$, a)

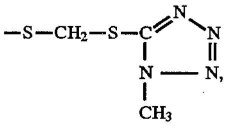 b)

$-Z_a-R_3$, c)

$R_2$ is selected from the group consisting of alkyl, alkenyl and alkynyl all optionally substituted with at least one member of the group consisting of nitro, carboxy free, esterified or salified, amino, —OH, azido, sulfo free or salified, halogen, carbamoyl, methyltetrazolylcarbamoyl, aryl selected from the group consisting of phenyl, diphenyl, naphthyl, thienyl, furyl, pyrrolyl, imidazolyl, pyrazolyl, thiazolyl, isothiazolyl, oxazolyl, isoxazolyl, triazolyl, thiadiazolyl, pyrannyl, oxadiazolyl, tetrazolyl, pyridinyl, pyrimidinyl, pyrazinyl, pyridazinyl, thiazinyl, oxazinyl, trazinyl, thiadiazinyl, oxadiazinyl, tetrazinyl, imidazolinyl, benzimidazolyl, benzothiazolyl and benzoxazol, all optionally substituted with at least one member of the group consisting of acetyl, nitrophenyl, 1-methyl-pyrrolidinium, methylpyridinium, trimethyl ammonium, pyridinium, methylthio-pyridinium, trifluoromethylphenyl and cyano-phenyl and $R_2$ can be optionally interrupted with optionally oxidized —S— or —O— or —NH— or —Se—, Z is selected from the group consisting of optionally oxidized —S— or —O— or —Se— or —NH—, Za is selected from the group consisting of $-CH_2$—, —O—, —S—, —Se—, —NH—, —$CH_2S$— and a simple bond, $R_3$ is selected from the group consisting of phenyl, diphenyl, naphthyl, heterocyclearyl selected from the group consisting of thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridinyl, pyrimidinyl, pyrazinyl, pyridazinyl, thiazinyl, oxazinyl, triazinyl, thiadiazinyl, oxadiazinyl, tetrazinyl, imidazolinyl, benzimidazolyl, benzothiazolyl, and benzoxazol, a quaternary ammonium pyridinium, quinolinium, isoquinolinium, 2,3-cyclopenteno pyridinium, thienopyridinium, cyclohexylpyridinium and trimethylammonium and optionally substituted with at least one member of the group consisting of alkyl optionally substituted with at least one member of the group consisting of phenyl, thienyl, phenoxy, alkoxycarbonyl, halogen, hydroxy, carboxy free, esterified or salified, amino, alkylamino, and dialkylamino; alkenyl; alkyl; phenyl; tolyl; halogen; nitro; alkoxy of 1 to 4 carbon atoms; alkylthio; hydroxy; mercapto; carboxyl free, esterified or salified; carbamoyl;

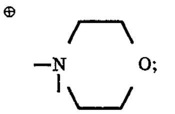

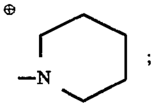

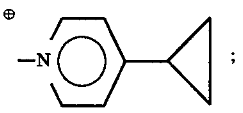

pyridinium substituted with cyano, $—CF_3$ or acetyl; (2-chloro-2-propenyl)-1,4,5,6-tetrahydro, 5,6-dioxo-1,2,4-triazin-3-yl and 1,2, 5,6-tetrahydro-2-methy-5,6-dioxo-1,2, 4-triazin-3-yl, d) alkyl, alkenyl or alkynyl of 2 to 4 carbon atoms optionally substituted with a member selected from the group consisting of phenyl, carboxy free, esterified or salified, cyano, amino, acyl, halogen and $—CF_3$ and optionally interrupted with optionally oxidized —S—, —O— or —NH—, e) halogen, nitrile, caboxy, free, esterified or salified, azide, thiocyanato, isothiocyanato and f) azidomethyl, amino, mono or dialkylaminomethyl, thiocyanatomethyl, isothiocyanatomethyl, carbamoyloxymethyl, semicarbazonomethine, arylhydrazonomethine optionally substituted with nitro, nitromethyl, di or trihalomethyl, $—CH_2—ONO_2$, $—CH^+{}_2P(alk_3)$,

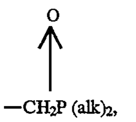

alk is alkyl of 1 to 4 carbon atoms, $R_4$ is hydrogen, COM is $CO_2A$ or A is hydrogen, an equivalent of alkali metal, alkaline earth metal, magnesium, ammonium or an organic amine or A is an ester or $CO_2A$ is $CO^-{}_2$, or $R_1$ and $CO_2A$ form with the carbon to which they are attached

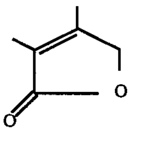

or

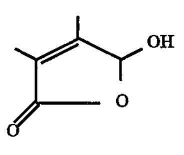

or COM is carbamoyl and their non-toxic, pharmaceutically acceptable acid addition salts.

2. A compound of claim 1 wherein Rd is selected from the group consisting of hydrogen, methyl and allyl and $R_1$ is selected from the group consisting of methoxymethyl, pyridinylthio, pyridinyl, phenyl or phenylthio optionally substituted by methyl, cyclopropyl, nitro, chloro or methoxy, phenyl-selenyl, methylthio or ethylthio optionally substituted by carboxy, ethoxy-carbonyl or amino, ethyl, isopropyl, methyltetrazolylthio, methyl or thiomethylthiadiazolylthio, trimethylammonium methyl and pyridinium optionally substituted with at least one member of the group consisting of dialkylamino of 1 to 4 carbon atoms, alkyl of 1 to 4 carbon atoms, cycloalkyl of 3 to 8 carbon atoms, alkoxy, alkoxyalkyl and alkylthio of 1 to 4 carbon atoms, cyano, acetyl, carboxy, phenyl, benzoyl, alkoxycarbonyl, acylamino, halogen, hydroxyalkyl, thiocyanate, phenylthio, hydroxy, amino, phenoxy, methylimidazolinium, pyrazinium, alkyl thienopyridinium, benzopyridinium, vinylimidazolinium, thiazolinium, methyl methylthio imidazolinium and cyclohexyl pyridinium or dihydro-pyridinium.

3. A compound of claim 1, wherein $R_1$ is $Z'_a—R'_3$ in which $Z'_a$ is sulfur and $R'_3$ is a heterocyclic aryl with 5 to 6 links optionally substituted, or $Z'_a$ is methylene and $R'_3$ is selected from the group consisting of pyridinium, thienopyridinium, quinolinium, isoquinolinium, cyclohexylpyridinium and phenyl optionally substituted with $—NO_2$, chlorine or $CH_3O—$ and its non-toxic, pharmaceutically acceptable salts.

4. A compound of claim 1 selected from the group consisting of racemic or optically active forms of the syn isomer of 7-[2-(2-aminothiazol-4-yl)-2-methoxyimino-acetamido]-3-(3-nitro-phenylthio)-8-oxo-4-thia-1-azabicyclo[4,2,0]-oct-2-ene-2-carboxylic acid and its non-toxic, pharmaceutically acceptable salts.

5. A compound of claim 1 selected from the group consisting of racemic or optically active forms of the syn isomer of 7-[2-(2-aminothiazol-4-yl)-2-methoxyimino-acetamido]-3-(4-nitro-phenyl)-8-oxo-4-thia-1-azabicyclo[4, 2,0]-oct-2-ene-2-carboxylic acid and its non-toxic, pharmaceutically acceptable salts.

6. A compound of claim 1 selected from the group consisting of racemic or optically active forms of the syn isomer of 7-[2-(2-aminothiazol-4-yl)-2-methoxyimino-acetamido]-3-[1-methyl-(1H)-tetrazol-5-yl)-thio]-8-oxo-4-thia-1-azabicyclo[4,2,0]oct-2-ene-2-carboxylic acid and its non-toxic, pharmaceutically acceptable salts.

7. A compound of claim 1 selected from the group consisting of racemic or optically active forms of the syn isomer of 7-[2-(2-aminothiazol-4-yl)-2-methoxyimino-acetamido]-3-[1-methyl-(1H)-tetrazol-5-yl)-thiomethyl)-8-oxo-4-thia-1-azabicyclo[4,2,0]oct-2-ene-2-carboxylic acid and its non-toxic, pharmaceutically acceptable salts.

8. A compound of claim 1 selected from the group consisting of racemic or optically active forms of the syn isomer of 1-[7-[2-(2-aminothiazol-4-yl)-2-methoxyimino-acetamido]-2-carboxy-8-oxo-4-thia-1-azabicyclo[4,2,0]oct-2-ene-3-yl]-methyl-pyridinium and its non-toxic, pharmaceutically acceptable salts.

9. A compound of claim 1 selected from the group consisting of racemic or optically active forms of the syn isomer of 1-[7-[2-(2-aminothiazol-4-yl)-2-methoxyimino-acetamido]-2-carboxy-8-oxo-4-thia-1-azabicyclo[4,2,0]oct-2-ene-3-yl]-methyl-(6,7,-dihydro)-5H-1-pyrindinium and its non-toxic, pharmaceutically acceptable salts.

10. A compound of claim 1 selected from the group consisting of racemic or optically active forms of the syn isomer of 6-[7-[2-(2-aminothiazol-4-yl)-2-methoxyimino-acetamido]-2-carboxy-8-oxo-4-thia-1-azabicyclo[4,2,0]oct- 2-ene-3-yl]-methyl-thieno[2,3-c]pyridinium and its non-toxic, pharmaceutically acceptable salts.

11. A compound of claim 1 selected from the group consisting of racemic or optically active forms of the syn isomer of 7-[2-(2-aminothiazol-4-yl)-2-methoxyimino-acetamido]-8-oxo-2-carboxy-4-thia-1-azabicyclo[4,2,0]oct-2-ene-3-yl]-methyl-trimethyl ammonium and its non-toxic, pharmaceutically acceptable salts.

12. A compound of claim 1 selected from the group consisting of racemic or optically active forms of the syn isomer of 7-[2-(2-aminothiazol-4-yl)-2-methoxyimino-acetamido]-8-oxo-4-thia-2-carboxy-1-azabicyclo[4,2,0]oct-2-ene-3-yl]-methyl-4-cyclopropylpyridinium and its non-toxic, pharmaceutically acceptable salts.

13. A compound of claim 1 selected from the group consisting of racemic or optically active forms of the syn isomer of 6-[7-[2-(2-aminothiazol-4-yl)-2-methoxyimino-acetamido]-8-oxo-4-thia-2-carboxy-1-azabicyclo[4,2,0]oct-2-ene-3-yl]-methyl-7-methylthieno[2,3-c]pyridinium and its non-toxic, pharmaceutically acceptable salts.

14. A compound of claim 1 selected from the group consisting of racemic or optically active forms of the syn isomer of 7-[7-[2-(2-aminothiazol-4-yl)-2-methoxyimino-acetamido]-8-oxo-4-thia-2-carboxy-1-azabicyclo[4,2,0]oct-2-ene-3-yl]-methylthieno[2,3-b]pyridinium and its non-toxic, pharmaceutically acceptable salts.

15. A compound of claim 1 selected from the group consisting of racemic or optically active forms of the syn isomer of 7-[2-(2-aminothiazol-4-yl)-2-(2-propenyloxy)-imino-acetamido]-2-carboxy-8-oxo-4-thia-1-azabicyclo[4,2,0]oct-2-ene-3-yl]-methyl pyridinium and its non-toxic, pharmaceutically acceptable salts.

16. A compound of claim 1 selected from the group consisting of racemic or optically active forms of the syn isomer of 1-[(7-[2-(2-aminothiazol-4-yl)-2-methoxyimino-acetamido]-2-carboxy-8-oxo-4-thia-1-azabicyclo[4,2,0]oct-2-ene-3-yl]-methyl-(2-methylthio]-pyridinium and its non-toxic, pharmaceutically acceptable salts.

17. A compound of claim 1 selected from the group consisting of racemic or optically active forms of the syn isomer of 5-[7-[2-(2-aminothiazol-4-yl)-[(difluoromethoxy)-imino-acetamido]-2-carboxy-8-oxo-4-thia-1-azabicyclo[4,2,0]oct-2-ene-3-yl]-methylthieno[2,3-b]pyridinium and its non-toxic, pharmaceutically acceptable salts.

18. A compound of claim 1 selected from the group consisting of racemic or optically active forms of the syn isomer of 7-[7-[2-(2-aminothiazol-4-yl-[(propenyloxy-imino]-acetamido]-2-carboxy-8-oxo-4-thia-1-azabicyclo[4,2,0]oct-2-ene-3-yl]-methyl]-thieno[2,3-b]pyridinium (6RS, 7RS) and its non-toxic, pharmaceutically acceptable salts.

19. An antibiotic composition comprising an antibiotically effective amount of at least one compound of claim 1 and an excipient.

20. A composition of claim 19 wherein Rd is selected from the group consisting of hydrogen, methyl and allyl and $R_1$ is selected from the group consisting of methoxymethyl, pyridiniylthio, pyridinyl, phenyl or phenylthio optionally substituted by methyl, cyclopropyl, nitro, chloro or methoxy, phenylselenyl, methylthio or ethylthio optionally substituted by carboxy, ethoxy-carbonyl or amino radical, ethyl, isopropyl, methyltetrazolylthio, methyl or thiomethylthiadiazolylthio, trimethylammonium methyl, pyridinium optionally substituted with at least one member of the group consisting of dialkylamino of 1 to 4 carbon atoms, alkyl of 1 to 4 carbon atoms, cycloalkyl of 3 to 8 carbon atoms, alkoxy, alkoxyalkyl and alkylthio of 1 to 4 carbon atoms, cyano, acetyl, carboxy, phenyl, benzoyl, alkoxycarbonxyl, acylamino, halogen, hydroxyalkyl, thiocyanato, phenylthio, hydroxy, amino, phenoxy, methylimidazolinium, pyrazinium, alkyl thienopyridinium, benzopyridinium, vinylimidazolinium, thiazolinium, methyl methylthio imidazolinium, cyclohexylpyridinium and dihydropyridinium.

21. A composition of claim 19 wherein $R_1$ is —$Z'_a$—$R'_3$ in which $Z'_a$ is sulfur and $R'_3$ is a heterocyclic aryl with 5 to 6 links optionally substituted, or $Z'_a$ is methylene and $R'_3$ is selected from the group consisting of pyridinium, thienopyridinium, quinolinium, isoquinolinium and phenyl optionally substituted with —$NO_2$, chlorine or $CH_3O$.

22. A composition of claim 19 wherein the active compound is selected from the group consisting of racemic or optically active forms of the syn isomer of 7-[2-(2-aminothiazol-4-yl)-2-methoxy-imino-acetamido]-3-(3-nitrophenylthio)-8-oxo-4-thia-1-azabicyclo (4,2,0]oct-2-ene-2-carboxylic acid and its non-toxic, pharmaceutically acceptable salts.

23. A composition of claim 21 wherein the active compound is selected from the group consisting of racemic or optically active forms of the syn isomer of 7-[2-(2-aminothiazol-4-yl)-2-methoxy-imino-acetamido]-3-(4-nitrophenyl)-8-oxo-4-thia-1-azabicyclo [4,2,0]oct-2-ene-2-carboxylic acid and its non-toxic, pharmaceutically acceptable salts.

24. A composition of claim 19 wherein the active compound is selected from the group consisting of racemic or optically active forms of the syn isomer of 7-[2-(2-aminothiazol-4-yl)-2-methoxy-imino-acetamido]-3-[(1-methyl-(1H)-tetrazol-5-yl)-thio]-8-oxo-4-thia-1-azabicyclo [4,2,0]oct-2-ene-2-carboxylic acid and its non-toxic, pharmaceutically acceptable salts.

25. A composition of claim 19 wherein the active compound is selected from the group consisting of racemic or optically active forms of the syn isomer of7-[2-(2-aminothiazol-4-yl)-2-methoxy-imino-acetamido]-3-[(1-methyl-(1H)-tetrazol-5-yl)-thiomethy]-8-oxo-4-thia-1-azabicyclo[4,2,0]oct-2-ene-2-carboxylic acid and its non-toxic, pharmaceutically acceptable salts.

26. A composition of claim 19 wherein the active compound is selected from the group consisting of racemic or optically active forms, of the syn isomer of 1-[7-[(2-aminothiazol-4-yl)-2-methoxy-imino-acetamido]-2-carboxy-8-oxo-4-thia-1-azabicyclo[4,2,0]oct-2-ene-3-yl]-methylpyridiniuim and its non-toxic, pharmaceutically acceptable salts.

27. A composition of claim 19 wherein the active compound is selected from the group consisting of racemic or optically active forms of the syn isomer of 1-[7-[(2-aminothiazol-4-yl)-2-methoxy-imino-acetamido]-2-carboxy-8-oxo-4-thia-1-azabicyclo[4,2,0]oct-2-en-3-yl]-methyl(6,7-dihydro)-5H-1-pyrindinium and its non-toxic, pharmaceutically acceptable salts.

28. A composition of claim 19 wherein the active compound is selected from the group consisting of racemic or optically active forms of the syn isomer of 6-[7-[(2-(2-aminothiazol-4-yl)-2-methoxy-imino-acetamido]-2-carboxy-8-oxo-4-thia-1-azabicyclo[4,2,0]oct-2-en-3-yl)-methylthieno[2,3-c]pyridinium and its non-toxic, pharmaceutically acceptable salts.

29. A composition of claim 19 wherein the active compound is selected from the group consisting of racemic or optically active forms of the syn isomer of 7-[2-(2-aminothiazol-4-yl)-2-methoxy-imino-acetamido]-8-oxo-2-carboxy-4-thia-1-azabicyclo[4,2,0]oct-2-en-3-yl)-methyl-trimethyl ammonium and its non-toxic, pharmaceutically acceptable salts.

30. A composition of claim 19 wherein the active compound is selected from the group consisting of racemic or optically active forms of the syn isomer of 7-[2-(2-aminothiazol-4-y)-2-methoxy-imino-acetamido]-8-oxo-4-thia-2-carboxy-1-azabicyclo[4,2,0]oct-2-en-3-yl)-methyl-4-cyclopropyl-pyridinium and its non-toxic, pharmaceutically acceptable salts.

31. A composition of claim 19 wherein the active compound is selected from the group consisting of racemic or optically active forms of the syn isomer of 6-[7-[2-(2-aminothiazol-4-yl)-2-methoxyimino-acetamido]-8-oxo-4-thia-2-carboxy-1-azabicyclo[4,2,0]oct-2-en-3-yl]-methyl-7-methylthieno[2,3-c]pyridinium and its non-toxic, pharmaceutically acceptable salts.

32. A composition of claim 19 wherein the active compound is selected from the group consisting of racemic or optically forms of the syn isomer of 7-[7-[2-(2-aminothiazol-4-yl)-2-methoxyimino-acetamido]-8-oxo-4-thia-2-carboxy-1-azabicyclo[4,2,0]oct-2-en-3-yl]-methylthieno[2,3-b]pyridinium and its non-toxic, pharmaceutically acceptable salts.

33. A composition of claim 19 wherein the active compound is selected from the group consisting of racemic or optically active forms of the syn isomer of 7-[2-(2-aminothiazol-4-yl)-2-propenyloxy)-imino-acetamido]-2-carboxy-8-oxo-4-thia-1-azabicyclo[4,2,0]oct-2-ene-3-yl]-methyl pyridinium and its non-toxic, pharmaceutically acceptable salts.

34. A composition of claim 19 wherein the active compound is selected from the group consisting of racemic or optically forms of the syn isomer of 1-[(7-[2-(2-aminothiazol-4-yl)-2-methoxyimino-acetamido]-2-carboxy-8-oxo-4-thia-1-azabicyclo[4,2,0]oct-2-en-3-yl]-methyl-(2-methylthio)-pyridinium and its non-toxic, pharmaceutically acceptable salts.

35. A composition of claim 19 wherein the active compound is selected from the group consisting of racemic or optically forms of the syn isomer of 5-[7-(2-aminothiazol-4-yl)-[(difluoromethoxy)-imino]-acetamido]-2-carboxy-8-oxo-4-thia-1-azabicyclo[4,2,0]oct-2-ene- 3-yl]-methylthieno[2,3-b]pyridinium and its non-toxic, pharmaceutically acceptable salts.

36. A composition of claim 19 wherein the active compound is selected from the group consisting of racemic or optically forms of the syn isomer of 7-[7-[2-(2-aminothiazol-4-yl)-2-[(propenyloxy)-imino]-acetamido-2-carboxy-8-oxo-4-thia-1-azabicyclo[4,2,0]oct-2-en-3-yl]-methyl]-thieno[2,3-b]-pyridinium (6RS,7RS) and its non-toxic, pharmaceutically acceptable salts.

37. A method of treating bacterial infections in warm-blooded animals comprising administering to warm-blooded animals an anti-bactericidally effective amount of at least one compound of claim 1.

38. A method of claim 37 wherein Rd is selected from the group consisting hydrogen, methyl and allyl and $R_1$ is selected from the group consisting of methoxymethyl, pyridinylthio, pyridinyl, phenyl or, phenylthio optionally substituted by methyl, cyclopropyl, nitro, chloro or methoxy, phenyl-selenyl, methylthio optionally substituted by carboxy, ethoxycarbonyl, or amino radical, ethyl, isopropyl, methyltetrazolylthio, methyl or thiomethyl-thiadiazolylthio, trimethyl-ammonium methyl, pyridinium optionally substituted with at least one member of the group consisting of dialkylamino of 1 to 4 carbon atoms, alkyl of 1 to 4 carbon atoms, cycloalkyl of 3 to 8 carbon atoms, alkoxy, alkoxyalkyl and alkylthio of 1 to 4 carbon atoms, cyano, acetyl, carboxy, phenyl, benzoyl, alkoxycarbonyl, acylamino, halogen, hydroxyalkyl, thiocyanate, phenylthio, hydroxy, amino, phenoxy, methylimidazolinium, pyrazinium, alkyl thienopyridinium, benzopyridinium, vinylimidazolinium, thiazolinium, methyl methylthio imidiazolinium and cyclohexyl-pyridinium or dihydropyridinium.

39. A method of claim 37 wherein $R_1$ is $Z_a—R_3$ in which $Z_a$ is sulfur and $R_3$ is a heterocyclic aryl with 5 to 6 links optionally substituted, or $Z_a$ is methylene and $R_3$ is selected from the group consisting of pyridinium, thienopyridinium, quinolinium, isoquinolinium and phenyl optionally substituted with $—NO_2$, chlorine or $CH_3O—$.

40. A method of claim 35 wherein the active compound is selected from the group consisting of racemic or optically active forms of the syn isomer of 7-[2-(2-amino-thiazol-4-yl)-2-methoxy-imino-acetamido]-3-(3-nitrophenylthio)-8-oxo-4-thia-1-azabicyclo[4,2,0]oct-2-ene-2-carboxylic acid and its non-toxic, pharmaceutically acceptable salts.

41. A method of claim 35 wherein the active compound is selected from the group consisting of racemic or optically active forms of the syn isomer of 7-[2-(2-amino-thiazol-4-yl)-2-methoxy-imino-acetamido]-3-(4-nitrophenyl)-8-oxo-4-thia-1-azabicyclo[4,2,0]oct-2-ene-2-carboxylic acid and its non-toxic, pharmaceutically acceptable salts.

42. A method of claim 37 wherein the active compound is selected from the group consisting of racemic or optically active forms of the syn isomer of 7-[2-(2-aminothiazol-4-yl)-2-methoxy-imino-acetamido]-3-[(1-methyl-(1H)-tetrazol-5-yl)-thio]-8-oxo-4-thia-1-azabicyclo[4,2,0]oct-2-ene-2-carboxylic acid and its non-toxic, pharmaceutically acceptable salts.

43. A method of claim 37 wherein the active compound is selected from the group consisting of racemic or optically active forms of the syn isomer of 7-[2-(2-aminothiazol-4-yl)-2-methoxy-imino-acetamido]-3-[(1-methyl-(1H)-tetrazol-5-yl)-thiomethyl]-8-oxo-4-thia-1-azabicyclo[4,2,0]oct-2-ene-2-carboxylic acid and its non-toxic, pharmaceutically acceptable salts.

44. A method of claim 37 wherein the active compound is selected from the group consisting of racemic or optically active forms of the syn isomer of 1-[7-[(2-aminothiazol-4-yl)-2-methoxy-imino-acetamido]-2-carboxy-8-oxo-4-thia-1-azabicyclo[4,2,0]oct-2-ene-3-yl]-methylpyridinium and its non-toxic, pharmaceutically acceptable salts.

45. A method of claim 37 wherein the active compound is selected from the group consisting of racemic or optically active forms of the syn isomer of 1-[7-[(2-aminothiazol-4-yl)-2-methoxy-imino-acetamido]-2-carboxy-8-oxo-4-thia-1-azabicyclo[4,2,0]oct-2-ene- 3-yl]-methyl-(6,7-dihydro)-5H-1-pyrindinium and its non-toxic, pharmaceutically acceptable salts.

46. A method of claim 37 wherein the active compound is selected from the group consisting of racemic or optically active forms of the syn isomer of 6-(7-[2-(2-aminothiazol-4-yl)-2-methoxy-imino-acetamido]-2-carboxy-8-oxo-4-thia-1-azabicyclo[4,2,0]oct-2-ene-3-yl]-methylthieno[2,3-c] pyridinium and its non-toxic, pharmaceutically acceptable salts.

47. A method of claim 37 wherein the active compound is selected from the group consisting of racemic or optically active forms of the syn isomer of 7-[2-(2-aminothiazol-4-yl)-2-methoxy-imino-acetamido]-8-oxo-2-carboxy-4-thia-1-azabicyclo[4,2,0]oct-2-ene-3-yl]-methyl-trimethyl ammonium and its non-toxic, pharmaceutically acceptable salts.

48. A method of claim 13 wherein the active compound is selected from the group consisting of racemic or optically active forms of the syn isomer of 7-[2-(2-aminothiazol-4-yl)-2-methoxy-imino-acetamido]-8-oxo-4-thia-2-carboxy- 1-azabicyclo[4,2,0]oct-2-ene-3-yl]-methyl-4-cyclopropyl-pyridinium and its non-toxic, pharmaceutically acceptable salts.

49. A method of treating bacterial infections in warm-blooded animals comprising administering to warm-blooded animals an anti-bactericidally effective amount of at least one compound of claim 13.

50. A method of treating bacterial infections in warm-blooded animals comprising administering to warm-blooded animals an anti-bactericidally effective amount of at least one compound of claim 14.

51. A method of treating bacterial infections in warm-blooded animals comprising administering to warm-blooded animals an anti-bactericidally effective amount of at least one compound of claim 15.

52. A method of treating bacterial infections in warm-blooded animals comprising administering to warm-blooded animals an anti-bactericidally effective amount of at least one compound of claim 16.

53. A method of treating bacterial infections in warm-blooded animals comprising administering to warm-blooded animals an anti-bactericidally effective amount of at least one compound of claim 17.

54. A method of treating bacterial infections in warm-blooded animals comprising administering to warm-blooded animals an anti-bactericidally effective amount of at least one compound of claim 18.

* * * * *